(12) United States Patent
Meyer et al.

(10) Patent No.: US 9,347,066 B2
(45) Date of Patent: May 24, 2016

(54) PLANTS AND SEEDS WITH ALTERED STORAGE COMPOUND LEVELS, RELATED CONSTRUCTS AND METHODS INVOLVING GENES ENCODING PROTEINS WITH SIMILARITY TO BACTERIAL 2,4-DIHYDROXY-HEPT-2-ENE-1,7-DIOIC ACID CLASS II-LIKE ALDOLASE PROTEINS

(76) Inventors: Knut Meyer, Wilmington, DE (US); Kevin L. Stecca, New Castle, DE (US)

(*) Notice: Subject to any disclaimer, the term of this patent is extended or adjusted under 35 U.S.C. 154(b) by 620 days.

(21) Appl. No.: 13/504,982

(22) PCT Filed: Nov. 1, 2010

(86) PCT No.: PCT/US2010/054932
§ 371 (c)(1),
(2), (4) Date: Oct. 15, 2012

(87) PCT Pub. No.: WO2011/053898
PCT Pub. Date: May 5, 2011

(65) Prior Publication Data
US 2013/0111633 A1     May 2, 2013

Related U.S. Application Data

(60) Provisional application No. 61/256,323, filed on Oct. 30, 2009.

(51) Int. Cl.
*C12N 15/82* (2006.01)
*C12N 9/88* (2006.01)
*C07K 14/415* (2006.01)

(52) U.S. Cl.
CPC .......... *C12N 15/8247* (2013.01); *C07K 14/415* (2013.01); *C12N 9/88* (2013.01); *C12N 15/8218* (2013.01); *C12N 15/8243* (2013.01); *C12N 15/8245* (2013.01); *C12N 15/8251* (2013.01)

(58) Field of Classification Search
None
See application file for complete search history.

(56) References Cited

U.S. PATENT DOCUMENTS

| 2004/0031072 | A1* | 2/2004 | La Rosa et al. ............... 800/278 |
| 2006/0107345 | A1 | 5/2006 | Alexandrov et al. |
| 2006/0135758 | A1 | 6/2006 | Wu |

FOREIGN PATENT DOCUMENTS

| EP | 1033405 A2 | 9/2000 |

OTHER PUBLICATIONS

Focks and Benning, 1998, Plant Physiology 118: 91-101.*
Arabidopsis thaliana sequence encoding HpcH/Hpal aldolase family protein, GenBank Accession No. NP_192813, published May 22, 2008.*
Chanprame et al., 1998, In Vitro Cell Dev. Biol.-Plant 34: 64-68.*
Flores et al., 2008, Transgenic Res. 17: 839-850.*
Barbara Mazur et al., Gene Discovery and Product Development for Grain Quality Traits, Science, Jul. 16, 1999, pp. 372-375, vol. 285.
Weijun Wang et al., Purification and Biochemical Characterization of a Pyruvate-Specific Class II Aldolase, Hpal, Biochemistry, Jul. 2005, pp. 9447-9455, vol. 44, No. 27.
International Search Report for PCT/US2010/054932.
Written Opinion for PCT/US2010/054932.

\* cited by examiner

*Primary Examiner* — David T Fox
*Assistant Examiner* — Bratislav Stankovic

(57) ABSTRACT

This invention is in the field of plant molecular biology. More specifically, this invention pertains to isolated nucleic acid fragments encoding proteins with similarity to bacterial 2,4-dihydroxy-hept-2-ene-1,7-dioic acid class II-like aldolase proteins in plants and seeds and the use of such fragments to modulate expression of a gene encoding proteins with similarity to bacterial 2,4-dihydroxy-hept-2-ene-1,7-dioic acid class II-like aldolase proteins in a transformed host cell.

20 Claims, 7 Drawing Sheets

FIG. 1A

FIG. 1B

Figure 3:
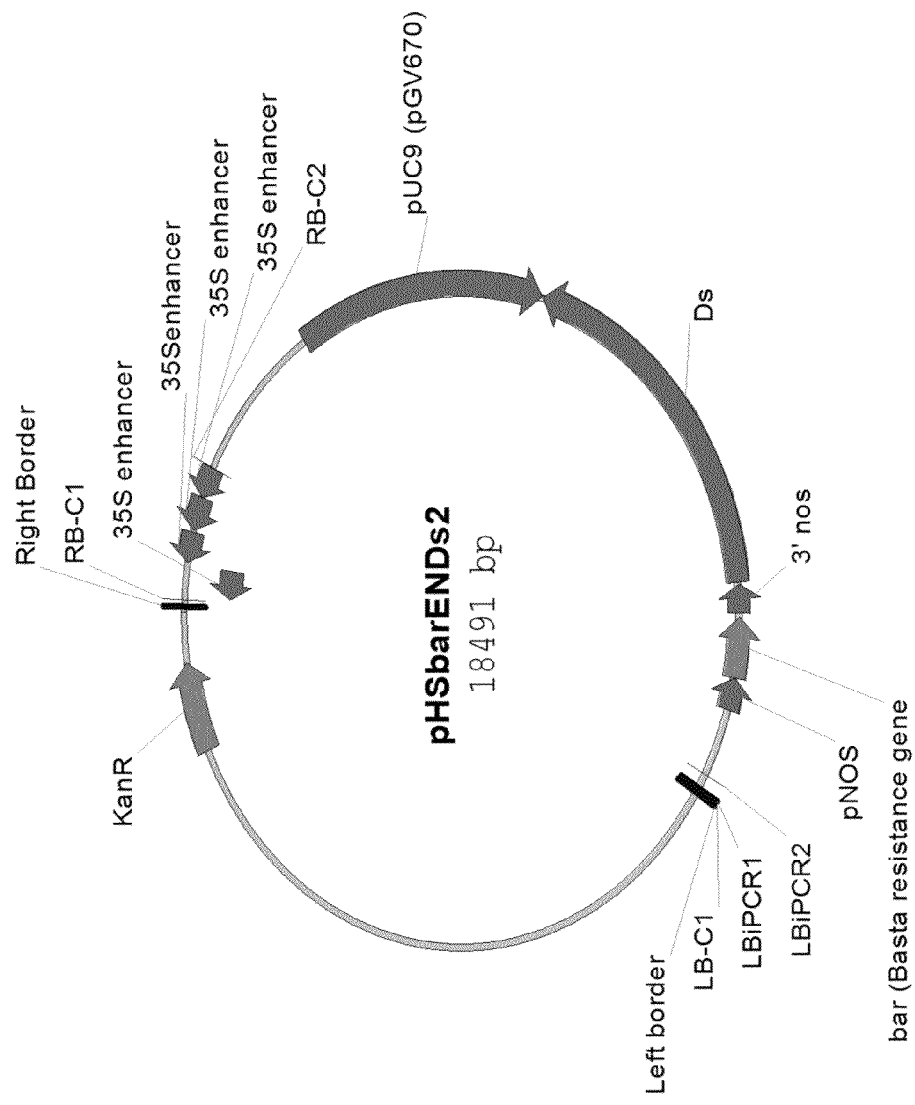

```
Majority       IAAVDGVDCVQMGPLDLSASXGYLWDPGHKKVREMLREAEKKVLXXXXD-------XXXXGAYLXGFAMPXDGAEQLRLR
                      250            260            270            280            290            300            310            320

SEQ ID NO 29.pro  IAAVDGVDCVQMGPLDLSASIGYLWDPGHKKVREMMRRAEKAVLTS--D-------PEKGGAYLSGFAMPHDGPAAIRER    306
SEQ ID NO 31.pro  IAAVDGVDCVQMGPLDLSASLGYLWDPGHKKVREVLREAENKVLESRND------DVESGAYLAGFATAYDGARDLRSR    302
SEQ ID NO 33.pro  IAAVDGVDVVQMGPLDLSASMGYLWDPGNRKVRATLREAERKVLEAKKKKAAAAASGGNAAYLGGFAMQNDPPEQLKLR    296
SEQ ID NO 35.pro  IAAVDGVDGVQMGPLDLSASMGYLWDPGNRKVRARLREAEKKVLDARKKN---VTASDGNVAYLGGFAMPNDPAEQLKLR   294
SEQ ID NO 49.pro  IAAVDGVDCVQMGPLDLSASLGYLWDPGHKKVREMMKKAEKSVLTT--D------PAKGGAYLSGFAMPHDGAGEIRGR    305

Majority       GYHMVAGAVDIGLFRXAALEDVRRFKMXXXXXGDXEDSXEXEK-DXXDEKYWSE-
                      330            340            350            360            370

SEQ ID NO 29.pro  GYNMVAGTVDIGLFRNAAVEDVRRFKMGLVNESDGEDSLDNGK-DVDDEKYWSE.    360
SEQ ID NO 31.pro  GYHMVSGAVDVGLFRSAALEDVTRFKM----DGDGSESDEGEE-KEGDEKYWSE.   352
SEQ ID NO 33.pro  GYHMVAGAVDIAMFRKAALDDVRRFREAVMEI GEEDDKNEVEKCEKENDGYWSE.   351
SEQ ID NO 35.pro  GYHMVSGAVDIGMFRKAALEDVKRFKEAVMEI GEEEGEEDDEKKDKEDDGYWSE.   349
SEQ ID NO 49.pro  GYHMVAGAVDVGLFRNAAVEDVRRFKMGLVNESDSEDSSEHDK-DVDDEKYWSE.   359
```

FIG.2

| | 1 | 2 | 3 | 4 | 5 | |
|---|---|---|---|---|---|---|
| | | 56.0 | 49.6 | 51.0 | 81.1 | 1 SEQ ID NO 29.pro |
| | 54.5 | | 49.6 | 53.0 | 58.2 | 2 SEQ ID NO 31.pro |
| | 75.2 | 67.7 | | 76.5 | 50.1 | 3 SEQ ID NO 33.pro |
| | 69.4 | 62.9 | 21.3 | | 51.9 | 4 SEQ ID NO 35.pro |
| | 17.5 | 50.7 | 69.3 | 66.9 | | 5 SEQ ID NO 49.pro |
| | 1 | 2 | 3 | 4 | 5 | |

Percent Identity

FIG.4A

```
SEQ ID NO:107   MTTASIFPAAVVVTTDVTSLNPSSLLIGKSLSPSKFSSIRSSVSFSRK----TLTPIR
SEQ ID NO-108   MATLTYTAAA----AASPKLSLRNPLSFISSKSLSFPSSKPSISLKPLNSTKFPTLSPLK
SEQ ID NO-109   MPALTAAATTF-FLSSNHQNPNKPQCSSLPNLPFNF-KTLNPNTI-ITTTFKTLTPLK
SEQ ID NO-110   MAAMA---GFSSSSSSLSTIRKSFTSTSPIFP-SFHSLLPRIP---KFSSLKTVNPIF
SEQ ID NO-111   MATVTFFPSSLSTPPKPHFPKPSKTLIHLP-SPKFFGFSKPAFNLKT-LNPILSQSPAPLR
SEQ ID NO-112   MAARAILS---DLPLSSSFTKFSSSTSFSPRPPLSP---FSLPR-LKTLTFNSPSHLS
SEQ ID NO-113   -------AAAVTKLAQNKIISFPKSPLFNLNGNKSKIVFPK-LKLTPSVSRSP--
SEQ ID NO-114   MTTLTCSGSG-TAATVAKLAQNKISSFPKAPLFTLNGNKSKIVFPK-LKLTPSVSRSP--
SEQ ID NO-115   MAAFASSSA--SLSRLLRARKPSPSS--PPPSRRA------PALLPLP
SEQ ID NO-116   MAVSATA---TSLSHLLPAPKPKPRT--PPRL-------SLLPSN
SEQ ID NO-117   MAATAS----SLSHLLLAPKPRPKAQPNPSHLRSH------SITSPLP
SEQ ID NO-118   MAAASS------LSHPLLAPK----TQPNPSPLPSR------HIATPLP
SEQ ID NO-119   MAAAAS------LSHLLLAPKLKSK--PNPTPLPSR------RACVPLP
SEQ ID NO-120   ---------------------------------------------PSR
SEQ ID NO-121   -ARGSLSFSL---TVNTDSTHLFNSSSPIIGK-LSPSNSNSVRSTVTFSRK----TLTPIR
SEQ ID NO-29    MATATILS---TVNTDSTHLFNSSSPIIGK-LSPSNSNSVRSTVTFSRK----TLTPIR
SEQ ID NO-31    MGSIS--TSSIRAPPTRRTVVTPFSSLLPKP----KPHFLSLSTSKSHAFPLSKPLT
SEQ ID NO-33    MAATAS----FLSHLLLAPKRRPKTQPNPSHLPSQ------RITDRLP
SEQ ID NO-35    MAAASASATASLSHLLLARKPDPA----PLPSRRA------PALLPLP
SEQ ID NO-49    MATASIFPAAVTVIRDVTSLNPSSLLIGKSLSPSKFPSSIKSSVSFSRK----TLTPIR

**  **  + *****  **   ********  +  *
SEQ ID NO-107   YSSSPADHSPVAAV------EAITNRSKTSLKSRLRGGETLYGLFLLSFSPTLAEIAAHAG
SEQ ID NO-108   CSP-------NPS---PSPSTSSLKSRLRNGETLYGIFLLSFSPTLAEIAALSG
SEQ ID NO-109   -SSTSSDVDPTSSSTTPI---SAAASSFSLKSRLRNGETLYGIFLLSFSPTLAEISGLAG
SEQ ID NO-110   KPSLPRFSS-AVAATAD----SAEVRQSLKTRLKNGETLYGIFLLGFSPTLAEIAGLAG
SEQ ID NO-111   LSNTTSDLIAYDNSVPVP---VPVPSRSLKSRLHDGETLYGLFLLSFSPTLAEIAALAG
SEQ ID NO-112   PTITTA----AVTSA---SVSSSSLKSRLRNGDTLYGLFLLSFSPTLAEIAALAG
SEQ ID NO-113   ----SDLSP-GDFLSPS----PSPSPESIKYRLQSNETLYGLFLLSFSPTLAEISGLAG
SEQ ID NO-114   ----SDLSP-GDFLSPS----PSPSPESLKYRLQSNETLYGLFLLSFSPTLAEISGLAG
SEQ ID NO-115   RRGRRSASAV----SAATSELLSAAP--SLKSRLAAGKTLYGLFLLSFSPTLAEIAAHAG
SEQ ID NO-116   RKPSRAATSAIFAAAAAASDFLSPVP--SLKSRLAAGDTLYGLFLLSFSPTLAEIAALAG
SEQ ID NO-117   CRGRRSSLGV----SAAASDLLSPAP--SLKSRLAAGDTLYGLFLLSFSPTLAEIAALAG
SEQ ID NO-118   RGRRSAHAV----SAAASDLLSPAP--SLKSRLAAGDTLYGLFLLGFSPTLAEIAALAG
SEQ ID NO-119   -RSRRPTQAI----SAAASDLLAPAP--TLKSRLAAGDTLYGLFLLSFSPTLAEIAALAG
SEQ ID NO-120   ----TRQ--SLKSRLASGDTLLGIFLVSNSPTLAEIVGLSG
SEQ ID NO-121   SSCCCSSSMAPLLQ------SNITLKSRVASCETLYGLFLMSASPTIAEIAGLAG
SEQ ID NO-29    FSSSPADHSPAAAITSPTVEGIATRSKTSLKSRLQGGETLYGMFLLSFSPTLAEIAAHSG
SEQ ID NO-31    ISPNSHFLIPKS----IPTLSSSSPLNLKSRLRNGETLYGIFLLSFSPTLAEIAGHAG
SEQ ID NO-33    CRGRRSSVAV----SAAASDLLSPAP--SLKSRLAAGETLYGLFLLSFSPTLAEIAALAG
SEQ ID NO-35    RRRGQRPISA----AAAASDLLYAAP--SLKSRLAAGETLYGLFLLSFSPTLAEIAALAG
SEQ ID NO-49    YSSSPADHSPATAV------EAITNRSKTSLKSRLRGGETLYGLFLLSFSPTLAEIAAHAG

Motif I
```

FIG. 4B

```
               ** ++++++++++ *    *   +  ++++     ++++++++         ********** ** ***  *** +++ *
SEQ_ID_NO-107  YDYVVVDMEHGPGGIPEALDCIRALNAAGTSAILRLPENSSTWAKKALDLGPQGIMFPMI
SEQ_ID_NO-108  YDIFVVIDMEHGPGGIHESLQIILRTLSPTNTPAIIRLPEFSAAWAKKALDLGPQGIMFPMI
SEQ_ID_NO-109  YDFAVVDMEHGPGGITEALNCLRALASTQTPAIIRLPETCPTWAKKALDLGPQGIMFPMV
SEQ_ID_NO-110  YDFAVVDMEHGHGGISDALPCLHALAAIQTPAIIRLPESSATWAKKALDLGPQGIMFPMI
SEQ_ID_NO-111  YDFVVVDMEHGPGGVSDALPCLHALAAIRTPAIIRLPESCPTWAKKALDLGPQGIMFPMI
SEQ_ID_NO-112  YDFVVIDMEHGPGGISEALHCLRALSAAGTPGILRLPESCPTWAKKALDLGPQGIMFPMI
SEQ_ID_NO-113  YDFVVVDMEHGPGGISDALACLHALAAIGTPAILRLPESCPTWAKKALDLGPQGVMFPMI
SEQ_ID_NO-114  YDFVVVDMEHGPGGISDALACLHALAAIGTPAILRLPEACSIWAKKALDLGPQGVMFPMI
SEQ_ID_NO-115  YDYVVVDMEHGPGSITEALACLRALDAARTPAILRLPEACPVWAKKALDLGPAGLMLPAI
SEQ_ID_NO-116  YDYVVVDMEHGPGGIPEALACLRALDAARTPAVLRLPEASAVWAKKALDLGPAGLMLPAI
SEQ_ID_NO-117  YDYVVVDMEHGPGGIPEALSCLRALDAARTPAVLRLPEASAVWAKKALDLGPAGLMTPAV
SEQ_ID_NO-118  YDYVVVDMFHGPGGVPEALACLRALDAARTPAVLRLPEASPVWAKKALDLGPAGLMLPAV
SEQ_ID_NO-119  YDYVVVIDMEHGPGGIPEALACLRALAVTGTPAIIRVPELCAALAKKALDLGPQGIMFPMV
SEQ_ID_NO-120  YDYVVVIDMEHGPGDIIDSLSSIRALAAAGTPAIIRVPEKSAAWAKKALDLGPQGIMFPMV
SEQ_ID_NO-121  YDFVVVDMEHGHGGIPEALACLRALNAAGVAAVLRLPENCPTWAKKALDLGPQGIMFPMI
SEQ_ID_NO_29   YDFVVVDMEHGPGGIHDALPCLHALAAANTAAILRVPESTAAWAKKALDLGPAGLMLPAI
SEQ_ID_NO_31   YDFVVVDMEHGPGGIPEALACLRALDAARTPAVLRLPEASAVWAKKALDLGPAGLMLPAI
SEQ_ID_NO_33   YDYVVVDMFHGPGGVPEALACLRALDAARTPAVIRLPEAGPTWAKKALDLGPAGLMVPAV
SEQ_ID_NO_35   YDYVVVDMEHGPGGIPEALDCIRALNAAGTSAILRLPENSPTWAKKALDLGPQGIMFPMI
SEQ_ID_NO_49   YDYVVVDMEHGPGGIPEALDCIRALNAAGTSAILRLPENSPTWAKKALDLGPQGIMFPMI
                      Motif II                                        Motif III + +++      * *******   *                 ++  ++          *   +
SEQ_ID_NO-107  ESRKIDATKAVSYCRFPPDGIRGSAHTVVRASNYGIDEGYLSNYAEEILIMCQVESSEGVK
SEQ_ID_NO-108  DSPKDAKKAVSYCRFPPDGIRGSAHTVVRASNYGINEGYLSNYMEDLLIMCQVETVDAVK
SEQ_ID_NO-109  ESPRMAKKAVSYCRFPPEGIRGSAHTVVRASYGIDEGYLSNYGEDLLIMCQVESEGVK
SEQ_ID_NO-110  DGPFKSARKAVSYCRFPPNGVRGSAHTVVRASSYGIDEGYLSNYEDDLLIMCQVECVDGVK
SEQ_ID_NO-111  DSPKLARKAVSYCRFFPAGVRGSAHTVVRASSYGIDAGYLSNYEEELLIMCQVESEEAVK
SEQ_ID_NO-112  DSPKDAKKAVSYCHFPPKGIRGSAHTVVRASNYGVDEEYLSTYEFEQLIMCQVESEEGVK
SEQ_ID_NO-113  DSPEAAKEAVSYCRFPPSGVRGSAHTVVRASGYGIDEGYLSNYEEEILIMCQVESEEGVK
SEQ_ID_NO-114  DSPEAAKEAVSYCRFPPSGVRGSAHTVVRASGYGIDEGYLSNYEEELLIMCQVESEEGVK
SEQ_ID_NO-115  ESPAAAAAAVSHCRYPPRGVRGAAHPIVRASVYGLDDSYLSRCEDDTLIICQVETAAGIA
SEQ_ID_NO-116  ESPAAAAEAVSHCRYPPRGVRGAAHPIVRASAYGIDDSYISRCEDDTLVICQVETATGIA
SEQ_ID_NO-117  ESPAAAAEAVSYXRYPPRGVRGAAHPIVRASAYGLDDSYLSRCEDDTLLICQVEETAAGIA
SEQ_ID_NO-118  ESPAAAAEAVSYCRYPPRGVRGAAHTVVRASAYGLDDSYLSRCEDETLIMCQVETAAGIA
SEQ_ID_NO-119  ESADQAELAVSYCRYPPKGIRGAAN--VVRASAYGFDEGYLKWCREELIVFCQVESEAGVA
SEQ_ID_NO-120  ENAKTAEQLVSYCRYPPRGIRGTAHVMVRASGYGTDDTYVHRCEEDLLILCMVETETGVD
SEQ_ID_NO-121  ESRKIDATKAVSYCRFPPDGIRGSAHTVVRASKYGLDEGYLGNYADELLIMCQVESAEGVK
SEQ_ID_NO_29   DSLQSAQDAVSYCRFPTGLRGAAHPIPPASKYGLDEGYLGNYLDELLIMCQVESEEGVA
SEQ_ID_NO_31   ESPEAAAEAVSHCRYPPRGVRGAAHPIVRASAYGFDDSYLSRCEDDTLVICQVETATAIA
SEQ_ID_NO_33   ESPAAAAAAVSHCRYPPRGVRGAAHPIVRASAYGLDDSYLSRCEDETLIICQVETAAGIA
SEQ_ID_NO_35   ESRKIDATKAVSYCRFPPDGIRGSAHTVVRASNYGIDEGYLSNYAEEILIMCQVESGEGVK
SEQ_ID_NO_49   ESRKIDATKAVSYCRFPPDGIRGSAHTVVRASNYGIDEGYLSNYAEEILIMCQVESGEGVK
                                                                      Motif IV
```

FIG. 4C

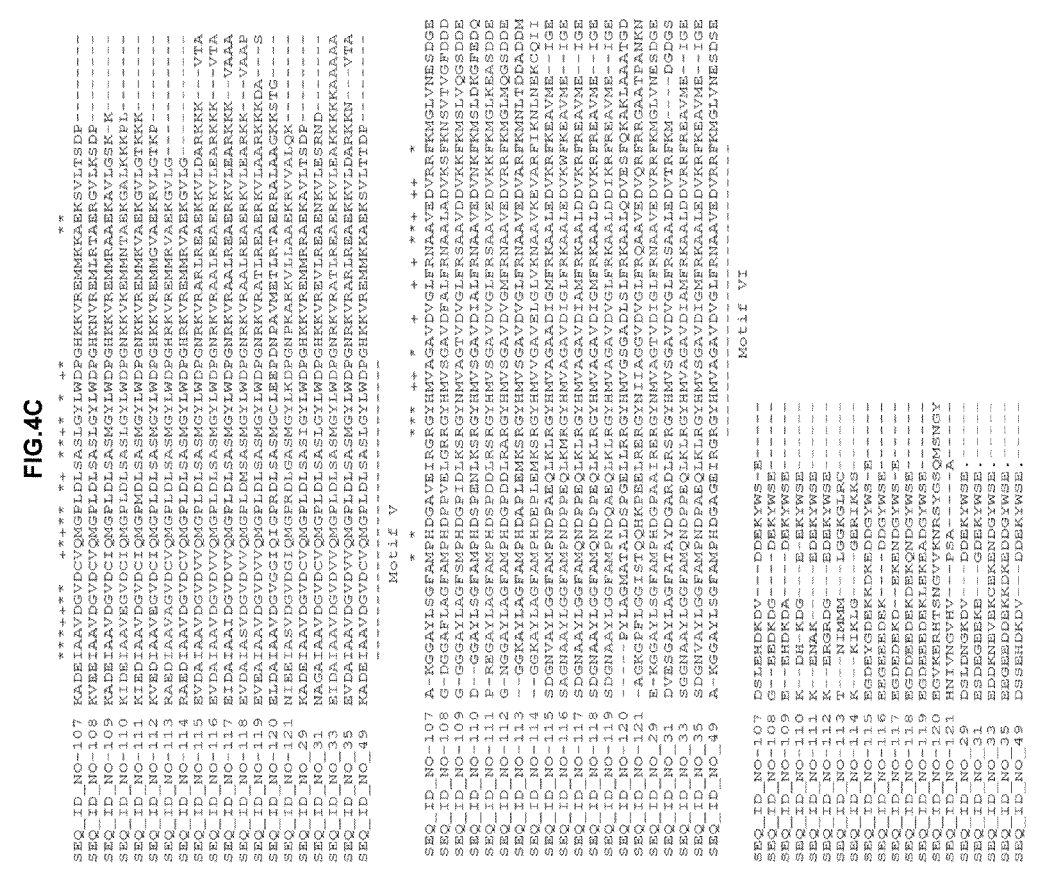

[Sequence alignment figure showing multiple protein sequences labeled SEQ_ID_NO-107 through SEQ_ID_NO-121, and SEQ_ID_NO-29, 31, 33, 35, 49, with conserved regions labeled Motif V and Motif VI.]

PLANTS AND SEEDS WITH ALTERED STORAGE COMPOUND LEVELS, RELATED CONSTRUCTS AND METHODS INVOLVING GENES ENCODING PROTEINS WITH SIMILARITY TO BACTERIAL 2,4-DIHYDROXY-HEPT-2-ENE-1,7-DIOIC ACID CLASS II-LIKE ALDOLASE PROTEINS

This application claims priority benefit of provisional application No. 61/256,323 filed Oct. 30, 2009, the entire contents of which are hereby incorporated by reference.

FIELD OF THE INVENTION

This invention is in the field of plant molecular biology. More specifically, this invention pertains to isolated nucleic acid fragments encoding proteins with similarity to bacterial 2,4-dihydroxy-hept-2-ene-1,7-diolic acid class II-like aldolase proteins in plants and seeds and the use of such fragments to modulate expression of a gene encoding plastidic Class II aldolase-like activity.

BACKGROUND OF THE INVENTION

At maturity, about 40% of soybean seed dry weight is protein and 20% extractable oil. These constitute the economically valuable products of the soybean crop. Plant oils for example are the most energy-rich biomass available from plants; they have twice the energy content of carbohydrates. It also requires very little energy to extract plant oils and convert them to fuels. Of the remaining 40% of seed weight, about 10% is soluble carbohydrate. The soluble carbohydrate portion contributes little to the economic value of soybean seeds and the main component of the soluble carbohydrate fraction, raffinosaccharides, are deleterious both to processing and to the food value of soybean meal in monogastric animals (Coon et al., (1988) Proceedings Soybean Utilization Alternatives, Univ. of Minnesota, pp. 203-211).

As the pathways of storage compound biosynthesis in seeds are becoming better understood it is clear that it may be possible to modulate the size of the storage compound pools in plant cells by altering the catalytic activity of specific enzymes in the oil, starch and soluble carbohydrate biosynthetic pathways (Taiz L., et al. *Plant Physiology*; The Benjamin/Cummings Publishing Company: New York, 1991). For example, studies investigating the over-expression of LPAT and DAGAT showed that the final steps acylating the glycerol backbone exert significant control over flux to lipids in seeds. Seed oil content could also be increased in oil-seed rape by overexpression of a yeast glycerol-3-phosphate dehydrogenase, whereas over-expression of the individual genes involved in de novo fatty acid synthesis in the plastid, such as acetyl-CoA carboxylase and fatty acid synthase, did not substantially alter the amount of lipids accumulated (Vigeolas H., et al, *Plant Biotechnology J.* 5, 431-441 (2007). A low-seed-oil mutant, wrinkled 1, has been identified in *Arabidopsis*. The mutation apparently causes a deficiency in the seed-specific regulation of carbohydrate metabolism (Focks, Nicole at al., Plant Physiol. (1998), 118(1), 91-101. There is a continued interest in identifying the genes that encode proteins that can modulate the synthesis of storage compounds, such as oil, protein, starch and soluble carbohydrates, in plants.

Aldolases represent a diverse class of enzymes that differ in their catalytic mechanism and carbonyl donor preference (Wang et al. Biochemistry:44, 9447-9455 (2005)). There are Class I and Class II aldolases. Class II aldolases can be further divided into those that have a preference for dihydroxyacetone phosphate (DHAP) and those that prefer pyruvate as the carbonyl donor. The former represent the best characterized subgroup of Class II aldolases and includes for example fructose-1,6-bisphosphate aldolase, which catalyzes the cleavage of fructose 1,6-bisphosphate into D-glyceraldehyde 3-phosphate and dihydroxyacetone phosphate, which is the third committed step in glycolysis.

Class II pyruvate-specific aldolases include for example HpaI, a bacterial class II aldolase that catalyzes the reversible cleavage of 2,4-dihydroxy-hept-2-ene-1,7-dioic acid to pyruvate and succinic semialdehyde.

No studies on plant enzymes with similarity to bacterial 2,4-dihydroxy-hept-2-ene-1,7-dioic class II-like aldolase have been conducted and further investigation of the role of this subgroup of proteins in the regulation of storage compounds is therefore merited.

Diacylglycerol acyltransferase ("DGAT") is an integral membrane protein that catalyzes the final enzymatic step in the production of triacylglycerols in plants, fungi and mammals. This enzyme is responsible for transferring an acyl group from acyl-coenzyme-A to the sn-3 position of 1,2-diacylglycerol ("DAG") to form triacylglycerol ("TAG"). DGAT is associated with membrane and lipid body fractions in plants and fungi, particularly, in oilseeds where it contributes to the storage of carbon used as energy reserves. TAG is believed to be an important chemical for storage of energy in cells. DGAT is known to regulate TAG synthesis. Furthermore, it is known that the DGAT reaction is specific for oil synthesis.

TAG is the primary component of vegetable oil in plants_ It is used by the seed as a stored form of energy to be used during seed germination.

Two different families of DGAT proteins have been identified. The first family of DGAT proteins ("DGAT1") is related to the acyl-coenzyme A:cholesterol acyltransferase ("ACAT") and has been described in U.S. Pat. Nos. 6,100,077 and 6,344,548. A second family of DGAT proteins ("DGAT2") is unrelated to the DGAT1 family and is described in PCT Patent Publication WO 2004/011671 published Feb. 5, 2004. Other references to DGAT genes and their use in plants include PCT Publication Nos. WO2004/011, 671, WO1998/055,631, and WO2000/001,713, and US Patent Publication No. 20030115632.

Applicants Assignee's copending published patent application US 2006-0094088 describes genes for DGATs of plants and fungi and their use is in modifying levels of polyunsaturated fatty acids ("PUFAs") in edible oils.

Applicants' Assignee's published PCT application WO 2005/003322 describes the cloning of phosphatidylcholine diacylglycerol acyltransferase and DGAT2 for altering PUFA and oil content in oleaginous yeast.

Applicants' Assignee's copending published U.S. application Ser. No. 12/470,509 describes DGAT genes from *Yarrowia lipolytica* combined with plastidic phosphoglucomutase down regulation for increased seed storage lipid production and altered fatty acid profiles in oilseed plants.

SUMMARY OF THE INVENTION

In a first embodiment the present invention concerns a transgenic plant comprising a recombinant DNA construct comprising a polynucleotide operably linked to at least one regulatory element, wherein said polynucleotide encodes a polypeptide having an amino acid sequence of at least 85% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 and wherein seeds from said transgenic plant have an altered oil, protein, starch and/or soluble carbohydrate content and/or altered seed weight, when compared to seeds from a control plant not comprising said recombinant DNA construct.

In a second embodiment the present invention concerns transgenic seed comprising a recombinant DNA construct comprising a polynucleotide operably linked to at least one regulatory element, wherein said polynucleotide encodes a polypeptide having an amino acid sequence of at least 85% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 and wherein said transgenic seed has an altered oil, protein, starch and/or soluble carbohydrate content and/or altered seed weight when compared to a control seed not comprising said recombinant DNA construct.

In a third embodiment the present invention concerns transgenic seed comprising a recombinant DNA construct comprising a polynucleotide operably linked to at least one regulatory element, wherein said polynucleotide encodes a polypeptide having an amino acid sequence of at least 85% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 and wherein said transgenic seed has an increased protein content of at least 0.5% content on a dry weight basis when compared to a control seed not comprising said recombinant DNA construct.

In a fourth embodiment the present invention concerns transgenic seed comprising:
a recombinant DNA construct comprising: (a) a polynucleotide operably linked to at least one regulatory element, wherein said polynucleotide encodes a polypeptide having an amino acid sequence of at least 85% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 or (b) a suppression DNA construct comprising at least one regulatory element operably linked to: (i) all or part of: (A) a nucleic acid sequence encoding a polypeptide having an amino acid sequence of at least 85% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 or (B) a full complement of the nucleic add sequence of (b)(i)(A); or (ii) a region derived from all or part of a sense strand or antisense strand of a target gene of interest, said region having a nucleic acid sequence of at least 85% sequence identity, based on the Clustal V method of alignment, when compared to said all or part of a sense strand or antisense strand from which said region is derived, and wherein said target gene of interest encodes a plastidic HpaIL aldolase, and wherein said plant has an altered oil, protein, starch and/or soluble carbohydrate content and/or altered seed weight when compared to a control plant not comprising said recombinant DNA construct.

In a fifth embodiment the invention concerns transgenic seed having an increased oil content of at least 2% on a dry-weight basis when compared to the oil content of a non-transgenic seed, wherein said transgenic seed comprises a recombinant DNA construct comprising: (a) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (b) the full-length complement of (a): wherein (a) or (b) is of sufficient length to inhibit expression of endogenous plastidic HpaIL aldolase activity in a transgenic plant and further wherein said seed has an increase in oil content of at least 2% on a dry-weight basis, as compared to seed obtained from a non-transgenic plant.

In a sixth embodiment the invention concerns transgenic seed comprising a recombinant DNA construct comprising: (a) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (b) the full-length complement of (a): wherein (a) or (b) is of sufficient length to inhibit expression of endogenous plastidic HpaIL aldolase activity in a transgenic plant and further wherein said seed has an increase in oil content of at least 2% on a dry-weight basis, as compared to seed obtained from a non-transgenic plant.

In a seventh embodiment the present invention concerns a method for producing transgenic seeds, the method comprising: (a) transforming a plant cell with a recombinant DNA construct comprising a polynucleotide operably linked to at least one regulatory sequence, wherein the polynucleolide encodes a polypeptide having an amino acid sequence of at least 85% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, and 123; and (b) regenerating a transgenic plant from the transformed plant cell of (a); and (c) selecting a transgenic plant that produces a transgenic seed having an altered oil, protein, starch and/or soluble carbohydrate content and/or altered seed weight, as compared to a transgenic seed obtained from a non-transgenic plant.

In an eighth embodiment the present invention concerns a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 85% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, and 123; and (b) regenerating a transgenic plant from the transformed plant cell of (a); and (c) selecting a transgenic plant that produces a transgenic seed having an increased protein content of at least 0.5% on a dry weight basis, as compared to a transgenic seed obtained from a non-transgenic plant.

In a ninth embodiment this invention concerns a method for producing transgenic seed, the method comprising: (a) transforming a plant cell with a recombinant DNA construct comprising: (i) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (ii) the full-length complement of (i); wherein (i) or (ii) is of sufficient length to inhibit expression of endogenous plastidic HpaIL aldolase activity in a transgenic plant; (b) regenerating a transgenic plant from the transformed plant cell of (a); and (c) selecting a transgenic plant that produces a transgenic seed having an altered oil, protein, starch and/or soluble carbohydrate content and/or altered seed weight, as compared to a transgenic seed obtained from a non-transgenic plant. In a seventh embodiment, the present invention concerns a method for producing transgenic seed, the method comprising: (a) transforming a plant cell with a recombinant DNA construct comprising: (i) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (ii) the full-length complement of (i); wherein (i) or (ii) is of sufficient length to inhibit expression of endogenous plastidic HpaIL aldolase activity in a transgenic plant; (b) regenerating a transgenic plant from the transformed plant cell of (a); and (c) selecting a transgenic plant that produces a transgenic seed having an increase in oil content of at least 2% on a dry-weight basis, as compared to a transgenic seed obtained from a non-transgenic plant.

In a tenth embodiment this invention concerns transgenic plants comprising at least one DGAT sequences and a construct downregulating plastidic HpaI or HpaI-like activity, wherein the DGAT sequence and the plastidic HpaI or HpaI-like construct can be in the same recombinant construct or in separate recombinant constructs, and wherein seed obtained from said transgenic plant has an increased oil content when compared to the oil content of seed obtained from a control plant not comprising said construct or when compared to transgenic seed obtained from a transgenic plant comprising either said DGAT sequences alone or said construct downregulating HpaIL activity alone.

In an eleventh embodiment this invention concerns transgenic seed obtained from the transgenic plant comprising at least one DGAT sequence and a construct downregulating HpaIL activity, wherein the DGAT sequence and the plastidic HpaI or HpaI-like construct can be in the same recombinant construct or in separate recombinant constructs and wherein the oil content of said transgenic seed is increased when compared to the oil content of control seed not comprising said construct or null segregant or transgenic seed comprising either said DGAT sequences alone or said construct downregulating HpaIL activity alone.

In a twelfth embodiment this invention concerns a method for increasing the oil content of a seed comprising: (a) transforming at least one cell with at least one recombinant construct having at least one DGAT sequences and a construct downregulating plastidic HpaIL activity wherein the DGAT sequence and HpaIL construct can be in the same recombinant construct or in separate recombinant constructs; (b) selecting the transformed soybean cell(s) of step (a) having an increased oil acid content when compared to the oil content of a control cell not comprising said construct or when compared to a null segregant seed or when compared to transgenic seed obtained from a transgenic plant comprising either said DGAT sequences alone or said construct downregulating HpaIL activity alone.

In a thirteenth embodiment this invention concerns an isolated polynucleotide comprising: (a) a nucleotide sequence encoding a polypeptide with HpaIL aldolase activity, wherein, based on the Clustal V method of alignment with pairwise alignment default parameters of KTUPLE=1, GAP PENALTY=3, WINDOW=5 and DIAGONALS SAVED=5, the polypeptide has an amino acid sequence of at least 75% sequence identity when compared to SEQ ID NO:120, 121, 122 or 123, or (b) the full complement of the nucleotide sequence of (a).

In a fourteenth embodiment this invention concerns an isolated polynucleotide comprising: (a) a nucleotide sequence encoding a polypeptide with HpaIL aldolase activity, wherein, based on the Clustal V method of alignment with pairwise alignment default parameters of KTUPLE=1, GAP PENALTY=3, WINDOW=5 and DIAGONALS SAVED=5, wherein the amino acid sequence of the polypeptide comprises SEQ ID NO: 120, 121, 122 or 123.

In a fifteenth embodiment this invention concerns an isolated polynucleotide comprising: (a) a nucleotide sequence encoding a polypeptide with HpaIL aldolase activity, wherein, based on the Clustal V method of alignment with pairwise alignment default parameters of KTUPLE=1, GAP PENALTY=3, WINDOW=5 and DIAGONALS SAVED=5, wherein the nucleotide sequence comprises SEQ ID NO:124, 125, 126, or 127.

In a sixteenth embodiment this invention concerns an isolated polynucleotide encoding a polypeptide, wherein said polynucleotide is capable of altering the endogenous expression of plastidic HpaIL aldolase activity and wherein said polypeptide comprises a chloroplast transit peptide and at least one motif selected from the group consisting of: SEQ ID NO: 128, 129, 130, 131, or 132.

In a seventeenth embodiment this invention concerns an isolated polynucleotide encoding a plant HpaIL aldolase polypeptide, wherein said polynucleotide is capable of altering the endogenous expression of plastidic HpaI-like activity and wherein said polypeptide has a Km (acetaldehyde) at least 1.7 fold lower than the Km (acetaldehyde) of bacterial HpaIL aldolase activity and a Vmax of at least 15 fold lower than the bacterial HpaIL aldolase activity.

In an eighteenth embodiment this invention concerns a method of altering i.e. increasing or decreasing oil, protein, starch and/or soluble carbohydrate content and or altering seed weight, comprising: a) transforming a plant with the recombinant DNA construct of claim 34; b) growing the transformed plant under conditions suitable for the expression of the recombinant DNA construct; and c) selecting those plant having altered i.e. increased or decreased oil, protein, starch and/or soluble carbohydrate content and/or altered seed weight when compared to a control plant not comprising said recombinant DNA construct. In a nineteenth embodiment the present invention concerns a method to isolate nucleic acid fragments encoding plastidic HpaI-like polypeptides, comprising: a) comparing SEQ ID NOs: 128, 129, 130, 131, or 132 with other polypeptide sequences encoding a plastidic HpaI-like polypeptides; b) identifying the conserved sequences obtained in step (a); c) making region-specific nucleotide probe(s) or oligomer(s) based on the conserved sequences identified in step (b); and (d) using the nucleotide probe(s) or oligomer(s) of step (c) to isolate HpaI-like sequences; e) selecting those sequences comprising a chloroplast transit peptide.

Seeds obtained from monocot and dicot plants (such as for example maize and soybean, respectively) comprising the recombinant constructs of the invention are within the scope of the present invention. Also included are seed-specific or seed-preferred promoters driving the expression of the nucleic acid sequences of the invention. Embryo or endosperm specific promoters driving the expression of the nucleic acid sequences of the invention are also included. Furthermore the methods of the present inventions are useful for obtaining transgenic seeds from monocot plants (such as maize and rice) and dicot plants (such as soybean and canola).

Also plants or seed comprising the recombinant DNA construct of the present invention are useful to alter i.e. increase or decrease oil, protein, starch and/or soluble carbohydrate content and/or altered seed weight when compared to a control plant not comprising the recombinant DNA construct(s) of the present invention.

Also within the scope of the invention are product(s) and/or by-product(s) obtained from the transgenic seed obtained from monocot or dicot plants, such as maize and soybean, respectively.

In another embodiment, this invention relates to a method for suppressing in a plant the level of expression of a gene encoding a polypeptide having plastidic HpaIL aldolase activity, wherein the method comprises transforming a monocot or dicot plant with any of the nucleic acid fragments of the present invention.

Progeny plants derived from the transgenic plant, wherein said progeny plant comprises in its genome the recombinant DNA construct and seed obtained from said progeny plant exhibit an altered i.e. increased or decreased oil, protein, starch and/or soluble carbohydrate content and/or altered seed weight when compared to a control plant not comprising said recombinant DNA construct are also included in the present invention.

Furthermore the present invention includes a vector comprising any of the isolated polynucleotides of the present invention. Also included are methods for transforming a cell comprising transforming a cell with any of the isolated polynucleotides of the present invention. The cell transformed by this method is also included. Advantageously, the cell is eukaryotic, e.g., a yeast, insect or plant cell, or prokaryotic, e.g., a bacterium.

In another embodiment, the present invention includes a method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

BRIEF DESCRIPTION OF THE DRAWING AND SEQUENCE LISTING

The invention can be more fully understood from the following detailed description and the accompanying Drawing and Sequence Listing which form a part of this application.

Figure 1A:
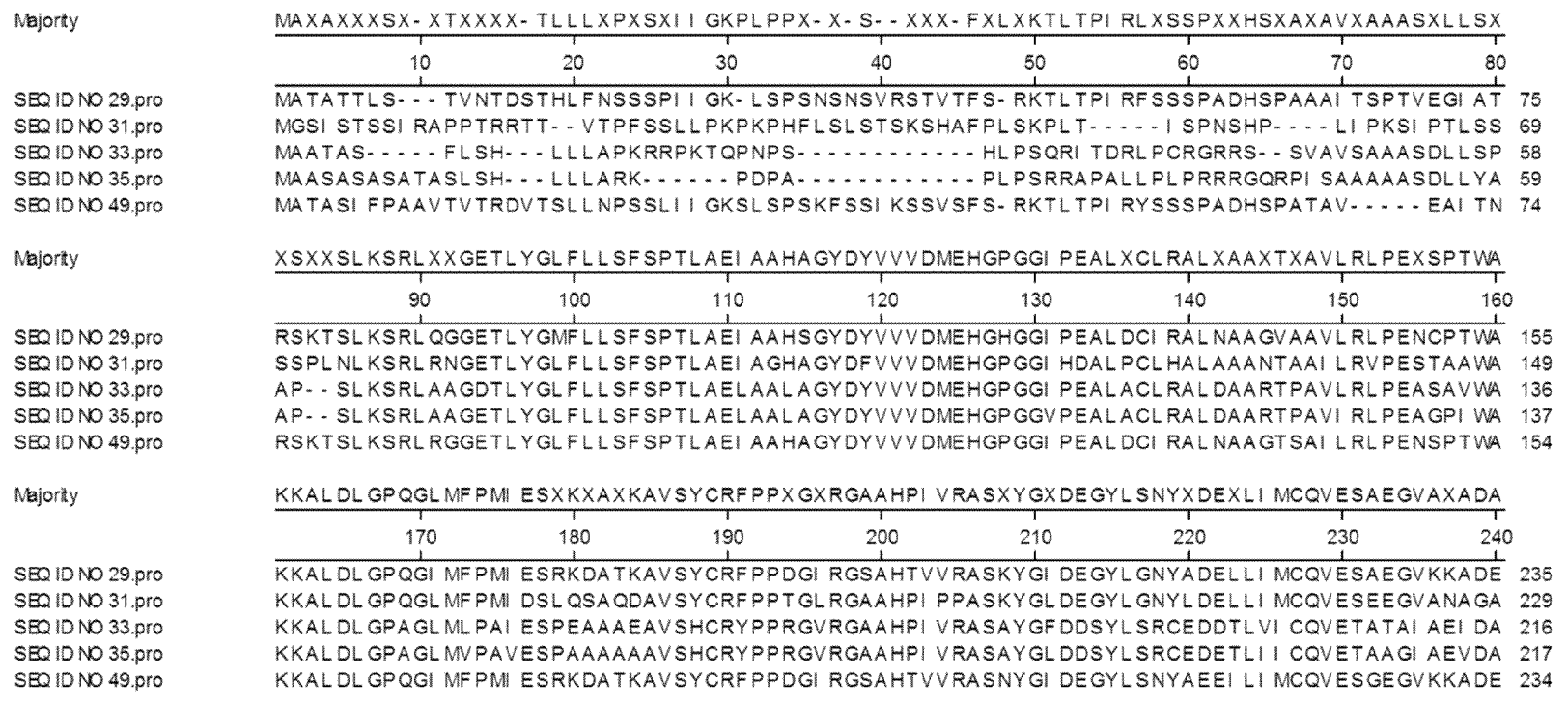

FIGS. 1A-1B shows an alignment of the amino acid sequences of plastidic HpaIL aldolases encoded by the nucleotide sequences derived from the following: *Arahidopsis thaliana* (SEQ ID NO: 49); canola (SEQ ID NO:29); soybean (SEQ ID NO:31); corn (SEQ ID NO:33), and rice (SEQ ID NO:35). For the consensus alignment, amino acids which are conserved among all sequences at a given position, and which are contained in at least two sequences, are indicated with an asterisk (*). Dashes are used by the program to maximize alignment of the sequences. Amino acid positions for a given SEQ ID NO are given to the left of the corresponding line of sequence. Amino acid positions for the consensus alignment are given below each section of sequence.

FIG. 2 shows a chart of the percent sequence identity for each pair of amino acid sequences displayed in FIGS. 1A-1B.

FIG. 3 corresponds to vector pHSbarENDS2.

FIGS. 4A-C show an alignment of the amino acid sequences of plastidic HpaIL aldolases encoded by the nucleotide sequences derived from the following: *Arabidopsis lyrata* (SEQ ID NO: 107); *Theobroma cacao* (SEQ ID NO:108); *Ricinus communis* (SEQ ID NO:109); *Solanum lycopersicum* (SEQ ID NO:110), *Vitis vinifera* (SEQ ID NO:111), *Carica papaya* (SEQ ID NO:112), *Citrus clementina* (SEQ ID NOs:113 and 114), *Oryza brachyata* (SEQ ID NO:115), *Brachypodium distayon* (SEQ ID NO:116), *Sorghum* (SEQ ID NO:117), *Paspalurn notaturn* (SEQ ID NO:118), *Eragrostis nindensis* (SEQ ID NO:119), *Tulipa gesneriana* (SEQ ID NOs:120 and 121), *Brassica napus* (SEQ ID NO:29), *Glycine max* (SEQ ID NO:31), *Zea Mays* (SEQ ID NO:33), *Oryza saliva* (SEQ ID NO:35), and *Arabidopsis thaliana* (SEQ ID NO:49). Amino acids conserved among all sequences are indicated with an asterix above the conserved residues. Conservative amino acids substitutions are indicated by a plus sign (+) above the conserved residues. Dashes are used by the program to maximize alignment of the sequences. Conserved sequence motifs I, II, III, IV and V are underlined. The active site residue "R83" is indicated by a triangle under the alignment.

The sequence descriptions and Sequence Listing attached hereto comply with the rules governing nucleotide and/or amino acid sequence disclosures in patent applications as set forth in 37 C.F.R. §1.821-1.825.

SEQ ID NO:1 corresponds to the nucleotide sequence of vector PHSbarENDS2.
SEQ ID NO:2 corresponds to the nucleotide sequence of vector pUC9 and a polylinker.
SEQ ID NO:3 corresponds to the nucleotide sequence of vector pKR85.
SEQ ID NO:4 corresponds to the nucleotide sequence of vector pKR278.
SEQ ID NO:5 corresponds to the nucleotide sequence of vector pKR407.
SEQ ID NO:6 corresponds to the nucleotide sequence of vector pKR1468,
SEQ ID NO:7 corresponds to the nucleotide sequence of vector pKR1475,
SEQ ID NO:8 corresponds to the nucleotide sequence of vector pKR92.
SEQ ID NO:9 corresponds to the nucleotide sequence of vector pKR1478.
SEQ ID NO:10 corresponds to SAIFF and genomic DNA of lo22048,
SEQ ID NO:11 corresponds to the forward primer HpaILORF FWD.
SEQ ID NO:12 corresponds to the reverse primer for HpaILORF REV.
SEQ ID NO:13 corresponds to the nucleotide sequence of vector pENTR-HpaIL.
SEQ ID NO:14 corresponds to the nucleotide sequence of vector pKR1478-HpaIL.
SEQ ID NO:15 corresponds to the nucleotide sequence of PKR1482.
SEQ ID NO:16 corresponds to the AthLcc In forward primer.
SEQ ID NO; 17 corresponds to the AthLcc In reverse primer.
SEQ ID NO:18 corresponds to the PCR product with the laccase intron.
SEQ ID NO:19 corresponds to the nucleotide sequence of PSM1318.
SEQ ID NO:20 corresponds to the nucleotide sequence of pMBL18 ATTR12 INT.
SEQ ID NO:21 corresponds to the nucleotide sequence of PMS1789.
SEQ ID NO:22 corresponds to the nucleotide sequence of pMBL18 ATTR12 INT ATTR21.
SEQ ID NO:23 corresponds to the nucleotide sequence of vector pKR1480.
SEQ ID NO:24 corresponds to the HpaIL UTR FWD forward primer,
SEQ ID NO:25 corresponds to the HpaIL UTR REV reverse primer.
SEQ ID NO:26 corresponds to the nucleotide sequence of pENTR containing the HpaIL 3'UTR.
SEQ ID NO:27 corresponds to the nucleotide sequence of pKR1482 containing the HpaIL 3"UTR.

Table 1 lists the polypeptides that are described herein, the designation of the clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire or functional protein derived from an FIS, a contig, an EST and PCR, or an FIS and PCR ("CGS").

TABLE 1

Identification of plant genes with similarity to At4g10750 (HpaIL aldolases)

| Protein (Plant Source) | Clone Designation | Status | SEQ ID NO: (Nucleotide) | (Amino Acid) |
|---|---|---|---|---|
| HpaIL aldolase (*Brassica napus*) | TC25873 | CGS | 28 | 29 |
| HpaIL aldolase (*Glycine max*) | Glyma09g21760 | CGS | 30 | 31 |
| HpaIL aldolase (*Zea mays*) | PCO651314 | CGS | 32 | 33 |
| HpaIL aldolase (*Oryza sativa*) | Os09g36030 | CGS | 34 | 35 |
| HpaIL aldolase (*Zea mays*) | cfp2npk070b11.fis1 | CGS | 146 | 147 |

SEQ ID NO:36 is the linker sequence described in Example 14.
SEQ ID NO:37 is the nucleic acid sequence of vector pKS133 described in Example 15.
SEQ ID NO:38 corresponds to synthetic complementary region of pKS106 and pKS124,
SEQ ID NO:39 corresponds to a synthetic complementary region of pKS133.
SEQ ID NO:40 corresponds to a synthetic PCR primer.
SEQ ID NO:41 corresponds to a synthetic PCR primer.
SEQ ID NO:42 corresponds to a synthetic PCR primer (SA64).
SEQ ID NO:43 corresponds to a synthetic PCR primer (SA65).
SEQ ID NO:44 corresponds to a synthetic PCR primer (SA66).
SEQ ID NO:45 is the nucleic acid sequence of vector pKS423.
SEQ ID NO:46 corresponds to the nucleic acid sequence of plasmid pKS120.
SEQ ID NO:47 corresponds to the nucleic acid sequence of At4g10750.
SEQ ID NO:48 corresponds to the ORF of SEQ ID NO:47.
SEQ ID NO:49 corresponds to the amino acid sequence encoded by SEQ ID NO:48.
SEQ ID NO:50 corresponds to the nucleotide sequence of pENTR-At4g10750.
SEQ ID NO:51 corresponds to the nucleotide sequence of pKR1478-At4g10750.
SEQ ID NO:52 corresponds to the nucleotide sequence of pKR1478-At4g10750-ORF.
SEQ ID NO:53 corresponds to the amino acid sequence encoded by the ORF in SEQ ID NO:52.
SEQ ID NO:54 corresponds to the nucleotide sequence of pKR1482-At4g10750.
SEQ ID NO:55 corresponds to the nucleotide sequence of KS387.
SEQ ID NO:56 corresponds to the nucleotide sequence artificial microRNA (amiRNA) aldo A.
SEQ ID NO:57 corresponds to the nucleotide sequence amiRNA aldo B.
SEQ ID NO:58 corresponds to the nucleotide sequence amiRNA aldo A star.
SEQ ID NO: 59 corresponds to the nucleotide sequence amiRNA aldo B star.
SEQ ID NO:60 corresponds to the nucleotide sequence of microRNA 159 precursor.
SEQ ID NO:61 corresponds to the nucleotide sequence of in-fusion ready microRNA 159.
SEQ ID NO:62 corresponds to the nucleotide sequence of in-fusion ready microRNA 159-KS126 plasmid.
SEQ ID NO:63 corresponds to the nucleotide sequence of the gmir159ALDO A1 primer.
SEQ ID NO:64 corresponds to the nucleotide sequence of the gmir159ALDO A2 primer.
SEQ ID NO:65 corresponds to the nucleotide sequence of the 159-ALDO A DNA microRNA precursor.
SEQ ID NO:66 corresponds to the nucleotide sequence of the gmir159ALDO B1 primer.
SEQ ID NO:67 corresponds to the nucleotide sequence of the gmir159ALDO B2 primer.
SEQ ID NO:68 corresponds to the nucleotide sequence of the 159-ALDO B DNA microRNA precursor.
SEQ ID NO:69 corresponds to the nucleotide sequence of 159 ALDO A-KS126.
SEQ ID NO:70 corresponds to the nucleotide sequence of 159 ALDO B-KS126
SEQ ID NO:71 corresponds to the nucleotide sequence of the AthHpaIL fwd primer.
SEQ ID NO:72 corresponds to the nucleotide sequence of the AthHpaIL rev primer.
SEQ ID NO:73 corresponds to the nucleotide sequence of pGEM®-T At4g10750.
SEQ ID NO:74 corresponds to the nucleotide sequence of pET28a At4g10750
SEQ ID NO:75 corresponds to the amino acid sequence of At4g10750 His TAG AA.
SEQ ID NO:76 corresponds to the nucleotide sequence of the Soy HpaIL fwd primer.
SEQ ID NO:77 corresponds to the nucleotide sequence of the Soy HpaIL rev primer.
SEQ ID NO:78 corresponds to the nucleotide sequence pGEM®-T Glyma09g21760.
SEQ ID NO:79 corresponds to the nucleotide sequence pET29a Glyma09g21760.
SEQ ID NO:80 corresponds to the amino acid sequence of Glyma09g21760 His TAG.
SEQ ID NO:81 corresponds to the nucleotide sequence of the Rice HpaIL fwd primer.
SEQ ID NO:82 corresponds to the nucleotide sequence of the Rice HpaIL rev primer.
SEQ ID NO:83 corresponds to the nucleotide sequence of pGEM®-T Os09g36030.
SEQ ID NO:84 corresponds to the nucleotide sequence of pET28a Os09g36030.
SEQ ID NO:85 corresponds to amino acid sequence of Os09g36030 His TAG.
SEQ ID NO:86 corresponds to the nucleotide sequence of the PP FWD primer.
SEQ ID NO:87 corresponds to the nucleotide sequence of the PP REV primer.
SEQ ID NO:88 corresponds to the nucleotide sequence of pCR blunt HpaI PP.
SEQ ID NO:89 corresponds to the nucleotide sequence HpaI PP.
SEQ ID NO:90 corresponds to the amino acid sequence of HpaI PP.
SEQ ID NO:91 corresponds to the nucleotide sequence of HpaI PP fwd primer.

SEQ ID NO:92 corresponds to nucleotide sequence of HpaI PP rev primer.
SEQ ID NO:93 corresponds to the nucleotide sequence of pGEM®-T HpaI PP.
SEQ ID NO:94 corresponds to the nucleotide sequence of pET29a HpaI PP.
SEQ ID NO:95 corresponds to the amino acid sequence of HpaI PP His TAG.
SEQ ID NO:96 corresponds to the nucleotide sequence of the AthHpaIL G83 rev primer.
SEQ ID NO:97 corresponds to the nucleotide sequence of the AthHpaIL G83 fwd primer.
SEQ ID NO:98 corresponds to the nucleotide sequence of pGEM®-T At4g10750-G83
SEQ ID NO:99 corresponds to the nucleotide sequence of pET28a At4g10750-G83.
SEQ ID NO:100 corresponds to the amino acid sequence of At4g10750-G83 His TAG.
SEQ ID NO:101 corresponds to the nucleotide sequence of the FUSION REV primer.
SEQ ID NO:102 corresponds to the nucleotide sequence of FUSION FWD primer.
SEQ ID NO:103 corresponds to the nucleotide sequence of pET29a 3primer.
SEQ ID NO:104 corresponds to the nucleotide sequence of pCR8GW-plastid HpaI PP.
SEQ ID NO:105 corresponds to the nucleotide sequence of pKR1478-plastid HpaI PP.
SEQ ID NO:106 corresponds to the amino acid sequence of pKR1478 plastid HpaI PP AA.
SEQ ID NO:107 corresponds to the amino acid sequence of the plastidic HpaIL from *Arabidopsis lyrata* (NCBI GI NO: 297809303).
SEQ ID NO:108 corresponds to the amino acid sequence of the plastidic HpaIL from *Theobroma cacao* (NCBI GI NO: 212319639).
SEQ ID NO:109 corresponds to the amino acid sequence of the plastidic HpaIL aldolase from *Ricinus communis* (NCBI GI NO: 255587508).
SEQ ID NO:110 corresponds to the amino acid sequence of the plastidic HpaIL aldolase from *Solarium iycopersicum* (NCBI GI NO: 47105574).
SEQ ID NO:111 corresponds to the amino acid sequence of the plastidic HpaIL aldolase from *Vitis vinifera* (NCBI GI NO: 225426623 and proprietary done vpl1c.pk008.013).
SEQ ID NO:112 corresponds to the amino acid sequence of the plastidic HpaIL aldolase from *Carica papaya* (C_papaya Tu SC 175.15).
SEQ ID NO:113 corresponds to the amino acid sequence of the plastidic HpaIL aldolase from *Citrus clementine* (NCBI GI NO: 110855269).
SEQ ID NO:114 corresponds to the amino acid sequence of the plastidic HpaIL from *Citrus clementina* (NCBI GI NO: 110843679).
SEQ ID NO:115 corresponds to the amino acid sequence of the plastidic HpaIL from *Oryza brachyata* (NCBI GI NO: 110430657).
SEQ ID NO:116 corresponds to the amino acid sequence of the plastidic HpaIL from *Brachypodium distachyon* (Brad i4g35820).
SEQ ID NO:117 corresponds to the amino acid sequence of the plastidic HpaIL from *Sorghum* (Sb02g030560).
SEQ ID NO:118 corresponds to the amino acid sequence of the plastidic HpaIL from *Paspalum notatum* (Bahia-force joined).
SEQ ID NO:119 corresponds to the amino acid sequence of the plastidic HpaIL from *Eragrostis nindensis* (resurrection grass-force joined).
SEQ ID NO:120 corresponds to the amino acid sequence of the plastidic HpaIL from *Tulipa gesneriana* (proprietary clone etp1c.pk001.g3:fis).
SEQ ID NO:121 corresponds to the amino acid sequence of the plastidic HpaIL from *Tulipa gesneriana* (proprietary clone etp1c.pk003.b22:fis).
SEQ ID NO:122 corresponds to the amino acid sequence of the plastidic HpaIL from *Asclepias syriaca* (proprietary clone mas1c.pk012.d9.f).
SEQ ID NO:123 corresponds to the amino acid sequence of the plastidic HpaIL from *Momordica charantia* (proprietary clone fds1n.pk007.i18).
SEQ ID NO:124 corresponds to the nucleic acid sequence of the plastid HpaIL from *Tulipa gesneriana* (proprietary clone etp1c.pk001.g3:fis) encoding the amino acid sequence set forth in SEQ ID NO:120.
SEQ ID NO:125 corresponds to the nucleic acid sequence of the plastid HpaIL from *Tulipa gesneriana* (proprietary clone etp1c.pk003.b22:fis) encoding the amino acid sequence set forth in SEQ ID NO:121.
SEQ ID NO:126 corresponds to the nucleic acid sequence of the plastid HpaIL from *Asclepias syriaca* (proprietary clone mas1c.pk012.d9.f) encoding the amino acid sequence set forth in SEQ ID NO:122.
SEQ ID NO:127 corresponds to the nucleic acid sequence of the plastid HpaIL from *Momordica charantia* (proprietary clone fds1n.pk007.i18) encoding the amino acid sequence set forth in SEQ ID NO:123.
SEQ ID NO:128 is a conserved sequence motif useful in identifying genes belonging to the HpaIL family of genes.
SEQ ID NO:129 is a conserved sequence motif useful in identifying genes belonging to the HpaIL family of genes.
SEQ ID NO:130 is a conserved sequence motif useful in identifying genes belonging to the HpaIL family of genes.
SEQ ID NO:131 is a conserved sequence motif useful in identifying genes belonging to the HpaIL family of genes.
SEQ ID NO:132 is a conserved sequence motif useful in identifying genes belonging to the HpaIL family of genes.
SEQ ID NO:133 corresponds to the nucleic acid sequence of the plastidic HpAIL from *Arabidopsis lyrata* encoding SEQ ID NO:107.
SEQ ID NO:134 corresponds to the nucleic acid sequence of the plastidic HpAIL from *Theobroma cacao* encoding SEQ ID NO:108.
SEQ ID NO:135 corresponds to the nucleic acid sequence of the plastidic HpAIL from *Ricinus communis* encoding SEQ ID NO:109.
SEQ ID NO:136 corresponds to the nucleic acid sequence of the plastidic HpAIL from *Soianum lycopersicum* encoding SEQ ID NO:110.
SEQ ID NO:137 corresponds to the nucleic acid sequence of the plastidic HpAIL from *Vitis vinifera* encoding SEQ ID NO:111.
SEQ ID NO:138 corresponds to the nucleic acid sequence of the plastidic HpAIL from *Carica papaya* (C_papaya Tu SC 175.15) encoding SEQ ID NO:112.
SEQ ID NO:139 corresponds to the nucleic acid sequence of the plastidic HpAIL from *Citrus clementina* encoding SEQ ID NO:113.
SEQ ID NO:140 corresponds to the nucleic acid sequence of the plastidic HpAIL from *Citrus clementina* encoding SEQ ID NO:114.

SEQ ID NO:141 corresponds to the nucleic acid sequence of the plastidic HpAIL from *Oryza brachyata* encoding SEQ ID NO:115.

SEQ ID NO:142 corresponds to the nucleic acid sequence of the plastidic HpAIL from *Brachypodium distachyon* (Bradi4g35820) encoding SEQ ID NO:116.

SEQ ID NO:143 corresponds to the nucleic acid sequence of the plastidic HpAIL from *Sorghum* (Sb02g030560) encoding SEQ ID NO:117.

SEQ ID NO:144 corresponds to the nucleic acid sequence of the plastidic HpAIL from *Paspalum notatum* (Bahia-force joined) encoding SEQ ID NO:118.

SEQ ID NO:145 corresponds to the nucleic acid sequence of the plastidic HpAIL from *Eragrostis nindensis* (resurrection grass-force joined) encoding SEQ ID NO:119.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

All patents, patent applications, and publications cited throughout the application are hereby incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure a number of terms and abbreviations are used. The following definitions are provided.

"Open reading frame" is abbreviated ORF.

"Polymerase chain reaction" is abbreviated PCR.

"Triacylglycerols" are abbreviated TAGs.

"Co-enzyme A" is abbreviated CoA.

"Diacylglycerol acyltransferase" is abbreviated DAG AT or DGAT.

"Diacylglycerol" is abbreviated DAG.

The term "HpaI-like aldolase", "HpaIL", "HpaIL aldolase" and "Class II or class II-like aldolase" proteins refers to proteins identified based on their similarity to bacterial 2,4-dihydroxy-hept-2-ene-1,7-dioic acid class II-like aldolase.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

The term "DAG AT" or "DGAT" refers to a diacylglycerol acyltransferase (also known as an acyl-CoA-diacylglycerol acyltransferase or a diacylglycerol O-acyltransferase) (EC 2.3.1.20). This enzyme is responsible for the conversion of acyl-CoA and 1,2-diacylglycerol to TAG and CoA (thereby involved in the terminal step of TAG biosynthesis). Two families of DAG AT enzymes exist: DGAT1 and DGAT2. The former family shares homology with the acyl-CoA:cholesterol acyltransferase (ACAT) gene family, while the latter family is unrelated (Lardizabal et al., *J. Biol. Chem.* 276(42): 38862-28869 (2001)).

The term "modulation" or "alteration" in the context of the present invention refers to increases or decreases of plastidic HpaIL aldolase expression, protein level or enzyme activity, as well as to an increase or decrease in the storage compound levels, such as oil, protein, starch or soluble carbohydrates.

The term "plant" includes reference to whole plants, plant parts or organs (e.g., leaves, stems, roots, etc.), plant cells, seeds and progeny of same. Plant cell, as used herein includes, without limitation, cells obtained from or found in the following: seeds, suspension cultures, embryos, meristematic regions, callus tissue, leaves, roots, shoots, gametophytes, sporophytes, pollen and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Examples of monocots include, but are not limited to (corn) maize, wheat, rice, sorghum, millet, barley, palm, lily, Alstroemeria, rye, and oat.

Examples of dicots include, but are not limited to, soybean, rape, sunflower, canola, grape, guayule, columbine, cotton, tobacco, peas, beans, flax, safflower, and alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue.

The term "plant organ" refers to plant tissue or group of tissues that constitute a morphologically and functionally distinct part of a plant.

The term "genome" refers to the following: 1. The entire complement of genetic material (genes and non-coding sequences) is present in each cell of an organism, or virus or organelle. 2. A complete set of chromosomes inherited as a (haploid) unit from one parent. The term "stably integrated" refers to the transfer of a nucleic acid fragment into the genome of a host organism or cell resulting in genetically stable inheritance.

The terms "polynucleotide", "polynucleotide sequence", "nucleic acid", nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" refers to materials, such as "isolated nucleic acid fragments" and/or "isolated polypeptides", which are substantially free or otherwise removed from components that normally accompany or interact with the materials in a naturally occurring environment isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "isolated" nucleic acid fragment is used interchangeably with "isolated polynucleotide" and is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T. "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of recombinant DNA constructs to produce the desired phenotype in a transformed plant. Recombinant DNA constructs can be designed for use in co-suppression or antisense by linking a nucleic add fragment or subfragment thereof, whether or not it encodes an active enzyme, in the appropriate orientation relative to a plant promoter sequence.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive; and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107, 065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

Previously described is the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication No. WO 99/61632 published on Dec. 2, 1999).

The use of poly-T and poly-A sequences to generate the stem in the stem-loop structure has also been described (PCT Publication No. WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication No. WO 02/00904, published Jan. 3, 2002.

RNA interference refers to the process of sequence-specific post-transcriptional gene silencing in animals mediated by short interfering RNAs (siRNAs) (Fire et al., *Nature* 391: 806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., *Nature* 409:363 (2001)). Short interfering RNAs derived from dicer activity are typically about 21 to about 23 nucleotides in length and comprise about 19 base pair duplexes (Elbashir et al., *Genes Dev.* 15:188 (2001)). Dicer has also been implicated in the excision of 21- and 22-nucleotide small temporal RNAs (stRNAs) from precursor RNA of conserved structure that are implicated in translational control (Hutvagner et al., *Science* 293:834 (2001)). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex. In addition, RNA interference can also involve small RNA (e.g., miRNA) mediated gene silencing, presumably through cellular mechanisms that regulate chromatin structure and thereby prevent transcription of target gene sequences (see, e.g., Allshire, *Science* 297:1818-1819 (2002); Volpe et al., *Science* 297:1833-1837 (2002); Jenuwein, *Science* 297:2215-2218 (2002); and Hall et al., *Science* 297:2232-2237 (2002)). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 (1998)) were the first to observe RNAi in *Caenorhabditis elegans*. Wianny and Goetz (*Nature Cell Biol.* 2:70 (1999)) describe RNAi mediated by dsRNA in mouse embryos. Hammond et al. (*Nature* 404:293 (2000)) describe RNAi in *Drosophila* cells transfected with dsRNA. Elbashir et al., (*Nature* 411:494 (2001)) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., *Science* 294:853-858 (2001), Lagos-Quintana et al., *Curr. Biol.* 12:735-739 (2002); Lau et al., *Science* 294; 858-862 (2001); Lee and Ambros, *Science* 294:862-864 (2001); Llave et al., *Plant Cell* 14:1605-1619 (2002); Mourelatos et al., *Genes. Dev.* 16:720-728 (2002); Park et al., *Curr. Biol.* 12:1484-1495 (2002); Reinhart et al., *Genes. Dev.* 16:1616-1626 (2002)). They are processed from longer precursor transcripts that range in size from approximately 70 to 200 nt, and these precursor transcripts have the ability to form stable hairpin structures. In animals, the enzyme involved in processing miRNA precursors is called dicer, an RNAse III-like protein (Grishok et al., *Cell* 106:23-34 (2001); Hutvagner et al., *Science* 293:834-838 (2001); Ketting et al., *Genes. Dev.* 15:2654-2659 (2001)). Plants also have a dicer-like enzyme, DCLI (previously named CARPEL FACTORY/SHORT INTEGUMENTS1/SUSPENSOR1), and recent evidence indicates that it, like dicer, is involved in processing the hairpin precursors to generate mature miRNAs (Park et al., *Curr. Biol.* 12:1484-1495 (2002); Reinhart et al., *Genes Dev.* 16:1616-1626 (2002)). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 (2001); Lee et al., *EMBO J.* 21:4663-4670 (2002)).

Recent work has also examined the selection of the miRNA strand from the dsRNA product arising from processing of the hairpin by DICER (Schwartz et al., *Cell* 115:199-208 (2003)). It appears that the stability (i.e. G:C versus A:U content, and/or mismatches) of the two ends of the processed dsRNA affects the strand selection, with the low stability end being easier to unwind by a helicase activity. The 5 end strand at the low stability end is incorporated into the RISC complex, while the other strand is degraded.

MicroRNAs (miRNAs) appear to regulate target genes by binding to complementary sequences located in the transcripts produced by these genes. In the case of lin-4 and let-7, the target sites are located in the 3' UTRs of the target mRNAs (Lee et al., *Cell* 75:843-854 (1993); Wightman at al., *Cell* 75:855-862 (1993); Reinhart et al., *Nature* 403:901-906 (2000); Slack et al., *Mol. Cell.* 5:659-669 (2000)), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 (1999)). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, *Science* 297:2056-2060 (2002); Llave et al., *Plant Cell* 14:1605-1619 (2002)). It seems likely that miRNAs can enter at least two pathways of target gene regulation: (1) protein downregulation when target complementarily is <100%; and (2) RNA cleavage when target complementarity is 100%. MicroRNAs entering the RNA cleavage pathway are analogous to the 21-25 nt short interfering RNAs (siRNAs) generated during RNA interference (RNAi) in animals and post-transcriptional gene silencing (PTGS) in plants, and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 (2002); Park at al., *Curr. Biol.* 12:1484-1495 (2002); Rhoades et al., *Cell* 110:513-520 (2002)), and thus it appears that plant miR-NAs have higher overall complementarity with their putative targets than do animal miRNAs. Most of these predicted target transcripts of plant miRNAs encode members of transcription factor families implicated in plant developmental patterning or cell differentiation.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. For example, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes that result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 1×SSC, 0.1% SDS, 60° C.) with the sequences exemplified herein, or to any portion of the nucleotide sequences reported herein and which are functionally equivalent to the gene or the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SOS at 50° C. for 30 min. A more preferred set of stringent conditions involves the use of higher temperatures in which the washes are identical to those above except for the temperature of the final two 30 min washes in 0.2×SSC, 0.5% SOS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length: and should be at least 80% identical, preferably at least 85% identical, more preferably at least 90% identical, and most preferably at least 95% identical.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 85% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%.

Sequence alignments and percent similarity calculations may be determined using a variety of comparison methods designed to detect homologous sequences including, but not limited to, the MEGALIGN® program of the LASERGENE® bioinformatics computing suite (DNASTAR Inc., Madison, Wis.). Unless stated otherwise, multiple alignment of the sequences provided herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain a "percent identity" by viewing the "sequence distances" table on the same program.

Unless otherwise stated, the Basic Local Alignment Search Tool (BLAST)® sequence identity/similarity values provided herein refer to the value obtained using the BLAST® 2.0 suite of programs using default parameters (Altschul et al., *Nucleic Acids Res*. 25:3389-3402 (1997)). Software for performing BLAST® search tool analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® search tool algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

"Sequence identity" or "identity" in the context of nucleic acid or polypeptide sequences refers to the nucleic acid bases or amino acid residues in the two sequences that are the same when aligned for maximum correspondence over a specified comparison window.

Thus, "Percentage of sequence identity" refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 55% to 100%. These identities can be determined using any of the programs described herein.

Sequence alignments and percent identity or similarity calculations may be determined using a variety of comparison methods designed to detect homologous sequences including, but not limited to, the MEGALIGN® program of the LASERGENE® bioinformatics computing suite (DNASTAR Inc., Madison, Wis.). Multiple alignments of the sequences are performed using the Clustal V method of alignment (Higgins, D. G. and Sharp, P. M. (1989) *Comput. Appl. Biosci*. 5:151-153; Higgins, D. G. et al. (1992) *Comput. Appl. Biosci*. 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other plant species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 55% to 100%. Indeed, any integer amino acid identity from 50%-100% may be useful in describing the present invention. Also, of interest is any full or partial complement of this isolated nucleotide fragment.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The terms "synthetic nucleic acid" or "synthetic genes" refer to nucleic acid molecules assembled either in whole or in part from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that is capable of directing expression a specific protein or functional RNA.

"Native gene" refers to a gene as found in nature with its own regulatory sequences.

"Chimeric gene" or "recombinant DNA construct" are used interchangeably herein, and refers to any gene that is not a native gene, comprising regulatory and coding sequences that are not found together in nature, or to an isolated native gene optionally modified and reintroduced into a host cell.

A chimeric gene may comprise regulatory sequences and coding sequences that are derived from different sources, or regulatory sequences and coding sequences derived from the same source, but arranged in a manner different than that found in nature. In one embodiment, a regulatory region and a coding sequence region are assembled from two different sources. In another embodiment, a regulatory region and a coding sequence region are derived from the same source but arranged in a manner different than that found in nature. In another embodiment, the coding sequence region is assembled from at least two different sources. In another embodiment, the coding region is assembled from the same source but not found in nature.

The term "endogenous gene" refers to a native gene in its natural location in the genome of an organism.

The term "foreign gene" refers to a gene not normally found in the host organism that is introduced into the host organism by gene transfer.

The term "transgene" refers to a gene that has been introduced into a host cell by a transformation procedure. Transgenes may become physically inserted into a genome of the host cell (e.g., through recombination) or may be maintained outside of a genome of the host cell (e.g., on an extrachromosomal array).

An "allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The term "coding sequence" refers to a DNA fragment that codes for a polypeptide having a specific amino acid sequence, or a structural RNA. The boundaries of a protein coding sequence are generally determined by a ribosome binding site (prokaryotes) or by an ATG start codon (eukaryotes) located at the 5' end of the mRNA and a transcription terminator sequence located just downstream of the open reading frame at the 3' end of the mRNA. A coding sequence can include, but is not limited to, DNA, cDNA, and recombinant nucleic acid sequences.

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be and are not limited to intracellular localization signals.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence, "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Sense" RNA refers to RNA transcript that includes the mRNA and can be translated into protein within a cell or in vitro.

"Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5 non-coding sequence, 3' non-coding sequence, introns, or the coding sequence.

"Functional RNA" refers to antisense RNA, ribozyme RNA, or other RNA that may not be translated, yet has an effect on cellular processes. The terms "complement" and "reverse complement" are used interchangeably herein with respect to mRNA transcripts, and are meant to define the antisense RNA of the message.

The term "recombinant DNA construct" refers to a DNA construct assembled from nucleic acid fragments obtained from different sources. The types and origins of the nucleic acid fragments may be very diverse.

A "recombinant expression construct" contains a nucleic acid fragment operably linked to at least one regulatory element, that is capable of effecting expression of the nucleic acid fragment. The recombinant expression construct may also affect expression of a homologous sequence in a host cell.

In one embodiment the choice of recombinant expression construct is dependent upon the method that will be used to transform host cells. The skilled artisan is well aware of the genetic elements that must be present on the recombinant expression construct in order to successfully transform, select and propagate host cells. The skilled artisan will also recognize that different independent transformation events may be screened to obtain lines displaying the desired expression level and pattern. Such screening may be accomplished by, but is not limited to, Southern analysis of DNA, Northern analysis of mRNA expression, Western analysis of protein expression, or phenotypic analysis.

The term "operably linked" refers to the association of nucleic acid fragments on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3" to the target mRNA, or within the target mRNA, or a first complementary region is 5' and its complement is 3' to the target mRNA.

"Regulatory sequences" refer to nucleotides located upstream (5 non-coding sequences), within, or downstream (3 non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters which cause an isolated nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) Biochemistry of Plants 15:1-82. It is further recognized that since in most cases the exact boundaries of regulatory sequences have not been completely defined, DNA fragments of some variation may have identical promoter activity.

Specific examples of promoters that may be useful in expressing the nucleic acid fragments of the invention include, but are not limited to, the oleosin promoter (PCT Publication WO99/65479, published Dec. 12, 1999), the maize 27 kD zein promoter (Ueda et al (1994) *Mol. Cell. Biol.* 14:4350-4359), the ubiquitin promoter (Christensen at al (1992) *Plant Mol. Biol.* 18:675-680), the SAM synthetase promoter (PCT Publication WO00/37662, published Jun. 29, 2000), the CaMV 35S (Odell at al (1985) *Nature* 313:810-812), and the promoter described in PCT Publication WO02/099063 published Dec. 12, 2002.

The "translation leader sequence" refers to a polynucleotide fragment located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Mol. Biotechnol.* 3:225-236).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

A "signal peptide" is an amino acid sequence that is translated in conjunction with a protein and directs the protein to the secretory system (Chrispeels, M. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel, N. (1992) *Plant Phys.* 100:1627-1632). A "chloroplast transit peptide" is an amino acid sequence that is translated in conjunction with a protein and directs the protein to the chloroplast or other plastid types present in the cell in which the protein is made. "Chloroplast transit sequence" refers to a nucleotide sequence that encodes a chloroplast transit peptide.

Chloroplast transit sequences can be predicted for example by using ChloroP at the online ChloroP 1.1. Server, which predicts the presence of chloroplast transit peptides (cTP) in protein sequences and the location of potential cTP cleavage sites.

An "intron" is an intervening sequence in a gene that does not encode a portion of the protein sequence. Thus, such sequences are transcribed into RNA but are then excised and are not translated. The term is also used for the excised RNA sequences.

The "3 non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) *Plant Cell* 1:671-680.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989. Transformation methods are well known to those skilled in the art and are described below.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

"Stable transformation" refers to the transfer of a nucleic acid fragment into a genome of a host organism, including nuclear and organellar genomes, resulting in genetically stable inheritance.

In contrast, "transient transformation" refers to the transfer of a nucleic acid fragment into the nucleus, or DNA-containing organelle, of a host organism resulting in gene expression without integration or stable inheritance.

Host organisms comprising the transformed nucleic acid fragments are referred to as "transgenic" organisms.

The term "amplified" means the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology Principles and Applications, D. H. Persing et al., Ed., American Society for Microbiology, Washington, D.C. (1993). The product of amplification is termed an amplicon.

The term "chromosomal location" includes reference to a length of a chromosome which may be measured by reference to the linear segment of DNA which it comprises. The chromosomal location can be defined by reference to two unique DNA sequences, i.e., markers.

The term "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

The present invention includes, inter alia, compositions and methods for altering or modulating (i.e., increasing or decreasing) the level of plastidic HpaIL aldolase polypeptides described herein in plants. The size of the oil, protein, starch and soluble carbohydrate pools in soybean seeds as well as the seed weight can be modulated or altered (i.e. increased or decreased) by altering the expression of a specific gene, plastidic HpaI aldolase polypeptides.

In one embodiment, the present invention concerns a transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 and wherein seed obtained from said transgenic plant has an altered oil, protein, starch and/or soluble carbohydrate content and/or altered seed weight when compared to seed obtained from a control plant not comprising said recombinant DNA construct.

In a second embodiment the present invention concerns a transgenic seed obtained from the transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 and wherein said transgenic seed has an altered oil, protein, starch and/or soluble carbohydrate content and/or altered seed weight when compared to a control plant not comprising said recombinant DNA construct.

In a third embodiment the present invention concerns a transgenic seed obtained from the transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 and wherein said transgenic seed has an increased protein content of at least 0.5%, 1%, 1.5%, 2%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11%, 11.5%, 12.0% 12.5%, 13.0, 13.5%. 14.0%, 14.5%, 15.0%, 15.5%, 15.0%, 16.5%, 17.0%, 17.5% 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29%, 29.5%, 30.0%, 30.5%, 31.0%, 31.5%, 32.0%, 32.5%, 33.0%, 33.5%, 34.0%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, or 50.0% on a dry weight basis when compared to a control seed not comprising said recombinant DNA construct.

In a third embodiment the present invention concerns a transgenic seed obtained from the transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 and wherein said transgenic seed has an increased starch content of at least 0.5%, 1%, 1.5%, 2%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11%, 11.5%, 12.0% 12.5%, 13.0, 13.5%. 14.0%, 14.5%, 15.0%, 15.5%, 15.0%, 16.5%, 17.0%, 17.5% 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29%, 29.5%, 30.0%, 30.5%, 31.0%, 31.5%, 32.0%, 32.5%, 33.0%, 33.5%, 34.0%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, or 50.0% on a dry weight basis when compared to a control seed not comprising said recombinant DNA construct.

In another embodiment, the present invention relates to a recombinant DNA construct comprising any of the isolated polynucleotides of the present invention operably linked to at least one regulatory sequence.

In another embodiment of the present invention, a recombinant construct of the present invention further comprises an enhancer.

In another embodiment, the present invention relates to a vector comprising any of the polynucleotides of the present invention.

In another embodiment, the present invention relates to an isolated polynucleotide fragment comprising a nucleotide sequence comprised by any of the polynucleotides of the present invention, wherein the nucleotide sequence contains at least 30, 40, 60, 100, 200, 300, 400, 500 or 600 nucleotides.

In another embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In yet another embodiment, the present invention relates to a method for transforming a cell, comprising transforming a cell with a polynucleotide of the present invention.

In another embodiment, the present invention relates to a method for producing a transgenic plant comprising transforming a plant cell with any of the isolated polynucleotides of the present invention and regenerating a transgenic plant from the transformed plant cell.

In another embodiment, a cell, plant, or seed comprising a recombinant DNA construct of the present invention.

In another embodiment, an isolated polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, and 123; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. The polypeptide can be a HpaIL aldolase protein.

In another embodiment, an isolated polynucleotide comprising: (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 28, 30, 32, 34, 48, 124, 125, 126, 127, 133, 134, 135, 136, 137, 138, 139, 140, 141, 142, 143, 144, 145, or 146; or (ii) a full complement of the nucleic acid sequence of (i). Any of the foregoing isolated polynucleotides may be utilized in any recombinant DNA constructs (including suppression DNA constructs) of the present invention. The polypeptide can be a HpaIL aldolase.

In one aspect, the present invention includes recombinant DNA constructs (including suppression DNA constructs).

In another embodiment, the present invention relates to a method of selecting an isolated polynucleotide that alters, i.e. increases or decreases, the level of expression of a HpaIL aldolase gene, protein or enzyme activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the HpaIL aldolase RNA, protein or enzyme activity in the host cell containing the isolated polynucleotide or recombinant DNA construct; (d) comparing the level of the HpaIL aldolase RNA, protein or enzyme activity in the host cell containing the isolated polynucleotide or recombinant DNA construct with the level of the HpaIL aldolase RNA, protein or enzyme activity in a host cell that does not contain the isolated polynucleotide or recombinant DNA construct, and selecting the isolated polynucleotide or recombinant DNA construct that alters, i.e., increases or decreases, the level of expression of the HpaIL aldolase gene, protein or enzyme activity in the plant cell.

In another embodiment, this invention concerns a method for suppressing the level of expression of a gene encoding a plastidic HpaIL aldolase in a transgenic plant, wherein the method comprises:
  (a) transforming a plant cell with a fragment of the isolated polynucleotide of the invention;
  (b) regenerating a transgenic plant from the transformed plant cell of 9a); and
  (c) selecting a transgenic plant wherein the level of expression of a gene encoding a plastidic polypeptide having HpaIL aldolase activity has been suppressed.

Preferably, the gene encodes a plastidic polypeptide having HpaI aldolase activity, and the plant is a soybean plant.

In another embodiment, the invention concerns a method for producing transgenic seed, the method comprising: a) transforming a plant cell with the recombinant DNA construct of (i) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146, or (ii) the complement of (i); wherein (i) or (ii) is useful in co-suppression or antisense suppression of endogenous HpaIL aldolase in a transgenic plant; (b) regenerating a transgenic plant from the transformed plant cell of (a); and (c) selecting a transgenic plant that produces transgenic seeds having an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% compared to seed obtained from a non-transgenic plant. Preferably, the seed is a soybean plant.

In another embodiment, a plant comprising in its genome a recombinant DNA construct comprising: (a) a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, 123, and 147 or (b) a suppression DNA construct comprising at least one regulatory element operably linked to: (i) all or part of: (A) a nucleic acid sequence encoding a polypeptide having an amino acid sequence of at least 70% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, and 123, or (B) a full complement of the nucleic acid sequence of (b)(i)(A); or (ii) a region derived from all or part of a sense strand or antisense strand of a target gene of interest, said region having a nucleic acid sequence of at least 70% sequence identity, based on the Clustal V method of alignment, when compared to said all or part of a sense strand or antisense strand from which said region is derived, and wherein said target gene of interest encodes a plastidic HpaIL aldolase, and wherein said plant has an altered oil, protein, starch and/or soluble carbohydrate content and/or altered seed weight, when compared to a control plant not comprising said recombinant DNA construct.

A transgenic seed having an increased oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% when compared to the oil content of a non-transgenic seed, wherein said transgenic seed comprises a recombinant DNA construct comprising: (a) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (b) the full-length complement of (a):wherein (a) or (b) is of sufficient length to inhibit expression of endogenous plastidic HpaIL aldolase in a transgenic plant and further wherein said seed has an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% on a dry-weight basis, as compared to seed obtained from a non-transgenic plant.

Yet another embodiment of the invention concerns a transgenic seed comprising a recombinant DNA construct comprising:

(a) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (b) the full-length complement of (a): wherein (a) or (b) is of sufficient length to inhibit expression of plastidic HpaIL aldolase in a transgenic plant and further wherein said seed has an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30° A on a dry-weight basis, as compared to seed obtained from a non-transgenic plant.

In another embodiment, the invention concerns a method for producing a transgenic plant, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, and 123; and (b) regenerating a plant from the transformed plant cell.

The method may further comprise (c) obtaining a progeny plant derived from the transgenic plant, wherein said progeny plant comprises in its genome the recombinant DNA construct and exhibits an altered oil, protein, starch and/or soluble carbohydrate content and/or altered seed weight, when compared to a control plant not comprising the recombinant DNA construct.

Another embodiment of the invention concerns, a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, and 123; and (b) regenerating a transgenic plant from the transformed plant cell of (a); and (c) selecting a transgenic plant that produces a transgenic seed having an altered oil, protein, starch and/or soluble carbohydrate content and/or altered seed weight, as compared to a transgenic seed obtained from a non-transgenic plant.

Another embodiment of the invention concerns, a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% 100% sequence identity, based on the Clustal V method of alignment, when compared to SEQ ID NO: 29, 31, 33, 35, 49, 107, 108, 109, 110, 111, 112, 113, 114, 115, 116, 117, 118, 119, 120, 121, 122, and 123; and (b) regenerating a transgenic plant from the transformed plant cell of (a); and (c) selecting a transgenic plant that produces a transgenic seed having an increased protein content of at least 0.5%, 1%, 1.5%, 2%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11%, 11.5%, 12.0% 12.5%, 13.0, 13.5%. 14.0%, 14.5%, 15.0%, 15.5%, 15.0%, 16.5%, 17.0%, 17.5% 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29%, 29.5%, 30.0%, 30.5%, 31.0%, 31.5%, 32.0%, 32.5%, 33.0%, 33.5%, 34.0%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, or 50.0% on a dry weight basis as compared to a transgenic seed obtained from a non-transgenic plant.

In another embodiment, the invention concerns a method for producing transgenic seed, the method comprising: (a) transforming a plant cell with a recombinant DNA construct comprising: (i) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (ii) the full-length complement of (i); wherein (i) or (ii) is of sufficient length to inhibit expression of plastidic HpaIL aldolase in a transgenic plant; (b) regenerating a transgenic plant from the transformed plant cell of (a); and (c) selecting a transgenic plant that produces a transgenic seed having an altered oil, protein, starch and/or soluble carbohydrate content and/or altered seed weight, as compared to a transgenic seed obtained from a non-transgenic plant.

A method for producing transgenic seed, the method comprising: (a) transforming a plant cell with a recombinant DNA construct comprising: (i) all or part of the nucleotide sequence set forth in SEQ ID NO: 28, 30, 32, 34, 48, 124, 125, 126, 127, 133, 134, 135, 136, 137, 138, 139, 140, 141, 142, 143, 144, 145, or 146; or (ii) the full-length complement of (i);
wherein (i) or (ii) is of sufficient length to inhibit expression of plastidic HpaIL aldolase in a transgenic plant; (b) regenerating a transgenic plant from the transformed plant cell of (a); and (c) selecting a transgenic plant that produces a transgenic seed having an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, on a dry-weight basis, as compared to a transgenic seed obtained from a non-transgenic plant.

A transgenic oilseed of the invention can comprise at least one DGAT sequence and a construct downregulating plastidic HpaI or HpaI-like activity, wherein the DGAT sequence and the plastidic HpaI or HpaI-like construct can be in the same recombinant construct or in separate recombinant constructs, and wherein seed obtained from said transgenic plant has an increased oil content when compared to the oil content of seed obtained from a control plant not comprising said construct or when compared to transgenic seed obtained from a transgenic plant comprising either said DGAT sequences alone or said construct downregulating HpaI or HpaI-like activity alone.

Those skilled in the art will appreciate that the instant invention includes, but is not limited to, the DGAT and plastidic HpaI and HpaI-like sequences disclosed herein. For example, the DGAT sequence can be selected from the group consisting of DGAT1, DGAT2 and DGAT1 in combination with DGAT2.

In one embodiment the present invention concerns a transgenic plant comprising at least one DGAT sequence and a construct downregulating plastidic HpaI or HpaI-like activity, wherein the DGAT sequence and the plastidic HpaI or HpaI-like construct can be in the same recombinant construct or in separate recombinant constructs, and wherein seed obtained from said transgenic plant has an increased oil content when compared to the oil content of seed obtained from a control plant not comprising said construct or when compared to transgenic seed obtained from a transgenic plant comprising either said DGAT sequences alone or said construct downregulating HpaI-like activity alone. Such increases in the oil content would include, but are not limited to, at least 0.5%, 0.6%, 0.7%, 0.8%, 0.9%, 1%, 1.1, %, 1.2%, 1.3%, 1.4%, 1.5%, 1.6%, 1.7%, 1.8%, 1.9%, 2%, 2.1, %, 2.2%, 2.3%, 2.4%, 2.5%, 2.6%, 2.7%, 2.8%, 2.9%, 3%, 3.1, %, 3.2%, 3.3%, 3.4%, 3.5%, 3.6%, 3.7%, 3.8%, 3.9%, 4%, 4.1, %, 4.2%, 4.3%, 4.4%, 4.5%, 4.6%, 4.7%, 4.8%, 4.9%, 5%, 5.1, %, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 7.1%, 7.2%, 7.3%, 7.4%, 7.5%, 7.6%, 7.7%, 7.8%, 7.9%, 8%, 8.1, %, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9%, 10%, 10.1%, 10.2%, 10.3%, 10.4%, 10.5%, 10.6%, 10.7%, 10.8%, 10.9%, 11%, 11.1%, 11.2%, 11.3%, 11.4%, 11.5%, 11.6%, 11.7%, 11.8%, 11.9%, 12%, 12.1%, 12.2%, 12.3%, 12.4%, 12.5%, 12.6%, 12.7%, 12.8%, 12.9%, 13%, 13.1%, 13.2%, 13.3%, 13.4%, 13.5%, 13.6%, 13.7%, 13.8%, 13.9%, 14%, 14.1%, 14.2%, 14.3%, 14.4%, 14.5%, 14.6%, 14.7%, 14.8%, 14.9%, 15%, 15.1%, 15.2%, 15.3%, 15.4%, 15.5%, 15.6%, 15.7%, 15.8%, 15.9%, 16%, 16.1%, 16.2%, 16.3%, 16.4%, 16.5%, 16.6%, 16.7%, 16.8%, 16.9%, 17%, 17.1%, 17.2%, 17.3%, 17.4%, 17.5%, 17.6%, 17.7%, 17.8%, 17.9%, 18%, 18.1%, 18.2%, 18.3%, 18.4%, 18.5%, 18.6%, 18.7%, 18.8%, 18.9%, 19%, 19.1%, 19.2%, 19.3%, 19.4%, 19.5%, 19.6%, 19.7%, 19.8%, 19.9%, 20%, 20.1%, 20.2%, 20.3%, 20.4%, 20.5%, 20.6%, 20.7%, 20.8%, 20.9%, 21%, 21.1%, 21.2%, 21.3%, 21.4%, 21.5%, 21.6%, 21.7%, 21.8%, 21.9%, 22%, 22.1%, 22.2%, 22.3%, 22.4%, 22.5%, 22.6%, 22.7%, 22.8%, 22.9%, 23%, 23.1%, 23.2%, 23.3%, 23.4%, 23.5%, 23.6%, 23.7%, 23.8%, 23.9%, 24%, 24.1%, 24.2%, 24.3%, 24.4%, 24.5%, 24.6%, 24.7%, 24.8%, 24.9%, 25%, 25.1%, 25.2%, 25.3%, 25.4%, 25.5%, 25.6%, 25.7%, 25.8%, 25.9%, 26%, 26.1%, 26.2%, 26.3%, 26.4%, 26.5%, 26.6%, 26.7%, 26.8%, 26.9%, 27%, 27.1%, 27.2%, 27.3%, 27.4%, 27.5%, 27.6%, 27.7%, 27.8%, 27.9%, 28%, 28.1%, 28.2%, 28.3%, 28.4%, 28.5%, 28.6%, 28.7%, 28.8%, 28.9%, 29%, 29.1%, 29.2%, 29.3%, 29.4%, 29.5%, 29.6%, 29.7%, 29.8%, 29.9%, or 30%, on a dry-weight basis.

Further embodiments include transgenic seed obtained from the transgenic plant of claim 1 comprising at least one DGAT sequence and a construct downregulating HpaI or HpaI-like activity, wherein the DGAT sequence and the plastidic HpaI-like construct can be in the same recombinant construct or in separate recombinant constructs and wherein the oil content of said transgenic seed is increased when compared to the oil content of control seed not comprising said construct or transgenic seed comprising either said DGAT sequence alone or said construct downregulating HpaI or HpaI-like activity alone.

Transgenic seed obtained from a monocot or dicot plant are included in the invention, e.g. maize or soybean.

Another embodiment of the present invention comprises a seed-specific or seed-preferred promoter as the at least one regulatory element linked to the nucleic acid sequences of the present invention. Also, endosperm or embryo-specific promoter are included.

Another embodiment of the present invention comprises q method for increasing the oil content of a seed comprising: a) transforming at least one cell with at least one recombinant construct having at least one DGAT sequence and a construct downregulating plastidic HpaI or HpaI-like activity wherein the DGAT sequence and the HpaI or HpaI-like construct can be in the same recombinant construct or in separate recombinant constructs; (b) selecting the transformed soybean cell(s) of step (a) having an increased oil content when compared to the oil content of a control cell not comprising said construct or when compared to transgenic seed obtained from a transgenic plant comprising either said DGAT sequences alone or said construct downregulating HpaI or HpaI-like activity alone.

Product and/or by-product obtained from the transgenic seed of transformed with any of the recombinant construct of the present invention are also included.

Soybeans can be processed into a number of products. For example, "soy protein products" can include, and are not limited to, those items listed in Table 2. "Soy protein products".

TABLE 2

Soy Protein Products Derived from Soybean Seeds[a]

Whole Soybean Products

Roasted Soybeans
Baked Soybeans
Soy Sprouts
Soy Milk
Specialty Soy Foods/Ingredients Soy Milk
Tofu
Tempeh
Miso
Soy Sauce
Hydrolyzed Vegetable Protein
Whipping Protein
Processed Soy Protein Products Full Fat and Defatted Flours
Soy Grits
Soy Hypocotyls
Soybean Meal
Soy Milk
Soy Protein Isolates
Soy Protein Concentrates
Textured Soy Proteins
Textured Flours and Concentrates
Textured Concentrates
Textured Isolates

[a]See Soy Protein Products: Characteristics, Nutritional Aspects and Utilization (1987). Soy Protein Council.
"Processing" refers to any physical and chemical methods used to obtain the products listed in Table A and includes, and is not limited to, heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy foodproducts. Trading Standards and Specifications have been established for many of these products (see National Oilseed Processors Association Yearbook and Trading Rules 1991-1992).
"White" flakes refer to flaked, dehulled cotyledons that have been defatted and treated with controlled moist heat to have a PDI (AOCS: Ba10-65) of about 85 to 90. This term can also refer to a flour with a similar PDI that has been ground to pass through a No. 100 U.S. Standard Screen size.
"Grits" refer to defatted, dehulled cotyledons having a U.S. Standard screen size of between No. 10 and 80.
"Soy Protein Concentrates" refer to those products produced from dehulled, defatted soybeans by three basic processes: acid leaching (at about pH 4.5), extraction with alcohol (about 55-80%), and denaturing the protein with moist heat prior to extraction with water. Conditions typically used to prepare soy protein concentrates have been described by Pass ((1975) U.S. Pat. No. 3,897,574; Campbell et al., (1985) in New Protein Foods, ed. by Altschul and Wilcke, Academic Press,Vol. 5, Chapter 10, Seed Storage Proteins, pp 302-338).
"Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously (Atkinson (1970) U.S. Pat.No. 3,488,770, Horan (1985) In New Protein Foods, ed. by Altschul and Wilcke, Academic Press, Vol. 1A, Chapter 8, pp 367-414). Moreover, conditions used during extrusion processing of complex foodstuff mixtures that include soy protein products have been described previously (Rokey (1983) Feed Manufacturing Technology III, 222-237; McCulloch, U.S. Pat. No. 4,454,804).

TABLE 3

Generalized Steps for Soybean Oil and Byproduct Production

| Process Step | Process | Impurities Removed and/or By-Products Obtained |
|---|---|---|
| #1 | soybean seed | |
| #2 | oil extraction | meal |
| #3 | Degumming | lecithin |
| #4 | alkali or physical refining | gums, free fatty acids, pigments |
| #5 | water washing | soap |
| #6 | Bleaching | color, soap, metal |
| #7 | (hydrogenation) | |
| #8 | (winterization) | stearine |
| #9 | Deodorization | free fatty acids, tocopherols, sterols, volatiles |
| #10 | oil products | |

More specifically, soybean seeds are cleaned, tempered, dehulled, and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production, and byproduct utilization can be found in Erickson, Practical Handbook of Soybean Processing and Utilization, The American Oil Chemists Society and United Soybean Board (1995). Soybean oil is liquid at room temperature because it is relatively low in saturated fatty acids when compared with oils such as coconut, palm, palm kernel, and cocoa butter.

For example, plant and microbial oils containing polyunsaturated fatty acids (PUFAs) that have been refined and/or purified can be hydrogenated, thereby resulting in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, linoleic, and linolenic fatty acids, and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation, and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

In another embodiment, the invention concerns a transgenic seed produced by any of the above methods. Preferably, the seed is a soybean seed.

The present invention concerns a transgenic soybean seed having increased total fatty acid content of at least 1%, 2%, 3%, 4%, 5%, 6%, 7%, 8%, 9%, 11%, 12%, 13%, 14%, 15%, 16%, 17%, 18%, 19%, 20%, 21%, 22%, 23%, 24%, 25%, 26%, 27%, 28%, 29%, or 30% when compared to the total fatty acid content of a non-transgenic, null segregant soybean seed. It is understood that any measurable increase in the total fatty acid content of a transgenic versus a non-transgenic, null segregant, or a control not comprising the recombinant construct would be useful. Such increases in the total fatty acid content would include, but are not limited to, at least 1%, 2%, 3%, 4%, 5%, 6%, 7%, 8%, 9%, 11%, 12%, 13%, 14%, 15%, 16%, 17%, 18%, 19%, 20%, 21%, 22%, 23%, 24%, 25%, 26%, 27%, 28%, 29%, or 30%.

Regulatory sequences may include, and are not limited to, promoters, translation leader sequences, introns, and polyadenylation recognition sequences.

"Tissue-specific" promoters direct RNA production preferentially in particular types of cells or tissues. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (*Biochemistry of Plants* 15:1-82 (1989)). It is further recognized that since in most cases the exact boundaries of regulatory sequences have not been completely defined, DNA fragments of some variation may have identical promoter activity.

A number of promoters can be used to practice the present invention. The promoters can be selected based on the desired outcome. The nucleic acids can be combined with constitutive, tissue-specific (preferred), inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 353 promoter (Odell et al., *Nature* 313:810-812 (1985)); rice actin (McElroy et al., *Plant Cell* 2:163-171 (1990)); ubiquitin (Christensen et al., *Plant Mol.* *Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in particular cells/tissues of a plant. Any identifiable promoter may be used in the methods of the present invention which causes the desired temporal and spatial expression.

Promoters which are seed or embryo specific and may be useful in the invention include patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol, Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J. 6:3559-3564 (1987)).

A plethora of promoters is described in WO 00/18963, published on Apr. 6, 2000, the disclosure of which is hereby incorporated by reference. Examples of seed-specific promoters include, and are not limited to, the promoter for soybean Kunitz trypsin inhibitor (Kti3, Jofuku and Goldberg, *Plant Cell* 1:1079-1093 (1989)) β-conglycinin (Chen et al., *Dev. Genet.* 10:112-122 (1989)), the napin promoter, and the phaseolin promoter.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention includes compositions, and methods for making, heterologous promoters and/or enhancers operably linked to a native, endogenous (i.e., non-heterologous) form of a polynucleotide of the present invention.

An intron sequence can be added to the 5 untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell. Biol.* 8:4395-4405 (1988); Callis et al., *Genes Dev.* 1:1183-1200 (1987)). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994). A vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. in Enzymol.* 153:253-277 (1987).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

Preferred recombinant DNA constructs include the following combinations: a) a nucleic acid fragment corresponding to a promoter operably linked to at least one nucleic acid fragment encoding a selectable marker, followed by a nucleic acid fragment corresponding to a terminator, b) a nucleic acid fragment corresponding to a promoter operably linked to a nucleic acid fragment capable of producing a stem-loop structure, and followed by a nucleic acid fragment corresponding to a terminator, and c) any combination of a) and b) above. Preferably, in the stem-loop structure at least one nucleic acid fragment that is capable of suppressing expression of a native gene comprises the "loop" and is surrounded by nucleic acid fragments capable of producing a stem.

Preferred methods for transforming dicots and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al. (1996) *Plant Cell Rep.* 15:653-657, McKently et al. (1995) *Plant Cell Rep.* 14:699-703); papaya (Ling, K. et al. (1991) *Bio/technology* 9:752-758); and pea (Grant et al. (1995) *Plant Cell Rep.* 15:254-258). For a review of other commonly used methods of plant transformation see Newell, C. A. (2000) *Mol. Biotechnol.* 16:53-65. One of these methods of transformation uses *Agrobacterium rhizogenes* (Tepfler, M. and Casse-Delbart, F. (1987) *Microbiol. Sci.* 4:24-28), Transformation of soybeans using direct delivery of DNA has been published using PEG fusion (PCT publication WO 92/17598), electroporation (Chowrira, G. M. et al. (1995) *Mol. Biotechnol.* 3:17-23; Christou, P. et al. (1987) *Proc. Natl. Acad. Sci. U.S.A.* 84:3962-3966), microinjection, or particle bombardment (McCabe, D. E. et. Al. (1988) *Bio/Technology* 6:923; Christou et al. (1988) *Plant Physiol.* 87:671-674).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants are well known in the art (Weissbach and Weissbach, (1988) In.: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants may be self-pollinated. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide(s) is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al. (1989) Molecular Cloning: A Laboratory Manual, Cold Spring Harbor Press; Maliga et al. (1995) Methods in Plant Molecular Biology, Cold Spring Harbor Press; Birren et al, (1998) Genome Analysis: Detecting Genes, 1, Cold Spring Harbor, N.Y.; Birren et al. (1998) Genome Analysis: Analyzing DNA, 2, Cold Spring Harbor, N.Y.; Plant Molecular Biology: A Laboratory Manual, eds. Clark, Springer, N.Y. (1997)).

Assays to detect proteins may be performed by SDS-polyacrylamide gel electrophoresis or immunological assays. Assays to detect levels of substrates or products of enzymes may be performed using gas chromatography or liquid chromatography for separation and UV or visible spectrometry or mass spectrometry for detection, or the like. Determining the levels of mRNA of the enzyme of interest may be accomplished using northern-blotting or RT-PCR techniques. Once plants have been regenerated, and progeny plants homozygous for the transgene have been obtained, plants will have a stable phenotype that will be observed in similar seeds in later generations.

Typically, when a transgenic plant comprising a recombinant DNA construct or suppression DNA construct in its genome exhibits an altered, e.g. increased/or decreased oil, protein, soluble carbohydrate or starch content relative to a reference or control plant, the reference or control plant does not comprise in its genome the recombinant DNA construct or suppression DNA construct.

In another aspect, this invention includes a polynucleotide of this invention or a functionally equivalent subfragment thereof useful in antisense inhibition or cosuppression of expression of nucleic acid sequences encoding proteins having plastidic HpaIL aldolase, most preferably in antisense inhibition or cosuppression of an plastidic HpaIL aldolase gene.

Protocols for antisense inhibition or co-suppression are well known to those skilled in the art.

The sequences of the polynucleotide fragments used for suppression do not have to be 100% identical to the sequences of the polynucleotide fragment found in the gene to be suppressed. For example, suppression of all the subunits of the soybean seed storage protein β-conglycinin has been accomplished using a polynucleotide derived from a portion of the gene encoding the α subunit (U.S. Pat. No. 6,362,399). β-conglycinin is a heterogeneous glycoprotein composed of varying combinations of three highly negatively charged subunits identified as α,α' and β. The polynucleotide sequences encoding the α and α' subunits are 85% identical to each other while the polynucleotide sequences encoding the β subunit are 75 to 80% identical to the α and α' subunits, respectively. Thus, polynucleotides that are at least 75% identical to a region of the polynucleotide that is target for suppression have been shown to be effective in suppressing the desired target. The polynucleotide may be at least 80% identical, at least 90% identical, at least 95% identical, or about 100% identical to the desired target sequence.

One embodiment of the invention comprises an isolated polynucleotide comprising: (a) a nucleotide sequence encoding a polypeptide with HpaIL aldolase activity, wherein, based on the Clustal V method of alignment with pairwise alignment default parameters of KTUPLE=1, GAP PENALTY=3, WINDOW=5 and DIAGONALS SAVED=5, the polypeptide has an amino acid sequence of at least 75% sequence identity when compared to SEQ ID NO:120, 121, 122 or 123, or (b) the full complement of the nucleotide sequence of (a).

Furthermore, the amino acid sequence of the polypeptide can comprise SEQ ID NO: 120, 121, 122 or 123.

The present invention further comprises an isolated polynucleotide encoding a polypeptide, wherein said polynucleotide is capable of altering the endogenous expression of plastidic HpaI-like activity and wherein said polypeptide comprises a chloroplast transit peptide and at least one motif selected from the group consisting of: SEQ ID NO: 128, 129, 130, 131, or 132.

Another embodiment includes an isolated polynucleotide encoding a plant HpaI-like polypeptide, wherein said polynucleotide is capable of altering the endogenous expression of plastidial HpaI-like activity and wherein said polypeptide has a Km (acetaldehyde) at least 1.7 fold lower than the Km (acetaldehyde) of bacterial HpaIL aldolase activity and a Vmax of at least 15 fold lower than the bacterial HpaIL aldolase activity. Useful Km values of plastidial HpaI-like activity are at least 1.7, 1.75, 1.8, 1.85, 1.9, 1.95, 2.0, or 2.5 fold lower compared to the bacterial HpaII aldolase activity, in particular the aldolase of *P. putida*. Useful Vmax values for plastidial HpaI-like activity are at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 fold lower compared to the bacterial HpaII aldolase activity, in particular the aldolase of *P. putida*.

In another embodiment, the present invention includes a vector comprising any of the isolated polynucleotides of the present invention.

In another embodiment, the present invention concerns a method for transforming a cell comprising transforming a cell with any of the isolated polynucleotides of the present invention. The cell transformed by this method is also included. Advantageously, the cell is eukaryotic, e.g., a yeast, insect or plant cell, or prokaryotic, e.g., a bacterium.

In another embodiment, the present invention includes a method for producing a transgenic plant comprising transforming a plant cell with any of the isolated polynucleotides or recombinant DNA constructs of the present invention and regenerating a transgenic plant from the transformed plant cell. The invention is also directed to the transgenic plant produced by this method, and transgenic seed obtained from this transgenic plant.

The isolated nucleic acids and proteins and any embodiments of the present invention can be used over a broad range of plant types, particularly dicots such as the species of the genus *Glycine*.

It is believed that the nucleic acids and proteins and any embodiments of the present invention can be with monocots as well including, but not limited to, Graminiae including *Sorghum bicolor* and *Zea mays*.

The isolated nucleic acid and proteins of the present invention can also be used in species from the following dicot genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Antirrhinum, Pelargonium, Ranunculus, Senecio, Salpiglossis, Cucumis, Browallia, Glycine, Pisum, Phaseolus*, and from the following monocot genera: *Bromus, Asparagus, Hemerocallis, Panicum, Pennisetum, Lolium, Oryza, Avena, Hordeum, Secale, Triticum, Bambusa, Dendrocalamus*, and *Melocanna*.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Creation of an *Arabidopsis* Population with Activation-Tagged Genes

An 18.49-kb T-DNA based binary construct was created, pHSbarENDs2 (SEQ ID NO:1; FIG. 1), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a poly-linker (SEC) ID NO:2) to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHS-barENDs2 (SEQ ID NO:1) construct was transformed into *Agrobacterium tumefaciens* strain C58, grown in lysogeny broth medium at 25° C. to OD600~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting T1 seed were sown on soil, and transgenic seedlings were selected by spraying with glufosinate (FINALE®; AgrEvo; Bayer Environmental Science). A total of 100,000 glufosinate resistant T1 seedlings were selected. T2 seed from each line was kept separate. Small aliquots of T2 seed from independently generated activation-tagged lines were pooled. The pooled seed were planted in soil and plants were grown to maturity producing T3 seed pools each comprised of seed derived from 96 activation-tagged lines.

Example 2

Identification and Characterization of Mutant Line lo22048

A method for screening *Arabidopsis* seed density was developed based on Focks and Benning (1998) with significant modifications. *Arabidopsis* seeds can be separated according to their density. Density layers were prepared by a mixture of 1,6 dibromohexane (d=1.6), 1-bromohexane (d=1.17) and mineral oil (d=0.84) at different ratios. From the bottom to the top of the tube, 6 layers of organic solvents each comprised of 2 mL were added sequentially. The ratios of 1,6 dibromohexane:1-bromohexane:mineral oil for each layer were 1:1:0, 1:2:0, 0:1:0, 0:5:1, 0:3:1, 0:0:1. About 600 mg of T3 seed of a given pool of 96 activation-tagged lines corresponding to about 30,000 seeds were loaded on to the surface layer of a 15 ml glass tube containing said step gradient. After centrifugation for 5 min at 2000×g, seeds were separated according to their density. The seeds in the lower two layers of the step gradient and from the bottom of the tube were collected. Organic solvents were removed by sequential washing with 100% and 80% ethanol and seeds were sterilized using a solution of 5% hypochloride (NaOCl) in water. Seed were rinsed in sterile water and plated on MS-1 media comprised of 0.5×MS salts, 1% (W/V) sucrose, 0.05 MES/KOH (pH 5.8), 200 µg/mL, 10 g/L agar and 15 mg $L^{-1}$ glufosinate ammonium (Basta; Sigma Aldrich, USA). A total of 520 T3 pools each derived from 96 T2 activation-tagged lines were screened in this manner. Seed pool 500 when subjected to density gradient centrifugation as described above produced about 20 seed with increased density. These seed were sterilized and plated on selective media containing Basta. Basta-resistant seedlings were transferred to soil and plants were grown in a controlled environment (22° C., 16 h light/8 h dark, 100-200 µE $m^{-2}s^{-1}$) to maturity for about 8-10 weeks alongside three untransformed wild type plants of the Columbia ecotype. Oil content of T4 seed and control seed was measured by NMR as follows.

NMR Based Analysis of Seed Oil Content:

Seed oil content was determined using a Maran Ultra NMR analyzer (Resonance Instruments Ltd, Whitney, Oxfordshire, UK). Samples (e.g., batches of *Arabidopsis* seed ranging in weight between 5 and 200 mg) were placed into pre-weighed 2 mL polypropylene tubes (Corning Inc, Corning N.Y., USA; Part no. 430917) previously labeled with unique bar code identifiers. Samples were then placed into 96 place carriers and processed through the following series of steps by an ADEPT COBRA 600™ M SCARA robotic system:
1. pick up tube (the robotic arm was fitted with a vacuum pickup devise);
2. read bar code;
3. expose tube to antistatic device (ensured that *Arabidopsis* seed were not adhering to the tube walls);
4. weigh tube (containing the sample), to 0.0001 g precision;
5. take NMR reading; measured as the intensity of the proton spin echo 1 msec after a 22.95 MHz signal had been applied to the sample (data was collected for 32 NMR scans per sample);
6. return tube to rack; and
7. repeat process with next tube.

Bar codes, tubes weights and NMR readings were recorded by a computer connected to the system. Sample weight was determined by subtracting the polypropylene tube weight from the weight of the tube containing the sample.

Seed oil content of soybeans seed or soybean somatic embryos was calculated as follows:

$$\% \text{ oil (\% wt basis)} = \frac{(NMR \text{ signal/sample wt (g)}) - 70.58}{351.45}$$

Calibration parameters were determined by precisely weighing samples of soy oil (ranging from 0.0050 to 0.0700 g at approximately 0.0050 g intervals; weighed to a precision of 0.0001 g) into Corning tubes (see above) and subjecting them to NMR analysis. A calibration curve of oil content (% seed wt basis; assuming a standard seed weight of 0.1500 g) to NMR value was established.

The relationship between seed oil contents measured by NMR and absolute oil contents measured by classical analytical chemistry methods was determined as follows. Fifty soybean seed, chosen to have a range of oil contents, were dried at 40° C. in a forced air oven for 48 h. Individual seeds were subjected to NMR analysis, as described above, and were then ground to a fine powder in a GenoGrinder (SPEX Centriprep (Metuchen, N.J., U.S.A.); 1500 oscillations per minute, for 1 minute). Aliquots of between 70 and 100 mg were weighed (to 0.0001 g precision) into 13×100 mm glass tubes fitted with Teflon® lined screw caps; the remainder of the powder from each bean was used to determine moisture content, by weight difference after 18 h in a forced air oven at 105° C. Heptane (3 mL) was added to the powders in the tubes and after vortex mixing samples were extracted, on an end-over-end agitator, for 1 h at room temperature. The extracts were centrifuged, 1500×g for 10 min, the supernatant decanted into a clean tube and the pellets were extracted two more times (1 h each) with 1 mL heptane. The supernatants from the three extractions were combined and 50 µL internal standard (triheptadecanoic acid; 10 mg mL toluene) was added prior to evaporation to dryness at room temperature under a stream of nitrogen gas; standards containing 0, 0.0050, 0.0100, 0.0150, 0.0200 and 0.0300 g soybean oil, in 5 mL heptane, were prepared in the same manner. Fats were converted to fatty acid methyl esters (FAMEs) by adding 1 mL 5% sulfuric acid (v:v. in anhydrous methanol) to the dried pellets and heating them at 80° C. for 30 min, with occasional vortex mixing. The samples were allowed to cool to room temperature and 1 mL 25% aqueous sodium chloride was added followed by 0.8 mL heptane. After vortex mixing the phases were allowed to separate and the upper organic phase was transferred to a sample vial and subjected to GC analysis.

Plotting NMR determined oil contents versus GC determined oil contents resulted in a linear relationship between 9.66 and 26.27% oil (GC values; % seed wt basis) with a slope of 1.0225 and an $R^2$ of 0.9744; based on a seed moisture content that averaged 2.6+/−0.8%.

Seed oil content (on a % seed weight basis) of *Arabidopsis* seed was calculated as follows:

mg oil=(*NMR* signal−2.1112)/37.514;

% oil [(mg oil)/1000]/[g of seed sample weight]×100.

Prior to establishing this formula, *Arabidopsis* seed oil was extracted as follows. Approximately 5 g of mature *Arabidopsis* seed (cv Columbia) were ground to a fine powder using a mortar and pestle. The powder was placed into a 33×94 mm paper thimble (Ahlstrom #7100-3394; Ahlstrom, Mount Holly Springs, Pa., USA) and the oil extracted during approximately 40 extraction cycles with petroleum ether (BP 39.9-51.7° C.) in a Soxhlet apparatus. The extract was allowed to cool and the crude oil was recovered by removing the solvent under vacuum in a rotary evaporator. Calibration parameters were determined by precisely weighing 11 standard samples of partially purified *Arabidopsis* oil (samples contained 3.6, 6.3, 7.9, 9.6, 12, 8, 16.3, 20.3, 28.2, 32.1, 39.9 and 60 mg of partially purified *Arabidopsis* oil) weighed to a precision of 0.0001 g) into 2 mL polypropylene tubes (Corning Inc, Corning N.Y., USA; Part no. 430917) and subjecting them to NMR analysis. A calibration curve of oil content (% seed weight basis) to NMR value was established.

Table 4 shows that the seed oil content of T4 activation-tagged line with Bar code ID K22048 is only 90% of that of WT control plants (pooled seed of six WT plants) grown in the same flat.

TABLE 4

Oil Content of T4 activation-tagged lines derived from T3 pool 500

| BARCODE | % Oil | T3 pool ID # | oil content % of WT |
|---|---|---|---|
| K22048 | 33.6 | 500 | 90 |
| K22049 | 41.6 | 500 | 111.3 |
| K22050 | 38.7 | 500 | 103.5 |
| K22051 | 41 | 500 | 109.8 |
| K22052 | 38.7 | 500 | 103.5 |
| K22053 | 41 | 500 | 109.6 |
| K22054 | 38.8 | 500 | 103.8 |
| K22055 | 41.7 | 500 | 111.5 |
| K22056 | 40 | 500 | 107 |
| K22057 | 39.8 | 500 | 106.4 |
| K22058 | 39.4 | 500 | 105.4 |
| K22059 | 34.4 | 500 | 92.1 |
| K22060 | 39.8 | 500 | 106.4 |
| K22061 | 37.6 | 500 | 100.6 |
| K22062 | 40.4 | 500 | 108.1 |
| K22063 | 37.9 | 500 | 101.3 |
| K22064 | 39.8 | 500 | 106.4 |
| K22065 | 41 | 500 | 109.7 |
| K22066 | 41.2 | 500 | 110.2 |
| K22067 | 39.7 | 500 | 106.3 |
| K22068 | 37.7 | 500 | 100.8 |
| K22069 | 36.4 | 500 | 97.4 |
| K22070 | 38.1 | 500 | 102 |
| K22071 | 40.9 | 500 | 109.3 |
| K22072 | 41.3 | 500 | 110.4 |
| K22073 | 40.1 | 500 | 107.4 |
| K22074 | 35.7 | 500 | 95.6 |
| K22075 | 39.3 | 500 | 105.2 |
| K22076 | 38.4 | 500 | 102.8 |
| wt | 37.4 | | |

K22048 was renamed lo22048. T4 seed were plated on selective media and a total of 10 glufosinate-resistant seedlings were planted in the same flat as four untransformed WT plants.

TABLE 5

Oil Content of T5 activation-tagged line lo22048

| BARCODE | % Oil | Average % oil | T5 activation-tagged line ID | oil content % of WT | Average oil content % of WT |
|---|---|---|---|---|---|
| | 37.3 | | lo22048 | 103.5 | |
| | 35.6 | | lo22048 | 98.9 | |
| | 34.5 | | lo22048 | 96.0 | |
| | 34.5 | | lo22048 | 95.8 | |
| | 34.4 | | lo22048 | 95.6 | |
| | 34.4 | | lo22048 | 95.5 | |
| | 33.8 | | lo22048 | 93.8 | |
| | 33.5 | | lo22048 | 93.1 | |
| | 33.4 | | lo22048 | 92.7 | |
| | 32.8 | 34.4 | lo22048 | 91.1 | 95.6 |
| | 37.1 | | WT | | |
| | 36.7 | | WT | | |
| | 35.9 | | WT | | |
| | 35.8 | | WT | | |
| | 34.6 | 36 | WT | | |

Table 5 shows that the seed oil content of T5 activation-tagged line lo22048 is between 91.1 and 103.5% of that of WT control plants grown in the same flat. The average oil content of all T5 lines of lo22048 was 95.6% of the WT control plants. When plated on Basta-containing media all 10 T5 seed selections shown in Table 5 produced about 25% of herbicide sensitive seedlings and 25% of non-germinating seed. Applicants conclude that despite repeated selection on Basta containing media no lines homozygous for the lo22048-specific transgene could be recovered. It is believed that a gene that is important for development of viable seed was disrupted by the transgene insertion in lo22048. Twenty-four Basta-resistant T5 seedling of lo22048 were planted in the same flat alongside 12 untransformed WT control plants of the Columbia ecotype. Plants were grown to maturity and seed was bulk harvested from all 24 lo22048 and 12 WT plants. Oil content of lo22048 and WT seed was measured by NMR (Table 6).

TABLE 6

Oil Content of T6 activation-tagged line lo22048

| Barcode | % Oil | Seed ID | oil content % of WT |
|---|---|---|---|
| K35910 | 40.1 | lo22048 | 90.7 |
| K35911 | 44.2 | WT | |

T6 seed of lo22048 and WT seed produced under identical conditions were subjected to compositional analysis as described below. Seed weight was measured by determining the weight of 100 seed. This analysis was performed in triplicate.

Tissue Preparation:

*Arabidopsis* seed (approximately 0.5 g in a ½×2" polycarbonate vial) was ground to a homogeneous paste in a GENO-GRINDER® (3×30 sec at 1400 strokes per minute, with a 15 sec interval between each round of agitation). After the second round of agitation the vials were removed and the *Arabidopsis* paste was scraped from the walls with a spatula prior to the last burst of agitation.

Determination of Protein Content:

Protein contents were estimated by combustion analysis on a Thermo FINNIGAN™ Flash 1112EA combustion analyzer running in the NCS mode (vanadium pentoxide was omitted) according to instructions of the manufacturer. Triplicate samples of the ground pastes, 4-8 mg, weighed to an accuracy of 0.001 mg on a METTLER-TOLEDO® MX5 micro balance, were used for analysis. Protein contents were calculated by multiplying % N, determined by the analyzer, by 6.25. Final protein contents were expressed on a % tissue weight basis.

Determination of Non-Structural Carbohydrate Content:

Sub-samples of the ground paste were weighed (to an accuracy of 0.1 mg) into 13×100 mm glass tubes; the tubes had TEFLON® lined screw-cap closures. Three replicates were prepared for each sample tested.

Lipid extraction was performed by adding 2 ml aliquots of heptane to each tube. The tubes were vortex mixed and placed into an ultrasonic bath (VWR Scientific Model 750D) filled with water heated to 60° C. The samples were sonicated at full-power (~360 W) for 15 min and were then centrifuged (5 min×1700 g). The supernatants were transferred to clean 13×100 mm glass tubes and the pellets were extracted 2 more times with heptane (2 ml, second extraction; 1 ml third extraction) with the supernatants from each extraction being pooled. After lipid extraction 1 ml acetone was added to the pellets and after vortex mixing, to fully disperse the material, they were taken to dryness in a Speedvac.

Non-Structural Carbohydrate Extraction and Analysis:

Two ml of 80% ethanol was added to the dried pellets from above. The samples were thoroughly vortex mixed until the plant material was fully dispersed in the solvent prior to sonication at 60° C. for 15 min. After centrifugation, 5 min× 1700 g, the supernatants were decanted into clean 13×100 mm glass tubes. Two more extractions with 80% ethanol were performed and the supernatants from each were pooled. The extracted pellets were suspended in acetone and dried (as above). An internal standard β-phenyl glucopyranoside (100 µl of a 0.5000+/−0.0010 g/100 ml stock) was added to each extract prior to drying in a Speedvac. The extracts were maintained in a desiccator until further analysis.

The acetone dried powders from above were suspended in 0.9 ml MOPS (3-N[Morpholino]propane-sulfonic acid; 50 mM, 5 mM $CaCl_2$, pH 7.0) buffer containing 100 U of heat-stable α-amylase (from *Bacillus licheniformis*; Sigma A-4551). Samples were placed in a heat block (90° C.) for 75 min and were vortex mixed every 15 min. Samples were then allowed to cool to room temperature and 0.6 ml acetate buffer (285 mM, pH 4.5) containing 5 U amyloglucosidase (Roche 110 202 367 001) was added to each. Samples were incubated for 15-18 h at 55° C. in a water bath fitted with a reciprocating shaker; standards of soluble potato starch (Sigma S-2630) were included to ensure that starch digestion went to completion.

Post-digestion the released carbohydrates were extracted prior to analysis. Absolute ethanol (6 ml) was added to each tube and after vortex mixing the samples were sonicated for 15 min at 60° C. Samples were centrifuged (5 min×1700 g) and the supernatants were decanted into clean 13×100 mm glass tubes. The pellets were extracted 2 more times with 3 ml of 80% ethanol and the resulting supernatants were pooled. Internal standard (100 µl β-phenyl glucopyranoside, as above) was added to each sample prior to drying in a Speedvac.

Sample Preparation and Analysis:

The dried samples from the soluble and starch extractions described above were solubilized in anhydrous pyridine (Sigma-Aldrich P57506) containing 30 mg/ml of hydroxylamine HCl (Sigma-Aldrich 159417). Samples were placed on an orbital shaker (300 rpm) overnight and were then heated for 1 hr (75° C.) with vigorous vortex mixing applied every 15 min. After cooling to room temperature. 1 ml hexamethyldisilazane (Sigma-Aldrich H-4875) and 100 µl trifluoroacetic acid (Sigma-Aldrich T-6508) were added. The samples were vortex mixed and the precipitates were allowed to settle prior to transferring the supernatants to GC sample vials.

Samples were analyzed on an Agilent 6890 gas chromatograph fitted with a DB-17MS capillary column (15 m×0.32 mm×0.25 um film). Inlet and detector temperatures were both 275° C. After injection (2 µl, 20:1 split) the initial column temperature (150° C.) was increased to 180° C. at a rate of 3° C./min and then at 25° C./min to a final temperature of 320° C. The final temperature was maintained for 10 min. The carrier gas was $H_2$ at a linear velocity of 51 cm/sec. Detection was by flame ionization. Data analysis was performed using Agilent ChemStation software. Each sugar was quantified relative to the internal standard and detector responses were applied for each individual carbohydrate (calculated from standards run with each set of samples). Final carbohydrate concentrations were expressed on a tissue weight basis.

Carbohydrates were identified by retention time matching with authentic samples of each sugar run in the same chromatographic set and by GC-MS with spectral matching to the NIST Mass Spectral Library Version 2a, build Jul. 1, 2002.

TABLE 7

Composition Analysis of lo22048 and WT Control Seed

| Genotype | Bar code ID | Oil (%, NMR) | Protein % | Seed Weight (µg) | fructose (µg $mg^{-1}$ seed) |
|---|---|---|---|---|---|
| lo22048 | K35910 | 40.1 | 16.3 | 26.0 | 0.65 |
| WT | K35911 | 44.2 | 15.22 | 23.7 | 0.59 |
|  | Δ TG/WT % | −9.2 | +7.1 | +10 | +10.1 |

| Genotype | Bar code ID | glucose (µg $mg^{-1}$ seed) | sucrose (µg $mg^{-1}$ seed) | raffinose (µg $mg^{-1}$ seed) | stachyose (µg $mg^{-1}$ seed) |
|---|---|---|---|---|---|
| lo22048 | K35910 | 9.17 | 28.13 | 0.16 | 3.3 |
| WT | K35911 | 7.45 | 26.25 | 0.52 | 2.9 |
|  | ΔTG/WT % | +23.1 | +7.1 | +17.3 | +13.8 |

The oil decrease in seed oil content of lo22048 is associated with an increase in seed weight and protein. The soluble carbohydrate profile of lo22048 differs from that of WT seed. The former shows increase in soluble carbohydrates including fructose, glucose, raffinose and stachyose. Herbicide-resistant seedlings were grown in soil. Pollen of lo22048 plant was used to fertilize emasculated immature flowers of WT plants. F1 seed were germinated on selective media, transferred to soil and 10 herbicide-resistant F1 plants were grown alongside four WT plants and four lo22048 parent plants in the same flat. Parent seed were bulk harvested. F2 seed of lo22048 were harvested from individual plants. Table 8 shows that 8 out of 10 $F_1$ plants produced seed with an oil content that was lower than that of WT seed grown in the same flat. The average decrease in seed oil content (compared to WT) of all F1 plants was 92.4% which is very close to 94.2% which was observed for the lo22048 parent.

TABLE 8

Seed oil content of F1 plants derived from a cross of lo22048 to WT plants of ecotype Columbia

| genotype | BARCODE | % oil | oil content % of wt | avg. oil content % of WT |
|---|---|---|---|---|
| lo22048xCOL F$_1$ | K41190 | 41.9 | 105.3 | |
| | K41188 | 39.8 | 100.0 | |
| | K41187 | 37.8 | 95.1 | |
| | K41195 | 37.7 | 94.8 | |
| | K41186 | 37.1 | 93.2 | |
| | K41189 | 36.8 | 92.6 | |
| | K41191 | 35.3 | 88.8 | |
| | K41192 | 35.3 | 88.7 | |
| | K41194 | 33.1 | 83.3 | |
| | K41193 | 32.9 | 82.7 | 92.4 |
| lo22048 | K41196 | 37.5 | 94.3 | |
| wt | K41197 | 39.8 | | |

In summary the lo22048 contains a single genetic locus that confers glufosinate herbicide resistance. Presence of this transgene is associated with a dominant low oil trait (reduction in oil content of 5-10% compared to WT) that is accompanied by increased seed size, protein content and increased levels of soluble carbohydrate in mature dry seed.

Example 3

Identification of Activation-Tagged Genes

Genes flanking the T-DNA insert in the lo22048 lines were identified using one, or both, of the following two standard procedures: (1) thermal asymmetric interlaced (TAIL) PCR (Liu et al., Plant J. 8:457-63 (1995)); and (2) SAIFF PCR (Siebert et al., Nucleic Acids Res. 23:1087-1088 (1995)). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and Arabidopsis genomic sequence. Once a tag of genomic sequence flanking a T-DNA insert is obtained, candidate genes are identified by alignment to publicly available Arabidopsis genome sequence. Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged Genes in lo22048 Construction of pKR1478 for Seed Specific Overexpression of Genes in Arabidopsis Plasmid pKR85 (SEQ ID NO:3; described in US Patent Application Publication US 2007/0118929 published on May 24, 2007) was digested with HindIII and the fragment containing the hygromycin selectable marker was re-ligated together to produce pKR278 (SEQ ID NO:4).

Plasmid pKR407 (SEQ ID NO:5; described in PCT Int. Appl. WO 2008/124048 published on Oct. 16, 2008) was digested with BamHI/HindIII and the fragment containing the Gy1 promoter/NotI/LegA2 terminator cassette was effectively cloned into the BamHI/HindIII fragment of pKR278 (SEQ ID NO:4) to produce pKR1468 (SEC) ID NO:6).

Plasmid pKR1468 (SEQ ID NO:6) was digested with NotI and the resulting DNA ends were filled using Klenow. After filling to form blunt ends, the DNA fragments were treated with calf intestinal alkaline phosphatase and separated using agarose gel electrophoresis. The purified fragment was ligated with cassette frmA containing a chloramphenicol resistance and ccdB genes flanked by attR1 and attR2 sites, using the Gateway® Vector Conversion System (Cat. No. 11823-029, Invitrogen Corporation) following the manufacturer's protocol to pKR1475 (SEQ ID NO:7).

Plasmid pKR1475 (SEQ ID NO:7) was digested with AscI and the fragment containing the Gy1 promoter/NotI/LegA2 terminator Gateway® L/R cloning cassette was cloned into the AscI fragment of binary vector pKR92 (SEQ ID NO:8; described in US Patent Application Publication US 2007/0118929 published on May 24, 2007) to produce pKR1478 (SEQ ID NO:9).

In this way, genes flanked by attL1 and attL2 sites could be cloned into pKR1478 (SEQ ID NO:9) using Gateway® technology (Invitrogen Corporation) and the gene could be expressed in Arabidopsis from the strong, seed-specific soybean Gy1 promoter in soy.

The activation tagged-line (lo22048) showing reduced oil content was further analyzed. DNA from the line was extracted, and genes flanking the T-DNA insert in the mutant line were identified using ligation-mediated PCR (Siebert et al., Nucleic Acids Res. 23:1087-1088 (1995)). A single amplified fragment was identified that contained a T-DNA border sequence and Arabidopsis genomic sequence. The sequence of this PCR product which contains part of the left border of the inserted T-DNA is set forth as SEQ ID NO:10. Once a tag of genomic sequence flanking a T-DNA insert was obtained, a candidate gene was identified by alignment to the completed Arabidopsis genome. Specifically, the SAIFF PCR product generated with PCR primers corresponding to the left border sequence of the T-DNA present in pHSbarENDs2 aligns with nucleotides 1347-1543 of the Arabidopsis gene At4g10760. lo22048 carries a T-DNA insertion in the first intron of At4g10760 which very likely disrupts the function of this gene. Disruption of this gene is known to result in an embryo defective phenotype characterized by developmental arrest at the globular stage. (Zhong S. et al Plant Cell (2008), 20, 1278-1288). Because of the location of the T-DNA in lo22048 we conclude that like the emb1706 alleles of At4g10760 the lo22048-T DNA insertion allele of At4g10760 encodes a non-functional product of said gene which leads to embryo lethality. The low seed oil phenotype of herbicide resistant F1 plants that are heterozygous for the lo22048 transgene suggests that the disruption of At4g10760 is not related to the low seed oil phenotype of lo22048.

Validation of Candidate Arabidopsis Gene (At4g10750) via Transformation into Arabidopsis The gene At4g10750, specifically its inferred start codon is 3.25 kb upstream of the SAIFF sequence corresponding to sequence adjacent to the left T-DNA border in lo22048. This gene is annotated as encoding a possibly plastidic, soluble protein with similarity to bacterial 2,4-dihydroxy-hept-2-ene-1,7-dioic acid and is subsequently called HpaI-like (HpaIL).

Primers HpaILORF FWD (SEQ ID NO:11) and HpaIL ORF REV (SEQ ID NO:12) were used to amplify the At4g10750 ORF from genomic DNA of *Arabidopsis* plants of the Columbia ecotyope. The PCR product was cloned into pENTR (Invitrogen, USA) to give pENTR-HpaIL (SEQ ID NO:13). The HpaIL ORF was inserted in the sense orientation downstream of the GY1 promoter in binary plant transformation vector pKR1478 using GATEWAY® LR recombinase (Invitrogen, USA) using manufacturer instructions. The sequence of the resulting plasmid pKR1478-HpaIL is set forth as SEQ ID NO:14.

pKR1478-HpaIL (SEQ ID NO:14) was introduced into *Agrobacterium tumefaciens* NTL4 (Luo et al, *Molecular Plant-Microbe Interactions* (2001) 14(1):98-103) by electroporation. Briefly, 1 µg plasmid DNA was mixed with 100 µL of electro-competent cells on ice. The cell suspension was transferred to a 100 µL electroporation cuvette (1 mm gap width) and electroporated using a BIORAD electroporator set to 1 kV, 400Ω and 25 µF. Cells were transferred to 1 mL LB medium and incubated for 2 h at 30° C. Cells were plated onto LB medium containing 50 µg/mL kanamycin. Plates were incubated at 30° C. for 60 h. Recombinant *Agrobacterium* cultures (500 mL LB, 50 µg/mL kanamycin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 cm² pot in METRO-MIX® 360 soil mixture for 4 weeks (22° C., 16 h light/8 h dark, 100 µE m$^{-2}$s$^{-1}$). Plants were repeatedly dipped into the *Agrobacterium* suspension harboring the binary vector pKR1478-HpaIL and kept in a dark, high humidity environment for 24 h. Post dipping, plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20× 20 cm) containing 150 mL of sterile plant growth medium comprised of 0.5×MS salts, 0.53% (W/V) sorbitol, 0.05 MES/KOH (pH 5.8), 200 µg/mL TIMENTIN®, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. T1 Plants are grown to maturity alongside wt control plants and T2 seeds are harvested.

Example 5

Seed-Specific RNAi of A 4q10750, Generation and Phenotypic Characterization of Transgenic Lines A binary plant transformation vector pKR1482 (SEQ ID NO:15) for generation of hairpin constructs facilitating seed-specific RNAi was constructed. The RNAi related expression cassette that can be used for cloning of a given DNA fragment flanked by ATTL sites in sense and antisense orientation downstream of the GY1 promoter (see Example 4). The two gene fragments are interrupted by a sliceable intron sequence derived from the *Arabidopsis* gene At2g38080.

An intron of an *Arabidopsis* laccase gene (At2g38080) was amplified from genomic *Arabidopsis* DNA of ecotype Columbia using primers AthLcc IN FWD (SEQ ID NO:16) and AthLcc IN REV (SEQ ID NO:17). PCR products were cloned into pGEM T EASY (Promega, USA) according to manufacturer instructions and sequenced. The DNA sequence of the PCR product containing the laccase intron is set forth as SEQ ID NO:18. The PCR primers introduce an HpaI restriction site at the 5' end of the intron and restriction sites for NruI and SpeI at the 3 end of the intron. A three-way ligation of DNA fragments was performed as follows. XbaI digested, dephosphorylated DNA of pMBL18 (Nakano, Yoshio: Yoshida, Yasuo; Yamashita, Yoshihisa; Koga, Toshihiko. Construction of a series of pACYC-derived plasmid vectors. Gene (1995), 162(1), 157-8.) was ligated to the XbaI, EcoRV DNA fragment of PSM1318 (SEQ ID NO:19) containing ATTR12 sites a DNA Gyrase inhibitor gene (ccdB), a chloramphenicol acetyltransferase gene, an HpaI/SpeI restriction fragment excised from pGEM T EASY Lacc INT (SEQ ID NO:18) containing intron 1 of At2g38080. Ligation products were transformed into the DB 3.1 strain of *E. coli* (Invitrogen, USA). Recombinant clones were characterized by restriction digests and sequenced. The DNA sequence of the resulting plasmid pMBL18 ATTR12 INT is set forth as SEQ ID NO:20. DNA of pMBL18 ATTR12 INT was linearized with NruI, dephosphorylated and ligated to the XbaI, EcoRV DNA fragment of PSM1789 (SEQ ID NO: 21) containing ATTR12 sites and a DNA Gyrase inhibitor gene (ccdB). Prior to ligation ends of the PSM1789 restriction fragment had been filled in with T4 DNA polymerase (Promega, USA). Ligation products were transformed into the DB 31 strain of *E. coli*/(Invitrogen, USA). Recombinant clones were characterized by restriction digests and sequenced. The DNA sequence of the resulting plasmid pMBL18 ATTR12 INT ATTR21 is set forth as SEQ ID NO:22.

Plasmid pMBL18 ATTR12 INT ATTR21 (SEQ ID NO:22) was digested with XbaI and after filling to blunt the XbaI site generated, the resulting DNA was digested with Ecl136II and the fragment containing the attR cassettes was cloned into the NotI/BsiWI (where the NotI site was completely filled in) fragment of pKR1468 (SEQ ID NO:6), containing the Gy1 promoter, to produce pKR1480 (SEQ ID NO:23).

pKR1480 (SEQ ID NO:23) was digested with AscI and the fragment containing the Gy1 promoter/attR cassettes was cloned into the AscI fragment of binary vector pKR92 (SEQ ID NO:8) to produce pKR1482 (SEQ ID NO:15).

Primers HpaIL UTR FWD (SEQ ID NO:24) and HpaIL UTR REV (SEQ ID NO:25) were used to amplify the At4g10750 3'UTR from applicants cDNA library of developing *Arabidopsis* seeds of the *erecta* mutant of the Landsberg ecotype. The PCR product was cloned into pENTR (Invitrogen, USA) to give pENTR-HpaIL 3'UTR (SEQ ID NO:26).

5 µg of plasmid DNA of pENTR-HpaIL1 3'UTR (SEQ ID NO:26) was digested with EcoRV/HpaI. A restriction fragment of 528 bp (derived from pENTR-HpaIL1 3'UTR) was excised from an agarose gel. Purified gene fragments of the 3'UTR sequence were inserted into vector pKR1482 using LR clonase (Invitrogen) according to the manufacturers instructions, to give pKR1482HpaIL 3'UTR (SEQ ID NO:27)

pKR1482HpaIL 3'UTR (SEQ ID NO:27) was introduced into *Agrobacterium tumefaciens* NTL4 (Luo et al, *Molecular*

Plant-Microbe Interactions (2001) 14(1):98-103) by electroporation. Briefly, 1 μg plasmid DNA was mixed with 100 μL of electro-competent cells on ice. The cell suspension was transferred to a 100 μL electroporation cuvette (1 mm gap width) and electroporated using a BIORAD electroporator set to 1 kV, 400Ω and 25 μF. Cells were transferred to 1 mL LB medium and incubated for 2 h at 30° C. Cells were plated onto LB medium containing 50 μg/mL kanamycin. Plates were incubated at 30° C. for 60 h. Recombinant *Agrobacterium* cultures (500 mL LB, 50 μg/mL kanamycin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 cm² pot in METRO-MIX® 360 soil mixture for 4 weeks (22° C., 16 h light/8 h dark, 100 μE m$^{-2}$s$^{-1}$). Plants were repeatedly dipped into the *Agrobacterium* suspension harboring the binary vector pKR1482HpaIL 3'UTR (SEQ ID NO:27) and kept in a dark, high humidity environment for 24 h. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20× 20 cm) containing 150 mL of sterile plant growth medium comprised of 0.5×MS salts, 0.53% (W/V) sorbitol, 0.05 MES/KOH (pH 5.8), 200 μg/mL TIMENTIN®, and 50 μg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. Plants were grown to maturity and T2 seeds were harvested. A total of 16 events were generated with pKR1482HpaIL. Four wild-type (WT) control plants were grown in the same flat. WT seeds were bulk harvested and T2 seeds of individual transgenic lines were harvested and oil content was measured by NMR as described above.

TABLE 10

Seed oil content of T1 plants generated with binary vector pKR1482-HpaIL 3'UTR for seed specific gene suppression of At4g10750

| Construct | BARCODE | % oil | oil content % of WT | avg. oil content % of WT |
|---|---|---|---|---|
| pKR1482 HpaIL 3'UTR | K14724 | 42.2 | 107.4 | |
| | K14729 | 41.6 | 106.0 | |
| | K14734 | 41.6 | 105.9 | |
| | K14733 | 41.6 | 105.9 | |
| | K14719 | 41.4 | 105.5 | |
| | K14732 | 41.4 | 105.4 | |
| | K14727 | 41.4 | 105.4 | |
| | K14721 | 41.0 | 104.4 | |
| | K14730 | 40.5 | 103.2 | |
| | K14728 | 40.4 | 102.9 | |
| | K14725 | 40.4 | 102.7 | |
| | K14723 | 38.1 | 97.0 | |
| | K14731 | 38.1 | 97.0 | |
| | K14720 | 38.0 | 96.7 | |
| | K14726 | 37.3 | 94.9 | |
| | K14735 | 35.3 | 89.9 | 101.9 |
| wt | K14736 | 39.6 | | |
| | K14737 | 39.0 | | |

Table 10 shows that seed-specific down regulation of At4g10750 leads to increased oil content in *Arabidopsis* seed.

T2 seed of events K14733 and K14734 that both carry transgenes pKR1482 HpaIL 3'UTR were plated on plant growth media containing kanamycin. For event K14733 and K14734 21 and 23 kanamycin-resistant T2 seedlings, respectively, were grown to maturity alongside WT plants of the Columbia ecotype grown in the same flats. Oil content of T3 seed is depicted in Table 11. Table 11 demonstrates that the oil increase associated with seed-specific down regulation of At4g10750 is heritable.

TABLE 11

Seed oil content of T2 plants generated with binary vectors pKR1482-HpaIL 3'UTR for seed specific gene suppression of At4g10750

| Construct | Event | T2 plant # | % oil | Oil content % of wt | Avg. oil content % of wt |
|---|---|---|---|---|---|
| pKR1482 HpaIL 3'UTR | K14733 | 1 | 44.6 | 109.0 | |
| | | 2 | 44.3 | 108.2 | |
| | | 3 | 44.2 | 107.8 | |
| | | 4 | 43.9 | 107.2 | |
| | | 5 | 43.4 | 105.9 | |
| | | 6 | 43.4 | 105.9 | |
| | | 7 | 43.3 | 105.8 | |
| | | 8 | 42.2 | 103.1 | |
| | | 9 | 42.1 | 102.8 | |
| | | 10 | 42.0 | 102.5 | |
| | | 11 | 42.0 | 102.5 | |
| | | 12 | 41.9 | 102.4 | |
| | | 13 | 41.9 | 102.4 | |
| | | 14 | 41.9 | 102.3 | |
| | | 15 | 41.4 | 101.0 | |
| | | 16 | 41.2 | 100.5 | |
| | | 17 | 41.1 | 100.4 | |
| | | 18 | 40.9 | 99.8 | |
| | | 19 | 40.0 | 97.7 | |
| | | 20 | 39.9 | 97.4 | |
| | | 21 | 39.7 | 96.9 | 102.9 |
| Wt | | 1 | 42.8 | | |
| | | 2 | 42.6 | | |
| | | 3 | 42.4 | | |
| | | 4 | 42.3 | | |
| | | 5 | 41.9 | | |
| | | 6 | 41.6 | | |
| | | 7 | 41.3 | | |
| | | 8 | 40.9 | | |
| | | 9 | 40.3 | | |
| | | 10 | 39.8 | | |
| | | 11 | 38.2 | | |
| | | 12 | 37.4 | | |
| pKR1482 HpaIL 3'UTR | K14734 | 1 | 43.5 | | |
| | | 2 | 43.3 | 113.2 | |
| | | 3 | 43.2 | 112.7 | |
| | | 4 | 43.0 | 112.5 | |
| | | 5 | 42.9 | 111.9 | |
| | | 6 | 42.8 | 111.5 | |
| | | 7 | 42.8 | 111.4 | |

TABLE 11-continued

Seed oil content of T2 plants generated with binary vectors pKR1482-HpaIL 3'UTR for seed specific gene suppression of At4g10750

| Construct | Event | T2 plant # | % oil | Oil content % of wt | Avg. oil content % of wt |
|---|---|---|---|---|---|
| | | 8 | 42.7 | 111.3 | |
| | | 9 | 42.0 | 111.0 | |
| | | 10 | 41.7 | 109.2 | |
| | | 11 | 41.4 | 108.6 | |
| | | 12 | 41.2 | 107.6 | |
| | | 13 | 41.2 | 107.3 | |
| | | 14 | 40.7 | 107.2 | |
| | | 15 | 40.7 | 105.8 | |
| | | 16 | 40.7 | 105.8 | |
| | | 17 | 40.2 | 105.8 | |
| | | 18 | 39.9 | 104.7 | |
| | | 19 | 39.8 | 103.9 | |
| | | 20 | 38.9 | 103.4 | |
| | | 21 | 38.6 | 101.3 | |
| | | 22 | 37.4 | 100.5 | |
| | | 23 | 36.3 | 97.3 | 106.9 |
| Wt | | 1 | 39.9 | | |
| | | 2 | 39.8 | | |
| | | 3 | 39.6 | | |
| | | 4 | 39.3 | | |
| | | 5 | 39.2 | | |
| | | 6 | 38.8 | | |
| | | 7 | 38.2 | | |
| | | 8 | 37.6 | | |
| | | 9 | 37.4 | | |
| | | 10 | 36.7 | | |
| | | 11 | 36.5 | | |

Example 6

Identification of Genes of *Brassica napus* Closely-Related to At4g10750

Public DNA sequences (NCBI and *Brassica napus* EST assembly (N) *Brassica napus* EST assembly version 3.0 (Jul. 30, 2007) from the Gene Index Project at Dana-Farber Cancer Institute were searched using the predicted amino acid sequence of At4g10750 and tBLASTn. The assembly encompasses about 558465 public ESTs and has a total of 90310 sequences (47591 assemblies and 42719 singletons). There is one gene which shares 84.5% amino acid sequence identity to At4g10750. This genes, its % identity to At4g10750 and SEQ ID NOs are listed in Table 12.

TABLE 12

*Brassica napus* gene closely related to At4g10750

| Gene name | % AA sequence identity to At4g10750 | SEQ ID NO: NT | SEQ ID NO: AA |
|---|---|---|---|
| TC 25873 | 84.5 | 28 | 29 |

Example 7

Identification of Genes of Soybean (*Glycine max*) Closely-Related to At4g10750

Public DNA sequences (Soybean cDNAs Glyma1.01 (JGI) (N) Predicted cDNAs from Soybean JGI Glyma1.01 genomic sequence, FGENESH predictions, and EST PASA analysis.) were searched using the predicted amino acid sequence of At4g10750 and tBLASTn. There is one gene which shares 61.3% amino acid sequence identity At4g10750. This gene, its properties and SEQ ID NO is listed in Table 13

TABLE 13

Soybean gene closely related to At4g10750

| Gene name | % AA sequence identity to At4g10750 | SEQ ID NO: NT | SEQ ID NO: AA |
|---|---|---|---|
| Glyma09g21760 | 61.3 | 30 | 31 |

Example 8

Identification of Genes of Maize (*Zea mays*) Closely-Related to At4g10750

An assembly of proprietary and public maize EST DNA sequences (UniCorn 7.0 (N) Corn UniGene dataset, July 2007) was searched using the predicted amino acid sequence of At4g10750 and tBLASTn. There is one gene which shares 56.3% amino acid sequence identity to At4g10750, its properties and SEQ ID NOs are listed in Table 14

TABLE 14

Maize gene closely related to At4g10750

| Gene name | % AA sequence identity to At4g10750 | SEQ ID NO: NT | SEQ ID NO: AA |
|---|---|---|---|
| PCO651314 | 56.3 | 32 | 33 |

Example 9

Identification of Genes of Rice (*Oryza sativa*) Closely-Related to At4q10750

A public database of transcripts from rice gene models (*Oryza sativa* (japonica cultivar-group) MSU Rice Genome Annotation Project Osa1 release 6 (January 2009)) which includes untranslated regions (UTR) but no introns was searched using the predicted amino acid sequence of At4g10750 and IBLASTn. There is gene which share at least 56.4% amino acid sequence identity to At4g10750. This gene, its properties and SEQ ID NOs is listed in Table 15.

TABLE 15

Rice genes closely related to At4g10750

| Gene name | % AA sequence identity to At4g10750 | SEQ ID NO: NT | SEQ ID NO: AA |
|---|---|---|---|
| Os09g36030 | 56.4 | 34 | 35 |

Example 10

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668).

The embryos are kept in the dark at 27° C. Friable embryogenic callus consisting of undifferentiated masses of cells with somatic proembryoids and embryoids borne on suspensor structures proliferate from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a BIOLISTIC® PDS-1000/He particle delivery system (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi. Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 11

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5 and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872 can be cultured in the light or dark at 26° C. on an appropriate agar medium for 6-10 weeks. Somatic embryos which produce secondary embryos are then excised and placed into a suitable liquid medium.

After repeated selection for clusters of somatic embryos which multiplied as early, globular staged embryos, the suspensions are maintained as described below. Soybean embryogenic suspension cultures can be maintained in 35 mL of liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A BIOLISTIC® PDS1000/HE instrument particle delivery system (helium retrofit; Bio-Rad Instruments, Hercules Calif., developed by E.I. du Pont de Nemours and Company, Willington, Del.) can be used for these transformations.

A selectable marker gene which can be used to facilitate soybean transformation is a chimeric gene composed of the 353 promoter from Cauliflower Mosaic Virus (Odell et al. (1985) *Nature* 313:810-812), the hygroniycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene. To 50 μL of a 60 mg/mL 1 μm gold particle suspension is added (in order): 5 μL DNA (1 μg/μL), 20 μL spermidine (0.1 M), and 50 μL CaCl$_2$ (2.5M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk. Approximately 300400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 12

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis. For high level expression, a plasmid clone with the cDNA insert in the correct orientation relative to the 17 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 13

Transformation of Somatic Soybean Embryo Cultures

Generic Stable Soybean Transformation Protocol:
Soybean embryogenic suspension cultures are maintained in 35 ml liquid media (SB55 or SBP6) on a rotary shaker, 150 rpm, at 28° C. with mixed fluorescent and incandescent lights on a 16:8 h day/night schedule. Cultures are subcultured every four weeks by inoculating approximately 35 mg of tissue into 35 ml of liquid medium.

TABLE 17

Stock Solutions (g/L):

MS Sulfate 100X Stock

| | |
|---|---|
| $MgSO_4\ 7H_2O$ | 37.0 |
| $MnSO_4\ H_2O$ | 1.69 |
| $ZnSO_4\ 7H_2O$ | 0.86 |
| $CuSO_4\ 5H_2O$ | 0.0025 |

MS Halides 100X Stock

| | |
|---|---|
| $CaCl_2\ 2H_2O$ | 44.0 |
| KI | 0.083 |
| $CoCl_2\ 6H_2O$ | 0.00125 |
| $KH_2PO_4$ | 17.0 |
| $H_3BO_3$ | 0.62 |
| $Na_2MoO_4\ 2H_2O$ | 0.025 |

MS FeEDTA 100X Stock

| | |
|---|---|
| $Na_2EDTA$ | 3.724 |
| $FeSO_4\ 7H_2O$ | 2.784 |

B5 Vitamin Stock 10 g m-inositol
100 mg nicotinic acid
100 mg pyridoxine HCl
1 g thiamine SB55 (per Liter, pH 5.7)

10 ml each MS stocks
1 ml B5 Vitamin stock
0.8 g $NH_4NO_3$
3.033 g $KNO_3$
1 ml 2,4-D (10 mg/mL stock)
60 g sucrose
0.667 g asparagine
SBP6
same as SB55 except 0.5 ml 2,4-D
SB103 (per Liter, pH 5.7)

1X MS Salts
6% maltose
750 mg $MgCl_2$
0.2% Gelrite
SB71-1 (per Liter, pH 5.7)

1X B5 salts
1 ml B5 vitamin stock
3% sucrose
750 mg $MgCl_2$
0.2% Gelrite

Soybean embryogenic suspension cultures are transformed with plasmid DNA by the method of particle gun bombardment (Klein et al (1987) *Nature* 327:70). A DuPont Biolistic PDS1000/HE instrument (helium retrofit) is used for these transformations.

To 50 ml of a 60 mg/ml 1 μm gold particle suspension is added (in order); 5 μL DNA (1 μg/μl), 20 μl spermidine (0.1 M), and 50 μl $CaCl_2$ (2.5 M). The particle preparation is agitated for 3 min, spun in a microfuge for 10 sec and the supernatant removed. The DNA-coated particles are then washed once in 400 μl 70% ethanol and re suspended in 40 μl of anhydrous ethanol. The DNA/particle suspension is sonicated three times for 1 sec each. Five μl of the DNA-coated gold particles are then loaded on each macro carrier disk. For selection, a plasmid conferring resistance to hygromycin phosphotransferase (HPT) may be co-bombarded with the silencing construct of interest.

Approximately 300-400 mg of a four week old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1000 psi and the chamber is evacuated to a vacuum of 28 inches of mercury. The tissue is placed approximately 3.5 inches away from the retaining screen and bombarded three times. Following bombardment, the tissue is placed back into liquid and cultured as described above.

Eleven days post bombardment, the liquid media is exchanged with fresh SB55 containing 50 mg/ml hygromycin. The selective media is refreshed weekly. Seven weeks post bombardment, green, transformed tissue is observed growing from untransformed, necrotic embryogenic clusters. Isolated green tissue is removed and inoculated into individual flasks to generate new, clonally propagated, transformed embryogenic suspension cultures. Thus each new line is treated as an independent transformation event. These suspensions can then be maintained as suspensions of embryos maintained in an immature developmental stage or regenerated into whole plants by maturation and germination of individual somatic embryos.

Independent lines of transformed embryogenic clusters are removed from liquid culture and placed on a solid agar media (SB103) containing no hormones or antibiotics. Embryos are cultured for four weeks at 26° C. with mixed fluorescent and incandescent lights on a 16:8 h day/night schedule. During this period, individual embryos are removed from the clusters and screened for alterations in gene expression.

It should be noted that any detectable phenotype, resulting from the co-suppression of a target gene, can be screened at this stage. This would include, but not be limited to, alterations in oil content, protein content, carbohydrate content, growth rate, viability, or the ability to develop normally into a soybean plant.

Example 14

Plasmid DNAs for "Complementary Region" Co-Suppression

The plasmids in the following experiments are made using standard cloning methods well known to those skilled in the art (Sambrook et al (1989) *Molecular Cloning*, CSHL Press, New York). A starting plasmid pKS18HH (U.S. Pat. No. 5,846,784 the contents of which are hereby incorporated by reference) contains a hygromycin B phosphotransferase (HPT) obtained from *E. coli* strain W677 under the control of a T7 promoter and the 35S cauliflower mosaic virus promoter. Plasmid pKS18HH thus contains the T7 promoter/HPT/T7 terminator cassette for expression of the HPT enzyme in certain strains of *E. coli* such as NovaBlue(DE3) [from Novagen], that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restriction endonuclease sites suitable for the cloning other chimeric genes into this vector, Plasmid ZBL100 (PCT Application No. WO 00/11176 published on Mar. 2, 2000) is a derivative of pKS18HH with a reduced NOS 3' terminator. Plasmid pKS67 is a ZBL100 derivative with the insertion of a beta-conglycinin promoter, in front of a NotI cloning site, followed by a phaseolin 3' terminator (described in PCT Application No. WO 94/11516, published on May 26, 1994).

The 2.5 kb plasmid pKS17 contains pSP72 (obtained from Promega Biosystems) and the T7 promoter/HPT/T7 3' terminator region, and is the original vector into which the 3.2 kb BamHI-SalI fragment containing the 35S/HPT/NOS cassette was cloned to form pKS18HH. The plasmid pKS102 is a pKS17 derivative that is digested with XhoI and SalI, treated with mung-bean nuclease to generate blunt ends, and ligated to insert the following linker:

SEQ ID NO: 36
GGCGCGCCAAGCTTGGATCCGTCGACGGCGCGCC

The plasmid pKS83 has the 2.3 kb BamHI fragment of ML70 containing the Kti3 promoter/NotI/Kti3 3' terminator region (described in PCT Application No. WO 94/11516, published on May 26, 1994) ligated into the BamHI site of pKS17. Additional methods for suppression of endogenous genes are well known in the art and have been described in the detailed description of the instant invention and can be used to reduce the expression of endogenous plastidic HpaIL aldolase gene expression, protein or enzyme activity in a plant cell.

Example 15

Suppression by ELVISLIVES Complementary Region

Constructs can be made which have "synthetic complementary regions" (SCR). In this example the target sequence is placed between complementary sequences that are not known to be part of any biologically derived gene or genome (i.e. sequences that are "synthetic" or conjured up from the mind of the inventor). The target DNA would therefore be in the sense or antisense orientation and the complementary RNA would be unrelated to any known nucleic acid sequence. It is possible to design a standard "suppression vector" into which pieces of any target gene for suppression could be dropped. The plasmids pKS106, pKS124, and pKS133 (SEQ ID NO:37) exemplify this. One skilled in the art will appreciate that all of the plasmid vectors contain antibiotic selection genes such as, but not limited to, hygromycin phosphotransferase with promoters such as the T7 inducible promoter.

pKS106 uses the beta-conglycinin promoter while the pKS124 and pKS133 plasmids use the Kti promoter, both of these promoters exhibit strong tissue specific expression in the seeds of soybean. pKS106 uses a 3' termination region from the phaseolin gene, and pKS124 and pKS133 use a Kti 3' termination region. pKS106 and pKS124 have single copies of the 36 nucleotide EagI-ELVISLIVES (SEQ ID NO:148) sequence surrounding a NotI site (the amino acids given in parentheses are back-translated from the complementary strand):

The idea is that the single EL linker (SCR) can be duplicated to increase stem lengths in increments of approximately 40 nucleotides. A series of vectors will cover the SCR lengths between 40 bp and the 300 bp. Various target gene lengths can also be evaluated. It is believed that certain combinations of target lengths and complementary region lengths will give optimum suppression of the target, however, it is expected that the suppression phenomenon works well over a wide range of sizes and sequences. It is also believed that the lengths and ratios providing optimum suppression may vary somewhat given different target sequences and/or complementary regions.

The plasmid pKS106 is made by putting the EagI fragment (SEQ ID NO:39) of ELVISLIVES (SEQ ID NO:148) into the NotI site of pKS67. The ELVISLIVES fragment (SEQ ID NO:39) is made by PCR using two primers and no other DNA:

SEQ ID NO: 40
5'-
GAATTCCGGCCGGAGCTGGTCATCTCGCTCATCGTCGAGTCGGCGGCC

GCCGACTCGACGATGAGCGAGATGACCAGCTCCGGCCGGAATTC-3'

SEQ ID NO: 41
5'-GAATTCCGGCCGGAG-3'

The product of the PCR reaction is digested with EagI (5'-CGGCCG-3') and then liqated into NotI digested pKS67. The term "ELVISLIVES" (SEQ ID NO:148) and "EL" are used interchangeably herein.

Additional plasmids can be used to test this example and any synthetic sequence, or naturally occurring sequence, can be used in an analogous manner.

Example 16

Screening of Transgenic Lines for Alterations in Oil, Protein, Starch and Soluble Carbohydrate Content Transgenic lines can be selected from soybean transformed with a suppression plasmid, such as those described in Example 15 and Example 18. Transgenic lines can be screened for down regulation of plastidic HpaIL aldolase in

```
                                          SEQ ID NO: 38
EagI E L V I S L I V E S (SEQ ID NO: 148)NotI
CGGCCG GAG CTG GTC ATC TCG CTC ATC GTC GAG TCG GCGGCCGC (S) (E) (V) (I) (L) (S) (I) (V) (L) (E)(SEQ ID NO: 149)EagI
CGA CTC GAC GAT GAG CGA GAT GAC CAG CTC CGGCCG
```

CGA CTC GAC GAT GAG CGA GAT GAC CAG CTC CGGCCG pKS133 has 2x copies of ELVISLIVES (SEQ ID NO:148) surrounding the NotI site:

soybean, by measuring alteration in oil, starch, protein, soluble carbohydrate and/or seed weight. Compositional analysis including measurements of seed compositional

```
                                                    SEQ ID NO: 39
EagI E L V I S L I V E S (SEQ ID NO: 148)EagI E L V I S
                                                    (SEQ ID NO: 150)
cggccggagctggtcatctcgctcatcgtcgagtcg gcggccg gagctggtcatctcg L I V E S (SEQ ID NO: 151)NotI
(S)(E (V)(I)(L)(S)(I)(V)(L)(E)  (SEQ ID NO: 149)EagI
ctcatcgtcgagtcg gcggccgc cgactgacgatgagcgagatgaccagctc cggccgc (S)(E)(V)(I)(L)(S)(I)(V)(L)(E)  (SEQ ID NO: 149)EagI
cgactcgacgatgagcgagatgaccagctc cggccg
``` parameters such as protein content and content of soluble carbohydrates of soybean seed derived from transgenic events that show seed-specific down-regulation of plastidic HpaIL aldolase genes is performed as follows: Oil content of mature soybean seed or lyophilized soybean somatic embryos can be measured by NMR as described in Example 2.

Non-Structural Carbohydrate and Protein Analysis.

Dry soybean seed are ground to a fine powder in a Geno-Grinder and subsamples are weighed (to an accuracy of 0.0001 g) into 13×100 mm glass tubes; the tubes have Teflon® lined screw-cap closures. Three replicates are prepared for each sample tested. Tissue dry weights are calculated by weighing sub-samples before and after drying in a forced air oven for 18 h at 105 C. Lipid extraction is performed by adding 2 ml aliquots of heptane to each tube.

The tubes are vortex mixed and placed into an ultrasonic bath (VWR Scientific Model 750D) filled with water heated to 6° C. The samples are sonicated at full-power (~360W) for 15 min and were then centrifuged (5 min×1700 g). The supernatants are transferred to clean 13×100 mm glass tubes and the pellets are extracted 2 more times with heptane (2 ml, second extraction, 1 ml third extraction) with the supernatants from each extraction being pooled. After lipid extraction 1 ml acetone is added to the pellets and after vortex mixing, to fully disperse the material, they are taken to dryness in a Speedvac.

Non-Structural Carbohydrate Extraction and Analysis.

Two ml of 80% ethanol is added to the acetone dried pellets from above. The samples are thoroughly vortex mixed until the plant material was fully dispersed in the solvent prior to sonication at 600 for 15 min. After centrifugation, 5 min× 1700 g, the supernatants are decanted into clean 13×100 mm glass tubes. Two more extractions with 80% ethanol are performed and the supernatants from each are pooled. The extracted pellets are suspended in acetone and dried (as above). An internal standard β-phenyl glucopyranoside (100 ul of a 0.5000+/−0.0010 g/100 ml stock) is added to each extract prior to drying in a Speedvac. The extracts are maintained in a desiccator until further analysis.

The acetone dried powders from above were suspended in 0.9 ml MOPS (3-N[Morpholino]propane-sulfonic acid; 50 mM, 5 mM $CaCl_2$, pH 7.0) buffer containing 100 U of heat stable α-amylase (from *Bacillus licheniformis*; Sigma A-4551). Samples are placed in a heat block (90 C) for 75 min and were vortex mixed every 15 min. Samples are then allowed to cool to room temperature and 0.6 ml acetate buffer (285 mM, pH 4.5) containing 5 U amyloglucosidase (Roche 110 202 367 001) is added to each. Samples are incubated for 15-18 h at 550 in a water bath fitted with a reciprocating shaker; standards of soluble potato starch (Sigma 5-2630) are included to ensure that starch digestion went to completion.

Post-digestion the released carbohydrates are extracted prior to analysis. Absolute ethanol (6 ml) is added to each tube and after vortex mixing the samples were sonicated for 15 min at 600. Samples were centrifuged (5 min×1700 g) and the supernatants were decanted into clean 13×100 mm glass tubes. The pellets are extracted 2 more times with 3 ml of 80% ethanol and the resulting supernatants are pooled. Internal standard (100 ul β-phenyl glucopyranoside, as above) is added to each sample prior to drying in a Speedvac.

Sample Preparation and Analysis

The dried samples from the soluble and starch extractions described above are solubilized in anhydrous pyridine (Sigma-Aldrich P57506) containing 30 mg/ml of hydroxylamine HCl (Sigma-Aldrich 159417). Samples are placed on an orbital shaker (300 rpm) overnight and are then heated for 1 hr (750) with vigorous vortex mixing applied every 15 min.

After cooling to room temperature 1 ml hexamethyldisilazane (Sigma-Aldrich H-4875) and 100 ul trifluoroacetic acid (Sigma-Aldrich T-6508) are added. The samples are vortex mixed and the precipitates are allowed to settle prior to transferring the supernatants to GC sample vials. Samples are analyzed on an Agilent 6890 gas chromatograph fitted with a DB-17MS capillary column (15m×0.32 mm×0.25 um film). Inlet and detector temperatures are both 275 C. After injection (2 ul, 20:1 split) the initial column temperature (150 C) is increased to 180 C at a rate 3 C/min and then at 25 C/min to a final temperature of 320 C. The final temperature is maintained for 10 min. The carrier gas is $H_2$ at a linear velocity of 51 cm/sec. Detection is by flame ionization. Data analysis is performed using Agilent ChemStation software. Each sugar is quantified relative to the internal standard and detector responses were applied for each individual carbohydrate (calculated from standards run with each set of samples). Final carbohydrate concentrations are expressed on a tissue dry weight basis.

Protein Analysis

Protein contents are estimated by combustion analysis on a Thermo Finnigan Flash 1112EA combustion analyzer. Samples, 4-8 mg, weighed to an accuracy of 0.001 mg on a Mettler-Toledo MX5 micro balance are used for analysis. Protein contents were calculated by multiplying % N, determined by the analyzer, by 6.25. Final protein contents are expressed on a % tissue dry weight basis.

Additionally, the composition of intact single seed and bulk quantities of seed or powders derived from them, may be measured by near-infrared analysis. Measurements of moisture, protein and oil content in soy and moisture, protein, oil and starch content in corn can be measured when combined with the appropriate calibrations.

Example 17

Screening of Transgenic Maize Lines for Alterations in Oil, Protein, Starch and Soluble Carbohydrate Content Transgenic maize lines prepared by the method described in Examples 11 can be screened essentially as described in Example 17. Embryo-specific downregulation of plastidic HpaIL aldolase expression is expected to lead to an increase in seed oil content. In contrast overexpression of HpaIL aldolase in the endosperm-specific is expected to lead to an increase in seed starch content.

Example 18

Seed Specific RNAi of HpaIL in Soybean

A plasmid vector (pKS423) for generation of transgenic soybean events that show seed specific down-regulation of the soy HpaIL (Glyma09g21760) gene was constructed.

Briefly plasmid DNA of applicants EST clone sfp1n.pk034.b9 corresponding to Glyma09g21760 (SEQ ID NO:30) was used in two PCR reactions with either Primers SA64 (SEQ ID NO:42) and SA65 (SEQ ID NO:43) or SA66 (SEQ ID NO:44) and SA64 (Seq ID NO:42). PCR products from both reactions were gel purified and a mixture of 100 ng of each PCR product was used in a third PCR reaction using only the SA64 PCR primer. A PCR product of approximately 1 kb was gel purified, digested with NotI and ligated to NotI linearized, dephosphorylated pBSKS+(Stratagene, USA). Plasmid DNA was isolated from recombinant clones and digested with NotI. The NotI restriction fragment of 0.968 kb was gel purified and cloned in the sense orientation behind the Kti promoter, to DNA of KS126 (PCT Publication No. WO 04/071467) linearized with the restriction enzyme NotI to give pKS423 (SEQ ID NO:45).

Plasmid DNA of pKS423 can be used to generate transgenic somatic embryos or seed of soybean using hygromycin selection as described in Example 14. Composition of transgenic somatic embryos or soybean seed generated with pKS423 determined as described in Example 17.

The plasmid vector pKS123 is described in PCT Application No. WO 02/08269. Plasmid pKS120 (SEQ ID NO: 46) is identical to pKS123 (supra) with the exception that the HindIII fragment containing Bcon/NotI/Phas3' cassette was removed.

Generation of Transgenic Somatic Embryos:

Soybean somatic embryos soybean tissue was co-bombarded as described below with a plasmid DNA of pKS120 or pKS423.

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 h day/night photoperiod at light intensity of 60-85 µE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., *Nature* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time, secondary embryos were cut and placed into SB196 liquid media for 7 days.

Preparation of DNA for Bombardment:

Plasmid DNA of pKS120 or pKS423 were used for bombardment.

A 50 µL aliquot of sterile distilled water containing 1 mg of gold particles was added to 5 µL of a 1 µg/µL plasmid DNA solution 50 µL 2.5M CaCl$_2$ and 20 µL of 0.1 M spermidine. The mixture was pulsed 5 times on level 4 of a vortex shaker and spun for 5 sec in a bench microfuge. After a wash with 150 µL of 100% ethanol, the pellet was suspended by sonication in 85 µL of 100% ethanol. Five µL of DNA suspension was dispensed to each flying disk of the Biolistic PDS1000/HE instrument disk. Each 5 µL aliquot contained approximately 0.058 mg gold particles per bombardment (i.e., per disk).

Tissue Preparation and Bombardment with DNA:

Approximately 100-150 mg of 7 day old embryonic suspension cultures were placed in an empty, sterile 60×15 mm petri dish and the dish was placed inside of an empty 150×25 mm Petri dish. Tissue was bombarded 1 shot per plate with membrane rupture pressure set at 650 PSI and the chamber was evacuated to a vacuum of 27-28 inches of mercury. Tissue was placed approximately 2.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six to eight days post-bombardment, the SB196 is exchanged with fresh SB196 containing 30 mg/L hygromycin. The selection media was refreshed weekly. Four to six weeks post-selection, green, transformed tissue was observed growing from untransformed, necrotic embryogenic clusters isolated, green tissue was removed and inoculated into multi-well plates to generate new, clonally propagated, transformed embryogenic suspension cultures.

Embryo Maturation:

Transformed embryogenic clusters were cultured for one-three weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 µE/m$^2$s. After this time embryo clusters were removed to a solid agar media, SB166, for 1 week. Then subcultured to medium SB103 for 3 weeks. Alternatively, embryo clusters were removed to SB228 (SHaM) liquid media, 35 mL in 250 mL Erlenmeyer flask, for 2-3 weeks. Tissue cultured in SB228 was maintained on a rotary shaker, 130 rpm, 26° C. with cool white fluorescent lights on 16:8 h day/night photoperiod at light intensity of 60-85 ρE/m2/s. During this period, individual embryos were removed from the clusters and screened for alterations in their fatty acid compositions as described supra.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| KNO$_3$ | 2.83 gm |
| (NH$_4$)$_2$SO$_4$ | 0.463 gm |
| Asparagine | 1.0 gm |
| Sucrose (1%) | 10 gm |
| pH 5.8 | |

FN Lite Stock Solutions

| Stock Number | | 1000 mL | 500 mL |
|---|---|---|---|
| 1 | MS FeEDTA 100x Stock | | |
| | Na$_2$EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |

-continued

| Stock Number | | 1000 mL | 500 mL |
|---|---|---|---|
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SBI Solid Medium (Per Liter)

1 package MS salts (Gibco/BRL—Cat. No, 11117-066)
1 mL 35 vitamins 1000× stock
31.5 g Glucose
2 mL 2,4-D (20 mg/L final concentration)
pH 5.7
8 g TC agar

SB199 Solid Medium (Per Liter)

1 package MS salts (Gibco/BRL—Cat. No. 11117-066)
1 mL B5 vitamins 1000× stock
30 g Sucrose
4 ml 2,4-D (40 mg/L final concentration)
pH 7.0
2 gm Gelrite

SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g Activated charcoal
pH 5.7
2 g Gelrite

SB 103 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
pH 5.7
2 g Gelrite

SB 71-4 Solid Medium (Per Liter)

1 bottle Gamborg's B5 salts w/sucrose (Gibco/BRL—Cat. No. 21153-036)
pH 5.7
5 g TC agar

2,4-D Stock

Obtain premade from Phytotech Cat. No. D 295—concentration 1 mg/mL

B5 Vitamins Stock (Per 100 mL)

Store aliquots at −20° C.
  10 g Myo-inositol
  100 mg Nicotinic acid
  100 mg Pyridoxine HCl
  1 g Thiamine
If the solution does not dissolve quickly enough, apply a low level of heat via the hot stir plate.

SB 228—Soybean Histodifferentiation & Maturation (SHaM) (Per Liter)

| | |
|---|---|
| DDI H2O | 600 ml |
| FN-Lite Macro Salts for SHaM 10X | 100 ml |
| MS Micro Salts 1000x | 1 ml |
| MS FeEDTA 100x | 10 ml |
| CaCl 100x | 6.82 ml |
| B5 Vitamins 1000x | 1 ml |
| L-Methionine | 0.149 g |
| Sucrose | 30 g |
| Sorbitol | 30 g |
| Adjust volume to 900 mL | |
| pH 5.8 | |
| Autoclave | |
| Add to cooled media (≤30 C.): | |
| *Glutamine (Final conc. 30 mM) 4% | 110 mL |

*Note: Final volume will be 1010 mL after glutamine addition.

Because glutamine degrades relatively rapidly, it may be preferable to add immediately prior to using media. Expiration 2 weeks after glutamine is added; base media can be kept longer w/o glutamine.

FN-Lite Macro for SHAM 10×—Stock #1 (Per Liter)

| | |
|---|---|
| $(NH_4)2SO_4$ (Ammonium Sulfate) | 4.63 g |
| $KNO_3$ (Potassium Nitrate) | 28.3 g |
| $MgSO_4*7H_2O$ (Magnesium Sulfate Heptahydrate) | 3.7 g |
| $KH_2PO_4$ (Potassium Phosphate, Monobasic) | 1.85 g |
| Bring to volume | |
| Autoclave | |

MS Micro 1000×—Stock #2 (Per 1 Liter)

| | |
|---|---|
| $H_3BO_3$ (Boric Acid) | 6.2 g |
| $MnSO_4*H_2O$ (Manganese Sulfate Monohydrate) | 16.9 g |
| $ZnSO4*7H20$ (Zinc Sulfate Heptahydrate) | 8.6 g |
| $Na_2MoO_4*2H20$ (Sodium Molybdate Dihydrate) | 0.25 g |
| $CuSO_4*5H_2O$ (Copper Sulfate Pentahydrate) | 0.025 g |
| $CoCl_2*6H_2O$ (Cobalt Chloride Hexahydrate) | 0.025 g |
| KI (Potassium Iodide) | 0.8300 g |
| Bring to volume | |
| Autoclave | |

FeEDTA 100×—Stock #3 (Per Liter)

| | |
|---|---|
| $Na_2EDTA*$ (Sodium EDTA) | 3.73 g |
| $FeSO_4*7H_2O$ (Iron Sulfate Heptahydrate) | 2.78 g |
| *EDTA must be completely dissolved before adding iron. | |
| Bring to Volume | |
| Solution is photosensitive. Bottle(s) should be wrapped in foil to omit light. | |
| Autoclave | |

Ca 100×—Stock #4 (Per Liter)

| | |
|---|---|
| CaCl$_2$*2H$_2$0 (Calcium Chloride Dihydrate) | 44 g |
| Bring to Volume | |
| Autoclave | |

B5 Vitamin 1000×—Stock #5 (Per Liter)

| | |
|---|---|
| Thiamine*HCl | 10 g |
| Nicotinic Acid | 1 g |
| Pyridoxine*HCl | 1 g |
| Myo-Inositol | 100 g |
| Bring to Volume | |
| Store frozen | |

4% Glutamine—Stock #6 (Per Liter)

| | |
|---|---|
| DDI water heated to 30° C. | 900 ml |
| L-Glutamine | 40 g |
| Gradually add while stirring and applying low heat. | |
| Do not exceed 35° C. | |
| Bring to Volume | |
| Filter Sterilize | |
| Store frozen* | |

*Note: Warm thawed stock in 31° C. bath to fully dissolve crystals.

Oil Analysis:

Oil content of somatic embryos was measured using NMR. Briefly lyophilized soybean somatic embryo tissue was pulverized in genogrinder vial as described previously (Example 2). 20-200 mg of tissue powder were transferred to NMR tubes. Oil content of the somatic embryo tissue powder was calculated from the NMR signal as described in Example 2. A total of 29 and 26 event were generated with plasmids pKS120 and pKS423, respectively and oil content of somatic embryos was measured (Table 18)

TABLE 18

Oil content of soybean somatic embryos generated with pKS120 or pKS423

| event ID | plasmid | % oil (NMR) | event ID | plasmid | % oil (NMR) |
|---|---|---|---|---|---|
| 2598-14 | pKS120 | 7.3 | 2599-6 | pKS423 | 8.0 |
| 2598-17 | pKS120 | 6.1 | 2599-2 | pKS423 | 6.5 |
| 2598-21 | pKS120 | 6.0 | 2599-24 | pKS423 | 6.3 |
| 2598-7 | pKS120 | 5.6 | 2599-1 | pKS423 | 6.2 |
| 2598-2 | pKS120 | 5.2 | 2599-13 | pKS423 | 6.1 |
| 2598-18 | pKS120 | 4.7 | 2599-22 | pKS423 | 6.0 |
| 2598-23 | pKS120 | 4.7 | 2599-3 | pKS423 | 5.7 |
| 2598-26 | pKS120 | 4.6 | 2599-4 | pKS423 | 5.7 |
| 2598-27 | pKS120 | 4.5 | 2599-19 | pKS423 | 5.5 |
| 2598-8 | pKS120 | 4.4 | 2599-20 | pKS423 | 5.4 |
| 2598-13 | pKS120 | 4.3 | 2599-10 | pKS423 | 5.4 |
| 2598-6 | pKS120 | 4.3 | 2599-25 | pKS423 | 5.3 |
| 2598-10 | pKS120 | 4.3 | 2599-11 | pKS423 | 5.2 |
| 2598-22 | pKS120 | 4.2 | 2599-9 | pKS423 | 5.2 |
| 2598-9 | pKS120 | 4.1 | 2599-16 | pKS423 | 5.2 |
| 2598-30 | pKS120 | 4.0 | 2599-12 | pKS423 | 4.8 |
| 2598-28 | pKS120 | 3.9 | 2599-7 | pKS423 | 4.4 |
| 2598-1 | pKS120 | 3.5 | 2599-15 | pKS423 | 4.2 |
| 2598-19 | pKS120 | 3.1 | 2599-14 | pKS423 | 4.0 |
| 2598-29 | pKS120 | 3.1 | 2599-8 | pKS423 | 3.8 |
| 2598-24 | pKS120 | 2.9 | 2599-23 | pKS423 | 3.7 |
| 2598-12 | pKS120 | 2.8 | 2599-17 | pKS423 | 3.5 |
| 2598-5 | pKS120 | 2.7 | 2599-26 | pKS423 | 3.3 |
| 2598-15 | pKS120 | 2.5 | 2599-5 | pKS423 | 3.2 |
| 2598-4 | pKS120 | 2.4 | 2599-18 | pKS423 | 3.1 |
| 2598-16 | pKS120 | 2.4 | 2599-21 | pKS423 | 3.0 |
| 2598-20 | pKS120 | 2.4 | | | average % oil |
| 2598-11 | pKS120 | 2.3 | | | |
| 2598-3 | pKS120 | 2.2 | | | 4.9 |
| | | average % oil | | | |
| | | 3.9 | | | |

Table 18 demonstrates that total fatty acid content in soybean somatic embryos is increased as result of down-regulation of a soy HpaIL gene (Glyma09g21760).

Example 19

Compositional Analysis of *Arabidopsis* Events Transformed with DNA Constructs for Seed-Preferred Silencing of HpaIL Gene The example describes seed composition of transgenic events generated with pKR1482HpaIL 3'UTR (SEQ ID NO: 27). It demonstrates that transformation with DNA constructs for silencing of genes encoding plastidic HpaI-like genes leads to increased oil content that is accompanied by a reduction in seed storage protein and soluble carbohydrate content.

Two transgenic events 14733 and 14734 were generated by agrobacterium-mediated transformation with pKR1482HpaIL 3'UTR (SEQ ID NO:27) as described in Example 5.

T3 seed of K14733 and 14734 were germinated on selective plant growth media containing kanamycin. Kanamycin-resistant seedlings were transferred to soil and grown alongside untransformed control plants as described in Example 5. At maturity T4 seeds were bulk-harvested from transgenic lines and control plants and subjected to oil analysis by NMR as described in Example 2. The seed samples were subjected to compositional analysis of protein and soluble carbohydrate content of triplicate samples as described in Example 2. The results of this analysis are summarized in Table 19.

TABLE 19

Seed composition of Arabidospis events transformed with DNA constructs for silencing of plastidic HpaIL genes

| Genotype | Event ID | Oil (%, NMR) | Protein % | fructose (µg mg$^{-1}$ seed) | glucose (µg mg$^{-1}$ seed) |
|---|---|---|---|---|---|
| pKR1482 HpaIL 3'UTR (T4) | K14733 | 43.8 | 16.9 | 0.5 | 3.2 |
| | WT | 40.4 | 18.9 | 0.5 | 4.0 |
| | Δ TG/WT % | 8.4 | −10.3 | 4.9 | −20.5 |

TABLE 19-continued

Seed composition of Arabidospis events transformed with DNA constructs for silencing of plastidic HpaIL genes

| Genotype | Bar code ID | sucrose (µg mg$^{-1}$ seed) | raffinose (µg mg$^{-1}$ seed) | stachyose (µg mg$^{-1}$ seed) | total soluble CHO (µg mg$^{-1}$ seed) |
|---|---|---|---|---|---|
| pKR1482 HpaIL 3'UTR (T4) | K14733 | 15.0 | 0.4 | 1.6 | 21.4 |
| | WT | 15.3 | 0.5 | 1.8 | 22.7 |
| | Δ TG/WT % | −2.0 | −6.5 | −8.8 | −5.8 |

| Genotype | Event ID | Oil (%, NMR) | Protein % | fructose (µg mg$^{-1}$ seed) | glucose (µg mg$^{-1}$ seed) |
|---|---|---|---|---|---|
| pKR1482 HpaIL 3'UTR (T4) | K14733 | 43.3 | 16.5 | 0.4 | 2.6 |
| | WT | 41.9 | 18.2 | 0.5 | 4.0 |
| | Δ TG/WT % | 3.3 | −9.6 | −10.5 | −34.5 |

| Genotype | Event ID | sucrose (µg mg$^{-1}$ seed) | raffinose (µg mg$^{-1}$ seed) | stachyose (µg mg$^{-1}$ seed) | total soluble CHO (µg mg$^{-1}$ seed) |
|---|---|---|---|---|---|
| pKR1482 HpaIL 3'UTR (T4) | K14733 | 15.0 | 0.4 | 1.4 | 20.6 |
| | WT | 14.9 | 0.4 | 1.6 | 22.0 |
| | Δ TG/WT % | 0.6 | −3.2 | −10.3 | −6.5 |

| Genotype | Event ID | Oil (%, NMR) | Protein % | fructose (µg mg$^{-1}$ seed) | glucose (µg mg$^{-1}$ seed) |
|---|---|---|---|---|---|
| pKR1482 HpaIL 3'UTR (T4) | K14734 | 41.4 | 17.0 | 0.5 | 4.4 |
| | WT | 38.0 | 20.6 | 0.4 | 4.7 |
| | Δ TG/WT % | 8.9 | −17.4 | 7.8 | −7.0 |

| Genotype | Event ID | sucrose (µg mg$^{-1}$ seed) | raffinose (µg mg$^{-1}$ seed) | stachyose (µg mg$^{-1}$ seed) | total soluble CHO (µg mg$^{-1}$ seed) |
|---|---|---|---|---|---|
| pKR1482 HpaIL 3'UTR (T4) | K14734 | 14.5 | 0.4 | 1.7 | 22.2 |
| | WT | 15.3 | 0.5 | 1.5 | 23.0 |
| | TG/WT % | −5.0 | −12.0 | 14.9 | −3.7 |

Table 18 demonstrates that the oil increase associated with the presence of the pKR1482HpaIL 3'UTR transgene (SEQ ID NO:27) is accompanied by a reduction in seed protein content and a small reduction in soluble carbohydrate content. The latter was calculated by summarizing the content of pinitol, sorbitol, fructose, glucose, myo-Inositol, sucrose, raffinose and stachyose.

Example 20

Compositional Analysis of *Arabidopsis* Events Transformed with DNA Constructs for Seed-Preferred Over-Expression of Hail Genes The example describes seed composition of transgenic events generated with pKR1478-At4g10750 (SEQ ID NO:51). It demonstrates that transformation with DNA constructs for seed-preferred overexpression genes encoding plastidic HpaI-like genes leads to decreased oil content that is accompanied by increased seed storage protein content.

Primers Hailer FWD (SEQ ID NO:11) and HpaIL ORF REV (SEQ ID NO:12) were used to amplify the At4g10750 ORF from genomic DNA of *Arabidopsis* plants of the Landsberg *erecta* genotype. The PCR product was cloned into pENTR (Invitrogen, USA) to give pENTR-At4g10750 (SEQ ID NO:50). The HpaIL ORF was inserted in the sense orientation downstream of the GY1 promoter in binary plant transformation vector pKR1478 using GATEWAY®LR recombinase (Invitrogen, USA) using manufacturer instructions. A gel-purified DNA fragment of 2222 bp was excised from pENTR-At4g10750 with the restriction enzymes EcoR V and ApaL I and used in the recombination reaction. The sequence of the resulting plasmid pKR1478-At4g10750 is set forth as SEQ ID NO:51. The HpaIL ORF present in pKR1478-At4g10750 and its deduced amino acid sequence are set forth in SEQ ID NO: 52 and SEQ ID NO: 53, respectively. They represent the At4g10750 gene sequence of *Arabidopsis thaliana* of genotype Landsberg *erecta*. Said sequences are 99.6 and 99.4% identical to the nucleotide sequence and deduced amino acid sequence of SEQ ID NOs: 48 and 49, respectively. The latter represent the nucleotide and deduced amino acid sequence of the At4g10750 sequence of *Arabidopsis thaliana* of genotype Columbia. As stated in the current example genomic DNA of *Arabidopsis thaliana* of genotype Landsberg *erecta* and not of genotype Columbia (as was stated erroneously in Example 4 of the instant specification) was used as a template to PCR amplify the ORF present in pENTR-At4g10750 and pKR1478-At4g10750.

pKR1478-At4g10750 (SEQ ID NO:51) was introduced into *Agrobacterium tumefaciens* NTL4 (Luo et al, *Molecular Plant-Microbe Interactions* (2001) 14(1):98-103) by electroporation. Briefly, 100 ng plasmid DNA was mixed with 100 µL of electro-competent cells on ice. The cell suspension was transferred to a 100 µL electroporation cuvette (1 mm gap width) and electroporated using a BIORAD electroporator set to 1 kV, 1kΩ and 25 µF. Cells were transferred to 1 mL LB medium and incubated for 3 h at 30° C. Cells were plated onto LB medium containing 50 µg/mL kanamycin. Plates were incubated at 30° C. for 60 h. Recombinant *Agrobacterium* cultures (500 mL LB, 50 µg/mL kanamycin) were inoculated from single colonies of transformed *agrobacterium* cells and grown at 30° C. for 60 h. Cells were harvested by centrifugation (5000×g, 10 min) and resuspended in 250 mL of 5% (W/V) sucrose containing 0.05% (V/V) Silwet. *Arabidopsis* plants were grown in soil at a density of 30 plants per 100 cm$^2$ pot in METRO-MIX® 360 soil mixture for 4 weeks (22° C., 16 h light/8 h dark, 100 µE m$^{-2}$s$^{-1}$). Plants were repeatedly dipped into the *Agrobacterium* suspension harboring the binary vector pKR1478-HpaIL and kept in a dark, high humidity environment for 24 h. Post dipping, plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20× 20 cm) containing 250 mL of sterile plant growth medium comprised of 0.5×MS salts, 0.53% (W/V) sorbitol, 0.05 MES/KOH (pH 5.8), 200 µg/mL TIMENTIN®, and 50 µg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. T1 Plants were grown to maturity alongside wt control plants and T2 seeds were harvested and oil content was analyzed by NMR as described above (Example 2).

TABLE 20

Seed oil content of T1 plants generated with binary vector pKR1478-At4g10750 for seed preferred overexpression of At4g10750

| Construct | BARCODE | % oil | oil content % of WT | avg. oil content % of WT |
|---|---|---|---|---|
| pKR1478-At4g10750 | K50660 | 40.6 | 99.9 | |
| pKR1478-At4g10750 | K50655 | 40.5 | 99.6 | |
| pKR1478-At4g10750 | K50672 | 40.4 | 99.5 | |
| pKR1478-At4g10750 | K50663 | 40.1 | 98.8 | |
| pKR1478-At4g10750 | K50661 | 39.0 | 96.0 | |
| pKR1478-At4g10750 | K50653 | 38.6 | 94.9 | |
| pKR1478-At4g10750 | K50669 | 38.4 | 94.5 | |
| pKR1478-At4g10750 | K50662 | 38.3 | 94.3 | |
| pKR1478-At4g10750 | K50667 | 38.0 | 93.6 | |
| pKR1478-At4g10750 | K50652 | 37.7 | 92.8 | |
| pKR1478-At4g10750 | K50668 | 31.5 | 77.5 | 94.7 |
| wt | K50679 | 42.6 | | |
| wt | K50676 | 40.6 | | |
| wt | K50680 | 40.4 | | |
| wt | K50678 | 39.8 | | |
| wt | K50677 | 39.6 | | |
| pKR1478-At4g10750 | K50696 | 41.2 | 100.4 | |
| pKR1478-At4g10750 | K50687 | 40.8 | 99.5 | |
| pKR1478-At4g10750 | K50697 | 40.3 | 98.1 | |
| pKR1478-At4g10750 | K50683 | 40.2 | 97.9 | |
| pKR1478-At4g10750 | K50686 | 40.1 | 97.8 | |
| pKR1478-At4g10750 | K50692 | 39.9 | 97.1 | |
| pKR1478-At4g10750 | K50681 | 39.5 | 96.3 | |
| pKR1478-At4g10750 | K50693 | 39.5 | 96.2 | |
| pKR1478-At4g10750 | K50689 | 38.2 | 93.2 | |
| pKR1478-At4g10750 | K50684 | 38.1 | 92.8 | 96.9 |
| wt | K50701 | 42.3 | | |
| wt | K50698 | 41.1 | | |
| wt | K50700 | 40.7 | | |
| wt | K50699 | 40.1 | | |

TABLE 21

Seed oil content of T2 plants generated with binary vector pKR1478-At4g10750 for seed preferred overexpression of At4g10750

| | BARCODE | % oil | oil content % of WT | avg. oil content % of WT |
|---|---|---|---|---|
| event | | | | |
| K50668 | K53363 | 40.1 | 98.9 | |
| K50668 | K53361 | 40.0 | 98.7 | |
| K50668 | K53359 | 39.9 | 98.4 | |
| K50668 | K53375 | 39.1 | 96.4 | |
| K50668 | K53377 | 39.1 | 96.3 | |

TABLE 21-continued

Seed oil content of T2 plants generated with binary vector pKR1478-At4g10750 for seed preferred overexpression of At4g10750

| | BARCODE | % oil | oil content % of WT | avg. oil content % of WT |
|---|---|---|---|---|
| K50668 | K53376 | 38.8 | 95.6 | |
| K50668 | K53365 | 38.7 | 95.4 | |
| K50668 | K53362 | 37.7 | 92.9 | |
| K50668 | K53371 | 36.8 | 90.7 | |
| K50668 | K53370 | 36.6 | 90.2 | |
| K50668 | K53366 | 36.5 | 90.1 | |
| K50668 | K53369 | 36.0 | 88.8 | |
| K50668 | K53373 | 35.9 | 88.6 | |
| K50668 | K53372 | 31.9 | 78.7 | 92.8 |
| wt | K53379 | 42.3 | | |
| wt | K53382 | 42.2 | | |
| wt | K53388 | 41.8 | | |
| wt | K53385 | 41.3 | | |
| wt | K53381 | 40.3 | | |
| wt | K53387 | 39.8 | | |
| wt | K53384 | 39.8 | | |
| wt | K53383 | 39.6 | | |
| wt | K53380 | 39.5 | | |
| wt | K53386 | 39.0 | | |
| Construct | | | | |
| K50689 | K53259 | 39.5 | 96.4 | |
| K50689 | K53257 | 39.0 | 95.2 | |
| K50689 | K53251 | 38.7 | 94.4 | |
| K50689 | K53253 | 38.3 | 93.5 | |
| K50689 | K53249 | 38.1 | 93.1 | |
| K50689 | K53256 | 37.7 | 92.1 | |
| K50689 | K53247 | 37.5 | 91.6 | |
| K50689 | K53248 | 37.2 | 90.7 | |
| K50689 | K53261 | 36.8 | 90.0 | |
| K50689 | K53260 | 36.8 | 89.8 | |
| K50689 | K53246 | 35.8 | 87.3 | |
| K50689 | K53258 | 35.4 | 86.5 | 91.7 |
| wt | K53270 | 42.8 | | |
| wt | K53266 | 42.2 | | |
| wt | K53271 | 41.9 | | |
| wt | K53267 | 41.7 | | |
| wt | K53272 | 41.3 | | |
| wt | K53275 | 41.3 | | |
| wt | K53273 | 41.2 | | |
| wt | K53264 | 40.7 | | |
| wt | K53269 | 40.5 | | |
| wt | K53268 | 40.4 | | |
| wt | K53265 | 40.1 | | |
| wt | K53274 | 37.2 | | |

T3 seed of events K50668 and K50689 with oil contents shown in Table 21 were combined and seed composition of the events was analyzed and compared to seed composition of untransformed WT plants gown in the same flat. Analysis of seed composition was performed as described in Example 2.

TABLE 22

Seed composition of Arabidospis events transformed with DNA constructs for seed-preferred overexpression of plastidic HpaIL genes

| Genotype | Event ID | Oil (%, NMR) | Protein % | fructose (µg mg$^{-1}$ seed) | glucose (µg mg$^{-1}$ seed) |
|---|---|---|---|---|---|
| pKR1478-At410750 | K50668 | 35.9 | 20.6 | 0.5 | 5.7 |
| | WT | 39.3 | 18.5 | 0.6 | 3.9 |
| | Δ | −8.7 | 11.6 | −6.3 | 48.0 |
| | TG/WT % | | | | |

TABLE 22-continued

Seed composition of Arabidospis events transformed with DNA constructs for seed-preferred overexpression of plastidic HpaIL genes

| Genotype | Event ID | sucrose (μg mg$^{-1}$ seed) | raffinose (μg mg$^{-1}$ seed) | stachyose (μg mg$^{-1}$ seed) | total soluble CHO (μg mg$^{-1}$ seed) |
|---|---|---|---|---|---|
| pKR1478-At4910750 | K50668 | 15.0 | 0.5 | 1.5 | 24.0 |
|  | WT | 17.2 | 0.5 | 1.5 | 24.2 |
|  | Δ TG/WT % | −12.4 | 4.1 | 0.0 | −0.7 |

| Genotype | Event ID | Oil (%, NMR) | Protein % | fructose (μg mg$^{-1}$ seed) | glucose (μg mg$^{-1}$ seed) |
|---|---|---|---|---|---|
| pKR1478-At4910750 | K50689 | 37.3 | 18.2 | 0.5 | 4.5 |
|  | WT | 39.5 | 17.0 | 0.5 | 4.1 |
|  | Δ TG/WT % | −5.5 | 7.0 | −2.1 | 10.1 |

| Genotype | Event ID | sucrose (μg mg$^{-1}$ seed) | raffinose (μg mg$^{-1}$ seed) | stachyose (μg mg$^{-1}$ seed) | total soluble CHO (μg mg$^{-1}$ seed) |
|---|---|---|---|---|---|
| pKR1478-At4g10750 | K50689 | 16.6 | 0.5 | 1.6 | 24.3 |
|  | WT | 16.9 | 0.4 | 1.6 | 24.3 |
|  | Δ TG/WT % | −1.8 | 1.4 | 1.9 | 0.3 |

Tables 20 and 21 demonstrate that seed-preferred over-expression of HpaIL genes such as At4g10750 leads to a heritable reduction in seed oil content. Table 22 shows that this oil reduction is accompanied by an increase in seed storage protein.

Example 21

Characterization of *Arabidopsis* Events Transformed with DNA Constructs that Contain the Complete HpaIL Gene ORF for Seed-Preferred Silencing of HpaIL Genes The example describes seed composition of transgenic events generated with pKR1482At4g10750 (SEQ ID NO:54). It demonstrates that transformation with DNA constructs for silencing of genes encoding plastidic HpaI-like genes such as At4g10750 leads to increased oil content.

5 μg of plasmid DNA of pENTR-At4g10750 (SEQ ID NO:50) was digested with PvuII. A restriction fragment of 1715 bp (derived from pENTR-At4g10750) was excised from an agarose gel. The entire protein coding sequence of the HpaIL gene represented by SEQ ID NO: 52 was inserted in the sense and anti-sense orientation into vector pKR1482 (SEQ ID NO:15) using LR clonase (Invitrogen) according to the manufacturer's instructions, to give pKR1482-At4g10750 (SEQ ID NO:54). Transgenic *Arabidopsis* lines were generated as described previously (Example 19) and oil content of transgenic T2 seed and untransformed control seed from plants grown in the same flat alongside the transgenic lines was analyzed by NMR as described in Example 2.

TABLE 23

Seed oil content of T1 plants generated with binary vector pKR1482-At4g10750 for seed preferred silencing of At4g10750

| Construct | BARCODE | % oil | oil content % of WT | avg. oil content % of WT |
|---|---|---|---|---|
| pKR1482-At4g10750 | K50819 | 43.4 | 106.5 |  |
| pKR1482-At4g10750 | K50816 | 43.3 | 106.2 |  |
| pKR1482-At4g10750 | K50807 | 43.2 | 106.0 |  |
| pKR1482-At4g10750 | K50814 | 43.2 | 106.0 |  |
| pKR1482-At4g10750 | K50796 | 42.9 | 105.3 |  |
| pKR1482-At4g10750 | K50817 | 42.9 | 105.2 |  |
| pKR1482-At4g10750 | K50798 | 42.8 | 105.0 |  |
| pKR1482-At4g10750 | K50808 | 42.7 | 104.7 |  |
| pKR1482-At4g10750 | K50800 | 42.6 | 104.4 |  |
| pKR1482-At4g10750 | K50804 | 42.1 | 103.3 |  |
| pKR1482-At4g10750 | K50820 | 42.0 | 103.0 |  |
| pKR1482-At4g10750 | K50794 | 41.9 | 102.8 |  |
| pKR1482-At4g10750 | K50810 | 41.7 | 102.4 |  |
| pKR1482-At4g10750 | K50818 | 41.6 | 102.1 |  |
| pKR1482-At4g10750 | K50815 | 41.6 | 101.9 |  |
| pKR1482-At4g10750 | K50801 | 41.4 | 101.5 |  |
| pKR1482-At4g10750 | K50806 | 41.0 | 100.7 |  |
| pKR1482-At4g10750 | K50799 | 40.8 | 100.0 |  |
| pKR1482-At4g10750 | K50821 | 40.8 | 100.0 |  |
| pKR1482-At4g10750 | K50812 | 40.8 | 100.0 |  |
| pKR1482-At4g10750 | K50795 | 40.6 | 99.6 |  |
| pKR1482-At4g10750 | K50813 | 40.1 | 98.5 |  |
| pKR1482-At4g10750 | K50809 | 39.5 | 96.9 |  |
| pKR1482-At4g10750 | K50802 | 39.1 | 95.9 |  |
| pKR1482-At4g10750 | K50811 | 38.9 | 95.4 |  |
| pKR1482-At4g10750 | K50803 | 38.7 | 94.9 |  |
| pKR1482-At4g10750 | K50805 | 37.8 | 92.8 |  |
| pKR1482-At4g10750 | K50822 | 35.7 | 87.5 |  |
| pKR1482-At4g10750 | K50797 | 35.1 | 86.2 | 100.5 |
| wt | K50824 | 41.7 |  |  |
| wt | K50823 | 41.5 |  |  |
| wt | K50825 | 41.1 |  |  |
| wt | K50826 | 40.8 |  |  |
| wt | K50827 | 38.6 |  |  |

T2 seed of event K50819 were germinated on selective plant growth media containing kanamycin, planted in soil alongside WT plants and grown to maturity. T3 seed oil content was measured by NMR.

TABLE 24

Seed oil content of T2 plants generated with binary vector pKR1482-At4g10750 for seed preferred silencing of At4g10750

| Event ID | BARCODE | % oil | oil content % of WT | avg. oil content % of WT |
|---|---|---|---|---|
| K50819 | K53078 | 42.2 | 108.4 |  |
| K50819 | K53070 | 41.9 | 107.8 |  |
| K50819 | K53064 | 41.8 | 107.5 |  |
| K50819 | K53069 | 41.5 | 106.8 |  |
| K50819 | K53077 | 40.9 | 105.2 |  |
| K50819 | K53062 | 40.4 | 104.0 |  |
| K50819 | K53075 | 40.3 | 103.8 |  |
| K50819 | K53068 | 39.4 | 101.4 |  |
| K50819 | K53063 | 39.2 | 100.8 |  |
| K50819 | K53061 | 39.1 | 100.6 |  |
| K50819 | K53066 | 39.0 | 100.4 |  |
| K50819 | K53060 | 38.8 | 99.9 |  |
| K50819 | K53076 | 38.6 | 99.2 |  |
| K50819 | K53072 | 38.4 | 98.8 |  |
| K50819 | K53067 | 38.3 | 98.5 |  |
| K50819 | K53065 | 38.1 | 97.9 |  |
| K50819 | K53074 | 38.0 | 97.7 |  |
| K50819 | K53073 | 37.6 | 96.7 |  |
| K50819 | K53071 | 37.0 | 95.1 | 101.6 |
| wt | K53084 | 40.1 |  |  |
| wt | K53083 | 39.9 |  |  |

TABLE 24-continued

Seed oil content of T2 plants generated with binary vector pKR1482-At4g10750 for seed preferred silencing of At4g10750

| Event ID | BARCODE | % oil | oil content % of WT | avg. oil content % of WT |
|---|---|---|---|---|
| wt | K53087 | 39.8 | | |
| wt | K53089 | 39.6 | | |
| wt | K53080 | 39.6 | | |
| wt | K53079 | 39.5 | | |
| wt | K53086 | 39.1 | | |
| wt | K53081 | 39.0 | | |
| wt | K53090 | 38.8 | | |
| wt | K53088 | 38.3 | | |
| wt | K53082 | 38.2 | | |
| wt | K53091 | 37.9 | | |
| wt | K53085 | 35.6 | | |

T3 seed of lines K53078, K53070, K53064 and K53069 derived event from event K50819 were germinated on selective plant growth media containing kanamycin, planted in soil alongside WT plants and grown to maturity. T4 Seed oil content was measured by NMR.

TABLE 25

Seed oil content of T3 plants generated with binary vector pKR1482-At4g10750 for seed preferred silencing of At4g10750

| T4 line ID | BARCODE | % oil | oil content % of WT | avg. oil content % of WT |
|---|---|---|---|---|
| K50819/K53078 | K59771 | 44.8 | 115.6 | |
| K50819/K53078 | K59778 | 43.7 | 112.9 | |
| K50819/K53078 | K59780 | 43.4 | 112.2 | |
| K50819/K53078 | K59786 | 42.9 | 110.9 | |
| K50819/K53078 | K59775 | 42.5 | 109.8 | |
| K50819/K53078 | K59774 | 42.5 | 109.7 | |
| K50819/K53078 | K59777 | 42.5 | 109.7 | |
| K50819/K53078 | K59769 | 42.4 | 109.5 | |
| K50819/K53078 | K59784 | 42.2 | 109.1 | |
| K50819/K53078 | K59781 | 42.2 | 108.9 | |
| K50819/K53078 | K59770 | 42.0 | 108.4 | |
| K50819/K53078 | K59785 | 41.6 | 107.6 | |
| K50819/K53078 | K59779 | 41.2 | 106.3 | |
| K50819/K53078 | K59768 | 40.9 | 105.7 | |
| K50819/K53078 | K59776 | 40.6 | 104.9 | |
| K50819/K53078 | K59765 | 40.1 | 103.5 | |
| K50819/K53078 | K59772 | 39.9 | 103.0 | |
| K50819/K53078 | K59767 | 38.8 | 100.2 | |
| K50819/K53078 | K59773 | 38.7 | 100.1 | |
| K50819/K53078 | K59783 | 37.9 | 98.0 | |
| K50819/K53078 | K59766 | 37.3 | 96.3 | |
| K50819/K53078 | K59782 | 36.8 | 95.0 | 106.2 |
| wt | K59791 | 40.6 | | |
| wt | K59792 | 39.9 | | |
| wt | K59788 | 39.7 | | |
| wt | K59787 | 38.9 | | |
| wt | K59789 | 38.7 | | |
| wt | K59793 | 38.4 | | |
| wt | K59794 | 38.3 | | |
| wt | K59790 | 35.3 | | |
| K50819/K53070 | K58902 | 45.4 | 112.4 | |
| K50819/K53070 | K58906 | 45.1 | 111.7 | |
| K50819/K53070 | K58886 | 45.0 | 111.6 | |
| K50819/K53070 | K58896 | 44.9 | 111.4 | |
| K50819/K53070 | K58894 | 44.8 | 111.0 | |
| K50819/K53070 | K58904 | 44.6 | 110.6 | |
| K50819/K53070 | K58895 | 44.4 | 110.1 | |
| K50819/K53070 | K58887 | 44.3 | 109.7 | |
| K50819/K53070 | K58889 | 44.1 | 109.3 | |
| K50819/K53070 | K58888 | 44.1 | 109.3 | |
| K50819/K53070 | K58897 | 43.9 | 108.7 | |
| K50819/K53070 | K58901 | 43.9 | 108.7 | |
| K50819/K53070 | K58905 | 43.7 | 108.2 | |
| K50819/K53070 | K58903 | 43.5 | 107.8 | |
| K50819/K53070 | K58891 | 43.5 | 107.7 | |
| K50819/K53070 | K58900 | 43.2 | 107.0 | |
| K50819/K53070 | K58892 | 42.8 | 106.0 | |
| K50819/K53070 | K58893 | 42.8 | 105.9 | |
| K50819/K53070 | K58898 | 42.1 | 104.3 | |
| K50819/K53070 | K58899 | 41.7 | 103.3 | |
| K50819/K53070 | K58890 | 38.7 | 95.9 | |
| K50819/K53070 | K58907 | 35.2 | 87.1 | 107.2 |
| wt | K58915 | 42.3 | | |
| wt | K58908 | 42.1 | | |
| wt | K58909 | 42.0 | | |
| wt | K58913 | 41.5 | | |
| wt | K58911 | 41.2 | | |
| wt | K58910 | 40.2 | | |
| wt | K58914 | 40.0 | | |
| wt | K58917 | 39.7 | | |
| wt | K58916 | 38.2 | | |
| wt | K58912 | 36.4 | | |
| K50819/K53064 | K58936 | 45.2 | 114.3 | |
| K50819/K53064 | K58934 | 45.2 | 114.3 | |
| K50819/K53064 | K58933 | 45.1 | 114.0 | |
| K50819/K53064 | K58919 | 45.0 | 113.7 | |
| K50819/K53064 | K58921 | 44.9 | 113.6 | |
| K50819/K53064 | K58924 | 44.8 | 113.2 | |
| K50819/K53064 | K58927 | 44.5 | 112.5 | |
| K50819/K53064 | K58925 | 44.4 | 112.2 | |
| K50819/K53064 | K58918 | 44.1 | 111.4 | |
| K50819/K53064 | K58928 | 44.0 | 111.3 | |
| K50819/K53064 | K58929 | 43.7 | 110.3 | |
| K50819/K53064 | K58926 | 43.0 | 108.8 | |
| K50819/K53064 | K58930 | 43.0 | 108.6 | |
| K50819/K53064 | K58923 | 42.7 | 108.0 | |
| K50819/K53064 | K58931 | 42.6 | 107.7 | |
| K50819/K53064 | K58922 | 41.4 | 104.5 | |
| K50819/K53064 | K58920 | 39.0 | 98.5 | |
| K50819/K53064 | K58935 | 38.8 | 98.0 | |
| K50819/K53064 | K58932 | 37.2 | 94.1 | 108.9 |
| wt | K58945 | 41.8 | | |
| wt | K58944 | 40.8 | | |
| wt | K58941 | 40.5 | | |
| wt | K58937 | 40.5 | | |
| wt | K58939 | 40.2 | | |
| wt | K58942 | 39.5 | | |
| wt | K58943 | 38.7 | | |
| wt | K58940 | 38.2 | | |
| wt | K58938 | 35.8 | | |
| K50819/K53069 | K60122 | 44.1 | 112.0 | |
| K50819/K53069 | K60127 | 44.1 | 112.0 | |
| K50819/K53069 | K60125 | 44.0 | 111.6 | |
| K50819/K53069 | K60123 | 43.8 | 111.3 | |
| K50819/K53069 | K60117 | 43.7 | 111.1 | |
| K50819/K53069 | K60120 | 43.6 | 110.7 | |
| K50819/K53069 | K60114 | 43.4 | 110.4 | |
| K50819/K53069 | K60113 | 43.4 | 110.2 | |
| K50819/K53069 | K60128 | 43.3 | 110.1 | |
| K50819/K53069 | K60124 | 43.3 | 110.1 | |
| K50819/K53069 | K60126 | 43.1 | 109.6 | |
| K50819/K53069 | K60119 | 42.4 | 107.7 | |
| K50819/K53069 | K60115 | 42.2 | 107.2 | |
| K50819/K53069 | K60116 | 41.6 | 105.6 | |
| K50819/K53069 | K60121 | 41.0 | 104.0 | |
| K50819/K53069 | K60129 | 39.4 | 100.2 | |
| K50819/K53069 | K60118 | 39.3 | 99.9 | 108.4 |
| wt | K60138 | 41.1 | | |
| wt | K60135 | 40.5 | | |
| wt | K60132 | 40.2 | | |
| wt | K60131 | 39.8 | | |

TABLE 25-continued

Seed oil content of T3 plants generated with binary vector pKR1482-At4g10750 for seed preferred silencing of At4g10750

| T4 line ID | BARCODE | % oil | oil content % of WT | avg. oil content % of WT |
|---|---|---|---|---|
| wt | K60130 | 39.6 | | |
| wt | K60134 | 39.6 | | |
| wt | K60133 | 39.6 | | |
| wt | K60137 | 39.2 | | |
| wt | K60136 | 34.7 | | |

Table 23-25 show that silencing of HpaI-like genes such as At4910750 using hairpin constructs comprised of the entire protein coding region of the gene lead to a heritable oil increase. InT4 lines that are homozygous for the T-DNA insertion the average oil content was 6-9% higher than that of WT control plants.

Example 22

Combination HpaI-Like Gene Silencing and Over-Expression of acylCoA: Diacylglycerol Acyltransferase (DGAT) in Soybean Somatic Embryos The example describes generation of transgenic soybean somatic embryos that contain either constructs for down-regulation of soybean HpaIL genes, or constructs for overexpression of acylCoA: diacyl glycerol acyltransferase (DGAT) genes. Moreover transgenic soybean somatic embryos are described that show both, over-expression of DGAT and down-regulation of soybean HpaIL genes. The latter embryos have a total oil content that exceeds the oil content observed in embryos harboring single transgenes responsible for DGAT overexpression or silencing of HpaIL genes.

Patent application number WO 2009143398 A1 describes plasmid KS387 (SEQ ED NO:55) for co-expression of DGAT1 and DGAT2 genes of *Yarrowia lipolytica* in developing soybean seed. Plasmids KS120 (SEQ ID NO:46) and KS423 (SEQ ID NO:45) are described in Example 18.

For experiments MSE 2650 and MSE 2653 purified plasmid DNA of KS120 and KS423 was used for generation of transgenic soybean somatic embryos exactly as described in Example 18. For experiment MSE2651 a 10:1 ratio of DNA of plasmids KS387 and KS120 was used for generation of transgenic soybean somatic embryos exactly as described in Example 18. For experiment MSE2652 a 10:1 ratio of DNA of plasmids KS387 and KS423 was used for generation of transgenic soybean somatic embryos exactly as described in Example 18. Oil content of lyophilized soybean somatic embryos of experiments MSE2650-2653 was analyzed by NMR as described in Examples 2 and is reported in Table 26.

TABLE 26

Oil content of somatic embryos generated with plasmids KS120, KS387, KS423 or a combination thereof

| experiment name | plasmid | event id | % oil | average % oil |
|---|---|---|---|---|
| MSE 2650 | KS120 | K52130 | 6.6 | |
| | | K52140 | 5.6 | |
| | | K52137 | 5.5 | |
| | | K52136 | 5.2 | |
| | | K52131 | 4.8 | |
| | | K52139 | 4.8 | |
| | | K52122 | 4.7 | |
| | | K52146 | 4.6 | |
| | | K52133 | 4.5 | |
| | | K52151 | 4.4 | |
| | | K52145 | 4.3 | |
| | | K52147 | 4.0 | |
| | | K52132 | 3.8 | |
| | | K52143 | 3.8 | |
| | | K52124 | 3.7 | |
| | | K52149 | 3.6 | |
| | | K52129 | 3.6 | |
| | | K52134 | 3.6 | |
| | | K52128 | 3.6 | |
| | | K52150 | 3.3 | |
| | | K52148 | 3.3 | |
| | | K52138 | 3.2 | |
| | | K52127 | 3.2 | |
| | | K52135 | 3.1 | |
| | | K52126 | 3.1 | |
| | | K52123 | 3.0 | |
| | | K52142 | 3.0 | |
| | | K52141 | 2.9 | |
| | | K52121 | 2.9 | |
| | | K52144 | 2.8 | |
| | | K52125 | 2.8 | 3.9 |
| 2653 | KS423 | K52237 | 9.8 | |
| | | K52243 | 7.8 | |
| | | K52214 | 6.2 | |
| | | K52227 | 6.1 | |
| | | K52233 | 5.9 | |
| | | K52236 | 5.6 | |
| | | K52231 | 5.4 | |
| | | K52228 | 5.3 | |
| | | K52230 | 5.0 | |
| | | K52238 | 4.9 | |
| | | K52239 | 4.8 | |
| | | K52218 | 4.7 | |
| | | K52215 | 4.7 | |
| | | K52220 | 4.7 | |
| | | K52235 | 4.6 | |
| | | K52242 | 4.5 | |
| | | K52232 | 4.5 | |
| | | K52221 | 4.5 | |
| | | K52241 | 4.4 | |
| | | K52229 | 4.1 | |
| | | K52226 | 4.0 | |
| | | K52224 | 3.8 | |
| | | K52217 | 3.8 | |
| | | K52225 | 3.5 | |
| | | K52222 | 3.4 | |
| | | K52240 | 3.3 | |
| | | K52219 | 3.0 | |
| | | K52219 | 3.0 | |
| | | K52234 | 2.6 | |
| | | K52234 | 2.6 | |
| | | K52223 | 2.5 | |
| | | K52223 | 2.5 | |
| | | K52216 | 2.2 | 4.5 |
| 2651 | KS387/KS120 | K52171 | 9.7 | |
| | | K52166 | 9.5 | |
| | | K52159 | 9.0 | |
| | | K52179 | 8.9 | |
| | | K52178 | 8.7 | |
| | | K52158 | 8.0 | |
| | | K52153 | 8.0 | |
| | | K52157 | 7.9 | |
| | | K52173 | 7.7 | |
| | | K52155 | 7.5 | |
| | | K52163 | 7.3 | |
| | | K52180 | 7.3 | |
| | | K52177 | 7.2 | |
| | | K52182 | 6.5 | |
| | | K52170 | 5.6 | |

TABLE 26-continued

Oil content of somatic embryos generated with plasmids
KS120, KS387, KS423 or a combination thereof

| experiment name | plasmid | event id | % oil | average % oil |
|---|---|---|---|---|
| | | K52169 | 5.5 | |
| | | K52165 | 5.4 | |
| | | K52161 | 5.3 | |
| | | K52172 | 5.1 | |
| | | K52175 | 5.0 | |
| | | K52174 | 4.4 | |
| | | K52181 | 4.2 | |
| | | K52168 | 3.7 | |
| | | K52152 | 3.6 | |
| | | K52156 | 3.3 | |
| | | K52164 | 3.3 | |
| | | K52176 | 3.0 | |
| | | K52160 | 2.7 | 6.2 |
| 2652 | KS387/KS423 | K52188 | 12.7 | |
| | | K52190 | 11.5 | |
| | | K52186 | 11.1 | |
| | | K52206 | 11.1 | |
| | | K52197 | 10.6 | |
| | | K52203 | 10.4 | |
| | | K52193 | 9.5 | |
| | | K52183 | 9.5 | |
| | | K52211 | 9.1 | |
| | | K52201 | 9.0 | |
| | | K52204 | 8.5 | |
| | | K52187 | 8.3 | |
| | | K52213 | 7.7 | |
| | | K52207 | 6.7 | |
| | | K52196 | 6.7 | |
| | | K52208 | 6.5 | |
| | | K52194 | 6.3 | |
| | | K52192 | 6.2 | |
| | | K52185 | 6.2 | |
| | | K52202 | 6.1 | |
| | | K52212 | 5.4 | |
| | | K52198 | 5.0 | |
| | | K52191 | 4.9 | |
| | | K52195 | 4.8 | |
| | | K52199 | 4.3 | |
| | | K52189 | 4.1 | |
| | | K52205 | 3.9 | |
| | | K52200 | 3.8 | |
| | | K52210 | 3.6 | |
| | | K52184 | 3.2 | |
| | | K52209 | 3.0 | 7.1 |

In summary Table 26 demonstrates that transformation with constructs for silencing of HpaIL genes increased average oil content of soybean somatic embryos by 14.5%, transformation with constructs for co-expression of *Yarrowia* DGAT genes increased average oil of soybean somatic embryos by 58% and transformation with constructs for co-expression of *Yarrowia* DGAT genes and silencing of HpaIL genes increased oil content by 81%. Thus the additive effect of both metabolic engineering approaches on soybean oil content provides clear evidence that HpaL gene silencing and DGAT overexpression direct carbohydrates towards oil biosynthesis through independent, i.e. distinct routes.

Example 24

Seed-Preferred Silencing of HpaIL Genes in Soybean Using Artificial miRNAs

The example describes the construction of a plasmid vector for soybean transformation. The plasmid provides seed-preferred expression of two artificial microRNAs that both target soybean gene Glyma09g21760 (SEQ ID NO: 30). Soybean somatic embryos transformed with plasmid constructs containing either one of the two artificial microRNA showed increased oil content compared to embryos that harbor a control plasmid.

Vectors were made to silence HpaIL genes using an artificial microRNA largely as described in U.S. patent application Ser. No. 12/335,717, filed Dec. 16, 2008. The following briefly explains the procedure.

Design of Artificial MicroRNA Sequences

Artificial microRNAs (amiRNAs) that would have the ability to silence the desired target genes were designed largely according to rules described in Schwab R, et al. (2005) *Dev Cell* 8: 517-27. To summarize, microRNA sequences are 21 nucleotides in length, start at their 5'-end with a "U", display 5° instability relative to their star sequence which is achieved by including a C or G at position 19, and their 10th nucleotide is either an "A" or an "U". An additional requirement for artificial microRNA design was that the amiRNA have a high free delta-G as calculated using the ZipFold algorithm (Markham, N. R. & Zuker, M. (2005) *Nucleic Acids Res.* 33: W577-W581.) The DNA sequence corresponding to the first amiRNA (ALDO A) that was used to silence aldolase is set forth in SEQ ID NO:56. The DNA sequence corresponding to the second amiRNA (ALDO B) that was used to silence the aldolase gene is set forth in SEQ ID NO:57.

Design an Artificial Star Sequences

"Star sequences" are those that base pair with the amiRNA sequences, in the precursor RNA, to form imperfect stem structures. To form a perfect stem structure the star sequence would be the exact reverse complement of the amiRNA. The soybean precursor sequence as described in "Novel and nodulation-regulated microRNAs in soybean roots" Subramanian 5, Fu Y, Sunkar R, Barbazuk W B, Zhu J K, Yu O BMC Genomics. 9:160 (2008) and accessed on mirBase (Conservation and divergence of microRNA families in plants" Dezulian T, Palatnik J F, Huson D H, Weigel D (2005) Genome Biology 6:P13) was folded using mfold (M. Zuker (2003) *Nucleic Acids Res.* 31: 3406-15; and D. H. Mathews, J. et al. (1999) *J. Mol. Biol.* 288: 911-940). The miRNA sequence was then replaced with the amiRNA sequence and the endogenous star sequence was replaced with the exact reverse complement of the amiRNA. Changes in the artificial star sequence were introduced so that the structure of the stem would remain the same as the endogenous structure. The altered sequence was then folded with mfold and the original and altered structures were compared by eye. If necessary, further alternations to the artificial star sequence were introduced to maintain the original structure. The first amiRNA star sequence (ALDO A star) that was used to silence aldolase is set forth as SEQ ID NO:58. The $2^{nd}$ amiRNA star sequence (ALDO B star) that was used to silence aldolase is set forth as SEQ ID NO:59.

Conversion of Genomic MicroRNA Precursors to Artificial MicroRNA Precursors

Genomic mRNA precursor genes were converted to amiRNA precursors using In-Fusion™ as described above. In brief, the microRNA 159 precursor (SEQ ID NO:60) was altered to include Pme I sites immediately flanking the star and microRNA sequences to form the in-fusion ready microRNA 159 precursor (SEQ ID NO:61). This sequence was cloned into the Not I site of KS126 to form the in-fusion ready microRNA 159-KS126 plasmid (SEQ ID NO:62). KS126 is described in PCT Publication No. WO 04/071467.

The microRNA 159 precursor (SEQ ID NO:60) was used as a PCR template. The primers (gmir159ALDO A1, SEQ ID NO:63 and gmir159ALDO A2, SEQ ID NO:64) were designed according to the protocol provided by Clontech and do not leave any footprint of the Pme I sites after the In-Fusion recombination reaction. The sequence of resulting amplified 159-ALDO A DNA is shown in SEQ ID NO:65.

The microRNA 159 precursor (SEQ ID NO:60) was used as a PCR template. The primers (gmir159ALDO B1, SEQ ID NO:66 and gmir159ALDO B2, SEQ ID NO:67) were designed according to the protocol provided by Clontech and do not leave any footprint of the Pme I sites after the In-Fusion recombination reaction. The sequence of resulting amplified 159-ALDO B DNAs is shown in SEQ ID NO:68.

The sequences of 159-ALDO A (SEQ ID NO:65) and 159-ALDO B (SEQ ID NO:67) were recombined into the in-fusion ready microRNA 159-KS126 plasmid (SEQ ID NO:62) digested with PmeI. This was done using protocols provided with the In-Fusion™ kit. The resulting plasmid are 159 ALDO A-KS126 (SEQ ID NO:69) and 159 ALDO B-KS126 (SEQ ID NO:70).

Plasmid DNA of 159 ALDO A-KS126 (SEQ ID NO:69) 159 ALDO B-KS126 (SEQ ID NO:70) and a control plasmid KS120 (SEQ ID NO:46) was used for transformation soybean cell suspensions and subsequent generation of soybean somatic embryos as described in Example 18. Oil content of soybean somatic embryos was measured by NMR and is summarized in Table 27.

TABLE 27

Oil content of somatic embryos generated with plasmids KS120, 159 ALDO A-KS126 and 159 ALDO B-KS126

| experiment name | plasmid | event id | % oil | average % oil |
|---|---|---|---|---|
| 2672 | KS120 | K54409 | 5.7 | |
| | | K54408 | 4.6 | |
| | | K54386 | 4.5 | |
| | | K54389 | 4.4 | |
| | | K54401 | 4.2 | |
| | | K54405 | 4.2 | |
| | | K54393 | 4.1 | |
| | | K54394 | 3.9 | |
| | | K54387 | 3.7 | |
| | | K54406 | 3.6 | |
| | | K54390 | 3.6 | |
| | | K54400 | 3.6 | |
| | | K54398 | 3.5 | |
| | | K54397 | 3.5 | |
| | | K54410 | 3.5 | |
| | | K54395 | 3.5 | |
| | | K54382 | 3.4 | |
| | | K54381 | 3.4 | |
| | | K54391 | 3.3 | |
| | | K54399 | 3.2 | |
| | | K54385 | 3.2 | |
| | | K54402 | 3.0 | |
| | | K54407 | 3.0 | |
| | | K54388 | 3.0 | |
| | | K54392 | 3.0 | |
| | | K54396 | 2.8 | |
| | | K54404 | 2.8 | 3.6 |
| 2670 | 159 ALDO A-KS126 | K54326 | 11.4 | |
| | | K54346 | 9.5 | |
| | | K54322 | 8.6 | |
| | | K54325 | 8.2 | |
| | | K54340 | 7.1 | |
| | | K54345 | 6.8 | |
| | | K54324 | 6.8 | |
| | | K54329 | 6.4 | |
| | | K54333 | 6.4 | |
| | | K54337 | 6.2 | |
| | | K54343 | 6.0 | |
| | | K54336 | 6.0 | |
| | | K54331 | 5.9 | |
| | | K54349 | 5.9 | |
| | | K54328 | 5.9 | |
| | | K54341 | 5.8 | |
| | | K54327 | 5.8 | |
| | | K54339 | 5.6 | |
| | | K54348 | 5.3 | |
| | | K54334 | 5.2 | |
| | | K54332 | 5.0 | |
| | | K54342 | 4.8 | |
| | | K54323 | 4.7 | |
| | | K54338 | 4.3 | |
| | | K54347 | 4.3 | |
| | | K54320 | 4.2 | |
| | | K54335 | 4.0 | |
| | | K54321 | 3.7 | |
| | | K54330 | 3.4 | |
| | | K54344 | 3.2 | 5.9 |
| 2671 | 159 ALDO B-KS126 | K54378 | 8.0 | |
| | | K54368 | 7.6 | |
| | | K54350 | 7.0 | |
| | | K54363 | 5.6 | |
| | | K54361 | 5.5 | |
| | | K54373 | 5.5 | |
| | | K54360 | 5.4 | |
| | | K54371 | 5.3 | |
| | | K54375 | 5.2 | |
| | | K54365 | 5.0 | |
| | | K54357 | 4.9 | |
| | | K54355 | 4.4 | |
| | | K54372 | 4.4 | |
| | | K54358 | 4.3 | |
| | | K54380 | 4.2 | |
| | | K54352 | 4.2 | |
| | | K54374 | 4.2 | |
| | | K54376 | 4.2 | |
| | | K54364 | 4.0 | |
| | | K54369 | 3.8 | |
| | | K54356 | 3.7 | |
| | | K54379 | 3.7 | |
| | | K54362 | 3.7 | |
| | | K54353 | 3.6 | |
| | | K54370 | 3.6 | |
| | | K54359 | 3.5 | |
| | | K54354 | 3.4 | |
| | | K54366 | 3.3 | |
| | | K54377 | 3.3 | |
| | | K54351 | 3.2 | |
| | | K54367 | 2.7 | 4.5 |

Table 27 demonstrates that total fatty acid content in soybean somatic embryos was increased as result of down-regulation of a soy HpaIL gene (Glyma09g21760) mediated by expression of artificial microRNAs targeting said gene.

Example 25

Expression of Bacterial HpaI and Plant HpaIL Genes in *E. coli* and Analysis of Enzyme Activity of Recombinantly-Produced Proteins The example describes expression of bacterial HpaI and plant HpaIL genes in *E. coli*, purification of recombinantly-produced bacterial HpaI and plant HpaIL enzymes and analysis of enzyme properties such as divalent ion and pH requirements and kinetic properties with pyruvate and acetaldehyde substrates. The example demonstrates that plant HpaIL enzymes, like distantly related bacterial HpaI enzymes can catalyze aldol additions using pyruvate and short chain aldehydes. Similar to bacterial HpaI enzymes, catalysis by plant HpaI-like enzymes requires presence of divalent ions. In these reactions catalytic efficiency (Kcat/Km) of plant HpaI-like enzyme is about 20-30 fold lower than of bacterial HpaI enzymes. Finally it is shown that in plant HpaI-like enzymes, similar to prokaryotic HpaI enzyme, a certain n-terminal arginine residue is required for aldol addition enzyme activity.

The amino acid sequence of the *Arabidopsis* HpaIL protein derived from At4g10750 SEQ ID NO:48 was analyzed using ChloroP at the online ChloroP 1.1. Server, which predicts the presence of chloroplast transit peptides (cTP) in protein sequences and the location of potential cTP cleavage sites. An n-terminal chloroplast targeting signal peptide of 65 amino acids was identified. Primers AthHpaIL fwd (SEQ ID NO:71) and AthHpaIL rev (SEQ ID NO:72) and plasmid DNA of pKR1478-At4g10750 (SEQ ID NO:51) were used to PCR amplify a fragment of the At4g10750 transcript that corresponds to the processed, plastid-localized At4g10750 gene product. PCR products were cloned into pGEM®-T Easy to give pGEM®-T At4g10750 (SEQ ID NO:73).

pGEM®-T At4g10750 was digested with NcoI SalI. A restriction fragment of 890 bp was gel-purified and ligated to NcoI SalI linearized plasmid DNA of pET28a (Novagen/EMD4Biosciences, NJ, USA) to give pET28a At4g10750 (SEQ ID NO:74). The amino acid sequence of the At4g10750 gene product including a c-terminal pET28A-derived hexa-histidine tag are set forth as SEQ ID NO:75.

The amino acid sequence of soy HpaIL protein derived from Glyma09g21760 was analyzed using ChloroP (supra). An n-terminal chloroplast targeting signal peptide of 60 amino acids was identified. Primers Soy HpaIL fwd (SEQ ID NO:76) and Soy HpaIL rev (SEQ ID NO:77) and plasmid of applicants EST clone sfp1n.pk022.m19 were used to PCR amplify a fragment of the Glyma09g21760 transcript that corresponds to the processed, plastid-localized Glyma09g21760 gene product. PCR products were cloned into pGEM®-T Easy to give pGEM®-T Glyma09g21760 (SEQ ID NO:78).

pGEM®-T Glyma09g21760 was digested with NdeI SacI. A restriction fragment of 884 bp was gel-purified and ligated to NdeI SacI-linearized plasmid DNA of pET29a (Novagen/EMD4Biosciences, NJ, USA) to give pET29a Glyma09g21760 (SEQ ID NO:79). The amino acid sequence of the Glyma09g21760 gene product including a c-terminal pET29a-derived hexa-histidine tag are set forth as SEQ ID NO:80.

The amino acid sequence of the rice HpaIL protein derived from Os09g36030 was analyzed using ChloroP (supra). An n-terminal chloroplast targeting signal peptide of 47 amino acids was identified. Primers Rice HpaIL fwd (SEQ ID NO:81) and Rice HpaIL rev (SEQ ID NO:82) and plasmid applicants EST clone rdi2c.pk005.c17 were used to PCR amplify a fragment of the Os09g36030 transcript that corresponds to the processed, plastid-localized Os09g36030 gene product. PCR products were cloned into pGEM®-T Easy to give pGEM®-T Os09g36030 (SEQ ID NO:83).

pGEM®-T Os09g36030 was digested with NcoI and HindIII. A restriction fragment of 884 bp was gel-purified and ligated to NcoI HindIII-linearized plasmid DNA of pET28a (supra) to give pET28a Os09g36030 (SEQ ID NO:84). The amino acid sequence of the Os09g36030 gene product including a c-terminal pET28a-derived hexa-histidine tag are set forth as SEQ ID NO:85.

A bacterial HpaI gene was amplified from genomic DNA of *Pseudomonas putida* strain DSM 12585 described in: Muheim, A.; Lerch, K. Towards a high-yield bioconversion of ferulic acid to vanillin. Applied Microbiology and Biotechnology (1999), 51(4), 456-461. Briefly, a PCR product of 900 bp was PCR amplified with primer PP FWD (SEQ ID NO:86) and PP REV (SEQ ID NO:87) and genomic DNA of *Pseudomonas putida* strain DSM 12585. PCR products were cloned into pCR Blunt-II-Topo (Invitrogen, USA) according to manufacturer instructions to give pCR blunt HpaI PP (SEQ ID NO:88). Recombinant plasmid DNA was sequenced. The DNA and deduced amino acid sequence of HpaI ORF of *Pseudomonas putida* strain DSM 12585 henceforth named HpaI PP is set forth as SEQ ID NO:89 and SEQ ID NO:90, respectively. A DNA fragment for expression cloning into pET29a was generated. Briefly, a PCR product of 800 bp was PCR amplified with primer HpaI PP FWD (SEQ ID NO:91) and HpaI PP REV (SEQ ID NO:92) and plasmid DNA of pCR blunt HpaI PP (SEQ ID NO:88). PCR products were cloned into pGEM®-T Easy vector to give pGEM®-T HpaI PP vector (SEQ ID NO:93).

pGEM®-T HpaI PP (SEQ ID NO:93) was digested with NdeI SacI. A restriction fragment of 800 bp was gel-purified and ligated to NdeI SacI-linearized plasmid DNA of pET29a (supra) to give pET29a HpaI PP (SEQ ID NO:94). The amino acid sequence of the HpaI PP gene product including a c-terminal pET29a-derived hexa-histidine tag are set forth as SEQ ID NO:95.

Competent *E. coli* cells of strain Rosetta™ (DE3)pLysS (Novagen/EMD4Biosciences, NJ, USA) were transformed with pET28a At4g10750 (SEQ ID NO:74) using electroporation. Four 500 mL flasks each containing 250 mL of LB medium supplemented with 50 µg/mL kanamycin were inoculated with *E. coli* cells of strain Rosetta™ (DE3)pLysS carrying pET28a At4g10750 (SEQ ID NO:74). The culture was grown at 37° C. until a cell density ($OD_{\lambda=600\ nm}$) of 0.6 was achieved. The cultures were cooled to 16° C. on ice. Isopropyl β-D-1-thiogalactopyranoside (IPTG) was then added to a final concentration of 0.1 mM followed by continued culture at 16° C. for 36 h. Cells were harvested by centrifugation (5000×g, 10 min) and resuspended in 30 mL of 50 mM Hepes/KOH (pH 8), 0.5M NaCl, 10 mM Imidazole, 2 mM DTT. The cell suspension was passed twice through a French press and cleared by centrifugation (30000×g, 20 min, 4° C.). The enzyme extract (30 mL) was buffer-exchanged in 2.5 mL aliquots on PD10 columns (GE Healthcare, USA) into 50 mM Hepes/KOH (pH 8), 500 mM NaCl, 20 mM Imidazole. Buffer-exchanged extract (40 mL) was loaded onto a HiTrap chelating HP column with 5 mL gel bed volume (GE Healthcare, Uppsala, Sweden). The HiTrap chelating HP column had previously been charged with $Ni^{2+}$ according to manufacturer instructions. The column was developed at a flow rate of 2 mL/min at 22° C. as follows: Solvent A (50 mM Hepes/KOH (pH 8), 500 mM NaCl, 20 mM Imidazole), Solvent B (50 mM Hepes/KOH (pH 8), 500 mM NaCl, 500 mM Imidazole); 0-20 min 0% B, 20-35 min 20% B, 35-50 min (linear gradient) 20-100% B, 50-55 min 100% B, 55-60 min 0% B. 1.5 mL fractions were collected from beginning to end of the linear imidazole gradient. 10 µL fractions were analyzed by sodium dodecyl sulfate polyacrylamide gel electrophoresis (PAGE). A protein of 33 kDA was observed in fractions 11-15 indicating that the expected 6xhistagged At4g10750 protein variant (SEQ ID NO:75) was present in the *E. coli* extract and could be purified by $Ni^{2+}$ affinity column chromatography.

Bacterial HpaI enzymes catalyze aldol addition reactions using substrates such as pyruvate and acetaldehyde leading to the formation of 4-hydroxy-2-oxovalerate with said substrates (Wang, Weijun; Baker, Perrin; Seah, Stephen Y. K. Comparison of Two Metal-Dependent Pyruvate Aldolases Related by Convergent Evolution: Substrate Specificity, Kinetic Mechanism, and Substrate Channeling. Biochemistry (2010), 49(17), 3774-3782).

Next, $Ni^{2+}$ affinity column chromatography fractions of protein extracts of *E. coli* expressing pET28a At4g10750 were assayed for this activity. Briefly 20 μL of fraction 9 with undetectable levels of 6xhistagged At4g10750 protein and fraction 12 with very high levels of said protein were combined with 80 mM pyruvate, 80 mM acetaldehyde, 100 mM Hepes, KOH, pH 8, 2 mM $CoCl_2$ in a final volume of 100 μL. Reactions were incubated at 27° C. for 20 min. 20 μL of HCl was added, samples were incubated at 100° C. for 3 min, quenched on ice, cleared by centrifugation an analyzed by HPLC as follows.

10 μL of sample were separated using an HP Agilent 1100 HPLC system equipped with an Aminex fast-acid analysis ion-exchange column, 100 mm length, 7.8 mm diameter (Biorad, Hercules, Calif., USA). The column was developed at a flow rate of 2 mL $min^{-1}$ using 10 mM $H_2SO_4$ and reaction products were detected using a diode array UV detector at λ=210 nm and λ=230 nm.

Reaction products of fraction 9 contained two predominant peaks with retention times of 2.1 and 2.6 min. The former shared its retention time with an unmodified pyruvate standard. The latter absorbed more strongly at λ=230 nm. Applicants assume that the latter compound is the lactone of γ-hydroxy γ-methyl α-keto glutarate. It is well established that two molecules of pyruvate can spontaneously react at alkaline pH to form one molecule of γ-hydroxy γ-methyl α-keto glutarate (Formation of γ-hydroxy-γ-methylglutamic acid from a common impurity in pyruvic acid. Goldfine, H Biochimica et Biophysica Acta (1960), 40:557-9). Compared to reaction products obtained with fraction 9, products obtained with fraction 12 showed a great reduction in pyruvate and putative γ-hydroxy γ-methyl α-keto glutarate-lactone peaks and a new, predominant peak with a retention time of 6.06 min that absorbed strongly at λ=230 nm. Subsequent enzyme assays revealed that the production of the compound with a retention time of 6.06 min was only observed when both pyruvate and acetaldehyde were provided to recombinantly produced At4g10750 protein. Applicants conclude that, most likely, the peak with a retention time of 6.06 min is the lactonized product of an aldol addition reaction between acetaldehyde and pyruvate catalyzed by the At4g10750 protein. The expected molecule would be the lactone of 4-hydroxy-2-oxovalerate with an expected MW of 114.1. Large scale synthesis of the compound with a retention time of 6.06 min was performed as follows. The final reaction mixture contained 80 mM pyruvate, 80 mM acetaldehyde, 100 mM Hepes/KOH pH 8, 2 mM $CoCl_2$, and 100 μL of fraction 12, corresponding to approximately 50 μg of recombinantly-produced At4g10750 protein in a final volume of 5 mL. The reaction was incubated at 27° C. for 16h. One mL of concentrated HCl was added and the reaction mixture was heated to 100° C. for 3 min. The aqueous reaction was extracted three times with 5 mL of ethylacetate. 100 μL of the ethylacetate extract was dried down using $N_2$ and resuspended in 100 μL of water. Ten μL were analyzed by HPLC as described above. When analyzed by HPLC the ethyl acetate extracted reaction products contained one predominant peak with a retention time of 6.06 min. The entire ethylacetate extract was dried down and analyzed by GC/electron impact MS. Reaction products were dissolved in 3 mL of dichloromethane and 1 μL was subjected to GC/MS analysis. Reaction products were separated on a DB-5MS column using an Agilent 6890 GC using the following temperature program: initial temperature 70° C., hold 4 min, temperature ramp 10° C. $min^{-1}$ to 300° C., hold 7 min. Mass spectroscopy was performed using a Hewlett-Packard mass selective detector according to manufacturer instructions with ms source and ms quad temperatures at −150° C. and 230° C., respectively. Total icon current chromatograms revealed the presence of two peaks with retention times of 6.5 and 6.9 min. Mass spectra of booth peaks reveal the presence of a molecular ion with a mass to charge ratio (m/z) of 114.1. MS spectra of both peaks contain fragments with m/z of 86.2, 58.1 and 43.1. 6.5 and 6.8 min peaks show differences in the mass spectra the former contains two fragments with m/z of 69.2 and 99.0, whereas the latter instead contains two fragments with m/z of 71.2 and 97.2. A second preparative synthesis of the compound with a retention time of 6.06 min was performed in a volume of 5 mL exactly as described above. Reaction products were resuspended in $D_2O$ and analyzed by $^1H$ NMR (500 MHz). The following shifts were identified: chem. shift $^1H$=5.25 (=C—H), 2.07 (—$CH_2$—), 1.60 (—CH), 1.50 (C—H), 1.23 (—$CH_3$). In summary, both GC/MS and $^1H$ NMR analysis of reaction products generated with recombinantly-produced At4g10750 enzyme, pyruvate and acetaldehyde reveal that the reaction product with a HPLC retention time of 6.06 min is a mixture of 5-Methyl-dihydro-furan-2,3-dione and the enol form of this molecule which is 3-Hydroxy-5-methyl-5H-furan-2-one. These molecules can also be referred to as 4-hydroxy-2-oxovalerate-lactone and the enol isomer of said molecule.

Purification of Recombinantly-Produced At4g10750 Protein

Four 500 mL flasks each containing 333 mL of LB medium supplemented with 50 μg/mL kanamycin were inoculated with *E. coli* cells of strain Rosetta™ (DE3)pLysS carrying pET28a At4g10750 (SEQ ID NO:74). The culture was grown at 37° C. until a cell density ($OD_{\lambda=600\ nm}$) of 0.6 was achieved. The cultures were cooled to 16° C. on ice. Isopropyl β-D-1-thiogalactopyranoside (IPTG) was then added to a final concentration of 0.1 mM followed by continued culture at 16° C. for 36 h. Cells were harvested by centrifugation (5000×g, 10 min) and recombinantly-produced At4g10750 protein was purified from the cell pellet as described above. 10 μL aliquots of $Ni^{2+}$ affinity chromatography fractions were analyzed by SDS page and coomassie staining. Fractions containing the recombinantly produced At4g10750 protein were pooled and buffer exchanged into 20 mM Hepes/NaOH, pH8, 5% w/v glycerol and stored at −80° C. The protein concentration of the buffer exchanged $Ni^{2+}$ affinity chromatography fractions was measured at 3.5 mg $mL^{-1}$ using the Bradford assay (Biorad, USA) according to manufacturer instructions. Visual inspection of overloaded Coomassie-stained gels indicated that the purified recombinant At4g10750 protein was at least 95% pure. In summary approximately 36 mg of recombinantly produced At4g10750 protein were purified from 750 mg of total protein of *E. coli* cells carrying pET28a At4g10750.

Purification of Recombinantly-Produced Glyma09d21760 Protein

Four 500 mL flasks each containing 333 mL of LB medium supplemented with 50 μg/mL kanamycin were inoculated with *E. coli* cells of strain Rosetta™ (DE3) pLysS carrying pET29a Glyma09g21760 (SEQ ID NO:79). The culture was grown at 37° C. until a cell density ($OD_{\lambda=600\ nm}$) of 0.6 was achieved. The cultures were cooled to 16° C. on ice. Isopropyl β-D-1-thiogalactopyranoside (IPTG) was then added to a final concentration of 0.1 mM followed by continued culture at 16° C. for 36 h. Cells were harvested by centrifugation (5000×g, 10 min) and recombinantly produced Glyma09g21760 protein was purified from the cell pellet as described above. 10 uL aliquots of $Ni^{2+}$ affinity chromatography fractions were analyzed by SDS page and coomassie staining. Fractions containing the recombinantly-produced Glyma09g21760 protein were pooled and buffer exchanged into 20 mM Hepes/NaOH, pH8, 5% w/v glycerol and stored at −80° C. The protein concentration of the buffer exchanged $Ni^{2+}$ affinity chromatography fractions was measured at 1.96 mg $mL^{-1}$ using the Bradford assay (Biorad, USA) according to manufacturer instructions. Visual inspection of overloaded Coomassie-stained gels indicated that the purified recombinant Glyma09g21760 protein was at least 95% pure. In summary approximately 20 mg of recombinantly produced Glyma09g21760 protein were purified from 750 mg of total protein of E. coli cells carrying pET29a Glyma09g21760.

Purification of Recombinantly Produced Os09q36030 Protein

Six 500 mL flasks each containing 333 mL of LB medium supplemented with 50 μg/mL kanamycin were inoculated with E. coli cells of strain Rosetta™ (DE3) pLysS carrying pET28a Os09g36030 (SEC ID NO:84). The culture was grown at 37° C. until a cell density $(OD_{\lambda=600\ nm})$ of 0.6 was achieved. The cultures were cooled to 16° C. on ice. Isopropyl β-D-1-thiogalactopyranoside (IPTG) was then added to a final concentration of 0.1 mM followed by continued culture at 16° C. for 36 h. Cells were harvested by centrifugation (5000×g, 10 min) and recombinantly-produced Os09g36030 protein was purified from the cell pellet as described above. 10 pt aliquots of $Ni^{2+}$ affinity chromatography fractions were analyzed by SOS page and coomassie staining. Fractions containing the recombinantly-produced Os09g36030 protein were pooled and buffer exchanged into 20 mM Hepes/NaOH, pH8, 5% w/v glycerol and stored at −80° C. The buffer exchanged $Ni^{2+}$ affinity chromatography fractions were further concentrated to a final volume of 1.3 mL using Centriprep YM 10 centrifugal concentrators (Millipore, USA) according to manufacturer instructions. The protein concentration of the buffer exchanged $Ni^{2+}$ affinity chromatography fractions was measured at 1.9 mg $mL^{-1}$ using the Bradford assay (Biorad, USA) according to manufacturer instructions. Visual inspection of overloaded Coomassie-stained gels indicated that the purified recombinant Os09g36030 protein was at least 50% pure. In summary, approximately 2.5 mg of recombinantly-produced Os09g36030 protein were purified from 900 mg of total protein of E. coli cells carrying pET28a Os09g36030.

Purification of Recombinantly Produced P. putida HpaI Protein

Five 500 mL flasks each containing 333 mL of LB medium supplemented with 50 μg/mL kanamycin were inoculated with E. coli cells of strain Rosett™ (DE3) pLysS carrying pET29a HpaI PP (SEQ ID NO:94). The culture was grown at 37° C. until a cell density $(OD_{\lambda=600\ nm})$ of 0.6 was achieved. The cultures were cooled to 16° C. on ice. Isopropyl β-D-1-thiogalactopyranoside (IPTG) was then added to a final concentration of 0.1 mM followed by continued culture at 16° C. for 36 h. Cells were harvested by centrifugation (5000×g, 10 min) and recombinantly-produced P. putida HpaI protein was purified from the cell pellet as described above. 10 μL aliquots of $Ni^{2+}$ affinity chromatography fractions were analyzed by SDS page and coomassie staining. Fractions containing the recombinantly-produced P. putida HpaI protein were pooled and buffer exchanged and stored at −80° C. The protein concentration of the buffer exchanged $Ni^{2+}$ affinity chromatography fractions was measured at 6.75 mg $mL^{-1}$ using the Bradford assay (Biorad, USA) according to manufacturer instructions. Visual inspection of overloaded Coomassie-stained gels indicated that the purified recombinant P. putida HpaI protein was at least 95% pure. In summary approximately 110 mg of recombinantly-produced P. putida HpaI protein were purified from 1200 mg of total protein of E. coli cells carrying pET29a HpaI PP.

HPLC-Based Quantitation of the Lactone of 4-hydroxy-2-oxovalerate

100 μL samples (50 mM Hepes/KOH, pH8) with pyruvate concentrations of 2.5, 5, 7.5, 10, 15 and 20 mM were supplemented with 20 μL of concentrated HCl, heated to 100° C. for 3 min, quenched in ice water. 30 μL of each sample was separated by HPLC on a Fast Acid on exchange column as described above. The peak areas of pyruvate (RT 2.1 min, I=210 nm) and putatively identified γ-hydroxy γ-methyl α-keto glutarate-lactone (RT 2.1 min, I=230 nm) were recorded. The sum of both peak areas is henceforth referred to as Peak area Pyr−E. The same range of pyruvate concentrations (2.5-20 mM) was incubated with 2.5 μg of recombinantly-produced P. putida HpaI protein in a final volume of 100 μL in the presence of 50 mM Hepes/KOH, pH8, 20 mM acetaldehyde, 2 mM $CoCl_2$ for 15 min at 27° C. Enzyme reactions were supplemented with 20 μL of concentrated HCl, heated to 100° C. for 3 min, quenched in ice water. 30 μL of each sample was separated by HPLC on a Fast Acid ion exchange column as described above. Peak areas of pyruvate (RT 2.1 min, λ=210 nm), putatively identified γ-hydroxy γ-methyl α-keto glutarate-lactone (RT 2.1 min, λ=230 nm) and the lactone of 4-hydroxy-2-oxovalerate (RT 6.1 min, λ=230 nm) were recorded. The sum of peak areas of pyruvate (RT 2.1 min, λ=210 nm) and putatively identified γ-hydroxy γ-methyl α-keto glutarate-lactone (RT 2.1 min, λ=230 nm) derived from the enzyme treated sample is henceforth referred to as Peak area Pyr+E. The concentration of pyruvate consumed by the HpaI enzyme-catalyzed aldol condensation of pyruvate and acetaldehyde in each enzyme-treated sample can be calculated using the following formula: [Pyr consumed]=(Peak area Pyr−E−Peak area Pyr+E)/Peak area Pyr−E×[Pyr $T_0$]. In each HpaI-enzyme-treated sample [Pyr consumed] calculated in this manner is equal to the concentration of 4-hydroxy-2-oxovalerate-lactone produced.

TABLE 28

Values for HPLC-based quantitation of 4-hydroxy-2-oxovalerate-lactone

| μM pyruvate [Pyr $T_0$] | μM pyruvate consumed [Pyr consumed] | peak area 4-hydroxy-2-oxovalerate-lactone (mAU, λ = 230 nm) |
|---|---|---|
| 2500 | 392 | 1260 |
| 5000 | 549 | 2069 |
| 7500 | 799 | 2981 |
| 10000 | 1220 | 3774 |
| 15000 | 1279 | 4582 |
| 20000 | 1751 | 5562 |

A calibration curve for quantitation of 4-hydroxy-2-oxovalerate-lactone was established using the values shown in column 2 and 3 of Table 28. According to this calibration curve the concentration (μM) of 4-hydroxy-2-oxovalerate-lactone in a given HPLC sample can be calculated by multiplying the peak area of RT 6.1 at λ=230 with 0.2993.

Divalent Ion Requirements of a Bacterial HpaI Enzyme and Plant-Derived HpaIL Enzymes Divalent ion requirements of recombinantly-produced At4g10750 enzyme were determined as follows: 25 μg of recombinantly-produced At4g10750 protein were incubated in the presence of no added divalent ion or 2 mM of either $CoCl_2$, $CaCl_2$, $MnCl_2$ or $MgCl_2$ in a final volume of 100 μL of 10 mM pyruvate, 10 mM acetaldehyde. 50 mM Hepes/KOH, pH 8.0. Enzyme assays were performed at 27° C. for 20 min. Reactions were stopped by addition of 20 μL concentrated HCl and incubation at 100° C. for 3 min. Reaction products were separated by HPLC and 4-hydroxy-2-oxovalerate-lactone production was quantitated using the previously described calibration curve.

TABLE 29

Divalent ion requirements of recombinantly-produced At4g10750 enzyme

| ion | specific activity (pmol $s^{-1}$ $mg^{-1}$ protein) |
|---|---|
| no on | 152.5 |
| $Co^{2+}$ | 2866.6 |
| $Ca^{2+}$ | 647.0 |
| $Mn^{2+}$ | 2832.3 |
| $Mg^{2+}$ | 5489.6 |

Divalent on requirements of recombinantly-produced Glyma09g21760 enzyme were determined as follows: 50 μg of recombinantly-produced Glyma09g21760 protein were incubated in the presence of no added divalent on or 2 mM of either $CoCl_2$, $CaCl_2$, $MnCl_2$ or $MgCl_2$ in a final volume of 100 μL of 10 mM pyruvate, 10 mM acetaldehyde. 50 mM Hepes/KOH, pH 8.0. Enzyme assays were performed at 27° C. for 20 min. Reactions were stopped by addition of 20 μL concentrated HCl and incubation at 100° C. for 3 min. Reaction products were separated by HPLC and 4-hydroxy-2-oxovalerate-lactone production was quantitated using the previously described calibration curve.

TABLE 30

Divalent ion requirements of recombinantly produced Glyma09g21760 enzyme

| ion | specific activity (pmol $s^{-1}$ $mg^{-1}$ protein) |
|---|---|
| no ion | 0.0 |
| $Co^{2+}$ | 986.1 |
| $Ca^{2+}$ | 847.1 |
| $Mn^{2+}$ | 1155.8 |
| $Mg^{2+}$ | 1890.2 |

Divalent on requirements of recombinantly-produced Os09g36030 enzyme were determined as follows: 25 μg of recombinantly-produced Os09g36030 protein were incubated in the presence of no added divalent ion or 2 mM of either $CoCl_2$, $CaCl_2$, $MnCl_2$ or $MgCl_2$ in a final volume of 100 μL of 10 mM pyruvate, 10 mM acetaldehyde and 50 mM Hepes/KOH, pH 8.0. Enzyme assays were performed at 27° C. for 18 min. Reactions were stopped by addition of 20 μL concentrated HCl and incubation at 100° C. for 3 min. Reaction products were separated by HPLC and 4-hydroxy-2-oxovalerate-lactone production was quantitated using the previously described calibration curve.

TABLE 31

Divalent ion requirements of recombinantly produced Os09g36030 enzyme

| ion | specific activity (pmol $s^{-1}$ $mg^{-1}$ protein) |
|---|---|
| no ion | 89.3 |
| $Co^{2+}$ | 1344.4 |
| $Ca^{2+}$ | 119.7 |
| $Mn^{2+}$ | 1669.1 |
| $Mg^{2+}$ | 667.6 |

Divalent on requirements of recombinantly-produced *P. putida* HpaI enzyme 2.5 μg of recombinantly-produced *P. putida* HpaI protein were incubated in the presence of no added divalent ion or 2 mM of either $CoCl_2$, $CaCl_2$, $MnCl_2$ or $MCl_2$ in a final volume of 100 μL of 10 mM pyruvate, 10 mM acetaldehyde and 50 mM Hepes/KOH, pH 7.25. Enzyme assays were performed at 27° C. for 15 min. Reactions were stopped by addition of 20 μL concentrated HCl and incubation at 100° C. for 3 min. Reaction products were separated by HPLC and 4-hydroxy-2-oxovalerate-lactone production was quantitated using the previously described calibration curve.

TABLE 32

Divalent ion requirements of recombinantly-produced *P. putida* HpaI enzyme

| ion | specific activity (pmol $s^{-1}$ $mg^{-1}$ protein) |
|---|---|
| no ion | 5155.7 |
| $Co^{2+}$ | 95304.8 |
| $Ca^{2+}$ | 6282.4 |
| $Mn^{2+}$ | 62343.5 |
| $Mg^{2+}$ | 38026.4 | pH Requirements of a Bacterial HpaI Enzyme and Plant-Derived HpaIL Enzymes pH requirements of recombinantly produced At4g10750 enzyme were determined as follows: 25 μg of recombinantly produced At4g10750 protein were incubated in the presence 100 mM Bis-Tris-Propane/HCl covering a pH range form 7-9.5 in 0.25 pH point increments in a final volume of 100 μL of 10 mM pyruvate, 10 mM acetaldehyde and 2 mM $MgCl_2$. Enzyme assays were performed at 27° C. for 10 min. Reactions were stopped by addition of 20 μL concentrated HCl and incubation at 100° C. for 3 min. Reaction products were separated by HPLC and 4-hydroxy-2-oxovalerate-lactone production was quantitated using the previously described calibration curve.

TABLE 33 pH requirements of recombinantly produced At4g10750 enzyme

| pH | specific activity (pmol $s^{-1}$ $mg^{-1}$ protein) |
|---|---|
| 7 | 955.3 |
| 7.25 | 1121.4 |
| 7.5 | 1206.1 |
| 7.75 | 1354.3 |
| 8 | 1380.5 |
| 8.25 | 1375.8 |
| 8.75 | 1254.8 |
| 9.25 | 1129.3 |
| 9.5 | 1077.2 | pH requirements of recombinantly produced Glyrna09g21760 enzyme were determined as follows: 25 µg of recombinantly produced Glyma09g21760protein were incubated in the presence 100 mM Bis-Tris-Propane/HCl covering a pH range form 7-9.5 in 0.25 pH point increments in a final volume of 100 µL of 10 mM pyruvate, 10 mM acetaldehyde and 2 mM MgCl$_2$, Enzyme assays were performed at 27° C. for 10 min. Reactions were stopped by addition of 20 µL concentrated HCl and incubation at 100° C. for 3 min. Reaction products were separated by HPLC and 4-hydroxy-2-oxovalerate-lactone production was quantitated using the previously described calibration curve.

TABLE 34 pH requirements of recombinantly produced Glyma09g21760 enzyme

| pH | specific activity (pmol s$^{-1}$ mg$^{-1}$ protein) |
|---|---|
| 7 | 883.1 |
| 7.25 | 1151.0 |
| 7.5 | 1442.3 |
| 7.75 | 2161.3 |
| 8 | 2321.3 |
| 8.25 | 2273.5 |
| 8.5 | 2046.1 |
| 8.75 | 1894.0 |
| 9 | 1882.3 |
| 9.25 | 1813.0 |
| 9.5 | 1798.5 | pH requirements of recombinantly produced Os09g36030 enzyme were determined as follows: 25 µg of recombinantly produced Os09g36030 protein were incubated in the presence 100 mM Bis-Tris-Propane/HCl covering a pH range form 7-9.5 in 0.25 pH point increments in a final volume of 100 µL of 10 mM pyruvate, 10 mM acetaldehyde and 2 mM MnCl$_2$. Enzyme assays were performed at 27° C. for 10 min. Reactions were stopped by addition of 20 µL concentrated HCl and incubation at 100° C. for 3 min. Reaction products were separated by HPLC and 4-hydroxy-2-oxovalerate-lactone production was quantitated using the previously described calibration curve.

TABLE 35 pH requirements of recombinantly produced Os09g36030 enzyme

| pH | specific activity (pmol s$^{-1}$ mg$^{-1}$ protein) |
|---|---|
| 7 | 271.6 |
| 7.25 | 265.9 |
| 7.5 | 337.7 |
| 7.75 | 406.9 |
| 8 | 461.8 |
| 8.25 | 486.4 |
| 8.5 | 456.2 |
| 8.75 | 408.7 |
| 9 | 382.4 |
| 9.25 | 251.4 |
| 9.5 | 144.8 | pH requirements of recombinantly produced *P. putida* HpaI enzyme were determined as follows: 2.5 of recombinantly produced *P. putida* HpaI protein were incubated in the presence 100 mM MES/KOH or Bis-Tris-Propane/HCl covering a pH range of 4.5-8 in a final volume of 100 µL of 10 mM pyruvate, 100M acetaldehyde and 2 mM CoCl$_2$. Enzyme assays were performed at 27° C. for 15 min. Reactions were stopped by addition of 20 µL concentrated HCl and incubation at 100° C. for 3 min. Reaction products were separated by HPLC and 4-hydroxy-2-oxovalerate-lactone production was quantitated using the previously described calibration curve.

TABLE 36 pH requirements of recombinantly produced *P. putida* HpaI enzyme

| pH | Buffer | specific activity (pmol s$^{-1}$ mg$^{-1}$ protein) |
|---|---|---|
| 4.5 | MES | 31770.7 |
| 5 | MES | 39220.9 |
| 5.5 | MES | 48823.0 |
| 6 | MES | 46708.5 |
| 6.5 | MES | 54927.3 |
| 7 | HEPES | 75939.2 |
| 7.25 | HEPES | 78898.3 |
| 7.5 | HEPES | 73605.4 |
| 7.75 | HEPES | 68430.3 |
| 8 | HEPES | 65166.7 |

Analysis of Kinetic Properties of Recombinantly Produced At4g10750 Enzyme with Pyruvate Kinetic properties of recombinantly produced At4g10750 enzyme with the substrate pyruvate were determined as follows. Formation of 4-hydroxy-2-oxovalerate was assayed using 25 µg of recombinantly produced At4g10750 enzyme in a final volume of 100 microliters in the presence of 50 mM Hepes/KOH pH8, 10 mM acetaldehyde, 2 mM MgCl$_2$ and pyruvate concentrations ranging from 1 to 32 mM. Assays were performed for 15 min at 27° C. 4-hydroxy-2-oxovalerate was quantitated by HPLC analysis as described above. Under these conditions, apparent Km and Vmax values were 3.79 mM and 3139 pmol s$^{-1}$ mg$^{-1}$ protein, respectively. These parameters were determined using the Eadie-Hofstee plot by plotting velocity/substrate concentration versus velocity using velocities determined at pyruvate concentrations of 2, 4, 6, 8 and 10 mM. In this plot an estimate of the Km is provided as the slope of the line representing the linear regression curve through the points and the Vmax by the intercept of the regression curve with the y axis.

Analysis of Kinetic Properties of Recombinantly Produced At4g10750 Enzyme with Acetaldehyde Kinetic properties of recombinantly produced At4g10750 enzyme with the substrate acetaldehyde were determined as follows. Formation of 4-hydroxy-2-oxovalerate was assayed using 25 µg of recombinantly produced At4g10750 enzyme in a final volume of 100 µL in the presence of 50 mM Hepes/KOH pH8, 10 mM pyruvate, 2 mM MgCl$_2$ and acetaldehyde concentrations ranging from 1 to 32 mM. Assays were performed for 15 min at 27° C. 4-hydroxy-2-oxovalerate was quantitated by HPLC analysis as described above. Under these conditions, apparent Km and Vmax values were 1.37 mM and 2253 pmol s$^{-1}$ mg$^{-1}$ protein, respectively. These parameters were determined using the Eadie-Hofstee plot by plotting velocity/substrate concentration versus velocity using velocities determined at pyruvate concentrations 1, 2, 4, 6, 8, 10, 12, 14, 16, 18 and 32 mM. In this plot an estimate of the Km is provided as the slope of the line representing the linear regression curve through the points and the Vmax by the intercept of the regression curve with the y axis.

Analysis of Kinetic Properties of Recombinantly Produced Glyma09g21760 Enzyme with Pyruvate Kinetic properties of recombinantly produced Glyma09g21760 enzyme with the substrate pyruvate were determined as follows. Formation of 4-hydroxy-2-oxovalerate was assayed using 25 µg of recombinantly produced At4g10750 enzyme in a final volume of 100 µL in the presence of 50 mM Hepes/KOH pH8, 10 mM acetaldehyde, 2 mM $MgCl_2$ and pyruvate concentrations ranging from 1 to 32 mM. Assays were performed for 15 min at 27° C. 4-hydroxy-2-oxovalerate was quantitated by HPLC analysis as described above. Under these conditions, apparent Km and Vmax values were 13.2 mM and 7853 pmol $s^{-1}$ $mg^{-1}$ protein, respectively. These parameters were determined using the Hofstee plot by plotting velocity/substrate concentration versus velocity using velocities determined at pyruvate concentrations of 2, 4, 6, 8, 10, 12, 14, 16, 18 and 32. In this plot an estimate of the Km is provided as the slope of the line representing the linear regression curve through the points and the Vmax by the intercept of the regression curve with the y axis.

Analysis of Kinetic Properties of Recombinantly Produced Glyma09g21760 Enzyme with Acetaldehyde Kinetic properties of recombinantly produced Glyma09g21760 enzyme with the substrate pyruvate were determined as follows. Formation of 4-hydroxy-2-oxovalerate was assayed using 25 µg of recombinantly produced Glyma09g21760 enzyme in a final volume of 100 µL in the presence of 50 mM Hepes/KOH pH8, 10 mM pyruvate, 2 mM $MgCl_2$ and acetaldehyde concentrations ranging from 1 to 32 mM. Assays were performed for 15 min at 27° C. 4-hydroxy-2-oxovalerate was quantitated by HPLC analysis as described above. Under these conditions, apparent Km and Vmax values were 1.74 mM and 5366 pmol $s^{-1}$ $mg^{-1}$ protein, respectively. These parameters were determined using the Hofstee plot by plotting velocity/substrate concentration versus velocity using velocities determined at pyruvate concentrations 2,4,6,8,10,12,14,16,18 and 32 mM. In this plot an estimate of the Km is provided as the slope of the line representing the linear regression curve through the points and the Vmax by the intercept of the regression curve with the y axis.

Analysis of Kinetic Properties of Recombinantly Produced Os09g36030 Enzyme with Pyruvate Kinetic properties of recombinantly produced Os09g36030 enzyme with the substrate pyruvate were determined as follows. Formation of 4-hydroxy-2-oxovalerate was assayed using 25 µg of recombinantly produced Os09g36030 enzyme in a final volume of 100 µL in the presence of 50 mM Hepes/KOH pH8, 10 mM acetaldehyde, 2 mM $MnCl_2$ and pyruvate concentrations ranging from 1 to 32 mM. Assays were performed for 15 min at 27° C. 4-hydroxy-2-oxovalerate was quantitated by HPLC analysis as described above. Under these conditions, apparent Km and Vmax values were 7.5 mM and 2104 pmol $s^{-1}$ $mg^{-1}$ protein, respectively. These parameters were determined using the Hofstee plot by plotting velocity/substrate concentration versus velocity using velocities determined at pyruvate concentrations of 1, 2, 4, 6, 8, 10, 12, 14, 16, 18 and 32. In this plot an estimate of the Km is provided as the slope of the line representing the linear regression curve through the points and the Vmax by the intercept of the regression curve with the y axis.

Analysis of Kinetic Properties of Recombinantly Produced Os09g36030 Enzyme with Acetaldehyde Kinetic properties of recombinantly produced Os09g36030 enzyme with the substrate pyruvate were determined as follows. Formation of 4-hydroxy-2-oxovalerate was assayed using 25 µg of recombinantly produced Os09g36030 enzyme in a final volume of 100 µL in the presence of 50 mM Hepes/KOH, pH 7.25, 10 mM pyruvate, 2 mM $MgCl_2$ and acetaldehyde concentrations ranging from 1 to 32 mM. Assays were performed for 15 min at 27° C. 4-hydroxy-2-oxovalerate was quantitated by HPLC analysis as described above. Under these conditions, apparent Km and Vmax values were 1.48 mM and 1304 pmol $s^{-1}$ $mg^{-1}$ protein, respectively. These parameters were determined using the Hofstee plot by plotting velocity/substrate concentration versus velocity using velocities determined at pyruvate concentrations 1,2,4,6,8 and 10 mM. In this plot an estimate of the Km is provided as the slope of the line representing the linear regression curve through the points and the Vmax by the intercept of the regression curve with the y axis.

Analysis of Kinetic Properties of Recombinantly Produced P. putida HpaI Enzyme with Pyruvate Kinetic properties of recombinantly produced P. putida HpaI enzyme with the substrate pyruvate were determined as follows. Formation of 4-hydroxy-2-oxovalerate was assayed using 1.25 µg of recombinantly-produced P. putida HpaI enzyme in a final volume of 100 µL in the presence of 50 mM Hepes/KOH, pH 7.25, 10 mM acetaldehyde, 2 mM $CoCl_2$ and pyruvate concentrations ranging from 1 to 80 mM. Assays were performed for 15 min at 27° C. 4-hydroxy-2-oxovalerate was quantitated by HPLC analysis as described above. Under these conditions, apparent Km and Vmax values were 5.3 mM and 122866 pmol $s^{-1}$ $mg^{-1}$ protein, respectively. These parameters were determined using the Hofstee plot by plotting velocity/substrate concentration versus velocity using velocities determined at pyruvate concentrations of 1, 2, 4, 6, 8, 10, 12, 16, 20, 25, 30, 40, 60 and 80 mM, In this plot an estimate of the Km is provided as the slope of the line representing the linear regression curve through the points and the Vmax by the intercept of the regression curve with the y axis.

Analysis of Kinetic Properties of Recombinantly-Produced P. putida HpaI Enzyme with Acetaldehyde Kinetic properties of recombinantly produced P. putida HpaI enzyme with the substrate pyruvate were determined as follows. Formation of 4-hydroxy-2-oxovalerate was assayed using 1.25 µg of recombinantly produced P. putida HpaI enzyme in a final volume of 100 microliters in the presence of 50 mM Hepes/KOH, pH 7.25, 10 mM pyruvate, 2 mM $CoCl_2$ and acetaldehyde concentrations ranging from 1 to 80 mM. Assays were performed for 15 min at 27° C. 4-hydroxy-2-oxovalerate was quantitated by HPLC analysis as described above. Under these conditions, apparent Km and Vmax values were 2.98 mM and 93010 pmol $s^{-1}$ $mg^{-1}$ protein, respectively. These parameters were determined using the Eadie-Hofstee plot by plotting velocity/substrate concentration versus velocity using velocities determined at pyruvate concentrations of 1, 2, 4, 6, 8,10, 12, 16, 20, 25, 30, 40, 60 and 80 mM. In this plot an estimate of the Km is provided as the slope of the line representing the linear regression curve through the points and the Vmax by the intercept of the regression curve with the y axis.

Table 37 compares properties of a prokaryotic HpaI enzyme (P. putida HpaI) to that of HpaI-like enzyme of Arabidopsis (At4g10750) soybean (Glyma09g21760) and rice (Os09g36030).

Table 37 compares properties of a prokaryotic HpaI enzyme (P. putida HpaI) to that of HpaI-like enzyme of arabidopsis (At4g10750) soybean (Glyma09g21760) and rice (Os09g36030).

TABLE 37

Comparison of properties of a prokaryotic HpaI enzyme (P. putida HpaI) to that of Hpal-like enzyme of Arabidopsis (At4g10750) soybeans (Glyma09g21760) and rice (Os09g36030).

| enzyme/gene | pH optimum | preferred divalent ion |
|---|---|---|
| At4g10750 | 8 | Mg2+ |
| Glyma09g21760 | 8 | Mg2+ |

TABLE 37-continued

Comparison of properties of a prokaryotic HpaI enzyme (*P. putida* HpaI) to that of HpaI-like enzyme of Arabidopsis (At4g10750) soybeans (Glyma09g21760) and rice (Os09g36030).

| | | | |
|---|---|---|---|
| Os09g36030 | 8.25 | Mn2+ | |
| *P putida* HpaI | 7.25 | Co2+ | |

| enzyme/gene | v max (pmol s$^{-1}$ mg$^{-1}$ protein) | Kcat (s$^{-1}$) | Km pyruvate (mM) | Km acetaldehyde (mM) |
|---|---|---|---|---|
| At4g10750 | 3139 | 0.6 | 3.97 | 1.37 |
| Glyma09g21760 | 7853 | 1.6 | 13.18 | 1.74 |
| Os09g36030 | 2104 | 0.4 | 7.49 | 1.48 |
| *P putida* HpaI | 122886 | 22.4 | 5.29 | 2.98 |

| enzyme/gene | Kcat/Km (pyr) | Kcat/Km (acetaldehyde) |
|---|---|---|
| At4g10750 | 0.2 | 0.5 |
| Glyma09g21760 | 0.1 | 0.9 |
| Os09g36030 | 0.1 | 0.3 |
| *P putida* HpaI | 4.2 | 7.5 |

A DNA sequence encoding a variant of the processed, plastid localized At4g10750 protein in which arginine 83 (R83) is replaced by glycine (G83) was generated as follows: The n-terminal fragment of the gene was PCR amplified using PCR primers AthHpaIL fwd (SEQ ID NO:71) and AthHpaIL G83 rev (SEQ ID NO: 96) and plasmid DNA of pKR1478-At4g10750 (SEQ ID NO:53). The c-terminal fragment of the gene was PCR amplified using PCR primers AthHpaIL rev (SEQ ID NO:72) AthHpaIL G83 fwd (SEQ ID NO: 97) and plasmid DNA of pKR1478-At4g10750 (SEQ ID NO:53). PCR products of both reactions were combined and used as template in a PCR reactions with primers AthHpaIL fwd (SEQ ID NO:71) and AthHpaIL rev (SEQ ID NO:72). PCR products were cloned into pGEM®-T Easy to give pGEM®-T At4g10750-G83 (SEQ ID NO:98).

pGEM®-T At4g10750-G83 (SEQ ID NO:98) was digested with NcoI SalI. A restriction fragment of 890 bp was gel-purified and ligated to NcoI SalI-linearized plasmid DNA of pET28a to give pET28a At4g10750-G83 (SEQ ID NO: 99). The amino acid sequence of the At4g10750-G83 gene product including a c-terminal pET28A-derived hexa-histidine tag are set forth as SEQ ID NO:100.

100 mL flasks each containing 25 of LB medium supplemented with 50 µg/mL kanamycin were inoculated with *E. coli* cells of strain Rosetta™ (DE3) pLysS carrying either pET28a At4g10750 (SEQ ID NO:74) or pET28a At4g10750-G83 (SEQ ID NO:99). The cultures were grown at 37° C. until a cell density (OD$_{\lambda=600\,nm}$) of 0.6 was achieved. The cultures were cooled to 16° C. on ice. Isopropyl β-D-1-thiogalactopyranoside (IPTG) was then added to a final concentration of 0.1 mM followed by continued culture at 16° C. for 36 h. From each culture duplicate sample of 1.5 mL were harvested by centrifugation and resuspended in 200 µL of 50 mM Hepes/KOH pH8. 20 µL of toluene were added to each cell suspension. Toluene-treated cell suspensions were incubated at 37° C. for 20 min. Aldol addition enzyme activity of toluene-treated cell suspensions was assayed as follows. Enzyme assays consisted of 2 mM MgCl$_2$, 10 mM acetaldehyde, 10 mM pyruvate, 50 mM Hepes/KOH pH8 and 50 µL of toluene treated cell suspensions in a final volume of 100 µL. Enzyme assays were incubated at 27° C. for 20 min and stopped by addition of 20 µL of concentrated HCl followed by incubation at 100° C. Enzyme assays were cleared by centrifugation and 4-hydroxy-2-oxovalerate was quantitated by HPLC as described above. Table 38 shows that that there is a 14-fold reduction of aldol addition activity in *E. coli* cell suspensions transformed with pET28a At4g10750-G83 compared to *E. coli* cell suspensions transformed with pET28a At4g10750. SDS/PAGE analysis of protein extracts of both cultures showed similar levels of recombinantly produced protein.

TABLE 38

Aldol addition activity of *E. coli* cultures carrying pET28a At4g10750 or pET28a At4g10750-G83

| sample | aldol addition activity (nmol mL$^{-1}$ min$^{-1}$) |
|---|---|
| pET28a At4g10750 | 26.5 |
| pET28a At4g10750 | 26.7 |
| pET28a At4g10750-G83 | 1.9 |
| pET28a At4g10750-G83 | 1.8 |

Example 26

Expression of Plastid Targeted, Bacterial HpaI Enzymes in Developing Seed

The following example describes DNA constructs for plastid-targeted expression of bacterial HpaI enzymes in developing seed. Transgenic plants generated with these DNA constructs have altered composition of seed storage compounds such as oil, protein and carbohydrate.

A DNA sequence encoding a signal sequence for plastid targeting was PCR-amplified from pKR1478-At4g10750 using primers HpaILORF FWD (SEQ ID NO:11) and FUSION REV (SEQ ID NO: 101)

to give PCR product 1. A DNA sequence encoding the *P. putida* HpaI protein and a pET29a-derived c-terminal 6xHIS tag was amplified from plasmid DNA of pET29a HpaI PP (SEQ ID NO:94) using primers FUSION FWD: (SEQ ID NO: 102) and pET29a 3prime:

(SEQ ID NO: 103) to give PCR product 2. PCR products 1 and 2 were combined and used as template in a PCR reaction with HpaILORF FWD (SEQ ID NO:11) and pET29a 3prime (SEQ ID NO: 102). A PCR product of 1070 bp was extracted form agarose gels and cloned into the pCR®8/GW/TOPO® vector (Invitrogen) to give pCR8GW-plastid HpaI PP (SEQ ID NO:104). The ORF comprised of DNA sequences encoding plastid targeting signal, *P. putida* HpaI enzyme and pET29a-derived 6xHis tag was inserted in the sense orientation downstream of the GY1 promoter in binary plant transformation vector pKR1478 using GATEWAY® LR recombinase (Invitrogen, USA) using manufacturer instructions. The sequence of the resulting plasmid pKR1478-plastid HpaI PP is set forth as SEQ ID NO:105. The fusion protein expressed by this plant transformation vector is set forth as SEQ ID NO:106. It is comprised of plastid targeting signal of At4g10750, the catalytic domain of HpaI of *Pseudomonas putida* (DSM 12585) and a c-terminal pET29a-derived hexa-histidine tag. The plasmid was used for *agrobacterium*-mediated transformation of *Arabidopsis* plants as described in Example 4. Seed oil content of wt control plants and T1 plants generated with plasmid pKR1478-plastid HpaI PP can be measured by NMR as described in Example 2.

Example 27

Composition of cDNA Libraries: Isolation and Sequencing of cDNA Clones cDNA libraries representing mRNAs from various tissues of *Momordica charantia* (balsam pear), *Aclepsia syriaca* (milkweed), and *Tulipa gesnenana* (tulip) were prepared. The characteristics of the libraries are described below.

TABLE 39 cDNA Libraries from Tulip, milkweed, Balsam pear and mays

| Library | Tissue | Clone |
|---|---|---|
| etp1c | *Tulipa* (*Gesneriana*, Apeldoorn) stage 3 pistil | etp1c.pk001.g3:fis etp1c.pk003.b22:fis |
| mas1c | developing fibers of common milkweed stage 1 | mas1c.pk012.d9.f |
| fds1n | Balsam pear (*Momordica charantia*) developing seeds | fds1n.pk007.i18 |
| cfp2n | Maize Silk pollinated and unpollinated, pooled, Full-length enriched, normalized | cfp2n.pk070b11.fis1 | cDNA libraries may be prepared by any one of many methods available. For example, the cDNAs may be introduced into plasmid vectors by first preparing the cDNA libraries in UniZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res,* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred and Phrap (Ewing et al. (1998) *Genome Res.* 8:175-185; Ewing and Green (1998) *Genome Res.* 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen™ (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 28

Identification of cDNA Clones cDNA clones encoding HpaI-like polypeptides were identified by conducting BLAST® (Basic Local Alignment Search Tool; Altschul et al. (1993) *J. Mol. Biol.* 215:403-410; see also the explanation of the BLAST® search tool algorithm on the world wide web site for the National Center for Biotechnology Information at the National Library of Medicine of the National Institutes of Health) searches for similarity to sequences contained in the BLAST® search tool "nr" database (comprising all non-redundant GENBANK® database CDS translations, sequences derived from the 3-dimensional structure Brookhaven Protein Data Bank, the last major release of the SWISS-PROT protein sequence database, EMBL, and DDBJ databases). The cDNA sequences obtained as described in Example 6 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST BLAST® search tool are reported herein as "pLog" values, which represent the negative of the logarithm of the reported P-value. Accordingly, the greater the pLog value, the greater the likelihood that the cDNA sequence and the BLAST® search tool "hit" represent homologous proteins.

ESTs submitted for analysis are compared to the GEN-BANK® database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 6. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 29

Characterization of cDNA Clones Encoding HpaI-Like Polypeptides

The BLASTX search using the EST sequences from clones listed in Table xx revealed similarity of the polypeptides encoded by the cDNAs to HpaI-like polypeptide from *Arabidopsis* (At4g10750) corresponding to SEQ ID NO's:47), Shown in Table 40 are the percent identities results for the proteins encoded by individual ESTs ("EST"), the sequences of the entire cDNA inserts comprising the indicated cDNA clones ("FIS"), the sequences of contigs assembled from two or more EST, FIS or PCR sequences ("Contig"), or sequences encoding an entire or functional protein derived from an FIS or a contig ("CGS"):

TABLE 40

Percent Identity for HpaI-like Polypeptides

| Sequence | Status | NCBI GI No. | % identity |
| --- | --- | --- | --- |
| etp1c.pk001.g4:fis SEQ ID NO: 120 | FIS | 255587508 (*Ricinus communis*) SEQ ID NO: 109 | 53.6 |
| etp1c.pk003.b22:fis SEQ ID NO: 121 | FIS | 225426623 (*Vitis vinifera*) SEQ ID NO: 111 | 53.4 |
| mas1c.pk012.d9.f SEQ ID NO: 122 | FIS | 225426623 (*Vitis vinifera*) SEQ ID NO: 111 | 55.8 |
| fds1n.pk007.i18 SEQ ID NO: 123 | CGS | 225426623 (*Vitis vinifera*) SEQ ID NO: 111 | 54.0 |
| cfp2n.pk070b11.fis1 SEQ ID NO: 147 | CGS | 226510158 (*Zea mays*) SEQ ID NO: 33 | 99.7 |

Sequence alignments and percent identity calculations were performed using the MEGALIGN® computer program of the LASERGENE® bioinformatics computing suite software (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST® search tool scores and probabilities indicate that the nucleic acid fragments comprising the instant cDNA clones encode HpaI-like polypeptides.

What is claimed is:

1. A transgenic plant comprising a suppression DNA construct, which is capable of suppressing expression of an aldolase-encoding gene, the construct comprising at least one heterologous regulatory element operably linked to:
    (a) a polynucleotide encoding a polypeptide having an amino acid sequence of at least 95% sequence identity, based on the Clustal V method of alignment, when compared to SEQ ID NO: 31 or 49; or
    (b) a polynucleotide comprising at least 21 contiguous nucleotides of SEQ ID NO: 30 or 48; or
    (c) a full complement of the nucleic acid sequence of (a) or (b);
    wherein the suppression DNA construct is expressed in the plant to reduce endogenous aldolase activity and wherein seed of the plant has an increase in oil-content of at least 1%, on a dry-weight basis, when compared to a seed of a control plant not comprising said suppression DNA construct.

2. A transgenic seed comprising a suppression DNA construct, which is capable of suppressing expression of an aldolase-encoding gene, the construct comprising at least one heterologous regulatory element operably linked to:
    (a) a polynucleotide encoding a polypeptide having an amino acid sequence of at least 95% sequence identity, based on the Clustal V method of alignment, when compared to SEQ ID NO: 31 or 49;
    (b) a polynucleotide comprising at least 21 contiguous nucleotides of SEQ ID NO: 30 or 48; or
    (c) a full complement of the nucleic acid sequence of (a) or (b);
    wherein the suppression DNA construct is expressed in the seed to reduce endogenous aldolase activity and wherein the soybean seed has an increase in oil content of at least 1%, on a dry-weight basis when compared to a seed not comprising said suppression DNA construct.

3. A method for producing a transgenic plant, the method comprising:
    growing a transgenic plant regenerated from a plant cell transformed with a suppression DNA construct, which is capable of suppressing expression of an aldolase-encoding gene, the construct comprising at least one heterologous regulatory element operably linked to:
    (a) a polynucleotide encoding a polypeptide having an amino acid sequence of at least 95% sequence identity, based on the Clustal V method of alignment, when compared to SEQ ID NO: 31 or 49;
    (b) a polynucleotide comprising at least 21 contiguous nucleotides of SEQ ID NO: 30 or 48; or
    (c) the full-length complement of (a) or (b);
    wherein the suppression DNA construct is expressed in the seed to reduce endogenous aldolase activity in the transgenic plant; and wherein the transgenic plant produces a transgenic seed having an increase in oil content of at least 2%, on a dry-weight basis, as compared to a seed obtained from a non-transgenic plant.

4. The method of claim 3, wherein the DNA construct comprises:
    (a) a polynucleotide comprising at least 21 contiguous nucleotides of SEQ ID NO: 30 or 48; or
    (b) the full-length complement of (a);
wherein (a) or (b) is suppresses expression of an aldolase-encoding gene in the transgenic plant.

5. The transgenic plant obtained by the method of claim 3.

6. The transgenic plant obtained by the method of claim 4.

7. The transgenic plant of claim 1, which is a dicot plant.

8. The transgenic plant of claim 7, which is a soybean plant.

9. The transgenic seed of claim 2, which is a dicot seed.

10. The transgenic seed of claim 9, which is a soybean seed.

11. The transgenic plant of claim 1, wherein the at least one regulatory element is a seed-specific or seed-preferred promoter.

12. The transgenic seed of claim 2, wherein the at least one regulatory element is a seed-specific or seed-preferred promoter.

13. The method of claim 3, wherein the seed is a soybean seed, and wherein the method further comprises processing the transgenic seed to produce soybean oil or a soy protein product.

14. The method of claim 4, wherein the seed is a soybean seed, wherein the method further comprises processing the transgenic seed to produce soybean oil or a soy protein product.

15. The transgenic plant of claim 1, wherein the seed of the plant has an increase in oil content of at least 2%.

16. The transgenic seed of claim 2, wherein the increase in the oil content in the seed is at least 2%.

17. The transgenic plant of claim 1, wherein the seed of the plant has an increase in oil content of at least 5%.

18. The transgenic seed of claim 2, wherein the increase in the oil content in the seed is at least 5%.

19. The transgenic plant of claim 1, wherein the seed of the plant has an increase in oil content of at least 10%.

20. The transgenic seed of claim 2, wherein the increase in the oil content in the seed is at least 10%.

\* \* \* \* \*

SEQUENCE LISTING

<160> NUMBER OF SEQ ID NOS: 151

<210> SEQ ID NO 1
<211> LENGTH: 18491
<212> TYPE: DNA
<213> ORGANISM: Artificial Sequence
<220> FEATURE:
<223> OTHER INFORMATION: pHSbarEND2s activation tagging vector

<400> SEQUENCE: 1

```
catgaatcaa acaaacatac acagcgactt attcacacga gctcaaatta caacggtata      60
tatcctgccg tcgacaacca tggtctagac aggatcccg ggtaccgagc tcgaatttgc      120
aggtcgactg cgtcatccct tacgtcagtg gagatatcac atcaatccac ttgctttgaa      180
```

```
gacgtggttg gaacgtcttc ttttccacg atgctcctcg tgggtggggg tccatctttg    240
ggaccactgt cggcagaggc atcttgaacg atagcctttc ctttatcgca atgatggcat    300
ttgtaggtgc caccttcctt ttctactgtc cttttgatga agtgacagat agctgggcaa    360
tggaatccga ggaggtttcc cgatattacc ctttgttgaa aagtctcaat tgcccttggg    420
tcttctgaga ctgttgcgtc atcccttacg tcagtggaga tatcacatca atccacttgc    480
tttgaagacg tggttggaac gtcttctttt tccacgatgc tcctcgtggg tggggtcca    540 tctttgggac cactgtcggc agaggcatct tgaacgatag cctttccttt atcgcaatga    600
tggcatttgt aggtgccacc ttccttttct actgtccttt tgatgaagtg acagatagct    660
gggcaatgga atccgaggag gtttcccgat attaccctt tgttgaaaagt ctcagttaac    720 ccgcgatcct gcgtcatccc ttacgtcagt ggagatatca catcaatcca cttgcttgaa    780
agacgtggtt ggaacgtctt cttttccac gatgctcctc gtgggtgggg gtccatcttt    840
gggaccactg tcggcagagg catcttgaac gatagccttt cctttatcgc aatgatggca    900
tttgtaggtg ccaccttcct tttctactgt ccttttgatg aagtgacaga tagctgggca    960
atggaatccg aggaggtttc ccgatattac cctttgttga aaagtctcaa ttgcccttg    1020 gtcttctgag actgttgcgt catcccttac gtcagtggag atatcacatc aatccacttg    1080
ctttgaagac gtggttggaa cgtcttcttt tccacgatg ctcctcgtgg gtggggtcc    1140 atctttggga ccactgtcgg cagaggcatc ttgaacgata gcctttcctt tatcgcaatg    1200
atggcatttg taggtgccac cttccttttc tactgtcctt ttgatgaagt gacagatagc    1260
tgggcaatgg aatccgagga ggtttcccga tattaccctt tgttgaaaag tctcagttaa    1320
cccgcaattc actggccgtc gttttacaac gtcgtgactg ggaaaaccct ggcgttaccc    1380
aacttaatcg ccttgcagca catcccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctccccac tcctgcagtt cggggggcatg gatgcgcgga    1560 tagccgctgc tggtttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca tacaccaaaa aaatgctgca taattctcgg    1800
ggcagcaagt cggttacccg gccgccgtgc tggaccgggt tgaatggtgc ccgtaacttt    1860
cggtagagcg gacggccaat actcaacttc aaggaatctc acccatgcgc gccggcgggg    1920
aaccggagtt cccttcagtg aacgttatta gttcgccgct cggtgtgtcg tagatactag    1980
cccctggggc cttttgaaat tgaataaga tttatgtaat cagtctttta ggtttgaccg    2040
gttctgccgc ttttttaaaa attggatttg taataataaa acgcaattgt ttgttattgt    2100
ggcgctctat catagatgtc gctataaacc tattcagcac aatatattgt tttcatttta    2160
atattgtaca tataagtagt agggtacaat cagtaaattg aacggagaat attattcata    2220
aaaatacgat agtaacgggt gatatattca ttagaatgaa ccgaaaccgg cggtaaggat    2280
ctgagctaca catgctcagg ttttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
acctttcata gaaggcggcg gtggaatcga atctcgtga tggcaggttg ggcgtcgctt    2520
```

```
ggtcggtcat ttcgaacccc agagtcccgc tcagaagaac tcgtcaagaa ggcgatagaa    2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccggccac agtcgatgaa tccagaaaag cggccatttt ccaccatgat    2760
attcggcaag caggcatcgc catgggtcac gacgagatcc tcgccgtcgg gcatgccccc    2820
caattcactg gccgtcgttt tacaacgtcg tgactgggaa accctggcg ttacccaact    2880
taatcgcctt gcagcacatc cccctttcgc cagctggcgt aatagcgaag aggcccgcac    2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg    3120
acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga atgtgcgcg gaaccccat ttgtttattt ttctaaatac attcaaatat    3360
gtatccgctc atgagacaat aaccctgata atgcttcaa taatattgaa aaggaagag    3420
tatgagtatt caacatttcc gtgtcgccct tattcccttt tttgcggcat tttgccttcc    3480
tgttttgct cacccagaaa cgctggtgaa agtaaaagat gctgaagatc agttgggtgc    3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgcttttt gcacaacatg ggggatcatg taactcgcct    3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt catttttaat ttaaaaggat ctaggtgaag atcctttttg ataatctcat    4380
gaccaaaatc ccttaacgtg agttttcgtt ccactgagcg tcagacccg tagaaaagat    4440
caaaggatct tcttgagatc ctttttttct gcgcgtaatc tgctgcttgc aaacaaaaaa    4500
accaccgcta ccagcggtgg tttgtttgcc ggatcaagag ctaccaactc tttttccgaa    4560
ggtaactggc ttcagcagag cgcagatacc aaatactgtc cttctagtgt agccgtagtt    4620
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacggggggt tcgtgcacac agcccagctt    4800
ggagcgaacg acctacaccg aactgagata cctacagcgt gagcattgag aaagcgccac    4860
gcttcccgaa gggagaaagg cggacaggta tccggtaagc ggcagggtcg gaacaggaga    4920
```

```
gcgcacgagg gagcttccag ggggaaacgc ctggtatctt tatagtcctg tcgggtttcg    4980
ccacctctga cttgagcgtc gattttgtg atgctcgtca ggggggcgga gcctatggaa     5040
aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
gctcactcat taggcacccc aggctttaca ctttatgctt ccggctcgta tgttgtgtgg    5400
aattgtgagc ggataacaat ttcacacagg aaacagctat gaccatgatt acgccaagct    5460
ttctaggggg ggggtaccga tctgagatcg gtaacgaaaa cgaacgggta gggatgaaaa    5520
cggtcggtaa cggtcggtaa aatacctcta ccgttttcat tttcatattt aacttgcggg    5580
acggaaacga aaacgggata taccggtaac gaaaacgaac gggataaata cggtaatcga    5640
aaaccgatac gatccggtcg ggttaaagtc gaaatcggac gggaaccggt attttttgttc   5700 ggtaaaatca cacatgaaaa catatattca aaacttaaaa acaaatataa aaaattgtaa    5760
acacaagtct taatgatcac tagtggcgcg cctaggagat ctcgagtagg gataacaggg    5820
taatacatag ataaaatcca tataaatctg gagcacacat agtttaatgt agcacataag    5880
tgataagtct tgggctcttg gctaacataa gaagccatat aagtctacta gcacacatga    5940
cacaatataa agtttaaaac acatattcat aatcacttgc tcacatctgg atcacttagc    6000
atgctacagc tagtgcaata ttagacactt tccaatattt ctcaaacttt tcactcattg    6060
caacggccat tctcctaatg acaaattttt catgaacaca ccattggtca atcaaatcct    6120
ttatctcaca gaaacctttg taaaataaat ttgcagtgga atattgagta ccagatagga    6180
gttcagtgag atcaaaaaac ttcttcaaac acttaaaaag agttaatgcc atcttccact    6240
cctcggcttt aggacaaatt gcatcgtacc tacaataatt gacatttgat taattgagaa    6300
tttataatga tgcacatgtac aacaattgag acaaacatac ctgcgaggat cacttgtttt    6360
aagccgtgtt agtgcaggct tataatataa ggcatccctc aacatcaaat aggttgaatt    6420
ccatctagtt gagacatcat atgagatccc tttagattta tccaagtcac attcactagc    6480
acacttcatt agttcttccc actgcaaagg agaagatttt acagcaagaa caatcgcttt    6540
gattttctca attgttcctg caattacagc caagccatcc tttgcaacca agttcagtat    6600
gtgacaagca caccttcacat gaaagaaagc accatcacaa actagatttg aatcagtgtc    6660
ctgcaaatcc tcaattatat cgtgcacagc tacttcattt gcactagcat tatccaaaga    6720
caaggcaaac aattttttct caatgttcca cttaaccatg attgcagtga aggtttgtga    6780
taacctttgg ccagtgtggc gcccttcaac atgaaaaaag ccaacaattc ttttttggag    6840
acaccaatca tcatcaatcc aatggatggt gacacacatg tatgacttat tttgacaaga    6900
tgtccacata tccatagttg tactgaagcg agactgaaca tcttttagtt ttccatacaa    6960
cttttctttt tcttccaaat acaaatccat gatatatttt ctagcagtga cacgggactt    7020
tattggaaag tgagggcgca gagacttaac aaactcaaca aagtactcat gttctacaat    7080
attgaaagga tattcatgca tgattattgc caaatgaagc ttctttaggc taaccacttc    7140
atcgtactta taaggctcaa tgagattat gtctttgcca tgatccttttt cacttttttag    7200 acacaactga cctttaacta aactatgtga tgttctcaag tgatttcgaa atccgcttgt    7260
```

```
tccatgatga ccctcagccc tatacttagc cttgcaatta ggaaagttgc aatgtcccca    7320
tacctgaacg tatttctttc catcgacctc cacttcaatt tccttcttgg tgaaatgctg    7380
ccatacatcc gatgtgcact tctttgccct cttctgtggt gcttcttctt cgggttcagg    7440
ttgtggctgt ggttgtggtt ctggttgtgg ttgtggttgt ggttgtggtt catgaacaat    7500
agccatatca tcttgactcg gatctgtagc tgtaccattt gcattactac tgcttacact    7560
ctgaataaaa tgcctctcgg cctcagctgt tgatgatgat ggtgatgtgc ggccacatcc    7620
atgcccacgc gcacgtgcac gtacattctg aatccgacta aagaggctt cagcttttct     7680
tttcaaccct gttataaaca gattttttcgt attattctac agtcaatatg atgcttccca   7740
atctacaacc aattagtaat gctaatgcta ttgctactgt ttttctaata tataccttga    7800
gcatatgcag agaatacgga atttgttttg cgagtagaag gcgctcttgt ggtagacatc    7860
aacttggcca atcttatggc tgagcctgag ggaggattat ttccaaccgg aggcgtcatc    7920
tgaggaatgg agtcgtagcc ggctagccga agtggagagc agagccctgg acagcaggtg    7980
ttcagcaatc agcttggtgc tgtactgctg tgacttgtga gcacctggac ggctggacag    8040
caatcagcag gtgttgcaga gccctggac agcacacaaa tgacacaaca gcttggtgca     8100
atggtgctga cgtgctgtac tgctaagtgc tgtgagcctg tgagcagccg tggagacagg    8160
gagaccgcgg atggccggat gggcgagcgc cgagcagtgg aggtctggag gaccgctgac    8220
cgcagatggc ggatgcggga tgggcggacc gcggatgggc gagcagtgga gtggaggtct    8280
gggcggatgg gcggaccgcg gcgcggatgg gcgagtcgcg agcagtggag tggagggcgg    8340
accgtggatg gcggcgtctg cgtccggcgt gccgcgtcac ggccgtcacc gcgtgtggtg    8400
cctggtgcag cccagcggcc ggccggctgg gagacaggga gagtcggaga gagcaggcga    8460
gagcgagacg cgtcgccggc gtcggcgtgc ggctggcggc gtccggactc cggcgtgggc    8520
gcgtggcggc gtgtgaatgt gtgatgctgt tactcgtgtg gtgcctggcc gcctgggaga    8580
gaggcagagc agcgttcgct aggtatttct tacatgggct gggcctcagt ggttatggat    8640
gggagttgga gctggccata ttgcagtcat cccgaattag aaaatacggt aacgaaacgg    8700
gatcatcccg attaaaaacg ggatcccggt gaaacggtcg ggaaactagc tctaccgttt    8760
ccgtttccgt ttaccgtttt gtatatcccg tttccgttcc gttttcgttt tttacctcgg    8820
gttcgaaatc gatcgggata aaactaacaa aatcggttat acgataacgg tcggtacggg    8880
attttcccat cctactttca tccctgagat tattgtcgtt tctttcgcag atcggtaccc    8940
ccccccctaga gtcgacatcg atctagtaac atagatgaca ccgcgcgcga taatttatcc    9000
tagtttgcgc gctatatttt gttttctatc gcgtattaaa tgtataattg cgggactcta    9060
atcataaaaa cccatctcat aaataacgtc atgcattaca tgttaattat tacatgctta    9120
acgtaattca acagaaatta tatgataatc atcgcaagac cggcaacagg attcaatctt    9180
aagaaacttt attgccaaat gtttgaacga tctgcttcga cgcactcctt ctttaggtac    9240
ggactagatc tcggtgacgg gcaggaccgg acggggcggt accggcaggc tgaagtccag    9300
ctgccagaaa cccacgtcat gccagttccc gtgcttgaag ccggccgccc gcagcatgcc    9360
gcgggggca tatccgagcg cctcgtgcat gcgcacgctc gggtcgttgg gcagcccgat     9420
gacagcgacc acgctcttga agccctgtgc ctccagggac ttcagcaggt gggtgtagag    9480
cgtggagccc agtcccgtcc gctggtggcg gggggagacg tacacggtcg actcggccgt    9540
ccagtcgtag gcgttgcgtg ccttccaggg gcccgcgtag gcgatgccgg cgacctcgcc    9600
gtccacctcg gcgacgagcc agggatagcg ctcccgcaga cggacgaggt cgtccgtcca    9660
```

```
ctcctgcggt tcctgcggct cggtacggaa gttgaccgtg cttgtctcga tgtagtggtt    9720
gacgatggtg cagaccgccg gcatgtccgc ctcggtggca cggcggatgt cggccgggcg    9780
tcgttctggg ctcatggatc tggattgaga gtgaatatga gactctaatt ggataccgag    9840
gggaatttat ggaacgtcag tggagcattt ttgacaagaa atatttgcta gctgatagtg    9900
accttaggcg acttttgaac gcgcaataat ggtttctgac gtatgtgctt agctcattaa    9960
actccagaaa cccgcggctg agtggctcct tcaatcgttg cggttctgtc agttccaaac   10020
gtaaaacggc ttgtcccgcg tcatcggcgg gggtcataac gtgactccct taattctccg   10080
ctcatgatcc ccgggtaccg agctcgaatt gcggctgagt ggctccttca atcgttgcgg   10140
ttctgtcagt tccaaacgta aaacggcttg tcccgcgtca tcggcggggg tcataacgtg   10200
actcccttaa ttctccgctc atgatcttga tccctgcgc catcagatcc ttggcggcaa   10260
gaaagccatc cagtttactt tgcagggctt cccaaccttaa ccagagggcg ccccagctgg   10320
caattccggt tcgcttgctg tatcgatatg gtggatttat cacaaatggg acccgccgcc   10380
gacagaggtg tgatgttagg ccaggacttt gaaaatttgc gcaactatcg tatagtggcc   10440
gacaaattga cgccgagttg acagactgcc tagcatttga gtgaattatg tgaggtaatg   10500
ggctacactg aattggtagc tcaaactgtc agtatttatg tatatgagtg tatattttcg   10560
cataatctca gaccaatctg aagatgaaat gggtatctgg gaatggcgaa atcaaggcat   10620
cgatcgtgaa gtttctcatc taagccccca tttggacgtg aatgtagaca cgtcgaaata   10680
aagatttccg aattagaata atttgtttat tgctttcgcc tataaatacg acggatcgta   10740
atttgtcgtt ttatcaaaat gtactttcat tttataataa cgctgcggac atctacattt   10800
ttgaattgaa aaaaaattgg taattactct ttcttttttct ccatattgac catcatactc   10860
attgctgatc catgtagatt tcccggacat gaagccattt acaattgaat atatcctgcc   10920
gccgctgccg ctttgcaccc ggtggagctt gcatgttggt ttctacgcag aactgagccg   10980
gttaggcaga taatttccat tgagaactga gccatgtgca ccttccccc aacacggtga   11040 gcgacgggc aacggagtga tccacatggg acttttaaac atcatccgtc ggatggcgtt   11100
gcgagagaag cagtcgatcc gtgagatcag ccgacgcacc gggcaggcgc gcaacacgat   11160
cgcaaagtat ttgaacgcag gtacaatcga gccgacgttc accgtcaccc tggatgctgt   11220
aggcataggc ttggttatgc cggtactgcc gggcctcttg cgggatatcg tccattccga   11280
cagcatcgcc agtcactatg gcgtgctgct agcgctatat gcgttgatgc aatttctatg   11340
cgcacccgtt ctcggagcac tgtccgaccg ctttggccgc cgcccagtcc tgctcgcttc   11400
gctacttgga gccactatcg actacgcgat catggcgacc acaccgtcc tgtggtccaa   11460 ccctccgct gctatagtgc agtcggcttc tgacgttcag tgcagccgtc ttctgaaaac   11520
gacatgtcgc acaagtccta agttacgcga caggctgccg ccctgccctt tcctggcgt   11580 tttcttgtcg cgtgttttag tcgcataaag tagaatactt gcgactagaa ccggagacat   11640
tacgccatga acaagagcgc cgccgctggc ctgctgggct atgcccgcgt cagcaccgac   11700
gaccaggact tgaccaacca acgggccgaa ctgcacgcgg ccggctgcac caagctgttt   11760
tccgagaaga tcaccggcac caggcgcgac cgcccgagc tggccaggat gcttgaccac   11820
ctacgccctg gcgacgttgt gacagtgacc aggctagacc gcctggcccg cagcacccgc   11880
gacctactgg acattgccga gcgcatccag gaggccggcg cgggcctgcg tagcctggca   11940
gagccgtggg ccgacaccac cacgccggcc ggccgcatgg tgttgaccgt gttcgccggc   12000
```

```
attgccgagt tcgagcgttc cctaatcatc gaccgcaccc ggagcgggcg cgaggccgcc   12060
aaggcccgag gcgtgaagtt tggcccccgc cctaccctca ccccggcaca gatcgcgcac   12120
gcccgcgagc tgatcgacca ggaaggccgc accgtgaaag aggcggctgc actgcttggc   12180
gtgcatcgct cgaccctgta ccgcgcactt gagcgcagcg aggaagtgac gcccaccgag   12240
gccaggcggc gcggtgcctt ccgtgaggac gcattgaccg aggccgacgc cctggcggcc   12300
gccgagaatg aacgccaaga ggaacaagca tgaaaccgca ccaggacggc caggacgaac   12360 cgttttcat taccgaagag atcgaggcgg agatgatcgc ggccgggtac gtgttcgagc   12420
```



```
attgccgagt tcgagcgttc cctaatcatc gaccgcaccc ggagcgggcg cgaggccgcc   12060
aaggcccgag gcgtgaagtt tggcccccgc cctaccctca ccccggcaca gatcgcgcac   12120
gcccgcgagc tgatcgacca ggaaggccgc accgtgaaag aggcggctgc actgcttggc   12180
gtgcatcgct cgaccctgta ccgcgcactt gagcgcagcg aggaagtgac gcccaccgag   12240
gccaggcggc gcggtgcctt ccgtgaggac gcattgaccg aggccgacgc cctggcggcc   12300
gccgagaatg aacgccaaga ggaacaagca tgaaaccgca ccaggacggc caggacgaac   12360 cgttttcat taccgaagag atcgaggcgg agatgatcgc ggccgggtac gtgttcgagc   12420
cgcccgcgca cgtctcaacc gtgcggctgc atgaaatcct ggccggtttg tctgatgcca   12480
agctggcggc ctggccggcc agcttggccg ctgaagaaac cgagcgccgc cgtctaaaaa   12540
ggtgatgtgt atttgagtaa aacagcttgc gtcatgcggt cgctgcgtat atgatgcgat   12600
gagtaaataa acaaatacgc aagggaacgc atgaagttat cgctgtactt aaccagaaag   12660
gcgggtcagg caagacgacc atcgcaaccc atctagcccg cgccctgcaa ctcgccgggg   12720
ccgatgttct gttagtcgat tccgatcccc agggcagtgc ccgcgattgg gcggccgtgc   12780
gggaagatca accgctaacc gttgtcggca tcgaccgccc gacgattgac cgcgacgtga   12840
aggccatcgg ccggcgcgac ttcgtagtga tcgacggagc gccccaggcg gcggacttgg   12900
ctgtgtccgc gatcaaggca gccgacttcg tgctgattcc ggtgcagcca agcccttacg   12960
acatatgggc caccgccgac ctggtggagc tggttaagca gcgcattgag gtcacggatg   13020
gaaggctaca gcggcctttt gtcgtgtcgc gggcgatcaa aggcacgcgc atcggcggtg   13080
aggttgccga ggcgctggcc gggtacgagc tgcccattct tgagtcccgt atcacgcagc   13140
gcgtgagcta cccaggcact gccgccgccg gcacaaccgt tcttgaatca gaacccgagg   13200
gcgacgctgc ccgcgaggtc caggcgctgg ccgctgaaat taaatcaaaa ctcatttgag   13260
ttaatgaggt aaagagaaaa tgagcaaaag cacaaacacg ctaagtgccg gccgtccgag   13320
cgcacgcagc agcaaggctg caacgttggc cagcctggca gacacgccag ccatgaagcg   13380
ggtcaacttt cagttgccgg cggaggatca caccaagctg aagatgtacg cggtacgcca   13440
aggcaagacc attaccgagc tgctatctga atacatcgcg cagctaccag agtaaatgag   13500
caaatgaata aatgagtaga tgaattttag cggctaaagg aggcggcatg gaaaatcaag   13560
aacaaccagg caccgacgcc gtggaatgcc ccatgtgtgg aggaacgggc ggttggccag   13620
gcgtaagcgg ctgggttgtc tgccggccct gcaatggcac tggaaccccc aagcccgagg   13680
aatcggcgtg agcggtcgca aaccatccgg cccggtacaa atcggcgcgg cgctgggtga   13740
tgacctggtg gagaagttga aggccgcgca ggccgcccag cggcaacgca tcgaggcaga   13800
agcacgcccc ggtgaatcgt ggcaagcggc cgctgatcga atccgcaaag aatcccggca   13860
accgccggca gccggtgcgc cgtcgattag gaagccgccc aagggcgacg agcaaccaga   13920
ttttttcgtt ccgatgctct atgacgtggg cacccgcgat agtcgcagca tcatggacgt   13980
ggccgttttc cgtctgtcga agcgtgaccg acgagctggc gaggtgatcc gctacgagct   14040
tccagacggg cacgtagagg tttccgcagg ccggccggc atggccagtg tgtgggatta   14100
cgacctggta ctgatggcgg tttcccatct aaccgaatcc atgaaccgat accgggaagg   14160
gaagggagac aagcccggcc gcgtgttccg tccacacgtt gcggacgtac tcaagttctg   14220
ccggcgagcc gatggcggaa agcagaaaga cgacctggta gaaacctgca ttcggttaaa   14280
caccacgcac gttgccatgc agcgtacgaa gaaggccaag aacggccgcc tggtgacggt   14340
atccgagggt gaagccttga ttagccgcta caagatcgta aagagcgaaa ccgggcggcc   14400
```

```
ggagtacatc gagatcgagc tagctgattg gatgtaccgc gagatcacag aaggcaagaa    14460
cccggacgtg ctgacggttc accccgatta cttttttgatc gatcccggca tcggccgttt    14520
tctctaccgc ctggcacgcc gcgccgcagg caaggcagaa gccagatggt tgttcaagac    14580
gatctacgaa cgcagtggca gcgccggaga gttcaagaag ttctgtttca ccgtgcgcaa    14640
gctgatcggg tcaaatgacc tgccggagta cgatttgaag gaggaggcgg ggcaggctgg    14700
cccgatccta gtcatgcgct accgcaacct gatcgagggc gaagcatccg ccggttccta    14760
atgtacggag cagatgctag ggcaaattgc cctagcaggg gaaaaaggtc gaaaaggtct    14820 cttcctgtg gatagcacgt acattgggaa cccaaagccg tacattggga accggaaccc    14880
gtacattggg aacccaaagc cgtacattgg gaaccggtca cacatgtaag tgactgatat    14940
aaaagagaaa aaaggcgatt tttccgccta aaactcttta aaacttatta aaactcttaa    15000
aacccgcctg gcctgtgcat aactgtctgg ccagcgcaca gccgaagagc tgcaaaaagc    15060
gcctacccct cggtcgctgc gctccctacg ccccgccgct tcgcgtcggc ctatcgcggc    15120
cgctggccgc tcaaaaatgg ctggcctacg gccaggcaat ctaccagggc gcggacaagc    15180
cgcgccgtcg ccactcgacc gccggcgccc acatcaaggc accctgcctc gcgcgtttcg    15240
gtgatgacgg tgaaaacctc tgacacatgc agctcccgga gacggtcaca gcttgtctgt    15300
aagcggatgc cgggagcaga caagcccgtc agggcgcgtc agcgggtgtt ggcgggtgtc    15360
ggggcgcagc catgacccag tcacgtagcg atagcggagt gtatactggc ttaactatgc    15420
ggcatcagag cagattgtac tgagagtgca ccatatgcgg tgtgaaatac cgcacagatg    15480
cgtaaggaga aaataccgca tcaggcgctc ttccgcttcc tcgctcactg actcgctgcg    15540
ctcggtcgtt cggctgcggc gagcggtatc agctcactca aaggcggtaa tacggttatc    15600
cacagaatca ggggataacg caggaaagaa catgtgagca aaaggccagc aaaaggccag    15660
gaaccgtaaa aaggccgcgt tgctggcgtt tttccatagg ctccgccccc ctgacgagca    15720
tcacaaaaat cgacgctcaa gtcagaggtg gcgaaacccg acaggactat aaagatacca    15780
ggcgtttccc cctggaagct ccctcgtgcg ctctcctgtt ccgaccctgc cgcttaccgg    15840
atacctgtcc gcctttctcc cttcgggaag cgtggcgctt tctcatagct cacgctgtag    15900
gtatctcagt tcggtgtagg tcgttcgctc caagctgggc tgtgtgcacg aaccccccgt    15960
tcagcccgac cgctgcgcct tatccggtaa ctatcgtctt gagtccaacc cggtaagaca    16020
cgacttatcg ccactggcag cagccactgg taacaggatt agcagagcga ggtatgtagg    16080
cggtgctaca gagttcttga agtggtggcc taactacggc tacactagaa ggacagtatt    16140
tggtatctgc gctctgctga agccagttac cttcggaaaa agagttggta gctcttgatc    16200
cggcaaacaa accaccgctg gtagcggtgg tttttttgtt tgcaagcagc agattacgcg    16260
cagaaaaaaa ggatctcaag aagatccttt gatcttttct acggggtctg acgctcagtg    16320
gaacgaaaac tcacgttaag ggattttggt catgagatta caaaaagga tcttcaccta    16380 gatccttta aattaaaaat gaagttttaa atcaatctaa agtatatatg agtaaacttg    16440
gtctgacagt taccaatgct taatcagtga ggcacctatc tcagcgatct gtctatttcg    16500
ttcatccata gttgcctgac tccccgtcgt gtagataact acgatacggg agggcttacc    16560
atctggcccc agtgctgcaa tgataccgcg agacccacgc tcaccggctc cagatttatc    16620
agcaataaac cagccagccg gaagggccga gcgcagaagt ggtcctgcaa ctttatccgc    16680
ctccatccag tctattaatt gttgccggga agctagagta agtagttcgc cagttaatag    16740
```

-continued

```
tttgcgcaac gttgttgcca ttgctacagg catcgtggtg tcacgctcgt cgtttggtat    16800
ggcttcattc agctccggtt cccaacgatc aaggcgagtt acatgatccc ccatgttgtg    16860
caaaaaagcg gttagctcct tcggtcctcc gatcgttgtc agaagtaagt tggccgcagt    16920
gttatcactc atggttatgg cagcactgca taattctctt actgtcatgc catccgtaag    16980
atgcttttct gtgactggtg agtactcaac caagtcattc tgagaatagt gtatgcggcg    17040
accgagttgc tcttgcccgg cgtcaacacg ggataatacc cgccacata gcagaacttt     17100 aaaagtgctc atcattggaa aagacctgca gggggggggg ggaaagccac gttgtgtctc    17160
aaaatctctg atgttacatt gcacaagata aaaatatatc atcatgaaca ataaaactgt    17220
ctgcttacat aaacagtaat acaaggggtg ttatgagcca tattcaacgg gaaacgtctt    17280
gctcgaggcc gcgattaaat tccaacatgg atgctgattt atatgggtat aaatgggctc    17340
gcgataatgt cgggcaatca ggtgcgacaa tctatcgatt gtatgggaag cccgatgcgc    17400
cagagttgtt tctgaaacat ggcaaaggta gcgttgccaa tgatgttaca gatgagatgg    17460
tcagactaaa ctggctgacg gaatttatgc ctcttccgac catcaagcat tttatccgta    17520
ctcctgatga tgcatggtta ctcaccactg cgatccccgg gaaaacagca ttccaggtat    17580
tagaagaata tcctgattca ggtgaaaata ttgttgatgc gctggcagtg ttcctgcgcc    17640
ggttgcattc gattcctgtt tgtaattgtc cttttaacag cgatcgcgta tttcgtctcg    17700
ctcaggcgca atcacgaatg aataacggtt tggttgatgc gagtgatttt gatgacgagc    17760
gtaatggctg gcctgttgaa caagtctgga agaaaatgca taagctttg ccattctcac    17820 cggattcagt cgtcactcat ggtgatttct cacttgataa ccttattttt gacgagggga    17880
aattaatagg ttgtattgat gttggacgag tcggaatcgc agaccgatac caggatcttg    17940
ccatcctatg gaactgcctc ggtgagtttt ctccttcatt acagaaacgg ctttttcaaa    18000
aatatggtat tgataatcct gatatgaata aattgcagtt tcatttgatg ctcgatgagt    18060
ttttctaatc agaattggtt aattggttgt aacactggca gagcattacg ctgacttgac    18120
gggacggcgg ctttgttgaa taaatcgaac ttttgctgag ttgaaggatc agatcacgca    18180
tcttcccgac aacgcagacc gttccgtggc aaagcaaaag ttcaaaatca ccaactggtc    18240
cacctacaac aaagctctca tcaaccgtgg ctccctcact ttctggctgg atgatgggc     18300 gattcaggcc tggtatgagt cagcaacacc ttcttcacga ggcagacctc agcgcccccc    18360
cccccctgca ggtcaattcg gtcgatatgg ctattacgaa gaaggctcgt gcgcggagtc    18420
ccgtgaactt tcccacgcaa caagtgaacc gcaccgggtt tgccggaggc catttcgtta    18480
aaatgcgcag c                                                         18491
```

```
<210> SEQ ID NO 2
<211> LENGTH: 50
<212> TYPE: DNA
<213> ORGANISM: Artificial Sequence
<220> FEATURE:
<223> OTHER INFORMATION: poly-linker

<400> SEQUENCE: 2
gatcactagt ggcgcgccta ggagatctcg agtagggata acagggtaat                 50

<210> SEQ ID NO 3
<211> LENGTH: 7085
<212> TYPE: DNA
<213> ORGANISM: artificial sequence
<220> FEATURE:
<223> OTHER INFORMATION: plasmid
```

<400> SEQUENCE: 3

```
cgcgccaagc ttttgatcca tgcccttcat ttgccgctta ttaattaatt tggtaacagt    60
ccgtactaat cagttactta tccttccccc atcataatta atcttggtag tctcgaatgc   120
cacaacactg actagtctct tggatcataa gaaaaagcca aggaacaaaa gaagacaaaa   180
cacaatgaga gtatcctttg catagcaatg tctaagttca taaaattcaa acaaaaacgc   240
aatcacacac agtggacatc acttatccac tagctgatca ggatcgccgc gtcaagaaaa   300
aaaaactgga ccccaaaagc catgcacaac aacacgtact cacaaggtg tcaatcgagc    360
agcccaaaac attccaccaac tcacccatc atgagccctc acatttgttg tttctaaccc   420
aacctcaaac tcgtattctc ttccgccacc tcattttgt ttatttcaac acccgtcaaa    480
ctgcatgcca ccccgtggcc aaatgtccat gcatgttaac aagacctatg actataaata   540
gctgcaatct cggcccaggt tttcatcatc aagaaccagt tcaatatcct agtacaccgt   600
attaaagaat ttaagatata ctgcggccgc aagtatgaac taaatgcat gtaggtgtaa    660
gagctcatgg agagcatgga atattgtatc cgaccatgta acagtataat aactgagctc   720
catctcactt cttctatgaa taaacaaagg atgttatgat atattaacac tctatctatg   780
caccttattg ttctatgata aatttcctct tattattata aatcatctga atcgtgacgg   840
cttatggaat gcttcaaata gtacaaaaac aaatgtgtac tataagactt tctaaacaat   900
tctaaccta gcattgtgaa cgagacataa gtgttaagaa gacataacaa ttataatgga    960
agaagtttgt ctccatttat atattatata ttacccactt atgtattata ttaggatgtt  1020
aaggagacat aacaattata aagagagaag tttgtatcca tttatatatt atatactacc  1080
catttatata ttatacttat ccacttattt aatgtctta taaggtttga tccatgatat   1140
ttctaatatt ttagttgata tgtatatgaa agggtactat ttgaactctc ttactctgta  1200
taaaggttgg atcatcctta aagtgggtct atttaatttt attgcttctt acagataaaa  1260
aaaaaattat gagttggttt gataaaatat tgaaggattt aaaataataa taaataacat  1320
ataatatatg tatataaatt tattataata taacatttat ctataaaaaa gtaaatattg  1380
tcataaatct atacaatcgt ttagccttgc tggacgaatc tcaattattt aaacgagagt  1440
aaacatattt gacttttgg ttatttaaca aattattatt taacactata tgaaattttt   1500
tttttatca gcaaagaata aaattaaatt aagaaggaca atggtgtccc aatccttata  1560
caaccaactt ccacaagaaa gtcaagtcag agacaacaaa aaaacaagca aaggaaattt  1620
tttaatttga gttgtcttgt ttgctgcata atttatgcag taaaacacta cacataaccc  1680
ttttagcagt agagcaatgg ttgaccgtgt gcttagcttc ttttatttta ttttttatc   1740
agcaaagaat aaataaaata aaatgagaca cttcagggat gtttcaacaa gcttggatct  1800
cctgcaggat ctggccggcc ggatctcgta cggatccgtc gacggcgcgc cgatcatcc   1860
ggatatagtt cctcctttca gcaaaaaacc cctcaagacc cgtttagagg ccccaagggg  1920
ttatgctagt tattgctcag cggtggcagc agccaactca gcttcctttc gggctttgtt  1980
agcagccgga tcgatccaag ctgtacctca ctattccttt gccctcggac gagtgctggg  2040
gcgtcggttt ccactatcgg cgagtacttc tacacagcca tcggtccaga cggccgcgct  2100
tctgcgggcg atttgtgtac gcccgacagt cccggctccg gatcggacga ttgcgtcgca  2160
tcgaccctgc gcccaagctg catcatcgaa attgccgtca accaagctct gatagagttg  2220
gtcaagacca atgcggagca tatacgcccg gagccgcggc gatcctgcaa gctccggatg  2280
```

```
cctccgctcg aagtagcgcg tctgctgctc catacaagcc aaccacggcc tccagaagaa    2340
gatgttggcg acctcgtatt gggaatcccc gaacatcgcc tcgctccagt caatgaccgc    2400
tgttatgcgg ccattgtccg tcaggacatt gttggagccg aaatccgcgt gcacgaggtg    2460
ccggacttcg gggcagtcct cggcccaaag catcagctca tcgagagcct gcgcgacgga    2520
cgcactgacg gtgtcgtcca tcacagtttg ccagtgatac catgggggat cagcaatcgc    2580
gcatatgaaa tcacgccatg tagtgtattg accgattcct tgcggtccga atgggccgaa    2640
cccgctcgtc tggctaagat cggccgcagc gatcgcatcc atagcctccg cgaccggctg    2700
cagaacagcg ggcagttcgg tttcaggcag gtcttgcaac gtgacaccct gtgcacggcg    2760
ggagatgcaa taggtcaggc tctcgctgaa ttccccaatg tcaagcactt ccggaatcgg    2820
gagcgcggcc gatgcaaagt gccgataaac ataacgatct ttgtagaaac catcggcgca    2880
gctatttacc cgcaggacat atccacgccc tcctacatcg aagctgaaag cacgagattc    2940
ttcgccctcc gagagctgca tcaggtcgga gacgctgtcg aacttttcga tcagaaactt    3000
ctcgacagac gtcgcggtga gttcaggctt ttccatgggt atatctcctt cttaaagtta    3060
aacaaaatta tttctagagg gaaaccgttg tggtctccct atagtgagtc gtattaattt    3120
cgcgggatcg agatcgatcc aattccaatc ccacaaaaat ctgagcttaa cagcacagtt    3180
gctcctctca gagcagaatc gggtattcaa caccctcata tcaactacta cgttgtgtat    3240
aacggtccac atgccggtat atacgatgac tggggttgta caaaggcggc aacaaacggc    3300
gttcccggag ttgcacacaa gaaatttgcc actattacag aggcaagagc agcagctgac    3360
gcgtacacaa caagtcagca aacagacagg ttgaacttca tccccaaagg agaagctcaa    3420
ctcaagccca agagctttgc taaggcccta acaagcccac caaagcaaaa agcccactgg    3480
ctcacgctag gaaccaaaag gcccagcagt gatccagccc caaaagagat ctcctttgcc    3540
ccggagatta caatggacga tttcctctat ctttacgatc taggaaggaa gttcgaaggt    3600
gaaggtgacg acactatgtt caccactgat aatgagaagg ttagcctctt caatttcaga    3660
aagaatgctg acccacagat ggttagagag gcctacgcag caggtctcat caagacgatc    3720
tacccgagta caatctccag ggagatcaaa taccttccca agaaggttaa agatgcagtc    3780
aaaagattca ggactaattg catcaagaac acagagaaag acatatttct caagatcaga    3840
agtactattc cagtatggac gattcaaggc ttgcttcata aaccaaggca agtaatagag    3900
attggagtct ctaaaaaggt agttcctact gaatctaagg ccatgcatgg agtctaagat    3960
tcaaatcgag gatctaacag aactcgccgt gaagactggc gaacagttca tacagagtct    4020
tttacgactc aatgacaaga gaaaatcttc gtcaacatg gtggagcacg acactctggt    4080
ctactccaaa aatgtcaaag atacagtctc agaagaccaa agggctattg agacttttca    4140
acaaaggata atttcgggaa acctcctcgg attccattgc ccagctatct gtcacttcat    4200 cgaaggaca gtagaaaagg aaggtggctc ctacaaatgc catcattgcg ataaaggaaa    4260
ggctatcatt caagatgcct ctgccgacag tggtcccaaa gatggacccc cacccacgag    4320
gagcatcgtg aaaaagaag acgttccaac cacgtcttca aagcaagtgg attgatgtga    4380
catctccact gacgtaaggg atgacgcaca atcccactat ccttcgcaag acccttcctc    4440
tatataagga agttcatttc atttggagag gacacgctcg agctcatttc tctattactt    4500
cagccataac aaaagaactc ttttctcttc ttattaaacc atgaaaaagc ctgaactcac    4560
cgcgacgtct gtcgagaagt ttctgatcga aaagttcgac agcgtctccg acctgatgca    4620
gctctcggag ggcgaagaat ctcgtgcttt cagcttcgat gtaggagggc gtggatatgt    4680
```

-continued

```
cctgcgggta aatagctgcg ccgatggttt ctacaaagat cgttatgttt atcggcactt    4740
tgcatcggcc gcgctcccga ttccggaagt gcttgacatt ggggaattca gcagagcct    4800 gacctattgc atctcccgcc gtgcacaggg tgtcacgttg caagacctgc ctgaaaccga    4860
actgcccgct gttctgcagc cggtcgcgga ggccatggat gcgatcgctg cggccgatct    4920
tagccagacg agcgggttcg gcccattcgg accgcaagga atcggtcaat acactacatg    4980
gcgtgatttc atatgcgcga ttgctgatcc ccatgtgtat cactggcaaa ctgtgatgga    5040
cgacaccgtc agtgcgtccg tcgcgcaggc tctcgatgag ctgatgcttt gggccgagga    5100
ctgccccgaa gtccggcacc tcgtgcacgc ggatttcggc tccaacaatg tcctgacgga    5160
caatggccgc ataacagcgg tcattgactg gagcgaggcg atgttcgggg attcccaata    5220
cgaggtcgca aacatcttct tctggaggcc gtggttggct tgtatggagc agcagacgcg    5280
ctacttcgag cggaggcatc cggagcttgc aggatcgccg cggctccggg cgtatatgct    5340
ccgcattggt cttgaccaac tctatcagag cttggttgac ggcaatttcg atgatgcagc    5400
ttgggcgcag ggtcgatgcg acgcaatcgt ccgatccgga gccgggactg tcgggcgtac    5460
acaaatcgcc cgcagaagcg cggccgtctg gaccgatggc tgtgtagaag tactcgccga    5520
tagtggaaac cgacgcccca gcactcgtcc gagggcaaag gaatagtgag gtacctaaag    5580
aaggagtgcg tcgaagcaga tcgttcaaac atttggcaat aaagtttctt aagattgaat    5640
cctgttgccg gtcttgcgat gattatcata taatttctgt tgaattacgt taagcatgta    5700
ataattaaca tgtaatgcat gacgttattt atgagatggg tttttatgat tagagtcccg    5760
caattataca tttaatacgc gatagaaaac aaaatatagc gcgcaaacta ggataaatta    5820
tcgcgcgcgg tgtcatctat gttactagat cgatgtcgaa tcgatcaacc tgcattaatg    5880
aatcggccaa cgcgcgggga gaggcggttt gcgtattggg cgctcttccg cttcctcgct    5940
cactgactcg ctgcgctcgg tcgttcggct gcggcgagcg gtatcagctc actcaaaggc    6000
ggtaatacgg ttatccacag aatcagggga taacgcagga agaacatgt gagcaaaagg    6060 ccagcaaaag gccaggaacc gtaaaaaggc cgcgttgctg gcgttttcc ataggctccg    6120 ccccccctgac gagcatcaca aaaatcgacg ctcaagtcag aggtggcgaa acccgacagg    6180
actataaaga taccaggcgt ttccccctgg aagctccctc gtgcgctctc ctgttccgac    6240
cctgccgctt accggatacc tgtccgcctt tctcccttcg ggaagcgtgg cgctttctca    6300
atgctcacgc tgtaggtatc tcagttcggt gtaggtcgtt cgctccaagc tgggctgtgt    6360
gcacgaaccc cccgttcagc ccgaccgctg cgccttatcc ggtaactatc gtcttgagtc    6420
caacccggta agacacgact tatcgccact ggcagcagcc actggtaaca ggattagcag    6480
agcgaggtat gtaggcggtg ctacagagtt cttgaagtgg tggcctaact acggctacac    6540
tagaaggaca gtatttggta tctgcgctct gctgaagcca gttaccttcg gaaaaagagt    6600
tggtagctct tgatccggca aacaaaccac cgctggtagc ggtggttttt ttgtttgcaa    6660
gcagcagatt acgcgcagaa aaaaggatc tcaagaagat cctttgatct tttctacggg    6720
gtctgacgct cagtggaacg aaaactcacg ttaagggatt ttggtcatga cattaaccta    6780
taaaaatagg cgtatcacga ggccctttcg tctcgcgcgt ttcggtgatg acggtgaaaa    6840
cctctgacac atgcagctcc cggagacggt cacagcttgt ctgtaagcgg atgccgggag    6900
cagacaagcc cgtcagggcg cgtcagcggg tgttggcggg tgtcggggct ggcttaacta    6960
tgcggcatca gagcagattg tactgagagt gcaccatatg gacatattgt cgttagaacg    7020
```

-continued

```
cggctacaat taatacataa ccttatgtat catacacata cgatttaggt gacactatag    7080
aacgg                                                                7085

<210> SEQ ID NO 4
<211> LENGTH: 5303
<212> TYPE: DNA
<213> ORGANISM: artificial sequence
<220> FEATURE:
<223> OTHER INFORMATION: plasmid

<400> SEQUENCE: 4
agcttggatc tcctgcagga tctgccggc cggatctcgt acggatccgt cgacggcgcg      60
cccgatcatc cggatatagt tcctcctttc agcaaaaaac ccctcaagac ccgtttagag    120
gccccaaggg gttatgctag ttattgctca gcggtggcag cagccaactc agcttccttt    180
cgggctttgt tagcagccgg atcgatccaa gctgtacctc actattcctt tgccctcgga    240
cgagtgctgg ggcgtcggtt ccactatcg gcgagtactt ctacacagcc atcggtccag     300
acggccgcgc ttctgcgggc gatttgtgta cgcccgacag tcccggctcc ggatcggacg    360
attgcgtcgc atcgaccctg cgcccaagct gcatcatcga aattgccgtc aaccaagctc    420
tgatagagtt ggtcaagacc aatgcggagc atatacgccc ggagccgcgg cgatcctgca    480
agctccggat gcctccgctc gaagtagcgc gtctgctgct ccatacaagc caaccacggc    540
ctccagaaga agatgttggc gacctcgtat tgggaatccc cgaacatcgc ctcgctccag    600
tcaatgaccg ctgttatgcg gccattgtcc gtcaggacat tgttggagcc gaaatccgcg    660
tgcacgaggt gccggacttc ggggcagtcc tcggcccaaa gcatcagctc atcgagagcc    720
tgcgcgacgg acgcactgac ggtgtcgtcc atcacagttt gccagtgata cacatgggga    780
tcagcaatcg cgcatatgaa atcacgccat gtagtgtatt gaccgattcc ttgcggtccg    840
aatgggccga accgctcgt ctggctaaga tcggccgcag cgatcgcatc catagcctcc     900
gcgaccggct gcagaacagc gggcagttcg gtttcaggca ggtcttgcaa cgtgacaccc    960
tgtgcacggc gggagatgca ataggtcagg ctctcgctga attccccaat gtcaagcact   1020
tccggaatcg ggagcgcggc cgatgcaaag tgccgataaa cataacgatc tttgtagaaa   1080
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact tctcgacaga cgtcgcggtg agttcaggct tttccatggg tatatctcct   1260
tcttaaagtt aaacaaaatt atttctagag gaaaccgtt gtggtctccc tatagtgagt    1320
cgtattaatt tcgcgggatc gagatcgatc caattccaat cccacaaaaa tctgagctta   1380
acagcacagt tgctcctctc agagcagaat cgggtattca cacccctcat atcaactact   1440
acgttgtgta taacggtcca catgccggta tatacgatga ctggggttgt acaaaggcgg   1500
caacaaacgg cgttcccgga gttgcacaca agaaatttgc cactattaca gaggcaagag   1560
cagcagctga cgcgtacaca acaagtcagc aaacagacag gttgaacttc atccccaaag   1620
gagaagctca actcaagccc aagagctttg ctaaggccct aacaagccca ccaaagcaaa   1680
aagcccactg gctcacgcta ggaaccaaaa ggcccagcag tgatccagcc ccaaaagaga   1740
tctcctttgc cccggagatt acaatggacg atttcctcta tctttacgat ctaggaagga   1800
agttcgaagg tgaaggtgac gacactatgt tcaccactga taatgagaag gttagcctct   1860
tcaatttcag aaagaatgct gacccacaga tggttagaga ggcctacgca gcaggtctca   1920
tcaagacgat ctacccgagt aacaatctcc aggagatcaa ataccttccc aagaaggtta   1980
```

```
aagatgcagt caaaagattc aggactaatt gcatcaagaa cacagagaaa gacatatttc   2040
tcaagatcag aagtactatt ccagtatgga cgattcaagg cttgcttcat aaaccaaggc   2100
aagtaataga gattggagtc tctaaaaagg tagttcctac tgaatctaag gccatgcatg   2160
gagtctaaga ttcaaatcga ggatctaaca gaactcgccg tgaagactgg cgaacagttc   2220
atacagagtc ttttacgact caatgacaag aagaaaatct tcgtcaacat ggtggagcac   2280
gacactctgg tctactccaa aaatgtcaaa gatacagtct cagaagacca aagggctatt   2340
gagacttttc aacaaggat aatttcggga aacctcctcg gattccattg cccagctatc   2400
tgtcacttca tcgaaaggac agtagaaaag gaaggtggct cctacaaatg ccatcattgc   2460
gataaaggaa aggctatcat tcaagatgcc tctgccgaca gtggtcccaa agatggaccc   2520
ccacccacga ggagcatcgt ggaaaaagaa gacgttccaa ccacgtcttc aaagcaagtg   2580
gattgatgtg acatctccac tgacgtaagg gatgacgcac aatcccacta tccttcgcaa   2640
gacccttcct ctatataagg aagttcattt catttggaga ggacacgctc gagctcattt   2700
ctctattact tcagccataa caaaagaact cttttctctt cttattaaac catgaaaaag   2760
cctgaactca ccgcgacgtc tgtcgagaag tttctgatcg aaaagttcga cagcgtctcc   2820
gacctgatgc agctctcgga gggcgaagaa tctcgtgctt tcagcttcga tgtaggaggg   2880
cgtggatatg tcctgcgggt aaatagctgc gccgatggtt tctacaaaga tcgttatgtt   2940
tatcggcact ttgcatcggc cgcgctcccg attccggaag tgcttgacat tggggaattc   3000
agcgagagcc tgacctattg catctcccgc cgtgcacagg gtgtcacgtt gcaagacctg   3060
cctgaaaccg aactgcccgc tgttctgcag ccggtcgcgg aggccatgga tgcgatcgct   3120
gcggccgatc ttagccagac gagcgggttc ggcccattcg gaccgcaagg aatcggtcaa   3180
tacactacat ggcgtgattt catatgcgcg attgctgatc cccatgtgta tcactggcaa   3240
actgtgatgg acgacaccgt cagtgcgtcc gtcgcgcagg ctctcgatga gctgatgctt   3300
tgggccgagg actgccccga agtccggcac ctcgtgcacg cggatttcgg ctccaacaat   3360
gtcctgacgg acaatggccg cataacagcg gtcattgact ggagcgaggc gatgttcggg   3420
gattcccaat acgaggtcgc caacatcttc ttctggaggc cgtggttggc ttgtatggag   3480
cagcagacgc gctacttcga gcggaggcat ccggagcttg caggatcgcc gcggctccgg   3540
gcgtatatgc tccgcattgg tcttgaccaa ctctatcaga gcttggttga cggcaatttc   3600
gatgatgcag cttgggcgca gggtcgatgc gacgcaatcg tccgatccgg agccgggact   3660
gtcgggcgta cacaaatcgc ccgcagaagc gcggccgtct ggaccgatgg ctgtgtagaa   3720
gtactcgccg atagtggaaa ccgacgcccc agcactcgtc cgagggcaaa ggaatagtga   3780
ggtacctaaa gaaggagtgc gtcgaagcag atcgttcaaa catttggcaa taaagtttct   3840
taagattgaa tcctgttgcc ggtcttgcga tgattatcat ataatttctg ttgaattacg   3900
ttaagcatgt aataattaac atgtaatgca tgacgttatt tatgagatgg gtttttatga   3960
ttagagtccc gcaattatac atttaatacg cgatagaaaa caaaatatag cgcgcaaact   4020
aggataaatt atcgcgcgcg gtgtcatcta tgttactaga tcgatgtcga atcgatcaac   4080
ctgcattaat gaatcggcca acgcgcgggg agaggcggtt tgcgtattgg gcgctcttcc   4140
gcttcctcgc tcactgactc gctgcgctcg gtcgttcggc tgcggcgagc ggtatcagct   4200
cactcaaagg cggtaatacg gttatccaca gaatcagggg ataacgcagg aaagaacatg   4260
tgagcaaaag gccagcaaaa ggccaggaac cgtaaaaagg ccgcgttgct ggcgtttttc   4320
```

| | |
|---|---|
| cataggctcc gcccccctga cgagcatcac aaaaatcgac gctcaagtca gaggtggcga | 4380 |
| aacccgacag gactataaag ataccaggcg tttcccctg gaagctccct cgtgcgctct | 4440 |
| cctgttccga ccctgccgct taccggatac ctgtccgcct ttctcccttc gggaagcgtg | 4500 |
| gcgctttctc aatgctcacg ctgtaggtat ctcagttcgg tgtaggtcgt tcgctccaag | 4560 |
| ctgggctgtg tgcacgaacc ccccgttcag cccgaccgct gcgccttatc cggtaactat | 4620 |
| cgtcttgagt ccaacccggt aagacacgac ttatcgccac tggcagcagc cactggtaac | 4680 |
| aggattagca gagcgaggta tgtaggcggt gctacagagt tcttgaagtg gtggcctaac | 4740 |
| tacggctaca ctagaaggac agtatttggt atctgcgctc tgctgaagcc agttaccttc | 4800 |
| ggaaaaagag ttggtagctc ttgatccggc aaacaaacca ccgctggtag cggtggtttt | 4860 |
| tttgtttgca agcagcagat tacgcgcaga aaaaaggat ctcaagaaga tcctttgatc | 4920 |
| ttttctacgg ggtctgacgc tcagtggaac gaaaactcac gttaagggat tttggtcatg | 4980 |
| acattaacct ataaaaatag gcgtatcacg aggccctttc gtctcgcgcg tttcggtgat | 5040 |
| gacggtgaaa acctctgaca catgcagctc ccggagacgg tcacagcttg tctgtaagcg | 5100 |
| gatgccggga gcagacaagc ccgtcagggc gcgtcagcgg gtgttggcgg gtgtcggggc | 5160 |
| tggcttaact atgcggcatc agagcagatt gtactgagag tgcaccatat ggacatattg | 5220 |
| tcgttagaac gcggctacaa ttaatacata accttatgta tcatacacat acgatttagg | 5280 |
| tgacactata gaacggcgcg cca | 5303 |

<210> SEQ ID NO 5
<211> LENGTH: 4140
<212> TYPE: DNA
<213> ORGANISM: artificial sequence
<220> FEATURE:
<223> OTHER INFORMATION: plasmid

<400> SEQUENCE: 5

| | |
|---|---|
| ggccgcattt cgcaccaaat caatgaaagt aataatgaaa agtctgaata agaatactta | 60 |
| ggcttagatg cctttgttac ttgtgtaaaa taacttgagt catgtacctt tggcggaaac | 120 |
| agaataaata aaaggtgaaa ttccaatgct ctatgtataa gttagtaata cttaatgtgt | 180 |
| tctacggttg tttcaatatc atcaaactct aattgaaact ttagaaccac aaatctcaat | 240 |
| cttttcttaa tgaaatgaaa aatcttaatt gtaccatgtt tatgttaaac accttacaat | 300 |
| tggttggaga ggaggaccaa ccgatgggac aacattggga gaaagagatt caatggagat | 360 |
| ttggatagga gaacaacatt cttttttcact tcaatacaag atgagtgcaa cactaaggat | 420 |
| atgtatgaga ctttcagaag ctacgacaac atagatgagt gaggtggtga ttcctagcaa | 480 |
| gaaagacatt agaggaagcc aaaatcgaac aaggaagaca tcaagggcaa gagacaggac | 540 |
| catccatctc aggaaaagga gctttgggat agtccgagaa gttgtacaag aaattttttg | 600 |
| gagggtgagt gatgcattgc tggtgacttt aactcaatca aaattgagaa agaaagaaaa | 660 |
| gggaggggc tcacatgtga atagaaggga acgggagaa tttacagtt ttgatctaat | 720 |
| gggcatccca gctagtggta acatattcac catgtttaac cttcacgtac gtctagagga | 780 |
| tcccccgggg tgcaggaatt cactggccgt cgttttacaa cgtcgtgact gggaaaaccc | 840 |
| tggcgttacc caacttaatc gccttgcagc acatccccct ttcgccagct ggcgtaatag | 900 |
| cgaagaggcc cgcaccgatc gcccttccca acagttgcgc agcctgaatg gcgaatggcg | 960 |
| cctgatgcgg tattttctcc ttacgcatct gtgcggtatt tcacaccgca tatggtgcac | 1020 |
| tctcagtaca atctgctctg atgccgcata gttaagccag ccccgacacc cgccaacacc | 1080 |

```
cgctgacgcg ccctgacggg cttgtctgct cccggcatcc gcttacagac aagctgtgac    1140
cgtctccggg agctgcatgt gtcagaggtt ttcaccgtca tcaccgaaac gcgcgagacg    1200
aaagggcctc gtgatacgcc tatttttata ggttaatgtc atgataataa tggtttctta    1260
gacgtcaggt ggcactttc ggggaaatgt gcgcggaacc cctatttgtt tatttttcta    1320
aatacattca aatatgtatc cgctcatgag acaataaccc tgataaatgc ttcaataata    1380
ttgaaaaagg aagagtatga gtattcaaca tttccgtgtc gcccttattc cttttttgc    1440 ggcattttgc cttcctgttt ttgctcaccc agaaacgctg gtgaaagtaa aagatgctga    1500
agatcagttg ggtgcacgag tgggttacat cgaactggat ctcaacagcg gtaagatcct    1560
tgagagtttt cgccccgaag aacgttttcc aatgatgagc acttttaaag ttctgctatg    1620
tggcgcggta ttatcccgta ttgacgccgg gcaagagcaa ctcggtcgcc gcatacacta    1680
ttctcagaat gacttggttg agtactcacc agtcacagaa aagcatctta cggatggcat    1740
gacagtaaga gaattatgca gtgctgccat aaccatgagt gataacactg cggccaactt    1800
acttctgaca acgatcggag gaccgaagga gctaaccgct ttttgcaca acatggggga    1860 tcatgtaact cgccttgatc gttgggaacc ggagctgaat gaagccatac caaacgacga    1920
gcgtgacacc acgatgcctg tagcaatggc aacaacgttg cgcaaactat taactggcga    1980
actacttact ctagcttccc ggcaacaatt aatagactgg atggaggcgg ataaagttgc    2040
aggaccactt ctgcgctcgg cccttccggc tggctggttt attgctgata atctggagc    2100 cggtgagcgt gggtctcgcg gtatcattgc agcactgggg ccagatggta agccctcccg    2160
tatcgtagtt atctacacga cggggagtca ggcaactatg gatgaacgaa atagacagat    2220
cgctgagata ggtgcctcac tgattaagca ttggtaactg tcagaccaag tttactcata    2280
tatactttag attgatttaa aacttcattt ttaatttaaa aggatctagg tgaagatcct    2340
ttttgataat ctcatgacca aaatccctta acgtgagttt cgttccact gagcgtcaga    2400 ccccgtagaa aagatcaaag gatcttcttg agatcctttt tttctgcgcg taatctgctg    2460
cttgcaaaca aaaaaaccac cgctaccagc ggtggtttgt ttgccggatc aagagctacc    2520
aactcttttt ccgaaggtaa ctggcttcag cagagcgcag ataccaaata ctgtccttct    2580
agtgtagccg tagttaggcc accacttcaa gaactctgta gcaccgccta catacctcgc    2640
tctgctaatc ctgttaccag tggctgctgc cagtggcgat aagtcgtgtc ttaccgggtt    2700
ggactcaaga cgatagttac cggataaggc gcagcggtcg ggctgaacgg ggggttcgtg    2760
cacacagccc agcttggagc gaacgaccta caccgaactg agatacctac agcgtgagct    2820
atgagaaagc gccacgcttc ccgaaggag aaaggcggac aggtatccgg taagcggcag    2880
ggtcggaaca ggagagcgca cgagggagct tccaggggga aacgcctggt atctttatag    2940
tcctgtcggg tttcgccacc tctgacttga gcgtcgattt ttgtgatgct cgtcaggggg    3000
gcggagccta tggaaaaacg ccagcaacgc ggcctttta cggttcctgg ccttttgctg    3060
gccttttgct cacatgttct ttcctgcgtt atcccctgat tctgtggata accgtattac    3120
cgcctttgag tgagctgata ccgctcgccg cagccgaacg accgagcgca gcgagtcagt    3180
gagcgaggaa gcggaagagc gcccaatacg caaaccgcct ctccccgcgc gttggccgat    3240
tcattaatgc agctggcacg acaggtttcc cgactggaaa gcgggcagtg agcgcaacgc    3300
aattaatgtg agttagctca ctcattaggc accccaggct ttacacttta tgcttccggc    3360
tcgtatgttg tgtggaattg tgagcggata acaatttcac acaggaaaca gctatgacca    3420
```

| | |
|---|---:|
| tgattacgcc aagcttgcat gcctgcaggc tagcctaagt acgtactcaa aatgccaaca | 3480 |
| aataaaaaaa aagttgcttt aataatgcca aacaaatta ataaaacact acaacaccg | 3540 |
| gatttttttt aattaaaatg tgccatttag gataaatagt taatatttt aataattatt | 3600 |
| taaaaagccg tatctactaa aatgatttt atttggttga aaatattaat atgtttaaat | 3660 |
| caacacaatc tatcaaaatt aaactaaaaa aaaaataagt gtacgtggtt aacattagta | 3720 |
| cagtaatata agaggaaaat gagaaattaa gaaattgaaa gcgagtctaa ttttaaatt | 3780 |
| atgaacctgc atatataaaa ggaaagaaag aatccaggaa gaaagaaat gaaccatgc | 3840 |
| atggtcccct cgtcatcacg agtttctgcc atttgcaata gaaacactga acaccttc | 3900 |
| tctttgtcac ttaattgaga tgccgaagcc acctcacacc atgaacttca tgaggtgtag | 3960 |
| cacccaaggc ttccatagcc atgcatactg aagaatgtct caagctcagc accctacttc | 4020 |
| tgtgacgtgt ccctcattca ccttcctctc ttccctataa ataaccacgc ctcaggttct | 4080 |
| ccgcttcaca actcaaacat tctctccatt ggtccttaaa cactcatcag tcatcaccgc | 4140 |

<210> SEQ ID NO 6
<211> LENGTH: 6747
<212> TYPE: DNA
<213> ORGANISM: artificial sequence
<220> FEATURE:
<223> OTHER INFORMATION: plasmid

<400> SEQUENCE: 6

| | |
|---|---:|
| gatccgtcga cggcgcgccc gatcatccgg atatagttcc tcctttcagc aaaaaacccc | 60 |
| tcaagacccg tttagaggcc ccaagggtt atgctagtta ttgctcagcg gtggcagcag | 120 |
| ccaactcagc ttcctttcgg gctttgttag cagccggatc gatccaagct gtacctcact | 180 |
| attcctttgc cctcggacga gtgctgggc gtcggtttcc actatcggcg agtacttcta | 240 |
| cacagccatc ggtccagacg gccgcgcttc tgcgggcgat ttgtgtacgc ccgacagtcc | 300 |
| cggctccgga tcggacgatt gcgtcgcatc gaccctgcgc ccaagctgca tcatcgaaat | 360 |
| tgccgtcaac caagctctga tagagttggt caagaccaat gcggagcata tacgcccgga | 420 |
| gccgcggcga tcctgcaagc tccggatgcc tccgctcgaa gtagcgcgtc tgctgctcca | 480 |
| tacaagccaa ccacggcctc cagaagaaga tgttggcgac ctcgtattgg gaatccccga | 540 |
| acatcgcctc gctccagtca atgaccgctg ttatgcggcc attgtccgtc aggacattgt | 600 |
| tggagccgaa atccgcgtgc acgaggtgcc ggacttcggg gcagtcctcg gcccaaagca | 660 |
| tcagctcatc gagagcctgc gcgacggacg cactgacggt gtcgtccatc acagtttgcc | 720 |
| agtgatacac atggggatca gcaatcgcgc atatgaaatc acgccatgta gtgtattgac | 780 |
| cgattccttg cggtccgaat gggccgaacc cgctcgtctg gctaagatcg gccgcagcga | 840 |
| tcgcatccat agcctccgcg accggctgca gaacagcggg cagttcggtt tcaggcaggt | 900 |
| cttgcaacgt gacaccctgt gcacggcggg agatgcaata ggtcaggctc tcgctgaatt | 960 |
| ccccaatgtc aagcacttcc ggaatcggga gcgcggccga tgcaaagtgc cgataaacat | 1020 |
| aacgatcttt gtagaaacca tcggcgcagc tatttacccg caggacatat ccacgccctc | 1080 |
| ctacatcgaa gctgaaagca cgagattctt cgccctccga gagctgcatc aggtcggaga | 1140 |
| cgctgtcgaa cttttcgatc agaaacttct cgacagacgt cgcggtgagt tcaggctttt | 1200 |
| ccatgggtat atctccttct taaagttaaa caaaattatt tctagaggga aaccgttgtg | 1260 |
| gtctccctat agtgagtcgt attaatttcg cgggatcgag atcgatccaa ttccaatccc | 1320 |
| acaaaaatct gagcttaaca gcacagttgc tcctctcaga gcagaatcgg gtattcaaca | 1380 |

```
ccctcatatc aactactacg ttgtgtataa cggtccacat gccggtatat acgatgactg   1440
gggttgtaca aaggcggcaa caaacggcgt tcccggagtt gcacacaaga aatttgccac   1500
tattacagag gcaagagcag cagctgacgc gtacacaaca agtcagcaaa cagacaggtt   1560
gaacttcatc cccaaaggag aagctcaact caagcccaag agctttgcta aggccctaac   1620
aagcccacca aagcaaaaag cccactggct cacgctagga accaaaaggc ccagcagtga   1680
tccagcccca aaagagatct cctttgcccc ggagattaca atggacgatt cctctatct   1740 ttacgatcta ggaaggaagt tcgaaggtga aggtgacgac actatgttca ccactgataa   1800
tgagaaggtt agcctcttca atttcagaaa gaatgctgac ccacagatgg ttagagaggc   1860
ctacgcagca ggtctcatca agacgatcta cccgagtaac aatctccagg agatcaaata   1920
ccttcccaag aaggttaaag atgcagtcaa aagattcagg actaattgca tcaagaacac   1980
agagaaagac atatttctca agatcagaag tactattcca gtatggacga ttcaaggctt   2040
gcttcataaa ccaaggcaag taatagagat tggagtctct aaaaaggtag ttcctactga   2100
atctaaggcc atgcatggag tctaagattc aaatcgagga tctaacagaa ctcgccgtga   2160
agactggcga acagttcata cagagtcttt tacgactcaa tgacaagaag aaaatcttcg   2220
tcaacatggt ggagcacgac actctggtct actccaaaaa tgtcaaagat acagtctcag   2280
aagaccaaag ggctattgag acttttcaac aaaggataat tcgggaaaac ctcctcggat   2340
tccattgccc agctatctgt cacttcatcg aaaggacagt agaaaaggaa ggtggctcct   2400
acaaatgcca tcattgcgat aaaggaaagg ctatcattca agatgcctct gccgacagtg   2460
gtcccaaaga tggacccca cccacgagga gcatcgtgga aaaagaagac gttccaacca   2520
cgtcttcaaa gcaagtggat tgatgtgaca tctccactga cgtaagggat gacgcacaat   2580
cccactatcc ttcgcaagac ccttcctcta tataaggaag ttcatttcat ttggagagga   2640
cacgctcgag ctcatttctc tattacttca gccataacaa aagaactctt ttctcttctt   2700
attaaaccat gaaaaagcct gaactcaccg cgacgtctgt cgagaagttt ctgatcgaaa   2760
agttcgacag cgtctccgac ctgatgcagc tctcggaggg cgaagaatct cgtgctttca   2820
gcttcgatgt aggagggcgt ggatatgtcc tgcgggtaaa tagctgcgcc gatggttttct   2880 acaaagatcg ttatgtttat cggcacttttg catcggccgc gctcccgatt ccggaagtgc   2940
ttgacattgg ggaattcagc gagagcctga cctattgcat ctcccgccgt gcacagggtg   3000
tcacgttgca agacctgcct gaaaccgaac tgcccgctgt tctgcagccg gtcgcggagg   3060
ccatggatgc gatcgctgcg gccgatctta gccagacgag cgggttcggc ccattcggac   3120
cgcaaggaat cggtcaatac actacatggc gtgatttcat atgcgcgatt gctgatcccc   3180
atgtgtatca ctggcaaact gtgatggacg acaccgtcag tgcgtccgtc gcgcaggctc   3240
tcgatgagct gatgctttgg gccgaggact gccccgaagt ccggcacctc gtgcacgcgg   3300
atttcggctc caacaatgtc ctgacggaca atggccgcat aacagcggtc attgactgga   3360
gcgaggcgat gttcggggat tcccaatacg aggtcgccaa catcttcttc tggaggccgt   3420
ggttggcttg tatggagcag cagacgcgct acttcgagcg gaggcatccg gagcttgcag   3480
gatcgccgcg gctccgggcg tatatgctcc gcattggtct tgaccaactc tatcagagct   3540
tggttgacgg caatttcgat gatgcagctt gggcgcaggg tcgatgcgac gcaatcgtcc   3600
gatccggagc cgggactgtc gggcgtacac aaatcgcccg cagaagcgcg gccgtctgga   3660
ccgatggctg tgtagaagta ctcgccgata gtggaaaccg acgccccagc actcgtccga   3720
```

```
gggcaaagga atagtgaggt acctaaagaa ggagtgcgtc gaagcagatc gttcaaacat    3780
ttggcaataa agtttcttaa gattgaatcc tgttgccggt cttgcgatga ttatcatata    3840
atttctgttg aattacgtta agcatgtaat aattaacatg taatgcatga cgttatttat    3900
gagatgggtt tttatgatta gagtcccgca attatacatt taatacgcga tagaaaacaa    3960
aatatagcgc gcaaactagg ataaattatc gcgcgcggtg tcatctatgt tactagatcg    4020
atgtcgaatc gatcaacctg cattaatgaa tcggccaacg cgcggggaga ggcggtttgc    4080
gtattgggcg ctcttccgct tcctcgctca ctgactcgct gcgctcggtc gttcggctgc    4140
ggcgagcggt atcagctcac tcaaaggcgg taatacggtt atccacagaa tcagggggata   4200 acgcaggaaa gaacatgtga gcaaaaggcc agcaaaaggc caggaaccgt aaaaaggccg    4260
cgttgctggc gtttttccat aggctccgcc cccctgacga gcatcacaaa aatcgacgct    4320
caagtcagag gtggcgaaac ccgacaggac tataaagata ccaggcgttt ccccctggaa    4380
gctccctcgt gcgctctcct gttccgaccc tgccgcttac cggatacctg tccgcctttc    4440
tcccttcggg aagcgtggcg ctttctcaat gctcacgctg taggtatctc agttcggtgt    4500
aggtcgttcg ctccaagctg ggctgtgtgc acgaaccccc cgttcagccc gaccgctgcg    4560
ccttatccgg taactatcgt cttgagtcca acccggtaag acgacttta tcgccactgg    4620 cagcagccac tggtaacagg attagcagag cgaggtatgt aggcggtgct acagagttct    4680
tgaagtggtg gcctaactac ggctacacta aaggacagt atttggtatc tgcgctctgc    4740
tgaagccagt taccttcgga aaaagagttg gtagctcttg atccggcaaa caaaccaccg    4800
ctggtagcgg tggttttttt gtttgcaagc agcagattac gcgcagaaaa aaaggatctc    4860
aagaagatcc tttgatcttt tctacggggt ctgacgctca gtggaacgaa aactcacgtt    4920
aagggatttt ggtcatgaca ttaacctata aaaataggcg tatcacgagg ccctttcgtc    4980
tcgcgcgttt cggtgatgac ggtgaaaacc tctgacacat gcagctcccg gagacggtca    5040
cagcttgtct gtaagcggat gccgggagca gacaagcccg tcagggcgcg tcagcgggtg    5100
ttggcgggtg tcgggctgg cttaactatg cggcatcaga gcagattgta ctgagagtgc    5160
accatatgga catattgtcg ttagaacgcg gctacaatta atacataacc ttatgtatca    5220
tacacatacg atttaggtga cactatagaa cggcgcgcca agcttgcatg cctgcaggct    5280
agcctaagta cgtactcaaa atgccaacaa ataaaaaaaa agttgcttta ataatgccaa    5340
aacaaattaa taaaacactt acaacaccgg atttttttta attaaaatgt gccatttagg    5400
ataaatagtt aatattttta ataattattt aaaaagccgt atctactaaa atgattttta    5460
tttggttgaa aatattaata tgtttaaatc aacacaatct atcaaaatta aactaaaaaa    5520
aaaataagtg tacgtggtta acattagtac agtaatataa gaggaaaatg agaaattaag    5580
aaattgaaag cgagtctaat ttttaaatta tgaacctgca tatataaaag gaagaaaga    5640 atccaggaag aaaagaaatg aaaccatgca tggtccctc gtcatcacga gtttctgcca    5700
tttgcaatag aaacactgaa acacctttct ctttgtcact taattgagat gccgaagcca    5760
cctcacacca tgaacttcat gaggtgtagc acccaaggct tccatagcca tgcatactga    5820
agaatgtctc aagctcagca ccctacttct gtgacgtgtc cctcattcac cttcctctct    5880
tccctataaa taaccacgcc tcaggttctc cgcttcacaa ctcaaacatt ctctccattg    5940
gtccttaaac actcatcagt catcaccgcg gccgcatttc gcaccaaatc aatgaaagta    6000
ataatgaaaa gtctgaataa gaatacttag gcttagatgc ctttgttact tgtgtaaaat    6060
aacttgagtc atgtaccttt ggcggaaaca gaataaataa aaggtgaaat tccaatgctc    6120
```

-continued

```
tatgtataag ttagtaatac ttaatgtgtt ctacggttgt ttcaatatca tcaaactcta    6180
attgaaactt tagaaccaca aatctcaatc ttttcttaat gaaatgaaaa atcttaattg    6240
taccatgttt atgttaaaca ccttacaatt ggttggagag gaggaccaac cgatgggaca    6300
acattgggag aaagagattc aatggagatt tggataggaa acaacattc tttttcactt    6360 caatacaaga tgagtgcaac actaaggata tgtatgagac tttcagaagc tacgacaaca    6420
tagatgagtg aggtggtgat tcctagcaag aaagacatta gaggaagcca aaatcgaaca    6480
aggaagacat caagggcaag agacaggacc atccatctca ggaaaaggag ctttgggata    6540
gtccgagaag ttgtacaaga aattttttgg agggtgagtg atgcattgct ggtgacttta    6600
actcaatcaa aattgagaaa gaaagaaaag ggagggggct cacatgtgaa tagaagggaa    6660
acgggagaat tttacagttt tgatctaatg ggcatcccag ctagtggtaa catattcacc    6720
atgtttaacc ttcacgtacg tctagag                                       6747
```

<210> SEQ ID NO 7
<211> LENGTH: 8462
<212> TYPE: DNA
<213> ORGANISM: artificial sequence
<220> FEATURE:
<223> OTHER INFORMATION: plasmid

<400> SEQUENCE: 7

```
ggccgcattt cgcaccaaat caatgaaagt aataatgaaa agtctgaata agaatactta      60
ggcttagatg cctttgttac ttgtgtaaaa taacttgagt catgtacctt tggcggaaac     120
agaataaata aaaggtgaaa ttccaatgct ctatgtataa gttagtaata cttaatgtgt     180
tctacggttg tttcaatatc atcaaactct aattgaaact ttagaaccac aaatctcaat     240
cttttcttaa tgaaatgaaa atcttaattg gtaccatgtt tatgttaaac accttacaat     300
tggttggaga ggaggaccaa ccgatgggac aacattggga gaaagagatt caatggagat     360
ttggatagga gaacaacatt cttttcact tcaatacaag atgagtgcaa cactaaggat     420
atgtatgaga ctttcagaag ctacgacaac atagatgagt gaggtggtga ttcctagcaa     480
gaaagacatt agaggaagcc aaaatcgaac aaggaagaca tcaagggcaa gagacaggac     540
catccatctc aggaaaagga ctttgggat agtccgagaa ttgtacaag aaattttttg     600 gagggtgagt gatgcattgc tggtgacttt aactcaatca aaattgagaa agaaagaaaa     660
gggagggggc tcacatgtga atagaaggga acgggagaa ttttacagtt ttgatctaat     720
gggcatccca gctagtggta acatattcac catgtttaac cttcacgtac gtctagagga     780
tccgtcgacg gcgcgcccga tcatccggat atagttcctc ctttcagcaa aaaaccctc     840 aagacccgtt tagaggcccc aagggttat gctagttatt gctcagcggt ggcagcagcc     900
aactcagctt cctttcgggc tttgttagca gccggatcga tccaagctgt acctcactat     960
tcctttgccc tcggacgagt gctggggcgt cggtttccac tatcggcgag tacttctaca    1020
cagccatcgg tccagacggc cgcgcttctg cgggcgattt gtgtacgccc gacagtcccg    1080
gctccggatc ggacgattgc gtcgcatcga ccctgcgccc aagctgcatc atcgaaattg    1140
ccgtcaacca agctctgata gagttggtca agaccaatgc ggagcatata cgcccggagc    1200
cgcggcgatc ctgcaagctc cggatgcctc cgctcgaagt agcgcgtctg ctgctccata    1260
caagccaacc acggcctcca gaagaagatg ttggcgacct cgtatttggga atccccgaac    1320 atcgcctcgc tccagtcaat gaccgctgtt atgcggccat tgtccgtcag gacattgttg    1380
```

```
gagccgaaat ccgcgtgcac gaggtgccgg acttcggggc agtcctcggc ccaaagcatc      1440
agctcatcga gagcctgcgc gacggacgca ctgacggtgt cgtccatcac agtttgccag      1500
tgatacacat ggggatcagc aatcgcgcat atgaaatcac gccatgtagt gtattgaccg      1560
attccttgcg gtccgaatgg gccgaacccg ctcgtctggc taagatcggc cgcagcgatc      1620
gcatccatag cctccgcgac cggctgcaga acagcgggca gttcggtttc aggcaggtct      1680
tgcaacgtga caccctgtgc acggcgggag atgcaatagg tcaggctctc gctgaattcc      1740
ccaatgtcaa gcacttccgg aatcgggagc gcggccgatg caaagtgccg ataaacataa      1800
cgatctttgt agaaaccatc ggcgcagcta tttacccgca ggacatatcc acgccctcct      1860
acatcgaagc tgaaagcacg agattcttcg ccctccgaga gctgcatcag gtcggagacg      1920
ctgtcgaact tttcgatcag aaacttctcg acagacgtcg cggtgagttc aggcttttcc      1980
atgggtatat ctccttctta aagttaaaca aaattatttc tagagggaaa ccgttgtggt      2040
ctccctatag tgagtcgtat taatttcgcg ggatcgagat cgatccaatt ccaatcccac      2100
aaaaatctga gcttaacagc acagttgctc tctcagagac agaatcgggt attcaacacc      2160
ctcatatcaa ctactacgtt gtgtataacg gtccacatgc cggtatatac gatgactggg      2220
gttgtacaaa ggcggcaaca aacggcgttc ccggagttgc acacaagaaa tttgccacta      2280
ttacagaggc aagagcagca gctgacgcgt acacaacaag tcagcaaaca gacaggttga      2340
acttcatccc caaggagaa gctcaactca gcccaagag ctttgctaag gccctaacaa       2400
gcccaccaaa gcaaaagcc cactggctca cgctaggaac caaaaggccc agcagtgatc       2460
cagccccaaa agagatctcc tttgccccgg agattacaat ggacgatttc ctctatcttt      2520
acgatctagg aaggaagttc gaaggtgaag gtgacgacac tatgttcacc actgataatg      2580
agaaggttag cctcttcaat ttcagaaaga tgctgaccc acagatggtt agagaggcct       2640
acgcagcagg tctcatcaag acgatctacc cgagtaacaa tctccaggag atcaaatacc      2700
ttcccaagaa ggttaaagat gcagtcaaaa gattcaggac taattgcatc aagaacacag      2760
agaaagacat atttctcaag atcagaagta ctattccagt atggacgatt caaggcttgc      2820
ttcataaacc aaggcaagta atagagattg gagtctctaa aaaggtagtt cctactgaat      2880
ctaaggccat gcatggagtc taagattcaa atcgaggatc taacagaact cgccgtgaag      2940
actggcgaac agttcataca gagtctttta cgactcaatg acaagaagaa aatcttcgtc      3000
aacatggtgg agcacgacac tctggtctac tccaaaaatg tcaaagatac agtctcagaa      3060
gaccaaaggg ctattgagac ttttcaacaa aggataattt cgggaaacct cctcggattc      3120
cattgcccag ctatctgtca cttcatcgaa aggacagtag aaaaggaagg tggctcctac      3180
aaatgccatc attgcgataa aggaaaggct atcattcaag atgcctctgc cgacagtggt      3240
cccaaagatg gacccccacc cacgaggagc atcgtggaaa aagaagacgt tccaaccacg      3300
tcttcaaagc aagtggattg atgtgacatc tccactgacg taagggatga cgcacaatcc      3360
cactatcctt cgcaagaccc ttcctctata taaggaagtt catttcattt ggagaggaca      3420
cgctcgagct catttctcta ttacttcagc cataacaaaa gaactctttt ctcttcttat      3480
taaaccatga aaaagcctga actcaccgcg acgtctgtcg agaagtttct gatcgaaaag      3540
ttcgacagcg tctccgacct gatgcagctc tcggagggcg aagaatctcg tgctttcagc      3600
ttcgatgtag agggcgtgg atatgtcctg cgggtaaata gctgcgccga tggtttctac      3660
aaagatcgtt atgtttatcg gcactttgca tcggccgcgc tcccgattcc ggaagtgctt      3720
gacattgggg aattcagcga gagcctgacc tattgcatct cccgccgtgc acagggtgtc      3780
```

```
acgttgcaag acctgcctga aaccgaactg cccgctgttc tgcagccggt cgcggaggcc   3840
atggatgcga tcgctgcggc cgatcttagc cagacgagcg ggttcggccc attcggaccg   3900
caaggaatcg gtcaatacac tacatggcgt gatttcatat gcgcgattgc tgatccccat   3960
gtgtatcact ggcaaactgt gatggacgac accgtcagtg cgtccgtcgc gcaggctctc   4020
gatgagctga tgctttgggc cgaggactgc cccgaagtcc ggcacctcgt gcacgcggat   4080
ttcggctcca acaatgtcct gacgacaat ggccgcataa cagcggtcat tgactggagc    4140
gaggcgatgt tcggggattc ccaatacgag gtcgccaaca tcttcttctg gaggccgtgg   4200
ttggcttgta tggagcagca gacgcgctac ttcgagcgga ggcatccgga gcttgcagga   4260
tcgccgcggc tccgggcgta tatgctccgc attggtcttg accaactcta tcagagcttg   4320
gttgacggca atttcgatga tgcagcttgg gcgcagggtc gatgcgacgc aatcgtccga   4380
tccggagccg ggactgtcgg gcgtacacaa atcgcccgca gaagcgcggc cgtctggacc   4440
gatggctgtg tagaagtact cgccgatagt ggaaaccgac gccccagcac tcgtccgagg   4500
gcaaaggaat agtgaggtac ctaaagaagg agtgcgtcga agcagatcgt tcaaacattt   4560
ggcaataaag tttcttaaga ttgaatcctg ttgccggtct tgcgatgatt atcatataat   4620
ttctgttgaa ttacgttaag catgtaataa ttaacatgta atgcatgacg ttatttatga   4680
gatgggtttt tatgattaga gtcccgcaat tatacattta atacgcgata gaaaacaaaa   4740
tatagcgcgc aaactaggat aaattatcgc gcgcggtgtc atctatgtta ctagatcgat   4800
gtcgaatcga tcaacctgca ttaatgaatc ggccaacgcg cggggagagg cggtttgcgt   4860
attgggcgct cttccgcttc ctcgctcact gactcgctgc gctcggtcgt tcggctgcgg   4920
cgagcggtat cagctcactc aaaggcggta atacggttat ccacagaatc agggggataac   4980
gcaggaaaga acatgtgagc aaaaggccag caaaaggcca ggaaccgtaa aaaggccgcg   5040
ttgctggcgt ttttccatag gctccgcccc cctgacgagc atcacaaaaa tcgacgctca   5100
agtcagaggt ggcgaaaccc gacaggacta taaagatacc aggcgtttcc ccctggaagc   5160
tccctcgtgc gctctcctgt tccgaccctg ccgcttaccg gatacctgtc cgcctttctc   5220
ccttcgggaa gcgtggcgct ttctcaatgc tcacgctgta ggtatctcag ttcggtgtag   5280
gtcgttcgct ccaagctggg ctgtgtgcac gaaccccccg ttcagcccga ccgctgcgcc   5340
ttatccggta actatcgtct tgagtccaac ccggtaagac acgacttatc gccactggca   5400
gcagccactg gtaacaggat tagcagagcg aggtatgtag gcggtgctac agagttcttg   5460
aagtggtggc ctaactacgg ctacactaga aggacagtat ttggtatctg cgctctgctg   5520
aagccagtta ccttcggaaa aagagttggt agctcttgat ccggcaaaca accaccgct   5580
ggtagcggtg gtttttttgt ttgcaagcag cagattacgc gcagaaaaaa aggatctcaa   5640
gaagatcctt tgatctttc tacggggtct gacgctcagt ggaacgaaaa ctcacgttaa    5700
gggattttgg tcatgacatt aacctataaa aataggcgta tcacgaggcc ctttcgtctc   5760
gcgcgtttcg gtgatgacgg tgaaaacctc tgacacatgc agctcccgga cggtcaca    5820
gcttgtctgt aagcggatgc cgggagcaga caagcccgtc agggcgcgtc agcgggtgtt   5880
ggcgggtgtc ggggctggct taactatgcg gcatcagagc agattgtact gagagtgcac   5940
catatggaca tattgtcgtt agaacgcggc tacaattaat acataacctt atgtatcata   6000
cacatacgat ttaggtgaca ctatagaacg gcgcgccaag cttgcatgcc tgcaggctag   6060
cctaagtacg tactcaaaat gccaacaaat aaaaaaaaag ttgctttaat aatgccaaaa   6120
```

-continued

```
caaattaata aaacacttac aacaccggat ttttttaat taaaatgtgc catttaggat      6180
aaatagttaa tattttaat aattatttaa aaagccgtat ctactaaaat gatttttatt      6240
tggttgaaaa tattaatatg tttaaatcaa cacaatctat caaaattaaa ctaaaaaaaa     6300
aataagtgta cgtggttaac attagtacag taatataaga ggaaaatgag aaattaagaa      6360
attgaaagcg agtctaattt ttaaattatg aacctgcata tataaaagga agaaagaat      6420 ccaggaagaa aagaaatgaa accatgcatg gtcccctcgt catcacgagt ttctgccatt     6480
tgcaatagaa acactgaaac accttctct ttgtcactta attgagatgc cgaagccacc     6540
tcacaccatg aacttcatga ggtgtagcac ccaaggcttc catagccatg catactgaag     6600
aatgtctcaa gctcagcacc ctacttctgt gacgtgtccc tcattcacct tcctctcttc     6660
cctataaata accacgcctc aggttctccg cttcacaact caaacattct ctccattggt     6720
ccttaaacac tcatcagtca tcaccgcggc catcacaagt ttgtacaaaa aagctgaacg     6780
agaaacgtaa aatgatataa atatcaatat attaaattag attttgcata aaaaacagac     6840
tacataatac tgtaaaacac aacatatcca gtcatattgg cggccgcatt aggcacccca     6900
ggctttacac tttatgcttc cggctcgtat aatgtgtgga ttttgagtta ggatccgtcg     6960
agattttcag gagctaagga agctaaaatg gagaaaaaa tcactggata taccaccgtt      7020
gatatatccc aatggcatcg taaagaacat tttgaggcat ttcagtcagt tgctcaatgt     7080
acctataacc agaccgttca gctggatatt acggccttt taaagaccgt aaagaaaaat     7140
aagcacaagt tttatccggc ctttattcac attcttgccc gcctgatgaa tgctcatccg     7200
gaattccgta tggcaatgaa agacggtgag ctggtgatat gggatagtgt tcacccttgt     7260
tacaccgttt tccatgagca aactgaaacg ttttcatcgc tctggagtga ataccacgac     7320
gatttccggc agtttctaca catatattcg caagatgtgg cgtgttacgg tgaaaacctg     7380
gcctatttcc ctaaagggtt tattgagaat atgttttcg tctcagccaa tccctgggtg      7440
agtttcacca gttttgattt aaacgtggcc aatatggaca acttcttcgc ccccgttttc     7500
accatgggca aatattatac gcaaggcgac aaggtgctga tgccgctggc gattcaggtt     7560
catcatgccg tttgtgatgg cttccatgtc ggcagaatgc ttaatgaatt acaacagtac     7620
tgcgatgagt ggcagggcgg ggcgtaaacg cgtggatccg gcttactaaa agccagataa     7680
cagtatgcgt atttgcgcgc tgattttgc ggtataagaa tatatactga tatgtatacc      7740
cgaagtatgt caaaaagagg tatgctatga agcagcgtat tacagtgaca gttgacagcg     7800
acagctatca gttgctcaag gcatatatga tgtcaatatc tccggtctgg taagcacaac     7860
catgcagaat gaagcccgtc gtctgcgtgc cgaacgctgg aaagcggaaa atcaggaagg     7920
gatggctgag gtcgcccggt ttattgaaat gaacggctct tttgctgacg agaacagggg     7980
ctggtgaaat gcagtttaag gtttacacct ataaaagaga gagccgttat cgtctgtttg     8040
tggatgtaca gagtgatatt attgacacgc ccgggcgacg gatggtgatc cccctggcca     8100
gtgcacgtct gctgtcagat aaagtctccc gtgaactta cccggtggtg catatcgggg     8160
atgaaagctg gcgcatgatg accaccgata tggccagtgt gccggtctcc gttatcgggg     8220
aagaagtggc tgatctcagc caccgcgaaa atgcatcaa aaacgccatt aacctgatgt     8280
tctggggaat ataaatgtca ggctccctta tacacagcca gtctgcaggt cgaccatagt     8340
gactggatat gttgtgtttt acagcattat gtagtctgtt ttttatgcaa aatctaattt    8400
aatatattga tatttatatc attttacgtt tctcgttcag ctttcttgta caaagtggtg     8460
at                                                                    8462
```

<210> SEQ ID NO 8
<211> LENGTH: 13268
<212> TYPE: DNA
<213> ORGANISM: artificial sequence
<220> FEATURE:
<223> OTHER INFORMATION: plasmid

<400> SEQUENCE: 8

| | | | | | |
|---|---|---|---|---|---|
| cgcgcctcga | gtgggcggat | ccccgggct | gcaggaattc | actggccgtc | gttttacaac | 60 |
| gtcgtgactg | ggaaaaccct | ggcgttaccc | aacttaatcg | ccttgcagca | catccccctt | 120 |
| tcgccagctg | gcgtaatagc | gaagaggccc | gcaccgatcg | cccttcccaa | cagttgcgca | 180 |
| gcctgaatgg | cgaatggatc | gatccatcgc | gatgtacctt | tgttagtca | gcctctcgat | 240 |
| tgctcatcgt | cattacacag | taccgaagtt | tgatcgatc | agtaacatag | atgacaccgc | 300 |
| gcgcgataat | ttatcctagt | ttgcgcgcta | tattttgttt | tctatcgcgt | attaaatgta | 360 |
| taattgcggg | actctaatca | taaaaaccca | tctcataaat | aacgtcatgc | attacatgtt | 420 |
| aattattaca | tgcttaacgt | aattcaacag | aaattatatg | ataatcatcg | caagaccggc | 480 |
| aacaggattc | aatcttaaga | aactttattg | ccaaatgttt | gaacgatctg | cttgacgca | 540 |
| ctccttcttt | actccaccat | ctcgtcctta | ttgaaaacgt | gggtagcacc | aaaacgaatc | 600 |
| aagtcgctgg | aactgaagtt | accaatcacg | ctggatgatt | tgccagttgg | attaatcttg | 660 |
| cctttccccg | catgaataat | attgatgaat | gcatgcgtga | ggggtagttc | gatgttggca | 720 |
| atagctgcaa | ttgccgcgac | atcctccaac | gagcataatt | cttcagaaaa | atagcgatgt | 780 |
| tccatgttgt | cagggcatgc | atgatgcacg | ttatgaggtg | acggtgctag | gcagtattcc | 840 |
| ctcaaagttt | catagtcagt | atcatattca | tcattgcatt | cctgcaagag | agaattgaga | 900 |
| cgcaatccac | acgctgcggc | aaccttccgg | cgttcgtggt | ctatttgctc | ttggacgttg | 960 |
| caaacgtaag | tgttggatcg | atccggggtg | ggcgaagaac | tccagcatga | gatccccgcg | 1020 |
| ctggaggatc | atccagccgg | cgtcccggaa | aacgattccg | aagcccaacc | tttcatagaa | 1080 |
| ggcggcggtg | gaatcgaaat | ctcgtgatgg | caggttgggc | gtcgcttggt | cggtcatttc | 1140 |
| gaaccccaga | gtcccgctca | aagaactcg | tcaagaaggc | gatagaaggc | gatgcgctgc | 1200 |
| gaatcgggag | cggcgatacc | gtaaagcacg | aggaagcggt | cagcccattc | gccgccaagc | 1260 |
| tcttcagcaa | tatcacgggt | agccaacgct | atgtcctgat | agcggtccgc | cacacccagc | 1320 |
| cggccacagt | cgatgaatcc | agaaaagcgg | ccattttcca | ccatgatatt | cggcaagcag | 1380 |
| gcatcgccat | gggtcacgac | gagatcctcg | ccgtcgggca | tgcgcgcctt | gagcctggcg | 1440 |
| aacagttcgg | ctggcgcgag | cccctgatgc | tcttcgtcca | gatcatcctg | atcgacaaga | 1500 |
| ccggcttcca | tccgagtacg | tgctcgctcg | atgcgatgtt | tcgcttggtg | gtcgaatggg | 1560 |
| caggtagccg | gatcaagcgt | atgcagccgc | cgcattgcat | cagccatgat | ggatactttc | 1620 |
| tcggcaggag | caaggtgaga | tgacaggaga | tcctgccccg | gcacttcgcc | caatagcagc | 1680 |
| cagtcccttc | ccgcttcagt | gacaacgtcg | agcacagctg | cgcaaggaac | gcccgtcgtg | 1740 |
| gccagccacg | atagccgcgc | tgcctcgtcc | tgcagttcat | tcagggcacc | ggacaggtcg | 1800 |
| gtcttgacaa | aaagaaccgg | cgccctctgc | gctgacagcc | ggaacacggc | ggcatcagag | 1860 |
| cagccgattg | tctgttgtgc | ccagtcatag | ccgaatagcc | tctccaccca | agcggccgga | 1920 |
| gaacctgcgt | gcaatccatc | ttgttcaatc | atgcgaaacg | atccccgcaa | gcttggagac | 1980 |
| tggtgatttc | agcgtgtcct | ctccaaatga | aatgaacttc | cttatataga | ggaagggtct | 2040 |

```
tgcgaaggat agtgggattg tgcgtcatcc cttacgtcag tggagatatc acatcaatcc    2100
acttgctttg aagacgtggt tggaacgtct tctttttcca cgatgctcct cgtgggtggg    2160
ggtccatctt tgggaccact gtcggcagag gcatcttcaa cgatggcctt tcctttatcg    2220
caatgatggc atttgtagga gccaccttcc ttttccacta tcttcacaat aaagtgacag    2280
atagctgggc aatggaatcc gaggaggttt ccggatatta ccctttgttg aaaagtctca    2340
attgcccttt ggtcttctga gactgtatct ttgatatttt tggagtagac aagcgtgtcg    2400
tgctccacca tgttgacgaa gattttcttc ttgtcattga gtcgtaagag actctgtatg    2460
aactgttcgc cagtctttac ggcgagttct gttaggtcct ctatttgaat ctttgactcc    2520
atggcctttg attcagtggg aactaccttt ttagagactc caatctctat tacttgcctt    2580
ggtttgtgaa gcaagccttg aatcgtccat actggaatag tacttctgat cttgagaaat    2640
atatctttct ctgtgttctt gatgcagtta gtcctgaatc ttttgactgc atctttaacc    2700
ttcttgggaa ggtatttgat ctcctggaga ttattgctcg ggtagatcgt cttgatgaga    2760
cctgctgcgt aagcctctct aaccatcgtg gggttagcat tctttctgaa attgaaaagg    2820
ctaatcttct cattatcagt ggtgaacatg gtatcgtcac cttctccgtc gaacttcctg    2880
actagatcgt agagatagag gaagtcgtcc attgtgatct ctggggcaaa ggagtctgaa    2940
ttaattcgat atggtggatt tatcacaaat gggacccgcc gccgacagag gtgtgatgtt    3000
aggccaggac tttgaaaatt tgcgcaacta tcgtatagtg gccgacaaat tgacgccgag    3060
ttgacagact gcctagcatt tgagtgaatt atgtgaggta atgggctaca ctgaattggt    3120
agctcaaact gtcagtattt atgtatatga gtgtatattt tcgcataatc tcagaccaat    3180
ctgaagatga aatgggtatc tgggaatggc gaaatcaagg catcgatcgt gaagtttctc    3240
atctaagccc ccatttggac gtgaatgtag acacgtcgaa ataaagattt ccgaattaga    3300
ataatttgtt tattgctttc gcctataaat acgacggatc gtaatttgtc gttttatcaa    3360
aatgtacttt cattttataa taacgctgcg gacatctaca tttttgaatt gaaaaaaaat    3420
tggtaattac tctttctttt tctccatatt gaccatcata ctcattgctg atccatgtag    3480
atttcccgga catgaagcca tttacaattg aatatatcct gccgccgctg ccgcttttgca    3540
cccggtggag cttgcatgtt ggtttctacg cagaactgag ccggttaggc agataaattc    3600
cattgagaac tgagccatgt gcaccttccc cccaacacgg tgagcgacgg ggcaacggag    3660
tgatccacat gggactttta aacatcatcc gtcggatggc gttgcgagag aagcagtcga    3720
tccgtgagat cagccgacgc accgggcagg cgcgcaacac gatcgcaaag tatttgaacg    3780
caggtacaat cgagccgacg ttcacgcgga acgaccaagc aagctagctt taatgcggta    3840
gtttatcaca gttaaattgc taacgcagtc aggcaccgtg tatgaaatct aacaatgcgc    3900
tcatcgtcat cctcggcacc gtcaccctgg atgctgtagg cataggcttg gttatgccgg    3960
tactgccggg cctcttgcgg gatatcgtcc attccgacag catcgccagt cactatggcg    4020
tgctgctagc gctatatgcg ttgatgcaat ttctatgcgc acccgttctc ggagcactgt    4080
ccgaccgctt tggccgccgc ccagtcctgc tcgcttcgct acttggagcc actatcgact    4140
acgcgatcat ggcgaccaca cccgtcctgt ggtccaaccc ctccgctgct atagtgcagt    4200
cggcttctga cgttcagtgc agccgtcttc tgaaaacgac atgtcgcaca gtcctaagt    4260
tacgcgacag gctgccgccc tgcccttttc ctggcgtttt cttgtcgcgt gttttagtcg    4320
cataaagtag aatacttgcg actagaaccg gagacattac gccatgaaca agagcgccgc    4380
cgctggcctg ctgggctatg cccgcgtcag caccgacgac caggacttga ccaaccaacg    4440
```

-continued

```
ggccgaactg cacgcggccg gctgcaccaa gctgttttcc gagaagatca ccggcaccag    4500
gcgcgaccgc ccggagctgg ccaggatgct tgaccaccta cgccctggcg acgttgtgac    4560
agtgaccagg ctagaccgcc tggcccgcag cacccgcgac ctactggaca ttgccgagcg    4620
catccaggag gccggcgcgg gcctgcgtag cctggcagag ccgtgggccg acaccaccac    4680
gccggccggc cgcatggtgt tgaccgtgtt cgccggcatt gccgagttcg agcgttccct    4740
aatcatcgac cgcacccgga gcgggcgcga ggccgccaag gcccgaggcg tgaagtttgg    4800
cccccgccct accctcaccc cggcacagat cgcgcacgcc cgcgagctga tcgaccagga    4860
aggccgcacc gtgaaagagg cggctgcact gcttggcgtg catcgctcga ccctgtaccg    4920
cgcacttgag cgcagcgagg aagtgacgcc caccgaggcc aggcggcgcg gtgccttccg    4980
tgaggacgca ttgaccgagg ccgacgcccc ggcggccgcc gagaatgaac gccaaggagga    5040
acaagcatga aaccgcacca ggacggccag gacgaaccgt ttttcattac cgaagagatc    5100
gaggcggaga tgatcgcggc cgggtacgtg ttcgagccgc ccgcgcacgt ctcaaccgtg    5160
cggctgcatg aaatcctggc cggtttgtct gatgccaagc tggcggcctg ccggccagc     5220
ttggccgctg aagaaaccga gcgccgccgt ctaaaaaggt gatgtgtatt tgagtaaaac    5280
agcttgcgtc atgcggtcgc tgcgtatatg atgcgatgag taaataaaca aatacgcaag    5340
ggaacgcatg aagttatcgc tgtacttaac cagaaaggcg ggtcaggcaa gacgaccatc    5400
gcaacccatc tagcccgcgc cctgcaactc gccggggccg atgttctgtt agtcgattcc    5460
gatccccagg gcagtgcccg cgattgggcg ccgtgcggg aagatcaacc gctaaccgtt     5520
gtcggcatcg accgccgac gattgaccgc gacgtgaagg ccatcggccg gcgcgacttc     5580
gtagtgatcg acggagcgcc ccaggcggcg gacttggctg tgtccgcgat caaggcagcc    5640
gacttcgtgc tgattccggt gcagccaagc ccttacgaca tatgggccac cgccgacctg    5700
gtggagctgg ttaagcagcg cattgaggtc acggatggaa ggctacaagc ggcctttgtc    5760
gtgtcgcggg cgatcaaagg cacgcgcatc ggcggtgagg ttgccgaggc gctggccggg    5820
tacgagctgc ccattcttga gtcccgtatc acgcagcgcg tgagctaccc aggcactgcc    5880
gccgccggca caaccgttct tgaatcagaa cccgagggcg acgctgcccg cgaggtccag    5940
gcgctggccg ctgaaattaa atcaaaactc atttgagtta atgaggtaaa gagaaaatga    6000
gcaaaagcac aaaacacgcta agtgccggcc gtccgagcgc acgcagcagc aaggctgcaa    6060
cgttggccag cctggcagac acgccagcca tgaagcgggt caactttcag ttgccggcgg    6120
aggatcacac caagctgaag atgtacgcgg tacgccaagg caagaccatt accgagctgc    6180
tatctgaata catcgcgcag ctaccagagt aaatgagcaa atgaataaat gagtagatga    6240
attttagcgg ctaaaggagg cggcatggaa aatcaagaac aaccaggcac cgacgccgtg    6300
gaatgcccca tgtgtggagg aacgggcggt tggccaggcg taagcggctg ggttgtctgc    6360
cggcctgca atggcactgg aacccccaag cccgaggaat cggcgtgagc ggtcgcaaac    6420
catccggccc ggtacaaatc ggcgcggcgc tgggtgatga cctggtggag aagttgaagg    6480
ccgcgcaggc cgcccagcgg caacgcatcg aggcagaagc acgccccggt gaatcgtggc    6540
aagcggccgc tgatcgaatc cgcaaagaat cccggcaacc gccggcagcc ggtgcgccgt    6600
cgattaggaa gccgcccaag ggcgacgagc aaccagattt tttcgttccg atgctctatg    6660
acgtgggcac ccgcgatagt cgcagcatca tggacgtggc cgttttccgt ctgtcgaagc    6720
gtgaccgacg agctggcgag gtgatccgct acagcttcc agacgggcac gtagaggttt    6780
```

```
ccgcagggcc ggccggcatg gccagtgtgt gggattacga cctggtactg atggcggttt    6840
cccatctaac cgaatccatg aaccgatacc gggaagggaa gggagacaag cccggccgcg    6900
tgttccgtcc acacgttgcg gacgtactca agttctgccg gcgagccgat ggcggaaagc    6960
agaaagacga cctggtagaa acctgcattc ggttaaacac cacgcacgtt gccatgcagc    7020
gtacgaagaa ggccaagaac ggccgcctgg tgacggtatc cgagggtgaa gccttgatta    7080
gccgctacaa gatcgtaaag agcgaaaccg ggcggccgga gtacatcgag atcgagctag    7140
ctgattggat gtaccgcgag atcacagaag gcaagaaccc ggacgtgctg acggttcacc    7200
ccgattactt tttgatcgat cccggcatcg gccgttttct ctaccgcctg cacgccgcg     7260
ccgcaggcaa ggcagaagcc agatggttgt tcaagacgat ctacgaacgc agtggcagcg    7320
ccggagagtt caagaagttc tgtttcaccg tgcgcaagct gatcgggtca aatgacctgc    7380
cggagtacga tttgaaggag gaggcggggc aggctggccc gatcctagtc atgcgctacc    7440
gcaacctgat cgagggcgaa gcatccgccg gttcctaatg tacggagcag atgctagggc    7500
aaattgccct agcaggggaa aaaggtcgaa aaggtctctt tcctgtggat agcacgtaca    7560
ttgggaaccc aaagccgtac attgggaacc ggaacccgta cattgggaac ccaaagccgt    7620
acattgggaa ccggtcacac atgtaagtga ctgatataaa agagaaaaaa ggcgattttt    7680
ccgcctaaaa ctctttaaaa cttattaaaa ctcttaaaac ccgcctggcc tgtgcataac    7740
tgtctggcca gcgcacagcc gaagagctgc aaaaagcgcc tacccttcgg tcgctgcgct    7800
ccctacgccc cgccgcttcg cgtcggccta tcgcggccgc tggccgctca aaaatggctg    7860
gcctacggcc aggcaatcta ccagggcgcg acaagccgc cgtcgcca ctcgaccgcc        7920
ggcgcccaca tcaaggcacc ctgcctcgcg cgtttcggtg atgacggtga aaacctctga    7980
cacatgcagc tcccggagac ggtcacagct tgtctgtaag cggatgccgg gagcagacaa    8040
gcccgtcagg gcgcgtcagc gggtgttggc gggtgtcggg gcgcagccat gacccagtca    8100
cgtagcgata gcggagtgta tactggctta actatgcggc atcagagcag attgtactga    8160
gagtgcacca tatgcggtgt gaaataccgc acagatgcgt aaggagaaaa taccgcatca    8220
ggcgctcttc cgcttcctcg ctcactgact cgctgcgctc ggtcgttcgg ctgcggcgag    8280
cggtatcagc tcactcaaag gcggtaatac ggttatccac agaatcaggg gataacgcag    8340
gaaagaacat gtgagcaaaa ggccagcaaa aggccaggaa ccgtaaaaag gccgcgttgc    8400
tggcgttttt ccataggctc cgcccccctg acgagcatca caaaaatcga cgctcaagtc    8460
agaggtggcg aaacccgaca ggactataaa gataccaggc gtttccccct ggaagctccc    8520
tcgtgcgctc tcctgttccg accctgccgc ttaccggata cctgtccgcc tttctccctt    8580
cgggaagcgt ggcgctttct catagctcac gctgtaggta tctcagttcg gtgtaggtcg    8640
ttcgctccaa gctgggctgt gtgcacgaac cccccgttca gcccgaccgc tgcgccttat    8700
ccggtaacta tcgtcttgag tccaacccgg taagacacga cttatcgcca ctggcagcag    8760
ccactggtaa caggattagc agagcgaggt atgtaggcgg tgctacagag ttcttgaagt    8820
ggtggcctaa ctacggctac actagaagga cagtatttgg tatctgcgct ctgctgaagc    8880
cagttacctt cggaaaaaga gttggtagct cttgatccgg caaacaaacc accgctggta    8940
gcggtggttt ttttgtttgc aagcagcaga ttacgcgcag aaaaaaagga tctcaagaag    9000
atcctttgat cttttctacg ggtctgacgc tcagtggaa cgaaaactca cgttaaggga     9060
ttttggtcat gagattatca aaaaggatct tcacctagat cctttaaat taaaaatgaa      9120
gttttaaatc aatctaaagt atatatgagt aaacttggtc tgacagttac caatgcttaa    9180
```

```
tcagtgaggc acctatctca gcgatctgtc tatttcgttc atccatagtt gcctgactcc   9240
ccgtcgtgta gataactacg atacgggagg gcttaccatc tggccccagt gctgcaatga   9300
taccgcgaga cccacgctca ccggctccag atttatcagc aataaaccag ccagccggaa   9360
gggccgagcg cagaagtggt cctgcaactt tatccgcctc catccagtct attaattgtt   9420
gccgggaagc tagagtaagt agttcgccag ttaatagttt gcgcaacgtt gttgccattg   9480
ctacaggcat cgtggtgtca cgctcgtcgt ttggtatggc ttcattcagc tccgttccc    9540 aacgatcaag gcgagttaca tgatccccca tgttgtgcaa aaagcggtt agctccttcg    9600 gtcctccgat cgttgtcaga agtaagttgg ccgcagtgtt atcactcatg gttatggcag   9660
cactgcataa ttctcttact gtcatgccat ccgtaagatg cttttctgtg actggtgagt   9720
actcaaccaa gtcattctga gaatagtgta tgcggcgacc gagttgctct tgcccggcgt   9780
caacacggga taataccgcg ccacatagca gaactttaaa agtgctcatc attggaaaag   9840
acctgcaggg gggggggggc gctgaggtct gcctcgtgaa gaaggtgttg ctgactcata   9900
ccaggcctga atcgccccat catccagcca gaaagtgagg gagccacggt tgatgagagc   9960
tttgttgtag gtggaccagt tggtgatttt gaacttttgc tttgccacgg aacggtctgc  10020
gttgtcggga agatgcgtga tctgatcctt caactcagca aaagttcgat ttattcaaca  10080
aagccgccgt cccgtcaagt cagcgtaatg ctctgccagt gttacaacca attaaccaat  10140
tctgattaga aaaactcatc gagcatcaaa tgaaactgca atttattcat atcaggatta  10200
tcaataccat atttttgaaa aagccgtttc tgtaatgaag gagaaaactc accgaggcag  10260
ttccatagga tggcaagatc ctggtatcgg tctgcgattc cgactcgtcc aacatcaata  10320
caacctatta atttccctc gtcaaaaata aggttatcaa gtgagaaatc accatgagtg   10380
acgactgaat ccggtgagaa tggcaaaagc ttatgcattt ctttccagac ttgttcaaca  10440
ggccagccat tacgctcgtc atcaaaatca ctcgcatcaa ccaaaccgtt attcattcgt  10500
gattgcgcct gagcgagacg aaatacgcga tcgctgttaa aaggacaatt acaaacagga  10560
atcgaatgca accggcgcag gaacactgcc agcgcatcaa caatatttc acctgaatca  10620 ggatattctt ctaatacctg gaatgctgtt ttcccgggga tcgcagtggt gagtaaccat  10680
gcatcatcag gagtacggat aaaatgcttg atggtcggaa gaggcataaa ttccgtcagc  10740
cagtttagtc tgaccatctc atctgtaaca tcattggcaa cgctacctt gccatgttc    10800 agaaacaact ctggcgcatc gggcttccca tacaatcgat agattgtcgc acctgattgc  10860
ccgacattat cgcgagccca tttataccca tataaatcag catccatgtt ggaattaat   10920 cgcggcctcg agcaagacgt ttcccgttga atatggctca taacacccct tgtattactg  10980
tttatgtaag cagacagttt tattgttcat gatgatatat ttttatcttg tgcaatgtaa  11040
catcagagat tttgagacac aacgtggctt tcccccccccc ccctgcaggt caattcggtc  11100
gatatggcta ttacgaagaa ggctcgtgcg cggagtcccg tgaactttcc cacgcaacaa   11160
gtgaaccgca ccgggtttgc cggaggccat ttcgttaaaa tgcgcagcca tggctgcttc  11220
gtccagcatg gcgtaatact gatcctcgtc ttcggctggc ggtatattgc cgatgggctt  11280
caaaagccgc cgtggttgaa ccagtctatc cattccaagg tagcgaactc gaccgcttcg  11340
aagctcctcc atggtccacg ccgatgaatg acctcggcct tgtaaagacc gttgatcgct  11400
tctgcgaggg cgttgtcgtg ctgtcgccga cgcttccgat agatggctcg ataccttgctt 11460 ctgccaaccg ctcggaatag cgaaaggaca cgtattgaac accgcgatcc gagtgatgca  11520
```

| | |
|---|---|
| ctaggccgcc atgagcggga cgccgatcat gatgagcctc ctcgagggca tcgaggacaa | 11580 |
| agcctgcatg tgctgtccgg ctcgcccgcc atccgacaat gcgacgggcg aagacgtcga | 11640 |
| tcacgaaggc cacgtagacg aagccctccc aagtggcgac ataagtacgg acatgcgcaa | 11700 |
| aggctttccc ggtttgtcgc tgatggtgca agagacgctg aagcgcgatc cgatgcgcag | 11760 |
| gcatctgttc gtcttccgcg gtcgtggcgg tggcctgatc aaggtcactc gccgaagagc | 11820 |
| tgcatgattg gctcgaaacc gagcggggga aattgtcgcg cagttctccc gtcgccgagg | 11880 |
| cgataaatta catgctcaag cgatgggatg gcattacgtc attcctcgat gacggcccga | 11940 |
| tttgcctgac gaacaatgct gccgaacgaa cgctcagagg ctatgtactc ggcaggaagt | 12000 |
| catggctgtt tgccggatcg gatcgttgtg ctgaacgtgc ggcgttcatg gcgacactga | 12060 |
| tcatgagcgc caagctcaat aacatcgatc cgcaggcctg gcttgccgac gtccgcgccg | 12120 |
| accttgcgga cgctccgatc agcaggcttg agcaacagct gccgtggaac tggacatcca | 12180 |
| agacactgag tgctcaggcg gcctgacctg cggccttcac cggatactta ccccattatc | 12240 |
| gcagattgcg atgaagcatc agcgtcattc agcaatcttg ccaaagtatg caggctcgcg | 12300 |
| agaatcgacg tgcgaaaccg gctggttgcg ccaaagatcc gcttgcggag cggtcgaaca | 12360 |
| ttcatgctgg gacttcaaga ggtcgagtag aggaagaacc ggaaaggttg caccggaaaa | 12420 |
| tatgcgttcc tttggagagc gcctcatgga cgtgaacaaa tcgcccggac caaggatgcc | 12480 |
| acggatacaa aagctcgcga agctcggtcc cgtgggtgtt ctgtcgtctc gttgtacaac | 12540 |
| gaaatccatt cccattccgc gctcaagatg gcttcccctc ggcagttcat cagggctaaa | 12600 |
| tcaatctagc cgacttgtcc ggtgaaatgg gctgcactcc aacagaaaca atcaaacaaa | 12660 |
| catacacagc gacttattca cacgagctca aattacaacg gtatatatcc tgccagtcag | 12720 |
| catcatcaca ccaaaagtta ggcccgaata gtttgaaatt agaaagctcg caattgaggt | 12780 |
| ctacaggcca aattcgctct tagccgtaca atattactca ccggtgcgat gcccccatc | 12840 |
| gtaggtgaag gtgaaattta atgatccatc ttgagaccac aggcccacaa cagctaccag | 12900 |
| tttcctcaag ggtccaccaa aaacgtaagc gcttacgtac atggtcgata agaaaaggca | 12960 |
| atttgtagat gttaacatcc aacgtcgctt tcagggatcg atccaatacg caaaccgcct | 13020 |
| ctccccgcgc gttggccgat tcattaatgc agctggcacg acaggtttcc cgactggaaa | 13080 |
| gcgggcagtg agcgcaacgc aattaatgtg agttagctca ctcattaggc accccaggct | 13140 |
| ttacactta tgcttccggc tcgtatgttg tgtggaattg tgagcggata acaatttcac | 13200 |
| acaggaaaca gctatgacca tgattacgcc aagcttgcat gcctgcaggt cgactctaga | 13260 |
| ggatctgg | 13268 |

<210> SEQ ID NO 9
<211> LENGTH: 16490
<212> TYPE: DNA
<213> ORGANISM: artificial sequence
<220> FEATURE:
<223> OTHER INFORMATION: plasmid

<400> SEQUENCE: 9

| | |
|---|---|
| cgcgccagat cctctagagt cgacctgcag gcatgcaagc ttggcgtaat catggtcata | 60 |
| gctgtttcct gtgtgaaatt gttatccgct cacaattcca cacaacatac gagccggaag | 120 |
| cataaagtgt aaagcctggg gtgcctaatg agtgagctaa ctcacattaa ttgcgttgcg | 180 |
| ctcactgccc gctttccagt cgggaaacct gtcgtgccag ctgcattaat gaatcggcca | 240 |
| acgcgcgggg agaggcggtt tgcgtattgg atcgatccct gaaagcgacg ttggatgtta | 300 |

```
acatctacaa attgcctttt cttatcgacc atgtacgtaa gcgcttacgt ttttggtgga      360
cccttgagga aactggtagc tgttgtgggc ctgtggtctc aagatggatc attaatttcc      420
accttcacct acgatggggg gcatcgcacc ggtgagtaat attgtacggc taagagcgaa      480
tttggcctgt agacctcaat tgcgagcttt ctaatttcaa actattcggg cctaactttt      540
ggtgtgatga tgctgactgg caggatatat accgttgtaa tttgagctcg tgtgaataag      600
tcgctgtgta tgtttgtttg attgtttctg ttggagtgca gcccatttca ccggacaagt      660
cggctagatt gatttagccc tgatgaactg ccgagggaa gccatcttga gcgcggaatg      720
ggaatggatt tcgttgtaca acgagacgac agaacaccca cgggaccgag cttcgcgagc      780
ttttgtatcc gtggcatcct tggtccgggc gatttgttca cgtccatgag gcgctctcca      840
aaggaacgca tattttccgg tgcaaccttt ccggttcttc ctctactcga cctcttgaag      900
tcccagcatg aatgttcgac cgctccgcaa gcggatcttt ggcgcaacca gccggtttcg      960
cacgtcgatt ctcgcgagcc tgcatacttt ggcaagattg ctgaatgacg ctgatgcttc     1020
atcgcaatct gcgataatgg ggtaagtatc cggtgaaggc cgcaggtcag gccgcctgag     1080
cactcagtgt cttggatgtc cagttccacg gcagctgttg ctcaagcctg ctgatcggag     1140
cgtccgcaag gtcggcgcgg acgtcggcaa gccaggcctg cggatcgatg ttattgagct     1200
tggcgctcat gatcagtgtc gccatgaacg ccgcacgttc agcacaacga tccgatccgg     1260
caaacagcca tgacttcctg ccgagtacat agcctctgag cgttcgttcg gcagcattgt     1320
tcgtcaggca atcgggccg tcatcgagga atgacgtaat gccatcccat cgcttgagca     1380
tgtaatttat cgcctcggcg acgggagaac tgcgcgacaa tttccccgc tcggtttcga     1440 gccaatcatg cagctcttcg gcgagtgacc ttgatcaggc caccgccacg accgcggaag     1500
acgaacagat gcctgcgcat cggatcgcgc ttcagcgtct cttgcaccat cagcgacaaa     1560 ccggaaagc ctttgcgcat gtccgtactt atgtcgccac ttgggagggc ttcgtctacg     1620
tggccttcgt gatcgacgtc ttcgcccgtc gcattgtcgg atggcgggcg agccggacag     1680
cacatgcagg ctttgtcctc gatgccctcg aggaggctca tcatgatcgg cgtcccgctc     1740
atggcggcct agtgcatcac tcggatcgcg gtgttcaata cgtgtccttt cgctattccg     1800
agcggttggc agaagcaggt atcgagccat ctatcggaag cgtcggcgac agcacgacaa     1860
cgccctcgca gaagcgatca acggtctta caaggccgag gtcattcatc ggcgtggacc     1920
atggaggagc ttcgaagcgg tcgagttcgc taccttggaa tggatagact ggttcaacca     1980
cggcggcttt tgaagcccat cggcaatata ccgccagccg aagacgagga tcagtattac     2040
gccatgctgg acgaagcagc catggctgcg cattttaacg aaatggcctc cggcaaaccc     2100
ggtgcggttc acttgttgcg tgggaaagtt cacgggactc cgcgcacgag ccttcttcgt     2160
aatagccata tcgaccgaat tgacctgcag ggggggggg gaaagccacg ttgtgtctca     2220
aaatctctga tgttacattg cacaagataa aaatatatca tcatgaacaa taaaactgtc     2280
tgcttacata aacagtaata caagggggtgt tatgagccat attcaacggg aaacgtcttg     2340
ctcgaggccg cgattaaatt ccaacatgga tgctgattta tatgggtata aatgggctcg     2400
cgataatgtc gggcaatcag gtgcgacaat ctatcgattg tatgggaagc ccgatgcgcc     2460
agagttgttt ctgaaacatg gcaaaggtag cgttgccaat gatgttacag atgagatggt     2520
cagactaaac tggctgacgg aatttatgcc tcttccgacc atcaagcatt ttatccgtac     2580
tcctgatgat gcatggttac tcaccactgc gatccccggg aaaacagcat tccaggtatt     2640
```

```
agaagaatat cctgattcag gtgaaaatat tgttgatgcg ctggcagtgt tcctgcgccg    2700
gttgcattcg attcctgttt gtaattgtcc ttttaacagc gatcgcgtat ttcgtctcgc    2760
tcaggcgcaa tcacgaatga ataacggttt ggttgatgcg agtgattttg atgacgagcg    2820
taatggctgg cctgttgaac aagtctggaa agaaatgcat aagcttttgc cattctcacc    2880
ggattcagtc gtcactcatg gtgatttctc acttgataac cttatttttg acgaggggaa    2940
attaataggt tgtattgatg ttggacgagt cggaatcgca gaccgatacc aggatcttgc    3000
catcctatgg aactgcctcg gtgagttttc tccttcatta cagaaacggc ttttcaaaa     3060 atatggtatt gataatcctg atatgaataa attgcagttt catttgatgc tcgatgagtt    3120
tttctaatca gaattggtta attggttgta acactggcag agcattacgc tgacttgacg    3180
ggacggcggc tttgttgaat aaatcgaact tttgctgagt tgaaggatca gatcacgcat    3240
cttcccgaca acgcagaccg ttccgtggca aagcaaaagt tcaaaatcac caactggtcc    3300
acctacaaca aagctctcat caaccgtggc tccctcactt tctggctgga tgatggggcg    3360
attcaggcct ggtatgagtc agcaacacct tcttcacgag gcagacctca gcgccccccc    3420 cccctgcag gtcttttcca atgatgagca cttttaaagt tctgctatgt ggcgcggtat    3480
tatcccgtgt tgacgccggg caagagcaac tcggtcgccg catacactat tctcagaatg    3540
acttggttga gtactcacca gtcacagaaa agcatcttac ggatggcatg acagtaagag    3600
aattatgcag tgctgccata accatgagtg ataacactgc ggccaactta cttctgacaa    3660
cgatcggagg accgaaggag ctaaccgctt ttttgcacaa catgggggat catgtaactc    3720
gccttgatcg ttgggaaccg gagctgaatg aagccatacc aaacgacgag cgtgacacca    3780
cgatgcctgt agcaatggca acaacgttgc gcaaactatt aactggcgaa ctacttactc    3840
tagcttcccg gcaacaatta atagactgga tggaggcgga taaagttgca ggaccacttc    3900
tgcgctcggc ccttccggct ggctggttta ttgctgataa atctggagcc ggtgagcgtg    3960
ggtctcgcgg tatcattgca gcactggggc cagatggtaa gccctcccgt atcgtagtta    4020
tctacacgac ggggagtcag gcaactatgg atgaacgaaa tagacagatc gctgagatag    4080
gtgcctcact gattaagcat tggtaactgt cagaccaagt ttactcatat atactttaga    4140
ttgatttaaa acttcatttt taatttaaaa ggatctaggt gaagatcctt tttgataatc    4200
tcatgaccaa aatcccttaa cgtgagtttt cgttccactg agcgtcagac cccgtagaaa    4260
agatcaaagg atcttcttga tccttttttt ttctgcgcgt aatctgctgc ttgcaaacaa    4320
aaaaaccacc gctaccagcg gtggtttgtt tgccggatca agagctacca actctttttc    4380
cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccgggttg gactcaagac    4560
gatagttacc ggataaggcg cagcggtcgg gctgaacggg gggttcgtgc acacagccca    4620
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccaggggggaa acgcctggta tctttatagt cctgtcgggt    4800
ttcgccacct ctgacttgag cgtcgatttt tgtgatgctc gtcaggggg cggagcctat    4860 ggaaaaacgc cagcaacgcg gcctttttac ggttcctggc cttttgctgg ccttttgctc    4920
acatgttctt tcctgcgtta tcccctgatt ctgtggataa ccgtattacc gcctttgagt    4980
gagctgatac cgctcgccgc agccgaacga ccgagcgcag cgagtcagtg agcgaggaag    5040
```

```
cggaagagcg cctgatgcgg tattttctcc ttacgcatct gtgcggtatt tcacaccgca   5100
tatggtgcac tctcagtaca atctgctctg atgccgcata gttaagccag tatacactcc   5160
gctatcgcta cgtgactggg tcatggctgc gccccgacac ccgccaacac ccgctgacgc   5220
gccctgacgg gcttgtctgc tcccggcatc cgcttacaga caagctgtga ccgtctccgg   5280
gagctgcatg tgtcagaggt tttcaccgtc atcaccgaaa cgcgcgaggc agggtgcctt   5340
gatgtgggcg ccggcggtcg agtggcgacg gcgcggcttg tccgcgccct ggtagattgc   5400
ctggccgtag gccagccatt tttgagcggc cagcggccgc gataggccga cgcgaagcgg   5460
cggggcgtag ggagcgcagc gaccgaaggg taggcgcttt ttgcagctct tcggctgtgc   5520
gctggccaga cagttatgca caggccaggc gggttttaag agttttaata agttttaaag   5580
agttttaggc ggaaaaatcg ccttttttct cttttatatc agtcacttac atgtgtgacc   5640
ggttcccaat gtacggcttt gggttcccaa tgtacgggtt ccggttccca atgtacggct   5700
ttgggttccc aatgtacgtg ctatccacag gaaagagacc ttttcgacct ttttcccctg   5760
ctagggcaat ttgccctagc atctgctccg tacattagga accggcggat gcttcgccct   5820
cgatcaggtt gcggtagcgc atgactagga tcgggccagc ctgccccgcc tcctccttca   5880
aatcgtactc cggcaggtca tttgacccga tcagcttgcg cacggtgaaa cagaacttct   5940
tgaactctcc ggcgctgcca ctgcgttcgt agatcgtctt gaacaaccat ctggcttctg   6000
ccttgcctgc ggcgcggcgt gccaggcggt agagaaaacg gccgatgccg ggatcgatca   6060
aaaagtaatc ggggtgaacc gtcagcacgt ccgggttctt gccttctgtg atctcgcggt   6120
acatccaatc agctagctcg atctcgatgt actccggccg cccggtttcg ctctttacga   6180
tcttgtagcg gctaatcaag gcttcaccct cggataccgt caccaggcgg ccgttcttgg   6240
ccttcttcgt acgctgcatg gcaacgtgcg tggtgtttaa ccgaatgcag gtttctacca   6300
ggtcgtcttt ctgctttccg ccatcggctc gccggcagaa cttgagtacg tccgcaacgt   6360
gtggacggaa cacgcggccg ggcttgtctc ccttcccttc ccggtatcgg ttcatggatt   6420
cggttagatg ggaaaccgcc atcagtacca ggtcgtaatc ccacacactg gccatgccgg   6480
ccggccctgc ggaaacctct acgtgcccgt ctggaagctc gtagcggatc acctcgccag   6540
ctcgtcggtc acgcttcgac agacggaaaa cggccacgtc catgatgctg cgactatcgc   6600
gggtgcccac gtcatagagc atcggaacga aaaaatctgg ttgctcgtcg cccttgggcg   6660
gcttcctaat cgacggcgca ccggctgccg gcggttgccg ggattctttg cggattcgat   6720
cagcggccgc ttgccacgat tcaccggggc gtgcttctgc ctcgatgcgt tgccgctggg   6780
cggcctgcgc ggccttcaac ttctccacca ggtcatcacc cagcgccgcg ccgatttgta   6840
ccgggccgga tggtttgcga ccgctcacgc cgattcctcg ggcttggggg ttccagtgcc   6900
attgcagggc cggcagacaa cccagccgct tacgcctggc caaccgcccg ttcctccaca   6960 catgggcat tccacggcgt cggtgcctgg ttgttcttga ttttccatgc cgcctccttt   7020
agccgctaaa attcatctac tcatttattc atttgctcat ttactctggt agctgcgcga   7080
tgtattcaga tagcagctcg gtaatggtct tgccttggcg taccgcgtac atcttcagct   7140
tggtgtgatc ctccgccggc aactgaaagt tgacccgctt catggctggc gtgtctgcca   7200
ggctggccaa cgttgcagcc ttgctgctgc gtgcgctcgg acggccggca cttagcgtgt   7260
ttgtgctttt gctcattttc tctttacctc attaactcaa atgagttttg atttaatttc   7320
agcggccagc gcctggacct cgcgggcagc gtcgccctcg ggttctgatt caagaacggt   7380
```

```
tgtgccggcg gcggcagtgc ctgggtagct cacgcgctgc gtgatacggg actcaagaat    7440
gggcagctcg tacccggcca gcgcctcggc aacctcaccg ccgatgcgcg tgcctttgat    7500
cgcccgcgac acgacaaagg ccgcttgtag ccttccatcc gtgacctcaa tgcgctgctt    7560
aaccagctcc accaggtcgg cggtggccca tatgtcgtaa gggcttggct gcaccggaat    7620
cagcacgaag tcggctgcct tgatcgcgga cacagccaag tccgccgcct ggggcgctcc    7680
gtcgatcact acgaagtcgc gccggccgat ggccttcacg tcgcggtcaa tcgtcgggcg    7740
gtcgatgccg acaacggtta gcggttgatc ttcccgcacg gccgcccaat cgcgggcact    7800
gccctgggga tcggaatcga ctaacagaac atcggccccg gcgagttgca gggcgcgggc    7860
tagatgggtt gcgatggtcg tcttgcctga cccgcctttc tggttaagta cagcgataac    7920
ttcatgcgtt cccttgcgta tttgtttatt tactcatcgc atcatatacg cagcgaccgc    7980
atgacgcaag ctgttttact caaatacaca tcaccttttt agacggcggc gctcggtttc    8040
ttcagcggcc aagctggccg gccaggccgc cagcttggca tcagacaaac cggccaggat    8100
ttcatgcagc cgcacggttg agacgtgcgc gggcggctcg aacacgtacc cggccgcgat    8160
catctccgcc tcgatctctt cggtaatgaa aaacggttcg tcctggccgt cctggtgcgg    8220
tttcatgctt gttcctcttg gcgttcattc tcggcggccg ccagggcgtc ggcctcggtc    8280
aatgcgtcct cacggaaggc accgcgccgc ctggcctcgg tgggcgtcac ttcctcgctg    8340
cgctcaagtg cgcggtacag ggtcgagcga tgcacgccaa gcagtgcagc cgcctctttc    8400
acggtgcggc cttcctggtc gatcagctcg cgggcgtgcg cgatctgtgc cggggtgagg    8460
gtagggcggg ggccaaactt cacgcctcgg gccttggcgg cctcgcgccc gctccgggtg    8520
cggtcgatga ttagggaacg ctcgaactcg gcaatgccgg cgaacacggt caacaccatg    8580
cggccggccg gcgtggtggt gtcggcccac ggctctgcca ggctacgcag gcccgcgccg    8640
gcctcctgga tgcgctcggc aatgtccagt aggtcgcggg tgctgcgggc caggcggtct    8700
agcctggtca ctgtcacaac gtcgccaggg cgtaggtggt caagcatcct ggccagctcc    8760
gggcggtcgc gcctggtgcc ggtgatcttc tcggaaaaca gcttggtgca gccggccgcg    8820
tgcagttcgg cccgttggtt ggtcaagtcc tggtcgtcgg tgctgacgcg gcatagccc    8880
agcaggccag cggcggcgct cttgttcatg gcgtaatgtc tccggttcta gtcgcaagta    8940
ttctacttta tgcgactaaa acacgcgaca agaaaacgcc aggaaaaggg cagggcggca    9000
gcctgtcgcg taacttagga cttgtgcgac atgtcgtttt cagaagacgg ctgcactgaa    9060
cgtcagaagc cgactgcact atagcagcgg aggggttgga ccacaggacg ggtgtggtcg    9120
ccatgatcgc gtagtcgata gtggctccaa gtagcgaagc gagcaggact gggcggcggc    9180
caaagcggtc ggacagtgct ccgagaacgg gtgcgcatag aaattgcatc aacgcatata    9240
gcgctagcag cacgccatag tgactggcga tgctgtcgga atggacgata tcccgcaaga    9300
ggcccggcag taccggcata accaagccta tgcctacagc atccagggtg acggtgccga    9360
ggatgacgat gagcgcattg ttagatttca tacacggtgc ctgactgcgt tagcaattta    9420
actgtgataa actaccgcat taaagctagc ttgcttggtc gttccgcgtg aacgtcggct    9480
cgattgtacc tgcgttcaaa tactttgcga tcgtgttgcg cgcctgcccg gtgcgtcggc    9540
tgatctcacg gatcgactgc ttctctcgca acgccatccg acggatgatg tttaaaagtc    9600
ccatgtggat cactccgttg ccccgtcgct caccgtgttg ggggaaggt gcacatggct    9660
cagttctcaa tggaaattat ctgcctaacc ggctcagttc tgcgtagaaa ccaacatgca    9720
agctccaccg ggtgcaaagc ggcagcggcg gcaggatata ttcaattgta aatggcttca    9780
```

```
tgtccgggaa atctacatgg atcagcaatg agtatgatgg tcaatatgga gaaaagaaa    9840
gagtaattac caattttttt tcaattcaaa aatgtagatg tccgcagcgt tattataaaa    9900
tgaaagtaca ttttgataaa acgacaaatt acgatccgtc gtatttatag gcgaaagcaa    9960
taaacaaatt attctaattc ggaaatcttt atttcgacgt gtctacattc acgtccaaat   10020
gggggcttag atgagaaact tcacgatcga tgccttgatt tcgccattcc cagatacca    10080
tttcatcttc agattggtct gagattatgc gaaaatatac actctatatac ataaatactg   10140
acagtttgag ctaccaattc agtgtagccc attacctcac ataattcact caaatgctag   10200
gcagtctgtc aactcggcgt caatttgtcg gccactatac gatagttgcg caaattttca   10260
aagtcctggc ctaacatcac acctctgtcg gcggcgggtc ccatttgtga taaatccacc   10320
atatcgaatt aattcagact cctttgcccc agagatcaca atggacgact tcctctatct   10380
ctacgatcta gtcaggaagt tcgacggaga aggtgacgat accatgttca ccactgataa   10440
tgagaagatt agccttttca atttcagaaa gaatgctaac ccacagatgg ttagagaggc   10500
ttacgcagca ggtctcatca agacgatcta cccgagcaat aatctccagg agatcaaata   10560
ccttcccaag aaggttaaag atgcagtcaa aagattcagg actaactgca tcaagaacac   10620
agagaaagat atatttctca agatcagaag tactattcca gtatggacga ttcaaggctt   10680
gcttcacaaa ccaaggcaag taatagagat tggagtctct aaaaaggtag ttcccactga   10740
atcaaaggcc atggagtcaa agattcaaat agaggaccta acagaactcg ccgtaaagac   10800
tggcgaacag ttcatacaga gtctcttacg actcaatgac aagaagaaaa tcttcgtcaa   10860
catggtggag cacgacacgc ttgtctactc caaaaatatc aaagatacag tctcagaaga   10920
ccaaagggca attgagactt ttcaacaaag ggtaatatcc ggaaacctcc tcggattcca   10980
ttgcccagct atctgtcact ttattgtgaa gatagtggaa aaggaaggtg gctcctacaa   11040
atgccatcat tgcgataaag gaaaggccat cgttgaagat gcctctgccg acagtggtcc   11100
caaagatgga ccccacccca cgaggagcat cgtggaaaaa gaagacgttc caaccacgtc   11160
ttcaaagcaa gtggattgat gtgatatctc cactgacgta agggatgacg cacaatccca   11220
ctatccttcg caagaccctt cctctatata aggaagttca tttcatttgg agaggacacg   11280
ctgaaatcac cagtctccaa gcttgcgggg atcgtttcgc atgattgaac aagatggatt   11340
gcacgcaggt tctccggccg cttgggtgga gaggctattc ggctatgact gggcacaaca   11400
gacaatcggc tgctctgatg ccgccgtgtt ccggctgtca gcgcaggggc gcccggttct   11460
ttttgtcaag accgacctgt ccggtgccct gaatgaactg caggacgagg cagcgcggct   11520
atcgtggctg gccacgacgg gcgttccttg cgcagctgtg ctcgacgttg tcactgaagc   11580
gggaagggac tggctgctat tgggcgaagt gccggggcag gatctcctgt catctcacct   11640
tgctcctgcc gagaaagtat ccatcatggc tgatgcaatg cggcggctgc atacgcttga   11700
tccggctacc tgcccattcg accaccaagc gaaacatcgc atcgagcgag cacgtactcg   11760
gatggaagcc ggtcttgtcg atcaggatga tctggacgaa gagcatcagg ggctcgcgcc   11820
agccgaactg ttcgccaggc tcaaggcgcg catgcccgac ggcgaggatc tcgtcgtgac   11880
ccatggcgat gcctgcttgc cgaatatcat ggtggaaaat ggccgctttt ctggattcat   11940
cgactgtggc cggctgggtg tggcggaccg ctatcaggac atagcgttgg ctacccgtga   12000
tattgctgaa gagcttggcg gcgaatgggc tgaccgcttc ctcgtgcttt acggtatcgc   12060
cgctcccgat tcgcagcgca tcgccttcta tcgccttctt gacgagttct tctgagcggg   12120
```

```
actctggggt tcgaaatgac cgaccaagcg acgcccaacc tgccatcacg agatttcgat    12180
tccaccgccg ccttctatga aaggttgggc ttcggaatcg ttttccggga cgccggctgg    12240
atgatcctcc agcgcgggga tctcatgctg gagttcttcg cccaccccgg atcgatccaa    12300
cacttacgtt tgcaacgtcc aagagcaaat agaccacgaa cgccggaagg ttgccgcagc    12360
gtgtggattg cgtctcaatt ctctcttgca ggaatgcaat gatgaatatg atactgacta    12420
tgaaactttg agggaatact gcctagcacc gtcacctcat aacgtgcatc atgcatgccc    12480
tgacaacatg gaacatcgct attttttctga agaattatgc tcgttggagg atgtcgcggc    12540
aattgcagct attgccaaca tcgaactacc cctcacgcat gcattcatca atattattca    12600
tgcggggaaa ggcaagatta atccaactgg caaatcatcc agcgtgattg gtaacttcag    12660
ttccagcgac ttgattcgtt ttggtgctac ccacgttttc aataaggacg agatggtgga    12720
gtaaagaagg agtgcgtcga agcagatcgt tcaaacattt ggcaataaag tttcttaaga    12780
ttgaatcctg ttgccggtct tgcgatgatt atcatataat ttctgttgaa ttacgttaag    12840
catgtaataa ttaacatgta atgcatgacg ttatttatga gatgggtttt tatgattaga    12900
gtcccgcaat tatacattta atacgcgata gaaaacaaaa tatagcgcgc aaactaggat    12960
aaattatcgc gcgcggtgtc atctatgtta ctagatcgat caaacttcgg tactgtgtaa    13020
tgacgatgag caatcgagag gctgactaac aaaaggtaca tcgcgatgga tcgatccatt    13080
cgccattcag gctgcgcaac tgttgggaag ggcgatcggt gcgggcctct tcgctattac    13140
gccagctggc gaaaggggga tgtgctgcaa ggcgattaag ttgggtaacg ccagggtttt    13200
cccagtcacg acgttgtaaa acgacggcca gtgaattcct gcagcccggg ggatccgccc    13260
actcgaggcg cgccaagctt gcatgcctgc aggctagcct aagtacgtac tcaaaatgcc    13320
aacaaataaa aaaaagttg ctttaataat gccaaaacaa attaataaaa cacttacaac    13380
accggatttt ttttaattaa aatgtgccat ttaggataaa tagttaatat ttttaataat    13440
tatttaaaaa gccgtatcta ctaaaatgat ttttatttgg ttgaaaatat taatatgttt    13500
aaatcaacac aatctatcaa aattaaacta aaaaaaaaat aagtgtacgt ggttaacatt    13560
agtacagtaa tataagagga aaatgagaaa ttaagaaatt gaaagcgagt ctaattttta    13620
aattatgaac ctgcatatat aaaaggaaag aaagaatcca ggaagaaaag aaatgaaacc    13680
atgcatggtc ccctcgtcat cacgagtttc tgccatttgc aatagaaaca ctgaaacacc    13740
tttctctttg tcacttaatt gagatgccga agccacctca caccatgaac ttcatgaggt    13800
gtagcaccca aggcttccat agccatgcat actgaagaat gtctcaagct cagcacccta    13860
cttctgtgac gtgtccctca ttcaccttcc tctcttccct ataaataacc acgcctcagg    13920
ttctccgctt cacaactcaa acattctctc cattggtcct taaacactca tcagtcatca    13980
ccgcggccat cacaagtttg tacaaaaaag ctgaacgaga acgtaaaat gatataaata    14040
tcaatatatt aaattagatt ttgcataaaa aacagactac ataatactgt aaaacacaac    14100
atatccagtc atattggcgg ccgcattagg cacccccaggc tttacacttt atgcttccgg    14160
ctcgtataat gtgtggattt tgagttagga tccgtcgaga ttttcaggag ctaaggaagc    14220
taaaatggag aaaaaaatca ctggatatac caccgttgat atatcccaat ggcatcgtaa    14280
agaacatttt gaggcatttc agtcagttgc tcaatgtacc tataaccaga ccgttcagct    14340
ggatattacg gcctttttaa agaccgtaaa gaaaaataag cacaagtttt atccggcctt    14400
tattcacatt cttgcccgcc tgatgaatgc tcatccggaa ttccgtatgg caatgaaaga    14460
cggtgagctg gtgatatggg atagtgttca cccttgttac accgttttcc atgagcaaac    14520
```

| | | | | |
|---|---|---|---|---|
| tgaaacgttt | tcatcgctct | ggagtgaata | ccacgacgat | ttccggcagt ttctacacat | 14580 |
| atattcgcaa | gatgtggcgt | gttacggtga | aaacctggcc | tatttcccta aagggtttat | 14640 |
| tgagaatatg | tttttcgtct | cagccaatcc | ctgggtgagt | ttcaccagtt ttgatttaaa | 14700 |
| cgtggccaat | atggacaact | tcttcgcccc | cgttttcacc | atgggcaaat attatacgca | 14760 |
| aggcgacaag | gtgctgatgc | cgctggcgat | tcaggttcat | catgccgttt gtgatggctt | 14820 |
| ccatgtcggc | agaatgctta | atgaattaca | acagtactgc | gatgagtggc agggcggggc | 14880 |
| gtaaacgcgt | ggatccggct | tactaaaagc | cagataacag | tatgcgtatt tgcgcgctga | 14940 |
| tttttgcggt | ataagaatat | atactgatat | gtatacccga | agtatgtcaa aaagaggtat | 15000 |
| gctatgaagc | agcgtattac | agtgacagtt | gacagcgaca | gctatcagtt gctcaaggca | 15060 |
| tatatgatgt | caatatctcc | ggtctggtaa | gcacaaccat | gcagaatgaa gcccgtcgtc | 15120 |
| tgcgtgccga | acgctggaaa | gcggaaaatc | aggaagggat | ggctgaggtc gcccggttta | 15180 |
| ttgaaatgaa | cggctctttt | gctgacgaga | acaggggctg | gtgaaatgca gtttaaggtt | 15240 |
| tacacctata | aagagagag | ccgttatcgt | ctgtttgtgg | atgtacagag tgatattatt | 15300 |
| gacacgcccg | ggcgacggat | ggtgatcccc | ctggccagtg | cacgtctgct gtcagataaa | 15360 |
| gtctcccgtg | aactttaccc | ggtggtgcat | atcggggatg | aaagctggcg catgatgacc | 15420 |
| accgatatgg | ccagtgtgcc | ggtctccgtt | atcgggaag | aagtggctga tctcagccac | 15480 |
| cgcgaaaatg | acatcaaaaa | cgccattaac | ctgatgttct | ggggaatata aatgtcaggc | 15540 |
| tcccttatac | acagccagtc | tgcaggtcga | ccatagtgac | tggatatgtt gtgttttaca | 15600 |
| gcattatgta | gtctgttttt | tatgcaaaat | ctaatttaat | atattgatat ttatatcatt | 15660 |
| ttacgtttct | cgttcagctt | tcttgtacaa | agtggtgatg | gccgcatttc gcaccaaatc | 15720 |
| aatgaaagta | ataatgaaaa | gtctgaataa | gaatacttag | gcttagatgc ctttgttact | 15780 |
| tgtgtaaaat | aacttgagtc | atgtacccttt | ggcggaaaca | gaataaataa aaggtgaaat | 15840 |
| tccaatgctc | tatgtataag | ttagtaatac | ttaatgtgtt | ctacggttgt ttcaatatca | 15900 |
| tcaaactcta | attgaaactt | tagaaccaca | aatctcaatc | ttttcttaat gaaatgaaaa | 15960 |
| atcttaattg | taccatgttt | atgttaaaca | ccttacaatt | ggttggagag gaggaccaac | 16020 |
| cgatgggaca | acattgggag | aaagagattc | aatggagatt | tggataggag aacaacattc | 16080 |
| tttttcactt | caatacaaga | tgagtgcaac | actaaggata | tgtatgagac tttcagaagc | 16140 |
| tacgacaaca | tagatgagtg | aggtggtgat | tcctagcaag | aaagacatta gaggaagcca | 16200 |
| aaatcgaaca | aggaagacat | caagggcaag | agacaggacc | atccatctca ggaaaaggag | 16260 |
| ctttgggata | gtccgagaag | ttgtacaaga | aattttttgg | agggtgagtg atgcattgct | 16320 |
| ggtgacttta | actcaatcaa | aattgagaaa | gaaagaaaag | ggagggggct cacatgtgaa | 16380 |
| tagaagggaa | acgggagaat | tttacagttt | tgatctaatg | ggcatcccag ctagtggtaa | 16440 |
| catattcacc | atgtttaacc | ttcacgtacg | tctagaggat | ccgtcgacgg | 16490 |

<210> SEQ ID NO 10
<211> LENGTH: 209
<212> TYPE: DNA
<213> ORGANISM: artificial sequence
<220> FEATURE:
<223> OTHER INFORMATION: SAIFF and genomic DNA of lo22048

<400> SEQUENCE: 10
gccatcatac tttcttagta gttagtatcc atagtagttt gttatcaaga ttataggga      60

| | |
|---|---|
| gcagatacta tgccattttg tgaaaagcag tagggtgaaa agcaaagagc tatataactt | 120 |
| agatgtgtgt ttcttcggtt tggatgctga tagtgatgct cctatgtggc catatgttct | 180 |
| gaaagcaagg agccttctat tgaaaataa | 209 |

```
<210> SEQ ID NO 11
<211> LENGTH: 30
<212> TYPE: DNA
<213> ORGANISM: artificial sequence
<220> FEATURE:
<223> OTHER INFORMATION: primer

<400> SEQUENCE: 11
```

| | |
|---|---|
| caccatggcc accgcttcaa tcttccccgc | 30 |

```
<210> SEQ ID NO 12
<211> LENGTH: 29
<212> TYPE: DNA
<213> ORGANISM: artificial sequence
<220> FEATURE:
<223> OTHER INFORMATION: primer

<400> SEQUENCE: 12
```

| | |
|---|---|
| gcggccgctt attcgctcca gtacttctc | 29 |

```
<210> SEQ ID NO 13
<211> LENGTH: 3665
<212> TYPE: DNA
<213> ORGANISM: artificial sequence
<220> FEATURE:
<223> OTHER INFORMATION: primer

<400> SEQUENCE: 13
```

| | |
|---|---|
| aagggtgggc gcgccgaccc agctttcttg tacaaagttg gcattataag aaagcattgc | 60 |
| ttatcaattt gttgcaacga acaggtcact atcagtcaaa ataaaatcat tatttgccat | 120 |
| ccagctgata tcccctatag tgagtcgtat tacatggtca tagctgtttc ctggcagctc | 180 |
| tggcccgtgt ctcaaaatct ctgatgttac attgcacaag ataaaaatat atcatcatga | 240 |
| acaataaaac tgtctgctta cataaacagt aatacaaggg gtgttatgag ccatattcaa | 300 |
| cgggaaacgt cgaggccgcg attaaattcc aacatggatg ctgatttata tgggtataaa | 360 |
| tgggctcgcg ataatgtcgg gcaatcaggt gcgacaatct atcgcttgta tgggaagccc | 420 |
| gatgcgccag agttgtttct gaaacatggc aaaggtagcg ttgccaatga tgttacagat | 480 |
| gagatggtca gactaaactg gctgacggaa tttatgcctc ttccgaccat caagcatttt | 540 |
| atccgtactc ctgatgatgc atggttactc accactgcga tccccggaaa aacagcattc | 600 |
| caggtattag aagaatatcc tgattcaggt gaaaatattg ttgatgcgct ggcagtgttc | 660 |
| ctgcgccggt tgcattcgat tcctgtttgt aattgtcctt ttaacagcga tcgcgtattt | 720 |
| cgtctcgctc aggcgcaatc acgaatgaat aacggtttgg ttgatgcgag tgattttgat | 780 |
| gacgagcgta atggctggcc tgttgaacaa gtctggaaag aaatgcataa acttttgcca | 840 |
| ttctcaccgg attcagtcgt cactcatggt gatttctcac ttgataacct tatttttgac | 900 |
| gaggggaaat taataggttg tattgatgtt ggacgagtcg gaatcgcaga ccgataccag | 960 |
| gatcttgcca tcctatggaa ctgcctcggt gagttttctc cttcattaca gaaacggctt | 1020 |
| tttcaaaaat atggtattga taatcctgat atgaataaat tgcagtttca tttgatgctc | 1080 |
| gatgagtttt tctaatcaga attggttaat tggttgtaac actggcagag cattacgctg | 1140 |
| acttgacggg acggcgcaag ctcatgacca aaatccctta acgtgagtta cgcgtcgttc | 1200 |

```
cactgagcgt cagaccccgt agaaaagatc aaaggatctt cttgagatcc ttttttttctg    1260 cgcgtaatct gctgcttgca aacaaaaaaa ccaccgctac cagcggtggt ttgtttgccg    1320
gatcaagagc taccaactct ttttccgaag gtaactggct tcagcagagc gcagatacca    1380
aatactgtcc ttctagtgta gccgtagtta ggccaccact tcaagaactc tgtagcaccg    1440
cctacatacc tcgctctgct aatcctgtta ccagtggctg ctgccagtgg cgataagtcg    1500
tgtcttaccg ggttggactc aagacgatag ttaccggata aggcgcagcg gtcgggctga    1560
acggggggtt cgtgcacaca gcccagcttg gagcgaacga cctacaccga actgagatac    1620
ctacagcgtg agcattgaga aagcgccacg cttcccgaag ggagaaaggc ggacaggtat    1680
ccggtaagcg gcagggtcgg aacaggagag cgcacgaggg agcttccagg gggaaacgcc    1740
tggtatcttt atagtcctgt cgggtttcgc cacctctgac ttgagcgtcg attttgtga    1800 tgctcgtcag gggggcggag cctatggaaa aacgccagca acgcggcctt tttacggttc    1860
ctggcctttt gctggccttt tgctcacatg ttctttcctg cgttatcccc tgattctgtg    1920
gataaccgta ttaccgcctt tgagtgagct gataccgctc gccgcagccg aacgaccgag    1980
cgcagcgagt cagtgagcga ggaagcggaa gagcgcccaa tacgcaaacc gcctctcccc    2040
gcgcgttggc cgattcatta atgcagctgg cacgacaggt ttcccgactg gaaagcgggc    2100
agtgagcgca acgcaattaa tacgcgtacc gctagccagg aagagtttgt agaaacgcaa    2160
aaaggccatc cgtcaggatg gccttctgct tagtttgatg cctggcagtt tatggcgggc    2220
gtcctgcccg ccaccctccg ggccgttgct tcacaacgtt caaatccgct cccggcggat    2280
ttgtcctact caggagagcg ttcaccgaca acaacagat aaaacgaaag gcccagtctt    2340
ccgactgagc ctttcgtttt atttgatgcc tggcagttcc ctactctcgc gttaacgcta    2400
gcatggatgt tttcccagtc acgacgttgt aaaacgacgg ccagtcttaa gctcgggccc    2460
caaataatga ttttattttg actgatagtg acctgttcgt tgcaacaaat tgatgagcaa    2520 tgcttttttta taatgccaac tttgtacaaa aaagcaggct ccgcggccgc ccccttcacc    2580
atggccaccg cttcaatctt ccccgccgcc gtgaccgtca ccagagatgt gacatctctt    2640
cttaatccat cttctctgat catcggaaaa tcattatctc cttcaaagtt cagctcaatc    2700
aaatcctccg tttcattttc ccgcaaaacc ctaactccaa ttcgatactc ttcatctccc    2760
gccgatcact caccccgccac cgccgtggaa gcgatcacga atcgatccaa aaactccttg    2820
aaatctcgtc tccgtggagg agaaactctc tacggtctct ttttactctc cttctcgccg    2880
acattagccg agatcgctgc tcacgccggt tacgattacg tcgtcgttga tatggaacat    2940
ggtcccggag gtataccgga agctttggat tgtattcgag ctcttaacgc cgccggaaca    3000
tcagccattc tccgattacc ggaaaactca ccaacctggg ctaaaaaagc tctagatcta    3060
ggtccacaag gaatcatgtt cccaatgatc gaatctcgta aagacgctac caaagcggtg    3120
tcgtattgcc ggtttcctcc cgacggtatc cgtggatcgg cgcacacggt ggtgagagct    3180
tctaactacg gaatcgatga agggtattta agtaattacg cagaggagat tctgattatg    3240
tgccaggtgg aatcaggtga aggagtgaag aaagctgatg aaatcgcagc cgttgatggt    3300
gttgactgtg tgcaaatggg accgttggat cttagtgcga gtttagggta tttgtgggat    3360
cctggacata agaaagtgag agagatgatg aagaaggctg agaaatctgt gctgagcact    3420
gatccggcga aaggcgggc ttacttgtcg ggtttcgcga tgccgcacga tggaactggt    3480
gagattcggg gacgtggtta ccatatggtc gccggagctg ttgatgttgg attgtttagg    3540
```

```
aatgctgctg ttgaagatgt gaggagattc aagatgggtt tggtcaatga atcggacagt    3600
gaggattcgt cggaacatga taaagatgtt gatgatgaga agtactggag cgaataagcg    3660
gccgc                                                                3665

<210> SEQ ID NO 14
<211> LENGTH: 15948
<212> TYPE: DNA
<213> ORGANISM: artificial sequence
<220> FEATURE:
<223> OTHER INFORMATION: plasmid

<400> SEQUENCE: 14
acccagcttt cttgtacaaa gtggtgatgg ccgcatttcg caccaaatca atgaaagtaa      60
taatgaaaag tctgaataag aatacttagg cttagatgcc tttgttactt gtgtaaaata    120
acttgagtca tgtacctttg gcggaaacag aataaataaa aggtgaaatt ccaatgctct    180
atgtataagt tagtaatact taatgtgttc tacggttgtt tcaatatcat caaactctaa    240
ttgaaacttt agaaccacaa atctcaatct tttcttaatg aaatgaaaaa tcttaattgt    300
accatgttta tgttaaacac cttacaattg gttggagagg aggaccaacc gatgggacaa    360
cattgggaga aagagattca atggagattt ggataggaga caacattct ttttcacttc     420 aatacaagat gagtgcaaca ctaaggatat gtatgagact ttcagaagct acgacaacat    480
agatgagtga ggtggtgatt cctagcaaga aagacattag aggaagccaa aatcgaacaa    540
ggaagacatc aagggcaaga gacaggacca tccatctcag gaaaaggagc tttgggatag    600
tccgagaagt tgtacaagaa attttttgga gggtgagtga tgcattgctg gtgactttaa    660
ctcaatcaaa attgagaaag aaagaaaagg gaggggctc acatgtgaat agaagggaaa    720
cgggagaatt ttacagtttt gatctaatgg gcatcccagc tagtggtaac atattccacca   780 tgtttaacct tcacgtacgt ctagaggatc cgtcgacggc gcgccagatc ctctagagtc    840
gacctgcagg catgcaagct tggcgtaatc atggtcatag ctgtttcctg tgtgaaattg    900
ttatccgctc acaattccac acaacatacg agccggaagc ataaagtgta aagcctgggg    960
tgcctaatga gtgagctaac tcacattaat tgcgttgcgc tcactgcccg ctttccagtc   1020
gggaaacctg tcgtgccagc tgcattaatg aatcggccaa cgcgcgggga gaggcggttt   1080
gcgtattgga tcgatccctg aaagcgacgt tggatgttaa catctacaaa ttgccttttc   1140
ttatcgacca tgtacgtaag cgcttacgtt tttggtggac ccttgaggaa actggtagct   1200
gttgtgggcc tgtggtctca agatggatca ttaatttcca ccttcaccta cgatgggggg   1260
catcgcaccg gtgagtaata ttgtacggct aagagcgaat ttggcctgta gacctcaatt   1320
gcgagctttc taatttcaaa ctattcgggc ctaacttttg gtgtgatgat gctgactggc   1380
aggatatata ccgttgtaat ttgagctcgt gtgaataagt cgctgtgtat gtttgtttga   1440
ttgtttctgt tgggtgcag cccatttcac cggacaagtc ggctagattg atttagccct    1500
gatgaactgc cgaggggaag ccatcttgag cgcggaatgg gaatggatt cgttgtacaa    1560 cgagacgaca gaacacccac gggaccgagc ttcgcgagct tttgtatccg tggcatcctt   1620
ggtccgggcg atttgttcac gtccatgagg cgctctccaa aggaacgcat attttccggt   1680
gcaacctttc cggttcttcc tctactcgac ctcttgaagt cccagcatga atgttcgacc   1740
gctccgcaag cggatctttg gcgcaaccag ccggtttcgc acgtcgattc tcgcgagcct   1800
gcatactttg gcaagattgc tgaatgacgc tgatgcttca tcgcaatctg cgataatggg   1860
gtaagtatcc ggtgaaggcc gcaggtcagg ccgcctgagc actcagtgtc ttggatgtcc   1920
```

-continued

```
agttccacgg cagctgttgc tcaagcctgc tgatcggagc gtccgcaagg tcggcgcgga    1980
cgtcggcaag ccaggcctgc ggatcgatgt tattgagctt ggcgctcatg atcagtgtcg    2040
ccatgaacgc cgcacgttca gcacaacgat ccgatccggc aaacagccat gacttcctgc    2100
cgagtacata gcctctgagc gttcgttcgg cagcattgtt cgtcaggcaa atcgggccgt    2160
catcgaggaa tgacgtaatg ccatcccatc gcttgagcat gtaatttatc gcctcggcga    2220
cgggagaact gcgcgacaat ttcccccgct cggtttcgag ccaatcatgc agctcttcgg    2280
cgagtgacct tgatcaggcc accgccacga ccgcggaaga cgaacagatg cctgcgcatc    2340
ggatcgcgct tcagcgtctc ttgcaccatc agcgacaaac cgggaaagcc tttgcgcatg    2400
tccgtactta tgtcgccact tgggagggct tcgtctacgt ggccttcgtg atcgacgtct    2460
tcgcccgtcg cattgtcgga tggcgggcga gccggacagc acatgcaggc tttgtcctcg    2520
atgccctcga ggaggctcat catgatcggc gtcccgctca tggcggccta gtgcatcact    2580
cggatcgcgg tgttcaatac gtgtcctttc gctattccga gcggttggca gaagcaggta    2640
tcgagccatc tatcggaagc gtcggcgaca gcacgacaac gccctcgcag aagcgatcaa    2700
cggtctttac aaggccgagg tcattcatcg gcgtggacca tggaggagct tcgaagcggt    2760
cgagttcgct accttggaat ggatagactg gttcaaccac ggcggctttt gaagcccatc    2820
ggcaatatac cgccagccga agacgaggat cagtattacg ccatgctgga cgaagcagcc    2880
atggctgcgc attttaacga aatggcctcc ggcaaacccg gtgcggttca cttgttgcgt    2940
gggaaagttc acgggactcc gcgcacgagc cttcttcgta atagccatat cgaccgaatt    3000
gacctgcagg gggggggggg aaagccacgt tgtgtctcaa atctctgat gttacattgc    3060 acaagataaa aatatatcat catgaacaat aaaactgtct gcttacataa acagtaatac    3120 aagggtgtt atgagccata ttcaacggga aacgtcttgc tcgaggccgc gattaaattc    3180
caacatggat gctgatttat atgggtataa atgggctcgc gataatgtcg ggcaatcagg    3240
tgcgacaatc tatcgattgt atgggaagcc cgatgcgcca gagttgtttc tgaaacatgg    3300
caaaggtagc gttgccaatg atgttacaga tgagatggtc agactaaaact ggctgacgga    3360 atttatgcct cttccgacca tcaagcattt tatccgtact cctgatgatg catggttact    3420
caccactgcg atccccggga aaacagcatt ccaggtatta aagaatatc ctgattcagg    3480 tgaaaatatt gttgatgcgc tggcagtgtt cctgcgccgg ttgcattcga ttcctgtttg    3540
taattgtcct tttaacagcg atcgcgtatt tcgtctcgct caggcgcaat cacgaatgaa    3600
taacggtttg gttgatgcga gtgatttga tgacgagcgt aatggctggc ctgttgaaca    3660
agtctggaaa gaaatgcata agcttttgcc attctcaccg gattcagtcg tcactcatgg    3720
tgatttctca cttgataacc ttatttttga cgaggggaaa ttaataggtt gtattgatgt    3780
tggacgagtc ggaatcgcag accgatacca ggatcttgcc atcctatgga actgcctcgg    3840
tgagttttct ccttcattac agaaacggct ttttcaaaaa tatggtattg ataatcctga    3900
tatgaataaa ttgcagtttc atttgatgct cgatgagttt ttctaatcag aattggttaa    3960
ttggttgtaa cactggcaga gcattacgct gacttgacgg gacggcggct tgttgaata    4020 aatcgaactt ttgctgagtt gaaggatcag atcacgcatc ttcccgacaa cgcagaccgt    4080
tccgtggcaa agcaaaagtt caaaatcacc aactggtcca cctacaacaa agctctcatc    4140
aaccgtggct ccctcacttt ctggctggat gatgggcga ttcaggcctg gtatgagtca    4200 gcaacaccctt cttcacgagg cagacctcag cgcccccccc cccctgcagg tcttttccaa    4260
```

-continued

```
tgatgagcac ttttaaagtt ctgctatgtg gcgcggtatt atcccgtgtt gacgccgggc    4320
aagagcaact cggtcgccgc atacactatt ctcagaatga cttggttgag tactcaccag    4380
tcacagaaaa gcatcttacg gatggcatga cagtaagaga attatgcagt gctgccataa    4440
ccatgagtga taacactgcg gccaacttac ttctgacaac gatcggagga ccgaaggagc    4500
taaccgcttt tttgcacaac atgggggatc atgtaactcg ccttgatcgt tgggaaccgg    4560
agctgaatga agccatacca aacgacgagc gtgacaccac gatgcctgta gcaatggcaa    4620
caacgttgcg caaactatta actggcgaac tacttactct agcttcccgg caacaattaa    4680
tagactggat ggaggcggat aaagttgcag gaccacttct cgctcggccc ttccggctg     4740 gctggtttat tgctgataaa tctggagccg gtgagcgtgg gtctcgcggt atcattgcag    4800
cactggggcc agatggtaag ccctcccgta tcgtagttat ctacacgacg gggagtcagg    4860
caactatgga tgaacgaaat agacagatcg ctgagatagg tgcctcactg attaagcatt    4920
ggtaactgtc agaccaagtt tactcatata ctttagat tgatttaaaa cttcattttt      4980
aatttaaaag gatctaggtg aagatccttt ttgataatct catgaccaaa atcccttaac    5040
gtgagttttc gttccactga gcgtcagacc ccgtagaaaa gatcaaagga tcttcttgag    5100 atccttttttt tctgcgcgta atctgctgct tgcaaacaaa aaaaccaccg ctaccagcgg    5160
tggtttgttt gccggatcaa gagctaccaa ctctttttcc gaaggtaact ggcttcagca    5220
gagcgcagat accaaatact gtccttctag tgtagccgta gttaggccac cacttcaaga    5280
actctgtagc accgcctaca tacctcgctc tgctaatcct gttaccagtg gctgctgcca    5340
gtggcgataa gtcgtgtctt accgggttgg actcaagacg atagttaccg gataaggcgc    5400
agcggtcggg ctgaacgggg ggttcgtgca cacagcccag cttggagcga acgacctaca    5460
ccgaactgag atacctacag cgtgagctat gagaaagcgc cacgcttccc gaagggagaa    5520
aggcggacag gtatccggta agcggcaggg tcggaacagg agagcgcacg agggagcttc    5580 caggggggaaa cgcctggtat ctttatagtc ctgtcgggtt tcgccacctc tgacttgagc    5640
gtcgattttt gtgatgctcg tcagggggc ggagcctatg gaaaaacgcc agcaacgcgg    5700
cctttttacg gttcctggcc ttttgctggc cttttgctca catgttcttt cctgcgttat    5760
cccctgattc tgtggataac cgtattaccg cctttgagtg agctgatacc gctcgccgca    5820
gccgaacgac cgagcgcagc gagtcagtga gcgaggaagc ggaagagcgc ctgatgcggt    5880
attttctcct tacgcatctg tgcggtattt cacaccgcat atggtgcact ctcagtacaa    5940
tctgctctga tgccgcatag ttaagccagt atacactccg ctatcgctac gtgactgggt    6000
catggctgcg ccccgacacc cgccaacacc cgctgacgcg ccctgacggg cttgtctgct    6060
cccggcatcc gcttacagac aagctgtgac cgtctccggg agctgcatgt gtcagaggtt    6120
ttcaccgtca tcaccgaaac gcgcgaggca gggtgccttg atgtgggcgc cggcggtcga    6180
gtggcgacgg cgcggcttgt ccgcgccctg gtagattgcc tggccgtagg ccagccatt     6240 ttgagcggcc agcggccgcg ataggccgac gcgaagcggc gggcgtagg gagcgcagcg    6300 accgaagggt aggcgctttt tgcagctctt cggctgtgcg ctggccagac agttatgcac    6360
aggccaggcg ggttttaaga gttttaataa gttttaaaga gttttaggcg aaaaatcgc     6420 cttttttctc ttttatatca gtcacttaca tgtgtgaccg gttcccaatg tacgctttg     6480 ggttcccaat gtacgggttc cggttcccaa tgtacggctt tgggttccca atgtacgtgc    6540
tatccacagg aaaagaccct tttcgacctt ttccctgc tagggcaatt tgccctagca      6600
tctgctccgt acattaggaa ccggcggatg cttcgccctc gatcaggttg cggtagcgca    6660
```

```
tgactaggat cgggccagcc tgccccgcct cctccttcaa atcgtactcc ggcaggtcat   6720
ttgacccgat cagcttgcgc acggtgaaac agaacttctt gaactctccg cgcgctgccac  6780 tgcgttcgta gatcgtcttg aacaaccatc tggcttctgc cttgcctgcg cgcgggcgtg   6840
ccaggcggta gagaaaacgg ccgatgccgg gatcgatcaa aaagtaatcg gggtgaaccg   6900
tcagcacgtc cgggttcttg ccttctgtga tctcgcggta catccaatca gctagctcga   6960
tctcgatgta ctccggccgc ccggtttcgc tctttacgat cttgtagcgg ctaatcaagg   7020
cttcaccctc ggataccgtc accaggcggc cgttcttggc cttcttcgta cgctgcatgg   7080
caacgtgcgt ggtgtttaac cgaatgcagg tttctaccag gtcgtctttc tgctttccgc   7140
catcggctcg ccggcagaac ttgagtacgt ccgcaacgtg tggacggaac acgcggccgg   7200
gcttgtctcc cttcccttcc cggtatcggt tcatggattc ggttagatgg gaaaccgcca   7260
tcagtaccag gtcgtaatcc cacacactgg ccatgccggc cggccctgcg gaaacctcta   7320
cgtgcccgtc tggaagctcg tagcggatca cctcgccagc tcgtcggtca cgcttcgaca   7380
gacggaaaac ggccacgtcc atgatgctgc gactatcgcg ggtgcccacg tcatagagca   7440
tcggaacgaa aaaatctggt tgctcgtcgc ccttgggcgg cttcctaatc gacgcgcac    7500 cggctgccgg cggttgccgg gattctttgc ggattcgatc agcggccgct tgccacgatt   7560
caccggggcg tgcttctgcc tcgatgcgtt gccgctgggc ggcctgcgcg gccttcaact   7620
tctccaccag gtcatcaccc agcgccgcgc cgatttgtac cgggccggat ggtttgcgac   7680
cgctcacgcc gattcctcgg gcttgggggt tccagtgcca ttgcagggcc ggcagacaac   7740
ccagccgctt acgcctggcc aaccgcccgt tcctccacac atggggcatt ccacggcgtc   7800
ggtgcctggt tgttcttgat tttccatgcc gcctccttta gccgctaaaa ttcatctact   7860
catttattca tttgctcatt tactctggta gctgcgcgat gtattcagat agcagctcgg   7920
taatggtctt gccttggcgt accgcgtaca tcttcagctt ggtgtgatcc tccgccggca   7980
actgaaagtt gacccgcttc atggctggcg tgtctgccag gctggccaac gttgcagcct   8040
tgctgctgcg tgcgctcgga cggccggcac ttagcgtgtt tgtgcttttg ctcattttct   8100
ctttacctca ttaactcaaa tgagttttga tttaatttca gcggccagcg cctggacctc   8160 gcggcagcg tcgccctcgg gttctgattc aagaacggtt gtgccggcgg cggcagtgcc    8220
tgggtagctc acgcgctgcg tgatacggga ctcaagaatg ggcagctcgt acccggccag   8280
cgcctcggca acctcaccgc cgatgcgcgt gcctttgatc gcccgcgaca cgacaaaggc   8340
cgcttgtagc cttccatccg tgacctcaat gcgctgctta accagctcca ccaggtcggc   8400
ggtggcccat atgtcgtaag ggcttggctg caccggaatc agcacgaagt cggctgcctt   8460
gatcgcggac acagccaagt ccgccgcctg gggcgctccg tcgatcacta cgaagtcgcg   8520
ccggccgatg gccttcacgt cgcggtcaat cgtcgggcgg tcgatgccga caacggttag   8580
cggttgatct tcccgcacgg ccgcccaatc gcgggcactg ccctgggggat cggaatcgac  8640 taacagaaca tcggccccgg cgagttgcag ggcgcgggct agatggggttg cgatggtcgt  8700 cttgcctgac ccgcctttct ggttaagtac agcgataact tcatgcgttc ccttgcgtat   8760
ttgtttattt actcatcgca tcatatacgc agcgaccgca tgacgcaagc tgttttactc   8820
aaatacacat caccttttta gacggcggcg ctcggtttct tcagcggcca agctggccgg   8880
ccaggccgcc agcttggcat cagacaaacc ggccaggatt tcatgcagcc gcacggttga   8940
gacgtgcgcg ggcggctcga acacgtaccc ggccgcgatc atctccgcct cgatctcttc   9000
```

```
ggtaatgaaa aacggttcgt cctggccgtc ctggtgcggt ttcatgcttg ttcctcttgg   9060
cgttcattct cggcggccgc cagggcgtcg gcctcggtca atgcgtcctc acggaaggca   9120
ccgcgccgcc tggcctcggt gggcgtcact tcctcgctgc gctcaagtgc gcggtacagg   9180
gtcgagcgat gcacgccaag cagtgcagcc gcctcttca cggtgcggcc ttcctggtcg    9240
atcagctcgc gggcgtgcgc gatctgtgcc ggggtgaggg tagggcgggg gccaaacttc   9300
acgcctcggg ccttggcggc ctcgcgcccg ctccgggtgc ggtcgatgat tagggaacgc   9360
tcgaactcgg caatgccggc gaacacggtc aacaccatgc ggccggccgg cgtggtggtg   9420
tcggcccacg gctctgccag gctacgcagg cccgcgccgg cctcctggat gcgctcggca   9480
atgtccagta ggtcgcgggt gctgcgggcc aggcggtcta gcctggtcac tgtcacaacg   9540
tcgccagggc gtaggtggtc aagcatcctg gccagctccg ggcggtcgcg cctggtgccg   9600
gtgatcttct cggaaaacag cttggtgcag ccggccgcgt gcagttcggc ccgttggttg   9660
gtcaagtcct ggtcgtcggt gctgacgcgg gcatagccca gcaggccagc ggcggcgctc   9720
ttgttcatgg cgtaatgtct ccggttctag tcgcaagtat tctactttat gcgactaaaa   9780
cacgcgacaa gaaaacgcca ggaaagggc agggcggcag cctgtcgcgt aacttaggac    9840
ttgtgcgaca tgtcgttttc agaagacggc tgcactgaac gtcagaagcc gactgcacta   9900
tagcagcgga ggggttggac cacaggacgg gtgtggtcgc catgatcgcg tagtcgatag   9960
tggctccaag tagcgaagcg agcaggactg ggcggcggcc aaagcggtcg gacagtgctc   10020
cgagaacggg tgcgcataga aattgcatca acgcatatag cgctagcagc acgccatagt   10080
gactggcgat gctgtcggaa tggacgatat cccgcaagag gcccggcagt accggcataa   10140
ccaagcctat gcctacagca tccagggtga cggtgccgag gatgacgatg agcgcattgt   10200
tagatttcat acacggtgcc tgactgcgtt agcaatttaa ctgtgataaa ctaccgcatt   10260
aaagctagct tgcttggtcg ttccgcgtga acgtcggctc gattgtacct gcgttcaaat   10320
actttgcgat cgtgttgcgc gcctgccgg tgcgtcggct gatctcacgg atcgactgct    10380
tctctcgcaa cgccatccga cggatgatgt ttaaaagtcc catgtggatc actccgttgc   10440
cccgtcgctc accgtgttgg ggggaaggtg cacatggctc agttctcaat ggaaattatc   10500
tgcctaaccg gctcagttct gcgtagaaac caacatgcaa gctccaccgg gtgcaaagcg   10560
gcagcggcgg caggatatat tcaattgtaa atggcttcat gtccgggaaa tctacatgga   10620
tcagcaatga gtatgatggt caatatggag aaaaagaaag agtaattacc aatttttttt   10680
caattcaaaa atgtagatgt ccgcagcgtt attataaaat gaaagtacat tttgataaaa   10740
cgacaaatta cgatccgtcg tatttatagg cgaaagcaat aaacaaatta ttctaattcg   10800 gaaatctta tttcgacgtg tctacattca cgtccaaatg ggggcttaga tgagaaactt    10860
cacgatcgat gccttgattt cgccattccc agatacccat ttcatcttca gattggtctg   10920
agattatgcg aaaatataca ctcatataca taaatactga cagtttgagc taccaattca   10980
gtgtagccca ttacctcaca taattcactc aaatgctagg cagtctgtca actcggcgtc   11040
aatttgtcgg ccactatacg atagttgcgc aaattttcaa agtcctggcc taacatcaca   11100
cctctgtcgg cggcgggtcc catttgtgat aaatccacca tatcgaatta attcagactc   11160
ctttgcccca gagatcacaa tggacgactt cctctatctc tacgatctag tcaggaagtt   11220
cgacggagaa ggtgacgata ccatgttcac cactgataat gagaagatta gccttttcaa   11280
tttcagaaag aatgctaacc cacagatggt tagagaggct tacgcagcag gtctcatcaa   11340
gacgatctac ccgagcaata atctccagga gatcaaatac cttcccaaga aggttaaaga   11400
```

```
tgcagtcaaa agattcagga ctaactgcat caagaacaca gagaaagata tatttctcaa    11460
gatcagaagt actattccag tatggacgat tcaaggcttg cttcacaaac caaggcaagt    11520
aatagagatt ggagtctcta aaaaggtagt tcccactgaa tcaaaggcca tggagtcaaa    11580
gattcaaata gaggacctaa cagaactcgc cgtaaagact ggcgaacagt tcatacagag    11640
tctcttacga ctcaatgaca agaagaaaat cttcgtcaac atggtggagc acgacacgct    11700
tgtctactcc aaaaatatca aagatacagt ctcagaagac caaagggcaa ttgagacttt    11760
tcaacaaagg gtaatatccg gaaacctcct cggattccat tgcccagcta tctgtcactt    11820
tattgtgaag atagtggaaa aggaaggtgg ctcctacaaa tgccatcatt gcgataaagg    11880
aaaggccatc gttgaagatg cctctgccga cagtggtccc aaagatggac ccccacccac    11940
gaggagcatc gtgaaaaag aagacgttcc aaccacgtct tcaaagcaag tggattgatg    12000
tgatatctcc actgacgtaa gggatgacgc acaatcccac tatccttcgc aagacccttc    12060
ctctatataa ggaagttcat ttcatttgga gaggacacgc tgaaatcacc agtctccaag    12120
cttgcgggga tcgtttcgca tgattgaaca agatggattg cacgcaggtt ctccggccgc    12180
ttgggtggag aggctattcg gctatgactg ggcacaacag acaatcggct gctctgatgc    12240
cgccgtgttc cggctgtcag cgcaggggcg cccggttctt tttgtcaaga ccgacctgtc    12300
cggtgccctg aatgaactgc aggacgaggc agcgcggcta tcgtggctgg ccacgacggg    12360
cgttccttgc gcagctgtgc tcgacgttgt cactgaagcg ggaagggact ggctgctatt    12420
gggcgaagtg ccggggcagg atctcctgtc atctcacctt gctcctgccg agaaagtatc    12480
catcatggct gatgcaatgc ggcggctgca tacgcttgat ccggctacct gcccattcga    12540
ccaccaagcg aaacatcgca tcgagcgagc acgtactcgg atggaagccg gtcttgtcga    12600
tcaggatgat ctggacgaag agcatcaggg gctcgcgcca gccgaactgt tcgccaggct    12660
caaggcgcgc atgcccgacg gcgaggatct cgtcgtgacc catggcgatg cctgcttgcc    12720
gaatatcatg gtggaaaatg gccgcttttc tggattcatc gactgtggcc ggctgggtgt    12780
ggcggaccgc tatcaggaca tagcgttggc tacccgtgat attgctgaag agcttggcgg    12840
cgaatgggct gaccgcttcc tcgtgcttta cggtatcgcc gctcccgatt cgcagcgcat    12900
cgccttctat cgccttcttg acgagttctt ctgagcggga ctctgggtt cgaaatgacc    12960 gaccaagcga cgcccaacct gccatcacga gatttcgatt ccaccgccgc cttctatgaa    13020
aggttgggct tcggaatcgt tttccgggac gccggctgga tgatcctcca gcgcggggat    13080
ctcatgctgg agttcttcgc ccaccccgga tcgatccaac acttacgttt gcaacgtcca    13140
agagcaaata gaccacgaac gccggaaggt tgccgcagcg tgtggattgc gtctcaattc    13200
tctcttgcag gaatgcaatg atgaatatga tactgactat gaaactttga gggaatactg    13260
cctagcaccg tcacctcata acgtgcatca tgcatgccct gacaacatgg aacatcgcta    13320
tttttctgaa gaattatgct cgttggagga tgtcgcggca attgcagcta ttgccaacat    13380
cgaactaccc ctcacgcatg cattcatcaa tattattcat gcggggaaag gcaagattaa    13440
tccaactggc aaatcatcca gcgtgattgg taacttcagt tccagcgact tgattcgttt    13500
tggtgctacc cacgttttca ataaggacga gatggtggag taaagaagga gtgcgtcgaa    13560
gcagatcgtt caaacatttg gcaataaagt ttcttaagat tgaatcctgt tgccggtctt    13620
gcgatgatta tcatataatt tctgttgaat tacgttaagc atgtaataat taacatgtaa    13680
tgcatgacgt tatttatgag atgggttttt atgattagag tcccgcaatt atacatttaa    13740
```

| | | | | |
|---|---|---|---|---|
| tacgcgatag | aaaacaaaat | atagcgcgca | aactaggata | aattatcgcg cgcggtgtca 13800 |
| tctatgttac | tagatcgatc | aaacttcggt | actgtgtaat | gacgatgagc aatcgagagg 13860 |
| ctgactaaca | aaaggtacat | cgcgatggat | cgatccattc | gccattcagg ctgcgcaact 13920 |
| gttgggaagg | gcgatcggtg | cgggcctctt | cgctattacg | ccagctggcg aaaggggat 13980 |
| gtgctgcaag | gcgattaagt | tgggtaacgc | cagggttttc | ccagtcacga cgttgtaaaa 14040 |
| cgacggccag | tgaattcctg | cagcccgggg | gatccgccca | ctcgaggcgc gccaagcttg 14100 |
| catgcctgca | ggctagccta | agtacgtact | caaaatgcca | acaaataaaa aaaagttgc 14160 |
| tttaataatg | ccaaaacaaa | ttaataaaac | acttacaaca | ccggattttt tttaattaaa 14220 |
| atgtgccatt | taggataaat | agttaatatt | tttaataatt | atttaaaaag ccgtatctac 14280 |
| taaaatgatt | tttatttggt | tgaaaatatt | aaatatgttta | aatcaacaca atctatcaaa 14340 |
| attaaactaa | aaaaaaaata | agtgtacgtg | gttaacatta | gtacagtaat ataagaggaa 14400 |
| aatgagaaat | taagaaattg | aaagcgagtc | taattttaa | attatgaacc tgcatatata 14460 |
| aaaggaaaga | aagaatccag | gaagaaaaga | aatgaaacca | tgcatggtcc cctcgtcatc 14520 |
| acgagtttct | gccatttgca | atagaaacac | tgaaacacct | ttctctttgt cacttaattg 14580 |
| agatgccgaa | gccacctcac | accatgaact | tcatgaggtg | tagcacccaa ggcttccata 14640 |
| gccatgcata | ctgaagaatg | tctcaagctc | agcaccctac | ttctgtgacg tgtccctcat 14700 |
| tcaccttcct | ctcttcccta | taaataacca | cgcctcaggt | tctccgcttc acaactcaaa 14760 |
| cattctctcc | attggtcctt | aaacactcat | cagtcatcac | cgcggccatc acaagtttgt 14820 |
| acaaaaaagc | aggctccgcg | gccgcccccct | tcaccatggc | caccgcttca atcttccccg 14880 |
| ccgccgtgac | cgtcaccaga | gatgtgacat | ctcttcttaa | tccatcttct ctgatcatcg 14940 |
| gaaaatcatt | atctccttca | aagttcagct | caatcaaatc | ctccgtttca ttttcccgca 15000 |
| aaaccctaac | tccaattcga | tactcttcat | ctcccgccga | tcactcaccc gccaccgccg 15060 |
| tggaagcgat | cacgaatcga | tccaaaaact | ccttgaaatc | tcgtctccgt ggaggagaaa 15120 |
| ctctctacgg | tctcttttta | ctctccttct | cgccgacatt | agccgagatc gctgctcacg 15180 |
| ccggttacga | ttacgtcgtc | gttgatatgg | aacatggtcc | cggaggtata ccggaagctt 15240 |
| tggattgtat | tcgagctctt | aacgccgccg | gaacatcagc | cattctccga ttaccggaaa 15300 |
| actcaccaac | ctgggctaaa | aaagctctag | atctaggtcc | acaaggaatc atgttcccaa 15360 |
| tgatcgaatc | tcgtaaagac | gctaccaaag | cggtgtcgta | ttgccggttt cctcccgacg 15420 |
| gtatccgtgg | atcggcgcac | acggtggtga | gagcttctaa | ctacgaaatc gatgaagggt 15480 |
| atttaagtaa | ttacgcagag | gagattctga | ttatgtgcca | ggtggaatca ggtgaaggag 15540 |
| tgaagaaagc | tgatgaaatc | gcagccgttg | atggtgttga | ctgtgtgcaa atgggaccgt 15600 |
| tggatcttag | tgcgagttta | gggtatttgt | gggatcctgg | acataagaaa gtgagagaga 15660 |
| tgatgaagaa | ggctgagaaa | tctgtgctga | gcactgatcc | ggcgaaaggc ggggcttact 15720 |
| tgtcgggttt | cgcgatgccg | cacgatggaa | ctggtgagat | tcgggacgt ggttaccata 15780 |
| tggtcgccgg | agctgttgat | gttggattgt | ttaggaatgc | tgctgttgaa gatgtgagga 15840 |
| gattcaagat | gggtttggtc | aatgaatcgg | acagtgagga | ttcgtcggaa catgataaag 15900 |
| atgttgatga | tgagaagtac | tggagcgaat | aaaagggtgg | gcgcgccg 15948 |

<210> SEQ ID NO 15
<211> LENGTH: 17273
<212> TYPE: DNA
<213> ORGANISM: artificial sequence
<220> FEATURE:
<223> OTHER INFORMATION: plasmid

<400> SEQUENCE: 15

```
cgcgccagat cctctagagt cgacctgcag gcatgcaagc ttggcgtaat catggtcata        60
gctgtttcct gtgtgaaatt gttatccgct cacaattcca cacaacatac gagccggaag      120
cataaagtgt aaagcctggg gtgcctaatg agtgagctaa ctcacattaa ttgcgttgcg      180
ctcactgccc gctttccagt cgggaaacct gtcgtgccag ctgcattaat gaatcggcca      240
acgcgcgggg agaggcggtt tgcgtattgg atcgatccct gaaagcgacg ttggatgtta      300
acatctacaa attgcctttt cttatcgacc atgtacgtaa gcgcttacgt ttttggtgga      360
cccttgagga aactggtagc tgttgtgggc ctgtggtctc aagatggatc attaatttcc      420
accttcacct acgatggggg gcatcgcacc ggtgagtaat attgtacggc taagagcgaa      480
tttggcctgt agacctcaat tgcgagcttt ctaatttcaa actattcggg cctaacttt      540
ggtgtgatga tgctgactgg caggatatat accgttgtaa tttgagctcg tgtgaataag      600
tcgctgtgta tgtttgtttg attgtttctg ttggagtgca gcccatttca ccggacaagt      660
cggctagatt gatttagccc tgatgaactg ccgaggggaa gccatcttga gcgcggaatg      720
ggaatggatt tcgttgtaca acgagacgac agaacaccca cgggaccgag cttcgcgagc      780
ttttgtatcc gtggcatcct tggtccgggc gatttgttca cgtccatgag gcgctctcca      840
aaggaacgca tattttccgg tgcaaccttt ccggttcttc ctctactcga cctcttgaag      900
tcccagcatg aatgttcgac cgctccgcaa gcggatcttt ggcgcaacca gccggtttcg      960
cacgtcgatt ctcgcgagcc tgcatacttt ggcaagattg ctgaatgacg ctgatgcttc     1020
atcgcaatct gcgataatgg ggtaagtatc cggtgaaggc cgcaggtcag gccgcctgag     1080
cactcagtgt cttggatgtc cagttccacg gcagctgttg ctcaagcctg ctgatcggag     1140
cgtccgcaag gtcggcgcgg acgtcggcaa gccaggcctg cggatcgatg ttattgagct     1200
tggcgctcat gatcagtgtc gccatgaacg ccgcacgttc agcacaacga tccgatccgg     1260
caaacagcca tgacttcctg ccagtacat agcctctgag cgttcgttcg gcagcattgt     1320
tcgtcaggca atcgggccg tcatcgagga atgacgtaat gccatcccat cgcttgagca     1380
tgtaatttat cgcctcggcg acgggagaac tgcgcgacaa tttccccgc tcggtttcga     1440
gccaatcatg cagctcttcg gcgagtgacc ttgatcaggc caccgccacg accgcggaag     1500
acgaacagat gcctgcgcat cggatcgcgc ttcagcgtct cttgcaccat cagcgacaaa     1560
ccgggaaagc ctttgcgcat gtccgtactt atgtcgccac ttgggagggc ttcgtctacg     1620
tggccttcgt gatcgacgtc ttcgcccgtc gcattgtcgg atggcgggcg agccggacag     1680
cacatgcagg ctttgtcctc gatgccctcg aggaggctca tcatgatcgg cgtcccgctc     1740
atggcggcct agtgcatcac tcggatcgcg gtgttcaata cgtgtccttt cgctattccg     1800
agcggttggc agaagcaggt atcgagccat ctatcggaag cgtcggcgac agcacgacaa     1860
cgccctcgca gaagcgatca acggtcttta caaggccgag gtcattcatc ggcgtggacc     1920
atggaggagc ttcgaagcgg tcgagttcgc taccttggaa tggatagact ggttcaacca     1980
cggcggcttt tgaagcccat cggcaatata ccgccagccg aagacgagga tcagtattac     2040
gccatgctgg acgaagcagc catggctgcg cattttaacg aaatggcctc cggcaaaccc     2100
ggtgcggttc acttgttgcg tgggaaagtt cacgggactc cgcgcacgag ccttcttcgt     2160
aatagccata tcgaccgaat tgacctgcag ggggggggg gaaagccacg ttgtgtctca     2220
```

```
aaatctctga tgttacattg cacaagataa aaatatatca tcatgaacaa taaaactgtc    2280
tgcttacata aacagtaata caaggggtgt tatgagccat attcaacggg aaacgtcttg    2340
ctcgaggccg cgattaaatt ccaacatgga tgctgattta tatgggtata aatgggctcg    2400
cgataatgtc gggcaatcag gtgcgacaat ctatcgattg tatgggaagc ccgatgcgcc    2460
agagttgttt ctgaaacatg gcaaaggtag cgttgccaat gatgttacag atgagatggt    2520
cagactaaac tggctgacgg aatttatgcc tcttccgacc atcaagcatt ttatccgtac    2580
tcctgatgat gcatggttac tcaccactgc gatccccggg aaaacagcat tccaggtatt    2640
agaagaatat cctgattcag gtgaaaatat tgttgatgcg ctggcagtgt tcctgcgccg    2700
gttgcattcg attcctgttt gtaattgtcc ttttaacagc gatcgcgtat ttcgtctcgc    2760
tcaggcgcaa tcacgaatga ataacggttt ggttgatgcg agtgattttg atgacgagcg    2820
taatggctgg cctgttgaac aagtctggaa agaaatgcat aagcttttgc cattctcacc    2880
ggattcagtc gtcactcatg gtgatttctc acttgataac cttattttg acgaggggaa    2940 attaataggt tgtattgatg ttggacgagt cggaatcgca gaccgatacc aggatcttgc    3000
catcctatgg aactgcctcg gtgagttttc tccttcatta cagaaacggc ttttcaaaa    3060 atatggtatt gataatcctg atatgaataa attgcagttt catttgatgc tcgatgagtt    3120
tttctaatca gaattggtta attggttgta acactggcag agcattacgc tgacttgacg    3180
ggacggcggc tttgttgaat aaatcgaact tttgctgagt tgaaggatca gatcacgcat    3240
cttcccgaca acgcagaccg ttccgtggca aagcaaaagt tcaaaatcac caactggtcc    3300
acctacaaca aagctctcat caaccgtggc tccctcactt tctggctgga tgatggggcg    3360
attcaggcct ggtatgagtc agcaacacct tcttcacgag gcagacctca gcgcccccc    3420 ccccctgcag gtcttttcca atgatgagca cttttaaagt tctgctatgt ggcgcggtat    3480
tatcccgtgt tgacgccggg caagagcaac tcggtcgccg catacactat tctcagaatg    3540
acttggttga gtactcacca gtcacagaaa agcatcttac ggatggcatg acagtaagag    3600
aattatgcag tgctgccata accatgagtg ataacactgc ggccaactta cttctgacaa    3660
cgatcggagg accgaaggag ctaaccgctt ttttgcacaa catgggggat catgtaactc    3720
gccttgatcg ttgggaaccg gagctgaatg aagccatacc aaacgacgag cgtgacacca    3780
cgatgcctgt agcaatggca acaacgttgc gcaaactatt aactggcgaa ctacttactc    3840
tagcttcccg gcaacaatta atagactgga tgaggcgga taaagttgca ggaccacttc    3900
tgcgctcggc ccttccggct ggctggttta ttgctgataa atctggagcc ggtgagcgtg    3960
ggtctcgcgg tatcattgca gcactggggc cagatggtaa gccctcccgt atcgtagtta    4020
tctacacgac ggggagtcag gcaactatgg atgaacgaaa tagacagatc gctgagatag    4080
gtgcctcact gattaagcat tggtaactgt cagaccaagt ttactcatat atactttaga    4140
ttgatttaaa acttcatttt taatttaaaa ggatctaggt gaagatcctt tttgataatc    4200
tcatgaccaa aatcccttaa cgtgagtttt cgttccactg agcgtcagac cccgtagaaa    4260
agatcaaagg atcttcttga gatccttttt ttctgcgcgt aatctgctgc ttgcaaacaa    4320
aaaaaccacc gctaccagcg gtggtttgtt tgccggatca agagctacca actcttttc    4380 cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccgggttg actcaagac    4560 gatagttacc ggataaggcg cagcggtcgg gctgaacggg gggttcgtgc acacagccca    4620
```

```
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccagggggaa acgcctggta tctttatagt cctgtcgggt    4800
ttcgccacct ctgacttgag cgtcgatttt tgtgatgctc gtcagggggg cggagcctat    4860
ggaaaaacgc cagcaacgcg gccttttac ggttcctggc cttttgctgg ccttttgctc     4920
acatgttctt tcctgcgtta tcccctgatt ctgtggataa ccgtattacc gcctttgagt    4980
gagctgatac cgctcgccgc agccgaacga ccgagcgcag cgagtcagtg agcgaggaag    5040
cggaagagcg cctgatgcgg tattttctcc ttacgcatct gtgcggtatt tcacaccgca    5100
tatggtgcac tctcagtaca atctgctctg atgccgcata gttaagccag tatacactcc    5160
gctatcgcta cgtgactggg tcatggctgc gccccgacac cgccaacac ccgctgacgc     5220
gccctgacgg gcttgtctgc tcccggcatc cgcttacaga caagctgtga ccgtctccgg    5280
gagctgcatg tgtcagaggt tttcaccgtc atcaccgaaa cgcgcgaggc agggtgcctt    5340
gatgtgggcg ccggcggtcg agtggcgacg gcgcggcttg tccgcgccct ggtagattgc    5400
ctggccgtag gccagccatt tttgagcggc agcggccgc gataggccga cgcgaagcgg     5460
cggggcgtag ggagcgcagc gaccgaaggg taggcgcttt ttgcagctct tcggctgtgc    5520
gctggccaga cagttatgca caggccaggc gggttttaag agttttaata agttttaaag    5580
agttttaggc ggaaaaatcg cctttttttct cttttatatc agtcacttac atgtgtgacc    5640
ggttcccaat gtacgctttt gggttcccaa tgtacgggtt ccggttccca atgtacggct    5700
ttgggttccc aatgtacgtg ctatccacag gaaagagacc ttttcgacct ttttcccctg    5760
ctagggcaat ttgccctagc atctgctccg tacattagga accggcggat gcttcgccct    5820
cgatcaggtt gcggtagcgc atgactagga tcgggccagc ctgccccgcc tcctccttca    5880
aatcgtactc cggcaggtca tttgacccga tcagcttgcg cacggtgaaa cagaacttct    5940
tgaactctcc ggcgctgcca ctgcgttcgt agatcgtctt gaacaaccat ctggcttctg    6000
ccttgcctgc ggcgcggcgt gccaggcggt agagaaaacg gccgatgccg ggatcgatca    6060
aaaagtaatc ggggtgaacc gtcagcacgt ccgggttctt gccttctgtg atctcgcggt    6120
acatccaatc agctagctcg atctcgatgt actccggccg cccggtttcg ctctttacga    6180
tcttgtagcg gctaatcaag gcttcaccct cggataccgt caccaggcgg ccgttcttgg    6240
ccttcttcgt acgctgcatg gcaacgtgcg tggtgtttaa ccgaatgcag gtttctacca    6300
ggtcgtcttt ctgctttccg ccatcggctc gccggcagaa cttgagtacg tccgcaacgt    6360
gtggacggaa cacgcggccg ggcttgtctc ccttcccttc ccggtatcgg ttcatggatt    6420
cggttagatg gaaaccgcc atcagtacca ggtcgtaatc ccacacactg gccatgccgg     6480
ccggccctgc ggaaacctct acgtgcccgt ctggaagctc gtagcggatc acctcgccag    6540
ctcgtcggtc acgcttcgac agacggaaaa cggccacgtc catgatgctg cgactatcgc    6600
gggtgcccac gtcatagagc atcggaacga aaaaatctgg ttgctcgtcg cccttgggcg    6660
gcttcctaat cgacggcgca ccggctgccg gcggttgccg ggattctttg cggattcgat    6720
cagcggccgc ttgccacgat tcaccggggc gtgcttctgc ctcgatgcgt tgccgctggg    6780
cggcctgcgc ggccttcaac ttctccacca ggtcatcacc cagcgccgcg ccgatttgta    6840
ccgggccgga tggtttgcga ccgctcacgc cgattcctcg ggcttggggg ttccagtgcc    6900
attgcagggc cggcagacaa cccagccgct tacgcctggc caaccgcccg ttcctccaca    6960
```

```
catgggcat  tccacggcgt  cggtgcctgg  ttgttcttga  ttttccatgc  cgcctccttt    7020
agccgctaaa  attcatctac  tcatttattc  atttgctcat  ttactctggt  agctgcgcga    7080
tgtattcaga  tagcagctcg  gtaatggtct  tgccttggcg  taccgcgtac  atcttcagct    7140
tggtgtgatc  ctccgccggc  aactgaaagt  tgacccgctt  catggctggc  gtgtctgcca    7200
ggctggccaa  cgttgcagcc  ttgctgctgc  gtgcgctcgg  acggccggca  cttagcgtgt    7260
ttgtgctttt  gctcattttc  tctttacctc  attaactcaa  atgagttttg  atttaatttc    7320
agcggccagc  gcctggacct  cgcgggcagc  gtcgccctcg  ggttctgatt  caagaacggt    7380
tgtgccggcg  gcggcagtgc  ctgggtagct  cacgcgctgc  gtgatacggg  actcaagaat    7440
gggcagctcg  tacccggcca  gcgcctcggc  aacctcaccg  ccgatgcgcg  tgcctttgat    7500
cgcccgcgac  acgacaaagg  ccgcttgtag  ccttccatcc  gtgacctcaa  tgcgctgctt    7560
aaccagctcc  accaggtcgg  cggtggccca  tatgtcgtaa  gggcttggct  gcaccggaat    7620
cagcacgaag  tcggctgcct  tgatcgcgga  cacagccaag  tccgccgcct  ggggcgctcc    7680
gtcgatcact  acgaagtcgc  gccggccgat  ggccttcacg  tcgcggtcaa  tcgtcgggcg    7740
gtcgatgccg  acaacggtta  gcggttgatc  ttcccgcacg  gccgcccaat  cgcgggcact    7800
gccctgggga  tcggaatcga  ctaacagaac  atcggcccg   gcgagttgca  gggcgcgggc    7860
tagatgggtt  gcgatggtcg  tcttgcctga  cccgcctttc  tggttaagta  cagcgataac    7920
ttcatgcgtt  cccttgcgta  tttgtttatt  tactcatcgc  atcatatacg  cagcgaccgc    7980
atgacgcaag  ctgttttact  caaatacaca  tcacctttt   agacggcggc  gctcggtttc    8040
ttcagcggcc  aagctggccg  gccaggccgc  cagcttggca  tcagacaaac  cggccaggat    8100
ttcatgcagc  cgcacggttg  agacgtgcgc  gggcggctcg  aacacgtacc  cggccgcgat    8160
catctccgcc  tcgatctctt  cggtaatgaa  aaacggttcg  tcctggccgt  cctggtgcgg    8220
tttcatgctt  gttcctcttg  gcgttcattc  tcggcggccg  ccagggcgtc  ggcctcggtc    8280
aatgcgtcct  cacggaaggc  accgcgccgc  ctggcctcgg  tgggcgtcac  ttcctcgctg    8340
cgctcaagtg  cgcggtacag  ggtcgagcga  tgcacgccaa  gcagtgcagc  cgcctctttc    8400
acggtgcggc  cttcctggtc  gatcagctcg  cgggcgtgcg  cgatctgtgc  cggggtgagg    8460
gtagggcggg  ggccaaactt  cacgcctcgg  gccttggcgg  cctcgcgccc  gctccgggtg    8520
cggtcgatga  ttagggaacg  ctcgaactcg  gcaatgccgg  cgaacacggt  caacaccatg    8580
cggccggccg  gcgtggtggt  gtcggcccac  ggctctgcca  ggctacgcag  gcccgcgccg    8640
gcctcctgga  tgcgctcggc  aatgtccagt  aggtcgcggg  tgctgcgggc  caggcggtct    8700
agcctggtca  ctgtcacaac  gtcgccaggg  cgtaggtggt  caagcatcct  ggccagctcc    8760
gggcggtcgc  gcctggtgcc  ggtgatcttc  tcggaaaaca  gcttggtgca  gccggccgcg    8820
tgcagttcgg  cccgttggtt  ggtcaagtcc  tggtcgtcgg  tgctgacgcg  ggcatagccc    8880
agcaggccag  cggcggcgct  cttgttcatg  gcgtaatgtc  tccggttcta  gtcgcaagta    8940
ttctacttta  tgcgactaaa  acacgcgaca  agaaaacgcc  aggaaaaggg  cagggcggca    9000
gcctgtcgcg  taacttagga  cttgtgcgac  atgtcgtttt  cagaagacgg  ctgcactgaa    9060
cgtcagaagc  cgactgcact  atagcagcgg  aggggttgga  ccacaggacg  ggtgtggtcg    9120
ccatgatcgc  gtagtcgata  gtggctccaa  gtagcgaagc  gagcaggact  gggcggcggc    9180
caaagcggtc  ggacagtgct  ccgagaacgg  gtgcgcatag  aaattgcatc  aacgcatata    9240
gcgctagcag  cacgccatag  tgactggcga  tgctgtcgga  atggacgata  tcccgcaaga    9300
ggcccggcag  taccggcata  accaagccta  tgcctacagc  atccagggtg  acggtgccga    9360
```

```
ggatgacgat gagcgcattg ttagatttca tacacggtgc ctgactgcgt tagcaattta    9420
actgtgataa actaccgcat taaagctagc ttgcttggtc gttccgcgtg aacgtcggct    9480
cgattgtacc tgcgttcaaa tactttgcga tcgtgttgcg cgcctgcccg gtgcgtcggc    9540
tgatctcacg gatcgactgc ttctctcgca acgccatccg acggatgatg tttaaaagtc    9600
ccatgtggat cactccgttg ccccgtcgct caccgtgttg gggggaaggt gcacatggct    9660
cagttctcaa tggaaattat ctgcctaacc ggctcagttc tgcgtagaaa ccaacatgca    9720
agctccaccg ggtgcaaagc ggcagcggcg gcaggatata ttcaattgta aatggcttca    9780
tgtccgggaa atctacatgg atcagcaatg agtatgatgg tcaatatgga gaaaaagaaa    9840
gagtaattac caattttttt tcaattcaaa aatgtagatg tccgcagcgt tattataaaa    9900
tgaaagtaca ttttgataaa acgacaaatt acgatccgtc gtatttatag gcgaaagcaa    9960
taaacaaatt attctaattc ggaaatcttt atttcgacgt gtctacattc acgtccaaat    10020
gggggcttag atgagaaact tcacgatcga tgccttgatt tcgccattcc cagataccca    10080
tttcatcttc agattggtct gagattatgc gaaaatatac actcatatac ataaatactg    10140
acagtttgag ctaccaattc agtgtagccc attacctcac ataattcact caaatgctag    10200
gcagtctgtc aactcggcgt caatttgtcg gccactatac gatagttgcg caaattttca    10260
aagtcctggc ctaacatcac acctctgtcg gcggcgggtc ccatttgtga taaatccacc    10320
atatcgaatt aattcagact cctttgcccc agagatcaca atggacgact tcctctatct    10380
ctacgatcta gtcaggaagt tcgacggaga aggtgacgat accatgttca ccactgataa    10440
tgagaagatt agccttttca atttcagaaa gaatgctaac ccacagatgg ttagagaggc    10500
ttacgcagca ggtctcatca agacgatcta cccgagcaat aatctccagg agatcaaata    10560
ccttcccaag aaggttaaag atgcagtcaa aagattcagg actaactgca tcaagaacac    10620
agagaaagat atatttctca agatcagaag tactattcca gtatggacga ttcaaggctt    10680
gcttcacaaa ccaaggcaag taatagagat tggagtctct aaaaaggtag ttcccactga    10740
atcaaaggcc atggagtcaa agattcaaat agaggaccta acagaactcg ccgtaaagac    10800
tggcgaacag ttcatacaga gtctcttacg actcaatgac aagaagaaaa tcttcgtcaa    10860
catggtggag cacgcacgc ttgtctactc caaaaatatc aaagatacag tctcagaaga    10920
ccaaagggca attgagactt tcaacaaagg gtaatatcc ggaaacctcc tcggattcca    10980
ttgcccagct atctgtcact ttattgtgaa gatagtggaa aaggaaggtg gctcctacaa    11040
atgccatcat tgcgataaag gaaaggccat cgttgaagat gcctctgccg acagtggtcc    11100
caaagatgga cccccaccca cgaggagcat cgtggaaaaa gaagacgttc caaccacgtc    11160
ttcaaagcaa gtggattgat gtgatatctc cactgacgta agggatgacg cacaatccca    11220
ctatccttcg caagacccctt cctctatata aggaagttca tttcatttgg agaggacacg    11280
ctgaaatcac cagtctccaa gcttgcgggg atcgtttcgc atgattgaac aagatggatt    11340
gcacgcaggt tctccggccg cttgggtgga gaggctattc ggctatgact gggcacaaca    11400
gacaatcggc tgctctgatg ccgccgtgtt ccggctgtca gcgcaggggc gcccggttct    11460
ttttgtcaag accgacctgt ccggtgccct gaatgaactg caggacgagg cagcgcggct    11520
atcgtggctg gccacgacgg gcgttccttg cgcagctgtg ctcgacgttg tcactgaagc    11580
gggaagggac tggctgctat tgggcgaagt gccggggcag gatctcctgt catctcacct    11640
tgctcctgcc gagaaagtat ccatcatggc tgatgcaatg cggcggctgc atacgcttga    11700
```

```
tccggctacc tgcccattcg accaccaagc gaaacatcgc atcgagcgag cacgtactcg    11760
gatggaagcc ggtcttgtcg atcaggatga tctggacgaa gagcatcagg ggctcgcgcc    11820
agccgaactg ttcgccaggc tcaaggcgcg catgcccgac ggcgaggatc tcgtcgtgac    11880
ccatggcgat gcctgcttgc cgaatatcat ggtggaaaat ggccgctttt ctggattcat    11940
cgactgtggc cggctgggtg tggcggaccg ctatcaggac atagcgttgg ctacccgtga    12000
tattgctgaa gagcttggcg gcgaatgggc tgaccgcttc ctcgtgcttt acggtatcgc    12060
cgctcccgat tcgcagcgca tcgccttcta tcgccttctt gacgagttct tctgagcggg    12120
actctggggt tcgaaatgac cgaccaagcg acgcccaacc tgccatcacg agatttcgat    12180
tccaccgccg ccttctatga aggttgggc ttcggaatcg ttttccggga cgccggctgg    12240
atgatcctcc agcgcgggga tctcatgctg gagttcttcg cccacccggg atcgatccaa    12300
cacttacgtt tgcaacgtcc aagagcaaat agaccacgaa cgccggaagg ttgccgcagc    12360
gtgtggattg cgtctcaatt ctctcttgca ggaatgcaat gatgaatatg atactgacta    12420
tgaaactttg agggaatact gcctagcacc gtcacctcat aacgtgcatc atgcatgccc    12480
tgacaacatg gaacatcgct attttctga agaattatgc tcgttggagg atgtcgcggc    12540
aattgcagct attgccaaca tcgaactacc cctcacgcat gcattcatca atattattca    12600
tgcggggaaa ggcaagatta atccaactgg caaatcatcc agcgtgattg gtaacttcag    12660
ttccagcgac ttgattcgtt ttggtgctac ccacgttttc aataaggacg agatggtgga    12720
gtaaagaagg agtgcgtcga agcagatcgt tcaaacattt ggcaataaag tttcttaaga    12780
ttgaatcctg ttgccggtct tgcgatgatt atcatataat ttctgttgaa ttacgttaag    12840
catgtaataa ttaacatgta atgcatgacg ttatttatga gatgggtttt tatgattaga    12900
gtcccgcaat tatacattta atacgcgata gaaaacaaaa tatagcgcgc aaactaggat    12960
aaattatcgc gcgcggtgtc atctatgtta ctagatcgat caaacttcgg tactgtgtaa    13020
tgacgatgag caatcgagag gctgactaac aaaaggtaca tcgcgatgga tcgatccatt    13080
cgccattcag gctgcgcaac tgttgggaag ggcgatcggt gcgggcctct tcgctattac    13140
gccagctggc gaaaggggga tgtgctgcaa ggcgattaag ttgggtaacg ccagggtttt    13200
cccagtcacg acgttgtaaa acgacggcca gtgaattcct gcagcccggg ggatccgccc    13260
actcgaggcg cgccaagctt gcatgcctgc aggctagcct aagtacgtac tcaaaatgcc    13320
aacaaataaa aaaaagttg ctttaataat gccaaaacaa attaataaaa cacttacaac    13380
accggatttt ttttaattaa aatgtgccat ttaggataaa tagttaatat ttttaataat    13440
tatttaaaaa gccgtatcta ctaaaatgat ttttatttgg ttgaaaatat taatatgttt    13500
aaatcaacac aatctatcaa aattaaacta aaaaaaaaat aagtgtacgt ggttaacatt    13560
agtacagtaa tataagagga aaatgagaaa ttaagaaatt gaaagcgagt ctaatttta    13620
aattatgaac ctgcatatat aaaaggaaag aagaatcca ggaagaaaag aaatgaaacc    13680
atgcatggtc ccctcgtcat cacgagtttc tgccatttgc aatagaaaca ctgaaacacc    13740
tttctctttg tcacttaatt gagatgccga agccacctca caccatgaac ttcatgaggt    13800
gtagcaccca aggcttccat agccatgcat actgaagaat gtctcaagct cagcacccta    13860
cttctgtgac gtgtccctca ttcaccttcc tctcttccct ataaataacc acgcctcagg    13920
ttctccgctt cacaactcaa acattctctc cattggtcct taaacactca tcagtcatca    13980
ccgcggccct agacgcccat cacaagtttg tacaaaaaag ctgaacgaga aacgtaaaat    14040
gatataaata tcaatatatt aaattagatt ttgcataaaa aacagactac ataatactgt    14100
```

```
aaaacacaac atatccagtc atattggcgg ccgcattagg cacccagggc tttacacttt   14160
atgcttccgg ctcgtataat gtgtggattt tgagttagga tccgtcgaga ttttcaggag   14220
ctaaggaagc taaaatggag aaaaaaatca ctggatatac caccgttgat atatcccaat   14280
ggcatcgtaa agaacatttt gaggcatttc agtcagttgc tcaatgtacc tataaccaga   14340
ccgttcagct ggatattacg gccttttttaa agaccgtaaa gaaaaataag cacaagtttt   14400
atccggcctt tattcacatt cttgcccgcc tgatgaatgc tcatccggaa ttccgtatgg   14460
caatgaaaga cggtgagctg gtgatatggg atagtgttca cccttgttac accgttttcc   14520
atgagcaaac tgaaacgttt tcatcgctct ggagtgaata ccacgacgat ttccggcagt   14580
ttctacacat atattcgcaa gatgtggcgt gttacggtga aaacctggcc tatttcccta   14640
aagggtttat tgagaatatg ttttttcgtct cagccaatcc ctgggtgagt ttcaccagtt   14700
ttgatttaaa cgtggccaat atggacaact tcttcgcccc cgttttcacc atgggcaaat   14760
attatacgca aggcgacaag gtgctgatgc cgctggcgat tcaggttcat catgccgttt   14820
gtgatggctt ccatgtcggc agaatgctta atgaattaca acagtactgc gatgagtggc   14880
agggcggggc gtaaacgcgt ggatccggct tactaaaagc cagataacag tatgcgtatt   14940
tgcgcgctga ttttttgcggt ataagaatat atactgatat gtatacccga agtatgtcaa   15000
aaagaggtat gctatgaagc agcgtattac agtgacagtt gacagcgaca gctatcagtt   15060
gctcaaggca tatatgatgt caatatctcc ggtctggtaa gcacaaccat gcagaatgaa   15120
gcccgtcgtc tgcgtgccga acgctggaaa gcggaaaatc aggaagggat ggctgaggtc   15180
gcccggttta ttgaaatgaa cggctctttt gctgacgaga cagggggctg gtgaaatgca   15240
gtttaaggtt tacacctata aaagagagag ccgttatcgt ctgtttgtgg atgtacagag   15300
tgatattatt gacacgcccg gcgacggat ggtgatcccc ctggccagtg cacgtctgct   15360
gtcagataaa gtctcccgtg aactttaccc ggtggtgcat atcggggatg aaagctggcg   15420
catgatgacc accgatatgg ccagtgtgcc ggtctccgtt atcggggaag aagtggctga   15480
tctcagccac cgcgaaaatg acatcaaaaa cgccattaac ctgatgttct ggggaatata   15540
aatgtcaggc tcccttatac acagccagtc tgcaggtcga ccatagtgac tggatatgtt   15600
gtgttttaca gcattatgta gtctgttttt tatgcaaaat ctaatttaat atattgatat   15660
ttatatcatt ttacgtttct cgttcagctt tcttgtacaa agtggtgatg ataaccaagt   15720
ttaacgtgag tttatatatt cacagttcca tttacagatc ttatgctgat tgcagcatat   15780
aacatagtcg caacttaact ttatccctgc ttacgtaaag aaacatacat attgtttgtg   15840
gcttcgtagt ggaacatatg caattatgta atctttatat tatgagcctt tacttacaaa   15900
gattacttga gatttatgta cgtgtgctat tttcactttt caaacatgaa tttcctacgt   15960
ttacaatcat ttaatgtaaa agggatgata taatgtattt acgtacatgt gaacaaccaa   16020
gcatgttatt ttttccttttt tgttgcaac ttacaatcaa gtaatgatta tggttatgat   16080
tatgatattg gtgtgtgtct tttgccttat atatatattt atcccctttcg tttaactttg   16140
caatataatt attactgatc actatatttt ggtttgaaat ggcgcaggtt gtaatgatcg   16200
atcatcacca ctttgtacaa gaaagctgaa cgagaaacgt aaaatgatat aaatatcaat   16260
atattaaatt agattttgca taaaaaacag actacataat gctgtaaaac acaacatatc   16320
cagtcactat ggtcgacctg cagactggct gtgtataagg gagcctgaca tttatattcc   16380
ccagaacatc aggttaatgg cgtttttgat gtcatttcg cggtggctga gatcagccac   16440
```

```
ttcttccccg ataacggaga ccggcacact ggccatatcg gtggtcatca tgcgccagct   16500
ttcatccccg atatgcacca ccgggtaaag ttcacgggag actttatctg acagcagacg   16560
tgcactggcc aggggatca ccatccgtcg cccgggcgtg tcaataatat cactctgtac    16620
atccacaaac agacgataac ggctctctct tttataggtg taaaccttaa actgcatttc   16680
accagcccct gttctcgtca gcaaaagagc cgttcatttc aataaaccgg gcgacctcag   16740
ccatcccttc ctgatttttcc gctttccagc gttcggcacg cagacgacgg gcttcattct   16800
gcatggttgt gcttaccaga ccggagatat tgacatcata tatgccttga gcaactgata   16860
gctgtcgctg tcaactgtca ctgtaatacg ctgcttcata gcatacctct ttttgacata   16920
cttcgggtat acatatcagt atatattctt ataccgcaaa aatcagcgcg caaatacgca   16980
tactgttatc tggcttttag taagccggat cctaactcaa aatccacaca ttatacgagc   17040
cggaagcata aagtgtaaag cctggggtgc ctaatgcggc cgccaatatg actggatatg   17100
ttgtgtttta cagtattatg tagtctgttt tttatgcaaa atctaattta atatattgat    17160
atttatatca ttttacgttt ctcgttcagc ttttttgtac aaacttgtga tgggcgtcta   17220
gcgaactaga ggatccccgg gtaccgaggt acgtctagag gatccgtcga cgg          17273

<210> SEQ ID NO 16
<211> LENGTH: 38
<212> TYPE: DNA
<213> ORGANISM: artificial sequence
<220> FEATURE:
<223> OTHER INFORMATION: primer

<400> SEQUENCE: 16
cctagggtta accaagttta acgtgagttt atatattc                             38

<210> SEQ ID NO 17
<211> LENGTH: 38
<212> TYPE: DNA
<213> ORGANISM: artificial sequence
<220> FEATURE:
<223> OTHER INFORMATION: primer

<400> SEQUENCE: 17
actagttcgc gatcattaca acctgcgcca tttcaaac                             38

<210> SEQ ID NO 18
<211> LENGTH: 506
<212> TYPE: DNA
<213> ORGANISM: artificial sequence
<220> FEATURE:
<223> OTHER INFORMATION: PCR product with laccase intron

<400> SEQUENCE: 18
cctagggtta accaagttta acgtgagttt atatattcac agttccattt acagatctta     60
tgctgattgc agcatataac atagtcgcaa cttaacttta tccctgctta cgtaaagaaa    120
catacatatt gtttgtggct tcgtagtgga acatatgcaa ttatgtaatc tttatattat    180
gagcctttac ttacaaagat tacttgagat ttatgtacgt gtgctatttt cacttttcaa    240
acatgaattt cctacgttta caatcatttg atgtaaaagg gatgatataa tgtatttacg    300
tacatgtgaa caaccaagca tgttattttt tccttttttg ttgcaactta caatcaagta    360
atgattatgg ttatgattat gatattggtg tgtgtctttt gccttatata tatattatc     420 cctttcgttt aactttgcaa tataattatt actgatcact atatttttggt ttgaaatggc   480 gcaggttgta atgatcgcga actagt                                         506
```

<210> SEQ ID NO 19
<211> LENGTH: 1724
<212> TYPE: DNA
<213> ORGANISM: artificial sequence
<220> FEATURE:
<223> OTHER INFORMATION: EcoRV DNA fragment of plasmid PSM1318

<400> SEQUENCE: 19

| | | | | | |
|---|---|---|---|---|---|
| ctagacgccc | atcacaagtt | tgtacaaaaa | agctgaacga | gaaacgtaaa | atgatataaa | 60 |
| tatcaatata | ttaaattaga | ttttgcataa | aaaacagact | acataatact | gtaaaacaca | 120 |
| acatatccag | tcatattggc | ggccgcatta | ggcaccccag | gctttacact | ttatgcttcc | 180 |
| ggctcgtata | atgtgtggat | tttgagttag | gatccgtcga | gattttcagg | agctaaggaa | 240 |
| gctaaaatgg | agaaaaaaat | cactggatat | accaccgttg | atatatccca | atggcatcgt | 300 |
| aaagaacatt | ttgaggcatt | tcagtcagtt | gctcaatgta | cctataacca | gaccgttcag | 360 |
| ctggatatta | cggcctttt | aaagaccgta | aagaaaaata | agcacaagtt | ttatccggcc | 420 |
| tttattcaca | ttcttgcccg | cctgatgaat | gctcatccgg | aattccgtat | ggcaatgaaa | 480 |
| gacggtgagc | tggtgatatg | ggatagtgtt | cacccttgtt | acaccgtttt | ccatgagcaa | 540 |
| actgaaacgt | tttcatcgct | ctggagtgaa | taccacgacg | atttccggca | gtttctacac | 600 |
| atatattcgc | aagatgtggc | gtgttacggt | gaaaacctgg | cctatttccc | taaagggttt | 660 |
| attgagaata | tgttttttcgt | ctcagccaat | ccctgggtga | gtttcaccag | ttttgattta | 720 |
| aacgtggcca | atatggacaa | cttcttcgcc | cccgttttca | ccatgggcaa | atattatacg | 780 |
| caaggcgaca | aggtgctgat | gccgctggcg | attcaggttc | atcatgccgt | ttgtgatggc | 840 |
| ttccatgtcg | gcagaatgct | taatgaatta | caacagtact | gcgatgagtg | gcagggcggg | 900 |
| gcgtaaacgc | gtggatccgg | cttactaaaa | gccagataac | agtatgcgta | tttgcgcgct | 960 |
| gatttttgcg | gtataagaat | atatactgat | atgtataccc | gaagtatgtc | aaaaagaggt | 1020 |
| atgctatgaa | gcagcgtatt | acagtgacag | ttgacagcga | cagctatcag | ttgctcaagg | 1080 |
| catatatgat | gtcaatatct | ccggtctggt | aagcacaacc | atgcagaatg | aagcccgtcg | 1140 |
| tctgcgtgcc | gaacgctgga | aagcggaaaa | tcaggaaggg | atggctgagg | tcgcccggtt | 1200 |
| tattgaaatg | aacggctctt | tgctgacga | gaacaggggc | tggtgaaatg | cagtttaagg | 1260 |
| tttacaccta | taaaagagag | agccgttatc | gtctgtttgt | ggatgtacag | agtgatatta | 1320 |
| ttgacacgcc | cgggcgacgg | atggtgatcc | ccctggccag | tgcacgtctg | ctgtcagata | 1380 |
| aagtctcccg | tgaactttac | ccggtggtgc | atatcgggga | tgaaagctgg | cgcatgatga | 1440 |
| ccaccgatat | ggccagtgtg | ccggtctccg | ttatcgggga | agaagtggct | gatctcagcc | 1500 |
| accgcgaaaa | tgacatcaaa | aacgccatta | acctgatgtt | ctggggaata | taaatgtcag | 1560 |
| gctcccttat | acacagccag | tctgcaggtc | gaccatagtg | actggatatg | ttgtgtttta | 1620 |
| cagcattatg | tagtctgttt | tttatgcaaa | atctaattta | atatattgat | atttatatca | 1680 |
| ttttacgttt | ctcgttcagc | tttcttgtac | aaagtggtga | tgat | | 1724 |

<210> SEQ ID NO 20
<211> LENGTH: 4934
<212> TYPE: DNA
<213> ORGANISM: artificial sequence
<220> FEATURE:
<223> OTHER INFORMATION: plasmid

<400> SEQUENCE: 20

```
ctagaggatc cccgggtacc gagctcgaat tcgtaatcat ggtcatagct gtttcctgtg    60
tgaaattgtt atccgctcac aattccacac aacatacgag ccggaagcat aaagtgtaaa   120
gcctggggtg cctaatgagt gagctaactc acattaattg cgttgcgctc actgcccgct   180
ttccagtcgg gaaacctgtc gtgccagctg cattaatgaa tcggccaacg cgcgggaga    240 ggcggtttgc gtattgggcg ctagcggagt gtatactggc ttactatgtt ggcactgatg   300
agggtgtcag tgaagtgctt catgtggcag gagaaaaaag gctgcaccgg tgcgtcagca   360
gaatatgtga tacaggatat attccgcttc ctcgctcact gactcgctac gctcggtcgt   420
tcgactgcgg cgagcggaaa tggcttacga acggggcgga gatttcctgg aagatgccag   480
gaagatactt aacagggaag tgagagggcc gcggcaaagc cgttttttcca taggctccgc   540 cccccctgaca agcatcacga aatctgacgc tcaaatcagt ggtggcgaaa cccgacagga   600
ctataaagat accaggcgtt tccccctggc ggctccctcg tgcgctctcc tgttcctgcc   660
tttcggttta ccggtgtcat tccgctgtta tggccgcgtt tgtctcattc cacgcctgac   720
actcagttcc gggtaggcag ttcgctccaa gctggactgt atgcacgaac cccccgttca   780
gtccgaccgc tgcgccttat ccggtaacta tcgtcttgag tccaacccgg aaagacatgc   840
aaaagcacca ctggcagcag ccactggtaa ttgatttaga ggagttagtc ttgaagtcat   900
gcgccggtta aggctaaact gaaaggacaa gttttggtga ctgcgctcct ccaagccagt   960
tacctcggtt caaagagttg gtagctcaga gaaccttcga aaaaccgccc tgcaaggcgg  1020
ttttttcgtt ttcagagcaa gagattacgc gcagaccaaa acgatctcaa gaagatcatc  1080
ttattaaggg gtctgacgct cagtggaacg aaaactcacg ttaagggatt ttggtcatga  1140
gattatcaaa aaggatcttc acctagatcc ttttaaatta aaaatgaagt tttaaatcaa  1200
tctaaagtat atatgagtaa acttggtctg acagttacca atgcttaatc agtgaggcac  1260
ctatctcagc gatctgtcta tttcgttcat ccatagttgc ctgactcccc gtcgtgtaga  1320
taactacgat acgggagggc ttaccatctg gccccagtgc tgcaatgata ccgcgagacc  1380
cacgctcacc ggctccagat ttatcagcaa taaaccagcc agccggaagg gccgagcgca  1440
gaagtggtcc tgcaacttta tccgcctcca tccagtctat taattgttgc cgggaagcta  1500
gagtaagtag ttcgccagtt aatagtttgc gcaacgttgt tgccattgct acaggcatcg  1560
tggtgtcacg ctcgtcgttt ggtatggctt cattcagctc cggttcccaa cgatcaaggc  1620
gagttacatg atcccccatg ttgtgcaaaa aagcggttag ctccttcggt cctccgatcg  1680
ttgtcagaag taagttggcc gcagtgttat cactcatggt tatggcagca ctgcataatt  1740
ctcttactgt catgccatcc gtaagatgct tttctgtgac tggtgagtac tcaaccaagt  1800
cattctgaga atagtgtatg cggcgaccga gttgctcttg cccggcgtca atacgggata  1860
ataccgcgcc acatagcaga actttaaaag tgctcatcat tggaaaacgt tcttcggggc  1920
gaaaactctc aaggatctta ccgctgttga tccagttc gatgtaaccc actcgtgcac  1980
ccaactgatc ttcagcatct tttactttca ccagcgtttc tgggtgagca aaaacaggaa  2040
ggcaaaatgc cgcaaaaaag gaataagggc gacacggaa atgttgaata ctcatactct  2100 tccttttttca atattattga agcatttatc agggttattg tctcatgagc ggatacatat  2160
ttgaatgtat ttagaaaaat aaacaaatag gggttccgcg cacatttccc cgaaaagtgc  2220
cacctgacgt ctaagaaacc attattatca tgacattaac ctataaaaat aggcgtatca  2280
cgaggccctt tcgtctcgcg cgtttcggtg atgacggtga aaacctctga cacatgcagc  2340
tcccggagac ggtcacagct tgtctgtaag cggatgccgg gagcagacaa gcccgtcagg  2400
```

```
gcgcgtcagc gggtgttggc gggtgtcggg gctggcttaa ctatgcggca tcagagcaga    2460
ttgtactgag agtgcaccat atgcggtgtg aaataccgca cagatgcgta aggagaaaat    2520
accgcatcag gcgccattcg ccattcaggc tgcgcaactg ttgggaaggg cgatcggtgc    2580
gggcctcttc gctattacgc cagctggcga aggggggatg tgctgcaagg cgattaagtt    2640
gggtaacgcc agggttttcc cagtcacgac gttgtaaaac gacggccagt gccaagcttg    2700
catgcctgca ggtcgactct agacgcccat cacaagtttg tacaaaaaag ctgaacgaga    2760
aacgtaaaat gatataaata tcaatatatt aaattagatt ttgcataaaa aacagactac    2820
ataatactgt aaaacacaac atatccagtc atattggcgg ccgcattagg caccccaggc    2880
tttacacttt atgcttccgg ctcgtataat gtgtggattt tgagttagga tccgtcgaga    2940
ttttcaggag ctaaggaagc taaaatggag aaaaaaatca ctggatatac caccgttgat    3000
atatcccaat ggcatcgtaa agaacatttt gaggcatttc agtcagttgc tcaatgtacc    3060
tataaccaga ccgttcagct ggatattacg gcctttttaa agaccgtaaa gaaaaataag    3120
cacaagtttt atccggcctt tattcacatt cttgcccgcc tgatgaatgc tcatccggaa    3180
ttccgtatgg caatgaaaga cggtgagctg gtgatatggg atagtgttca cccttgttac    3240
accgttttcc atgagcaaac tgaaacgttt tcatcgctct ggagtgaata ccacgacgat    3300
ttccggcagt ttctacacat atattcgcaa gatgtggcgt gttacggtga aaacctggcc    3360
tatttcccta aagggtttat tgagaatatg ttttttcgtct cagccaatcc ctgggtgagt    3420
ttcaccagtt tgatttaaa cgtggccaat atggacaact tcttcgcccc cgttttcacc    3480
atgggcaaat attatacgca aggcgacaag gtgctgatgc cgctggcgat tcaggttcat    3540
catgccgttt gtgatggctt ccatgtcggc agaatgctta atgaattaca acagtactgc    3600
gatgagtggc agggcggggc gtaaacgcgt ggatccggct tactaaaagc cagataacag    3660
tatgcgtatt tgcgcgctga ttttttgcggt ataagaatat atactgatat gtatacccga    3720
agtatgtcaa aaagaggtat gctatgaagc agcgtattac agtgacagtt gacagcgaca    3780
gctatcagtt gctcaaggca tatatgatgt caatatctcc ggtctggtaa gcacaaccat    3840
gcagaatgaa gcccgtcgtc tgcgtgccga acgctggaaa gcggaaaatc aggaagggat    3900
ggctgaggtc gcccggttta ttgaaatgaa cggctctttt gctgacgaga cagggggctg    3960
gtgaaatgca gtttaaggtt tacacctata aaagagagag ccgttatcgt ctgtttgtgg    4020
atgtacagag tgatattatt gacacgcccg gcgacggat ggtgatcccc ctggccagtg    4080
cacgtctgct gtcagataaa gtctcccgtg aactttaccc ggtggtgcat atcggggatg    4140
aaagctggcg catgatgacc accgatatgg ccagtgtgcc ggtctccgtt atcggggaag    4200
aagtggctga tctcagccac cgcgaaaatg acatcaaaaa cgccattaac ctgatgttct    4260
ggggaatata aatgtcaggc tcccttatac acagccagtc tgcaggtcga ccatagtgac    4320
tggatatgtt gtgttttaca gcattatgta gtctgttttt tatgcaaaat ctaatttaat    4380
atattgatat ttatatcatt ttacgtttct cgttcagctt tcttgtacaa agtggtgatg    4440
ataaccaagt ttaacgtgag tttatatatt cacagttcca tttacagatc ttatgctgat    4500
tgcagcatat aacatagtcg caacttaact ttatccctgc ttacgtaaag aaacatacat    4560
attgtttgtg gcttcgtagt ggaacatatg caattatgta atctttatat tatgagcctt    4620
tacttacaaa gattacttga gatttatgta cgtgtgctat tttcacttttt caaacatgaa    4680 tttcctacgt ttacaatcat ttaatgtaaa agggatgata taatgtattt acgtacatgt    4740
```

| | |
|---|---|
| gaacaaccaa gcatgttatt ttttcctttt ttgttgcaac ttacaatcaa gtaatgatta | 4800 |
| tggttatgat tatgatattg gtgtgtgtct tttgccttat atatatattt atcccttcg | 4860 |
| tttaactttg caatataatt attactgatc actatatttt ggtttgaaat ggcgcaggtt | 4920 |
| gtaatgatcg cgaa | 4934 |

<210> SEQ ID NO 21
<211> LENGTH: 1021
<212> TYPE: DNA
<213> ORGANISM: artificial sequence
<220> FEATURE:
<223> OTHER INFORMATION: EcoRV DNA fragment of plasmid PSM1789

<400> SEQUENCE: 21

| | |
|---|---|
| ctagacgccc atcacaagtt tgtacaaaaa agctgaacga gaaacgtaaa atgatataaa | 60 |
| tatcaatata ttaaattaga ttttgcataa aaaacagact acataatact gtaaaacaca | 120 |
| acatatccag tcatattggc ggccgcatta ggcaccccag gctttacact ttatgcttcc | 180 |
| ggctcgtata atgtgtggat tttgagttag gatccggctt actaaaagcc agataacagt | 240 |
| atgcgtattt gcgcgctgat ttttgcggta taagaatata tactgatatg tatacccgaa | 300 |
| gtatgtcaaa aagaggtatg ctatgaagca gcgtattaca gtgacagttg acagcgacag | 360 |
| ctatcagttg ctcaaggcat atatgatgtc aatatctccg gtctggtaag cacaaccatg | 420 |
| cagaatgaag cccgtcgtct gcgtgccgaa cgctggaaag cggaaaatca ggaagggatg | 480 |
| gctgaggtcg cccggtttat tgaaatgaac ggctcttttg ctgacgagaa caggggctgg | 540 |
| tgaaatgcag tttaaggttt acacctataa aagagagagc cgttatcgtc tgtttgtgga | 600 |
| tgtacagagt gatattattg acacgcccgg gcgacggatg tgatccccc tggccagtgc | 660 |
| acgtctgctg tcagataaag tctcccgtga actttacccg gtggtgcata tcggggatga | 720 |
| aagctggcgc atgatgacca ccgatatggc cagtgtgccg gtctccgtta tcggggaaga | 780 |
| agtggctgat ctcagccacc gcgaaaatga catcaaaaac gccattaacc tgatgttctg | 840 |
| gggaatataa atgtcaggct cccttataca cagccagtct gcaggtcgac catagtgact | 900 |
| ggatatgttg tgttttacag cattatgtag tctgtttttt atgcaaaatc taatttaata | 960 |
| tattgatatt tatatcattt tacgtttctc gttcagcttt cttgtacaaa gtggtgatga | 1020 |
| t | 1021 |

<210> SEQ ID NO 22
<211> LENGTH: 5955
<212> TYPE: DNA
<213> ORGANISM: artificial sequence
<220> FEATURE:
<223> OTHER INFORMATION: plasmid

<400> SEQUENCE: 22

| | |
|---|---|
| atcatcacca ctttgtacaa gaaagctgaa cgagaaacgt aaaatgatat aaatatcaat | 60 |
| atattaaatt agattttgca taaaaaacag actacataat gctgtaaaac acaacatatc | 120 |
| cagtcactat ggtcgacctg cagactggct gtgtataagg gagcctgaca tttatattcc | 180 |
| ccagaacatc aggttaatgg cgttttttgat gtcatttcg cggtggctga atcagccac | 240 |
| ttcttccccg ataacggaga ccggcacact ggccatatcg gtggtcatca tgcgccagct | 300 |
| ttcatccccg atatgcacca ccgggtaaag ttcacgggag actttatctg acagcagacg | 360 |
| tgcactggcc aggggatca ccatccgtcg cccgggcgtg tcaataatat cactctgtac | 420 |
| atccacaaac agacgataac ggctctctct tttataggtg taaaccttaa actgcatttc | 480 |

-continued

```
accagcccct gttctcgtca gcaaaagagc cgttcatttc aataaaccgg gcgacctcag    540
ccatcccttc ctgattttcc gctttccagc gttcggcacg cagacgacgg gcttcattct    600
gcatggttgt gcttaccaga ccggagatat tgacatcata tatgccttga gcaactgata    660
gctgtcgctg tcaactgtca ctgtaatacg ctgcttcata gcatacctct ttttgacata    720
cttcgggtat acatatcagt atatattctt ataccgcaaa aatcagcgcg caaatacgca    780
tactgttatc tggcttttag taagccggat cctaactcaa aatccacaca ttatacgagc    840
cggaagcata aagtgtaaag cctggggtgc ctaatgcggc cgccaatatg actggatatg    900
ttgtgtttta cagtattatg tagtctgttt tttatgcaaa atctaattta atatattgat    960
atttatatca ttttacgttt ctcgttcagc tttttgtac aaacttgtga tgggcgtcta   1020
gcgaactaga ggatcccgg gtaccgagct cgaattcgta atcatggtca tagctgtttc   1080
ctgtgtgaaa ttgttatccg ctcacaattc cacacaacat acgagccgga agcataaagt   1140
gtaaagcctg gggtgcctaa tgagtgagct aactcacatt aattgcgttg cgctcactgc   1200
ccgctttcca gtcgggaaac ctgtcgtgcc agctgcatta atgaatcggc caacgcgcgg   1260
ggagaggcgg tttgcgtatt gggcgctagc ggagtgtata ctggcttact atgttggcac   1320
tgatgagggt gtcagtgaag tgcttcatgt ggcaggagaa aaaaggctgc accggtgcgt   1380
cagcagaata tgtgatacag gatatattcc gcttcctcgc tcactgactc gctacgctcg   1440
gtcgttcgac tgcggcgagc ggaaatggct tacgaacggg gcggagattt cctggaagat   1500
gccaggaaga tacttaacag ggaagtgaga gggccgcggc aaagccgttt ttccataggc   1560
tccgcccccc tgacaagcat cacgaaatct gacgctcaaa tcagtggtgg cgaaacccga   1620
caggactata aagataccag gcgtttcccc ctggcggctc cctcgtgcgc tctcctgttc   1680
ctgcctttcg gtttaccggt gtcattccgc tgttatggcc gcgtttgtct cattccacgc   1740
ctgacactca gttccgggta ggcagttcgc tccaagctgg actgtatgca cgaaccccc   1800 gttcagtccg accgctgcgc cttatccggt aactatcgtc ttgagtccaa cccggaaaga   1860
catgcaaaag caccactggc agcagccact ggtaattgat ttagaggagt tagtcttgaa   1920
gtcatgcgcc ggttaaggct aaactgaaag gacaagtttt ggtgactgcg ctcctccaag   1980
ccagttacct cggttcaaag agttggtagc tcagagaacc ttcgaaaaac cgccctgcaa   2040
ggcggttttt tcgttttcag agcaagagat tacgcgcaga ccaaaacgat ctcaagaaga   2100
tcatcttatt aaggggtctg acgctcagtg gaacgaaaac tcacgttaag ggattttggt   2160
catgagatta tcaaaaagga tcttcaccta gatcctttta aattaaaaat gaagttttaa   2220
atcaatctaa agtatatatg agtaaacttg gtctgacagt taccaatgct taatcagtga   2280
ggcacctatc tcagcgatct gtctatttcg ttcatccata gttgcctgac tccccgtcgt   2340
gtagataact acgatacggg agggcttacc atctggcccc agtgctgcaa tgataccgcg   2400
agacccacgc tcaccggctc cagatttatc agcaataaac cagccagccg aagggccga   2460 gcgcagaagt ggtcctgcaa ctttatccgc ctccatccag tctattaatt gttgccggga   2520
agctagagta agtagttcgc cagttaatag tttgcgcaac gttgttgcca ttgctacagg   2580
catcgtggtg tcacgctcgt cgtttggtat ggcttcattc agctccggtt cccaacgatc   2640
aaggcgagtt acatgatccc ccatgttgtg caaaaaagcg gttagctcct tcggtcctcc   2700
gatcgttgtc agaagtaagt tggccgcagt gttatcactc atggttatgg cagcactgca   2760
taattctctt actgtcatgc catccgtaag atgcttttct gtgactggtg agtactcaac   2820
```

```
caagtcattc tgagaatagt gtatgcggcg accgagttgc tcttgcccgg cgtcaatacg    2880
ggataatacc gcgccacata gcagaacttt aaaagtgctc atcattggaa acgttcttc    2940 ggggcgaaaa ctctcaagga tcttaccgct gttgagatcc agttcgatgt aacccactcg    3000
tgcacccaac tgatcttcag catcttttac tttcaccagc gtttctgggt gagcaaaaac    3060
aggaaggcaa aatgccgcaa aaagggaat aagggcgaca cggaaatgtt gaatactcat    3120
actcttcctt tttcaatatt attgaagcat ttatcaggt tattgtctca tgagcggata    3180
catatttgaa tgtatttaga aaataaaca aataggggtt ccgcgcacat ttccccgaaa    3240
agtgccacct gacgtctaag aaaccattat tatcatgaca ttaacctata aaaataggcg    3300
tatcacgagg ccctttcgtc tcgcgcgttt cggtgatgac ggtgaaaacc tctgacacat    3360
gcagctcccg gagacggtca cagcttgtct gtaagcggat gccggagca gacaagcccg    3420 tcagggcgcg tcagcgggtg ttggcgggtg tcggctgg cttaactatg cggcatcaga    3480
gcagattgta ctgagagtgc accatatgcg gtgtgaaata ccgcacagat gcgtaaggag    3540
aaaataccgc atcaggcgcc attcgccatt caggctgcgc aactgttggg aagggcgatc    3600
ggtgcgggcc tcttcgctat tacgccagct ggcgaaaggg ggatgtgctg caaggcgatt    3660
aagttgggta acgccagggt tttcccagtc acgacgttgt aaaacgacgg ccagtgccaa    3720
gcttgcatgc ctgcaggtcg actctagacg cccatcacaa gtttgtacaa aaaagctgaa    3780
cgagaaacgt aaaatgatat aaatatcaat atattaaatt agattttgca taaaaaacag    3840
actacataat actgtaaaac acaacatatc cagtcatatt ggcggccgca ttaggcaccc    3900
caggctttac actttatgct tccggctcgt ataatgtgtg gattttgagt taggatccgt    3960
cgagattttc aggagctaag gaagctaaaa tggagaaaaa aatcactgga tataccaccg    4020
ttgatatatc ccaatggcat cgtaaagaac attttgaggc atttcagtca gttgctcaat    4080
gtacctataa ccagaccgtt cagctggata ttacggcctt tttaaagacc gtaaagaaaa    4140
ataagcacaa gttttatccg gcctttattc acattcttgc ccgcctgatg aatgctcatc    4200
cggaattccg tatggcaatg aaagacggtg agctggtgat atgggatagt gttcacccct    4260
gttacaccgt tttccatgag caaactgaaa cgttttcatc gctctggagt gaataccacg    4320
acgatttccg gcagtttcta cacatatatt cgcaagatgt ggcgtgttac ggtgaaaacc    4380
tggcctattt ccctaaaggg tttattgaga atatgttttt cgtctcagcc aatccctggg    4440
tgagtttcac cagttttgat ttaaacgtgg ccaatatgga caacttcttc gcccccgttt    4500
tcaccatggg caaatattat acgcaaggcg acaaggtgct gatgccgctg gcgattcagg    4560
ttcatcatgc cgtttgtgat ggcttccatg tcggcagaat gcttaatgaa ttacaacagt    4620
actgcgatga gtggcagggc ggggcgtaaa cgcgtggatc cggcttacta aaagccagat    4680
aacagtatgc gtatttgcgc gctgattttt gcggtataag aatatatact gatatgtata    4740
cccgaagtat gtcaaaaaga ggtatgctat gaagcagcgt attacagtga cagttgacag    4800
cgacagctat cagttgctca aggcatatat gatgtcaata tctccggtct ggtaagcaca    4860
accatgcaga atgaagcccg tcgtctgcgt gccgaacgct ggaaagcgga aaatcaggaa    4920
gggatggctg aggtcgcccg gtttattgaa atgaacggct cttttgctga cgagaacagg    4980
ggctggtgaa atgcagttta aggtttacac ctataaaaga gagagccgtt atcgtctgtt    5040
tgtggatgta cagagtgata ttattgacac gcccgggcga cggatggtga tccccctggc    5100
cagtgcacgt ctgctgtcag ataaagtctc ccgtgaactt tacccggtgg tgcatatcgg    5160
ggatgaaagc tggcgcatga tgaccaccga tatggccagt gtgccggtct ccgttatcgg    5220
```

| | |
|---|---|
| ggaagaagtg gctgatctca gccaccgcga aaatgacatc aaaaacgcca ttaacctgat | 5280 |
| gttctgggga atataaatgt caggctccct tatacacagc cagtctgcag gtcgaccata | 5340 |
| gtgactggat atgttgtgtt ttacagcatt atgtagtctg ttttttatgc aaaatctaat | 5400 |
| ttaatatatt gatatttata tcattttacg tttctcgttc agctttcttg tacaaagtgg | 5460 |
| tgatgataac caagtttaac gtgagtttat atattcacag ttccatttac agatcttatg | 5520 |
| ctgattgcag catataacat agtcgcaact taactttatc cctgcttacg taaagaaaca | 5580 |
| tacatattgt ttgtggcttc gtagtggaac atatgcaatt atgtaatctt tatattatga | 5640 |
| gcctttactt acaaagatta cttgagattt atgtacgtgt gctattttca cttttcaaac | 5700 |
| atgaatttcc tacgtttaca atcatttaat gtaaaggga tgatataatg tatttacgta | 5760 |
| catgtgaaca accaagcatg ttattttttc cttttttgtt gcaacttaca atcaagtaat | 5820 |
| gattatggtt atgattatga tattggtgtg tgtcttttgc cttatatata tatttatccc | 5880 |
| tttcgtttaa ctttgcaata taattattac tgatcactat attttggttt gaaatggcgc | 5940 |
| aggttgtaat gatcg | 5955 |

<210> SEQ ID NO 23
<211> LENGTH: 9245
<212> TYPE: DNA
<213> ORGANISM: artificial sequence
<220> FEATURE:
<223> OTHER INFORMATION: plasmid

<400> SEQUENCE: 23

| | |
|---|---|
| gtacgtctag aggatccgtc gacggcgcgc ccgatcatcc ggatatagtt cctcctttca | 60 |
| gcaaaaaacc cctcaagacc cgtttagagg ccccaagggg ttatgctagt tattgctcag | 120 |
| cggtggcagc agccaactca gcttcctttc gggctttgtt agcagccgga tcgatccaag | 180 |
| ctgtacctca ctattccttt gccctcggac gagtgctggg gcgtcggttt ccactatcgg | 240 |
| cgagtacttc tacacagcca tcggtccaga cggccgcgct tctgcgggcg atttgtgtac | 300 |
| gcccgacagt cccggctccg gatcggacga ttgcgtcgca tcgaccctgc gcccaagctg | 360 |
| catcatcgaa attgccgtca accaagctct gatagagttg gtcaagacca atgcggagca | 420 |
| tatacgcccg gagccgcggc gatcctgcaa gctccggatg cctccgctcg aagtagcgcg | 480 |
| tctgctgctc catacaagcc aaccacggcc tccagaagaa gatgttggcg acctcgtatt | 540 |
| gggaatcccc gaacatcgcc tcgctccagt caatgaccgc tgttatgcgg ccattgtccg | 600 |
| tcaggacatt gttggagccg aaatccgcgt gcacgaggtg ccggacttcg ggcagtcct | 660 |
| cggcccaaag catcagctca tcgagagcct gcgcgacgga cgcactgacg gtgtcgtcca | 720 |
| tcacagtttg ccagtgatac acatgggat cagcaatcgc gcatatgaaa tcacgccatg | 780 |
| tagtgtattg accgattcct tgcggtccga atgggccgaa cccgctcgtc tggctaagat | 840 |
| cggccgcagc gatcgcatcc atagcctccg cgaccggctg cagaacagcg gcagttcgg | 900 |
| tttcaggcag gtcttgcaac gtgacaccct gtgcacggcg ggagatgcaa taggtcaggc | 960 |
| tctcgctgaa ttccccaatg tcaagcactt ccggaatcgg agcgcggcc gatgcaaagt | 1020 |
| gccgataaac ataacgatct tgtagaaac catcggcgca gctatttacc cgcaggacat | 1080 |
| atccacgccc tcctacatcg aagctgaaag cacgagattc ttcgccctcc gagagctgca | 1140 |
| tcaggtcgga gacgctgtcg aacttttcga tcagaaactt ctcgacagac gtcgcggtga | 1200 |
| gttcaggctt ttccatgggt atatctcctt cttaaagtta aacaaaatta tttctagagg | 1260 |

```
gaaaccgttg tggtctccct atagtgagtc gtattaattt cgcgggatcg agatcgatcc    1320
aattccaatc ccacaaaaat ctgagcttaa cagcacagtt gctcctctca gagcagaatc    1380
gggtattcaa caccctcata tcaactacta cgttgtgtat aacggtccac atgccggtat    1440
atacgatgac tggggttgta caaaggcggc aacaaacggc gttcccggag ttgcacacaa    1500
gaaatttgcc actattacag aggcaagagc agcagctgac gcgtacacaa caagtcagca    1560
aacagacagg ttgaacttca tccccaaagg agaagctcaa ctcaagccca agagctttgc    1620
taaggcccta acaagcccac caaagcaaaa agcccactgg ctcacgctag gaaccaaaag    1680
gcccagcagt gatccagccc caaaagagat ctcctttgcc ccggagatta caatggacga    1740
tttcctctat ctttacgatc taggaaggaa gttcgaaggt gaaggtgacg acactatgtt    1800
caccactgat aatgagaagg ttagcctctt caatttcaga aagaatgctg acccacagat    1860
ggttagagag gcctacgcag caggtctcat caagacgatc tacccgagta acaatctcca    1920
ggagatcaaa taccttccca agaaggttaa agatgcagtc aaaagattca ggactaattg    1980
catcaagaac acagagaaag acatatttct caagatcaga agtactattc cagtatggac    2040
gattcaaggc ttgcttcata aaccaaggca agtaatagag attggagtct ctaaaaaggt    2100
agttcctact gaatcaaagg ccatgcatgg agtctaagat tcaaatcgag gatctaacag    2160
aactcgccgt gaagactggc gaacagttca tacagagtct tttacgactc aatgacaaga    2220
agaaaatctt cgtcaacatg gtggagcacg acactctggt ctactccaaa aatgtcaaag    2280
atacagtctc agaagaccaa agggctattg agacttttca acaaggcata atttcgggaa    2340
acctcctcgg attccattgc ccagctatct gtcacttcat cgaaaggaca gtagaaaagg    2400
aaggtggctc ctacaaatgc catcattgcg ataaaggaaa ggctatcatt caagatgcct    2460
ctgccgacag tggtcccaaa gatggacccc caccccgag gagcatcgtg aaaaagaag     2520
acgttccaac cacgtcttca aagcaagtgg attgatgtga catctccact gacgtaaggg    2580
atgacgcaca atcccactat ccttcgcaag acccttcctc tatataagga agttcatttc    2640
atttggagag gacacgctcg agctcatttc tctattactt cagccataac aaaagaactc    2700
ttttctcttc ttattaaacc atgaaaaagc ctgaactcac cgcgacgtct gtcgagaagt    2760
ttctgatcga aaagttcgac agcgtctccg acctgatgca gctctcggag ggcgaagaat    2820
ctcgtgcttt cagcttcgat gtaggagggc gtggatatgt cctgcgggta atagctgcg     2880
ccgatggttt ctacaaagat cgttatgttt atcggcactt tgcatcggcc gcgctcccga    2940
ttccggaagt gcttgacatt ggggaattca gcgagagcct gacctattgc atctcccgcc    3000
gtgcacaggg tgtcacgttg caagacctgc ctgaaaccga actgcccgct gttctgcagc    3060
cggtcgcgga ggccatggat gcgatcgctg cggccgatct tagccagacg agcgggttcg    3120
gcccattcgg accgcaagga atcggtcaat acactacatg gcgtgatttc atatgcgcga    3180
ttgctgatcc ccatgtgtat cactggcaaa ctgtgatgga cgacaccgtc agtgcgtccg    3240
tcgcgcaggc tctcgatgag ctgatgcttt gggccgagga ctgccccgaa gtccggcacc    3300
tcgtgcacgc ggatttcggc tccaacaatg tcctgacgga caatggccgc ataacagcgg    3360
tcattgactg gagcgaggcg atgttcgggg attcccaata cgaggtcgcc aacatcttct    3420
tctggaggcc gtggttggct tgtatggagc agcagacgcg ctacttcgag cggaggcatc    3480
cggagcttgc aggatcgccg cggctccggg cgtatatgct ccgcattggt cttgaccaac    3540
tctatcagag cttggttgac ggcaatttcg atgatgcagc ttgggcgcag ggtcgatgcg    3600
acgcaatcgt ccgatccgga gccgggactg tcgggcgtac acaaatcgcc cgcagaagcg    3660
```

```
cggccgtctg gaccgatggc tgtgtagaag tactcgccga tagtggaaac cgacgcccca    3720
gcactcgtcc gagggcaaag gaatagtgag gtacctaaag aaggagtgcg tcgaagcaga    3780
tcgttcaaac atttggcaat aaagtttctt aagattgaat cctgttgccg gtcttgcgat    3840
gattatcata taatttctgt tgaattacgt taagcatgta ataattaaca tgtaatgcat    3900
gacgttattt atgagatggg ttttttatgat tagagtcccg caattataca tttaatacgc    3960
gatagaaaac aaaatatagc gcgcaaacta ggataaatta tcgcgcgcgg tgtcatctat    4020
gttactagat cgatgtcgaa tcgatcaacc tgcattaatg aatcggccaa cgcgcgggga    4080
gaggcggttt gcgtattggg cgctcttccg cttcctcgct cactgactcg ctgcgctcgg    4140
tcgttcggct gcggcgagcg gtatcagctc actcaaaggc ggtaatacgg ttatccacag    4200
aatcagggga taacgcagga aagaacatgt gagcaaaagg ccagcaaaag gccaggaacc    4260
gtaaaaaggc cgcgttgctg gcgttttttcc ataggctccg ccccctgac gagcatcaca    4320 aaaatcgacg ctcaagtcag aggtggcgaa acccgacagg actataaaga taccaggcgt    4380
ttccccctgg aagctccctc gtgcgctctc ctgttccgac cctgccgctt accggatacc    4440
tgtccgcctt tctcccttcg ggaagcgtgg cgctttctca atgctcacgc tgtaggtatc    4500
tcagttcggt gtaggtcgtt cgctccaagc tgggctgtgt gcacgaaccc cccgttcagc    4560
ccgaccgctg cgccttatcc ggtaactatc gtcttgagtc caacccggta agacacgact    4620
tatcgccact ggcagcagcc actggtaaca ggattagcag agcgaggtat gtaggcggtg    4680
ctacagagtt cttgaagtgg tggcctaact acggctacac tagaaggaca gtatttggta    4740
tctgcgctct gctgaagcca gttaccttcg gaaaagagt tggtagctct tgatccggca    4800
aacaaaccac cgctggtagc ggtggttttt ttgtttgcaa gcagcagatt acgcgcagaa    4860 aaaaggatc tcaagaagat cctttgatct tttctacggg gtctgacgct cagtggaacg    4920
aaaactcacg ttaagggatt ttggtcatga cattaaccta taaaaatagg cgtatcacga    4980 ggcccttttcg tctcgcgcgt ttcggtgatg acggtgaaaa cctctgacac atgcagctcc    5040
cggagacggt cacagcttgt ctgtaagcgg atgccgggag cagacaagcc cgtcagggcg    5100
cgtcagcggg tgttggcggg tgtcggggct ggcttaacta tgcggcatca gagcagattg    5160
tactgagagt gcaccatatg gacatattgt cgttagaacg cggctacaat taatacataa    5220
ccttatgtat catacacata cgatttaggt gacactatag aacggcgcgc caagcttgca    5280
tgcctgcagg ctagcctaag tacgtactca aaatgccaac aaataaaaaa aaagttgctt    5340
taataatgcc aaaacaaatt aataaaacac ttacaacacc ggattttttt taattaaaat    5400
gtgccattta ggataaatag ttaatatttt taataattat ttaaaagcc gtatctacta    5460 aaatgatttt tatttggttg aaaatattaa tatgtttaaa tcaacacaat ctatcaaaat    5520
taaactaaaa aaaaaataag tgtacgtggt taacattagt acagtaatat aagaggaaaa    5580
tgagaaatta agaaattgaa agcgagtcta atttttaaat tatgaacctg catatataaa    5640
aggaaagaaa gaatccagga agaaaagaaa tgaaaccatg catggtcccc tcgtcatcac    5700
gagtttctgc catttgcaat agaaacactg aaacacctttt ctctttgtca cttaattgag    5760
atgccgaagc cacctcacac catgaacttc atgaggtgta gcacccaagg cttccatagc    5820
catgcatact gaagaatgtc tcaagctcag caccctactt ctgtgacgtg tccctcattc    5880
accttcctct cttccctata ataaccacg cctcaggttc tccgcttcac aactcaaaca    5940
ttctctccat tggtccttaa acactcatca gtcatcaccg cggccctaga cgcccatcac    6000
```

```
aagtttgtac aaaaaagctg aacgagaaac gtaaaatgat ataaatatca atatattaaa    6060
ttagattttg cataaaaaac agactacata atactgtaaa acacaacata tccagtcata    6120
ttggcggccg cattaggcac cccaggcttt acactttatg cttccggctc gtataatgtg    6180
tggattttga gttaggatcc gtcgagattt caggagcta aggaagctaa aatggagaaa    6240
aaaatcactg gatataccac cgttgatata tcccaatggc atcgtaaaga acattttgag    6300
gcatttcagt cagttgctca atgtacctat aaccagaccg ttcagctgga tattacggcc    6360
tttttaaaga ccgtaaagaa aaataagcac aagttttatc cggcctttat tcacattctt    6420
gcccgcctga tgaatgctca tccggaattc cgtatggcaa tgaaagacgg tgagctggtg    6480
atatgggata gtgttcaccc ttgttacacc gttttccatg agcaaactga aacgttttca    6540
tcgctctgga gtgaatacca cgacgatttc cggcagtttc tacacatata ttcgcaagat    6600
gtggcgtgtt acggtgaaaa cctggcctat ttccctaaag ggtttattga gaatatgttt    6660
ttcgtctcag ccaatccctg ggtgagtttc accagttttg atttaaacgt ggccaatatg    6720
gacaacttct tcgcccccgt tttccaccatg gcaaatatt atacgcaagg cgacaaggtg    6780
ctgatgccgc tggcgattca ggttcatcat gccgtttgtg atggcttcca tgtcggcaga    6840
atgcttaatg aattcaaca gtactgcgat gagtggcagg gcggggcgta aacgcgtgga    6900
tccggcttac taaaagccag ataacagtat gcgtatttgc gcgctgattt ttgcggtata    6960
agaatatata ctgatatgta tacccgaagt atgtcaaaaa gaggtatgct atgaagcagc    7020
gtattacagt gacagttgac agcgacagct atcagttgct caaggcatat atgatgtcaa    7080
tatctccggt ctggtaagca caaccatgca gaatgaagcc cgtcgtctgc gtgccgaacg    7140
ctggaaagcg gaaaatcagg aagggatggc tgaggtcgcc cggtttattg aaatgaacgg    7200
ctcttttgct gacgagaaca ggggctggtg aaatgcagtt taaggtttac acctataaaa    7260
gagagagccg ttatcgtctg tttgtggatg tacagagtga tattattgac acgcccgggc    7320
gacggatggt gatcccccctg ccagtgcac gtctgctgtc agataaagtc tcccgtgaac    7380
tttacccggt ggtgcatatc ggggatgaaa gctggcgcat gatgaccacc gatatggcca    7440
gtgtgccggt ctccgttatc ggggaagaag tggctgatct cagccaccgc gaaaatgaca    7500
tcaaaaacgc cattaacctg atgttctggg aatataaat gtcaggctcc cttatacaca    7560
gccagtctgc aggtcgacca tagtgactgg atatgttgtg ttttacagca ttatgtagtc    7620
tgttttttat gcaaaatcta atttaatata ttgatattta tatcatttta cgtttctcgt    7680 tcagcttct tgtacaaagt ggtgatgata accaagttta acgtgagttt atatattcac    7740
agttccattt acagatctta tgctgattgc agcatataac atagtcgcaa cttaacttta    7800
tccctgctta cgtaaagaaa catacatatt gtttgtggct tcgtagtgga acatatgcaa    7860
ttatgtaatc tttatattat gagcctttac ttacaaagat tacttgagat ttatgtacgt    7920
gtgctatttt cacttttcaa acatgaattt cctacgttta caatcattta atgtaaaagg    7980
gatgatataa tgtatttacg tacatgtgaa caaccaagca tgttattttt tcctttttg    8040 ttgcaactta caatcaagta atgattatgg ttatgattat gatattggtg tgtgtcttt    8100 gccttatata tatatttatc cctttcgttt aactttgcaa tataattatt actgatcact    8160
atattttggt ttgaaatggc gcaggttgta atgatcgatc atcaccactt tgtacaagaa    8220
agctgaacga gaaacgtaaa atgatataaa tatcaatata ttaaattaga ttttgcataa    8280
aaaacagact acataatgct gtaaaacaca acatatccag tcactatggt cgacctgcag    8340
actggctgtg tataagggag cctgacattt atattcccca gaacatcagg ttaatggcgt    8400
```

```
tttttgatgtc attttcgcgg tggctgagat cagccacttc ttccccgata acggagaccg    8460
gcacactggc catatcggtg gtcatcatgc gccagctttc atccccgata tgcaccaccg    8520
ggtaaagttc acgggagact ttatctgaca gcagacgtgc actggccagg gggatcacca    8580
tccgtcgccc gggcgtgtca ataatatcac tctgtacatc cacaaacaga cgataacggc    8640
tctctctttt ataggtgtaa accttaaact gcatttcacc agcccctgtt ctcgtcagca    8700
aaagagccgt tcatttcaat aaaccgggcg acctcagcca tcccttcctg attttccgct    8760
ttccagcgtt cggcacgcag acgacgggct tcattctgca tggttgtgct taccagaccg    8820
gagatattga catcatatat gccttgagca actgatagct gtcgctgtca actgtcactg    8880
taatacgctg cttcatagca tacctctttt tgacatactt cgggtataca tatcagtata    8940
tattcttata ccgcaaaaat cagcgcgcaa atacgcatac tgttatctgg cttttagtaa    9000
gccggatcct aactcaaaat ccacacatta tacgagccgg aagcataaag tgtaaagcct    9060
ggggtgccta atgcggccgc caatatgact ggatatgttg tgttttacag tattatgtag    9120 tctgttttt atgcaaaatc taatttaata tattgatatt tatatcattt tacgtttctc    9180
gttcagcttt tttgtacaaa cttgtgatgg gcgtctagcg aactagagga tccccgggta    9240
ccgag                                                               9245

<210> SEQ ID NO 24
<211> LENGTH: 27
<212> TYPE: DNA
<213> ORGANISM: artificial sequence
<220> FEATURE:
<223> OTHER INFORMATION: primer

<400> SEQUENCE: 24
caccgatgtt ggattgttta ggaatgc                                         27

<210> SEQ ID NO 25
<211> LENGTH: 23
<212> TYPE: DNA
<213> ORGANISM: artificial sequence
<220> FEATURE:
<223> OTHER INFORMATION: primer

<400> SEQUENCE: 25
gccaaatgtc tcagctttgt tgg                                             23

<210> SEQ ID NO 26
<211> LENGTH: 2840
<212> TYPE: DNA
<213> ORGANISM: artificial sequence
<220> FEATURE:
<223> OTHER INFORMATION: plasmid

<400> SEQUENCE: 26
aagggtgggc gcgccgaccc agctttcttg tacaaagttg gcattataag aaagcattgc     60
ttatcaattt gttgcaacga acaggtcact atcagtcaaa ataaaatcat tatttgccat    120
ccagctgata tcccctatag tgagtcgtat tacatggtca tagctgtttc ctggcagctc    180
tggcccgtgt ctcaaaatct ctgatgttac attgcacaag ataaaaatat atcatcatga    240
acaataaaac tgtctgctta cataaacagt aatacaaggg gtgttatgag ccatattcaa    300
cgggaaacgt cgaggccgcg attaaattcc aacatggatg ctgatttata tgggtataaa    360
tgggctcgcg ataatgtcgg gcaatcaggt gcgacaatct atcgcttgta tgggaagccc    420
```

```
gatgcgccag agttgtttct gaaacatggc aaaggtagcg ttgccaatga tgttacagat    480
gagatggtca gactaaactg gctgacggaa tttatgcctc ttccgaccat caagcatttt    540
atccgtactc ctgatgatgc atggttactc accactgcga tccccggaaa aacagcattc    600
caggtattag aagaatatcc tgattcaggt gaaaatattg ttgatgcgct ggcagtgttc    660
ctgcgccggt tgcattcgat tcctgtttgt aattgtcctt ttaacagcga tcgcgtattt    720
cgtctcgctc aggcgcaatc acgaatgaat aacggtttgg ttgatgcgag tgattttgat    780
gacgagcgta atggctggcc tgttgaacaa gtctggaaag aaatgcataa acttttgcca    840
ttctcaccgg attcagtcgt cactcatggt gatttctcac ttgataacct tattttgac     900 gaggggaaat taataggttg tattgatgtt ggacgagtcg gaatcgcaga ccgataccag    960
gatcttgcca tcctatggaa ctgcctcggt gagttttctc cttcattaca gaaacggctt   1020
tttcaaaaat atggtattga taatcctgat atgaataaat tgcagtttca tttgatgctc   1080
gatgagtttt tctaatcaga attggttaat tggttgtaac actggcagag cattacgctg   1140
acttgacggg acggcgcaag ctcatgacca aaatccctta acgtgagtta cgcgtcgttc   1200
cactgagcgt cagaccccgt agaaaagatc aaaggatctt cttgagatcc ttttttttctg   1260 cgcgtaatct gctgcttgca acaaaaaaa ccaccgctac cagcggtggt ttgtttgccg    1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agcattgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg attttttgtga   1800 tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gctagccagg aagagtttgt agaaacgcaa   2160
aaaggccatc cgtcaggatg gccttctgct tagtttgatg cctggcagtt tatggcgggc   2220
gtcctgcccg ccacccteeg ggccgttgct tcacaacgtt caaatccgct cccggcggat   2280
ttgtcctact caggagagcg ttcaccgaca aacaacagat aaaacgaaag gcccagtctt   2340
ccgactgagc ctttcgtttt atttgatgcc tggcagttcc ctactctcgc gttaacgcta   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520 tgcttttta taatgccaac tttgtacaaa aaagcaggct ccgcggccgc cccctttcacc   2580 gatgttggat tgtttaggaa tgctgctgtt gaagatgtga ggagattcaa gatgggtttg   2640
gtcaatgaat cggacagtga ggattcgtcg gaacatgata agatgttga tgatgagaag    2700 tactggagcg aataagcaaa atttcaaatt tcgttaatgt tgtttccttt aactttcca    2760 taaagattta caaaatcatg atgccacaaa tgtttcaaaa acgaaagcaa catgaatcca   2820
```

-continued

```
acaaagctga gacatttggc                                               2840
```

<210> SEQ ID NO 27
<211> LENGTH: 15203
<212> TYPE: DNA
<213> ORGANISM: artificial sequence
<220> FEATURE:
<223> OTHER INFORMATION: plasmid

<400> SEQUENCE: 27

```
caccgatgtt ggattgttta ggaatgctgc tgttgaagat gtgaggagat tcaagatggg     60
tttggtcaat gaatcggaca gtgaggattc gtcggaacag gataaagatg ttgatgatga    120
gaagtactgg agcgaataag caaaatttca aatttcgtta atgttgtttc cttttaactt    180
tccataaaga tttacaaaat catgatgcca caaatgtttc aaaaacgaaa gcaacatgaa    240
tccaacaaag ctgagacatt tggcaagggt gggcgcgccg acccagcttt cttgtacaaa    300
gtggtgtgag tttatatatt cacagttcca tttacagatc ttatgctgat tgcagcatat    360
aacatagtcg caacttaact ttatccctgc ttacgtaaag aaacatacat attgtttgtg    420
gcttcgtagt ggaacatatg caattatgta atctttatat tatgagcctt tacttacaaa    480
gattacttga gatttatgta cgtgtgctat tttcactttt caaacatgaa tttcctacgt    540
ttacaatcat ttaatgtaaa agggatgata taatgtattt acgtacatgt gaacaaccaa    600
gcatgttatt ttttcctttt ttgttgcaac ttacaatcaa gtaatgatta tggttatgat    660
tatgatattg gtgtgtgtct tttgccttat atatatattt atcccttcg tttaactttg     720
caatataatt attactgatc actatatttt ggtttgaaat ggcgcagacc actttgtaca    780
agaaagctgg gtcggcgcgc ccaccccttgc caaatgtctc agctttgttg gattcatgtt    840
gctttcgttt ttgaaacatt tgtggcatca tgattttgta atctttatg gaaagttaaa     900
aggaaacaac attaacgaaa tttgaaattt tgcttattcg ctccagtact tctcatcatc    960
aacatcttta tcatgttccg acgaatcctc actgtccgat tcattgacca aacccatctt   1020
gaatctcctc acatcttcaa cagcagcatt cctaaacaat ccaacatcgg tgaaggggc   1080
ggccgcggag cctgcttttt tgtacaaact tgtgatgggc gtctagcgaa ctagaggatc   1140
cccgggtacc gaggtacgtc tagaggatcc gtcgacggcg cgccagatcc tctagagtcg   1200
acctgcaggc atgcaagctt ggcgtaatca tggtcatagc tgtttcctgt gtgaaattgt   1260
tatccgctca caattccaca acacatacga gccggaagca taaagtgtaa agcctgggt   1320
gcctaatgag tgagctaact cacattaatt gcgttgcgct cactgcccgc tttccagtcg   1380
ggaaacctgt cgtgccagct gcattaatga atcggccaac gcgcgggag aggcggtttg   1440
cgtattggat cgatccctga aagcgacgtt ggatgttaac atctacaaat tgcctttct   1500
tatcgaccat gtacgtaagc gcttacgttt ttggtggacc cttgaggaaa ctggtagctg   1560
ttgtgggcct gtggtctcaa gatggatcat taatttccac cttcacctac gatgggggc   1620
atcgcaccgg tgagtaatat tgtacggcta agagcgaatt tggcctgtag acctcaattg   1680
cgagctttct aatttcaaac tattcgggcc taacttttgg tgtgatgatg ctgactggca   1740
ggatatatac cgttgtaatt tgagctcgtg tgaataagtc gctgtgtatg tttgtttgat   1800
tgtttctgtt ggagtgcagc ccatttcacc ggacaagtcg gctagattga tttagccctg   1860
atgaactgcc gaggggaagc catcttgagc gcggaatggg aatggatttc gttgtacaac   1920
gagacgacag aacacccacg ggaccgagct tcgcgagctt ttgtatccgt ggcatccttg   1980
```

```
gtccgggcga tttgttcacg tccatgaggc gctctccaaa ggaacgcata ttttccggtg   2040
caacctttcc ggttcttcct ctactcgacc tcttgaagtc ccagcatgaa tgttcgaccg   2100
ctccgcaagc ggatctttgg cgcaaccagc cggtttcgca cgtcgattct cgcgagcctg   2160
catactttgg caagattgct gaatgacgct gatgcttcat cgcaatctgc gataatgggg   2220
taagtatccg gtgaaggccg caggtcaggc cgcctgagca ctcagtgtct tggatgtcca   2280
gttccacggc agctgttgct caagcctgct gatcggagcg tccgcaaggt cggcgcggac   2340
gtcggcaagc caggcctgcg gatcgatgtt attgagcttg gcgctcatga tcagtgtcgc   2400
catgaacgcc gcacgttcag cacaacgatc cgatccggca aacagccatg acttcctgcc   2460
gagtacatag cctctgagcg ttcgttcggc agcattgttc gtcaggcaaa tcgggccgtc   2520
atcgaggaat gacgtaatgc catcccatcg cttgagcatg taatttatcg cctcggcgac   2580
gggagaactg cgcgacaatt tccccgctc ggtttcgagc caatcatgca gctcttcggc   2640
gagtgacctt gatcaggcca ccgccacgac cgcggaagac gaacagatgc ctgcgcatcg   2700
gatcgcgctt cagcgtctct tgcaccatca gcgacaaacc gggaaagcct ttgcgcatgt   2760
ccgtacttat gtcgccactt gggagggctt cgtctacgtg gccttcgtga tcgacgtctt   2820
cgcccgtcgc attgtcggat ggcgggcgag ccggacagca catgcaggct ttgtcctcga   2880
tgccctcgag gaggctcatc atgatcggcg tcccgctcat ggcggcctag tgcatcactc   2940
ggatcgcggt gttcaatacg tgtcctttcg ctattccgag cggttggcag aagcaggtat   3000
cgagccatct atcggaagcg tcggcgacag cacgacaacg ccctcgcaga agcgatcaac   3060
ggtctttaca aggccgaggt cattcatcgg cgtggaccat ggaggagctt cgaagcggtc   3120
gagttcgcta ccttggaatg gatagactgg ttcaaccacg gcggcttttg aagcccatcg   3180
gcaatatacc gccagccgaa gacgaggatc agtattcgc catgctggac gaagcagcca   3240
tggctgcgca ttttaacgaa atggcctccg gcaaacccgg tgcggttcac ttgttgcgtg   3300
ggaaagttca cgggactccg cgcacgagcc ttcttcgtaa tagccatatc gaccgaattg   3360
acctgcaggg ggggggggga agccacgtt gtgtctcaaa atctctgatg ttacattgca   3420
caagataaaa atatatcatc atgaacaata aaactgtctg cttacataaa cagtaataca   3480
aggggtgtta tgagccatat tcaacgggaa acgtcttgct cgaggccgcg attaaattcc   3540
aacatggatc tgatttata tgggtataaa tgggctcgcg ataatgtcgg gcaatcaggt   3600
gcgacaatct atcgattgta tgggaagccc gatgcgccag agttgtttct gaaacatggc   3660
aaaggtagcg ttgccaatga tgttacagat gagatggtca gactaaactg gctgacggaa   3720
tttatgcctc ttccgaccat caagcatttt atccgtactc ctgatgatgc atggttactc   3780
accactgcga tccccgggaa aacagcattc caggtattag aagaatatcc tgattcaggt   3840
gaaaatattg ttgatgcgct ggcagtgttc ctgcgccggt tgcattcgat tcctgtttgt   3900
aattgtcctt ttaacagcga tcgcgtattt cgtctcgctc aggcgcaatc acgaatgaat   3960
aacggtttgg ttgatgcgag tgattttgat gacgagcgta atggctggcc tgttgaacaa   4020
gtctggaaag aaatgcataa gcttttgcca ttctcaccgg attcagtcgt cactcatggt   4080
gatttctcac ttgataacct tattttgac gaggggaaat taataggttg tattgatgtt   4140
ggacgagtcg gaatcgcaga ccgataccag gatcttgcca tcctatggaa ctgcctcggt   4200
gagttttctc cttcattaca gaaacggctt tttcaaaaat atggtattga taatcctgat   4260
atgaataaat tgcagtttca tttgatgctc gatgagtttt tctaatcaga attggttaat   4320
tggttgtaac actggcagag cattacgctg acttgacggg acggcggctt tgttgaataa   4380
```

```
atcgaacttt tgctgagttg aaggatcaga tcacgcatct tcccgacaac gcagaccgtt    4440
ccgtggcaaa gcaaaagttc aaaatcacca actggtccac ctacaacaaa gctctcatca    4500
accgtggctc cctcactttc tggctggatg atggggcgat tcaggcctgg tatgagtcag    4560
caacaccttc ttcacgaggc agacctcagc gcccccccccc ccctgcaggt cttttccaat    4620
gatgagcact tttaaagttc tgctatgtgg cgcggtatta tcccgtgttg acgccgggca    4680
agagcaactc ggtcgccgca tacactattc tcagaatgac ttggttgagt actcaccagt    4740
cacagaaaag catcttacgg atggcatgac agtaagagaa ttatgcagtg ctgccataac    4800
catgagtgat aacactgcgg ccaacttact tctgacaacg atcggaggac cgaaggagct    4860
aaccgctttt ttgcacaaca tgggggatca tgtaactcgc cttgatcgtt gggaaccgga    4920
gctgaatgaa gccataccaa acgacgagcg tgacaccacg atgcctgtag caatggcaac    4980
aacgttgcgc aaactattaa ctggcgaact acttactcta gcttcccggc aacaattaat    5040
agactggatg gaggcggata agttgcagg accacttctg cgctcggccc ttccggctgg    5100
ctggtttatt gctgataaat ctggagccgg tgagcgtggg tctcgcggta tcattgcagc    5160
actggggcca gatggtaagc cctcccgtat cgtagttatc tacacgacgg ggagtcaggc    5220
aactatggat gaacgaaata gacagatcgc tgagataggt gcctcactga ttaagcattg    5280
gtaactgtca gaccaagttt actcatatat actttagatt gatttaaaac ttcattttta    5340
atttaaaagg atctaggtga agatccttt tgataatctc atgaccaaaa tcccttaacg    5400
tgagttttcg ttccactgag cgtcagaccc cgtagaaaag atcaaaggat cttcttgaga    5460 tcctttttt ctgcgcgtaa tctgctgctt gcaaacaaaa aaaccaccgc taccagcggt    5520
ggtttgtttg ccggatcaag agctaccaac tctttttccg aaggtaactg gcttcagcag    5580
agcgcagata ccaaatactg tccttctagt gtagccgtag ttaggccacc acttcaagaa    5640
ctctgtagca ccgcctacat acctcgctct gctaatcctg ttaccagtgg ctgctgccag    5700
tggcgataag tcgtgtctta ccgggttgga ctcaagacga tagttaccgg ataaggcgca    5760
gcggtcgggc tgaacggggg gttcgtgcac acagcccagc ttggagcgaa cgacctacac    5820
cgaactgaga tacctacagc gtgagctatg agaaagcgcc acgcttcccg aagggagaaa    5880
ggcggacagg tatccggtaa gcggcagggt cggaacagga gagcgcacga gggagcttcc    5940
agggggaaac gcctggtatc tttatagtcc tgtcgggttt cgccacctct gacttgagcg    6000
tcgatttttg tgatgctcgt caggggggcg gagcctatgg aaaaacgcca gcaacgcggc    6060 cttttacgg ttcctggcct tttgctggcc ttttgctcac atgttctttc ctgcgttatc    6120
ccctgattct gtggataacc gtattaccgc ctttgagtga gctgataccg ctcgccgcag    6180
ccgaacgacc gagcgcagcg agtcagtgag cgaggaagcg gaagagcgcc tgatgcggta    6240
ttttctcctt acgcatctgt gcggtatttc acaccgcata tggtgcactc tcagtacaat    6300
ctgctctgat gccgcatagt taagccagta tacactccgc tatcgctacg tgactgggtc    6360
atggctgcgc cccgacaccc gccaacaccc gctgacgcgc cctgacgggc ttgtctgctc    6420
ccggcatccg cttacagaca agctgtgacc gtctccggga gctgcatgtg tcagaggttt    6480
tcaccgtcat caccgaaacg cgcgaggcag ggtgccttga tgtgggcgcc ggcggtcgag    6540
tggcgacggc gcggcttgtc cgcgccctgg tagattgcct ggccgtaggc cagccatttt    6600
tgagcggcca gcggccgcga taggccgacg cgaagcggcg gggcgtaggg agcgcagcga    6660
ccgaagggta ggcgcttttt gcagctcttc ggctgtgcgc tggccagaca gttatgcaca    6720
```

```
ggccaggcgg gttttaagag ttttaataag ttttaaagag ttttaggcgg aaaaatcgcc    6780
ttttttctct tttatatcag tcacttacat gtgtgaccgg ttcccaatgt acggctttgg    6840
gttcccaatg tacgggttcc ggttcccaat gtacggcttt gggttcccaa tgtacgtgct    6900
atccacagga aagagacctt ttcgaccttt ttcccctgct agggcaattt gccctagcat    6960
ctgctccgta cattaggaac cggcggatgc ttcgccctcg atcaggttgc ggtagcgcat    7020
gactaggatc gggccagcct gccccgcctc ctccttcaaa tcgtactccg gcaggtcatt    7080
tgacccgatc agcttgcgca cggtgaaaca gaacttcttg aactctccgg cgctgccact    7140
gcgttcgtag atcgtcttga caaccatct ggcttctgcc ttgcctgcgg cgcggcgtgc     7200
caggcggtag agaaaacggc cgatgccggg atcgatcaaa aagtaatcgg ggtgaaccgt    7260
cagcacgtcc gggttcttgc cttctgtgat ctcgcggtac atccaatcag ctagctcgat    7320
ctcgatgtac tccggccgcc cggtttcgct ctttacgatc ttgtagcggc taatcaaggc    7380
ttcaccctcg gataccgtca ccaggcggcc gttcttggcc ttcttcgtac gctgcatggc    7440
aacgtgcgtg gtgtttaacc gaatgcaggt ttctaccagg tcgtctttct gctttccgcc    7500
atcggctcgc cggcagaact tgagtacgtc cgcaacgtgt ggacggaaca cgcggccggg    7560
cttgtctccc ttcccttccc ggtatcggtt catggattcg gttagatggg aaaccgccat    7620
cagtaccagg tcgtaatccc acacactggc catgccggcc ggccctgcgg aaacctctac    7680
gtgcccgtct ggaagctcgt agcggatcac ctcgccagct cgtcggtcac gcttcgacag    7740
acggaaaacg gccacgtcca tgatgctgcg actatcgcgg gtgcccacgt catagagcat    7800
cggaacgaaa aaatctggtt gctcgtcgcc cttgggcggc ttcctaatcg acggcgcacc    7860
ggctgccggc ggttgccggg attctttgcg gattcgatca gcggccgctt gccacgattc    7920
accggggcgt gcttctgcct cgatgcgttg ccgctgggcg gcctgcgcgg ccttcaactt    7980
ctccaccagg tcatcaccca gcgccgcgcc gatttgtacc gggccggatg gtttgcgacc    8040
gctcacgccg attcctcggg cttgggggtt ccagtgccat gcagggccg gcagacaacc     8100 cagccgctta cgcctggcca accgccgtt cctccacaca tggggcattc cacggcgtcg     8160
gtgcctggtt gttcttgatt ttccatgccg cctcctttag ccgctaaaat tcatctactc    8220
atttattcat ttgctcattt actctggtag ctgcgcgatg tattcagata gcagctcggt    8280
aatggtcttg ccttggcgta ccgcgtacat cttcagcttg gtgtgatcct ccgcggcaa     8340 ctgaaagttg acccgcttca tggctggcgt gtctgccagg ctggccaacg ttgcagcctt    8400
gctgctgcgt gcgctcggac ggccggcact tagcgtgttt gtgcttttgc tcattttctc    8460
tttacctcat taactcaaat gagttttgat ttaatttcag cggccagcgc ctggacctcg    8520
cgggcagcgt cgccctcggg ttctgattca agaacggttg tgccggcggc ggcagtgcct    8580
gggtagctca cgcgctgcgt gatacgggac tcaagaatgg gcagctcgta cccggccagc    8640
gcctcggcaa cctcaccgcc gatgcgcgtg cctttgatcg cccgcgacac gacaaaggcc    8700
gcttgtagcc ttccatccgt gacctcaatg cgctgcttaa ccagctccac caggtcggcg    8760
gtggcccata tgtcgtaagg gcttggctgc accggaatca gcacgaagtc ggctgccttg    8820
atcgcggaca cagccaagtc cgccgcctgg ggcgctccgt cgatcactac gaagtcgcgc    8880
cggccgatgg ccttcacgtc gcggtcaatc gtcgggcggt cgatgccgac aacggttagc    8940
ggttgatctt cccgcacggc cgcccaatcg cgggcactgc cctggggatc ggaatcgact    9000 aacagaaacat cggccccggc gagttgcagg gcgcgggcta gatgggttgc gatggtcgtc    9060
ttgcctgacc cgcctttctg gttaagtaca gcgataactt catgcgttcc cttgcgtatt    9120
```

| | | | | | |
|---|---|---|---|---|---|
| tgtttatttta | ctcatcgcat | catatacgca | gcgaccgcat | gacgcaagct | gttttactca | 9180 |
| aatacacatc | accttttag | acggcggcgc | tcggtttctt | cagcggccaa | gctggccggc | 9240 |
| caggccgcca | gcttggcatc | agacaaaccg | gccaggattt | catgcagccg | cacggttgag | 9300 |
| acgtgcgcgg | gcggctcgaa | cacgtacccg | gccgcgatca | tctccgcctc | gatctcttcg | 9360 |
| gtaatgaaaa | acggttcgtc | ctggccgtcc | tggtgcggtt | tcatgcttgt | tcctcttggc | 9420 |
| gttcattctc | ggcggccgcc | agggcgtcgg | cctcggtcaa | tgcgtcctca | cggaaggcac | 9480 |
| cgcgccgcct | ggcctcggtg | ggcgtcactt | cctcgctgcg | ctcaagtgcg | cggtacaggg | 9540 |
| tcgagcgatg | cacgccaagc | agtgcagccg | cctctttcac | ggtgcggcct | tcctggtcga | 9600 |
| tcagctcgcg | ggcgtgcgcg | atctgtgccg | gggtgagggt | agggcggggg | ccaaacttca | 9660 |
| cgcctcgggg | cttggcggcc | tcgcgcccgc | tccgggtgcg | gtcgatgatt | agggaacgct | 9720 |
| cgaactcggc | aatgccggcg | aacacggtca | acaccatgcg | gccggccggc | gtggtggtgt | 9780 |
| cggcccacgg | ctctgccagg | ctacgcaggc | ccgcgccggc | ctcctggatg | cgctcggcaa | 9840 |
| tgtccagtag | gtcgcgggtg | ctgcgggcca | ggcggtctag | cctggtcact | gtcacaacgt | 9900 |
| cgccagggcg | taggtggtca | agcatcctgg | ccagctccgg | gcggtcgcgc | ctggtgccgg | 9960 |
| tgatcttctc | ggaaaacagc | ttggtgcagc | cggccgcgtg | cagttcggcc | cgttggttgg | 10020 |
| tcaagtcctg | gtcgtcggtg | ctgacgcggg | catagcccag | caggccagcg | gcggcgctct | 10080 |
| tgttcatggc | gtaatgtctc | cggttctagt | cgcaagtatt | ctactttatg | cgactaaaac | 10140 |
| acgcgacaag | aaaacgccag | gaaaagggca | gggcggcagc | ctgtcgcgta | acttaggact | 10200 |
| tgtgcgacat | gtcgttttca | gaagacggct | gcactgaacg | tcagaagccg | actgcactat | 10260 |
| agcagcggag | gggttggacc | acaggacggg | tgtggtcgcc | atgatcgcgt | agtcgatagt | 10320 |
| ggctccaagt | agcgaagcga | gcaggactgg | gcggcggcca | aagcggtcgg | acagtgctcc | 10380 |
| gagaacgggt | gcgcatagaa | attgcatcaa | cgcatatagc | gctagcagca | cgccatagtg | 10440 |
| actggcgatg | ctgtcggaat | ggacgatatc | ccgcaagagg | cccggcagta | ccggcataac | 10500 |
| caagcctatg | cctacagcat | ccagggtgac | ggtgccgagg | atgacgatga | gcgcattgtt | 10560 |
| agatttcata | cacggtgcct | gactgcgtta | gcaatttaac | tgtgataaac | taccgcatta | 10620 |
| aagctagctt | gcttggtcgt | tccgcgtgaa | cgtcggctcg | attgtacctg | cgttcaaata | 10680 |
| ctttgcgatc | gtgttgcgcg | cctgcccggt | gcgtcggctg | atctcacgga | tcgactgctt | 10740 |
| ctctcgcaac | gccatccgac | ggatgatgtt | taaaagtccc | atgtggatca | ctccgttgcc | 10800 |
| ccgtcgctca | ccgtgtttggg | gggaaggtgc | acatggctca | gttctcaatg | gaaattatct | 10860 |
| gcctaaccgg | ctcagttctg | cgtagaaacc | aacatgcaag | ctccaccggg | tgcaaagcgg | 10920 |
| cagcggcggc | aggatatatt | caattgtaaa | tggcttcatg | tccgggaaat | ctacatggat | 10980 |
| cagcaatgag | tatgatggtc | aatatggaga | aaagaaaga | gtaattacca | atttttttc | 11040 |
| aattcaaaaa | tgtagatgtc | cgcagcgtta | ttataaaatg | aaagtacatt | ttgataaaac | 11100 |
| gacaaattac | gatccgtcgt | atttataggc | gaaagcaata | acaaattat | tctaattcgg | 11160 |
| aaatctttat | ttcgacgtgt | ctacattcac | gtccaaatgg | gggcttagat | gagaaacttc | 11220 |
| acgatcgatg | ccttgatttc | gccattccca | gatacccatt | tcatcttcag | attggtctga | 11280 |
| gattatgcga | aaatatacac | tcatatacat | aaatactgac | agtttgagct | accaattcag | 11340 |
| tgtagcccat | tacctcacat | aattcactca | aatgctaggc | agtctgtcaa | ctcggcgtca | 11400 |
| atttgtcggc | cactatacga | tagttgcgca | aattttcaaa | gtcctggcct | aacatcacac | 11460 |

```
ctctgtcggc ggcgggtccc atttgtgata aatccaccat atcgaattaa ttcagactcc   11520
tttgccccag agatcacaat ggacgacttc ctctatctct acgatctagt caggaagttc   11580
gacggagaag gtgacgatac catgttcacc actgataatg agaagattag ccttttcaat   11640
ttcagaaaga atgctaaccc acagatggtt agagaggctt acgcagcagg tctcatcaag   11700
acgatctacc cgagcaataa tctccaggag atcaaatacc ttcccaagaa ggttaaagat   11760
gcagtcaaaa gattcaggac taactgcatc aagaacacag agaaagatat atttctcaag   11820
atcagaagta ctattccagt atggacgatt caaggcttgc ttcacaaacc aaggcaagta   11880
atagagattg gagtctctaa aaaggtagtt cccactgaat caaaggccat ggagtcaaag   11940
attcaaatag aggacctaac agaactcgcc gtaaagactg gcgaacagtt catacagagt   12000
ctcttacgac tcaatgacaa gaagaaaatc ttcgtcaaca tggtggagca cgacacgctt   12060
gtctactcca aaaatatcaa agatacagtc tcagaagacc aaagggcaat tgagactttt   12120
caacaagggg taatatccgg aaacctcctc ggattccatt gcccagctat ctgtcacttt   12180
attgtgaaga tagtggaaaa ggaaggtggc tcctacaaat gccatcattg cgataaagga   12240
aaggccatcg ttgaagatgc ctctgccgac agtggtccca agatggacc cccacccacg   12300 aggagcatcg tggaaaaaga agacgttcca accacgtctt caaagcaagt ggattgatgt   12360
gatatctcca ctgacgtaag ggatgacgca caatcccact atccttcgca agacccttcc   12420
tctatataag gaagttcatt tcatttggag aggcacgct gaaatcacca gtctccaagc   12480
ttgcggggat cgtttcgcat gattgaacaa gatggattgc acgcaggttc tccggccgct   12540
tgggtggaga ggctattcgg ctatgactgg gcacaacaga caatcggctg ctctgatgcc   12600
gccgtgttcc ggctgtcagc gcaggggcgc ccggttcttt ttgtcaagac cgacctgtcc   12660
ggtgccctga tgaactgca ggacgaggca gcgcggctat cgtggctggc cacgacgggc   12720
gttccttgcg cagctgtgct cgacgttgtc actgaagcgg gaagggactg ctgctattg   12780 ggcgaagtgc cggggcagga tctcctgtca tctcaccttg ctcctgccga aaagtatcc   12840 atcatggctg atgcaatgcg gcggctgcat acgcttgatc cggctacctg cccattcgac   12900
caccaagcga aacatcgcat cgagcgagca cgtactcgga tggaagccgg tcttgtcgat   12960
caggatgatc tggacgaaga gcatcagggg ctcgcgccag ccgaactgtt cgccaggctc   13020
aaggcgcgca tgcccgacgg cgaggatctc gtcgtgaccc atggcgatgc ctgcttgccg   13080
aatatcatgg tggaaaatgg ccgcttttct ggattcatcg actgtggccg ctgggtgtg   13140 gcggaccgct atcaggacat agcgttggct acccgtgata ttgctgaaga gcttggcggc   13200
gaatgggctg accgcttcct cgtgctttac ggtatcgccg ctcccgattc gcagcgcatc   13260
gccttctatc gccttcttga cgagttcttc tgagcgggac tctggggttc gaaatgaccg   13320
accaagcgac gcccaacctg ccatcacgag atttcgattc caccgccgcc ttctatgaaa   13380
ggttgggctt cggaatcgtt ttccgggacg ccggctggat gatcctccag cgcgggatc   13440 tcatgctgga gttcttcgcc caccccggat cgatccaaca cttacgtttg caacgtccaa   13500
gagcaaatag accacgaacg ccggaaggtt gccgcagcgt gtggattgcg tctcaattct   13560
ctcttgcagg aatgcaatga tgaatatgat actgactatg aaactttgag ggaatactgc   13620
ctagcaccgt cacctcataa cgtgcatcat gcatgccctg acaacatgga acatcgctat   13680
ttttctgaag aattatgctc gttggaggat gtcgcggcaa ttgcagctat tgccaacatc   13740
gaactacccc tcacgcatgc attcatcaat attattcatg cggggaaagg caagattaat   13800
ccaactggca aatcatccag cgtgattggt aacttcagtt ccagcgactt gattcgtttt   13860
```

```
ggtgctaccc acgttttcaa taaggacgag atggtggagt aaagaaggag tgcgtcgaag    13920
cagatcgttc aaacatttgg caataaagtt tcttaagatt gaatcctgtt gccggtcttg    13980
cgatgattat catataattt ctgttgaatt acgttaagca tgtaataatt aacatgtaat    14040
gcatgacgtt atttatgaga tgggttttta tgattagagt cccgcaatta tacatttaat    14100
acgcgataga aaacaaaata tagcgcgcaa actaggataa attatcgcgc gcggtgtcat    14160
ctatgttact agatcgatca aacttcggta ctgtgtaatg acgatgagca atcgagaggc    14220
tgactaacaa aaggtacatc gcgatggatc gatccattcg ccattcaggc tgcgcaactg    14280
ttgggaaggg cgatcggtgc gggcctcttc gctattacgc cagctggcga aaggggggatg    14340 tgctgcaagg cgattaagtt gggtaacgcc agggttttcc cagtcacgac gttgtaaaac    14400
gacggccagt gaattcctgc agcccggggg atccgcccac tcgaggcgcg ccaagcttgc    14460
atgcctgcag gctagcctaa gtacgtactc aaaatgccaa caaataaaaa aaaagttgct    14520
ttaataatgc caaacaaat taataaaaca cttacaacac cggattttttt ttaattaaaa    14580 tgtgccattt aggataaata gttaatattt ttaataatta tttaaaaagc cgtatctact    14640
aaaatgattt ttatttggtt gaaaatatta atatgtttaa atcaacacaa tctatcaaaa    14700
ttaaactaaa aaaaaaataa gtgtacgtgg ttaacattag tacagtaata taagaggaaa    14760
atgagaaatt aagaaattga aagcgagtct aatttttaaa ttatgaacct gcatatataa    14820
aaggaaagaa agaatccagg aagaaaagaa atgaaaccat gcatggtccc ctcgtcatca    14880 cgagttttctg ccatttgcaa tagaaacact gaaacaccttt tctctttgtc acttaattga    14940
gatgccgaag ccacctcaca ccatgaactt catgaggtgt agcacccaag gcttccatag    15000
ccatgcatac tgaagaatgt ctcaagctca gcaccctact tctgtgacgt gtccctcatt    15060
caccttcctc tcttccctat aaataaccac gcctcaggtt ctccgcttca caactcaaac    15120
attctctcca ttggtcctta aacactcatc agtcatcacc gcacaagttt gtacaaaaaa    15180
gcaggctccg cggccgcccc ctt    15203
```

<210> SEQ ID NO 28
<211> LENGTH: 1327
<212> TYPE: DNA
<213> ORGANISM: brassica napus

<400> SEQUENCE: 28

```
ggccactgtc gacacttccc aggtcataca ccgccatggc caccgctaca accctctcca      60
cagtcaacac agattcgaca catctcttta actcctcttc tccgatcatc gggaagctat     120 cacctttcaaa ttccaactcc gtcagatcca cggttacatt ttccaggaaa accctaactc     180
caatccgatt ctcttcatct cccgctgatc actcccccgc cgccgccatc acttctccca     240
ccgtggaggg aatcgccacc cgatccaaaa cctcattgaa atcccgcctc caaggaggcg     300
aaactctcta cggcatgttc ttgctctcct tttcgccgac tctagccgag atcgctgctc     360
actccggcta cgattacgtc gtcgttgaca tggaacacgg ccacggcggc ataccggaag     420
ctctagactg catccgagct cttaacgccg ccggtgtagc cgccgttctt cgcttaccgg     480
agaactgtcc tacatgggcc aaaaaggcct tagatctagg cccacaggga atcatgtttc     540
cgatgatcga atctcgcaag gacgcgacca aagcggtgtc gtactgccgg tttcctcccg     600
acgggatccg tggttcggcg cacacggtgg tgcgagcgtc caagtacgga atcgacgaag     660
ggtatttagg taattacgct gacgagttac tcatcatgtg ccaggtggag tcagccgaag     720
```

-continued

```
gagtgaagaa agctgatgag atcgcagccg tcgatggtgt tgactgcgtg cagatgggac   780
cgttggatct gagcgcgagc ataggatact tgtgggaccc ggggcataag aaagtgagag   840
agatgatgag gagagcggag aaggcggtgc tgacgtcaga tccagagaaa ggcggggcct   900
acttgtcagg gttcgccatg ccacacgacg gacctgccgc gatccgggaa cgtggttata   960
acatggtggc cggaaccgtc gatattgggc tgttcaggaa cgctgctgtg aagatgtca   1020 ggagattcaa gatgggtttg gtcaacgaat cggacggtga agattcgttg gataacggga   1080
aggatgttga cgatgagaag tactggagcg aataagcatg taattccgtc acagtttctt   1140
aaaaataaaa tgtgattttg cgttttcaa tgtttcgtta atgttgtttg gtcaatgttt    1200
ttattagaat catgtcacaa atgtttaact ctttcataaa ccaacatgat cacggtcgtt   1260
agctaatcag agactgcact ttcaacggtc tagatccaca aaattaacaa agctgagact   1320
tttggct                                                              1327
```

<210> SEQ ID NO 29
<211> LENGTH: 359
<212> TYPE: PRT
<213> ORGANISM: Brassica napus

<400> SEQUENCE: 29

```
Met Ala Thr Ala Thr Leu Ser Thr Val Asn Thr Asp Ser Thr His
1               5                   10                  15

Leu Phe Asn Ser Ser Pro Ile Ile Gly Lys Leu Ser Pro Ser Asn
            20                  25                  30

Ser Asn Ser Val Arg Ser Thr Val Thr Phe Ser Arg Lys Thr Leu Thr
        35                  40                  45

Pro Ile Arg Phe Ser Ser Pro Ala Asp His Ser Pro Ala Ala Ala
    50                  55                  60

Ile Thr Ser Pro Thr Val Glu Gly Ile Ala Thr Arg Ser Lys Thr Ser
65                  70                  75                  80

Leu Lys Ser Arg Leu Gln Gly Gly Glu Thr Leu Tyr Gly Met Phe Leu
                85                  90                  95

Leu Ser Phe Ser Pro Thr Leu Ala Glu Ile Ala Ala His Ser Gly Tyr
            100                 105                 110

Asp Tyr Val Val Val Asp Met Glu His Gly His Gly Ile Pro Glu
        115                 120                 125

Ala Leu Asp Cys Ile Arg Ala Leu Asn Ala Ala Gly Val Ala Ala Val
    130                 135                 140

Leu Arg Leu Pro Glu Asn Cys Pro Thr Trp Ala Lys Lys Ala Leu Asp
145                 150                 155                 160

Leu Gly Pro Gln Gly Ile Met Phe Pro Met Ile Glu Ser Arg Lys Asp
                165                 170                 175

Ala Thr Lys Ala Val Ser Tyr Cys Arg Phe Pro Pro Asp Gly Ile Arg
            180                 185                 190

Gly Ser Ala His Thr Val Val Arg Ala Ser Lys Tyr Gly Ile Asp Glu
        195                 200                 205

Gly Tyr Leu Gly Asn Tyr Ala Asp Glu Leu Leu Ile Met Cys Gln Val
    210                 215                 220

Glu Ser Ala Glu Gly Val Lys Lys Ala Asp Glu Ile Ala Ala Val Asp
225                 230                 235                 240

Gly Val Asp Cys Val Gln Met Gly Pro Leu Asp Leu Ser Ala Ser Ile
                245                 250                 255

Gly Tyr Leu Trp Asp Pro Gly His Lys Lys Val Arg Glu Met Met Arg
```

```
            260                 265                 270
Arg Ala Glu Lys Ala Val Leu Thr Ser Asp Pro Glu Lys Gly Gly Ala
            275                 280                 285

Tyr Leu Ser Gly Phe Ala Met Pro His Asp Gly Pro Ala Ala Ile Arg
            290                 295                 300

Glu Arg Gly Tyr Asn Met Val Ala Gly Thr Val Asp Ile Gly Leu Phe
305                 310                 315                 320

Arg Asn Ala Ala Val Glu Asp Val Arg Arg Phe Lys Met Gly Leu Val
                325                 330                 335

Asn Glu Ser Asp Gly Glu Asp Ser Leu Asp Asn Gly Lys Asp Val Asp
                340                 345                 350

Asp Glu Lys Tyr Trp Ser Glu
                355

<210> SEQ ID NO 30
<211> LENGTH: 1056
<212> TYPE: DNA
<213> ORGANISM: Glycine max

<400> SEQUENCE: 30
atggggagca taagcacaag cagcatcaga gctcccccaa cccgaagaac aacagtcact     60
cctttctctt cccttctccc caaacccaaa cctcattttc tctcccttc cacttccaaa    120 tcccacgcat tccctctctc caagccccta accatttccc ccaattcaca tcccctcatt    180
cccaaatcca tccccaccct ctcctcctcc tcccccctaa acctcaagtc ccgactccgc    240
aacggagaga ccctctacgg cctcttcctc ctctccttct cccccaccct cgccgagatc    300
gcgggccacg ccggctacga cttcgtcgtc gtcgacatgg agcacggtcc tggcggcatc    360
cacgacgccc tccctgcct ccacgccctc gccgccgcca caccgccgc catcctccgc    420 gtcccggagt ccaccgctgc ttgggccaag aaagccctcg acctcggccc acagggcctc    480
atgttcccca tgattgactc cctgcagtcg gcccaggacg cggtctccta ctgccgtttt    540
cctcccaccg gactccgcgg cgcggcccac cccatccccc cgcctccaa gtacggcctc    600 gacgaggggt atctcggtaa ttacctcgac gagctgttaa tcatgtgcca ggtggagtcc    660
gaggagggcg tggcgaacgc tggcgcgatc gccgctgttg atggtgtgga ctgcgtgcag    720
atggggccgt ggatctgag tgctagttta gggtacttgt gggaccctgg cacaagaaa    780 gtgagggagg tgttgaggga ggccgagaac aaggttttgg agagccgaaa cgacgacgtt    840
gagagtgggg cctacttggc gggtttcgct acgcgtatg atgggcgag ggatttgagg    900 tcgcgtgggt atcacatggt aagtggcgcc gtcgacgtgg ggctgttccg gagcgcggcc    960
ctggaggatg tcacgcggtt caagatgac ggggatgggt cggagagtga tgagggagag    1020
gagaaagagg gtgatgagaa gtactggagt gaatga                            1056

<210> SEQ ID NO 31
<211> LENGTH: 351
<212> TYPE: PRT
<213> ORGANISM: Glycine max

<400> SEQUENCE: 31

Met Gly Ser Ile Ser Thr Ser Ser Ile Arg Ala Pro Pro Thr Arg Arg
1               5                   10                  15

Thr Thr Val Thr Pro Phe Ser Ser Leu Leu Pro Lys Pro Lys Pro His
            20                  25                  30

Phe Leu Ser Leu Ser Thr Ser Lys Ser His Ala Phe Pro Leu Ser Lys
```

```
                    35                  40                  45
Pro Leu Thr Ile Ser Pro Asn Ser His Pro Leu Ile Pro Lys Ser Ile
 50                  55                  60

Pro Thr Leu Ser Ser Ser Pro Leu Asn Leu Lys Ser Arg Leu Arg
 65                  70                  75                  80

Asn Gly Glu Thr Leu Tyr Gly Leu Phe Leu Ser Phe Ser Pro Thr
                 85                  90                  95

Leu Ala Glu Ile Ala Gly His Ala Gly Tyr Asp Phe Val Val Asp
                100                 105                 110

Met Glu His Gly Pro Gly Ile His Asp Ala Leu Pro Cys Leu His
            115                 120                 125

Ala Leu Ala Ala Ala Asn Thr Ala Ala Ile Leu Arg Val Pro Glu Ser
130                 135                 140

Thr Ala Ala Trp Ala Lys Lys Ala Leu Asp Leu Gly Pro Gln Gly Leu
145                 150                 155                 160

Met Phe Pro Met Ile Asp Ser Leu Gln Ser Ala Gln Asp Ala Val Ser
                165                 170                 175

Tyr Cys Arg Phe Pro Pro Thr Gly Leu Arg Gly Ala Ala His Pro Ile
            180                 185                 190

Pro Pro Ala Ser Lys Tyr Gly Leu Asp Glu Gly Tyr Leu Gly Asn Tyr
        195                 200                 205

Leu Asp Glu Leu Leu Ile Met Cys Gln Val Ser Glu Gly Val
210                 215                 220

Ala Asn Ala Gly Ala Ile Ala Ala Val Asp Gly Val Asp Cys Val Gln
225                 230                 235                 240

Met Gly Pro Leu Asp Leu Ser Ala Ser Leu Gly Tyr Leu Trp Asp Pro
                245                 250                 255

Gly His Lys Lys Val Arg Glu Val Leu Arg Glu Ala Glu Asn Lys Val
            260                 265                 270

Leu Glu Ser Arg Asn Asp Asp Val Glu Ser Gly Ala Tyr Leu Ala Gly
        275                 280                 285

Phe Ala Thr Ala Tyr Asp Gly Ala Arg Asp Leu Arg Ser Arg Gly Tyr
290                 295                 300

His Met Val Ser Gly Ala Val Asp Val Gly Leu Phe Arg Ser Ala Ala
305                 310                 315                 320

Leu Glu Asp Val Thr Arg Phe Lys Met Asp Gly Asp Gly Ser Glu Ser
                325                 330                 335

Asp Glu Gly Glu Glu Lys Glu Gly Asp Glu Lys Tyr Trp Ser Glu
            340                 345                 350

<210> SEQ ID NO 32
<211> LENGTH: 1497
<212> TYPE: DNA
<213> ORGANISM: Zea mays

<400> SEQUENCE: 32
gccacgccag caagcgcacg gcggcaccgc agcacgtgac aaaacagtca cgccccacgc      60
ggccccactt ctccggccgc cggactcgcc gttcggcttg gcagtcgcag acggcagatc     120
ccaaaatcga acaaccacca cctcccctc cgccgaccgg ccggcggct tcgctcgcca       180 tggccgccac cgcttccttc ctctcccacc tcctcctcgc ccccaagcgc agacccaaaa     240
ctcagccaaa cccctcgcat cttccctccc agcgcatcac ggaccggctt ccctgccgtg     300
ggcggcgctc ctccgtcgcg gtctccgccg cggcatccga cctcctctct cccgcgccct    360
```

```
ccctcaagtc cgcctcgcc gccggagaca ccctgtacgg tctgttcctc ctctccttct    420
cccctacccct cgccgagctc gccgcccctcg ccggctacga ctacgtcgtc gtcgacatgg    480
agcacgggcc gggcgggatc cccgaggcgc tcgcctgcct tcgcgcgctg gacgccgcgc    540
gcaccccgc cgtgctccgc ctcccggagg ccagcgccgt ctgggccaag aaggcgctgg    600
acctcggccc cgcgggcctc atgctccccg ccatcgagtc ccccgaggcc gccgcggagg    660
cggtctccca ctgccgctac ccgccgcgcg gggtccgcgg cgccgcacac ccatcgtcc    720
gcgcctccgc ctacggcttc gacgactcct acctctcccg ctgcgaggac gatatccctcg    780
tcatctgcca ggtcgagacc gccaccgcga tcgcggagat cgacgccatc gccgccgtcg    840
acggcgtgga cgtcgtgcag atgggcccgc tcgacctgtc ggctagcatg ggatacctgt    900
gggaccccgg gaacaggaag gtccgggcta cgctgaggga ggccgagagg aaggtgctgg    960
aggccaagaa gaagaagaag gcggcggcag cagcctcggg tggcaatgct gcttacctgg    1020
gcgggtttgc aatgcagaat gacccgccgg agcagctcaa attgaggggt taccatatgg    1080
tagctggcgc agtagacatt gctatgttcc ggaaggcggc attggatgat gtcaggcggt    1140
tccgagaggc agtgatggag atcggcgagg aggatgataa aaatgaggtt gagaaatgtg    1200
agaaggaaaa tgacgggtac tggagtgagt gagtgaacag tgtagaacag agctgagctg    1260
aagcatggag agaagtggct atgggttttg ttctggtgat atgtttttg ttctgaattc    1320
agaggatcta ttcgagatct taaggagccc aagaatttct agctttagct gtactcttgt    1380
ttaggtcatc atttgatttt caggtgaaca atccgattgg gcatcttaaa catccctatt    1440
tgtaggatga aactcagaac tggtggctac caataaagtg ctgttttttt tcgcccc    1497
```

<210> SEQ ID NO 33
<211> LENGTH: 350
<212> TYPE: PRT
<213> ORGANISM: Zea mays

<400> SEQUENCE: 33

```
Met Ala Ala Thr Ala Ser Phe Leu Ser His Leu Leu Leu Ala Pro Lys
1               5                   10                  15

Arg Arg Pro Lys Thr Gln Pro Asn Pro Ser His Leu Pro Ser Gln Arg
            20                  25                  30

Ile Thr Asp Arg Leu Pro Cys Arg Gly Arg Arg Ser Ser Val Ala Val
        35                  40                  45

Ser Ala Ala Ala Ser Asp Leu Leu Ser Pro Ala Pro Ser Leu Lys Ser
    50                  55                  60

Arg Leu Ala Ala Gly Asp Thr Leu Tyr Gly Leu Phe Leu Leu Ser Phe
65                  70                  75                  80

Ser Pro Thr Leu Ala Glu Leu Ala Ala Leu Ala Gly Tyr Asp Tyr Val
                85                  90                  95

Val Val Asp Met Glu His Gly Pro Gly Gly Ile Pro Glu Ala Leu Ala
            100                 105                 110

Cys Leu Arg Ala Leu Asp Ala Ala Arg Thr Pro Ala Val Leu Arg Leu
        115                 120                 125

Pro Glu Ala Ser Ala Val Trp Ala Lys Lys Ala Leu Asp Leu Gly Pro
    130                 135                 140

Ala Gly Leu Met Leu Pro Ala Ile Glu Ser Pro Glu Ala Ala Ala Glu
145                 150                 155                 160

Ala Val Ser His Cys Arg Tyr Pro Pro Arg Gly Val Arg Gly Ala Ala
                165                 170                 175
```

His Pro Ile Val Arg Ala Ser Ala Tyr Gly Phe Asp Asp Ser Tyr Leu
            180                 185                 190

Ser Arg Cys Glu Asp Asp Thr Leu Val Ile Cys Gln Val Glu Thr Ala
        195                 200                 205

Thr Ala Ile Ala Glu Ile Asp Ala Ile Ala Ala Val Asp Gly Val Asp
    210                 215                 220

Val Val Gln Met Gly Pro Leu Asp Leu Ser Ala Ser Met Gly Tyr Leu
225                 230                 235                 240

Trp Asp Pro Gly Asn Arg Lys Val Arg Ala Thr Leu Arg Glu Ala Glu
                245                 250                 255

Arg Lys Val Leu Glu Ala Lys Lys Lys Lys Ala Ala Ala Ala
        260                 265                 270

Ser Gly Gly Asn Ala Ala Tyr Leu Gly Gly Phe Ala Met Gln Asn Asp
    275                 280                 285

Pro Pro Glu Gln Leu Lys Leu Arg Gly Tyr His Met Val Ala Gly Ala
    290                 295                 300

Val Asp Ile Ala Met Phe Arg Lys Ala Ala Leu Asp Asp Val Arg Arg
305                 310                 315                 320

Phe Arg Glu Ala Val Met Glu Ile Gly Glu Glu Asp Asp Lys Asn Glu
                325                 330                 335

Val Glu Lys Cys Glu Lys Glu Asn Asp Gly Tyr Trp Ser Glu
            340                 345                 350

<210> SEQ ID NO 34
<211> LENGTH: 1354
<212> TYPE: DNA
<213> ORGANISM: oryza sativa

<400> SEQUENCE: 34
acactgactg ggactcactc gccgcagatc cccaaacctc tccgccgccg cgccggctcg    60
cctcgcgcgc catggccgcc tccgcctccg cctccgccac cgcctccctc tcccacctcc   120
tcctcgcgcg caagccagac cccgcgcctc tcccctcccg ccgcgccccc gccctgctcc   180
ccttgccgcg gcggcgcggg cagcggccca tctccgccgc cgccgccgcc tccgacctcc   240
tctacgccgc accctccctc aagtcccggc tcgccgccgg ggagaccctg tacgggctct   300
tcctcctctc cttctccccc acgctcgccg agctcgccgc cctcgccggc tacgactacg   360
tcgtcgtcga catggagcac ggccccggcg gcgttcccga ggcgctggcc tgcctccgcg   420
ccctcgacgc cgcccgtacc ccagccgtca tccgcctccc cgaggccggc cccatctggg   480
ccaagaaggc cctcgacctc ggccccgcgg gcctcatggt ccccgccgtc gagtcccccg   540
ccgccgcggc cgccgccgtg tcgcactgcc gctacccgcc cgaggcgtt cgcggcgccg   600 cccaccccat cgtccgcgcc tccgcgtacg gcctcgacga ctcctacctc tcccgctgcg   660
aggacgagac gctaatcatc tgccaggtcg agaccgccgc tggcattgcg gaggtcgacg   720
ccattgccgc cgtcgacggc gtcgacgtcg tccagatggg accgctcgac ttgtcagcca   780
gcatggggta cctgtgggac ccagggaaca ggaaggtgcg agccaggctg agggaggccg   840
agaagaaggt gttggatgcc aggaagaaga atgtgacagc ttcagatggc aatgtcgcat   900
atctaggcgg attcgccatg ccgaacgacc cggcagagca gctcaagctg aggggttacc   960
acatggtgtc tggtgcagtg gacattggga tgttccggaa ggcggcgttg gaggatgtca  1020
agcggttcaa ggaggcagtg atggaaatcg gcgaggagga aggcgaggag gacgatgaaa  1080
agaaggacaa ggaagacgac gggtactgga gtgagtgagc actgagcaga gttgagctga  1140

-continued

```
agatgatcaa ggaactgtgg tgatggtgtc ttttgtttgt cttctgaatt cagattgaga      1200
ggtctaagtg gttccatttt ccagggggcct ctggtgtact cttgtttagt tgtcaggtcg      1260
attttgagaa catcatgttt gggcatctta ggattcccat ttgtaggtgg taacttctga      1320
gtaccaataa aagccagatt tttatatcat tcag                                   1354
```

<210> SEQ ID NO 35
<211> LENGTH: 348
<212> TYPE: PRT
<213> ORGANISM: Oryza sativa

<400> SEQUENCE: 35

```
Met Ala Ala Ser Ala Ser Ala Ser Ala Thr Ala Ser Leu Ser His Leu
1               5                   10                  15

Leu Leu Ala Arg Lys Pro Asp Pro Ala Pro Leu Pro Ser Arg Arg Ala
            20                  25                  30

Pro Ala Leu Leu Pro Leu Pro Arg Arg Arg Gly Gln Arg Pro Ile Ser
        35                  40                  45

Ala Ala Ala Ala Ala Ser Asp Leu Leu Tyr Ala Ala Pro Ser Leu Lys
    50                  55                  60

Ser Arg Leu Ala Ala Gly Glu Thr Leu Tyr Gly Leu Phe Leu Leu Ser
65                  70                  75                  80

Phe Ser Pro Thr Leu Ala Glu Leu Ala Ala Leu Ala Gly Tyr Asp Tyr
                85                  90                  95

Val Val Val Asp Met Glu His Gly Pro Gly Gly Val Pro Glu Ala Leu
            100                 105                 110

Ala Cys Leu Arg Ala Leu Asp Ala Ala Arg Thr Pro Ala Val Ile Arg
        115                 120                 125

Leu Pro Glu Ala Gly Pro Ile Trp Ala Lys Lys Ala Leu Asp Leu Gly
    130                 135                 140

Pro Ala Gly Leu Met Val Pro Ala Val Glu Ser Pro Ala Ala Ala Ala
145                 150                 155                 160

Ala Ala Val Ser His Cys Arg Tyr Pro Pro Arg Gly Val Arg Gly Ala
                165                 170                 175

Ala His Pro Ile Val Arg Ala Ser Ala Tyr Gly Leu Asp Asp Ser Tyr
            180                 185                 190

Leu Ser Arg Cys Glu Asp Glu Thr Leu Ile Ile Cys Gln Val Glu Thr
        195                 200                 205

Ala Ala Gly Ile Ala Glu Val Asp Ala Ile Ala Ala Val Asp Gly Val
    210                 215                 220

Asp Val Val Gln Met Gly Pro Leu Asp Leu Ser Ala Ser Met Gly Tyr
225                 230                 235                 240

Leu Trp Asp Pro Gly Asn Arg Lys Val Arg Ala Arg Leu Arg Glu Ala
                245                 250                 255

Glu Lys Lys Val Leu Asp Ala Arg Lys Lys Asn Val Thr Ala Ser Asp
            260                 265                 270

Gly Asn Val Ala Tyr Leu Gly Gly Phe Ala Met Pro Asn Asp Pro Ala
        275                 280                 285

Glu Gln Leu Lys Leu Arg Gly Tyr His Met Val Ser Gly Ala Val Asp
    290                 295                 300

Ile Gly Met Phe Arg Lys Ala Ala Leu Glu Asp Val Lys Arg Phe Lys
305                 310                 315                 320

Glu Ala Val Met Glu Ile Gly Glu Glu Gly Glu Glu Asp Asp Glu
                325                 330                 335
```

Lys Lys Asp Lys Glu Asp Asp Gly Tyr Trp Ser Glu
     340             345

<210> SEQ ID NO 36
<211> LENGTH: 34
<212> TYPE: DNA
<213> ORGANISM: artificial sequence
<220> FEATURE:
<223> OTHER INFORMATION: linker

<400> SEQUENCE: 36
ggcgcgccaa gcttggatcc gtcgacggcg cgcc        34

<210> SEQ ID NO 37
<211> LENGTH: 4974
<212> TYPE: DNA
<213> ORGANISM: artificial sequence
<220> FEATURE:
<223> OTHER INFORMATION: vector
<220> FEATURE:
<221> NAME/KEY: misc_feature
<222> LOCATION: (3951)..(3951)
<223> OTHER INFORMATION: n=a,c,g,or t

<400> SEQUENCE: 37

```
ggccgccgac tcgacgatga gcgagatgac cagctccggc cgcgacacaa gtgtgagagt     60
actaaataaa tgctttggtt gtacgaaatc attacactaa ataaataat caaagcttat     120
atatgccttc cgctaaggcc gaatgcaaag aaattggttc tttctcgtta tcttttgcca    180
cttttactag tacgtattaa ttactactta atcatctttg tttacggctc attatatccg    240
tcgacggcgc gcccgatcat ccggatatag ttcctccttt cagcaaaaaa cccctcaaga    300
cccgtttaga ggcccaagg ggttatgcta gttattgctc agcggtggca gcagccaact     360
cagcttcctt tcgggctttg ttagcagccg gatcgatcca agctgtacct cactattcct    420
ttgccctcgg acgagtgctg gggcgtcggt ttccactatc ggcgagtact tctacacagc    480
catcggtcca gacggccgcg cttctgcggg cgatttgtgt acgcccgaca gtcccggctc    540
cggatcggac gattgcgtcg catcgaccct gcgcccaagc tgcatcatcg aaattgccgt    600
caaccaagct ctgatagagt tggtcaagac caatgcggag catatacgcc cggagccgcg    660
gcgatcctgc aagctccgga tgcctccgct cgaagtagcg cgtctgctgc tccatacaag    720
ccaaccacgg cctccagaag aagatgttgg cgacctcgta ttgggaatcc ccgaacatcg    780
cctcgctcca gtcaatgacc gctgttatgc ggccattgtc cgtcaggaca ttgttggagc    840
cgaaatccgc gtgcacgagg tgccggactt cggggcagtc ctcggcccaa gcatcagct    900
catcgagagc ctgcgcgacg acgcactga cggtgtcgtc catcacagtt gccagtgat    960
acacatgggg atcagcaatc gcgcatatga atcacgccat gtagtgtat tgaccgattc   1020
cttgcggtcc gaatgggccg aacccgctcg tctggctaag atcggccgca gcgatcgcat   1080
ccatagcctc cgcgaccggc tgcagaacag cgggcagttc ggtttcaggc aggtcttgca   1140
acgtgacacc ctgtgcacgg cgggagatgc aataggtcag gctctcgctg aattccccaa   1200
tgtcaagcac ttccggaatc gggagcgcgg ccgatgcaaa gtgccgataa acataacgat   1260
ctttgtagaa accatcggcg cagctattta cccgcaggac atatccacgc cctcctacat   1320
cgaagctgaa agcacgagat tcttcgccct ccgagagctg catcaggtcg agacgctgt    1380
cgaacttttc gatcagaaac ttctcgacag acgtcgcggt gagttcaggc ttttccatgg   1440
gtatatctcc ttcttaaagt taaacaaaat tatttctaga gggaaaccgt tgtggtctcc   1500
```

```
ctatagtgag tcgtattaat ttcgcgggat cgagatctga tcaacctgca ttaatgaatc   1560
ggccaacgcg cggggagagg cggtttgcgt attgggcgct cttccgcttc ctcgctcact   1620
gactcgctgc gctcggtcgt tcggctgcgg cgagcggtat cagctcactc aaaggcggta   1680
atacggttat ccacagaatc aggggataac gcaggaaaga acatgtgagc aaaaggccag   1740
caaaaggcca ggaaccgtaa aaaggccgcg ttgctggcgt ttttccatag gctccgcccc   1800
cctgacgagc atcacaaaaa tcgacgctca agtcagaggt ggcgaaaccc gacaggacta   1860
taaagatacc aggcgtttcc ccctggaagc tccctcgtgc gctctcctgt tccgaccctg   1920
ccgcttaccg gatacctgtc cgcctttctc ccttcgggaa gcgtggcgct ttctcaatgc   1980
tcacgctgta ggtatctcag ttcggtgtag gtcgttcgct ccaagctggg ctgtgtgcac   2040
gaaccccccg ttcagcccga ccgctgcgcc ttatccggta actatcgtct tgagtccaac   2100
ccggtaagac acgacttatc gccactggca gcagccactg gtaacaggat tagcagagcg   2160
aggtatgtag gcggtgctac agagttcttg aagtggtggc ctaactacgg ctacactaga   2220
aggacagtat ttggtatctg cgctctgctg aagccagtta ccttcggaaa aagagttggt   2280
agctcttgat ccggcaaaca aaccaccgct ggtagcggtg gtttttttgt ttgcaagcag   2340
cagattacgc gcagaaaaaa aggatctcaa gaagatcctt tgatcttttc tacggggtct   2400
gacgctcagt ggaacgaaaa ctcacgttaa gggattttgg tcatgacatt aacctataaa   2460
aataggcgta tcacgaggcc ctttcgtctc gcgcgtttcg gtgatgacgg tgaaaacctc   2520
tgacacatgc agctcccgga gacggtcaca gcttgtctgt aagcggatgc cgggagcaga   2580
caagcccgtc agggcgcgtc agcgggtgtt ggcgggtgtc ggggctggct taactatgcg   2640
gcatcagagc agattgtact gagagtgcac catatggaca tattgtcgtt agaacgcggc   2700
tacaattaat acataacctt atgtatcata cacatacgat ttaggtgaca ctatagaacg   2760
gcgcgccaag cttggatcct cgaagagaag ggttaataac acatttttta acatttttaa   2820
cacaaatttt agttatttaa aaatttatta aaaaatttaa aataagaaga ggaactctttt   2880 aaataaatct aacttacaaa atttatgatt tttaataagt tttcaccaat aaaaaatgtc   2940
ataaaaatat gttaaaaagt atattatcaa tattctcttt atgataaata aaagaaaaa   3000 aaaaataaaa gttaagtgaa aatgagattg aagtgacttt aggtgtgtat aaatatatca   3060
accccgccaa caatttattt aatccaaata tattgaagta tattattcca tagcctttat   3120
ttatttatat atttattata taaaagcttt atttgttcta ggttgttcat gaaatatttt   3180
tttggtttta tctccgttgt aagaaaatca tgtgctttgt gtcgccactc actattgcag   3240 cttttttcatg cattggtcag attgacggtt gattgtattt ttgttttta tggttttgtg   3300 ttatgactta agtcttcatc tctttatctc ttcatcaggt ttgatggtta cctaatatgg   3360
tccatgggta catgcatggt taaattaggt ggccaacttt gttgtgaacg atagaatttt   3420
ttttatatta agtaaactat ttttatatta tgaaataata ataaaaaaaa tattttatca   3480
ttattaacaa aatcatatta gttaatttgt taactctata ataaaagaaa tactgtaaca   3540
ttcacattac atggtaacat ctttccaccc tttcatttgt tttttgtttg atgactttt    3600 ttcttgttta aatttatttc ccttctttta aatttggaat acattatcat catatataaa   3660
ctaaaatact aaaaacagga ttacacaaat gataaataat aacacaaata tttataaatc   3720
tagctgcaat atatttaaac tagctatatc gatattgtaa aataaaacta gctgcattga   3780
tactgataaa aaaatatcat gtgctttctg gactgatgat gcagtatact tttgacattg   3840 ccttttatttt atttttcaga aaagctttct tagttctggg ttcttcatta tttgtttccc   3900
```

```
atctccattg tgaattgaat catttgcttc gtgtcacaaa tacaatttag ntaggtacat    3960
gcattggtca gattcacggt ttattatgtc atgacttaag ttcatggtag tacattacct    4020
gccacgcatg cattatattg gttagatttg ataggcaaat ttggttgtca acaatataaa    4080
tataaataat gtttttatat tacgaaataa cagtgatcaa aacaaacagt tttatcttta    4140
ttaacaagat tttgttttg tttgatgacg tttttaatg tttacgcttt ccccttctt      4200 ttgaatttag aacactttat catcataaaa tcaaatacta aaaaattac atatttcata    4260 aataataaca caaatatttt taaaaaatct gaaataataa tgaacaatat tacatattat    4320
cacgaaaatt cattaataaa aatattatat aaataaaatg taatagtagt tatatgtagg    4380
aaaaaagtac tgcacgcata atatatacaa aaagattaaa atgaactatt ataaataata    4440
acactaaatt aatggtgaat catatcaaaa taatgaaaaa gtaaataaaa tttgtaatta    4500
acttctatat gtattacaca cacaaataat aaataatagt aaaaaaaatt atgataaata    4560
tttaccatct cataagatat ttaaaataat gataaaaata tagattatt tttatgcaac    4620 tagctagcca aaagagaac acgggtatat ataaaaagag tacctttaaa ttctactgta    4680
cttcctttat tcctgacgtt tttatatcaa gtggacatac gtgaagatt taattatcag    4740 tctaaatatt tcattagcac ttaatacttt tctgttttat tcctatccta aagtagtcc    4800 cgattctccc aacattgctt attcacacaa ctaactaaga aagtcttcca tagccccca    4860 agcggccgga gctggtcatc tcgctcatcg tcgagtcggc ggccggagct ggtcatctcg    4920
ctcatcgtcg agtcggcggc cgccgactcg acgatgagcg agatgaccag ctcc          4974
```

<210> SEQ ID NO 38
<211> LENGTH: 80
<212> TYPE: DNA
<213> ORGANISM: artificial sequence
<220> FEATURE:
<223> OTHER INFORMATION: synthetic complementary region of pKS106 and pKS124

<400> SEQUENCE: 38

```
cggccggagc tggtcatctc gctcatcgtc gagtcggcgg ccgccgactc gacgatgagc    60
gagatgacca gctccggccg                                                80
```

<210> SEQ ID NO 39
<211> LENGTH: 154
<212> TYPE: DNA
<213> ORGANISM: artificial sequence
<220> FEATURE:
<223> OTHER INFORMATION: corresponds to a synthetic complementary region of pKS133

<400> SEQUENCE: 39

```
cggccggagc tggtcatctc gctcatcgtc gagtcggcgg ccggagctgg tcatctcgct    60
catcgtcgag tcggcggccg ccgactcgac gatgagcgag atgaccagct ccggccgccg   120
actcgacgat gagcgagatg accagctccg gccg                                154
```

<210> SEQ ID NO 40
<211> LENGTH: 92
<212> TYPE: DNA
<213> ORGANISM: artificial sequence
<220> FEATURE:
<223> OTHER INFORMATION: primer

<400> SEQUENCE: 40

```
gaattccggc cggagctggt catctcgctc atcgtcgagt cggcggccgc cgactcgacg    60
atgagcgaga tgaccagctc cggccggaat tc                                  92
```

<210> SEQ ID NO 41
<211> LENGTH: 15
<212> TYPE: DNA
<213> ORGANISM: artificial sequence
<220> FEATURE:
<223> OTHER INFORMATION: primer

<400> SEQUENCE: 41

```
gaattccggc cggag                                                     15
```

<210> SEQ ID NO 42
<211> LENGTH: 28
<212> TYPE: DNA
<213> ORGANISM: artificial sequence
<220> FEATURE:
<223> OTHER INFORMATION: primer

<400> SEQUENCE: 42

```
gcggccgcta agcacaagca gcatcaga                                       28
```

<210> SEQ ID NO 43
<211> LENGTH: 30
<212> TYPE: DNA
<213> ORGANISM: artificial sequence
<220> FEATURE:
<223> OTHER INFORMATION: primer

<400> SEQUENCE: 43

```
gggcgtggcg aacgcgatct cggcgagggt                                     30
```

<210> SEQ ID NO 44
<211> LENGTH: 30
<212> TYPE: DNA
<213> ORGANISM: artificial sequence
<220> FEATURE:
<223> OTHER INFORMATION: priemr

<400> SEQUENCE: 44

```
accctcgccg agatcgcgtt cgccacgccc                                     30
```

<210> SEQ ID NO 45
<211> LENGTH: 8522
<212> TYPE: DNA
<213> ORGANISM: artificial sequence
<220> FEATURE:
<223> OTHER INFORMATION: plasmid
<220> FEATURE:
<221> NAME/KEY: misc_feature
<222> LOCATION: (6642)..(6642)
<223> OTHER INFORMATION: n=a,c,g,or t

<400> SEQUENCE: 45

```
ggccgcgaca caagtgtgag agtactaaat aaatgctttg gttgtacgaa atcattacac    60
taaataaaat aatcaaagct tatatatgcc ttccgctaag gccgaatgca agaaattgg    120 ttctttctcg ttatcttttg ccacttttac tagtacgtat taattactac ttaatcatct   180
ttgtttacgg ctcattatat ccgtcgacgg cgcgcccgat catccggata tagttcctcc   240
tttcagcaaa aaaccctca agacccgttt agaggcccca aggggttatg ctagttattg    300
ctcagcggtg gcagcagcca actcagcttc ctttcgggct tgttagcag ccggatcgat    360 ccaagctgta cctcactatt cctttgccct cggacgagtg ctggggcgtc ggtttccact   420
```

-continued

```
atcggcgagt acttctacac agccatcggt ccagacggcc gcgcttctgc gggcgatttg    480
tgtacgcccg acagtcccgg ctccggatcg gacgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc gcgtgcacg aggtgccgga cttcggggca    840
gtcctcggcc aaagcatca gctcatcgag agcctgcgcg acgacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct   1020
aagatcggcc gcagcgatcg catccatagc ctccgcgacc ggctgcagaa cagcgggcag   1080
ttcggtttca ggcaggtctt gcaacgtgac accctgtgca cggcgggaga tgcaataggt   1140
caggctctcg ctgaattccc caatgtcaag cacttccgga atcgggagcg cggccgatgc   1200
aaagtgccga taaacataac gatctttgta gaaaccatcg gcgcagctat ttacccgcag   1260
gacatatcca cgccctccta catcgaagct gaaagcacga gattcttcgc cctccgagag   1320
ctgcatcagg tcggagacgc tgtcgaactt ttcgatcaga aacttctcga cagacgtcgc   1380
ggtgagttca ggcttttcca tgggtatatc tccttcttaa agttaaacaa aattatttct   1440
agagggaaac cgttgtggtc tccctatagt gagtcgtatt aatttcgcgg gatcgagatc   1500
gatccaattc caatcccaca aaaatctgag cttaacagca cagttgctcc tctcagagca   1560
gaatcgggta ttcaacaccc tcatatcaac tactacgttg tgtataacgg tccacatgcc   1620
ggtatatacg atgactgggg ttgtacaaag gcggcaacaa acggcgttcc cggagttgca   1680
cacaagaaat ttgccactat tacagaggca agagcagcag ctgacgcgta cacaacaagt   1740
cagcaaacag acaggttgaa cttcatcccc aaaggagaag ctcaactcaa gcccaagagc   1800
tttgctaagg ccctaacaag cccaccaaag caaaaagccc actggctcac gctaggaacc   1860
aaaaggccca gcagtgatcc agccccaaaa gagatctcct tgccccggga gattacaatg   1920
gacgatttcc tctatctta cgatctagga aggaagttcg aaggtgaagg tgacgacact   1980
atgttccacca ctgataatga aaggttagc ctcttcaatt tcagaaagaa tgctgaccca   2040
cagatggtta gagaggccta cgcagcaggt ctcatcaaga cgatctaccc gagtaacaat   2100
ctccaggaga tcaaatacct tcccaagaag gttaaagatg cagtcaaaag attcaggact   2160
aattgcatca agaacacaga gaaagacata tttctcaaga tcagaagtac tattccagta   2220
tggacgattc aaggcttgct tcataaacca aggcaagtaa tagagattgg agtctctaaa   2280
aaggtagttc ctactgaatc taaggccatg catggagtct aagattcaaa tcgaggatct   2340
aacagaactc gccgtgaaga ctggcgaaca gttcatacag agtcttttac gactcaatga   2400
caagaagaaa atcttcgtca acatggtgga gcacgacact ctggtctact ccaaaaatgt   2460
caaagataca gtctcagaag accaaagggc tattgagact tttcaacaaa ggataatttc   2520
gggaaacctc ctcggattcc attgcccagc tatctgtcac ttcatcgaaa ggacagtaga   2580
aaaggaaggt ggctcctaca aatgccatca ttgcgataaa ggaaaggcta tcattcaaga   2640
tgcctctgcc gacagtggtc ccaaagatgg acccccaccc acgaggagca tcgtggaaaa   2700
agaagacgtt ccaaccacgt cttcaaagca agtggattga tgtgacatct ccactgacgt   2760
```

```
aagggatgac gcacaatccc actatccttc gcaagaccct tcctctatat aaggaagttc    2820
atttcatttg gagaggacac gctcgagctc atttctctat tacttcagcc ataacaaaag    2880
aactcttttc tcttcttatt aaaccatgaa aaagcctgaa ctcaccgcga cgtctgtcga    2940
gaagtttctg atcgaaaagt tcgacagcgt ctccgacctg atgcagctct cggagggcga    3000
agaatctcgt gctttcagct tcgatgtagg agggcgtgga tatgtcctgc gggtaaatag    3060
ctgcgccgat ggtttctaca agatcgtta tgtttatcgg cactttgcat cggccgcgct    3120
cccgattccg gaagtgcttg acattgggga attcagcgag agcctgacct attgcatctc    3180
ccgccgtgca cagggtgtca cgttgcaaga cctgcctgaa accgaactgc ccgctgttct    3240
gcagccggtc gcggaggcca tggatgcgat cgctgcggcc gatcttagcc agacgagcgg    3300
gttcggccca ttcggaccgc aaggaatcgg tcaatacact acatggcgtg atttcatatg    3360
cgcgattgct gatccccatg tgtatcactg gcaaactgtg atggacgaca ccgtcagtgc    3420
gtccgtcgcg caggctctcg atgagctgat gctttgggcc gaggactgcc ccgaagtccg    3480
gcacctcgtg cacgcggatt tcggctccaa caatgtcctg acgacaatg gccgcataac    3540
agcggtcatt gactggagcg aggcgatgtt cggggattcc caatacgagg tcgccaacat    3600
cttcttctgg aggccgtggt tggcttgtat ggagcagcag acgcgctact cgagcggag    3660
gcatccggag cttgcaggat cgccgcggct ccgggcgtat atgctccgca ttggtcttga    3720
ccaactctat cagagcttgg ttgacggcaa tttcgatgat gcagcttggg cgcagggtcg    3780
atgcgacgca atcgtccgat ccggagccgg gactgtcggg cgtacacaaa tcgcccgcag    3840
aagcgcggcc gtctggaccg atggctgtgt agaagtactc gccgatagtg aaaccgacg    3900
ccccagcact cgtccgaggg caaaggaata gtgaggtacc taaagaagga gtgcgtcgaa    3960
gcagatcgtt caaacatttg gcaataaagt ttcttaagat tgaatcctgt tgccggtctt    4020
gcgatgatta tcatataatt tctgttgaat tacgttaagc atgtaataat taacatgtaa    4080
tgcatgacgt tatttatgag atgggttttt atgattagag tcccgcaatt atacatttaa    4140
tacgcgatag aaaacaaaat atagcgcgca aactaggata aattatcgcg cgcggtgtca    4200
tctatgttac tagatcgatg tcgaatctga tcaacctgca ttaatgaatc ggccaacgcg    4260
cggggagagg cggtttgcgt attgggcgct cttccgcttc ctcgctcact gactcgctgc    4320
gctcggtcgt tcggctgcgg cgagcggtat cagctcactc aaaggcggta atacggttat    4380
ccacagaatc aggggataac gcaggaaaga acatgtgagc aaaaggccag caaaaggcca    4440
ggaaccgtaa aaaggccgcg ttgctggcgt ttttccatag gctccgcccc cctgacgagc    4500
atcacaaaaa tcgacgctca agtcagaggt ggcgaaaccc gacaggacta taaagatacc    4560
aggcgtttcc ccctggaagc tccctcgtgc gctctcctgt tccgaccctg ccgcttaccg    4620
gatacctgtc cgcctttctc ccttcgggaa gcgtggcgct ttctcaatgc tcacgctgta    4680
ggtatctcag ttcggtgtag tcgttcgct ccaagctggg ctgtgtgcac gaaccccccg    4740
ttcagcccga ccgctgcgcc ttatccgta actatcgtct tgagtccaac ccggtaagac    4800
acgacttatc gccactggca gcagccactg gtaacaggat tagcagagcg aggtatgtag    4860
gcggtgctac agagttcttg aagtggtggc ctaactacgg ctacactaga aggacagtat    4920
ttggtatctg cgctctgctg aagccagtta ccttcggaaa aagagttggt agctcttgat    4980
ccggcaaaca aaccaccgct ggtagcggtg ttttttttgt ttgcaagcag cagattacgc    5040
gcagaaaaaa aggatctcaa gaagatcctt tgatcttttc tacggggtct gacgctcagt    5100
ggaacgaaaa ctcacgttaa gggattttgg tcatgacatt aacctataaa aataggcgta    5160
```

```
tcacgaggcc ctttcgtctc gcgcgtttcg gtgatgacgg tgaaaacctc tgacacatgc    5220
agctcccgga gacggtcaca gcttgtctgt aagcggatgc cgggagcaga caagcccgtc    5280
agggcgcgtc agcgggtgtt ggcgggtgtc ggggctggct taactatgcg gcatcagagc    5340
agattgtact gagagtgcac catatggaca tattgtcgtt agaacgcggc tacaattaat    5400
acataacctt atgtatcata cacatacgat ttaggtgaca ctatagaacg gcgcgccaag    5460
cttggatcct cgaagagaag ggttaataac acactttttt aacattttta acacaaattt    5520
tagttattta aaaatttatt aaaaaattta aataagaag aggaactctt taaataaatc    5580
taacttacaa aatttatgat ttttaataag ttttcaccaa taaaaaatgt cataaaaata    5640
tgttaaaaag tatattatca atattctctt tatgataaat aaaaagaaaa aaaaaataaa    5700
agttaagtga aaatgagatt gaagtgactt taggtgtgta taaatatatc aaccccgcca    5760
acaatttatt taatccaaat atattgaagt atattattcc atagccttta tttatttata    5820
tatttattat ataaaagctt tatttgttct aggttgttca tgaaatattt ttttggtttt    5880
atctccgttg taagaaaatc atgtgctttg tgtcgccact cactattgca gcttttcat    5940 gcattggtca gattgacggt tgattgtatt tttgttttt atggttttgt gttatgactt    6000
aagtcttcat ctctttatct cttcatcagg tttgatggtt acctaatatg gtccatgggt    6060
acatgcatgg ttaaattagg tggccaactt tgttgtgaac gatagaattt tttttatatt    6120
aagtaaacta ttttatatt atgaaataat aataaaaaaa atattttatc attattaaca    6180
aaatcatatt agttaatttg ttaactctat aataaaagaa atactgtaac attcacatta    6240
catggtaaca tctttccacc ctttcatttg ttttttgttt gatgactttt tttcttgttt    6300
aaatttattt cccttctttt aaatttggaa tacattatca tcatatataa actaaaatac    6360
taaaaacagg attacacaaa tgataaataa taacacaaat atttataaat ctagctgcaa    6420
tatatttaaa ctagctatat cgatattgta aaataaaact agctgcattg atactgataa    6480
aaaaatatca tgtgctttct ggactgatga tgcagtatac ttttgacatt gcctttattt    6540 tattttttcag aaaagctttc ttagttctgg gttcttcatt atttgtttcc catctccatt    6600
gtgaattgaa tcatttgctt cgtgtcacaa atacaattta gntaggtaca tgcattggtc    6660
agattcacgg tttattatgt catgacttaa gttcatggta gtacattacc tgccacgcat    6720
gcattatatt ggttagattt gataggcaaa tttggttgtc aacaatataa atataaataa    6780 tgttttttata ttacgaaata acagtgatca aaacaaacag ttttatcttt attaacaaga    6840
ttttgttttt gttgatgac gtttttaat gtttacgctt tcccccttct tttgaattta    6900
gaacacttta tcatcataaa atcaaatact aaaaaaatta catatttcat aaataataac    6960
acaaatattt ttaaaaatc tgaaataata atgaacaata ttacatatta tcacgaaaat    7020
tcattaataa aaatattata taaataaaat gtaatagtag ttatatgtag gaaaaaagta    7080
ctgcacgcat aatatataca aaagattaa aatgaactat tataaataat aacactaaat    7140
taatggtgaa tcatatcaaa ataatgaaaa agtaaataaa atttgtaatt aacttctata    7200
tgtattacac acacaaataa taaataatag taaaaaaaat tatgataaat atttaccatc    7260
tcataagata tttaaaataa tgataaaaat atagattatt ttttatgcaa ctagctagcc    7320
aaaaagagaa cacgggtata tataaaaaga gtacctttaa attctactgt acttccttta    7380
ttcctgacgt ttttatatca agtggacata cgtgaagatt ttaattatca gtctaaatat    7440
ttcattagca cttaatactt ttctgtttta ttcctatcct ataagtagtc ccgattctcc    7500
```

```
caacattgct tattcacaca actaactaag aaagtcttcc atagccccc aagcggccgc   7560
taagcacaag cagcatcaga gctcccccaa cccgaagaac aacagtcact cctttctctt   7620
cccttctccc caaacccaaa cctcatttc tctccctttc cacttccaaa tcccacgcat    7680
tccctctctc caagccccta accatttccc ccaattcaca tccctcatt cccaaatcca    7740
tccccaccct ctcctcctcc tccccctaa acctcaagtc ccgactccgc aacggagaga   7800
ccctctacgg cctcttcctc ctctccttct cccccaccct cgccgagatc gcggccacg    7860
ccggctacga cttcgtcgtc gtcgacatgg agcacggtcc tggcggcatc cacgacgccc   7920
tccctgcct ccacgccctc gccgccgcca acaccgccgc catcctccgc gtcccggagt    7980
ccaccgctgc ttgggccaag aaagccctcg acctcggccc acagggcctc atgttcccca   8040
tgattgactc cctgcagtcg gcccaggacg cggtctccta ctgccgtttt cctcccaccg   8100
gactccgcgg cgcggcccac cccatcgtcc gggcctccaa gtacgcctc gacgaggggt    8160
atctcggtaa ttacctcgac gagctgttaa tcatgtgcca ggtggagtcc gaggagggcg   8220
tggcgaacgc gatctcggcg agggtggggg agaaggagag gaggaagagg ccgtagaggg   8280
tctctccgtt gcggagtcgg gacttgaggt ttagggggga ggaggaggag agggtgggga   8340
tggatttggg aatgagggga tgtgaattgg gggaaatggt tagggcttg gagagaggga    8400
atgcgtggga tttggaagtg gaaagggaga gaaatgagg tttgggtttg gggagaaggg   8460
aagagaaagg agtgactgtt gttcttcggg ttggggagc tctgatgctg cttgtgctta    8520
gc                                                                    8522
```

<210> SEQ ID NO 46
<211> LENGTH: 5267
<212> TYPE: DNA
<213> ORGANISM: artificial sequence
<220> FEATURE:
<223> OTHER INFORMATION: plasmid

<400> SEQUENCE: 46

```
atctgatcaa cctgcattaa tgaatcggcc aacgcgcggg gagaggcggt ttgcgtattg     60
ggcgctcttc cgcttcctcg ctcactgact cgctgcgctc ggtcgttcgg ctgcggcgag    120
cggtatcagc tcactcaaag gcggtaatac ggttatccac agaatcaggg gataacgcag    180
gaaagaacat gtgagcaaaa ggccagcaaa aggccaggaa ccgtaaaaag gccgcgttgc    240
tggcgttttt ccataggctc cgcccccctg acgagcatca caaaaatcga cgctcaagtc    300
agaggtggcg aaacccgaca ggactataaa gataccaggc gtttccccct ggaagctccc    360
tcgtgcgctc tcctgttccg accctgccgc ttaccggata cctgtccgcc tttctccctt    420
cgggaagcgt ggcgctttct caatgctcac gctgtaggta tctcagttcg gtgtaggtcg    480
ttcgctccaa gctgggctgt gtgcacgaac cccccgttca gcccgaccgc tgcgccttat    540
ccggtaacta tcgtcttgag tccaacccgg taagacacga cttatcgcca ctggcagcag    600
ccactggtaa caggattagc agagcgaggt atgtaggcgg tgctacagag ttcttgaagt    660
ggtggcctaa ctacggctac actagaagga cagtatttgg tatctgcgct ctgctgaagc    720
cagttacctt cggaaaaaga gttggtagct cttgatccgg caaacaaacc accgctggta    780
gcggtggttt ttttgtttgc aagcagcaga ttacgcgcag aaaaaaagga tctcaagaag    840
atcctttgat cttttctacg ggtctgacg ctcagtggaa cgaaaactca cgttaaggga    900
ttttggtcat gacattaacc tataaaaata ggcgtatcac gaggcccttt cgtctcgcgc    960
gtttcggtga tgacggtgaa aacctctgac acatgcagct cccggagacg gtcacagctt   1020
```

```
gtctgtaagc ggatgccggg agcagacaag cccgtcaggg cgcgtcagcg ggtgttggcg    1080
ggtgtcgggg ctggcttaac tatgcggcat cagagcagat tgtactgaga gtgcaccata    1140
tggacatatt gtcgttagaa cgcggctaca attaatacat aaccttatgt atcatacaca    1200
tacgatttag gtgacactat agaacggcgc gccaagcttg gatccgtcga cggcgcgccc    1260
gatcatccgg atatagttcc tcctttcagc aaaaaccccc tcaagacccg tttagaggcc    1320
ccaaggggtt atgctagtta ttgctcagcg gtggcagcag ccaactcagc ttcctttcgg    1380
gctttgttag cagccggatc gatccaagct gtacctcact attcctttgc cctcggacga    1440
gtgctggggc gtcggtttcc actatcggcg agtacttcta cacagccatc ggtccagacg    1500
gccgcgcttc tgcgggcgat ttgtgtacgc ccgacagtcc cggctccgga tcggacgatt    1560
gcgtcgcatc gaccctgcgc ccaagctgca tcatcgaaat tgccgtcaac caagctctga    1620
tagagttggt caagaccaat gcggagcata tacgcccgga gccgcggcga tcctgcaagc    1680
tccggatgcc tccgctcgaa gtagcgcgtc tgctgctcca tacaagccaa ccacggcctc    1740
cagaagaaga tgttggcgac ctcgtattgg gaatccccga acatcgcctc gctccagtca    1800
atgaccgctg ttatgcggcc attgtccgtc aggacattgt tggagccgaa atccgcgtgc    1860
acgaggtgcc ggacttcggg gcagtcctcg gcccaaagca tcagctcatc gagagcctgc    1920
gcgacggacg cactgacggt gtcgtccatc acagtttgcc agtgatacac atggggatca    1980
gcaatcgcgc atatgaaatc acgccatgta gtgtattgac cgattccttg cggtccgaat    2040
gggccgaacc cgctcgtctg gctaagatcg gccgcagcga tcgcatccat agcctccgcg    2100
accggctgca gaacagcggg cagttcggtt tcaggcaggt cttgcaacgt gacaccctgt    2160
gcacggcggg agatgcaata ggtcaggctc tcgctgaatt ccccaatgtc aagcacttcc    2220
ggaatcggga gcgcggccga tgcaaagtgc cgataaacat aacgatcttt gtagaaacca    2280
tcggcgcagc tatttacccg caggacatat ccacgccctc ctacatcgaa gctgaaagca    2340
cgagattctt cgccctccga gagctgcatc aggtcggaga cgctgtcgaa cttttcgatc    2400
agaaacttct cgacagacgt cgcggtgagt tcaggctttt ccatgggtat atctccttct    2460
taaagttaaa caaaattatt tctagaggga aaccgttgtg gtctccctat agtgagtcgt    2520
attaatttcg cgggatcgag atcgatccaa ttccaatccc acaaaaatct gagcttaaca    2580
gcacagttgc tcctctcaga gcagaatcgg gtattcaaca ccctcatatc aactactacg    2640
ttgtgtataa cggtccacat gccggtatat acgatgactg gggttgtaca aaggcggcaa    2700
caaacggcgt tccggagtt gcacacaaga aatttgccac tattacagag gcaagagcag    2760
cagctgacgc gtacacaaca agtcagcaaa cagacaggtt gaacttcatc cccaaaggag    2820
aagctcaact caagcccaag agctttgcta aggccctaac aagcccacca agcaaaaag    2880 cccactggct cacgctagga accaaaaggc ccagcagtga tccagcccca aaagagatct    2940
cctttgcccc ggagattaca atggacgatt tcctctatct ttacgatcta ggaaggaagt    3000
tcgaaggtga aggtgacgac actatgttca ccactgataa tgagaaggtt agcctcttca    3060
atttcagaaa gaatgctgac ccacagatgg ttagagaggc ctacgcagca ggtctcatca    3120
agacgatcta cccgagtaac aatctccagg agatcaaata ccttcccaag aaggttaaag    3180
atgcagtcaa aagattcagg actaattgca tcaagaacac agagaaagac atatttctca    3240
agatcagaag tactattcca gtatggacga ttcaaggctt gcttcataaa ccaaggcaag    3300
taatagagat tggagtctct aaaaaggtag ttcctactga atctaaggcc atgcatggag    3360
```

| | |
|---|---|
| tctaagattc aaatcgagga tctaacagaa ctcgccgtga agactggcga acagttcata | 3420 |
| cagagtcttt tacgactcaa tgacaagaag aaaatcttcg tcaacatggt ggagcacgac | 3480 |
| actctggtct actccaaaaa tgtcaaagat acagtctcag aagaccaaag ggctattgag | 3540 |
| acttttcaac aaaggataat ttcgggaaac ctcctcggat tccattgccc agctatctgt | 3600 |
| cacttcatcg aaaggacagt agaaaaggaa ggtggctcct acaaatgcca tcattgcgat | 3660 |
| aaaggaaagg ctatcattca agatgcctct gccgacagtg gtcccaaaga tggaccccca | 3720 |
| cccacgagga gcatcgtgga aaaagaagac gttccaacca cgtcttcaaa gcaagtggat | 3780 |
| tgatgtgaca ctccactga cgtaagggat gacgcacaat cccactatcc ttcgcaagac | 3840 |
| ccttcctcta tataaggaag ttcatttcat ttggagagga cacgctcgag ctcatttctc | 3900 |
| tattacttca gccataacaa aagaactctt ttctcttctt attaaaccat gaaaaagcct | 3960 |
| gaactcaccg cgacgtctgt cgagaagttt ctgatcgaaa agttcgacag cgtctccgac | 4020 |
| ctgatgcagc tctcggaggg cgaagaatct cgtgctttca gcttcgatgt aggagggcgt | 4080 |
| ggatatgtcc tgcgggtaaa tagctgcgcc gatggtttct acaaagatcg ttatgtttat | 4140 |
| cggcactttg catcggccgc gctcccgatt ccggaagtgc ttgacattgg ggaattcagc | 4200 |
| gagagcctga cctattgcat ctcccgccgt gcacagggtg tcacgttgca agacctgcct | 4260 |
| gaaaccgaac tgcccgctgt tctgcagccg gtcgcggagg ccatggatgc gatcgctgcg | 4320 |
| gccgatctta ccagacgag cgggttcggc ccattcggac cgcaaggaat cggtcaatac | 4380 |
| actacatggc gtgatttcat atgcgcgatt gctgatcccc atgtgtatca ctggcaaact | 4440 |
| gtgatggacg acaccgtcag tgcgtccgtc gcgcaggctc tcgatgagct gatgctttgg | 4500 |
| gccgaggact gccccgaagt ccggcacctc gtgcacgcgg atttcggctc caacaatgtc | 4560 |
| ctgacgaca atggccgcat aacagcggtc attgactgga gcgaggcgat gttcggggat | 4620 |
| tcccaatacg aggtcgccaa catcttcttc tggaggccgt ggttggcttg tatggagcag | 4680 |
| cagacgcgct acttcgagcg gaggcatccg gagcttgcag atcgccgcg gctccgggcg | 4740 |
| tatatgctcc gcattggtct tgaccaactc tatcagagct tggttgacgg caatttcgat | 4800 |
| gatgcagctt gggcgcaggg tcgatgcgac gcaatcgtcc gatccggagc cgggactgtc | 4860 |
| gggcgtacac aaatcgcccg cagaagcgcg gccgtctgga ccgatggctg tgtagaagta | 4920 |
| ctcgccgata gtggaaaccg acgccccagc actcgtccga gggcaaagga atagtgaggt | 4980 |
| acctaaagaa ggagtgcgtc gaagcagatc gttcaaacat ttggcaataa agtttcttaa | 5040 |
| gattgaatcc tgttgccggt cttgcgatga ttatcatata atttctgttg aattacgtta | 5100 |
| agcatgtaat aattaacatg taatgcatga cgttatttat gagatgggtt tttatgatta | 5160 |
| gagtcccgca attatacatt taatacgcga tagaaaacaa aatatagcgc gcaaactagg | 5220 |
| ataaattatc gcgcgcggtg tcatctatgt tactagatcg atgtcga | 5267 |

<210> SEQ ID NO 47
<211> LENGTH: 1264
<212> TYPE: DNA
<213> ORGANISM: Arabidopsis thaliana

<400> SEQUENCE: 47

| | |
|---|---|
| aacactttgt cttttaccac ttcttcgata cttcccaagt tcaccgcaat ggccaccgct | 60 |
| tcaatcttcc ccgccgccgt gaccgtcacc agagatgtga catctcttct taatccatct | 120 |
| tctctgataa tcggaaaatc attatctcct tcaaagttca gctcaatcaa atcctccgtt | 180 |
| tcatttttccc gcaaaaccct aactccaatt cgatactctt catctcccgc cgatcactca | 240 |

```
cccgccaccg ccgtggaagc gatcacgaat cgatccaaaa cctccttgaa atctcgtctc      300
cgtggaggag aaactctcta cggtctcttt ttactctcct tctcgccgac attagccgag      360
atcgctgctc acgccggtta cgattacgtc gtcgttgata tggaacatgg tcccggaggt      420
ataccggaag ctttggattg tattcgagct cttaacgccg ccggaacatc agccattctc      480
cgattaccgg aaaactcacc aacctgggct aaaaagctc tagatctagg tccacaagga       540
atcatgttcc caatgatcga atctcgtaaa gacgctacca agcggtgtc gtattgccgg       600 tttcctcccg acggtatccg tggatcggcg cacacggtgg tgagagcttc taactacgga      660
atcgatgaag ggtatttaag taattacgca gaggagattc tgattatgtg ccaggtggaa      720
tcaggtgaag gagtgaagaa agctgatgaa atcgcagccg ttgatggtgt tgactgtgtg      780
caaatgggac cgttggatct tagtgcgagt ttagggtatt tgtgggatcc tggacataag      840
aaagtgagag agatgatgaa gaaggctgag aaatctgtgc tgaccactga tccggcgaaa      900 ggcgggctt acttgtcggg tttcgcgatg ccgcacgacg gagctggtga gattcgggga       960
cgtggttacc atatggtcgc cggagctgtt gatgttggat tgtttaggaa tgctgctgtt     1020
gaagatgtga ggagattcaa gatgggttg gtcaatgaat cggacagtga ggattcgtcg      1080
gaacatgata agatgttga tgatgagaag tactggagcg aataagcaaa atttcaaatt      1140
tcgttaatgt tgtttccttt taactttcca taaagattta caaatcatg atgccacaaa      1200 tgtttcaaaa acgaaagcaa catgaatcca acaaagctga gacatttggc tttgtttttt     1260
ttgg                                                                  1264

<210> SEQ ID NO 48
<211> LENGTH: 1077
<212> TYPE: DNA
<213> ORGANISM: Arabidopsis thaliana

<400> SEQUENCE: 48
atggccaccg cttcaatctt ccccgccgcc gtgaccgtca ccagagatgt gacatctctt       60
cttaatccat cttctctgat aatcggaaaa tcattatctc cttcaaagtt cagctcaatc      120
aaatcctccg tttcattttc ccgcaaaacc ctaactccaa ttcgatactc ttcatctccc      180
gccgatcact cacccgccac cgccgtggaa gcgatcacga atcgatccaa aacctccttg      240
aaatctcgtc tccgtggagg agaaactctc tacggtctct tttactctc cttctcgccg      300 acattagccg agatcgctgc tcacgccggt tacgattacg tcgtcgttga tatggaacat      360
ggtcccggag gtataccgga agctttggat tgtattcgag ctcttaacgc cgccggaaca      420
tcagccattc tccgattacc ggaaaactca ccaacctggg ctaaaaaagc tctagatcta     480
ggtccacaag gaatcatgtt cccaatgatc gaatctcgta agacgctac caagcggtg      540 tcgtattgcc ggtttcctcc cgacggtatc cgtggatcgg cgcacacggt ggtgagagct      600
tctaactacg gaatcgatga agggtattta agtaattacg cagaggagat tctgattatg      660
tgccaggtgg aatcaggtga aggagtgaag aaagctgatg aaatcgcagc cgttgatggt      720
gttgactgtg tgcaaatggg accgttggat cttagtgcga gtttagggta tttgtgggat      780
cctggacata gaaagtgag agagatgatg aagaaggctg aaatctgt gctgaccact       840 gatccggcga aaggcgggc ttacttgtcg ggtttcgcga tgccgcacga cggagctggt      900
gagattcggg gacgtggtta ccatatggtc gccggagctg ttgatgttgg attgtttagg      960
aatgctgctg ttgaagatgt gaggagattc aagatgggtt tggtcaatga atcggacagt     1020
```
gaggattcgt cggaacatga taaagatgtt gatgatgaga agtactggag cgaataa    1077

<210> SEQ ID NO 49
<211> LENGTH: 358
<212> TYPE: PRT
<213> ORGANISM: Arabidopsis thaliana

<400> SEQUENCE: 49

```
Met Ala Thr Ala Ser Ile Phe Pro Ala Ala Val Thr Val Thr Arg Asp
1               5                   10                  15

Val Thr Ser Leu Leu Asn Pro Ser Ser Leu Ile Ile Gly Lys Ser Leu
            20                  25                  30

Ser Pro Ser Lys Phe Ser Ser Ile Lys Ser Ser Val Ser Phe Ser Arg
        35                  40                  45

Lys Thr Leu Thr Pro Ile Arg Tyr Ser Ser Ser Pro Ala Asp His Ser
    50                  55                  60

Pro Ala Thr Ala Val Glu Ala Ile Thr Asn Arg Ser Lys Thr Ser Leu
65                  70                  75                  80

Lys Ser Arg Leu Arg Gly Gly Glu Thr Leu Tyr Gly Leu Phe Leu Leu
                85                  90                  95

Ser Phe Ser Pro Thr Leu Ala Glu Ile Ala Ala His Ala Gly Tyr Asp
            100                 105                 110

Tyr Val Val Asp Met Glu His Gly Pro Gly Gly Ile Pro Glu Ala
        115                 120                 125

Leu Asp Cys Ile Arg Ala Leu Asn Ala Ala Gly Thr Ser Ala Ile Leu
    130                 135                 140

Arg Leu Pro Glu Asn Ser Pro Thr Trp Ala Lys Lys Ala Leu Asp Leu
145                 150                 155                 160

Gly Pro Gln Gly Ile Met Phe Pro Met Ile Glu Ser Arg Lys Asp Ala
                165                 170                 175

Thr Lys Ala Val Ser Tyr Cys Arg Phe Pro Pro Asp Gly Ile Arg Gly
            180                 185                 190

Ser Ala His Thr Val Val Arg Ala Ser Asn Tyr Gly Ile Asp Glu Gly
        195                 200                 205

Tyr Leu Ser Asn Tyr Ala Glu Glu Ile Leu Ile Met Cys Gln Val Glu
    210                 215                 220

Ser Gly Glu Gly Val Lys Lys Ala Asp Glu Ile Ala Ala Val Asp Gly
225                 230                 235                 240

Val Asp Cys Val Gln Met Gly Pro Leu Asp Leu Ser Ala Ser Leu Gly
                245                 250                 255

Tyr Leu Trp Asp Pro Gly His Lys Lys Val Arg Glu Met Met Lys Lys
            260                 265                 270

Ala Glu Lys Ser Val Leu Thr Thr Asp Pro Ala Lys Gly Gly Ala Tyr
        275                 280                 285

Leu Ser Gly Phe Ala Met Pro His Asp Gly Ala Gly Glu Ile Arg Gly
    290                 295                 300

Arg Gly Tyr His Met Val Ala Gly Ala Val Asp Val Gly Leu Phe Arg
305                 310                 315                 320

Asn Ala Ala Val Glu Asp Val Arg Arg Phe Lys Met Gly Leu Val Asn
                325                 330                 335

Glu Ser Asp Ser Glu Asp Ser Ser Glu His Asp Lys Asp Val Asp Asp
            340                 345                 350

Glu Lys Tyr Trp Ser Glu
        355
```

<210> SEQ ID NO 50
<211> LENGTH: 3665
<212> TYPE: DNA
<213> ORGANISM: artificial sequence
<220> FEATURE:
<223> OTHER INFORMATION: pENTR-At4g10750 -plasmid

<400> SEQUENCE: 50

```
aactttgtac aaaaaagcag gctccgcggc cgccccttc accatggcca ccgcttcaat      60
cttcccccgcc gccgtgaccg tcaccagaga tgtgacatct cttcttaatc catcttctct    120
gatcatcgga aaatcattat ctccttcaaa gttcagctca atcaaatcct ccgtttcatt    180
ttcccgcaaa accctaactc caattcgata ctcttcatct cccgccgatc actcacccgc    240
caccgccgtg aagcgatca cgaatcgatc caaaaactcc ttgaaatctc gtctccgtgg    300
aggagaaact ctctacggtc tcttttttact ctccttctcg ccgacattag ccgagatcgc    360
tgctcacgcc ggttacgatt acgtcgtcgt tgatatggaa catggtcccg gaggtatacc    420
ggaagctttg gattgtattc gagctcttaa cgccgccgga acatcagcca ttctccgatt    480
accggaaaac tcaccaacct gggctaaaaa agctctagat ctaggtccac aaggaatcat    540
gttcccaatg atcgaatctc gtaaagacgc taccaaagcg tgtcgtatt gccggtttcc    600
tcccgacggt atccgtggat cggcgcacac ggtggtgaga gcttctaact acggaatcga    660
tgaagggtat ttaagtaatt acgcagagga gattctgatt atgtgccagg tggaatcagg    720
tgaaggagtg aagaaagctg atgaaatcgc agccgttgat ggtgttgact gtgtgcaaat    780
gggaccgttg gatcttagtg cgagtttagg gtatttgtgg gatcctggac ataagaaagt    840
gagagagatg atgaagaagg ctgagaaatc tgtgctgagc actgatccgg cgaaaggcgg    900
ggcttacttg tcgggtttcg cgatgccgca cgatggagct ggtgagattc ggggacgtgg    960
ttaccatatg gtcgccggag ctgttgatgt tggattgttt aggaatgctg ctgttgaaga   1020
tgtgaggaga ttcaagatgg gtttggtcaa tgaatcggac agtgaggatt cgtcggaaca   1080
tgataaagat gttgatgatg agaagtactg gagcgaataa gcggccgcaa gggtgggcgc   1140
gccgacccag ctttcttgta caaagttggc attataagaa agcattgctt atcaatttgt   1200
tgcaacgaac aggtcactat cagtcaaaat aaaatcatta tttgccatcc agctgatatc   1260
ccctatagtg agtcgtatta catggtcata gctgtttcct ggcagctctg gcccgtgtct   1320
caaaatctct gatgttacat tgcacaagat aaaaatatat catcatgaac aataaaactg   1380
tctgcttaca taaacagtaa tacaaggggg ttatgagcc atattcaacg ggaaacgtcg   1440
aggccgcgat taaattccaa catggatgct gatttatatg ggtataaatg gctcgcgat   1500
aatgtcgggc aatcaggtgc gacaatctat cgcttgtatg ggaagcccga tgcgccagag   1560
ttgtttctga acatggcaa aggtagcgtt gccaatgatg ttacagatga gatggtcaga   1620
ctaaactggc tgacggaatt tatgcctctt ccgaccatca agcattttat ccgtactcct   1680
gatgatgcat ggttactcac cactgcgatc cccggaaaaa cagcattcca ggtattagaa   1740
gaatatcctg attcaggtga aatattgtt gatgcgctgg cagtgttcct gcgccggttg   1800
cattcgattc ctgttttgtaa ttgtccttttt aacagcgatc gcgtatttcg tctcgctcag   1860
gcgcaatcac gaatgaataa cggtttggtt gatgcgagtg attttgatga cgagcgtaat   1920
ggctggcctg ttgaacaagt ctggaaagaa atgcataaac ttttgccatt ctcaccggat   1980
tcagtcgtca ctcatggtga tttctcactt gataaccta ttttttgacga ggggaaatta   2040
ataggttgta ttgatgttgg acgagtcgga atcgcagacc gataccagga tcttgccatc   2100
```

| | |
|---|---:|
| ctatggaact gcctcggtga gttttctcct tcattacaga aacggctttt tcaaaaatat | 2160 |
| ggtattgata atcctgatat gaataaattg cagtttcatt tgatgctcga tgagttttc | 2220 |
| taatcagaat tggttaattg gttgtaacac tggcagagca ttacgctgac ttgacgggac | 2280 |
| ggcgcaagct catgaccaaa atcccttaac gtgagttacg cgtcgttcca ctgagcgtca | 2340 |
| gaccccgtag aaaagatcaa aggatcttct tgagatcctt ttttctgcg cgtaatctgc | 2400 |
| tgcttgcaaa caaaaaaacc accgctacca gcggtggttt gtttgccgga tcaagagcta | 2460 |
| ccaactcttt ttccgaaggt aactggcttc agcagagcgc agataccaaa tactgtcctt | 2520 |
| ctagtgtagc cgtagttagg ccaccacttc aagaactctg tagcaccgcc tacatacctc | 2580 |
| gctctgctaa tcctgttacc agtggctgct gccagtggcg ataagtcgtg tcttaccggg | 2640 |
| ttggactcaa gacgatagtt accggataag gcgcagcggt cgggctgaac ggggggttcg | 2700 |
| tgcacacagc ccagcttgga gcgaacgacc tacaccgaac tgagatacct acagcgtgag | 2760 |
| cattgagaaa gcgccacgct tcccgaaggg agaaaggcgg acaggtatcc ggtaagcggc | 2820 |
| agggtcggaa caggagagcg cacgagggag cttccagggg gaaacgcctg gtatctttat | 2880 |
| agtcctgtcg ggtttcgcca cctctgactt gagcgtcgat ttttgtgatg ctcgtcaggg | 2940 |
| gggcggagcc tatggaaaaa cgccagcaac gcggccttt tacggttcct ggccttttgc | 3000 |
| tggccttttg ctcacatgtt ctttcctgcg ttatccctg attctgtgga taaccgtatt | 3060 |
| accgcctttg agtgagctga taccgctcgc cgcagccgaa cgaccgagcg cagcgagtca | 3120 |
| gtgagcgagg aagcggaaga cgccaata cgcaaaccgc ctctccccgc gcgttggccg | 3180 |
| attcattaat gcagctggca cgacaggttt cccgactgga aagcgggcag tgagcgcaac | 3240 |
| gcaattaata cgcgtaccgc tagccaggaa gagtttgtag aaacgcaaaa aggccatccg | 3300 |
| tcaggatggc cttctgctta gtttgatgcc tggcagttta tggcgggcgt cctgcccgcc | 3360 |
| accctccggg ccgttgcttc acaacgttca aatccgctcc cggcggattt gtcctactca | 3420 |
| ggagagcgtt caccgacaaa caacagataa aacgaaaggc ccagtcttcc gactgagcct | 3480 |
| ttcgttttat ttgatgcctg gcagttccct actctcgcgt taacgctagc atggatgttt | 3540 |
| tcccagtcac gacgttgtaa aacgacggcc agtcttaagc tcgggcccca aataatgatt | 3600 |
| ttattttgac tgatagtgac ctgttcgttg caacaaattg atgagcaatg ctttttata | 3660 |
| atgcc | 3665 |

<210> SEQ ID NO 51
<211> LENGTH: 15956
<212> TYPE: DNA
<213> ORGANISM: artificial sequence
<220> FEATURE:
<223> OTHER INFORMATION: pKR1478-At4g10750-plasmid

<400> SEQUENCE: 51

| | |
|---|---:|
| acccagcttt cttgtacaaa gtggtgatgg ccgcatttcg caccaaatca atgaaagtaa | 60 |
| taatgaaaag tctgaataag aatacttagg cttagatgcc tttgttactt gtgtaaaata | 120 |
| acttgagtca tgtacctttg gcggaaacag aataaataaa aggtgaaatt ccaatgctct | 180 |
| atgtataagt tagtaatact taatgtgttc tacggttgtt tcaatatcat caaactctaa | 240 |
| ttgaaacttt agaaccacaa atctcaatct tttcttaatg aaatgaaaaa tcttaattgt | 300 |
| accatgtttta tgttaaacac cttacaattg gttggagagg aggaccaacc gatgggacaa | 360 |
| cattgggaga aagagattca atggagattt ggataggaga acaacattct ttttcacttc | 420 |

```
aatacaagat gagtgcaaca ctaaggatat gtatgagact ttcagaagct acgacaacat    480
agatgagtga ggtggtgatt cctagcaaga aagacattag aggaagccaa aatcgaacaa    540
ggaagacatc aagggcaaga gacaggacca tccatctcag gaaaaggagc tttgggatag    600
tccgagaagt tgtacaagaa attttttgga gggtgagtga tgcattgctg gtgactttaa    660
ctcaatcaaa attgagaaag aaagaaaagg gaggggctc acatgtgaat agaagggaaa    720
cgggagaatt ttacagtttt gatctaatgg gcatcccagc tagtggtaac atattcacca    780
tgtttaacct tcacgtacgt ctagaggatc cgtcgacggc gcgccagatc ctctagagtc    840
gacctgcagg catgcaagct tggcgtaatc atggtcatag ctgtttcctg tgtgaaattg    900
ttatccgctc acaattccac acaacatacg agccggaagc ataaagtgta aagcctgggg    960
tgcctaatga gtgagctaac tcacattaat tgcgttgcgc tcactgcccg ctttccagtc   1020
gggaaacctg tcgtgccagc tgcattaatg aatcggccaa cgcgcgggga gaggcggttt   1080
gcgtattgga tcgatccctg aaagcgacgt tggatgttaa catctacaaa ttgccttttc   1140
ttatcgacca tgtacgtaag cgcttacgtt tttggtggac ccttgaggaa actggtagct   1200
gttgtgggcc tgtggtctca agatggatca ttaatttcca ccttcaccta cgatgggggg   1260
catcgcaccg gtgagtaata ttgtacggct aagagcgaat ttggcctgta gacctcaatt   1320
gcgagctttc taatttcaaa ctattcgggc ctaacttttg gtgtgatgat gctgactggc   1380
aggatatata ccgttgtaat ttgagctcgt gtgaataagt cgctgtgtat gtttgtttga   1440
ttgtttctgt tggagtgcag cccatttcac cggacaagtc ggctagattg atttagccct   1500
gatgaactgc cgaggggaag ccatcttgag cgcggaatgg gaatggattt cgttgtacaa   1560
cgagacgaca gaacacccac gggaccgagc ttcgcgagct tttgtatccg tggcatcctt   1620
ggtccgggcg atttgttcac gtccatgagg cgctctccaa aggaacgcat attttccggt   1680
gcaacctttc cggttcttcc tctactcgac ctcttgaagt cccagcatga atgttcgacc   1740
gctccgcaag cggatctttg gcgcaaccag ccggtttcgc acgtcgattc tcgcgagcct   1800
gcatactttg caagattgc tgaatgacgc tgatgcttca tcgcaatctg cgataatggg   1860
gtaagtatcc ggtgaaggcc gcaggtcagg ccgcctgagc actcagtgtc ttggatgtcc   1920
agttccacgg cagctgttgc tcaagcctgc tgatcggagc gtccgcaagg tcggcgcgga   1980
cgtcggcaag ccaggcctgc ggatcgatgt tattgagctt ggcgtcatg atcagtgtcg   2040
ccatgaacgc cgcacgttca gcacaacgat ccgatccggc aaacagccat gacttcctgc   2100
cgagtacata gcctctgagc gttcgttcgg cagcattgtt cgtcaggcaa atcgggccgt   2160
catcgaggaa tgacgtaatg ccatcccatc gcttgagcat gtaatttatc gcctcggcga   2220
cgggagaact gcgcgacaat ttcccccgct cggtttcgag ccaatcatgc agctcttcgg   2280
cgagtgacct tgatcaggcc accgccacga ccgcggaaga cgaacagatg cctgcgcatc   2340
ggatcgcgct tcagcgtctc ttgcaccatc agcgacaaac cgggaaagcc tttgcgcatg   2400
tccgtactta tgtcgccact tgggagggct tcgtctacgt ggccttcgtg atcgacgtct   2460
tcgcccgtcg cattgtcgga tggcgggcga gccggacagc acatgcaggc tttgtcctcg   2520
atgccctcga ggaggctcat catgatcggc gtcccgctca tggcggccta gtgcatcact   2580
cggatcgcgg tgttcaatac gtgtcctttc gctattccga gcggttggca gaagcaggta   2640
tcgagccatc tatcggaagc gtcggcgaca gcacgacaac gccctcgcag aagcgatcaa   2700
cggtctttac aaggccgagg tcattcatcg gcgtggacca tggaggagct tcgaagcggt   2760
cgagttcgct accttggaat ggatagactg gttcaaccac ggcggctttt gaagcccatc   2820
```

```
ggcaatatac cgccagccga agacgaggat cagtattacg ccatgctgga cgaagcagcc    2880
atggctgcgc attttaacga aatggcctcc ggcaaacccg gtgcggttca cttgttgcgt    2940
gggaaagttc acgggactcc gcgcacgagc cttcttcgta atagccatat cgaccgaatt    3000
gacctgcagg ggggggggg aaagccacgt tgtgtctcaa aatctctgat gttacattgc    3060
acaagataaa aatatatcat catgaacaat aaaactgtct gcttacataa acagtaatac    3120
aaggggtgtt atgagccata ttcaacggga aacgtcttgc tcgaggccgc gattaaattc    3180
caacatggat gctgatttat atgggtataa atgggctcgc gataatgtcg ggcaatcagg    3240
tgcgacaatc tatcgattgt atgggaagcc cgatgcgcca gagttgtttc tgaaacatgg    3300
caaaggtagc gttgccaatg atgttacaga tgagatggtc agactaaact ggctgacgga    3360
atttatgcct cttccgacca tcaagcattt tatccgtact cctgatgatg catggttact    3420
caccactgcg atccccggga aaacagcatt ccaggtatta agaatatc ctgattcagg    3480 tgaaaatatt gttgatgcgc tggcagtgtt cctgcgccgg ttgcattcga ttcctgtttg    3540
taattgtcct tttaacagcg atcgcgtatt tcgtctcgct caggcgcaat cacgaatgaa    3600
taacggtttg gttgatgcga gtgattttga tgacgagcgt aatggctggc ctgttgaaca    3660
agtctggaaa gaaatgcata agcttttgcc attctcaccg gattcagtcg tcactcatgg    3720
tgatttctca cttgataacc ttatttttga cgaggggaaa ttaataggtt gtattgatgt    3780
tggacgagtc ggaatcgcag accgatacca ggatcttgcc atcctatgga actgcctcgg    3840
tgagttttct ccttcattac agaaacggct ttttcaaaaa tatggtattg ataatcctga    3900
tatgaataaa ttgcagtttc atttgatgct cgatgagttt ttctaatcag aattggttaa    3960
ttggttgtaa cactggcaga gcattacgct gacttgacgg gacggcggct ttgttgaata    4020
aatcgaactt tgctgagtt gaaggatcag atcacgcatc ttcccgacaa cgcagaccgt    4080
tccgtggcaa agcaaaagtt caaaatcacc aactggtcca cctacaacaa agctctcatc    4140
aaccgtggct ccctcacttt ctggctggat gatggggcga ttcaggcctg gtatgagtca    4200
gcaacaccct tcttcacgagg cagacctcag cgcccccccc ccctgcagg tcttttccaa    4260 tgatgagcac ttttaaagtt ctgctatgtg gcgcggtatt atcccgtgtt gacgccgggc    4320
aagagcaact cggtcgccgc atacactatt ctcagaatga cttggttgag tactcaccag    4380
tcacagaaaa gcatcttacg gatggcatga cagtaagaga attatgcagt gctgccataa    4440
ccatgagtga taacactgcg gccaacttac ttctgacaac gatcggagga ccgaaggagc    4500
taaccgcttt tttgcacaac atgggggatc atgtaactcg ccttgatcgt tgggaaccgg    4560
agctgaatga agccatacca aacgacgagc gtgacaccac gatgcctgta gcaatggcaa    4620
caacgttgcg caaactatta actggcgaac tacttactct agcttcccgg caacaattaa    4680
tagactggat ggaggcggat aaagttgcag gaccacttct gcgctcggcc cttccggctg    4740
gctggtttat tgctgataaa tctggagccg gtgagcgtgg gtctcgcggt atcattgcag    4800
cactggggcc agatggtaag ccctcccgta tcgtagttat ctacacgacg gggagtcagg    4860
caactatgga tgaacgaaat agacagatcg ctgagatagg tgcctcactg attaagcatt    4920
ggtaactgtc agaccaagtt tactcatata ctttagat tgatttaaaa cttcattttt    4980
aatttaaaag gatctaggtg aagatccttt ttgataatct catgaccaaa atcccttaac    5040
gtgagttttc gttccactga gcgtcagacc ccgtagaaaa gatcaaagga tcttcttgag    5100
atcctttttt tctgcgcgta atctgctgct tgcaaacaaa aaaaccaccg ctaccagcgg    5160
```

```
tggtttgttt gccggatcaa gagctaccaa ctcttttcc gaaggtaact ggcttcagca      5220
gagcgcagat accaaatact gtccttctag tgtagccgta gttaggccac cacttcaaga      5280
actctgtagc accgcctaca tacctcgctc tgctaatcct gttaccagtg gctgctgcca      5340
gtggcgataa gtcgtgtctt accgggttgg actcaagacg atagttaccg gataaggcgc      5400
agcggtcggg ctgaacgggg ggttcgtgca cacagcccag cttggagcga acgacctaca      5460
ccgaactgag atacctacag cgtgagctat gagaaagcgc cacgcttccc gaagggagaa      5520
aggcggacag gtatccggta agcggcaggg tcggaacagg agagcgcacg agggagcttc      5580
cagggggaaa cgcctggtat ctttatagtc ctgtcgggtt tcgccacctc tgacttgagc      5640
gtcgattttt gtgatgctcg tcagggggc ggagcctatg gaaaaacgcc agcaacgcgg       5700 ccttttacg gttcctggcc ttttgctggc cttttgctca catgttcttt cctgcgttat        5760
cccctgattc tgtggataac cgtattaccg cctttgagtg agctgatacc gctcgccgca      5820
gccgaacgac cgagcgcagc gagtcagtga gcgaggaagc ggaagagcgc ctgatgcggt      5880
attttctcct tacgcatctg tgcggtattt cacaccgcat atggtgcact ctcagtacaa      5940
tctgctctga tgccgcatag ttaagccagt atacactccg ctatcgctac gtgactgggt      6000
catggctgcg ccccgacacc cgccaacacc cgctgacgcg ccctgacggg cttgtctgct      6060
cccggcatcc gcttacagac aagctgtgac cgtctccggg agctgcatgt gtcagaggtt      6120
ttcaccgtca tcaccgaaac gcgcgaggca gggtgccttg atgtgggcgc cggcggtcga      6180
gtggcgacgg cgcggcttgt ccgcgccctg gtagattgcc tggccgtagg ccagccattt      6240 ttgagcggc agcggccgcg ataggccgac gcgaagcggc gggcgtagg gagcgcagcg       6300 accgaagggt aggcgctttt tgcagctctt cggctgtgcg ctggccagac agttatgcac      6360
aggccaggcg ggttttaaga gttttaataa gttttaaaga gttttaggcg gaaaaatcgc      6420
cttttttctc ttttatatca gtcacttaca tgtgtgaccg gttcccaatg tacggctttg       6480
ggttcccaat gtacgggttc cggttcccaa tgtacggctt tgggttccca atgtacgtgc      6540
tatccacagg aaagagacct ttcgacctt ttccctgc tagggcaatt tgccctagca        6600
tctgctccgt acattaggaa ccggcggatg cttcgccctc gatcaggttg cggtagcgca      6660
tgactaggat cgggccagcc tgccccgcct cctccttcaa atcgtactcc ggcaggtcat      6720
ttgacccgat cagcttgcgc acggtgaaac agaacttctt gaactctccg gcgctgccac      6780
tgcgttcgta gatcgtcttg aacaaccatc tggcttctgc cttgcctgcg gcgcggcgtg      6840
ccaggcggta gagaaaacgg ccgatgccgg gatcgatcaa aaagtaatcg gggtgaaccg      6900
tcagcacgtc cgggttcttg ccttctgtga tctcgcggta catccaatca gctagctcga      6960
tctcgatgta ctccggccgc ccggtttcgc tctttacgat cttgtagcgg ctaatcaagg      7020
cttcaccctc ggataccgtc accaggcggc cgttcttggc cttcttcgta cgctgcatgg      7080
caacgtgcgt ggtgtttaac cgaatgcagg tttctaccag gtcgtctttc tgctttccgc      7140
catcggctcg ccggcagaac ttgagtacgt ccgcaacgtg tggacggaac acgcggccgg      7200
gcttgtctcc cttcccttcc cggtatcggt tcatggattc ggttagatgg gaaccgcca       7260 tcagtaccag gtcgtaatcc cacacactgg ccatgccggc cggccctgcg gaaacctcta      7320
cgtgcccgtc tggaagctcg tagcggatca cctcgccagc tcgtcggtca cgcttcgaca      7380
gacggaaaac ggccacgtcc atgatgctgc gactatcgcg ggtgcccacg tcatagagca      7440
tcggaacgaa aaaatctggt tgctcgtcgc ccttgggcgg cttcctaatc gacgcgcac       7500 cggctgccgg cggttgccgg gattctttgc ggattcgatc agcggccgct tgccacgatt      7560
```

```
caccggggcg tgcttctgcc tcgatgcgtt gccgctgggc ggcctgcgcg gccttcaact    7620
tctccaccag gtcatcaccc agcgccgcgc cgatttgtac cgggccggat ggtttgcgac    7680
cgctcacgcc gattcctcgg gcttgggggt tccagtgcca ttgcagggcc ggcagacaac    7740
ccagccgctt acgcctggcc aaccgcccgt tcctccacac atggggcatt ccacggcgtc    7800
ggtgcctggt tgttcttgat tttccatgcc gcctccttta gccgctaaaa ttcatctact    7860
catttattca tttgctcatt tactctggta gctgcgcgat gtattcagat agcagctcgg    7920
taatggtctt gccttggcgt accgcgtaca tcttcagctt ggtgtgatcc tccgccggca    7980
actgaaagtt gacccgcttc atggctgcgc gtgtctgccag gctggccaac gttgcagcct    8040
tgctgctgcg tgcgctcgga cggccggcac ttagcgtgtt tgtgcttttg ctcattttct    8100
ctttacctca ttaactcaaa tgagttttga tttaatttca gcggccagcg cctgacctc     8160 gcgggcagcg tcgccctcgg gttctgattc aagaacggtt gtgccggcgg cggcagtgcc    8220
tgggtagctc acgcgctgcg tgatacggga ctcaagaatg ggcagctcgt acccggccag    8280
cgcctcggca acctcaccgc cgatgcgcgt gcctttgatc gcccgcgaca cgacaaaggc    8340
cgcttgtagc cttccatccg tgacctcaat gcgctgctta accagctcca ccaggtcggc    8400
ggtggcccat atgtcgtaag ggcttggctg caccggaatc agcacgaagt cggctgcctt    8460
gatcgcggac acagccaagt ccgccgcctg gggcgctccg tcgatcacta cgaagtcgcg    8520
ccggccgatg gccttcacgt cgcggtcaat cgtcgggcgg tcgatgccga caacggttag    8580
cggttgatct tcccgcacgg ccgcccaatc gcgggcactg ccctggggat cggaatcgac    8640
taacagaaca tcggccccgg cgagttgcag ggcgcgggct agatgggttg cgatggtcgt    8700
cttgcctgac ccgccttctct ggttaagtac agcgataact tcatgcgttc ccttgcgtat   8760
ttgtttattt actcatcgca tcatatacgc agcgaccgca tgacgcaagc tgttttactc    8820
aaatacacat cacctttta gacggcggcg ctcggtttct tcagcggcca agctggccgg     8880
ccaggccgcc agcttggcat cagacaaacc ggccaggatt tcatgcagcc gcacggttga    8940
gacgtgcgcg ggcggctcga acacgtaccc ggccgcgatc atctccgcct cgatctcttc    9000
ggtaatgaaa aacggttcgt cctggccgtc ctggtgcggt ttcatgcttg ttcctcttgg    9060
cgttcattct cggcggccgc cagggcgtcg gcctcggtca atgcgtcctc acggaaggca    9120
ccgcgccgcc tggcctcggt gggcgtcact tcctcgctgc gctcaagtgc gcggtacagg    9180
gtcgagcgat gcacgccaag cagtgcagcc gcctctttca cggtgcggcc ttcctggtcg    9240
atcagctcgc gggcgtgcgc gatctgtgcc ggggtgaggg tagggcgggg gccaaacttc    9300
acgcctcggg ccttggcggc ctcgcgcccg ctccgggtgc ggtcgatgat tagggaacgc    9360
tcgaactcgg caatgccggc gaacacggtc aacaccatgc ggccgccgg cgtggtggtg     9420 tcggcccacg gctctgccag gctacgcagg cccgcgccgg cctcctggat gcgctcggca    9480
atgtccagta ggtcgcgggt gctgcgggcc aggcggtcta gcctggtcac tgtcacaacg    9540
tcgccagggc gtaggtggtc aagcatcctg gccagctccg ggcggtcgcg cctggtgccg    9600
gtgatcttct cggaaaacag cttggtgcag ccggccgcgt gcagttcggc ccgttggttg    9660
gtcaagtcct ggtcgtcggt gctgacgcgg gcatagccca gcaggccagc ggcggcgctc    9720
ttgttcatgg cgtaatgtct ccggttctag tcgcaagtat tctactttat gcgactaaaa    9780
cacgcgacaa gaaacgcca ggaaaagggc agggcggcag cctgtcgcgt aacttaggac     9840
ttgtgcgaca tgtcgttttc agaagacggc tgcactgaac gtcagaagcc gactgcacta    9900
```

```
tagcagcgga ggggttggac cacaggacgg gtgtggtcgc catgatcgcg tagtcgatag    9960
tggctccaag tagcgaagcg agcaggactg ggcggcggcc aaagcggtcg gacagtgctc   10020
cgagaacggg tgcgcataga aattgcatca acgcatatag cgctagcagc acgccatagt   10080
gactggcgat gctgtcggaa tggacgatat cccgcaagag gcccggcagt accggcataa   10140
ccaagcctat gcctacagca tccagggtga cggtgccgag gatgacgatg agcgcattgt   10200
tagatttcat acacggtgcc tgactgcgtt agcaatttaa ctgtgataaa ctaccgcatt   10260
aaagctagct tgcttggtcg ttccgcgtga acgtcggctc gattgtacct gcgttcaaat   10320
actttgcgat cgtgttgcgc gcctgccggt gcgtcggct gatctcacgg atcgactgct    10380
tctctcgcaa cgccatccga cggatgatgt ttaaaagtcc catgtggatc actccgttgc   10440
cccgtcgctc accgtgttgg ggggaaggtg cacatggctc agttctcaat ggaaattatc   10500
tgcctaaccg gctcagttct gcgtagaaac caacatgcaa gctccaccgg gtgcaaagcg   10560
gcagcggcgg caggatatat tcaattgtaa atggcttcat gtccgggaaa tctacatgga   10620
tcagcaatga gtatgatggt caatatggag aaaagaaag agtaattacc aatttttttt    10680
caattcaaaa atgtagatgt ccgcagcgtt attataaaat gaaagtacat tttgataaaa   10740
cgacaaatta cgatccgtcg tatttatagg cgaaagcaat aaacaaatta ttctaattcg   10800
gaaatcttta tttcgacgtg tctacattca cgtccaaatg ggggcttaga tgagaaactt   10860
cacgatcgat gccttgattt cgccattccc agatacccat ttcatcttca gattggtctg   10920
agattatgcg aaaatataca ctcatataca taaatactga cagtttgagc taccaattca   10980
gtgtagccca ttacctcaca taattcactc aaatgctagg cagtctgtca actcggcgtc   11040
aatttgtcgg ccactatacg atagttgcgc aaattttcaa agtcctggcc taacatcaca   11100
cctctgtcgg cggcgggtcc catttgtgat aaatccacca tatcgaatta attcagactc   11160
ctttgcccca gagatcacaa tggacgactt cctctatctc tacgatctag tcaggaagtt   11220
cgacggagaa ggtgacgata ccatgttcac cactgataat gagaagatta gccttttcaa   11280
tttcagaaag aatgctaacc cacagatggt tagagaggct tacgcagcag gtctcatcaa   11340
gacgatctac ccgagcaata atctccagga gatcaaatac cttcccaaga aggttaaaga   11400
tgcagtcaaa agattcagga ctaactgcat caagaacaca gagaaagata tatttctcaa   11460
gatcagaagt actattccag tatggacgat tcaaggcttg cttcacaaac caaggcaagt   11520
aatagagatt ggagtctcta aaaaggtagt tcccactgaa tcaaaggcca tggagtcaaa   11580
gattcaaata gaggacctaa cagaactcgc cgtaaagact ggcgaacagt tcatacagag   11640
tctcttacga ctcaatgaca agaagaaaat cttcgtcaac atggtggagc acgacacgct   11700
tgtctactcc aaaaatatca agatacagt ctcagaagac caagggcaa ttgagacttt     11760
tcaacaaagg gtaatatccg gaaacctcct cggattccat tgcccagcta tctgtcactt   11820
tattgtgaag atagtggaaa aggaaggtgg ctcctacaaa tgccatcatt gcgataaagg   11880
aaaggccatc gttgaagatg cctctgccga cagtggtccc aaagatggac ccccacccac   11940
gaggagcatc gtggaaaaag aagacgttcc aaccacgtct tcaaagcaag tggattgatg   12000
tgatatctcc actgacgtaa gggatgacgc acaatcccac tatccttcgc aagacccttc   12060
ctctatataa ggaagttcat ttcatttgga gaggacacgc tgaaatcacc agtctccaag   12120
cttgcgggga tcgtttcgca tgattgaaca agatggattg cacgcaggtt ctccggccgc   12180
ttgggtggag aggctattcg gctatgactg ggcacaacag acaatcggct gctctgatgc   12240
cgccgtgttc cggctgtcag cgcaggggcg cccggttctt tttgtcaaga ccgacctgtc   12300
```

```
cggtgccctg aatgaactgc aggacgaggc agcgcggcta tcgtggctgg ccacgacggg   12360
cgttccttgc gcagctgtgc tcgacgttgt cactgaagcg ggaagggact ggctgctatt   12420
gggcgaagtg ccggggcagg atctcctgtc atctcacctt gctcctgccg agaaagtatc   12480
catcatggct gatgcaatgc ggcggctgca tacgcttgat ccggctacct gcccattcga   12540
ccaccaagcg aaacatcgca tcgagcgagc acgtactcgg atggaagccg gtcttgtcga   12600
tcaggatgat ctggacgaag agcatcaggg gctcgcgcca gccgaactgt tcgccaggct   12660
caaggcgcgc atgcccgacg gcgaggatct cgtcgtgacc catggcgatg cctgcttgcc   12720
gaatatcatg gtgaaaatg gccgcttttc tggattcatc gactgtggcc ggctgggtgt    12780
ggcggaccgc tatcaggaca tagcgttggc tacccgtgat attgctgaag agcttggcgg   12840
cgaatgggct gaccgcttcc tcgtgcttta cggtatcgcc gctcccgatt cgcagcgcat   12900
cgccttctat cgccttcttg acgagttctt ctgagcggga ctctggggtt cgaaatgacc   12960
gaccaagcga cgcccaacct gccatcacga gatttcgatt ccaccgccgc cttctatgaa   13020
aggttgggct tcggaatcgt tttccgggac gccggctgga tgatcctcca gcgcgggat    13080 ctcatgctgg agttcttcgc ccaccccgga tcgatccaac acttacgttt gcaacgtcca   13140
agagcaaata gaccacgaac gccggaaggt tgccgcagcg tgtggattgc gtctcaattc   13200
tctcttgcag gaatgcaatg atgaatatga tactgactat gaaactttga gggaatactg   13260
cctagcaccg tcacctcata acgtgcatca tgcatgccct gacaacatgg aacatcgcta   13320
tttttctgaa gaattatgct cgttggagga tgtcgcggca attgcagcta ttgccaacat   13380
cgaactaccc ctcacgcatg cattcatcaa tattattcat gcggggaaag gcaagattaa   13440
tccaactggc aaatcatcca gcgtgattgg taacttcagt tccagcgact tgattcgttt   13500
tggtgctacc cacgttttca ataaggacga gatggtggag taaagaagga gtgcgtcgaa   13560
gcagatcgtt caaacatttg gcaataaagt ttcttaagat tgaatcctgt tgccggtctt   13620
gcgatgatta tcatataatt tctgttgaat tacgttaagc atgtaataat taacatgtaa   13680
tgcatgacgt tatttatgag atgggttttt atgattagag tcccgcaatt atacatttaa   13740
tacgcgatag aaaacaaaat atagcgcgca aactaggata aattatcgcg cgcggtgtca   13800
tctatgttac tagatcgatc aaacttcggt actgtgtaat gacgatgagc aatcgagagg   13860
ctgactaaca aaaggtacat cgcgatggat cgatccattc gccattcagg ctgcgcaact   13920
gttgggaagg gcgatcggtg cgggcctctt cgctattacg ccagctggcg aaagggggat   13980
gtgctgcaag gcgattaagt tgggtaacgc cagggttttc ccagtcacga cgttgtaaaa   14040
cgacggccag tgaattcctg cagcccgggg gatccgccca ctcgaggcgc gccaagcttg   14100
catgcctgca ggctagccta agtacgtact caaaatgcca acaaataaaa aaaagttgc    14160 tttaataatg ccaaaacaaa ttaataaaac acttacaaca ccggattttt tttaattaaa   14220
atgtgccatt taggataaat agttaatatt tttaataatt atttaaaaag ccgtatctac   14280
taaaatgatt tttatttggt tgaaaatatt aatatgttta aatcaacaca atctatcaaa   14340
attaaactaa aaaaaaaata agtgtacgtg gttaacatta gtacagtaat ataagaggaa   14400
aatgagaaat taagaaattg aaagcgagtc taattttaa attatgaacc tgcatatata   14460
aaaggaaaga aagaatccag gaagaaaaga aatgaaacca tgcatggtcc cctcgtcatc   14520
acgagtttct gccatttgca atagaaacac tgaaacacct ttctctttgt cacttaattg   14580
agatgccgaa gccacctcac accatgaact tcatgaggtg tagcacccaa ggcttccata   14640
```

| | |
|---|---|
| gccatgcata ctgaagaatg tctcaagctc agcaccctac ttctgtgacg tgtccctcat | 14700 |
| tcaccttcct ctcttcccta taaataacca cgcctcaggt tctccgcttc acaactcaaa | 14760 |
| cattctctcc attggtcctt aaacactcat cagtcatcac cgcggccatc acaagtttgt | 14820 |
| acaaaaaagc aggctccgcg gccgcccccct tcaccatggc caccgcttca atcttccccg | 14880 |
| ccgccgtgac cgtcaccaga gatgtgacat ctcttcttaa tccatcttct ctgatcatcg | 14940 |
| gaaaatcatt atctccttca aagttcagct caatcaaatc ctccgtttca ttttcccgca | 15000 |
| aaaccctaac tccaattcga tactcttcat ctcccgccga tcactcaccc gccaccgccg | 15060 |
| tggaagcgat cacgaatcga tccaaaaact ccttgaaatc tcgtctccgt ggaggagaaa | 15120 |
| ctctctacgg tctcttttta ctctccttct cgccgacatt agccgagatc gctgctcacg | 15180 |
| ccggttacga ttacgtcgtc gttgatatgg aacatggtcc cggaggtata ccggaagctt | 15240 |
| tggattgtat tcgagctctt aacgccgccg gaacatcagc cattctccga ttaccggaaa | 15300 |
| actcaccaac ctgggctaaa aaagctctag atctaggtcc acaaggaatc atgttcccaa | 15360 |
| tgatcgaatc tcgtaaagac gctaccaaag cggtgtcgta ttgccggttt cctcccgacg | 15420 |
| gtatccgtgg atcggcgcac acggtggtga gagcttctaa ctacggaatc gatgaagggt | 15480 |
| atttaagtaa ttacgcagag gagattctga ttatgtgcca ggtggaatca ggtgaaggag | 15540 |
| tgaagaaagc tgatgaaatc gcagccgttg atggtgttga ctgtgtgcaa atgggaccgt | 15600 |
| tggatcttag tgcgagttta gggtatttgt gggatcctgg acataagaaa gtgagagaga | 15660 |
| tgatgaagaa ggctgagaaa tctgtgctga gcactgatcc ggcgaaaggc ggggcttact | 15720 |
| tgtcgggttt cgcgatgccg cacgatgagc tggtgagat tcgggacgt ggttaccata | 15780 |
| tggtcgccgg agctgttgat gttggattgt ttaggaatgc tgctgttgaa gatgtgagga | 15840 |
| gattcaagat gggtttggtc aatgaatcgg acagtgagga ttcgtcggaa catgataaag | 15900 |
| atgttgatga tgagaagtac tggagcgaat aagcggccgc aagggtgggc gcgccg | 15956 |

<210> SEQ ID NO 52
<211> LENGTH: 1077
<212> TYPE: DNA
<213> ORGANISM: Arabidopsis thaliana

<400> SEQUENCE: 52

| | |
|---|---|
| atggccaccg cttcaatctt ccccgccgcc gtgaccgtca ccagagatgt gacatctctt | 60 |
| cttaatccat cttctctgat catcggaaaa tcattatctc cttcaaagtt cagctcaatc | 120 |
| aaatcctccg tttcattttc ccgcaaaacc ctaactccaa ttcgatactc ttcatctccc | 180 |
| gccgatcact caccgccac cgccgtggaa gcgatcacga atcgatccaa aaactccttg | 240 |
| aaatctcgtc tccgtggagg agaaactctc tacggtctct ttttactctc cttctcgccg | 300 |
| acattagccg agatcgctgc tcacgccggt tacgattacg tcgtcgttga tatggaacat | 360 |
| ggtcccggag gtataccgga agctttggat tgtattcgag ctcttaacgc cgccggaaca | 420 |
| tcagccattc tccgattacc ggaaaactca ccaacctggg ctaaaaaagc tctagatcta | 480 |
| ggtccacaag gaatcatgtt cccaatgatc gaatctcgta agacgctac caaagcggtg | 540 |
| tcgtattgcc ggtttcctcc cgacggtatc cgtggatcgg cgcacacggt ggtgagagct | 600 |
| tctaactacg gaatcgatga agggtattta agtaattacg cagaggagat tctgattatg | 660 |
| tgccaggtgg aatcaggtga aggagtgaag aaagctgatg aaatcgcagc cgttgatggt | 720 |
| gttgactgtg tgcaaatggg accgttggat cttagtgcga gtttagggta tttgtgggat | 780 |
| cctggacata agaaagtgag agagatgatg aagaaggctg agaaatctgt gctgagcact | 840 |

```
gatccggcga aaggcggggc ttacttgtcg ggtttcgcga tgccgcacga tggagctggt    900
gagattcggg gacgtggtta ccatatggtc gccggagctg ttgatgttgg attgtttagg    960
aatgctgctg ttgaagatgt gaggagattc aagatgggtt tggtcaatga atcggacagt   1020
gaggattcgt cggaacatga taaagatgtt gatgatgaga agtactggag cgaataa     1077
```

<210> SEQ ID NO 53
<211> LENGTH: 358
<212> TYPE: PRT
<213> ORGANISM: Arabidopsis thaliana

<400> SEQUENCE: 53

```
Met Ala Thr Ala Ser Ile Phe Pro Ala Ala Val Thr Val Thr Arg Asp
1               5                   10                  15

Val Thr Ser Leu Leu Asn Pro Ser Ser Leu Ile Ile Gly Lys Ser Leu
            20                  25                  30

Ser Pro Ser Lys Phe Ser Ser Ile Lys Ser Ser Val Ser Phe Ser Arg
        35                  40                  45

Lys Thr Leu Thr Pro Ile Arg Tyr Ser Ser Ser Pro Ala Asp His Ser
    50                  55                  60

Pro Ala Thr Ala Val Glu Ala Ile Thr Asn Arg Ser Lys Asn Ser Leu
65                  70                  75                  80

Lys Ser Arg Leu Arg Gly Gly Glu Thr Leu Tyr Gly Leu Phe Leu Leu
                85                  90                  95

Ser Phe Ser Pro Thr Leu Ala Glu Ile Ala Ala His Ala Gly Tyr Asp
            100                 105                 110

Tyr Val Val Val Asp Met Glu His Gly Pro Gly Gly Ile Pro Glu Ala
        115                 120                 125

Leu Asp Cys Ile Arg Ala Leu Asn Ala Ala Gly Thr Ser Ala Ile Leu
    130                 135                 140

Arg Leu Pro Glu Asn Ser Pro Thr Trp Ala Lys Lys Ala Leu Asp Leu
145                 150                 155                 160

Gly Pro Gln Gly Ile Met Phe Pro Met Ile Glu Ser Arg Lys Asp Ala
                165                 170                 175

Thr Lys Ala Val Ser Tyr Cys Arg Phe Pro Pro Asp Gly Ile Arg Gly
            180                 185                 190

Ser Ala His Thr Val Val Arg Ala Ser Asn Tyr Gly Ile Asp Glu Gly
        195                 200                 205

Tyr Leu Ser Asn Tyr Ala Glu Glu Ile Leu Ile Met Cys Gln Val Glu
    210                 215                 220

Ser Gly Glu Gly Val Lys Lys Ala Asp Glu Ile Ala Ala Val Asp Gly
225                 230                 235                 240

Val Asp Cys Val Gln Met Gly Pro Leu Asp Leu Ser Ala Ser Leu Gly
                245                 250                 255

Tyr Leu Trp Asp Pro Gly His Lys Lys Val Arg Glu Met Met Lys Lys
            260                 265                 270

Ala Glu Lys Ser Val Leu Ser Thr Asp Pro Ala Lys Gly Gly Ala Tyr
        275                 280                 285

Leu Ser Gly Phe Ala Met Pro His Asp Gly Ala Gly Glu Ile Arg Gly
    290                 295                 300

Arg Gly Tyr His Met Val Ala Gly Ala Val Asp Val Gly Leu Phe Arg
305                 310                 315                 320

Asn Ala Ala Val Glu Asp Val Arg Arg Phe Lys Met Gly Leu Val Asn
                325                 330                 335
```

Glu Ser Asp Ser Glu Asp Ser Glu His Asp Lys Asp Val Asp Asp
            340                 345                 350

Glu Lys Tyr Trp Ser Glu
        355

<210> SEQ ID NO 54
<211> LENGTH: 16853
<212> TYPE: DNA
<213> ORGANISM: artificial sequence
<220> FEATURE:
<223> OTHER INFORMATION: pKR1482-At4g10750-plasmid

<400> SEQUENCE: 54

| | | | | | |
|---|---|---|---|---|---|
| ccgcggccgc | cccctcacc | atggccaccg | cttcaatctt | ccccgccgcc | gtgaccgtca | 60 |
| ccagagatgt | gacatctctt | cttaatccat | cttctctgat | catcggaaaa | tcattatctc | 120 |
| cttcaaagtt | cagctcaatc | aaatcctccg | tttcatttc | ccgcaaaacc | ctaactccaa | 180 |
| ttcgatactc | ttcatctccc | gccgatcact | caccgccac | cgccgtggaa | gcgatcacga | 240 |
| atcgatccaa | aaactccttg | aaatctcgtc | tccgtggagg | agaaactctc | tacggtctct | 300 |
| ttttactctc | cttctcgccg | acattagccg | agatcgctgc | tcacgccggt | tacgattacg | 360 |
| tcgtcgttga | tatggaacat | ggtcccggag | gtataccgga | agctttggat | tgtattcgag | 420 |
| ctcttaacgc | cgccggaaca | tcagccattc | tccgattacc | ggaaaactca | ccaacctggg | 480 |
| ctaaaaaagc | tctagatcta | ggtccacaag | gaatcatgtt | cccaatgatc | gaatctcgta | 540 |
| aagacgctac | caaagcggtg | tcgtattgcc | ggtttcctcc | cgacggtatc | cgtggatcgg | 600 |
| cgcacacggt | ggtgagagct | tctaactacg | gaatcgatga | agggtattta | agtaattacg | 660 |
| cagaggagat | tctgattatg | tgccaggtgg | aatcaggtga | aggagtgaag | aaagctgatg | 720 |
| aaatcgcagc | cgttgatggt | gttgactgtg | tgcaaatggg | accgttggat | cttagtgcga | 780 |
| gtttagggta | tttgtgggat | cctggacata | agaaagtgag | agagatgatg | aagaaggctg | 840 |
| agaaatctgt | gctgagcact | gatccggcga | aggcggggc | ttacttgtcg | ggtttcgcga | 900 |
| tgccgcacga | tggagctggt | gagattcggg | acgtggtta | ccatatggtc | gccggagctg | 960 |
| ttgatgttgg | attgtttagg | aatgctgctg | ttgaagatgt | gaggagattc | aagatgggtt | 1020 |
| tggtcaatga | atcggacagt | gaggattcgt | cggaacatga | taagatgtt | gatgatgaga | 1080 |
| agtactggag | cgaataagcg | gccgcaaggg | tgggcgcgcc | gacccagctt | tcttgtacaa | 1140 |
| agtggtctgc | gccatttcaa | accaaaatat | agtgatcagt | aataattata | ttgcaaagtt | 1200 |
| aaacgaaagg | gataaatata | tataaggc | aaaagacaca | caccaatatc | ataatcataa | 1260 |
| ccataatcat | tacttgattg | taagttgcaa | caaaaaagga | aaaataaca | tgcttggttg | 1320 |
| ttcacatgta | cgtaaataca | ttatatcatc | cctttacat | taaatgattg | taaacgtagg | 1380 |
| aaattcatgt | ttgaaaagtg | aaaatagcac | acgtacataa | atctcaagta | atctttgtaa | 1440 |
| gtaaaggctc | ataatataaa | gattacataa | ttgcatatgt | tccactacga | agccacaaac | 1500 |
| aatatgtatg | tttctttacg | taagcaggga | taaagttaag | ttgcgactat | gttatatgct | 1560 |
| gcaatcagca | taagatctgt | aaatggaact | gtgaatatat | aaactcacac | cactttgtac | 1620 |
| aagaaagctg | ggtcggcgcg | cccacccttg | cggccgctta | ttcgctccag | tacttctcat | 1680 |
| catcaacatc | tttatcatgt | tccgacgaat | cctcactgtc | cgattcattg | accaaaccca | 1740 |
| tcttgaatct | cctcacatct | tcaacagcag | cattcctaaa | caatccaaca | tcaacagctc | 1800 |
| cggcgaccat | atggtaacca | cgtccccgaa | tctcaccagc | tccatcgtgc | ggcatcgcga | 1860 |

```
aacccgacaa gtaagcccg cctttcgccg gatcagtgct cagcacagat ttctcagcct   1920
tcttcatcat ctctctcact ttcttatgtc caggatccca caaataccct aaactcgcac   1980
taagatccaa cggtcccatt tgcacacagt caacaccatc aacggctgcg atttcatcag   2040
ctttcttcac tccttcacct gattccacct ggcacataat cagaatctcc tctgcgtaat   2100
tacttaaata cccttcatcg attccgtagt tagaagctct caccaccgtg tgcgccgatc   2160
cacggatacc gtcgggagga aaccggcaat acgacaccgc tttggtagcg tctttacgag   2220
attcgatcat tgggaacatg attccttgtg gacctagatc tagagctttt ttagcccagg   2280
ttggtgagtt ttccggtaat cggagaatgg ctgatgttcc ggcggcgtta agagctcgaa   2340
tacaatccaa agcttccggt atacctccgg gaccatgttc catatcaacg acgacgtaat   2400
cgtaaccggc gtgagcagcg atctcggcta atgtcggcga aaggagagt aaaaagagac    2460
cgtagagagt ttctcctcca cggagacgag atttcaagga gttttggat cgattcgtga    2520
tcgcttccac ggcggtggcg ggtgagtgat cggcgggaga tgaagagtat cgaattggag   2580
ttagggtttt gcgggaaaat gaaacggagg atttgattga gctgaacttt gaaggagata   2640
atgattttcc gatgatcaga gaagatggat taagaagaga tgtcacatct ctggtgacgg   2700
tcacggcggc ggggaagatt gaagcggtgg ccatggtgaa gggggcggcc gcggagcctg   2760
ctttttgta caaacttgtg atgggcgtct agcgaactag aggatccccg ggtaccgagg   2820
tacgtctaga ggatccgtcg acggcgcgcc agatcctcta gagtcgacct gcaggcatgc   2880
aagcttggcg taatcatggt catagctgtt cctgtgtga aattgttatc cgctcacaat    2940
tccacacaac atacgagccg gaagcataaa gtgtaaagcc tggggtgcct aatgagtgag   3000
ctaactcaca ttaattgcgt tgcgctcact gcccgctttc cagtcgggaa acctgtcgtg   3060
ccagctgcat taatgaatcg gccaacgcgc ggggagaggc ggtttgcgta ttggatcgat   3120
ccctgaaagc gacgttggat gttaacatct acaaattgcc ttttcttatc gaccatgtac   3180
gtaagcgctt acgttttgg tggaccccttg aggaaactgg tagctgttgt gggcctgtgg   3240
tctcaagatg gatcattaat ttccaccttc acctacgatg gggggcatcg caccggtgag   3300
taatattgta cggctaagag cgaatttggc ctgtagacct caattgcgag cttctaatt    3360
tcaaactatt cgggcctaac ttttggtgtg atgatgctga ctggcaggat atataccgtt   3420
gtaatttgag ctcgtgtgaa taagtcgctg tgtatgtttg tttgattgtt tctgttggag   3480
tgcagcccat ttcaccggac aagtcggcta gattgattta gccctgatga actgccgagg   3540
ggaagccatc ttgagcgcgg aatgggaatg gatttcgttg tacaacgaga cgacagaaca   3600
cccacgggac cgagcttcgc gagcttttgt atccgtggca tccttggtcc gggcgatttg   3660
ttcacgtcca tgaggcgctc tccaaaggaa cgcatatttt ccggtgcaac ctttccggtt   3720
cttcctctac tcgacctctt gaagtcccag catgaatgtt cgaccgctcc gcaagcggat   3780
ctttggcgca accagccggt ttcgcacgtc gattctcgcg agcctgcata ctttggcaag   3840
attgctgaat gacgctgatg cttcatcgca atctgcgata atggggtaag tatccggtga   3900
aggccgcagg tcaggccgcc tgagcactca gtgtcttgga tgtccagttc cacggcagct   3960
gttgctcaag cctgctgatc ggagcgtccg caaggtcggc gcggacgtcg gcaagccagg   4020
cctgcggatc gatgttattg agcttggcgc tcatgatcag tgtcgccatg aacgccgcac   4080
gttcagcaca acgatccgat ccggcaaaca gccatgactt cctgccgagt acatagcctc   4140
tgagcgttcg ttcggcagca ttgttcgtca ggcaaatcgg gccgtcatcg aggaatgacg   4200
taatgccatc ccatcgcttg agcatgtaat ttatcgcctc ggcgacggga gaactgcgcg   4260
```

```
acaatttccc ccgctcggtt tcgagccaat catgcagctc ttcggcgagt gaccttgatc    4320
aggccaccgc cacgaccgcg gaagacgaac agatgcctgc gcatcggatc gcgcttcagc    4380
gtctcttgca ccatcagcga caaacccggga aagcctttgc gcatgtccgt acttatgtcg   4440
ccacttggga gggcttcgtc tacgtggcct tcgtgatcga cgtcttcgcc cgtcgcattg    4500
tcggatggcg ggcgagccgg acagcacatg caggctttgt cctcgatgcc ctcgaggagg    4560
ctcatcatga tcggcgtccc gctcatggcg gcctagtgca tcactcggat cgcggtgttc    4620
aatacgtgtc ctttcgctat tccgagcggt tggcagaagc aggtatcgag ccatctatcg    4680
gaagcgtcgg cgacagcacg acaacgccct cgcagaagcg atcaacggtc tttacaaggc    4740
cgaggtcatt catcggcgtg gaccatggag gagcttcgaa gcggtcgagt tcgctacctt    4800
ggaatggata gactggttca accacggcgg cttttgaagc ccatcggcaa tataccgcca    4860
gccgaagacg aggatcagta ttacgccatg ctggacgaag cagccatggc tgcgcatttt    4920
aacgaaatgg cctccggcaa acccgtgcg gttcacttgt tgcgtgggaa agttcacggg     4980
actccgcgca cgagccttct tcgtaatagc catatcgacc gaattgacct gcagggggg     5040
ggggaaagc cacgttgtgt ctcaaaatct ctgatgttac attgcacaag ataaaaatat     5100
atcatcatga acaataaaac tgtctgctta cataaacagt aatacaaggg gtgttatgag    5160
ccatattcaa cgggaaacgt cttgctcgag gccgcgatta aattccaaca tggatgctga    5220
tttatatggg tataaatggg ctcgcgataa tgtcgggcaa tcaggtgcga caatctatcg    5280
attgtatggg aagcccgatg cgccagagtt gtttctgaaa catggcaaag gtagcgttgc    5340
caatgatgtt acagatgaga tggtcagact aaactggctg acggaattta tgcctcttcc    5400
gaccatcaag cattttatcc gtactcctga tgatgcatgg ttactcacca ctgcgatccc    5460
cgggaaaaca gcattccagg tattagaaga atatcctgat tcaggtgaaa atattgttga    5520
tgcgctggca gtgttcctgc gccggttgca ttcgattcct gtttgtaatt gtccttttaa    5580
cagcgatcgc gtatttcgtc tcgctcaggc gcaatcacga atgaataacg gtttggttga    5640
tgcgagtgat tttgatgacg agcgtaatgg ctggcctgtt gaacaagtct ggaaagaaat    5700
gcataagctt ttgccattct caccggattc agtcgtcact catggtgatt tctcacttga    5760
taaccttatt tttgacgagg ggaaattaat aggttgtatt gatgttggac gagtcggaat    5820
cgcagaccga taccaggatc ttgccatcct atggaactgc ctcggtgagt tttctccttc    5880
attacagaaa cggctttttc aaaaatatgg tattgataat cctgatatga ataaattgca    5940
gtttcatttg atgctcgatg agtttttcta atcagaattg gttaattggt tgtaacactg    6000
gcagagcatt acgctgactt gacgggacgg cggctttgtt gaataaatcg aacttttgct    6060
gagttgaagg atcagatcac gcatcttccc gacaacgcag accgttccgt ggcaaagcaa    6120
aagttcaaaa tcaccaactg gtccacctac aacaaagctc tcatcaaccg tggctccctc    6180
actttctggc tggatgatgg ggcgattcag gcctggtatg agtcagcaac accttcttca    6240
cgaggcagac ctcagcgccc ccccccccct gcaggtcttt tccaatgatg agcacttttta   6300
aagttctgct atgtggcgcg gtattatccc gtgttgacgc cgggcaagag caactcggtc    6360
gccgcataca ctattctcag aatgacttgg ttgagtactc accagtcaca gaaaagcatc    6420
ttacggatgg catgacagta agagaattat gcagtgctgc cataaccatg agtgataaca    6480
ctgcggccaa cttacttctg acaacgatcg gaggaccgaa ggagctaacc gcttttttgc    6540
acaacatggg ggatcatgta actcgccttg atcgttggga accggagctg aatgaagcca    6600
```

```
taccaaacga cgagcgtgac accacgatgc ctgtagcaat ggcaacaacg ttgcgcaaac   6660
tattaactgg cgaactactt actctagctt cccggcaaca attaatagac tggatggagg   6720
cggataaagt tgcaggacca cttctgcgct cggcccttcc ggctggctgg tttattgctg   6780
ataaatctgg agccgtgag cgtgggtctc gcggtatcat tgcagcactg gggccagatg   6840
gtaagccctc ccgtatcgta gttatctaca cgacggggag tcaggcaact atggatgaac   6900
gaaatagaca gatcgctgag ataggtgcct cactgattaa gcattggtaa ctgtcagacc   6960
aagtttactc atatatactt tagattgatt taaaacttca ttttaatt aaaaggatct   7020
aggtgaagat cctttttgat aatctcatga ccaaaatccc ttaacgtgag ttttcgttcc   7080
actgagcgtc agacccgta gaaaagatca aggatcttc ttgagatcct ttttttctgc   7140
gcgtaatctg ctgcttgcaa acaaaaaaac caccgctacc agcggtggtt tgtttgccgg   7200
atcaagagct accaactctt tttccgaagg taactggctt cagcagagcg cagataccaa   7260
atactgtcct tctagtgtag ccgtagttag gccaccactt caagaactct gtagcaccgc   7320
ctacatacct cgctctgcta atcctgttac cagtggctgc tgccagtggc gataagtcgt   7380
gtcttaccgg gttggactca agacgatagt taccggataa ggcgcagcgg tcgggctgaa   7440
cggggggttc gtgcacacag cccagcttgg agcgaacgac ctacaccgaa ctgagatacc   7500
tacagcgtga gctatgagaa agcgccacgc ttcccgaagg gagaaaggcg gacaggtatc   7560
cggtaagcgg cagggtcgga acaggagagc gcacgaggga gcttccaggg ggaaacgcct   7620
ggtatcttta tagtcctgtc gggtttcgcc acctctgact tgagcgtcga ttttgtgat   7680
gctcgtcagg gggcggagc ctatggaaaa acgccagcaa gcggcctttt tacggttcc   7740
tggccttttg ctggccttt gctcacatgt tctttcctgc gttatcccct gattctgtgg   7800
ataaccgtat taccgccttt gagtgagctg ataccgctcg ccgcagccga acgaccgagc   7860
gcagcgagtc agtgagcgag gaagcggaag agcgcctgat gcggtatttt ctccttacgc   7920
atctgtgcgg tatttcacac cgcatatggt gcactctcag tacaatctgc tctgatgccg   7980
catagttaag ccagtataca ctccgctatc gctacgtgac tgggtcatgg ctgcgccccg   8040
acacccgcca cacccgctg acgcgccctg acgggcttgt ctgctcccgg catccgctta   8100
cagacaagct gtgaccgtct ccgggagctg catgtgtcag aggttttcac cgtcatcacc   8160
gaaacgcgcg aggcagggtg ccttgatgtg gcgccggcg tcgagtggc gacgcgcgg   8220
cttgtccgcg ccctggtaga ttgcctggcc gtaggccagc cattttttgag cggccagcgg   8280
ccgcgatagg ccgacgcgaa gcggcggggc gtagggagcg cagcgaccga agggtaggcg   8340
cttttttgcag ctcttcggct gtgcgctggc cagacagtta tgcacaggcc aggcgggttt   8400
taagagttt aataagtttt aaagagttt aggcggaaaa atcgccttt ttctctttta   8460
tatcagtcac ttacatgtgt gaccggttcc caatgtacgg ctttgggttc ccaatgtacg   8520
ggttccggtt cccaatgtac ggcttgggt cccaatgta cgtgctatcc acaggaaaga   8580
gacctttcg accttttcc cctgctaggg caatttgccc tagcatctgc tccgtacatt   8640
aggaaccggc ggatgcttcg ccctcgatca ggttgcggta gcgcatgact aggatcgggc   8700
cagcctgccc cgcctcctcc ttcaaatcgt actccggcag gtcatttgac ccgatcagct   8760
tgcgcacggt gaaacagaac ttcttgaact ctccggcgct gccactgcgt tcgtagatcg   8820
tcttgaacaa ccatctggct tctgccttgc ctgcggcgcg gcgtgccagg cggtagagaa   8880
aacgccgat gccgggatcg atcaaaaagt aatcggggtg aaccgtcagc acgtccgggt   8940
tcttgccttc tgtgatctcg cggtacatcc aatcagctag ctcgatctcg atgtactccg   9000
```

-continued

```
gccgcccggt tcgctctttt acgatcttgt agcggctaat caaggcttca ccctcggata    9060
ccgtcaccag gcggccgttc ttggccttct tcgtacgctg catggcaacg tgcgtggtgt    9120
ttaaccgaat gcaggtttct accaggtcgt ctttctgctt tccgccatcg gctcgccggc    9180
agaacttgag tacgtccgca acgtgtggac ggaacacgcg gccgggcttg tctcccttcc    9240
cttcccggta tcggttcatg gattcggtta gatgggaaac cgccatcagt accaggtcgt    9300
aatcccacac actggccatg ccggccggcc ctgcggaaac tctacgtgcc cgtctggaa    9360
gctcgtagcg gatcacctcg ccagctcgtc ggtcacgctt cgacagacgg aaaacggcca    9420
cgtccatgat gctgcgacta tcgcgggtgc ccacgtcata gagcatcgga acgaaaaaat    9480
ctggttgctc gtcgcccttg gcggcttcc taatcgacgg cgcaccggct gccggcggtt    9540
gccgggattc tttgcggatt cgatcagcgg ccgcttgcca cgattcaccg gggcgtgctt    9600
ctgcctcgat gcgttgccgc tgggcggcct gcgcggcctt caacttctcc accaggtcat    9660
cacccagcgc cgcgccgatt tgtaccgggc cggatggttt gcgaccgctc acgccgattc    9720
ctcgggcttg ggggttccag tgccattgca gggccggcag acaacccagc cgcttacgcc    9780
tggccaaccg cccgttcctc cacacatggg gcattccacg cgtcggtgc ctggttgttc    9840
ttgattttcc atgccgcctc ctttagccgc taaaattcat ctactcattt attcatttgc    9900
tcatttactc tggtagctgc gcgatgtatt cagatagcag ctcggtaatg gtcttgcctt    9960
ggcgtaccgc gtacatcttc agcttggtgt gatcctccgc cggcaactga aagttgaccc   10020
gcttcatggc tggcgtgtct gccaggctgg ccaacgttgc agccttgctg ctgcgtgcgc   10080
tcggacggcc ggcacttagc gtgtttgtgc ttttgctcat tttctcttta cctcattaac   10140
tcaaatgagt tttgatttaa tttcagcggc cagcgcctgg acctcgcggg cagcgtcgcc   10200
ctcgggttct gattcaagaa cggttgtgcc ggcggcggca gtgcctgggt agctcacgcg   10260
ctgcgtgata cgggactcaa gaatgggcag ctcgtacccg gccagcgcct cggcaacctc   10320
accgccgatg cgcgtgcctt tgatcgcccg cgacacgaca aaggccgctt gtagccttcc   10380
atccgtgacc tcaatgcgct gcttaaccag ctccaccagg tcggcggtgg cccatatgtc   10440
gtaagggctt ggctgcaccg gaatcagcac gaagtcggct gccttgatcg cggacacagc   10500
caagtccgcc gcctgggggcg ctccgtcgat cactacgaag tcgcgccggc cgatggcctt   10560
cacgtcgcgg tcaatcgtcg ggcggtcgat gccgacaacg gttagcggtt gatcttcccg   10620
cacggccgcc caatcgcggg cactgccctg gggatcggaa tcgactaaca gaacatcggc   10680
cccggcgagt tgcagggcgc gggctagatg ggttgcgatg tcgtcttgc ctgacccgcc   10740
tttctggtta agtacagcga taacttcatg cgttcccttg cgtatttgtt tatttactca   10800
tcgcatcata tacgcagcga ccgcatgacg caagctgttt tactcaaata cacatcacct   10860
ttttagacgg cggcgctcgg tttcttcagc ggccaagctg gccggccagg ccgccagctt   10920
ggcatcagac aaaccggcca ggatttcatg cagccgcacg gttgagacgt gcgcgggcgg   10980
ctcgaacacg tacccggccg cgatcatctc cgcctcgatc tcttcggtaa tgaaaaacgg   11040
ttcgtcctgg ccgtcctggt gcggtttcat gcttgttcct cttggcgttc attctcggcg   11100
gccgccaggg cgtcggcctc ggtcaatgcg tcctcacgga aggcaccgcg ccgcctggcc   11160
tcggtgggcg tcacttcctc gctgcgctca agtgcgcggt acagggtcga gcgatgcacg   11220
ccaagcagtg cagccgcctc tttcacggtg cggccttcct ggtcgatcag ctcgcgggcg   11280
tgcgcgatct gtgccggggt gagggtaggg cgggggccaa acttcacgcc tcgggccttg   11340
```

```
gcggcctcgc gcccgctccg ggtgcggtcg atgattaggg aacgctcgaa ctcggcaatg    11400
ccggcgaaca cggtcaacac catgcggccg gccggcgtgg tggtgtcggc ccacggctct    11460
gccaggctac gcaggcccgc gccggcctcc tggatgcgct cggcaatgtc cagtaggtcg    11520
cgggtgctgc gggccaggcg gtctagcctg gtcactgtca aacgtcgcc agggcgtagg     11580 tggtcaagca tcctggccag ctccgggcgg tcgcgcctgg tgccggtgat cttctcggaa    11640
aacagcttgg tgcagccggc cgcgtgcagt tcggcccgtt ggttggtcaa gtcctggtcg    11700
tcggtgctga cgcgggcata gcccagcagg ccagcggcgg cgctcttgtt catggcgtaa    11760
tgtctccggt tctagtcgca agtattctac tttatgcgac taaaacacgc gacaagaaaa    11820
cgccaggaaa agggcagggc ggcagcctgt cgcgtaactt aggacttgtg cgacatgtcg    11880
ttttcagaag acggctgcac tgaacgtcag aagccgactg cactatagca gcggaggggt    11940
tggaccacag gacgggtgtg gtcgccatga tcgcgtagtc gatagtggct ccaagtagcg    12000
aagcgagcag gactgggcgg cggccaaagc ggtcggacag tgctccgaga acgggtgcgc    12060
atagaaattg catcaacgca tatagcgcta gcagcacgcc atagtgactg gcgatgctgt    12120
cggaatggac gatatcccgc aagaggcccg gcagtaccgg cataaccaag cctatgccta    12180
cagcatccag ggtgacggtg ccgaggatga cgatgagcgc attgttagat tcatacacg     12240 gtgcctgact gcgttagcaa tttaactgtg ataaactacc gcattaaagc tagcttgctt    12300
ggtcgttccg cgtgaacgtc ggctcgattg tacctgcgtt caaatacttt gcgatcgtgt    12360
tgcgcgcctg cccggtgcgt cggctgatct cacggatcga ctgcttctct cgcaacgcca    12420
tccgacggat gatgtttaaa agtcccatgt ggatcactcc gttgcccgt cgctcaccgt     12480 gttgggggga aggtgcacat ggctcagttc tcaatggaaa ttatctgcct aaccggctca    12540
gttctgcgta gaaaccaaca tgcaagctcc accgggtgca aagcggcagc ggcggcagga    12600
tatattcaat tgtaaatggc ttcatgtccg ggaaatctac atggatcagc aatgagtatg    12660
atggtcaata tggagaaaaa gaaagagtaa ttaccaaattt tttttcaatt caaaaatgta    12720
gatgtccgca gcgttattat aaaatgaaag tacattttga taaaacgaca aattacgatc    12780
cgtcgtattt ataggcgaaa gcaataaaca aattattcta attcggaaat ctttatttcg    12840
acgtgtctac attcacgtcc aaatgggggc ttagatgaga aacttcacga tcgatgcctt    12900
gatttcgcca ttcccagata cccatttcat cttcagattg gtctgagatt atgcgaaaat    12960
atacactcat atacataaat actgacagtt tgagctacca attcagtgta gcccattacc    13020
tcacataatt cactcaaatg ctaggcagtc tgtcaactcg gcgtcaattt gtcggccact    13080
atacgatagt tgcgcaaatt ttcaaagtcc tggcctaaca tcacacctct gtcggcggcg    13140
ggtcccattt gtgataaatc caccatatcg aattaattca gactcctttg ccccagagat    13200
cacaatggac gacttcctct atctctacga tctagtcagg aagttcgacg gagaaggtga    13260
cgataccatg ttcaccactg ataatgagaa gattagcctt ttcaatttca gaaagaatgc    13320
taacccacag atggttagag aggcttacgc agcaggtctc atcaagacga tctacccgag    13380
caataatctc caggagatca atacccttcc caagaaggtt aaagatgcag tcaaaagatt    13440
caggactaac tgcatcaaga acacagagaa agatatattt ctcaagatca gaagtactat    13500
tccagtatgg acgattcaag gcttgcttca caaaccaagg caagtaatag agattggagt    13560
ctctaaaaag gtagttccca ctgaatcaaa ggccatggag tcaaagattc aaatagagga    13620
cctaacagaa ctcgccgtaa agactggcga acagttcata cagagtctct tacgactcaa    13680
tgacaagaag aaaaatcttcg tcaacatggt ggagcacgac acgcttgtct actccaaaaa    13740
```

```
tatcaaagat acagtctcag aagaccaaag ggcaattgag acttttcaac aaagggtaat    13800
atccggaaac ctcctcggat tccattgccc agctatctgt cactttattg tgaagatagt    13860
ggaaaaggaa ggtggctcct acaaatgcca tcattgcgat aaaggaaagg ccatcgttga    13920
agatgcctct gccgacagtg gtcccaaaga tggaccccca cccacgagga gcatcgtgga    13980
aaaagaagac gttccaacca cgtcttcaaa gcaagtggat tgatgtgata tctccactga    14040
cgtaagggat gacgcacaat cccactatcc ttcgcaagac ccttcctcta tataaggaag    14100
ttcatttcat ttggagagga cacgctgaaa tcaccagtct ccaagcttgc ggggatcgtt    14160
tcgcatgatt gaacaagatg gattgcacgc aggttctccg gccgcttggg tggagaggct    14220
attcggctat gactgggcac aacagacaat cggctgctct gatgccgccg tgttccggct    14280
gtcagcgcag gggcgcccgg ttcttttttgt caagaccgac ctgtccggtg ccctgaatga    14340
actgcaggac gaggcagcgc ggctatcgtg gctggccacg acgggcgttc cttgcgcagc    14400
tgtgctcgac gttgtcactg aagcgggaag ggactggctg ctattgggcg aagtgccggg    14460
gcaggatctc ctgtcatctc accttgctcc tgccgagaaa gtatccatca tggctgatgc    14520
aatgcggcgg ctgcatacgc ttgatccggc tacctgccca ttcgaccacc aagcgaaaca    14580
tcgcatcgag cgagcacgta ctcggatgga agccggtctt gtcgatcagg atgatctgga    14640
cgaagagcat caggggctcg cgccagccga actgttcgcc aggctcaagg cgcgcatgcc    14700
cgacggcgag gatctcgtcg tgacccatgg cgatgcctgc ttgccgaata tcatggtgga    14760
aaatggccgc ttttctggat tcatcgactg tggccggctg ggtgtggcgg accgctatca    14820
ggacatagcg ttggctaccc gtgatattgc tgaagagctt ggcggcgaat gggctgaccg    14880
cttcctcgtg ctttacggta tcgccgctcc cgattcgcag cgcatcgcct tctatcgcct    14940
tcttgacgag ttcttctgag cgggactctg gggttcgaaa tgaccgacca agcgacgccc    15000
aacctgccat cacgagattt cgattccacc gccgccttct atgaaaggtt gggcttcgga    15060
atcgttttcc gggacgccgg ctggatgatc ctccagcgcg ggatctcat gctggagttc    15120 ttcgcccacc ccggatcgat ccaacactta cgtttgcaac gtccaagagc aaatagacca    15180
cgaacgccgg aaggttgccg cagcgtgtgg attgcgtctc aattctctct tgcaggaatg    15240
caatgatgaa tatgatactg actatgaaac tttgagggaa tactgcctag caccgtcacc    15300
tcataacgtg catcatgcat gccctgacaa catggaacat cgctatttt ctgaagaatt    15360 atgctcgttg gaggatgtcg cggcaattgc agctattgcc aacatcgaac taccccctcac    15420 gcatgcattc atcaatatta ttcatgcggg gaaaggcaag attaatccaa ctggcaaatc    15480
atccagcgtg attggtaact tcagttccag cgacttgatt cgttttggtg ctacccacgt    15540
tttcaataag gacgagatgg tggagtaaag aaggagtgcg tcgaagcaga tcgttcaaac    15600
atttggcaat aaagtttctt aagattgaat cctgttgccg gtcttgcgat gattatcata    15660
taatttctgt tgaattacgt taagcatgta ataattaaca tgtaatgcat gacgttattt    15720
atgagatggg ttttatgat tagagtcccg caattataca tttaatacgc gatagaaaac    15780
aaaatatagc gcgcaaacta ggataaatta tcgcgcgcgg tgtcatctat gttactagat    15840
cgatcaaact tcggtactgt gtaatgacga tgagcaatcg agaggctgac taacaaaagg    15900
tacatcgcga tggatcgatc cattcgccat tcaggctgcg caactgttgg gaagggcgat    15960
cggtgcgggc ctcttcgcta ttacgccagc tggcgaaagg gggatgtgct gcaaggcgat    16020
taagttgggt aacgccaggg ttttcccagt cacgacgttg taaaacgacg ccagtgaatt    16080
```

| | | |
|---|---|---|
| tcctgcagcc cggggatcc gcccactcga ggcgcgccaa gcttgcatgc ctgcaggcta | 16140 |
| gcctaagtac gtactcaaaa tgccaacaaa taaaaaaaaa gttgctttaa taatgccaaa | 16200 |
| acaaattaat aaaacactta caacaccgga ttttttttaa ttaaaatgtg ccatttagga | 16260 |
| taaatagtta atattttaa taattattta aaaagccgta tctactaaaa tgattttat | 16320 |
| ttggttgaaa atattaatat gtttaaatca acacaatcta tcaaaattaa actaaaaaaa | 16380 |
| aaataagtgt acgtggttaa cattagtaca gtaatataag aggaaaatga gaaattaaga | 16440 |
| aattgaaagc gagtctaatt tttaaattat gaacctgcat atataaaagg aaagaaagaa | 16500 |
| tccaggaaga aaagaaatga aaccatgcat ggtcccctcg tcatcacgag tttctgccat | 16560 |
| ttgcaataga aacactgaaa cacctttctc tttgtcactt aattgagatg ccgaagccac | 16620 |
| ctcacaccat gaacttcatg aggtgtagca cccaaggctt ccatagccat gcatactgaa | 16680 |
| gaatgtctca agctcagcac cctacttctg tgacgtgtcc ctcattcacc ttcctctctt | 16740 |
| ccctataaat aaccacgcct caggttctcc gcttcacaac tcaaacattc tctccattgg | 16800 |
| tccttaaaca ctcatcagtc atcaccgcac aagtttgtac aaaaaagcag gct | 16853 |

<210> SEQ ID NO 55
<211> LENGTH: 13308
<212> TYPE: DNA
<213> ORGANISM: artificial sequence
<220> FEATURE:
<223> OTHER INFORMATION: KS387-plasmid

<400> SEQUENCE: 55

| | | |
|---|---|---|
| tcgacggcgc gcccgatcat ccggatatag ttcctccttt cagcaaaaaa cccctcaaga | 60 |
| cccgtttaga ggccccaagg ggttatgcta gttattgctc agcggtggca gcagccaact | 120 |
| cagcttcctt tcgggctttg ttagcagccg gatcgatcca agctgtacct cactattcct | 180 |
| ttgccctcgg acgagtgctg gggcgtcggt ttccactatc ggcgagtact tctacacagc | 240 |
| catcggtcca gacggccgcg cttctgcggg cgatttgtgt acgcccgaca gtcccggctc | 300 |
| cggatcggac gattgcgtcg catcgaccct gcgcccaagc tgcatcatcg aaattgccgt | 360 |
| caaccaagct ctgatagagt tggtcaagac caatgcggag catatacgcc cggagccgcg | 420 |
| gcgatcctgc aagctccgga tgcctccgct cgaagtagcg cgtctgctgc tccatacaag | 480 |
| ccaaccacgg cctccagaag aagatgttgg cgacctcgta ttgggaatcc ccgaacatcg | 540 |
| cctcgctcca gtcaatgacc gctgttatgc ggccattgtc cgtcaggaca ttgttggagc | 600 |
| cgaaatccgc gtgcacgagg tgccggactt cggggcagtc ctcggcccaa gcatcagct | 660 |
| catcgagagc ctgcgcgacg gacgcactga cggtgtcgtc catcacagtt tgccagtgat | 720 |
| acacatgggg atcagcaatc gcgcatatga aatcacgcca tgtagtgtat tgaccgattc | 780 |
| cttgcggtcc gaatgggccg aacccgctcg tctggctaag atcggccgca gcgatcgcat | 840 |
| ccatagcctc cgcgaccggc tgcagaacag cgggcagttc ggtttcaggc aggtcttgca | 900 |
| acgtgacacc ctgtgcacgg cgggagatgc aataggtcag gctctcgctg aattccccaa | 960 |
| tgtcaagcac ttccggaatc gggagcgcgg ccgatgcaaa gtgccgataa acataacgat | 1020 |
| ctttgtagaa accatcggcg cagctattta cccgcaggac atatccacgc cctcctacat | 1080 |
| cgaagctgaa agcacgagat cttcgccct ccgagagctg catcaggtcg agacgctgt | 1140 |
| cgaacttttc gatcagaaac ttctcgacag acgtcgcggt gagttcaggc ttttccatgg | 1200 |
| gtatatctcc ttcttaaagt taaacaaaat tatttctaga gggaaaccgt tgtggtctcc | 1260 |
| ctatagtgag tcgtattaat ttcgcgggat cgagatctga tcaacctgca ttaatgaatc | 1320 |

```
ggccaacgcg cggggagagg cggtttgcgt attgggcgct cttccgcttc ctcgctcact    1380
gactcgctgc gctcggtcgt tcggctgcgg cgagcggtat cagctcactc aaaggcggta    1440
atacggttat ccacagaatc agggggataac gcaggaaaga acatgtgagc aaaaggccag   1500
caaaaggcca ggaaccgtaa aaaggccgcg ttgctggcgt ttttccatag gctccgcccc    1560
cctgacgagc atcacaaaaa tcgacgctca agtcagaggt ggcgaaaccc gacaggacta    1620
taaagatacc aggcgtttcc ccctggaagc tccctcgtgc gctctcctgt tccgaccctg    1680
ccgcttaccg gatacctgtc cgcctttctc ccttcgggaa gcgtggcgct ttctcaatgc    1740
tcacgctgta ggtatctcag ttcggtgtag gtcgttcgct ccaagctggg ctgtgtgcac    1800
gaaccccccg ttcagcccga ccgctgcgcc ttatccggta actatcgtct tgagtccaac    1860
ccggtaagac acgacttatc gccactggca gcagccactg gtaacaggat tagcagagcg    1920
aggtatgtag gcggtgctac agagttcttg aagtggtggc ctaactacgg ctacactaga    1980
aggacagtat ttggtatctg cgctctgctg aagccagtta ccttcggaaa aagagttggt    2040
agctcttgat ccggcaaaca aaccaccgct ggtagcggtg gttttttgt ttgcaagcag    2100 cagattacgc gcagaaaaaa aggatctcaa gaagatcctt tgatcttttc tacgggtct    2160 gacgctcagt ggaacgaaaa ctcacgttaa gggattttgg tcatgacatt aacctataaa    2220
aataggcgta tcacgaggcc ctttcgtctc gcgcgtttcg gtgatgacgg tgaaaacctc    2280
tgacacatgc agctcccgga gacggtcaca gcttgtctgt aagcggatgc cgggagcaga    2340
caagcccgtc agggcgcgtc agcgggtgtt ggcgggtgtc ggggctggct taactatgcg    2400
gcatcagagc agattgtact gagagtgcac catatggaca tattgtcgtt agaacgcggc    2460
tacaattaat acataacctt atgtatcata cacatacgat ttaggtgaca ctatagaacg    2520
gcgcgccaag cttggatcct agaactagaa acgtgatgcc acttgttatt gaagtcgatt    2580
acagcatcta ttctgtttta ctatttataa ctttgccatt tctgactttt gaaaactatc    2640
tctggatttc ggtatcgctt tgtgaagatc gagcaaaaga gacgttttgt ggacgcaatg    2700
gtccaaatcc gttctacatg aacaaattgg tcacaatttc cactaaaagt aaataaatgg    2760
caagttaaaa aaggaatatg cattttactg attgcctagg tgagctccaa gagaagttga    2820
atctacacgt ctaccaaccg ctaaaaaaag aaaaacattg atatgtaacc tgattccatt    2880
agcttttgac ttcttcaaca gattctctac ttagatttct aacagaaata ttattactag    2940
cacatcattt tcagtctcac tacagcaaaa aatccaacgg cacaatacag acaacaggag    3000
atatcagact acagagatag atagatgcta ctgcatgtag taagttaaat aaaaggaaaa    3060
taaaatgtct tgctaccaaa actactacag actatgatgc tcaccacagg ccaaatcctg    3120
caactaggac agcattatct tatatatatt gtacaaaaca agcatcaagg aacatttggt    3180
ctaggcaatc agtacctcgt tctaccatca ccctcagtta tcacatcctt gaaggatcca    3240
ttactgggaa tcatcggcaa cacatgctcc tgatggggca caatgacatc aagaaggtag    3300
gggccagggg tgtccaacat tctctgaatt gccgctctaa gctcttcctt cttcgtcact    3360
cgcgctgccg gtatcccaca agcatcagca aacttgagca tgtttgggaa tatctcgctc    3420
tcgctagacg gatctccaag ataggtgtga gctctattgg acttgtagaa cctatcctcc    3480
aactgaacca ccatacccaa atgctgattg ttcaacaaca atatcttaac tgggagattc    3540
tccactctta tagtggccaa ctcctgaaca ttcatgatga aactaccatc cccatcaatg    3600
tcaaccacaa cagccccagg gttagcaaca gcagcaccaa tagccgcagg caatccaaaa    3660
```

```
cccatggctc caagacccccc tgaggtcaac cactgcctcg gtctcttgta cttgtaaaac    3720
tgcgcagccc acatttgatg ctgcccaacc ccagtactaa caatagcatc tccattagtc    3780
aactcatcaa gaacctcgat agcatgctgc ggagaaatcg cgtcctggaa tgtcttgtaa    3840
cccaatggaa acttgtgttt ctgcacatta atctcttctc tccaacctcc aagatcaaac    3900
ttaccctcca ctcctttctc ctccaaaatc atattaattc ccttcaaggc aacttcaaa    3960
tccgcgcaaa ccgacacgtg cgcctgcttg ttcttcccaa tctcggcaga atcaatatca    4020
atgtgaacaa tcttagccct actagcaaaa gcctcaagct tcccagtaac acggtcatca    4080
aaccttaccc caaaggcaag caacaaatca ctattgtcaa cagcatagtt agcataaaca    4140
gtaccatgca tacccagcat ctgaagggaa tattcatcac caataggaaa agttccaaga    4200
cccattaaag tgctagcaac gggaatacca gtgagttcaa caaagcgcct caattcagca    4260
ctggaattca aactgccacc gccgacgtag agaacgggct tttgggcctc catgatgagt    4320
ctgacaatgt gttccaattg ggcctcggcg ggggcctgg gcagcctggc gaggtaaccg    4380
gggaggttaa cgggctcgtc ccaattaggc acggcgagtt gctgctgaac gtctttggga    4440
atgtcgatga ggaccggacc ggggcggccg gaggtggcga cgaagaaagc ctcggcgacg    4500
acgcggggga tgtcgtcgac gtcgaggatg aggtagttgt gcttcgtgat ggatctgctc    4560
acctccacga tcggggtttc ttggaaggcg tcggtgccga tcatccggcg ggcgacctgg    4620
ccggtgatgg cgacgactgg gacgctgtcc attaaagcgt cggcgaggcc gctcacgagg    4680
ttggtggcgc cggggccgga ggtggcaatg cagacgccgg ggaggccgga ggaacgcgcg    4740
tagccttcgg cggcgaagac gccgccctgc tcgtggcgcg ggagcacgtt gcggatggcg    4800
gcggagcgcg tgagcgcctg gtggatctcc atcgacgcac cgccggggta cgcgaacacc    4860
gtcgtcacgc cctgcctctc cagcgcctcc acaaggatgt ccgcgccctt gcgaggttcg    4920
ccggaggcga accgtgacac gaagggctcc gtggtcggcg cttccttggt gaagggcgcc    4980
gccgtggggg gtttggagat ggaacatttg atttttgagag cgtggttggg tttggtgagg    5040
gtttgatgag agagagggag ggtggatcta gtaatgcgtt tggggaaggt ggggtgtgaa    5100
gaggaagaag agaatcgggt ggttctggaa gcggtggccg ccattgtgtt gtgtggcatg    5160
gttatacttc aaaaactgca caacaagcct agagttagta cctaaacagt aaatttacaa    5220
cagagagcaa agacacatgc aaaaatttca gccataaaaa aagttataat agaatttaaa    5280
gcaaaagttt cattttttaa acatatatac aaacaaactg gatttgaagg aagggattaa    5340
ttcccctgct caaagtttga attcctattg tgacctatac tcgaataaaa ttgaagccta    5400
aggaatgtat gagaaacaag aaaacaaaac aaaactacag acaaacaagt acaattacaa    5460
aattcgctaa aattctgtaa tcaccaaacc ccatctcagt cagcacaagg cccaaggttt    5520
attttgaaat aaaaaaaaag tgattttatt tctcataagc taaagaaag aaaggcaatt    5580
atgaaatgat ttcgactaga tctgaaagtc caacgcgtat tccgcagata ttaaagaaag    5640
agtagagttt cacatggatc ctagatggac ccagttgagg aaaaagcaag gcaaagcaaa    5700
ccagaagtgc aagatccgaa attgaaccac ggaatctagg attggtaga gggagaagaa    5760
aagtaccttg agaggtagaa gagaagagaa gagcagagag atatatgaac gagtgtgtct    5820
tggtctcaac tctgaagcga tacgagttta gagggagca ttgagttcca atttataggg    5880
aaaccgggtg gcagggtga gttaatgacg gaaaagcccc taagtaacga gattggattg    5940
tgggttagat tcaaccgttt gcatccgcgg cttagattgg ggaagtcaga gtgaatctca    6000
accgttgact gagttgaaaa ttgaatgtag caaccaattg agccaacccc agccctttgcc    6060
```

```
ctttgatttt gatttgtttg ttgcatactt tttatttgtc ttctggttct gactctcttt    6120
ctctcgtttc aatgccaggt tgcctactcc cacaccactc acaagaagat tctactgtta    6180
gtattaaata ttttttaatg tattaaatga tgaatgcttt tgtaaacaga acaagactat    6240
gtctaataag tgtcttgcaa catttttaa gaaattaaaa aaatatatt tattatcaaa     6300 atcaaatgta tgaaaaatca tgaataatat aattttatac attttttaa aaatcttt      6360 aatttcttaa ttaatatctt aaaaataatg attaatattt aacccaaaat aattagtatg    6420
attggtaagg aagatatcca tgttatgttt ggatgtgagt ttgatctaga gcaaagctta    6480
ctagagtcga cgcgccaagc ttttgatcca tgcccttcat ttgccgctta ttaattaatt    6540
tggtaacagt ccgtactaat cagttactta tccttccccc atcataatta atcttggtag    6600
tctcgaatgc cacaacactg actagtctct tggatcataa gaaaaagcca aggaacaaaa    6660
gaagacaaaa cacaatgaga gtatcctttg catagcaatg tctaagttca taaaattcaa    6720
acaaaaacgc aatcacacac agtggacatc acttatccac tagctgatca ggatcgccgc    6780
gtcaagaaaa aaaaactgga ccccaaaagc catgcacaac aacacgtact cacaaaggtg    6840
tcaatcgagc agcccaaaac attccccaac tcaacccatc atgagccctc acatttgttg    6900
tttctaaccc aacctcaaac tcgtattctc ttccgccacc tcattttgt ttatttcaac     6960 acccgtcaaa ctgcatgcca ccccgtggcc aaatgtccat gcatgttaac aagacctatg    7020
actataaata gctgcaatct cggcccaggt tttcatcatc aagaaccagt tcaatatcct    7080
agtacaccgt attaaagaat ttaagatata ctgcggccgc atgactatcg actcacaata    7140
ctacaagtcg cgagacaaaa acgacacggc acccaaaatc gcgggaatcc gatatgcccc    7200
gctatcgaca ccattactca accgatgtga gaccttctct ctggtctggc acattttcag    7260
cattcccact ttcctcacaa ttttcatgct atgctgcgca attccactgc tctggccatt    7320
tgtgattgcg tatgtagtgt acgctgttaa agacgactcc ccgtccaacg gaggagtggt    7380
caagcgatac tcgcctattt caagaaactt cttcatctgg aagctctttg gccgctactt    7440
ccccataact ctgcacaaga cggtggatct ggagcccacg cacacatact accctctgga    7500
cgtccaggag tatcacctga ttgctgagag atactggccg cagaacaagt acctccgagc    7560
aatcatctcc accatcgagt actttctgcc cgccttcatg aaacggtctc tttctatcaa    7620
cgagcaggag cagcctgccg agcgagatcc tctcctgtct cccgtttctc ccagctctcc    7680
gggttctcaa cctgacaagt ggattaacca cgacagcaga tatagccgtg gagaatcatc    7740
tggctccaac ggccacgcct cgggctccga acttaacggc aacggcaaca atggcaccac    7800
taaccgacga cctttgtcgt ccgcctctgc tggctccact gcatctgatt ccacgcttct    7860
taacgggtcc ctcaactcct acgccaacca gatcattggc gaaaacgacc cacagctgtc    7920
gcccacaaaa ctcaagccca ctggcagaaa atacatcttc ggctaccacc cccacggcat    7980
tatcggcatg ggagcctttg gtggaattgc caccgaggga gctggatggt ccaagctctt    8040
tccgggcatc cctgtttctc ttatgactct caccaacaac ttccgagtgc ctctctacag    8100
agagtacctc atgagtctgg gagtcgcttc tgtctccaag aagtcctgca aggccctcct    8160
caagcgaaac cagtctatct gcattgtcgt tggtggagca caggaaagtc ttctggccag    8220
acccggtgtc atggacctgg tgctactcaa gcgaaagggt tttgttcgac ttggtatgga    8280
ggtcggaaat gtcgcccttg ttcccatcat ggcctttggt gagaacgacc tctatgacca    8340
ggttagcaac gacaagtcgt ccaagctgta ccgattccag cagtttgtca agaacttcct    8400
```

```
tggattcacc cttcctttga tgcatgcccg aggcgtcttc aactacgatg tcggtcttgt    8460
cccctacagg cgacccgtca acattgtggt tggttccccc attgacttgc cttatctccc    8520
acaccccacc gacgaagaag tgtccgaata ccacgaccga tacatcgccg agctgcagcg    8580
aatctacaac gagcacaagg atgaatattt catcgattgg accgaggagg caaaggagc    8640 cccagagttc cgaatgattg agtaagcggc cgcaagtatg aactaaaatg catgtaggtg    8700
taagagctca tggagagcat ggaatattgt atccgaccat gtaacagtat aataactgag    8760
ctccatctca cttcttctat gaataaacaa aggatgttat gatatattaa cactctatct    8820
atgcacctta ttgttctatg ataaatttcc tcttattatt ataaatcatc tgaatcgtga    8880
cggcttatgg aatgcttcaa atagtacaaa aacaaatgtg tactataaga ctttctaaac    8940
aattctaacc ttagcattgt gaacgagaca taagtgttaa gaagacataa caattataat    9000
ggaagaagtt tgtctccatt tatatattat atattaccca cttatgtatt atattaggat    9060
gttaaggaga cataacaatt ataaagagag aagtttgtat ccatttatat attatatact    9120
acccatttat atattatact tatccactta tttaatgtct ttataaggtt tgatccatga    9180
tatttctaat attttagttg atatgtatat gaaagggtac tatttgaact ctcttactct    9240
gtataaaggt tggatcatcc ttaaagtggg tctatttaat tttattgctt cttacagata    9300
aaaaaaaaat tatgagttgg tttgataaaa tattgaagga tttaaaataa taataaataa    9360
catataatat atgtatataa atttattata atataacatt tatctataaa aaagtaaata    9420
ttgtcataaa tctatacaat cgtttagcct tgctggacga atctcaatta tttaaacgag    9480
agtaaacata tttgactttt tggttattta acaaattatt atttaacact atatgaaatt    9540
ttttttttta tcagcaaaga ataaaattaa attaagaagg acaatggtgt cccaatcctt    9600
atacaaccaa cttccacaag aaagtcaagt cagagacaac aaaaaaacaa gcaaaggaaa    9660 tttttaatt tgagttgtct tgtttgctgc ataatttatg cagtaaaaca ctacacataa    9720
cccttttagc agtagagcaa tggttgaccg tgtgcttagc ttcttttatt ttatttttt    9780 atcagcaaag aataaataaa ataaaatgag acacttcagg gatgtttcaa caagcttgga    9840
tcctagccta agtacgtact caaaatgcca acaaataaaa aaaagttgc tttaataatg    9900 ccaaaacaaa ttaataaaac acttacaaca ccggattttt tttaattaaa atgtgccatt    9960
taggataaat agttaatatt tttaataatt atttaaaaag ccgtatctac taaaatgatt    10020
tttatttggt tgaaaatatt aatatgttta aatcaacaca atctatcaaa attaaactaa    10080
aaaaaaaata agtgtacgtg gttaacatta gtacagtaat ataagaggaa aatgagaaat    10140
taagaaattg aaagcgagtc taattttaa attatgaacc tgcatatata aaggaaaga    10200 aagaatccag gaagaaaaga aatgaaacca tgcatggtcc cctcgtcatc acgagtttct    10260
gccatttgca atagaaacac tgaaacacct ttctctttgt cacttaattg agatgccgaa    10320
gccacctcac accatgaact tcatgaggtg tagcacccaa ggcttccata gccatgcata    10380
ctgaagaatg tctcaagctc agcaccctac ttctgtgacg tgtccctcat tcaccttcct    10440
ctcttcccta taaataacca cgcctcaggt tctccgcttc acaactcaaa cattctctcc    10500
attggtcctt aaacactcat cagtcatcac catggaggtc cgacgacgaa agatagacgt    10560
gctcaaggcc cagaaaaacg gctacgaatc gggcccacca tctcgacaat cgtcgcagcc    10620
ctcctcaaga gcatcgtcca gaacccgcaa caaacactcc tcgtccaccc tgtcgctcag    10680
cggactgacc atgaaagtcc agaagaaacc tgcgggaccc ccggcgaact ccaaaacgcc    10740
attcctacac atcaagcccg tgcacacgtg ctgctccaca tcaatgcttt cgcgcgatta    10800
```

```
tgacggctcc aaccccagct tcaagggctt caaaaacatc ggcatgatca ttctcattgt   10860
gggaaatcta cggctcgcat tcgaaaacta cctcaaatac ggcatttcca acccgttctt   10920
cgaccccaaa attactcctt ccgagtggca gctctcaggc ttgctcatag tcgtggccta   10980
cgcacatatc ctcatggcct acgctattga gagcgctgcc aagctgctgt tcctctctag   11040
caaacaccac tacatggccg tggggcttct gcataccatg aacactttgt cgtccatctc   11100
gttgctgtcc tacgtcgtct actactacct gcccaacccc gtggcaggca caatagtcga   11160
gtttgtggcc gttattctgt ctctcaaact cgcctcatac gccctcacta actcggatct   11220
ccgaaaagcc gcaattcatg cccagaagct cgacaagacg caagacgata acgaaaagga   11280
atccacctcg tcttcctctt cttcagatga cgcagagact ttggcagaca ttgacgtcat   11340
tcctgcatac tacgcacagc tgccctaccc ccagaatgtg acgctgtcga acctgctgta   11400
cttctggttt gctcccacac tggtctacca gcccgtgtac cccaagacgg agcgtattcg   11460
acccaagcac gtgatccgaa acctgtttga gctcgtctct ctgtgcatgc ttattcagtt   11520
tctcatcttc cagtacgcct accccatcat gcagtcgtgt ctggctctgt tcttccagcc   11580
caagctcgat tatgccaaca tctccgagcg cctcatgaag ttggcctccg tgtctatgat   11640
ggtctggctc attggattct acgctttctt ccagaacggt ctcaatctta ttgccgagct   11700
cacctgtttt ggaaacagaa ccttctacca gcagtggtgg aattcccgct ccattggcca   11760
gtactggact ctatggaaca agccagtcaa ccagtacttt agacaccacg tctacgtgcc   11820
tcttctcgct cggggcatgt cgcggttcaa tgcgtcggtg gtggtttttct ttttctccgc   11880 cgtcatccat gaactgcttg tcggcatccc cactcacaac atcatcggag ccgccttctt   11940
cggcatgatg tcgcaggtgc ctctgatcat ggctactgag aaccttcagc atattaactc   12000
ctctctgggc cccttccttg gcaactgtgc attctggttc acctttttcc tgggacaacc   12060
cacttgtgca ttcctttact atttggccta caactacaag cagaaccagt agcggccgca   12120
agtatgaact aaaatgcatg taggtgtaag agctcatgga gagcatggaa tattgtatcc   12180
gaccatgtaa cagtataata actgagctcc atctcacttc ttctatgaat aaacaaagga   12240
tgttatgata tattaacact ctatctatgc accttattgt tctatgataa atttcctctt   12300
attattataa atcatctgaa tcgtgacggc ttatggaatg cttcaaatag tacaaaaaca   12360
aatgtgtact ataagacttt ctaaacaatt ctaaccttag cattgtgaac gagacataag   12420
tgttaagaag acataacaat tataatggaa gaagtttgtc tccatttata tattatatat   12480
tacccactta tgtattatat taggatgtta aggagacata acaattataa agagagaagt   12540
ttgtatccat ttatatatta tatactaccc atttatatat tatacttatc cacttattta   12600
atgtctttat aaggtttgat ccatgatatt tctaatattt tagttgatat gtatatgaaa   12660
gggtactatt tgaactctct tactctgtat aaaggttgga tcatccttaa agtgggtcta   12720
tttaatttta ttgcttctta cagataaaaa aaaaattatg agttggtttg ataaaatatt   12780
gaaggattta aaataataat aaataacata taatatatgt atataaattt attataatat   12840
aacatttatc tataaaaaag taaatattgt cataaatcta tacaatcgtt tagccttgct   12900
ggacgaatct caattatttta aacgagagta acatatttg acttttggt tatttaacaa   12960 attattattt aacactatat gaaattttt tttttatcag caaagaataa aattaaatta   13020
agaaggacaa tggtgtccca atccttatac aaccaacttc cacaagaaag tcaagtcaga   13080
gacaacaaaa aaacaagcaa aggaaatttt ttaatttgag ttgtcttgtt tgctgcataa   13140
```
tttatgcagt aaaacactac acataacct tttagcagta gagcaatggt tgaccgtgtg    13200
cttagcttct tttattttat ttttttatca gcaaagaata aataaaataa aatgagacac    13260
ttcagggatg tttcaacaag ctctagactg gaattcgtcg acggcgcg                 13308

<210> SEQ ID NO 56
<211> LENGTH: 21
<212> TYPE: DNA
<213> ORGANISM: artificial sequence
<220> FEATURE:
<223> OTHER INFORMATION: amiRNA aldo A

<400> SEQUENCE: 56
tgggggagaa ggagaggagg a                                              21

<210> SEQ ID NO 57
<211> LENGTH: 21
<212> TYPE: DNA
<213> ORGANISM: artificial sequence
<220> FEATURE:
<223> OTHER INFORMATION: amiRNA aldo B

<400> SEQUENCE: 57
tcaaatccct cgccccatca t                                              21

<210> SEQ ID NO 58
<211> LENGTH: 21
<212> TYPE: DNA
<213> ORGANISM: artificial sequence
<220> FEATURE:
<223> OTHER INFORMATION: amiRNA aldo A star

<400> SEQUENCE: 58
tcctcctctc cacctccccc t                                              21

<210> SEQ ID NO 59
<211> LENGTH: 21
<212> TYPE: DNA
<213> ORGANISM: artificial sequence
<220> FEATURE:
<223> OTHER INFORMATION: amiRNA aldo B star

<400> SEQUENCE: 59
atgatggggc gtcggatttg t                                              21

<210> SEQ ID NO 60
<211> LENGTH: 974
<212> TYPE: DNA
<213> ORGANISM: artificial sequence
<220> FEATURE:
<223> OTHER INFORMATION: microRNA 159 precursor

<400> SEQUENCE: 60
gcggccgctt ctagctagct agggtttggg tagtgagtgt aataaagttg caaagttttt     60
ggttaggtta cgttttgacc ttattattat agttcaaagg gaaacattaa ttaaagggga    120
ttatgaagtg gagctccttg aagtccaatt gaggatctta ctgggtgaat tgagctgctt    180
agctatggat cccacagttc tacccatcaa taagtgcttt tgtggtagtc ttgtggcttc    240
catatctggg gagcttcatt tgcctttata gtattaacct tctttggatt gaagggagct    300 ctacacccttct cttcttttt ctctcataat aatttaaatt tgttatagac tctaaacttt    360
aaatgttttt tttgaagttt ttccgttttt ctcttttgcc atgatcccgt tcttgctgtg    420
gagtaacctt gtccgaggta tgtgcatgat tagatccata cttaattgt gtgcatcacg    480

```
aaggtgaggt tgaaatgaac tttgcttttt tgaccttttta ggaaagttct tttgttgcag    540
taatcaattt taattagttt taattgacac tattactttt attgtcatct ttgttagttt    600
tattgttgaa ttgagtgcat atttcctagg aaattctctt acctaacatt ttttatacag    660
atctatgctc ttggctcttg cccttactct tggccttgtg ttggttattt gtctacatat    720
ttattgactg gtcgatgaga catgtcacaa ttcttgggct tatttgttgg tctaataaaa    780
ggagtgctta ttgaaagatc aagacggaga ttcggtttta tataaataaa ctaaagatga    840
catattagtg tgttgatgtc tcttcaggat aattttttgtt tgaaataata tggtaatgtc    900
ttgtctaaat ttgtgtacat aattcttact gattttttgg attgttggat ttttataaac    960
aaatctgcgg ccgc                                                      974
```

<210> SEQ ID NO 61
<211> LENGTH: 990
<212> TYPE: DNA
<213> ORGANISM: artificial sequence
<220> FEATURE:
<223> OTHER INFORMATION: in-fusion ready microRNA 159

<400> SEQUENCE: 61

```
gcggccgctt ctagctagct agggtttggg tagtgagtgt aataaagttg caaagttttt     60
ggttaggtta cgttttgacc ttattattat agttcaaagg gaaacattaa ttaaaggggga   120 ttatgaagtg tttaaacgga gctccttgaa gtccaattga ggatcttact gggtgaattg    180
agctgcttag ctatggatcc cacagttcta cccatcaata agtgcttttg tggtagtctt    240
gtggcttcca tatctgggga gcttcatttg cctttatagt attaaccttc tttggattga    300
agggagctct agtttaaacc acccttctct tcttttctct cataataatt taaatttgtt    360
atagactcta aactttaaat gttttttttg aagttttttcc gtttttctct tttgccatga   420
tcccgttctt gctgtggagt aaccttgtcc gaggtatgtg catgattaga tccatactta    480
atttgtgtgc atcacgaagg tgaggttgaa atgaactttg ctttttttgac ctttttaggaa   540 agttcttttg ttgcagtaat caattttaat tagtttttaat tgacactatt acttttattg    600
tcatctttgt tagtttttatt gttgaattga gtgcatattt cctaggaaat tctcttacct    660 aacattttttt atacagatct atgctcttgg ctcttgccct tactcttggc cttgtgttgg    720
ttatttgtct acatatttat tgactggtcg atgagacatg tcacaattct tgggcttatt    780
tgttggtcta ataaaaggag tgcttattga aagatcaaga cggagattcg gttttatata    840
aataaactaa agatgacata ttagtgtgtt gatgtctctt caggataatt tttgtttgaa    900
ataatatggt aatgtcttgt ctaaatttgt gtacataatt cttactgatt ttttggattg    960
ttggattttt ataaacaaat ctgcggccgc                                     990
```

<210> SEQ ID NO 62
<211> LENGTH: 8536
<212> TYPE: DNA
<213> ORGANISM: artificial sequence
<220> FEATURE:
<223> OTHER INFORMATION: in-fusion ready microRNA 159-KS126 plasmid
<220> FEATURE:
<221> NAME/KEY: misc_feature
<222> LOCATION: (7624)..(7624)
<223> OTHER INFORMATION: n=a,c,g,or t

<400> SEQUENCE: 62

```
ggccgcttct agctagctag ggtttgggta gtgagtgtaa taaagttgca aagttttttgg    60
```

```
ttaggttacg ttttgacctt attattatag ttcaaaggga acattaatt aaaggggatt    120 atgaagtgtt taaacggagc tccttgaagt ccaattgagg atcttactgg gtgaattgag   180
ctgcttagct atggatccca cagttctacc catcaataag tgcttttgtg gtagtcttgt   240
ggcttccata tctggggagc ttcatttgcc tttatagtat taaccttctt tggattgaag   300
ggagctctag tttaaaccac ccttctcttc ttttctctca taataattta aatttgttat   360
agactctaaa ctttaaatgt ttttttttgaa gttttttccgt ttttctcttt tgccatgatc  420
ccgttcttgc tgtggagtaa ccttgtccga ggtatgtgca tgattagatc catacttaat   480
ttgtgtgcat cacgaaggtg aggttgaaat gaactttgct tttttgacct tttaggaaag   540
ttcttttgtt gcagtaatca atttttaatta gttttaattg acactattac ttttattgtc   600
atctttgtta gttttattgt tgaattgagt gcatatttcc taggaaattc tcttacctaa   660
cattttttat acagatctat gctcttggct cttgccctta ctcttggcct tgtgttggtt   720
atttgtctac atatttattg actggtcgat gagacatgtc acaattcttg ggcttatttg   780
ttggtctaat aaaaggagtg cttattgaaa gatcaagacg gagattcggt tttatataaa   840
taaactaaag atgacatatt agtgtgttga tgtctcttca ggataatttt tgtttgaaat   900
aatatggtaa tgtcttgtct aaatttgtgt acataattct tactgatttt ttggattgtt   960 ggattttttat aaacaaatct gcggccgcga cacaagtgtg agagtactaa ataaatgctt  1020
tggttgtacg aaatcattac actaaataaa ataatcaaag cttatatatg ccttccgcta  1080
aggccgaatg caaagaaatt ggttctttct cgttatcttt tgccactttt actagtacgt  1140
attaattact acttaatcat ctttgtttac ggctcattat atccgtcgac ggcgcgcccg  1200
atcatccgga tatagttcct cctttcagca aaaacccct caagaccgt ttagaggccc     1260 caaggggtta tgctagttat tgctcagcgg tggcagcagc caactcagct tcctttcggg  1320
ctttgttagc agccggatcg atccaagctg tacctcacta ttcctttgcc ctcggacgag  1380
tgctggggcg tcggtttcca ctatcggcga gtacttctac acagccatcg gtccagacgg  1440
ccgcgcttct gcgggcgatt tgtgtacgcc cgacagtccc ggctccggat cggacgattg  1500
cgtcgcatcg accctgcgcc caagctgcat catcgaaatt gccgtcaacc aagctctgat  1560
agagttggtc aagaccaatg cggagcatat acgcccggag ccgcggcgat cctgcaagct  1620
ccggatgcct ccgctcgaag tagcgcgtct gctgctccat acaagccaac cacgcctcc   1680 agaagaagat gttggcgacc tcgtattggg aatccccgaa catcgcctcg ctccagtcaa  1740
tgaccgctgt tatgcggcca ttgtccgtca ggacattgtt ggagccgaaa tccgcgtgca  1800
cgaggtgccg gacttcgggg cagtcctcgg cccaaagcat cagctcatcg agagcctgcg  1860
cgacggacgc actgacggtg tcgtccatca cagtttgcca gtgatacaca tggggatcag  1920
caatcgcgca tatgaaatca cgccatgtag tgtattgacc gattccttgc ggtccgaatg  1980
ggccgaaccc gctcgtctgg ctaagatcgg ccgcagcgat cgcatccata gcctccgcga  2040
ccggctgcag aacagcgggc agttcggttt caggcaggtc ttgcaacgtg acaccctgtg  2100
cacggcggga gatgcaatag gtcaggctct cgctgaattc cccaatgtca agcacttccg  2160
gaatcgggag cgcggccgat gcaaagtgcc gataaacata acgatctttg tagaaaccat  2220
cggcgcagct atttacccgc aggacatatc cacgccctcc tacatcgaag ctgaaagcac  2280
gagattcttc gccctccgag agctgcatca ggtcggagac gctgtcgaac ttttcgatca  2340
gaaacttctc gacagacgtc gcggtgagtt caggcttttc catgggtata tctccttctt  2400
aaagttaaac aaaattattt ctagagggaa accgttgtgg tctccctata gtgagtcgta  2460
```

```
ttaatttcgc gggatcgaga tcgatccaat tccaatccca caaaaatctg agcttaacag    2520
cacagttgct cctctcagag cagaatcggg tattcaacac cctcatatca actactacgt    2580
tgtgtataac ggtccacatg ccggtatata cgatgactgg ggttgtacaa aggcggcaac    2640
aaacggcgtt cccggagttg cacacaagaa atttgccact attacagagg caagagcagc    2700
agctgacgcg tacacaacaa gtcagcaaac agacaggttg aacttcatcc ccaaaggaga    2760
agctcaactc aagcccaaga gctttgctaa ggccctaaca agcccaccaa agcaaaaagc    2820
ccactggctc acgctaggaa ccaaaaggcc cagcagtgat ccagccccaa agagatctc    2880 cttgccccg gagattacaa tggacgattt cctctatctt tacgatctag aaggaagtt    2940 cgaaggtgaa ggtgacgaca ctatgttcac cactgataat gagaaggtta gcctcttcaa    3000
tttcagaaag aatgctgacc cacagatggt tagagaggcc tacgcagcag gtctcatcaa    3060
gacgatctac ccgagtaaca atctccagga gatcaaatac cttcccaaga aggttaaaga    3120
tgcagtcaaa agattcagga ctaattgcat caagaacaca gagaaagaca tatttctcaa    3180
gatcagaagt actattccag tatggacgat tcaaggcttg cttcataaac caaggcaagt    3240
aatagagatt ggagtctcta aaaaggtagt tcctactgaa tctaaggcca tgcatggagt    3300
ctaagattca aatcgaggat ctaacagaac tcgccgtgaa gactggcgaa cagttcatac    3360
agagtctttt acgactcaat gacaagaaga aaatcttcgt caacatggtg gagcacgaca    3420
ctctggtcta ctccaaaaat gtcaaagata cagtctcaga agaccaaagg gctattgaga    3480
cttttcaaca aaggataatt tcgggaaacc tcctcggatt ccattgccca gctatctgtc    3540
acttcatcga aggacagta gaaaaggaag gtggctccta caaatgccat cattgcgata    3600
aaggaaaggc tatcattcaa gatgcctctg ccgacagtgg tcccaaagat ggacccccac    3660
ccacgaggag catcgtggaa aaagaagacg ttccaaccac gtcttcaaag caagtggatt    3720
gatgtgacat ctccactgac gtaagggatg acgcacaatc ccactatcct tcgcaagacc    3780
cttcctctat ataaggaagt tcatttcatt tggagaggac acgctcgagc tcatttctct    3840
attacttcag ccataacaaa agaactcttt tctcttctta ttaaaccatg aaaaagcctg    3900
aactcaccgc gacgtctgtc gagaagtttc tgatcgaaaa gttcgacagc gtctccgacc    3960
tgatgcagct ctcggagggc gaagaatctc gtgctttcag cttcgatgta ggagggcgtg    4020
gatatgtcct gcgggtaaat agctgcgccg atggtttcta caaagatcgt tatgtttatc    4080
ggcactttgc atcggccgcg ctcccgattc cggaagtgct tgacattggg gaattcagcg    4140
agagcctgac ctattgcatc tcccgccgtg cacagggtgt cacgttgcaa gacctgcctg    4200
aaaccgaact gcccgctgtt ctgcagccgg tcgcggaggc catggatgcg atcgctgcgg    4260
ccgatcttag ccagacgagc gggttcggcc cattcggacc gcaaggaatc ggtcaataca    4320
ctacatggcg tgatttcata tgcgcgattg ctgatcccca tgtgtatcac tggcaaactg    4380
tgatggacga ccaccgtcagt gcgtccgtcg cgcaggctct cgatgagctg atgctttggg    4440
ccgaggactg ccccgaagtc cggcacctcg tgcacgcgga tttcggctcc aacaatgtcc    4500
tgacggacaa tggccgcata acagcggtca ttgactggag cgaggcgatg ttcggggatt    4560
cccaatacga ggtcgccaac atcttcttct ggaggccgtg gttggcttgt atggagcagc    4620
agacgcgcta cttcgagcgg aggcatccgg agcttgcagg atcgccgcgg ctccgggcgt    4680
atatgctccg cattggtctt gaccaactct atcagagctt ggttgacggc aatttcgatg    4740
atgcagcttg ggcgcagggt cgatgcgacg caatcgtccg atccggagcc gggactgtcg    4800
```

```
ggcgtacaca aatcgcccgc agaagcgcgg ccgtctggac cgatggctgt gtagaagtac    4860
tcgccgatag tggaaaccga cgccccagca ctcgtccgag ggcaaaggaa tagtgaggta    4920
cctaaagaag gagtgcgtcg aagcagatcg ttcaaacatt tggcaataaa gtttcttaag    4980
attgaatcct gttgccggtc ttgcgatgat tatcatataa tttctgttga attacgttaa    5040
gcatgtaata attaacatgt aatgcatgac gttatttatg agatgggttt ttatgattag    5100
agtcccgcaa ttatacattt aatacgcgat agaaaacaaa atatagcgcg caaactagga    5160
taaattatcg cgcgcggtgt catctatgtt actagatcga tgtcgaatct gatcaacctg    5220
cattaatgaa tcgccaacg cgcggggaga ggcggtttgc gtattgggcg ctcttccgct    5280
tcctcgctca ctgactcgct gcgctcggtc gttcggctgc ggcgagcggt atcagctcac    5340
tcaaaggcgg taatacggtt atccacagaa tcagggagata acgcaggaaa gaacatgtga    5400
gcaaaaggcc agcaaaaggc caggaaccgt aaaaaggccg cgttgctggc gtttttccat    5460
aggctccgcc ccctgacga gcatcacaaa aatcgacgct caagtcagag gtggcgaaac    5520
ccgacaggac tataaagata ccaggcgttt ccccctggaa gctccctcgt gcgctctcct    5580
gttccgaccc tgccgcttac cggatacctg tccgcctttc tcccttcggg aagcgtggcg    5640
ctttctcaat gctcacgctg taggtatctc agttcggtgt aggtcgttcg ctccaagctg    5700
ggctgtgtgc acgaaccccc cgttcagccc gaccgctgcg ccttatccgg taactatcgt    5760
cttgagtcca acccggtaag acacgactta tcgccactgg cagcagccac tggtaacagg    5820
attagcagag cgaggtatgt aggcggtgct acagagttct tgaagtggtg gcctaactac    5880
ggctacacta aaggacagt atttggtatc tgcgctctgc tgaagccagt taccttcgga    5940
aaaagagttg gtagctcttg atccggcaaa caaaccaccg ctggtagcgg tggttttttt    6000
gtttgcaagc agcagattac gcgcagaaaa aaaggatctc aagaagatcc tttgatcttt    6060
tctacggggt ctgacgctca gtggaacgaa aactcacgtt aagggatttt ggtcatgaca    6120
ttaacctata aaaataggcg tatcacgagg cccttcgtc tcgcgcgttt cggtgatgac    6180
ggtgaaaacc tctgacacat gcagctcccg gagacggtca gcttgtct gtaagcggat    6240 gccgggagca gacaagcccg tcaggcgcg tcagcgggtg ttggcgggtg tcggggctgg    6300
cttaactatg cggcatcaga gcagattgta ctgagagtgc accatatgga catattgtcg    6360
ttagaacgcg gctacaatta atacataacc ttatgtatca tacacatacg atttaggtga    6420
cactatagaa cggcgcgcca agcttggatc ctcgaagaga agggttaata acacacttt    6480 ttaacatttt taacacaaat tttagttatt taaaaattta ttaaaaaatt taaaataaga    6540
agaggaactc tttaaataaa tctaacttac aaaatttatg attttttaata agttttcacc    6600 aataaaaaat gtcataaaaa tatgttaaaa agtatattat caatattctc tttatgataa    6660
ataaaaagaa aaaaaaaata aagttaagt gaaatgaga ttgaagtgac tttaggtgtg    6720
tataaatata tcaaccccgc caacaattta tttaatccaa atatattgaa gtatattat    6780 ccatagcctt tatttattta tatatttatt atataaaagc tttatttgtt ctaggttgtt    6840
catgaaatat ttttttggtt ttatctccgt tgtaagaaaa tcatgtgctt tgtgtcgcca    6900
ctcactattg cagcttttc atgcattggt cagattgacg gttgattgta ttttgttt    6960 ttatggtttt gtgttatgac ttaagtcttc atctctttat ctcttcatca ggtttgatgg    7020
ttacctaata tggtccatgg gtacatgcat ggttaaatta ggtggccaac tttgttgtga    7080
acgatagaat ttttttata ttaagtaaac tatttttata ttatgaaata ataataaaaa    7140
aaatatttta tcattattaa caaaatcata ttagttaatt tgttaactct ataataaaag    7200
```

```
aaatactgta acattcacat tacatggtaa catctttcca cccttttcatt tgttttttgt    7260 ttgatgactt ttttttcttgt ttaaatttat ttcccttctt ttaaatttgg aatacattat    7320
catcatatat aaactaaaat actaaaaaca ggattacaca aatgataaat aataacacaa    7380
atatttataa atctagctgc aatatattta aactagctat atcgatattg taaaataaaa    7440
ctagctgcat tgatactgat aaaaaaatat catgtgcttt ctggactgat gatgcagtat    7500
acttttgaca ttgcctttat tttattttc agaaaagctt tcttagttct gggttcttca     7560
ttatttgttt cccatctcca ttgtgaattg aatcatttgc ttcgtgtcac aaatacaatt    7620
tagntaggta catgcattgg tcagattcac ggtttattat gtcatgactt aagttcatgg    7680
tagtacatta cctgccacgc atgcattata ttggttagat ttgataggca aatttggttg    7740
tcaacaatat aaatataaat aatgttttta tattacgaaa taacagtgat caaacaaac     7800 agttttatct ttattaacaa gattttgttt ttgtttgatg acgttttta atgtttacgc     7860 tttccccctt cttttgaatt tagaacactt tatcatcata aaatcaaata ctaaaaaaat    7920
tacatatttc ataaataata acacaaatat ttttaaaaaa tctgaaataa taatgaacaa    7980
tattacatat tatcacgaaa attcattaat aaaaatatta tataaataaa atgtaatagt    8040
agttatatgt aggaaaaaag tactgcacgc ataatatata caaaaagatt aaaatgaact    8100
attataaata ataacactaa attaatggtg aatcatatca aaataatgaa aaagtaaata    8160
aaatttgtaa ttaacttcta tatgtattac acacacaaat aataaataat agtaaaaaaa    8220
attatgataa atatttacca tctcataaga tatttaaaat aatgataaaa atatagatta    8280 tttttttatgc aactagctag ccaaaaagag aacacgggta tatataaaaa gagtacctt     8340 aaattctact gtacttcctt tattcctgac gtttttatat caagtggaca tacgtgaaga    8400
ttttaattat cagtctaaat atttcattag cacttaatac ttttctgttt tattcctatc    8460
ctataagtag tcccgattct cccaacattg cttattcaca caactaacta agaaagtctt    8520
ccatagcccc ccaagc                                                    8536

<210> SEQ ID NO 63
<211> LENGTH: 54
<212> TYPE: DNA
<213> ORGANISM: artificial sequence
<220> FEATURE:
<223> OTHER INFORMATION: gmir159ALDO A1 primer

<400> SEQUENCE: 63
attaaggggg attatgaagt cctcctctcc acctccccct tgaggatctt actg          54

<210> SEQ ID NO 64
<211> LENGTH: 54
<212> TYPE: DNA
<213> ORGANISM: artificial sequence
<220> FEATURE:
<223> OTHER INFORMATION: gmir159ALDO A2 primer

<400> SEQUENCE: 64
gagaaaagaa gagaagggtg tcctcctctc cttctccccc agaaggttaa tact          54

<210> SEQ ID NO 65
<211> LENGTH: 214
<212> TYPE: DNA
<213> ORGANISM: artificial sequence
<220> FEATURE:
<223> OTHER INFORMATION: 159-ALDO A DNA microRNA precursor
```

```
<400> SEQUENCE: 65
attaaagggg attatgaagt cctcctctcc acctccccct tgaggatctt actgggtgaa    60
ttgagctgct tagctatgga tcccacagtt ctacccatca ataagtgctt tgtggtagt    120 cttgtggctt ccatatctgg ggagcttcat ttgcctttat agtattaacc ttctggggga   180
gaaggagagg aggacaccct tctcttcttt tctc                                214

<210> SEQ ID NO 66
<211> LENGTH: 54
<212> TYPE: DNA
<213> ORGANISM: artificial sequence
<220> FEATURE:
<223> OTHER INFORMATION: gmir159ALDO B1 primer

<400> SEQUENCE: 66
attaaagggg attatgaaga tgatggggcg tcggatttgt tgaggatctt actg          54

<210> SEQ ID NO 67
<211> LENGTH: 54
<212> TYPE: DNA
<213> ORGANISM: artificial sequence
<220> FEATURE:
<223> OTHER INFORMATION: gmir159ALDO B2 primer

<400> SEQUENCE: 67
gagaaaagaa gagaagggtg atgatggggc gagggatttg agaaggttaa tact          54

<210> SEQ ID NO 68
<211> LENGTH: 213
<212> TYPE: DNA
<213> ORGANISM: artificial sequence
<220> FEATURE:
<223> OTHER INFORMATION: 159-ALDO B DNA microRNA precursor

<400> SEQUENCE: 68
attaaagggg attatgaaga tgatggggcg tcggatttgt tgaggatctt actgggtgaa    60
ttgagctgct tagctatgga tcccacagtt ctacccatca ataagtgctt tgtggtagt    120 cttgtggctt ccatatctgg ggagcttcat ttgcctttat agtattaacc ttctcaaatc   180
cctcgcccca tcatcaccct tctcttcttt tct                                 213

<210> SEQ ID NO 69
<211> LENGTH: 8520
<212> TYPE: DNA
<213> ORGANISM: artificial sequence
<220> FEATURE:
<223> OTHER INFORMATION: 159 ALDO A-KS126 -plasmid
<220> FEATURE:
<221> NAME/KEY: misc_feature
<222> LOCATION: (6642)..(6642)
<223> OTHER INFORMATION: n=a,c,g,or t

<400> SEQUENCE: 69
ggccgcgaca caagtgtgag agtactaaat aaatgctttg gttgtacgaa atcattacac    60
taaataaaat aatcaaagct tatatatgcc ttccgctaag gccgaatgca agaaattgg    120 ttctttctcg ttatcttttg ccacttttac tagtacgtat taattactac ttaatcatct   180
ttgtttacgg ctcattatat ccgtcgacgg cgcgcccgat catccggata tagttcctcc   240
tttcagcaaa aaaccctca agacccgttt agaggcccca aggggttatg ctagttattg    300
ctcagcggtg gcagcagcca actcagcttc ctttcgggct ttgttagcag ccggatcgat   360
ccaagctgta cctcactatt cctttgccct cggacgagtg ctggggcgtc ggtttccact   420
```

```
atcggcgagt acttctacac agccatcggt ccagacggcc gcgcttctgc gggcgatttg    480
tgtacgcccg acagtcccgg ctccggatcg gacgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc gcgtgcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct    1020
aagatcggcc gcagcgatcg catccatagc ctccgcgacc ggctgcagaa cagcgggcag    1080
ttcggtttca ggcaggtctt gcaacgtgac accctgtgca cggcgggaga tgcaataggt    1140
caggctctcg ctgaattccc caatgtcaag cacttccgga atcgggagcg cggccgatgc    1200
aaagtgccga taaacataac gatctttgta gaaaccatcg gcgcagctat ttacccgcag    1260
gacatatcca cgccctccta catcgaagct gaaagcacga gattcttcgc cctccgagag    1320
ctgcatcagg tcggagacgc tgtcgaactt ttcgatcaga aacttctcga cagacgtcgc    1380
ggtgagttca ggcttttcca tgggtatatc tccttcttaa agttaaacaa aattatttct    1440
agagggaaac cgttgtggtc tccctatagt gagtcgtatt aatttcgcgg gatcgagatc    1500
gatccaattc caatcccaca aaaatctgag cttaacagca cagttgctcc tctcagagca    1560
gaatcgggta ttcaacaccc tcatatcaac tactacgttg tgtataacgg tccacatgcc    1620
ggtatatacg atgactgggg ttgtacaaag gcggcaacaa acggcgttcc cggagttgca    1680
cacaagaaat ttgccactat tacagaggca agagcagcag ctgacgcgta cacaacaagt    1740
cagcaaacag acaggttgaa cttcatcccc aaaggagaag ctcaactcaa gcccaagagc    1800
tttgctaagg ccctaacaag cccaccaaag caaaaagccc actggctcac gctaggaacc    1860
aaaaggccca gcagtgatcc agccccaaaa gagatctcct tgccccggga gattacaatg    1920
gacgatttcc tctatcttta cgatctagga aggaagttcg aaggtgaagg tgacgacact    1980
atgttcacca ctgataatga aaggttagc ctcttcaatt tcagaaagaa tgctgaccca    2040
cagatggtta gagaggccta cgcagcaggt ctcatcaaga cgatctaccc gagtaacaat    2100
ctccaggaga tcaaatacct tcccaagaag gttaaagatg cagtcaaaag attcaggact    2160
aattgcatca agaacacaga gaaagacata tttctcaaga tcagaagtac tattccagta    2220
tggacgattc aaggcttgct tcataaacca aggcaagtaa tagagattgg agtctctaaa    2280
aaggtagttc ctactgaatc taaggccatg catggagtct aagattcaaa tcgaggatct    2340
aacagaactc gccgtgaaga ctggcgaaca gttcatacag agtcttttac gactcaatga    2400
caagaagaaa atcttcgtca acatggtgga gcacgacact ctggtctact ccaaaaatgt    2460
caaagataca gtctcagaag accaaagggc tattgagact tttcaacaaa ggataatttc    2520
gggaaacctc ctcggattcc attgcccagc tatctgtcac ttcatcgaaa ggacagtaga    2580
aaaggaaggt ggctcctaca aatgccatca ttgcgataaa ggaaaggcta tcattcaaga    2640
tgcctctgcc gacagtggtc ccaaagatgg acccccaccc acgaggagca tcgtggaaaa    2700
agaagacgtt ccaaccacgt cttcaaagca agtggattga tgtgacatct ccactgacgt    2760
```

-continued

```
aagggatgac gcacaatccc actatccttc gcaagaccct tcctctatat aaggaagttc   2820
atttcatttg gagaggacac gctcgagctc atttctctat tacttcagcc ataacaaaag   2880 aactctttc  tcttcttatt aaaccatgaa aaagcctgaa ctcaccgcga cgtctgtcga   2940
gaagtttctg atcgaaaagt tcgacagcgt ctccgacctg atgcagctct cggagggcga   3000
agaatctcgt gctttcagct tcgatgtagg agggcgtgga tatgtcctgc gggtaaatag   3060
ctgcgccgat ggtttctaca agatcgtta  tgtttatcgg cactttgcat cggccgcgct   3120
cccgattccg gaagtgcttg acattgggga attcagcgag agcctgacct attgcatctc   3180
ccgccgtgca cagggtgtca cgttgcaaga cctgcctgaa accgaactgc cgctgttct    3240 gcagccggtc gcggaggcca tggatgcgat cgctgcggcc gatcttagcc agacgagcgg   3300
gttcggccca ttcggaccgc aaggaatcgg tcaatacact acatggcgtg atttcatatg   3360
cgcgattgct gatccccatg tgtatcactg gcaaactgtg atggacgaca ccgtcagtgc   3420
gtccgtcgcg caggctctcg atgagctgat gctttgggcc gaggactgcc ccgaagtccg   3480
gcacctcgtg cacgcggatt tcggctccaa caatgtcctg acgacaatg  gccgcataac   3540 agcggtcatt gactggagcg aggcgatgtt cggggattcc caatacgagg tcgccaacat   3600
cttcttctgg aggccgtggt tggcttgtat ggagcagcag acgcgctact cgagcggag   3660 gcatccggag cttgcaggat cgccgcggct ccgggcgtat atgctccgca ttggtcttga   3720
ccaactctat cagagcttgg ttgacggcaa tttcgatgat gcagcttggg cgcagggtcg   3780
atgcgacgca atcgtccgat ccggagccgg gactgtcggg cgtacacaaa tcgcccgcag   3840
aagcgcggcc gtctggaccg atggctgtgt agaagtactc gccgatagtg aaaccgacg   3900 ccccagcact cgtccgaggg caaaggaata gtgaggtacc taaagaagga gtgcgtcgaa   3960
gcagatcgtt caaacatttg gcaataaagt ttcttaagat tgaatcctgt tgccggtctt   4020
gcgatgatta tcatataatt tctgttgaat tacgttaagc atgtaataat taacatgtaa   4080
tgcatgacgt tatttatgag atgggttttt atgattagag tcccgcaatt atacatttaa   4140
tacgcgatag aaaacaaaat atagcgcgca aactaggata aattatcgcg cgcggtgtca   4200
tctatgttac tagatcgatg tcgaatctga tcaacctgca ttaatgaatc ggccaacgcg   4260
cggggagagg cggtttgcgt attgggcgct cttccgcttc ctcgctcact gactcgctgc   4320
gctcggtcgt tcggctgcgg cgagcggtat cagctcactc aaaggcggta atacggttat   4380
ccacagaatc agggggataac gcaggaaaga acatgtgagc aaaaggccag caaaaggcca   4440
ggaaccgtaa aaaggccgcg ttgctggcgt ttttccatag gctccgcccc cctgacgagc   4500
atcacaaaaa tcgacgctca agtcagaggt ggcgaaaccc gacaggacta taaagatacc   4560
aggcgtttcc ccctggaagc tccctcgtgc gctctcctgt tccgaccctg ccgcttaccg   4620
gatacctgtc cgcctttctc ccttcgggaa gcgtggcgct ttctcaatgc tcacgctgta   4680
ggtatctcag ttcggtgtag tcgttcgct  ccaagctggg ctgtgtgcac gaaccccccg   4740
ttcagcccga ccgctgcgcc ttatccgta  actatcgtct tgagtccaac ccggtaagac   4800
acgacttatc gccactggca gcagccactg gtaacaggat tagcagagcg aggtatgtag   4860
gcggtgctac agagttcttg aagtggtggc ctaactacgg ctacactaga aggacagtat   4920
ttggtatctg cgctctgctg aagccagtta ccttcggaaa aagagttggt agctcttgat   4980
ccggcaaaca aaccaccgct ggtagcggtg gtttttttgt ttgcaagcag cagattacgc   5040
gcagaaaaaa aggatctcaa gaagatcctt tgatcttttc tacggggtct gacgctcagt   5100
ggaacgaaaa ctcacgttaa gggattttgg tcatgacatt aacctataaa aataggcgta   5160
```

```
tcacgaggcc ctttcgtctc gcgcgtttcg gtgatgacgg tgaaaacctc tgacacatgc   5220
agctcccgga gacggtcaca gcttgtctgt aagcggatgc cgggagcaga caagcccgtc   5280
agggcgcgtc agcgggtgtt ggcgggtgtc ggggctggct taactatgcg gcatcagagc   5340
agattgtact gagagtgcac catatggaca tattgtcgtt agaacgcggc tacaattaat   5400
acataacctt atgtatcata cacatacgat ttaggtgaca ctatagaacg gcgcgccaag   5460
cttggatcct cgaagagaag ggttaataac acactttttt aacatttta acacaaattt    5520
tagttattta aaaatttatt aaaaaattta aaataagaag aggaactctt taaataaatc   5580
taacttacaa aatttatgat ttttaataag ttttcaccaa taaaaaatgt cataaaaata   5640
tgttaaaaag tatattatca atattctctt tatgataaat aaaaagaaaa aaaaaataaa   5700
agttaagtga aaatgagatt gaagtgactt taggtgtgta taaatatatc aaccccgcca   5760
acaatttatt taatccaaat atattgaagt atattattcc atagccttta tttatttata   5820
tatttattat ataaaagctt tatttgttct aggttgttca tgaaatattt ttttggtttt   5880
atctccgttg taagaaaatc atgtgctttg tgtcgccact cactattgca gcttttcat    5940
gcattggtca gattgacggt tgattgtatt tttgtttttt atggttttgt gttatgactt   6000
aagtcttcat ctctttatct cttcatcagg tttgatggtt acctaatatg gtccatgggt   6060
acatgcatgg ttaaattagg tggccaactt tgttgtgaac gatagaattt tttttatatt   6120
aagtaaacta ttttttatatt atgaaataat aataaaaaaa atattttatc attattaaca   6180
aaatcatatt agttaatttg ttaactctat aataaaagaa atactgtaac attcacatta   6240
catggtaaca tctttccacc ctttcatttg tttttttgttt gatgactttt tttcttgttt   6300
aaatttattt cccttctttt aaatttggaa tacattatca tcatatataa actaaaaatac  6360
taaaaacagg attacacaaa tgataaataa taacacaaat atttataaat ctagctgcaa   6420
tatatttaaa ctagctatat cgatattgta aaataaaact agctgcattg atactgataa   6480
aaaaatatca tgtgctttct ggactgatga tgcagtatac ttttgacatt gcctttattt   6540
tatttttcag aaaagctttc ttagttctgg gttcttcatt atttgtttcc catctccatt   6600
gtgaattgaa tcatttgctt cgtgtcacaa atacaattta gntaggtaca tgcattggtc   6660
agattcacgg tttattatgt catgacttaa gttcatggta gtacattacc tgccacgcat   6720
gcattatatt ggttagattt gataggcaaa tttggttgtc aacaatataa atataaataa   6780
tgttttttata ttacgaaata acagtgatca aacaaacag ttttatcttt attaacaaga   6840
ttttgttttt gtttgatgac gttttttaat gtttacgctt tcccccttct tttgaattta   6900
gaacactta tcatcataaa atcaaatact aaaaaaatta catatttcat aaataataac   6960
acaaatattt ttaaaaaatc tgaaataata atgaacaata ttacatatta tcacgaaaat   7020
tcattaataa aaatattata taaataaaat gtaatagtag ttatatgtag gaaaaaagta   7080
ctgcacgcat aatatataca aaagattaa aatgaactat tataaataat aacactaaat   7140
taatggtgaa tcatatcaaa ataatgaaaa agtaaataaa atttgtaatt aacttctata   7200
tgtattacac acacaaataa taaataatag taaaaaaaat tatgataaat atttaccatc   7260
tcataagata tttaaaataa tgataaaaat atagattatt ttttatgcaa ctagctagcc   7320
aaaaagagaa cacgggtata tataaaaaga gtacctttaa attctactgt acttccttta   7380
ttcctgacgt ttttatatca agtggacata cgtgaagatt ttaattatca gtctaaatat   7440
ttcattagca cttaatactt ttctgtttta ttcctatcct ataagtagtc ccgattctcc   7500
```

| | |
|---|---|
| caacattgct tattcacaca actaactaag aaagtcttcc atagcccccc aagcggccgc | 7560 |
| ttctagctag ctagggtttg ggtagtgagt gtaataaagt tgcaaagttt ttggttaggt | 7620 |
| tacgttttga ccttattatt atagttcaaa gggaaacatt aattaaaggg gattatgaag | 7680 |
| tcctcctctc cacctccccc ttgaggatct tactgggtga attgagctgc ttagctatgg | 7740 |
| atcccacagt tctacccatc aataagtgct tttgtggtag tcttgtggct tccatatctg | 7800 |
| gggagcttca tttgccttta tagtattaac cttctggggg agaaggagag gaggacaccc | 7860 |
| ttctcttctt ttctctcata ataatttaaa tttgttatag actctaaact ttaaatgttt | 7920 |
| tttttgaagt ttttccgttt ttctcttttg ccatgatccc gttcttgctg tggagtaacc | 7980 |
| ttgtccgagg tatgtgcatg attagatcca tacttaattt gtgtgcatca cgaaggtgag | 8040 |
| gttgaaatga actttgcttt tttgaccttt taggaaagtt cttttgttgc agtaatcaat | 8100 |
| tttaattagt tttaattgac actattactt ttattgtcat ctttgttagt tttattgttg | 8160 |
| aattgagtgc atatttccta ggaaattctc ttacctaaca ttttttatac agatctatgc | 8220 |
| tcttggctct tgcccttact cttggccttg tgttggttat ttgtctacat atttattgac | 8280 |
| tggtcgatga gacatgtcac aattcttggg cttatttgtt ggtctaataa aaggagtgct | 8340 |
| tattgaaaga tcaagacgga gattcggttt tatataaata aactaaagat gacatattag | 8400 |
| tgtgttgatg tctcttcagg ataatttttg tttgaaataa tatggtaatg tcttgtctaa | 8460 |
| atttgtgtac ataattctta ctgattttttt ggattgttgg attttataaa acaaatctgc | 8520 |

<210> SEQ ID NO 70
<211> LENGTH: 8520
<212> TYPE: DNA
<213> ORGANISM: artificial sequence
<220> FEATURE:
<223> OTHER INFORMATION: 159 ALDO B-KS126 -plasmid
<220> FEATURE:
<221> NAME/KEY: misc_feature
<222> LOCATION: (6642)..(6642)
<223> OTHER INFORMATION: n=a,c,g,or t

<400> SEQUENCE: 70

| | |
|---|---|
| ggccgcgaca caagtgtgag agtactaaat aaatgctttg gttgtacgaa atcattacac | 60 |
| taaataaaat aatcaaagct tatatatgcc ttccgctaag gccgaatgca aagaaattgg | 120 |
| ttctttctcg ttatcttttg ccacttttac tagtacgtat taattactac ttaatcatct | 180 |
| ttgtttacgg ctcattatat ccgtcgacgg cgcgcccgat catccggata tagttcctcc | 240 |
| tttcagcaaa aaacccctca agacccgttt agaggcccca aggggttatg ctagttattg | 300 |
| ctcagcggtg gcagcagcca actcagcttc ctttcgggct ttgttagcag ccggatcgat | 360 |
| ccaagctgta cctcactatt cctttgccct cggacgagtg ctggggcgtc ggtttccact | 420 |
| atcggcgagt acttctacac agccatcggt ccagacggcc gcgcttctgc gggcgatttg | 480 |
| tgtacgcccg acagtcccgg ctccggatcg acgattgcg tcgcatcgac cctgcgccca | 540 |
| agctgcatca tcgaaattgc cgtcaaccaa gctctgatag agttggtcaa gaccaatgcg | 600 |
| gagcatatac gcccggagcc gcggcgatcc tgcaagctcc ggatgcctcc gctcgaagta | 660 |
| gcgcgtctgc tgctccatac aagccaacca cggcctccag aagaagatgt tggcgacctc | 720 |
| gtattgggaa tccccgaaca tcgcctcgct ccagtcaatg accgctgtta tgcggccatt | 780 |
| gtccgtcagg acattgttgg agccgaaatc cgcgtgcacg aggtgccgga cttcggggca | 840 |
| gtcctcggcc caaagcatca gctcatcgag agcctgcgcg acgacgcac tgacggtgtc | 900 |
| gtccatcaca gtttgccagt gatacacatg gggatcagca atcgcgcata tgaaatcacg | 960 |

```
ccatgtagtg tattgaccga ttccttgcgg tccgaatggg ccgaacccgc tcgtctggct   1020
aagatcggcc gcagcgatcg catccatagc ctccgcgacc ggctgcagaa cagcgggcag   1080
ttcggtttca ggcaggtctt gcaacgtgac accctgtgca cggcgggaga tgcaataggt   1140
caggctctcg ctgaattccc caatgtcaag cacttccgga atcgggagcg cggccgatgc   1200
aaagtgccga taaacataac gatctttgta gaaaccatcg gcgcagctat ttacccgcag   1260
gacatatcca cgccctccta catcgaagct gaaagcacga gattcttcgc cctccgagag   1320
ctgcatcagg tcggagacgc tgtcgaactt tcgatcaga aacttctcga cagacgtcgc    1380
ggtgagttca ggcttttcca tgggtatatc tccttcttaa agttaaacaa aattatttct   1440
agagggaaac cgttgtggtc tccctatagt gagtcgtatt aatttcgcgg gatcgagatc   1500
gatccaattc caatcccaca aaaatctgag cttaacagca cagttgctcc tctcagagca   1560
gaatcgggta ttcaacaccc tcatatcaac tactacgttg tgtataacgg tccacatgcc   1620
ggtatatacg atgactgggg ttgtacaaag gcggcaacaa acggcgttcc cggagttgca   1680
cacaagaaat ttgccactat tacagaggca agagcagcag ctgacgcgta cacaacaagt   1740
cagcaaacag acaggttgaa cttcatcccc aaaggagaag ctcaactcaa gcccaagagc   1800
tttgctaagg ccctaacaag cccaccaaag caaaaagccc actggctcac gctaggaacc   1860
aaaaggccca gcagtgatcc agccccaaaa gagatctcct ttgccccgga gattacaatg   1920
gacgatttcc tctatcttta cgatctagga aggaagttcg aaggtgaagg tgacgacact   1980
atgttcacca ctgataatga aaggttagc ctcttcaatt tcagaaagaa tgctgaccca    2040
cagatggtta gagaggccta cgcagcaggt ctcatcaaga cgatctaccc gagtaacaat   2100
ctccaggaga tcaaatacct tcccaagaag gttaaagatg cagtcaaaag attcaggact   2160
aattgcatca agaacacaga gaaagacata tttctcaaga tcagaagtac tattccagta   2220
tggacgattc aaggcttgct tcataaacca aggcaagtaa tagagattgg agtctctaaa   2280
aaggtagttc ctactgaatc taaggccatg catggagtct aagattcaaa tcgaggatct   2340
aacagaactc gccgtgaaga ctggcgaaca gttcatacag agtcttttac gactcaatga   2400
caagaagaaa atcttcgtca acatggtgga gcacgacact ctggtctact ccaaaaatgt   2460
caaagataca gtctcagaag accaaagggc tattgagact tttcaacaaa ggataatttc   2520
gggaaacctc ctcggattcc attgcccagc tatctgtcac ttcatcgaaa ggacagtaga   2580
aaaggaaggt ggctcctaca aatgccatca ttgcgataaa ggaaaggcta tcattcaaga   2640
tgcctctgcc gacagtggtc ccaaagatgg accccaccc acgaggagca tcgtggaaaa    2700
agaagacgtt ccaaccacgt cttcaaagca agtggattga tgtgacatct ccactgacgt   2760
aagggatgac gcacaatccc actatccttc gcaagaccct tcctctatat aaggaagttc   2820
atttcatttg gagaggacac gctcgagctc atttctctat tacttcagcc ataacaaaag   2880
aactcttttc tcttcttatt aaaccatgaa aaagcctgaa ctcaccgcga cgtctgtcga   2940
gaagtttctg atcgaaaagt tcgacagcgt ctccgacctg atgcagctct cggagggcga   3000
agaatctcgt gctttcagct tcgatgtagg agggcgtgga tatgtcctgc gggtaaatag   3060
ctgcgccgat ggtttctaca agatcgtta tgtttatcgg cactttgcat cggccgcgct    3120
cccgattccg gaagtgcttg acattgggga attcagcgag agcctgacct attgcatctc   3180
ccgccgtgca cagggtgtca cgttgcaaga cctgcctgaa accgaactgc ccgctgttct   3240
gcagccggtc gcggaggcca tggatgcgat cgctgcggcc gatcttagcc agacgagcgg   3300
```

```
gttcggccca ttcggaccgc aaggaatcgg tcaatacact acatggcgtg atttcatatg   3360
cgcgattgct gatccccatg tgtatcactg gcaaactgtg atggacgaca ccgtcagtgc   3420
gtccgtcgcg caggctctcg atgagctgat gctttgggcc gaggactgcc ccgaagtccg   3480
gcacctcgtg cacgcggatt tcggctccaa caatgtcctg acggacaatg ccgcataac    3540 agcggtcatt gactggagcg aggcgatgtt cggggattcc caatacgagg tcgccaacat   3600
cttcttctgg aggccgtggt tggcttgtat ggagcagcag acgcgctact tcgagcggag   3660
gcatccggag cttgcaggat cgccgcggct ccgggcgtat atgctccgca ttggtcttga   3720
ccaactctat cagagcttgg ttgacggcaa tttcgatgat gcagcttggg cgcagggtcg   3780
atgcgacgca atcgtccgat ccggagccgg gactgtcggg cgtacacaaa tcgcccgcag   3840
aagcgcggcc gtctggaccg atggctgtgt agaagtactc gccgatagtg aaaccgacg    3900 ccccagcact cgtccgaggg caaggaata gtgaggtacc taaagaagga gtgcgtcgaa    3960
gcagatcgtt caaacatttg gcaataaagt ttcttaagat tgaatcctgt tgccggtctt   4020
gcgatgatta tcatataatt tctgttgaat tacgttaagc atgtaataat taacatgtaa   4080
tgcatgacgt tattatgag atgggttttt atgattagag tcccgcaatt atacatttaa     4140
tacgcgatag aaaacaaaat atagcgcgca aactaggata aattatcgcg cgcggtgtca   4200
tctatgttac tagatcgatg tcgaatctga tcaacctgca ttaatgaatc ggccaacgcg   4260
cggggagagg cggtttgcgt attgggcgct cttccgcttc ctcgctcact gactcgctgc   4320
gctcggtcgt tcggctgcgg cgagcggtat cagctcactc aaaggcggta atacggttat   4380
ccacagaatc aggggataac gcaggaaaga acatgtgagc aaaaggccag caaaaggcca   4440
ggaaccgtaa aaaggccgcg ttgctggcgt ttttccatag gctccgcccc cctgacgagc   4500
atcacaaaaa tcgacgctca gtcagaggt ggcgaaaccc gacaggacta taaagatacc    4560
aggcgtttcc ccctggaagc tccctcgtgc gctctcctgt tccgaccctg ccgcttaccg   4620
gatacctgtc cgcctttctc ccttcgggaa gcgtggcgct ttctcaatgc tcacgctgta   4680
ggtatctcag ttcggtgtag gtcgttcgct ccaagctggg ctgtgtgcac gaaccccccg   4740
ttcagcccga ccgctgcgcc ttatccggta actatcgtct tgagtccaac ccggtaagac   4800
acgacttatc gccactggca gcagccactg gtaacaggat tagcagagcg aggtatgtag   4860
gcggtgctac agagttcttg aagtggtggc ctaactacgg ctacactaga aggacagtat   4920
ttggtatctg cgctctgctg aagccagtta ccttcggaaa aagagttggt agctcttgat   4980
ccggcaaaca aaccaccgct ggtagcggtg gtttttttgt ttgcaagcag cagattacgc   5040
gcagaaaaaa aggatctcaa gaagatcctt tgatcttttc tacggggtct gacgctcagt   5100
ggaacgaaaa ctcacgttaa gggattttgg tcatgacatt aacctataaa aataggcgta   5160
tcacgaggcc ctttcgtctc gcgcgtttcg gtgatgacgg tgaaaacctc tgacacatgc   5220
agctcccgga cggtcaca gcttgtctgt aagcggatgc cgggagcaga caagcccgtc    5280
agggcgcgtc agcgggtgtt ggcgggtgtc ggggctggct taactatgcg gcatcagagc   5340
agattgtact gagagtgcac catatggaca tattgtcgtt agaacgcggc tacaattaat   5400
acataacctt atgtatcata cacatacgat ttaggtgaca ctatagaacg gcgcgccaag   5460
cttggatcct cgaagagaag ggttaataac acactttttt aacattttta acacaaattt   5520
tagttattta aaatttatt aaaaatttta aataagaag aggaactctt taaataaatc      5580
taacttacaa aatttatgat ttttaataag ttttcaccaa taaaaatgt cataaaaata    5640 tgttaaaaag tatattatca atattctctt tatgataaat aaaaagaaaa aaaaaataaa   5700
```

```
agttaagtga aaatgagatt gaagtgactt taggtgtgta taaatatatc aaccccgcca    5760
acaatttatt taatccaaat atattgaagt atattattcc atagccttta tttatttata    5820
tatttattat ataaaagctt tatttgttct aggttgttca tgaaatattt ttttggtttt    5880
atctccgttg taagaaaatc atgtgctttg tgtcgccact cactattgca gcttttcat     5940 gcattggtca gattgacggt tgattgtatt tttgttttt atggttttgt gttatgactt     6000
aagtcttcat ctctttatct cttcatcagg tttgatggtt acctaatatg gtccatgggt    6060
acatgcatgg ttaaattagg tggccaactt tgttgtgaac gatagaattt tttttatatt    6120
aagtaaacta ttttatatt atgaaataat aataaaaaaa atattttatc attattaaca    6180
aaatcatatt agttaatttg ttaactctat aataaaagaa atactgtaac attcacatta    6240
catggtaaca tctttccacc ctttcatttg tttttgttt gatgactttt tttcttgttt     6300
aaatttattt cccttctttt aaatttggaa tacattatca tcatatataa actaaaatac    6360
taaaaacagg attacacaaa tgataaataa taacacaaat atttataaat ctagctgcaa    6420
tatatttaaa ctagctatat cgatattgta aaataaaact agctgcattg atactgataa    6480
aaaaatatca tgtgctttct ggactgatga tgcagtatac ttttgacatt gcctttattt    6540
tatttttcag aaaagctttc ttagttctgg gttcttcatt atttgtttcc catctccatt    6600
gtgaattgaa tcatttgctt cgtgtcacaa atacaaattta gntaggtaca tgcattggtc    6660
agattcacgg tttattatgt catgacttaa gttcatggta gtacattacc tgccacgcat    6720
gcattatatt ggttagattt gataggcaaa tttggttgtc aacaatataa atataaataa    6780 tgttttata ttacgaaata acagtgatca aaacaaacag ttttatcttt attaacaaga    6840
ttttgttttt gtttgatgac gttttttaat gtttacgctt tcccccttct tttgaattta    6900
gaacacttta tcatcataaa atcaaatact aaaaaaatta catatttcat aaataataac    6960
acaaatattt ttaaaaaatc tgaaataata atgaacaata ttacatatta tcacgaaaat    7020
tcattaataa aaatattata taaataaaat gtaatagtag ttatatgtag gaaaaaagta    7080
ctgcacgcat aatatataca aaagattaa aatgaactat tataaataat aacactaaat    7140
taatggtgaa tcatatcaaa ataatgaaaa agtaaataaa atttgtaatt aacttctata    7200
tgtattacac acacaaataa taaataatag taaaaaaaat tatgataaat atttaccatc    7260
tcataagata tttaaaataa tgataaaaat atagattatt tttatgcaa ctagctagcc      7320 aaaaagagaa cacgggtata tataaaaga gtacctttaa attctactgt acttcctta      7380 ttcctgacgt ttttatatca agtggacata cgtgaagatt ttaattatca gtctaaatat    7440
ttcattagca cttaatactt ttctgttta ttcctatcct ataagtagtc ccgattctcc     7500
caacattgct tattcacaca actaactaag aaagtcttcc atagcccccc aagcggccgc    7560
ttctagctag ctagggtttg ggtagtgagt gtaataaagt tgcaaagttt tggttaggt     7620 tacgttttga ccttattatt atagttcaaa gggaaacatt aattaaaggg gattatgaag    7680 atgatgggc gtcggatttg ttgaggatct tactgggtga attgagctgc ttagctatgg     7740
atcccacagt tctacccatc aataagtgct tttgtggtag tcttgtggct tccatatctg    7800
gggagcttca tttgccttta tagtattaac cttctcaaat ccctcgcccc atcatcaccc    7860
ttctcttctt ttctctcata ataatttaaa tttgttatag actctaaact ttaaatgttt    7920
tttttgaagt ttttccgttt ttctcttttg ccatgatccc gttcttgctg tggagtaacc    7980
ttgtccgagg tatgtgcatg attagatcca tacttaattt gtgtgcatca cgaaggtgag    8040
```

```
gttgaaatga actttgcttt tttgaccttt taggaaagtt cttttgttgc agtaatcaat    8100
tttaattagt tttaattgac actattactt ttattgtcat ctttgttagt tttattgttg    8160
aattgagtgc atatttccta ggaaattctc ttacctaaca tttttatac agatctatgc    8220 tcttggctct tgcccttact cttggccttg tgttggttat ttgtctacat atttattgac    8280
tggtcgatga gacatgtcac aattcttggg cttatttgtt ggtctaataa aaggagtgct    8340
tattgaaaga tcaagacgga gattcggttt tatataaata aactaaagat gacatattag    8400
tgtgttgatg tctcttcagg ataattttg tttgaaataa tatggtaatg tcttgtctaa    8460
atttgtgtac ataattctta ctgattttt ggattgttgg atttttataa acaaatctgc    8520

<210> SEQ ID NO 71
<211> LENGTH: 29
<212> TYPE: DNA
<213> ORGANISM: artificial sequence
<220> FEATURE:
<223> OTHER INFORMATION: AthHpaIL fwd primer

<400> SEQUENCE: 71
ccatggggcc cgccaccgcc gtggaagcg                                         29

<210> SEQ ID NO 72
<211> LENGTH: 30
<212> TYPE: DNA
<213> ORGANISM: artificial sequence
<220> FEATURE:
<223> OTHER INFORMATION: AthHpaIL rev primer

<400> SEQUENCE: 72
gtcgacttcg ctccagtact tctcatcatc                                        30

<210> SEQ ID NO 73
<211> LENGTH: 3913
<212> TYPE: DNA
<213> ORGANISM: artificial sequence
<220> FEATURE:
<223> OTHER INFORMATION: pGEM-T At4g10750 plasmid

<400> SEQUENCE: 73
aatcactagt gaattcgcgg ccgcctgcag gtcgaccata tgggagagct cccaacgcgt      60
tggatgcata gcttgagtat tctatagtgt cacctaaata gcttggcgta atcatggtca     120
tagctgtttc ctgtgtgaaa ttgttatccg ctcacaattc cacacaacat acgagccgga     180
agcataaagt gtaaagcctg gggtgcctaa tgagtgagct aactcacatt aattgcgttg     240
cgctcactgc ccgctttcca gtcgggaaac ctgtcgtgcc agctgcatta atgaatcggc     300
caacgcgcgg ggagaggcgg tttgcgtatt gggcgctctt ccgcttcctc gctcactgac     360
tcgctgcgct cggtcgttcg gctgcggcga gcggtatcag ctcactcaaa ggcggtaata     420
cggttatcca cagaatcagg ggataacgca ggaaagaaca tgtgagcaaa aggccagcaa     480
aaggccagga accgtaaaaa ggccgcgttg ctggcgtttt tccataggct ccgcccccct     540
gacgagcatc acaaaaatcg acgctcaagt cagaggtggc gaaacccgac aggactataa     600
agataccagg cgtttccccc tggaagctcc ctcgtgcgct ctcctgttcc gaccctgccg     660
cttaccggat acctgtccgc ctttctccct tcgggaagcg tggcgctttc tcatagctca     720
cgctgtaggt atctcagttc ggtgtaggtc gttcgctcca agctgggctg tgtgcacgaa     780
ccccccgttc agcccgaccg ctgcgcctta tccggtaact atcgtcttga gtccaacccg     840
gtaagacacg acttatcgcc actggcagca gccactggta acaggattag cagagcgagg     900
```

```
tatgtaggcg gtgctacaga gttcttgaag tggtggccta actacggcta cactagaaga    960
acagtatttg gtatctgcgc tctgctgaag ccagttacct tcggaaaaag agttggtagc   1020
tcttgatccg gcaaacaaac caccgctggt agcggtggtt ttttgtttg caagcagcag    1080
attacgcgca gaaaaaaagg atctcaagaa gatcctttga tcttttctac ggggtctgac   1140
gctcagtgga acgaaaactc acgttaaggg attttggtca tgagattatc aaaaaggatc   1200
ttcacctaga tccttttaaa ttaaaaatga agttttaaat caatctaaag tatatatgag   1260
taaacttggt ctgacagtta ccaatgctta atcagtgagg cacctatctc agcgatctgt   1320
ctatttcgtt catccatagt tgcctgactc cccgtcgtgt agataactac gatacgggag   1380
ggcttaccat ctggccccag tgctgcaatg ataccgcgag acccacgctc accggctcca   1440
gatttatcag caataaacca gccagccgga agggccgagc gcagaagtgg tcctgcaact   1500
ttatccgcct ccatccagtc tattaattgt tgccgggaag ctagagtaag tagttcgcca   1560
gttaatagtt tgcgcaacgt tgttgccatt gctacaggca tcgtggtgtc acgctcgtcg   1620
tttggtatgg cttcattcag ctccggttcc caacgatcaa ggcgagttac atgatccccc   1680
atgttgtgca aaaaagcggt tagctccttc ggtcctccga tcgttgtcag aagtaagttg   1740
gccgcagtgt tatcactcat ggttatggca gcactgcata attctcttac tgtcatgcca   1800
tccgtaagat gcttttctgt gactggtgag tactcaacca agtcattctg agaatagtgt   1860
atgcggcgac cgagttgctc ttgcccggcg tcaatacggg ataataccgc gccacatagc   1920
agaactttaa aagtgctcat cattggaaaa cgttcttcgg ggcgaaaact ctcaaggatc   1980
ttaccgctgt tgagatccag ttcgatgtaa cccactcgtg cacccaactg atcttcagca   2040
tcttttactt tcaccagcgt ttctgggtga gcaaaaacag gaaggcaaaa tgccgcaaaa   2100
aagggaataa gggcgacacg gaaatgttga atactcatac tcttcctttt tcaatattat   2160
tgaagcattt atcagggtta ttgtctcatg agcggataca tatttgaatg tatttagaaa   2220
aataaacaaa taggggttcc gcgcacattt ccccgaaaag tgccacctga tgcggtgtga   2280
aataccgcac agatgcgtaa ggagaaaata ccgcatcagg aaattgtaag cgttaatatt   2340
ttgttaaaat tcgcgttaaa ttttgttaa atcagctcat ttttaacca ataggccgaa     2400
atcggcaaaa tcccttataa atcaaaagaa tagaccgaga tagggttgag tgttgttcca   2460
gtttggaaca agagtccact attaagaac gtggactcca acgtcaaagg gcgaaaaacc    2520
gtctatcagg gcgatggccc actacgtgaa ccatcaccct aatcaagttt tttggggtcg   2580
aggtgccgta aagcactaaa tcggaaccct aaagggagcc cccgatttag agcttgacgg   2640
ggaaagccgg cgaacgtggc gagaaaggaa gggaagaaag cgaaaggagc gggcgctagg   2700
gcgctggcaa gtgtagcggt cacgctgcgc gtaaccacca cacccgccgc gcttaatgcg   2760
ccgctacagg gcgcgtccat tcgccattca ggctgcgcaa ctgttgggaa gggcgatcgg   2820
tgcgggcctc ttcgctatta cgccagctgg cgaaaggggg atgtgctgca aggcgattaa   2880
gttgggtaac gccagggttt tcccagtcac gacgttgtaa aacgacggcc agtgaattgt   2940
aatacgactc actatagggc gaattgggcc cgacgtcgca tgctcccggc cgccatggcg   3000
gccgcgggaa ttcgattcca tggggcccgc caccgccgtg gaagcgatca cgaatcgatc   3060
caaaaactcc ttgaaatctc gtctccgtgg aggagaaact ctctacggtc tcttttact    3120
ctccttctcg ccgacattag ccgagatcgc tgctcacgcc ggttacgatt acgtcgtcgt   3180
tgatatggaa catggtcccg gaggtatacc ggaagctttg gattgtattc gagctcttaa   3240
```

```
cgccgccgga acatcagcca ttctccgatt accggaaaac tcaccaacct gggctaaaaa    3300
agctctagat ctaggtccac aaggaatcat gttcccaatg atcgaatctc gtaaagacgc    3360
taccaaagcg gtgtcgtatt gccggtttcc tcccgacggt atccgtggat cggcgcacac    3420
ggtggtgaga gcttctaact acggaatcga tgaagggtat ttaagtaatt acgcagagga    3480
gattctgatt atgtgccagg tggaatcagg tgaaggagtg aagaaagctg atgaaatcgc    3540
agccgttgat ggtgttgact gtgtgcaaat gggaccgttg atcttagtg cgagtttagg     3600
gtatttgtgg gatcctggac ataagaaagt gagagagatg atgaagaagg ctgagaaatc    3660
tgtgctgagc actgatccgg cgaaaggcgg ggcttacttg tcgggtttcg cgatgccgca    3720
cgatggagct ggtgagattc ggggacgtgg ttaccatatg gtcgccggag ctgttgatgt    3780
tggattgttt aggaatgctg ctgttgaaga tgtgaggaga ttcaagatgg gtttggtcaa    3840
tgaatcggac agtgaggatt cgtcggaaca tgataaagat gttgatgatg agaagtactg    3900
gagcgaagtc gac                                                       3913

<210> SEQ ID NO 74
<211> LENGTH: 6142
<212> TYPE: DNA
<213> ORGANISM: artificial sequence
<220> FEATURE:
<223> OTHER INFORMATION: pET28a At4g10750 plasmid

<400> SEQUENCE: 74
tcgacaagct tgcggccgca ctcgagcacc accaccacca ccactgagat ccggctgcta      60
acaaagcccg aaaggaagct gagttggctg ctgccaccgc tgagcaataa ctagcataac     120
cccttggggc ctctaaacgg gtcttgaggg gttttttgct gaaaggagga actatatccg     180
gattggcgaa tgggacgcgc cctgtagcgg cgcattaagc gcggcgggtg tggtggttac     240
gcgcagcgtg accgctacac ttgccagcgc cctagcgccc gctcctttcg ctttcttccc     300
ttcctttctc gccacgttcg ccggctttcc ccgtcaagct ctaaatcggg gctcccttt      360
agggttccga tttagtgctt tacggcacct cgaccccaaa aaacttgatt agggtgatgg     420
ttcacgtagt gggccatcgc cctgatagac ggtttttcgc cctttgacgt tggagtccac     480
gttctttaat agtggactct tgttccaaac tggaacaaca ctcaacccta tctcggtcta     540
ttctttgat ttataaggga ttttgccgat ttcggcctat tggttaaaaa atgagctgat      600
ttaacaaaaa tttaacgcga attttaacaa aatattaacg tttacaattt caggtggcac     660
ttttcgggga aatgtgcgcg gaaccccat ttgtttattt ttctaaatac attcaaatat      720
gtatccgctc atgaattaat tcttagaaaa actcatcgag catcaaatga aactgcaatt     780
tattcatatc aggattatca ataccatatt tttgaaaaag ccgtttctgt aatgaaggag     840
aaaactcacc gaggcagttc cataggatgg caagatcctg gtatcggtct gcgattccga    900
ctcgtccaac atcaatacaa cctattaatt tcccctcgtc aaaaataagg ttatcaagtg     960
agaaatcacc atgagtgacg actgaatccg gtgagaatgg caaaagttta tgcatttctt    1020
tccagacttg ttcaacaggc cagccattac gctcgtcatc aaaatcactc gcatcaacca    1080
aaccgttatt cattcgtgat tgcgcctgag cgagacgaaa tacgcgatcg ctgttaaaag    1140
gacaattaca acaggaatc gaatgcaacc ggcgcaggaa cactgccagc gcatcaacaa     1200
tattttcacc tgaatcagga tattcttcta atacctggaa tgctgttttc ccggggatcg    1260
cagtggtgag taaccatgca tcatcaggag tacggataaa atgcttgatg gtcggaagag    1320
gcataaattc cgtcagccag tttagtctga ccatctcatc tgtaacatca ttggcaacgc    1380
```

```
tacctttgcc atgtttcaga aacaactctg gcgcatcggg cttcccatac aatcgataga   1440
ttgtcgcacc tgattgcccg acattatcgc gagcccattt atacccatat aaatcagcat   1500
ccatgttgga atttaatcgc ggcctagagc aagacgtttc ccgttgaata tggctcataa   1560
caccccttgt attactgttt atgtaagcag acagttttat tgttcatgac caaaatccct   1620
taacgtgagt tttcgttcca ctgagcgtca gaccccgtag aaaagatcaa aggatcttct   1680
tgagatcctt ttttctgcgc gtaatctgct gcttgcaaa caaaaaaacc accgctacca   1740
gcggtggttt gtttgccgga tcaagagcta ccaactcttt ttccgaaggt aactggcttc   1800
agcagagcgc agataccaaa tactgtcctt ctagtgtagc cgtagttagg ccaccacttc   1860
aagaactctg tagcaccgcc tacatacctc gctctgctaa tcctgttacc agtggctgct   1920
gccagtggcg ataagtcgtg tcttaccggg ttggactcaa gacgatagtt accgataag    1980
gcgcagcggt cgggctgaac ggggggttcg tgcacacagc ccagcttgga gcgaacgacc   2040
tacaccgaac tgagatacct acagcgtgag ctatgagaaa gcgccacgct tcccgaaggg   2100
agaaaggcgg acaggtatcc ggtaagcggc agggtcggaa caggagagcg cacgagggag   2160
cttccagggg gaaacgcctg gtatctttat agtcctgtcg ggtttcgcca cctctgactt   2220
gagcgtcgat ttttgtgatg ctcgtcaggg gggcggagcc tatggaaaaa cgccagcaac   2280
gcggcctttt tacggttcct ggccttttgc tggccttttg ctcacatgtt ctttcctgcg   2340
ttatcccctg attctgtgga taaccgtatt accgcctttg agtgagctga taccgctcgc   2400
cgcagccgaa cgaccgagcg cagcgagtca gtgagcgagg aagcggaaga gcgcctgatg   2460
cggtatttc tccttacgca tctgtgcggt atttcacacc gcatatatgg tgcactctca   2520
gtacaatctg ctctgatgcc gcatagttaa gccagtatac actccgctat cgctacgtga   2580
ctgggtcatg gctgcgcccc gacacccgcc aacacccgct gacgcgccct gacgggcttg   2640
tctgctcccg gcatccgctt acagacaagc tgtgaccgtc tccggagct gcatgtgtca    2700
gaggttttca ccgtcatcac cgaaacgcgc gaggcagctg cggtaaagct catcagcgtg   2760
gtcgtgaagc gattcacaga tgtctgcctg ttcatccgcg tccagctcgt tgagtttctc   2820
cagaagcgtt aatgtctggc ttctgataaa gcgggccatg ttaagggcgg ttttttcctg   2880
tttggtcact gatgcctccg tgtaaggggg atttctgttc atgggggtaa tgataccgat   2940
gaaacgagag aggatgctca cgatacgggt tactgatgat gaacatgccc ggttactgga   3000
acgttgtgag ggtaaacaac tggcggtatg gatgcggcgg gaccagagaa aaatcactca   3060
gggtcaatgc cagcgcttcg ttaatacaga tgtaggtgtt ccacagggta gccagcagca   3120
tcctgcgatg cagatccgga acataatggt gcagggcgct gacttccgcg tttccagact   3180
ttacgaaaca cggaaaccga agaccattca tgttgttgct caggtcgcag acgttttgca   3240
gcagcagtcg cttcacgttc gctcgcgtat cggtgattca ttctgctaac cagtaaggca   3300
accccgccag cctagccggg tcctcaacga caggagcacg atcatgcgca cccgtggggc   3360
cgccatgccg gcgataatgg cctgcttctc gccgaaacgt ttggtggcgg gaccagtgac   3420
gaaggcttga gcgagggcgt gcaagattcc gaataccgca agcgacaggc cgatcatcgt   3480
cgcgctccag cgaaagcggt cctcgccgaa aatgacccag agcgctgccg gcacctgtcc   3540
tacgagttgc atgataaaga agacagtcat aagtgcggcg acgatagtca tgccccgcgc   3600
ccaccggaag gagctgactg ggttgaaggc tctcaagggc atcggtcgag atccggtgc   3660
ctaatgagtg agctaactta cattaattgc gttgcgctca ctgcccgctt tccagtcggg   3720
```

```
aaacctgtcg tgccagctgc attaatgaat cggccaacgc gcggggagag gcggtttgcg   3780
tattgggcgc cagggtggtt tttcttttca ccagtgagac gggcaacagc tgattgccct   3840
tcaccgcctg gccctgagag agttgcagca agcggtccac gctggtttgc cccagcaggc   3900
gaaaatcctg tttgatggtg gttaacggcg ggatataaca tgagctgtct tcggtatcgt   3960
cgtatcccac taccgagata tccgcaccaa cgcgcagccc ggactcggta atggcgcgca   4020
ttgcgcccag cgccatctga tcgttggcaa ccagcatcgc agtgggaacg atgccctcat   4080
tcagcatttg catggtttgt tgaaaaccgg acatggcact ccagtcgcct tcccgttccg   4140
ctatcggctg aatttgattg cgagtgagat atttatgcca gccagccaga cgcagacgcg   4200
ccgagacaga acttaatggg cccgctaaca gcgcgatttg ctggtgaccc aatgcgacca   4260
gatgctccac gcccagtcgc gtaccgtctt catgggagaa aataatactg ttgatgggtg   4320
tctggtcaga gacatcaaga aataacgccg gaacattagt gcaggcagct tccacagcaa   4380
tggcatcctg gtcatccagc ggatagttaa tgatcagccc actgacgcgt tgcgcgagaa   4440
gattgtgcac cgccgcttta caggcttcga cgccgcttcg ttctaccatc gacaccacca   4500
cgctggcacc cagttgatcg gcgcgagatt taatcgccgc gacaatttgc gacggcgcgt   4560
gcagggccag actggaggtg gcaacgccaa tcagcaacga ctgtttgccc gccagttgtt   4620
gtgccacgcg gttgggaatg taattcagct ccgccatcgc cgcttccact ttttcccgcg   4680
ttttcgcaga aacgtggctg gcctggttca ccacgcggga aacggtctga taagagacac   4740
cggcatactc tgcgacatcg tataacgtta ctggtttcac attcaccacc ctgaattgac   4800
tctcttccgg gcgctatcat gccataccgc gaaaggtttt gcgccattcg atggtgtccg   4860
ggatctcgac gctctccctt atgcgactcc tgcattagga agcagcccag tagtaggttg   4920
aggccgttga gcaccgccgc cgcaaggaat ggtgcatgca aggagatggc gcccaacagt   4980
cccccggcca cggggcctgc caccataccc acgccgaaac aagcgctcat gagcccgaag   5040
tggcgagccc gatcttcccc atcggtgatg tcggcgatat aggcgccagc aaccgcacct   5100
gtggcgccgg tgatgccggc cacgatgcgt ccggcgtaga ggatcgagat ctcgatcccg   5160
cgaaattaat acgactcact ataggggaat tgtgagcgga taacaattcc cctctagaaa   5220
taattttgtt taactttaag aaggagatat accatggggc ccgccaccgc cgtggaagcg   5280
atcacgaatc gatccaaaaa ctccttgaaa tctcgtctcc gtggaggaga aactctctac   5340
ggtctctttt tactctcctt ctcgccgaca ttagccgaga tcgctgctca cgccggttac   5400
gattacgtcg tcgttgatat ggaacatggt cccggaggta taccggaagc tttggattgt   5460
attcgagctc ttaacgccgc cggaacatca gccattctcc gattaccgga aaactcacca   5520
acctgggcta aaaaagctct agatctaggt ccacaaggaa tcatgttccc aatgatcgaa   5580
tctcgtaaag acgctaccaa agcggtgtcg tattgccggt ttcctcccga cggtatccgt   5640
ggatcggcgc acacggtggt gagagcttct aactacggaa tcgatgaagg gtatttaagt   5700
aattacgcag aggagattct gattatgtgc caggtggaat caggtgaagg agtgaagaaa   5760
gctgatgaaa tcgcagccgt tgatggtgtt gactgtgtgc aaatgggacc gttggatctt   5820
agtgcgagtt tagggtattt gtgggatcct ggacataaga aagtgagaga gatgatgaag   5880
aaggctgaga atctgtgct gagcactgat ccggcgaaag gcggggctta cttgtcgggt   5940
ttcgcgatgc cgcacgatgg agctggtgag attcggggac gtggttacca tatggtcgcc   6000
ggagctgttg atgttggatt gtttaggaat gctgctgttg aagatgtgag gagattcaag   6060
atgggtttgg tcaatgaatc ggacagtgag gattcgtcgg aacatgataa agatgttgat   6120
```
gatgagaagt actggagcga ag    6142

<210> SEQ ID NO 75
<211> LENGTH: 311
<212> TYPE: PRT
<213> ORGANISM: artificial sequence
<220> FEATURE:
<223> OTHER INFORMATION: At4g10750 gene product including a c-terminal pET28A-derived hexa-histidine tag

<400> SEQUENCE: 75

Met Gly Pro Ala Thr Ala Val Glu Ala Ile Thr Asn Arg Ser Lys Asn
1               5                   10                  15

Ser Leu Lys Ser Arg Leu Arg Gly Gly Glu Thr Leu Tyr Gly Leu Phe
            20                  25                  30

Leu Leu Ser Phe Ser Pro Thr Leu Ala Glu Ile Ala Ala His Ala Gly
        35                  40                  45

Tyr Asp Tyr Val Val Asp Met Glu His Gly Pro Gly Ile Pro
    50                  55                  60

Glu Ala Leu Asp Cys Ile Arg Ala Leu Asn Ala Ala Gly Thr Ser Ala
65                  70                  75                  80

Ile Leu Arg Leu Pro Glu Asn Ser Pro Thr Trp Ala Lys Lys Ala Leu
                85                  90                  95

Asp Leu Gly Pro Gln Gly Ile Met Phe Pro Met Ile Glu Ser Arg Lys
            100                 105                 110

Asp Ala Thr Lys Ala Val Ser Tyr Cys Arg Phe Pro Pro Asp Gly Ile
        115                 120                 125

Arg Gly Ser Ala His Thr Val Val Arg Ala Ser Asn Tyr Gly Ile Asp
    130                 135                 140

Glu Gly Tyr Leu Ser Asn Tyr Ala Glu Glu Ile Leu Ile Met Cys Gln
145                 150                 155                 160

Val Glu Ser Gly Glu Gly Val Lys Lys Ala Asp Glu Ile Ala Ala Val
                165                 170                 175

Asp Gly Val Asp Cys Val Gln Met Gly Pro Leu Asp Leu Ser Ala Ser
            180                 185                 190

Leu Gly Tyr Leu Trp Asp Pro Gly His Lys Lys Val Arg Glu Met Met
        195                 200                 205

Lys Lys Ala Glu Lys Ser Val Leu Ser Thr Asp Pro Ala Lys Gly Gly
    210                 215                 220

Ala Tyr Leu Ser Gly Phe Ala Met Pro His Asp Gly Ala Gly Glu Ile
225                 230                 235                 240

Arg Gly Arg Gly Tyr His Met Val Ala Gly Ala Val Asp Val Gly Leu
                245                 250                 255

Phe Arg Asn Ala Ala Val Glu Asp Val Arg Arg Phe Lys Met Gly Leu
            260                 265                 270

Val Asn Glu Ser Asp Ser Glu Asp Ser Ser Glu His Asp Lys Asp Val
        275                 280                 285

Asp Asp Glu Lys Tyr Trp Ser Glu Val Asp Lys Leu Ala Ala Ala Leu
    290                 295                 300

Glu His His His His His His
305                 310

<210> SEQ ID NO 76
<211> LENGTH: 30
<212> TYPE: DNA
<213> ORGANISM: artificial sequence
<220> FEATURE:
<223> OTHER INFORMATION: Soy HpaIL fwd-primer

<400> SEQUENCE: 76
catatgccca aatccatccc caccctctcc                                30

<210> SEQ ID NO 77
<211> LENGTH: 31
<212> TYPE: DNA
<213> ORGANISM: artificial sequence
<220> FEATURE:
<223> OTHER INFORMATION: Soy HpaIL rev-primer

<400> SEQUENCE: 77
gagctcaatt cactccagta cttctcatca c                              31

<210> SEQ ID NO 78
<211> LENGTH: 3904
<212> TYPE: DNA
<213> ORGANISM: artificial sequence
<220> FEATURE:
<223> OTHER INFORMATION: pGEM-T Glyma09g21760 -plasmid

<400> SEQUENCE: 78

```
aatcactagt gaattcgcgg ccgcctgcag gtcgaccata tgggagagct cccaacgcgt    60
tggatgcata gcttgagtat tctatagtgt cacctaaata gcttggcgta atcatggtca   120
tagctgtttc ctgtgtgaaa ttgttatccg ctcacaattc cacacaacat acgagccgga   180
agcataaagt gtaaagcctg gggtgcctaa tgagtgagct aactcacatt aattgcgttg   240
cgctcactgc ccgctttcca gtcgggaaac ctgtcgtgcc agctgcatta atgaatcggc   300
caacgcgcgg ggagaggcgg tttgcgtatt gggcgctctt ccgcttcctc gctcactgac   360
tcgctgcgct cggtcgttcg ctgcggcga gcggtatcag ctcactcaaa ggcggtaata   420
cggttatcca cagaatcagg ggataacgca ggaaagaaca tgtgagcaaa aggccagcaa   480
aaggccagga accgtaaaaa ggccgcgttg ctggcgtttt tccataggct ccgcccccct   540
gacgagcatc acaaaaatcg acgctcaagt cagaggtggc gaaacccgac aggactataa   600
agataccagg cgtttccccc tggaagctcc ctcgtgcgct ctcctgttcc gaccctgccg   660
cttaccggat acctgtccgc ctttctccct tcgggaagcg tggcgctttc tcatagctca   720
cgctgtaggt atctcagttc ggtgtaggtc gttcgctcca agctgggctg tgtgcacgaa   780
ccccccgttc agcccgaccg ctgcgcctta tccggtaact atcgtcttga gtccaacccg   840
gtaagacacg acttatcgcc actggcagca gccactggta acaggattag cagagcgagg   900
tatgtaggcg gtgctacaga gttcttgaag tggtggccta actacggcta cactagaaga   960
acagtatttg gtatctgcgc tctgctgaag ccagttacct tcggaaaaag agttggtagc  1020
tcttgatccg gcaaacaaac caccgctggt agcggtggtt ttttgtttg caagcagcag   1080 attacgcgca gaaaaaaagg atctcaagaa gatcctttga tcttttctac ggggtctgac  1140
gctcagtgga acgaaaactc acgttaaggg attttggtca tgagattatc aaaaaggatc  1200
ttcacctaga tccttttaaa ttaaaaatga agttttaaat caatctaaag tatatatgag  1260
taaacttggt ctgacagtta ccaatgctta atcagtgagg cacctatctc agcgatctgt  1320
ctatttcgtt catccatagt tgcctgactc cccgtcgtgt agataactac gatacgggag  1380
ggcttaccat ctggccccag tgctgcaatg ataccgcgag acccacgctc accggctcca  1440
gatttatcag caataaacca gccagccgga agggccgagc gcagaagtgg tcctgcaact  1500
```

```
ttatccgcct ccatccagtc tattaattgt tgccgggaag ctagagtaag tagttcgcca    1560
gttaatagtt tgcgcaacgt tgttgccatt gctacaggca tcgtggtgtc acgctcgtcg    1620
tttggtatgg cttcattcag ctccggttcc caacgatcaa ggcgagttac atgatccccc    1680
atgttgtgca aaaagcggt tagctccttc ggtcctccga tcgttgtcag aagtaagttg     1740
gccgcagtgt tatcactcat ggttatggca gcactgcata attctcttac tgtcatgcca    1800
tccgtaagat gcttttctgt gactggtgag tactcaacca agtcattctg agaatagtgt    1860
atgcggcgac cgagttgctc ttgcccggcg tcaatacggg ataataccgc gccacatagc    1920
agaactttaa aagtgctcat cattggaaaa cgttcttcgg ggcgaaaact ctcaaggatc    1980
ttaccgctgt tgagatccag ttcgatgtaa cccactcgtg cacccaactg atcttcagca    2040
tcttttactt tcaccagcgt ttctgggtga gcaaaaacag gaaggcaaaa tgccgcaaaa    2100
aagggaataa gggcgacacg gaaatgttga atactcatac tcttcctttt tcaatattat    2160
tgaagcattt atcagggtta ttgtctcatg agcggataca tatttgaatg tatttagaaa    2220
aataaacaaa taggggttcc gcgcacattt ccccgaaaag tgccacctga tgcggtgtga    2280
aataccgcac agatgcgtaa ggagaaaata ccgcatcagg aaattgtaag cgttaatatt    2340
ttgttaaaat tcgcgttaaa ttttttgttaa atcagctcat tttttaacca ataggccgaa    2400
atcggcaaaa tcccttataa atcaaaagaa tagaccgaga tagggttgag tgttgttcca    2460
gtttggaaca agagtccact attaaagaac gtggactcca acgtcaaagg cgaaaaacc    2520 gtctatcagg gcgatggccc actacgtgaa ccatcaccct aatcaagttt tttggggtcg    2580
aggtgccgta aagcactaaa tcggaaccct aaagggagcc cccgatttag agcttgacgg    2640
ggaaagccgg cgaacgtggc gagaaaggaa gggaagaaag cgaaaggagc gggcgctagg    2700
gcgctggcaa gtgtagcggt cacgctgcgc gtaaccacca cacccgccgc gcttaatgcg    2760
ccgctacagg gcgcgtccat tcgccattca ggctgcgcaa ctgttgggaa gggcgatcgg    2820
tgcgggcctc ttcgctatta cgccagctgg cgaaaggggg atgtgctgca aggcgattaa    2880
gttgggtaac gccagggttt tcccagtcac gacgttgtaa aacgacggcc agtgaattgt    2940
aatacgactc actatagggc gaattgggcc cgacgtcgca tgctcccggc cgccatggcg    3000
gccgcgggaa ttcgattcat atgcccaaat ccatccccac cctctcctcc tcctcccccc    3060
taaacctcaa gtcccgactc cgcaacggag agacccttta cggcctcttc ctcctctcct    3120
tctcccccac cctcgccgag atcgcgggcc acgccggcta cgacttcgtc gtcgtcgaca    3180
tggagcacgg tcctggcggc atccacgacg ccctcccctg cctccacgcc ctcgccgccg    3240
ccaacaccgc cgccatcctc cgcgtcccgg agtccaccgc tgcttgggcc aagaaagccc    3300
tcgacctcgg cccacagggc ctcatgttcc ccatgattga ctccctgcag tcggcccagg    3360
acgcggtctc ctactgccgt tttcctccca ccggactccg cggcgcggcc caccccatcg    3420
tccgggcctc caagtacggc ctcgacgagg ggtatctcgg taattacctc gacgagctgt    3480
taatcatgtg ccaggtggag tccgaggagg gcgtggcgaa cgctggcgcg atcgccgctg    3540
ttgatggtgt ggactgcgtg cagatggggc cgttggatct gagtgctagt ttagggtact    3600
tgtgggaccc tgggcacaag aaagtgaggg aggtgttgag ggaggccgag aacaaggttt    3660
tggagagccg aaacgacgac gttgagagtg gggcctactt ggcgggtttc gctacggcgt    3720
atgatggggc gagggatttg aggtcgcgtg ggtatcacat ggtaagtggc gccgtcgacg    3780
tggggctgtt ccggagcgcg gccctggagg atgtcacgcg gttcaagatg gacggggatg    3840
ggtcggagag tgatgaggga gaggagaaag agggtgatga gaagtactgg agtgaattga    3900
```

<210> SEQ ID NO 79
<211> LENGTH: 6144
<212> TYPE: DNA
<213> ORGANISM: artificial sequence
<220> FEATURE:
<223> OTHER INFORMATION: pET29a Glyma09g21760 plasmid

<400> SEQUENCE: 79

```
gctc                                                                 3904 ccgtcgacaa gcttgcggcc gcactcgagc accaccacca ccaccactga gatccggctg      60
ctaacaaagc ccgaaaggaa gctgagttgg ctgctgccac cgctgagcaa taactagcat     120
aaccccttgg ggcctctaaa cgggtcttga ggggttttt gctgaaagga ggaactatat     180
ccggattggc gaatgggacg cgccctgtag cggcgcatta agcgcggcgg gtgtggtggt     240
tacgcgcagc gtgaccgcta cacttgccag cgccctagcg cccgctcctt tcgctttctt     300
cccttccttt ctcgccacgt tcgccggctt tccccgtcaa gctctaaatc ggggggctccc    360
tttagggttc cgatttagtg ctttacggca cctcgacccc aaaaaacttg attagggtga    420
tggttcacgt agtgggccat cgccctgata cggttttt cgccctttga cgttggagtc     480
cacgttcttt aatagtggac tcttgttcca aactggaaca cactcaacc ctatctcggt     540
ctattctttt gatttataag ggattttgcc gatttcggcc tattggttaa aaaatgagct     600
gatttaacaa aaatttaacg cgaattttaa caaaatatta cgtttacaa tttcaggtgg     660
cacttttcgg ggaaatgtgc gcggaacccc tatttgttta ttttttctaaa tacattcaaa     720
tatgtatccg ctcatgaatt aattcttaga aaaactcatc gagcatcaaa tgaaactgca     780
atttattcat atcaggatta tcaataccat attttttgaaa aagccgtttc tgtaatgaag     840
gagaaaactc accgaggcag ttccatagga tggcaagatc ctggtatcgg tctgcgattc     900
cgactcgtcc aacatcaata aacctatta atttccccctc gtcaaaaata aggttatcaa     960
gtgagaaatc accatgagtg acgactgaat ccggtgagaa tggcaaaagt ttatgcattt    1020
cttttccagac ttgttcaaca ggccagccat tacgctcgtc atcaaaatca ctcgcatcaa    1080
ccaaaccgtt attcattcgt gattgcgcct gagcgagacg aaatacgcga tcgctgttaa    1140
aaggacaatt acaaacagga atcgaatgca accggcgcag gaacactgcc agcgcatcaa    1200
caatatttttc acctgaatca ggatattctt ctaatacctg gaatgctgtt ttcccgggga    1260
tcgcagtggt gagtaaccat gcatcatcag gagtacggat aaaatgcttg atggtcggaa    1320
gaggcataaa ttccgtcagc cagtttagtc tgaccatctc atctgtaaca tcattggcaa    1380
cgctaccttt gccatgtttc agaaacaact ctggcgcatc gggcttccca tacaatcgat    1440
agattgtcgc acctgattgc ccgacattat cgcgagccca tttataccca tataaatcag    1500
catccatgtt ggaatttaat cgcggcctag agcaagacgt ttcccgttga atatggctca    1560
taacacccct tgtattactg tttatgtaag cagacagttt tattgttcat gaccaaaatc    1620
ccttaacgtg agttttcgtt ccactgagcg tcagaccccg tagaaaagat caaaggatct    1680
tcttgagatc ctttttttct gcgcgtaatc tgctgcttgc aaacaaaaaa accaccgcta    1740
ccagcggtgg tttgtttgcc ggatcaagag ctaccaactc tttttccgaa ggtaactggc    1800
ttcagcagag cgcagatacc aaatactgtc cttctagtgt agccgtagtt aggccaccac    1860
ttcaagaact ctgtagcacc gcctacatac ctcgctctgc taatcctgtt accagtggct    1920
gctgccagtg gcgataagtc gtgtcttacc gggttggact caagacgata gttaccggat    1980
```

```
aaggcgcagc ggtcgggctg aacgggggt tcgtgcacac agcccagctt ggagcgaacg    2040
acctacaccg aactgagata cctacagcgt gagctatgag aaagcgccac gcttcccgaa    2100
gggagaaagg cggacaggta tccggtaagc ggcagggtcg aacaggaga gcgcacgagg     2160 gagcttccag ggggaaacgc ctggtatctt tatagtcctg tcgggtttcg ccacctctga    2220
cttgagcgtc gattttgtg atgctcgtca ggggggcgga gcctatggaa aaacgccagc    2280
aacgcggcct ttttacggtt cctggccttt tgctggcctt ttgctcacat gttctttcct    2340
gcgttatccc ctgattctgt ggataaccgt attaccgcct ttgagtgagc tgataccgct    2400
cgccgcagcc gaacgaccga gcgcagcgag tcagtgagcg aggaagcgga agagcgcctg    2460
atgcggtatt ttctccttac gcatctgtgc ggtatttcac accgcatata tggtgcactc    2520
tcagtacaat ctgctctgat gccgcatagt taagccagta tacactccgc tatcgctacg    2580
tgactgggtc atggctgcgc cccgacaccc gccaacaccc gctgacgcgc cctgacgggc    2640
ttgtctgctc ccggcatccg cttacagaca agctgtgacc gtctccggga gctgcatgtg    2700
tcagaggttt tcaccgtcat caccgaaacg cgcgaggcag ctgcggtaaa gctcatcagc    2760
gtggtcgtga agcgattcac agatgtctgc ctgttcatcc gcgtccagct cgttgagttt    2820
ctccagaagc gttaatgtct ggcttctgat aaagcgggcc atgttaaggg cggttttttc    2880
ctgtttggtc actgatgcct ccgtgtaagg gggatttctg ttcatggggg taatgatacc    2940
gatgaaacga gagaggatgc tcacgatacg ggttactgat gatgaacatg cccggttact    3000
ggaacgttgt gagggtaaac aactggcggt atggatgcgg cgggaccaga gaaaaatcac    3060
tcagggtcaa tgccagcgct tcgttaatac agatgtaggt gttccacagg gtagccagca    3120
gcatcctgcg atgcagatcc ggaacataat ggtgcagggc gctgacttcc gcgtttccag    3180
actttacgaa acacggaaac cgaagaccat tcatgttgtt gctcaggtcg cagacgtttt    3240
gcagcagcag tcgcttcacg ttcgctcgcg tatcggtgat tcattctgct aaccagtaag    3300
gcaaccccgc cagcctagcc gggtcctcaa cgacaggagc acgatcatgc gcacccgtgg    3360
ggccgccatg ccggcgataa tggcctgctt ctcgccgaaa cgtttggtgg cgggaccagt    3420
gacgaaggct tgagcgaggg cgtgcaagat tccgaatacc gcaagcgaca ggccgatcat    3480
cgtcgcgctc cagcgaaagc ggtcctcgcc gaaaatgacc cagagcgctg ccggcacctg    3540
tcctacgagt tgcatgataa agaagacagt cataagtgcg gcgacgatag tcatgccccg    3600
cgcccaccgg aaggagctga ctgggttgaa ggctctcaag gcatcggtc gagatcccgg     3660 tgcctaatga gtgagctaac ttacattaat tgcgttgcgc tcactgcccg ctttccagtc    3720
gggaaacctg tcgtgccagc tgcattaatg aatcggccaa cgcgcgggga gaggcggttt    3780
gcgtattggg cgccagggtg ttttttcttt tcaccagtga cgggcaac agctgattgc      3840 ccttcaccgc ctggccctga gagagttgca gcaagcggtc cacgctggtt tgccccagca    3900
ggcgaaaatc ctgtttgatg gtggttaacg gcgggatata acatgagctg tcttcggtat    3960
cgtcgtatcc cactaccgag atgtccgcac caacgcgcag cccggactcg gtaatggcgc    4020
gcattgcgcc cagcgccatc tgatcgttgg caaccagcat cgcagtggga acgatgccct    4080
cattcagcat ttgcatggtt tgttgaaaac cggacatggc actccagtcg ccttcccgtt    4140
ccgctatcgg ctgaatttga ttgcgagtga atatttatg ccagccagcc agacgcagac     4200
gcgccgagac agaacttaat gggcccgcta acagcgcgat ttgctggtga cccaatgcga    4260
ccagatgctc cacgcccagt cgcgtaccgt cttcatggga gaaaataata ctgttgatgg    4320
gtgtctggtc agagacatca agaaataacg ccggaacatt agtgcaggca gcttccacag    4380
```

```
caatggcatc ctggtcatcc agcggatagt taatgatcag cccactgacg cgttgcgcga    4440
gaagattgtg caccgccgct ttacaggctt cgacgccgct tcgttctacc atcgacacca    4500
ccacgctggc acccagttga tcggcgcgag atttaatcgc cgcgacaatt tgcgacggcg    4560
cgtgcagggc cagactggag gtggcaacgc caatcagcaa cgactgtttg cccgccagtt    4620
gttgtgccac gcggttggga atgtaattca gctccgccat cgccgcttcc acttttccc     4680
gcgttttcgc agaaacgtgg ctggcctggt tcaccacgcg ggaaacggtc tgataagaga    4740
caccggcata ctctgcgaca tcgtataacg ttactggttt cacattcacc accctgaatt    4800
gactctcttc cgggcgctat catgccatac cgcgaaaggt tttgcgccat tcgatggtgt    4860
ccgggatctc gacgctctcc cttatgcgac tcctgcatta ggaagcagcc agtagtagg     4920
ttgaggccgt tgagcaccgc cgccgcaagg aatggtgcat gcaaggagat ggcgcccaac    4980
agtcccccgg ccacggggcc tgccaccata cccacgccga acaagcgct catgagcccg     5040
aagtggcgag cccgatcttc cccatcggtg atgtcggcga tataggcgcc agcaaccgca    5100
cctgtggcgc cggtgatgcc ggccacgatg cgtccggcgt agaggatcga gatcgatctc    5160
gatcccgcga aattaatacg actcactata ggggaattgt gagcggataa caattcccct    5220
ctagaaataa ttttgtttaa ctttaagaag gagatataca tatgcccaaa tccatcccca    5280
ccctctcctc ctcctccccc ctaaacctca gtcccgact ccgcaacgga gaccctt       5340
acggcctctt cctcctctcc ttctccccca ccctcgccga gatcgcgggc cacgccggct    5400
acgacttcgt cgtcgtcgac atggagcacg gtcctggcgg catccacgac gccctccct     5460
gcctccacgc cctcgccgcc gccaacaccg ccgccatcct ccgcgtcccg gagtccaccg    5520
ctgcttgggc caagaaagcc ctcgacctcg gcccacaggg cctcatgttc ccatgattg     5580
actccctgca gtcggcccag gacgcggtct cctactgccg ttttcctccc accggactcc    5640
gcggcgcggc ccaccccatc gtccgggcct ccaagtacgg cctcgacgag ggtatctcg     5700
gtaattacct cgacgagctg ttaatcatgt gccaggtgga gtccgaggag ggcgtggcga    5760
acgctggcgc gatcgccgct gttgatggtg tggactgcgt gcagatgggg ccgttggatc    5820
tgagtgctag tttagggtac ttgtgggacc ctgggcacaa gaaagtgagg gaggtgttga    5880
gggaggccga gaacaaggtt ttggagagcc gaaacgacga cgttgagagt ggggcctact    5940
tggcgggttt cgctacggcg tatgatgggg cgagggattt gaggtcgcgt gggtatcaca    6000
tggtaagtgg cgccgtcgac gtggggctgt tccggagcgc ggccctggag gatgtcacgc    6060
ggttcaagat ggacggggat gggtcggaga gtgatgaggg agaggagaaa gagggtgatg    6120
agaagtactg gagtgaattg agct                                            6144
```

<210> SEQ ID NO 80
<211> LENGTH: 310
<212> TYPE: PRT
<213> ORGANISM: artificial sequence
<220> FEATURE:
<223> OTHER INFORMATION: Glyma09g21760 His TAG

<400> SEQUENCE: 80

```
Met Pro Lys Ser Ile Pro Thr Leu Ser Ser Ser Pro Leu Asn Leu
1               5                  10                  15

Lys Ser Arg Leu Arg Asn Gly Glu Thr Leu Tyr Gly Leu Phe Leu Leu
            20                  25                  30

Ser Phe Ser Pro Thr Leu Ala Glu Ile Ala Gly His Ala Gly Tyr Asp
        35                  40                  45
```

```
Phe Val Val Asp Met Glu His Gly Pro Gly Ile His Asp Ala
     50                  55                  60

Leu Pro Cys Leu His Ala Leu Ala Ala Ala Asn Thr Ala Ala Ile Leu
 65                  70                  75                  80

Arg Val Pro Glu Ser Thr Ala Ala Trp Ala Lys Lys Ala Leu Asp Leu
                     85                  90                  95

Gly Pro Gln Gly Leu Met Phe Pro Met Ile Asp Ser Leu Gln Ser Ala
                    100                 105                 110

Gln Asp Ala Val Ser Tyr Cys Arg Phe Pro Pro Thr Gly Leu Arg Gly
                115                 120                 125

Ala Ala His Pro Ile Val Arg Ala Ser Lys Tyr Gly Leu Asp Glu Gly
            130                 135                 140

Tyr Leu Gly Asn Tyr Leu Asp Glu Leu Leu Ile Met Cys Gln Val Glu
145                 150                 155                 160

Ser Glu Glu Gly Val Ala Asn Ala Gly Ala Ile Ala Ala Val Asp Gly
                165                 170                 175

Val Asp Cys Val Gln Met Gly Pro Leu Asp Leu Ser Ala Ser Leu Gly
                180                 185                 190

Tyr Leu Trp Asp Pro Gly His Lys Lys Val Arg Glu Val Leu Arg Glu
                195                 200                 205

Ala Glu Asn Lys Val Leu Glu Ser Arg Asn Asp Val Glu Ser Gly
            210                 215                 220

Ala Tyr Leu Ala Gly Phe Ala Thr Ala Tyr Asp Gly Ala Arg Asp Leu
225                 230                 235                 240

Arg Ser Arg Gly Tyr His Met Val Ser Gly Ala Val Asp Val Gly Leu
                    245                 250                 255

Phe Arg Ser Ala Ala Leu Glu Asp Val Thr Arg Phe Lys Met Asp Gly
                260                 265                 270

Asp Gly Ser Glu Ser Asp Glu Gly Glu Lys Glu Gly Asp Glu Lys
                275                 280                 285

Tyr Trp Ser Glu Leu Ser Ser Val Asp Lys Leu Ala Ala Ala Leu Glu
                290                 295                 300

His His His His His His
305                 310

<210> SEQ ID NO 81
<211> LENGTH: 27
<212> TYPE: DNA
<213> ORGANISM: artificial sequence
<220> FEATURE:
<223> OTHER INFORMATION: Rice HpaIL fwd primer

<400> SEQUENCE: 81
ccatggccgc cgccgccgcc gcctccg                                    27

<210> SEQ ID NO 82
<211> LENGTH: 27
<212> TYPE: DNA
<213> ORGANISM: artificial sequence
<220> FEATURE:
<223> OTHER INFORMATION: Rice HpaIL rev primer

<400> SEQUENCE: 82
aagcttctca ctccagtacc cgtcgtc                                    27

<210> SEQ ID NO 83
<211> LENGTH: 3931
```

<212> TYPE: DNA
<213> ORGANISM: artificial sequence
<220> FEATURE:
<223> OTHER INFORMATION: pGEM-T Os09g36030 plasmid

<400> SEQUENCE: 83

| | | | | | |
|---|---|---|---|---|---|
| aatcactagt | gaattcgcgg | ccgcctgcag | gtcgaccata | tgggagagct | cccaacgcgt | 60 |
| tggatgcata | gcttgagtat | tctatagtgt | cacctaaata | gcttggcgta | atcatggtca | 120 |
| tagctgtttc | ctgtgtgaaa | ttgttatccg | ctcacaattc | cacacaacat | acgagccgga | 180 |
| agcataaagt | gtaaagcctg | gggtgcctaa | tgagtgagct | aactcacatt | aattgcgttg | 240 |
| cgctcactgc | ccgctttcca | gtcgggaaac | ctgtcgtgcc | agctgcatta | atgaatcggc | 300 |
| caacgcgcgg | ggagaggcgg | tttgcgtatt | gggcgctctt | ccgcttcctc | gctcactgac | 360 |
| tcgctgcgct | cggtcgttcg | gctgcggcga | gcggtatcag | ctcactcaaa | ggcggtaata | 420 |
| cggttatcca | cagaatcagg | ggataacgca | ggaaagaaca | tgtgagcaaa | aggccagcaa | 480 |
| aaggccagga | accgtaaaaa | ggccgcgttg | ctggcgtttt | tccataggct | ccgcccccct | 540 |
| gacgagcatc | acaaaaatcg | acgctcaagt | cagaggtggc | gaaacccgac | aggactataa | 600 |
| agataccagg | cgtttccccc | tggaagctcc | ctcgtgcgct | ctcctgttcc | gaccctgccg | 660 |
| cttaccggat | acctgtccgc | cttctccct | tcgggaagcg | tggcgctttc | tcatagctca | 720 |
| cgctgtaggt | atctcagttc | ggtgtaggtc | gttcgctcca | agctgggctg | tgtgcacgaa | 780 |
| ccccccgttc | agcccgaccg | ctgcgcctta | tccggtaact | atcgtcttga | gtccaacccg | 840 |
| gtaagacacg | acttatcgcc | actggcagca | gccactggta | acaggattag | cagagcgagg | 900 |
| tatgtaggcg | gtgctacaga | gttcttgaag | tggtggccta | actacggcta | cactagaaga | 960 |
| acagtatttg | gtatctgcgc | tctgctgaag | ccagttacct | tcggaaaaag | agttggtagc | 1020 |
| tcttgatccg | gcaaacaaac | caccgctggt | agcggtggtt | tttttgtttg | caagcagcag | 1080 |
| attacgcgca | gaaaaaaagg | atctcaagaa | gatcctttga | tcttttctac | ggggtctgac | 1140 |
| gctcagtgga | acgaaaactc | acgttaaggg | attttggtca | tgagattatc | aaaaaggatc | 1200 |
| ttcacctaga | tccttttaaa | ttaaaaatga | agttttaaat | caatctaaag | tatatatgag | 1260 |
| taaacttggt | ctgacagtta | ccaatgctta | atcagtgagg | cacctatctc | agcgatctgt | 1320 |
| ctatttcgtt | catccatagt | tgcctgactc | cccgtcgtgt | agataactac | gatacgggag | 1380 |
| ggcttaccat | ctggccccag | tgctgcaatg | ataccgcgag | acccacgctc | accggctcca | 1440 |
| gatttatcag | caataaacca | gccagccgga | agggccgagc | gcagaagtgg | tcctgcaact | 1500 |
| ttatccgcct | ccatccagtc | tattaattgt | tgccgggaag | ctagagtaag | tagttcgcca | 1560 |
| gttaatagtt | tgcgcaacgt | tgttgccatt | gctacaggca | tcgtggtgtc | acgctcgtcg | 1620 |
| tttggtatgg | cttcattcag | ctccggttcc | caacgatcaa | ggcgagttac | atgatccccc | 1680 |
| atgttgtgca | aaaaagcggt | tagctccttc | ggtcctccga | tcgttgtcag | aagtaagttg | 1740 |
| gccgcagtgt | tatcactcat | ggttatggca | gcactgcata | attctcttac | tgtcatgcca | 1800 |
| tccgtaagat | gcttttctgt | gactggtgag | tactcaacca | agtcattctg | agaatagtgt | 1860 |
| atgcggcgac | cgagttgctc | ttgcccggcg | tcaatacggg | ataataccgc | gccacatagc | 1920 |
| agaactttaa | aagtgctcat | cattggaaaa | cgttcttcgg | ggcgaaaact | ctcaaggatc | 1980 |
| ttaccgctgt | tgagatccag | ttcgatgtaa | cccactcgtg | cacccaactg | atcttcagca | 2040 |
| tcttttactt | tcaccagcgt | ttctgggtga | gcaaaaacag | gaaggcaaaa | tgccgcaaaa | 2100 |
| aagggaataa | gggcgacacg | gaaatgttga | atactcatac | tcttcctttt | tcaatattat | 2160 |

-continued

| | |
|---|---|
| tgaagcattt atcagggtta ttgtctcatg agcggataca tatttgaatg tatttagaaa | 2220 |
| aataaacaaa tagggttcc gcgcacattt ccccgaaaag tgccacctga tgcggtgtga | 2280 |
| aataccgcac agatgcgtaa ggagaaaata ccgcatcagg aaattgtaag cgttaatatt | 2340 |
| ttgttaaaat tcgcgttaaa tttttgttaa atcagctcat ttttttaacca ataggccgaa | 2400 |
| atcggcaaaa tcccttataa atcaaaagaa tagaccgaga tagggttgag tgttgttcca | 2460 |
| gtttggaaca agagtccact attaaagaac gtggactcca acgtcaaagg cgaaaaaacc | 2520 |
| gtctatcagg gcgatggccc actacgtgaa ccatcaccct aatcaagttt tttggggtcg | 2580 |
| aggtgccgta aagcactaaa tcggaaccct aaagggagcc cccgatttag agcttgacgg | 2640 |
| ggaaagccgg cgaacgtggc gagaaaggaa gggaagaaag cgaaaggagc gggcgctagg | 2700 |
| gcgctggcaa gtgtagcggt cacgctgcgc gtaaccacca cacccgccgc gcttaatgcg | 2760 |
| ccgctacagg gcgcgtccat tcgccattca ggctgcgcaa ctgttgggaa gggcgatcgg | 2820 |
| tgcgggcctc ttcgctatta cgccagctgg cgaaaggggg atgtgctgca aggcgattaa | 2880 |
| gttgggtaac gccagggttt tcccagtcac gacgttgtaa aacgacggcc agtgaattgt | 2940 |
| aatacgactc actatagggc gaattgggcc cgacgtcgca tgctcccggc cgccatggcg | 3000 |
| gccgcgggaa ttcgattcca tggccgccgc cgccgccgcc tccgacctcc tctacgccgc | 3060 |
| accctccctc aagtcccggc tcgccgccgg ggagaccctg tacgggctct tcctcctctc | 3120 |
| cttctccccc acgctcgccg agctcgccgc cctcgccggc tacgactacg tcgtcgtcga | 3180 |
| catggagcac ggccccggcg gcgttcccga ggcgctggcc tgcctccgcg ccctcgacgc | 3240 |
| cgcccgtacc ccagccgtca tccgcctccc cgaggccggc cccatctggg ccaagaaggc | 3300 |
| cctcgacctc ggccccgcgg gcctcatggt ccccgccgtc gagtcccccg ccgccgcggc | 3360 |
| cgccgccgtg tcgcactgcc gctaccgccc ccgaggcgtt cgcggcgccg cccacccccat | 3420 |
| cgtccgcgcc tccgcgtacg gcctcgacga ctcctacctc tcccgctgcg aggacgagac | 3480 |
| gctaatcatc tgccaggtcg agaccgccgc tggcattgcg gaggtcgacg ccattgccgc | 3540 |
| cgtcgacggc gtcgacgtcg tccagatggg accgctcgac ttgtcagcca gcatggggta | 3600 |
| cctgtgggac ccagggaaca ggaaggtgcg agccaggctg agggaggccg agaagaaggt | 3660 |
| gttggatgcc aggaagaaga atgtgacagc ttcagatggc aatgtcgcat atctaggcgg | 3720 |
| attcgccatg ccgaacgacc cggcagagca gctcaagctg aggggttacc acatggtgtc | 3780 |
| tggtgcagtg gacattggga tgttccggaa ggcggcgttg gaggatgtca agcggttcaa | 3840 |
| ggaggcagtg atggaaatcg gcgaggagga aggcgaggag gacgatgaaa agaaggacaa | 3900 |
| ggaagacgac gggtactgga gtgagaagct t | 3931 |

<210> SEQ ID NO 84
<211> LENGTH: 6154
<212> TYPE: DNA
<213> ORGANISM: artificial sequence
<220> FEATURE:
<223> OTHER INFORMATION: pET28a Os09g36030 plasmid

<400> SEQUENCE: 84

| | |
|---|---|
| agcttgcggc cgcactcgag caccaccacc accaccactg agatccggct gctaacaaag | 60 |
| cccgaaagga agctgagttg ctgctgccgcca ccgctgagca ataactagca taacccttg | 120 |
| gggcctctaa acgggtcttg aggggttttt tgctgaaagg aggaactata tccggattgg | 180 |
| cgaatgggac gcgccctgta gcggcgcatt aagcgcggcg ggtgtggtgg ttacgcgcag | 240 |
| cgtgaccgct acacttgcca gcgccctagc gcccgctcct ttcgctttct tcccttcctt | 300 |

```
tctcgccacg ttcgccggct ttccccgtca agctctaaat cggggctcc ctttagggtt      360 ccgatttagt gctttacggc acctcgaccc caaaaaactt gattagggtg atggttcacg      420
tagtgggcca tcgccctgat agacggtttt tcgcccttg acgttggagt ccacgttctt       480
taatagtgga ctcttgttcc aaactggaac aacactcaac cctatctcgg tctattcttt      540
tgatttataa gggattttgc cgatttcggc ctattggtta aaaatgagc tgatttaaca       600 aaaatttaac gcgaatttta acaaaatatt aacgtttaca atttcaggtg cacttttcg       660 gggaaatgtg cgcggaaccc ctatttgttt attttctaa atacattcaa atatgtatcc      720
gctcatgaat taattcttag aaaaactcat cgagcatcaa atgaaactgc aatttattca      780
tatcaggatt atcaatacca tattttgaa aaagccgttt ctgtaatgaa ggagaaaact       840
caccgaggca gttccatagg atggcaagat cctggtatcg gtctgcgatt ccgactcgtc      900
caacatcaat acaacctatt aatttcccct cgtcaaaaat aaggttatca agtgagaaat      960
caccatgagt gacgactgaa tccggtgaga atggcaaaag tttatgcatt tctttccaga     1020
cttgttcaac aggccagcca ttacgctcgt catcaaaatc actcgcatca accaaaccgt     1080
tattcattcg tgattgcgcc tgagcgagac gaaatacgcg atcgctgtta aaaggacaat     1140
tacaaacagg aatcgaatgc aaccggcgca ggaacactgc cagcgcatca acaatatttt     1200
cacctgaatc aggatattct tctaatacct ggaatgctgt tttcccgggg atcgcagtgg     1260
tgagtaacca tgcatcatca ggagtacgga taaaatgctt gatggtcgga agaggcataa     1320
attccgtcag ccagtttagt ctgaccatct catctgtaac atcattgca acgctacctt      1380 tgccatgttt cagaaacaac tctggcgcat cgggcttccc atacaatcga tagattgtcg     1440
cacctgattg cccgacatta tcgcgagccc atttatacc atataaatca gcatccatgt      1500
tggaatttaa tcgcggccta gagcaagacg tttcccgttg aatatggctc ataacacccc     1560
ttgtattact gtttatgtaa gcagacagtt ttattgttca tgaccaaaat cccttaacgt     1620
gagttttcgt tccactgagc gtcagacccc gtagaaaaga tcaaaggatc ttcttgagat     1680
cctttttttc tgcgcgtaat ctgctgcttg caaacaaaaa aaccaccgct accagcggtg     1740
gtttgtttgc cggatcaaga ctaccaact cttttttccga aggtaactgg cttcagcaga     1800
gcgcagatac caaatactgt ccttctagtg tagccgtagt taggccacca cttcaagaac     1860
tctgtagcac cgcctacata cctcgctctg ctaatcctgt taccagtggc tgctgccagt     1920
ggcgataagt cgtgtcttac cgggttggac tcaagacgat agttaccgga taaggcgcag     1980
cggtcgggct gaacggggg ttcgtgcaca cagcccagct tggagcgaac gacctacacc      2040
gaactgagat acctacagcg tgagctatga gaaagcgcca cgcttcccga agggagaaag     2100
gcggacaggt atccggtaag cggcaggtc ggaacaggag agcgcacgag ggagcttcca     2160
gggggaaacg cctggtatct ttatagtcct gtcgggttc gccacctctg acttgagcgt      2220 cgattttgt gatgctcgtc aggggggcgg agcctatgga aaaacgccag caacgcggcc     2280
tttttacggt tcctggcctt ttgctggcct tttgctcaca tgttctttcc tgcgttatcc     2340
cctgattctg tggataaccg tattaccgcc tttgagtgag ctgataccgc tcgccgcagc     2400
cgaacgaccg agcgcagcga gtcagtgagc gaggaagcgg aagagcgcct gatgcggtat     2460
tttctcctta cgcatctgtg cggtatttca caccgcatat atggtgcact ctcagtacaa     2520
tctgctctga tgccgcatag ttaagccagt atacactccg ctatcgctac gtgactgggt     2580
catggctgcg ccccgacacc cgccaacacc cgctgacgcg ccctgacggg cttgtctgct     2640
```

```
cccggcatcc gcttacagac aagctgtgac cgtctccggg agctgcatgt gtcagaggtt    2700
ttcaccgtca tcaccgaaac gcgcgaggca gctgcggtaa agctcatcag cgtggtcgtg    2760
aagcgattca cagatgtctg cctgttcatc cgcgtccagc tcgttgagtt tctccagaag    2820
cgttaatgtc tggcttctga taaagcgggc catgttaagg gcggtttttt cctgtttggt    2880
cactgatgcc tccgtgtaag ggggatttct gttcatgggg gtaatgatac cgatgaaacg    2940
agagaggatg ctcacgatac gggttactga tgatgaacat gcccggttac tggaacgttg    3000
tgagggtaaa caactggcgg tatggatgcg gcgggaccag agaaaaatca ctcagggtca    3060 atgccacgc ttcgttaata cagatgtagg tgttccacag ggtagccagc agcatcctgc    3120
gatgcagatc cggaacataa tggtgcaggg cgctgacttc cgcgtttcca gactttacga    3180
aacacgaaaa ccgaagacca ttcatgttgt tgctcaggtc gcagacgttt tgcagcagca    3240
gtcgcttcac gttcgctcgc gtatcggtga ttcattctgc taaccagtaa ggcaaccccg    3300
ccagcctagc cgggtcctca acgacaggag cacgatcatg cgcacccgtg gggccgccat    3360
gccggcgata atgcctgct tctcgccgaa acgtttggtg gcgggaccag tgacgaaggc    3420
ttgagcgagg gcgtgcaaga ttccgaatac cgcaagcgac aggccgatca tcgtcgcgct    3480
ccagcgaaag cggtcctcgc cgaaaatgac ccagagcgct gccggcacct gtcctacgag    3540
ttgcatgata aagaagacag tcataagtgc ggcgacgata gtcatgcccc gcgcccaccg    3600
gaaggagctg actgggttga aggctctcaa gggcatcggt cgagatcccg gtgcctaatg    3660
agtgagctaa cttacattaa ttgcgttgcg ctcactgccc gctttccagt cgggaaacct    3720
gtcgtgccag ctgcattaat gaatcggcca acgcgcgggg agaggcggtt tgcgtattgg    3780
gcgccagggt ggttttctt ttccaccagtg agacgggcaa cagctgattg cccttcaccg    3840
cctggccctg agagagttgc agcaagcggt ccacgctggt ttgccccagc aggcgaaaat    3900
cctgtttgat ggtggttaac ggcgggatat aacatgagct gtcttcggta tcgtcgtatc    3960
ccactaccga gatatccgca ccaacgcgca gcccggactc ggtaatggcg cgcattgcgc    4020
ccagcgccat ctgatcgttg gcaaccagca tcgcagtggg aacgatgccc tcattcagca    4080
tttgcatggt ttgttgaaaa ccggacatgg cactccagtc gccttcccgt tccgctatcg    4140
gctgaatttg attgcgagtg agatatttat gccagccagc cagacgcaga gcgcccgaga    4200
cagaacttaa tgggcccgct aacagcgcga tttgctggtg acccaatgcg accagatgct    4260
ccacgcccag tcgcgtaccg tcttcatggg agaaaataat actgttgatg ggtgtctggt    4320
cagagacatc aagaaataac gccggaacat tagtgcaggc agcttccaca gcaatggcat    4380
cctggtcatc cagcggatag ttaatgatca gcccactgac gcgttgcgcg agaagattgt    4440
gcaccgccgc tttacaggct tcgacgccgc ttcgttctac catcgacacc accacgctgg    4500
cacccagttg atcggcgcga gatttaatcg ccgcgacaat ttgcgacggc gcgtgcaggg    4560
ccagactgga ggtggcaacg ccaatcagca acgactgttt gcccgccagt tgttgtgcca    4620
cgcggttggg aatgtaattc agctccgcca tcgccgcttc acttttttcc cgcgttttcg    4680
cagaaacgtg gctggcctgg ttcaccacgc gggaaacggt ctgataagag acaccggcat    4740
actctgcgac atcgtataac gttactggtt tcacattcac caccctgaat tgactctctt    4800
ccgggcgcta tcatgccata ccgcgaaagg ttttgcgcca ttcgatggtg tccgggatct    4860
cgacgctctc ccttatgcga ctcctgcatt aggaagcagc ccagtagtag gttgaggccg    4920
ttgagcaccg ccgccgcaag gaatggtgca tgcaaggaga tggcgcccaa cagtcccccg    4980
gccacggggc ctgccaccat acccacgccg aaacaagcgc tcatgagccc gaagtggcga    5040
```

-continued

```
gcccgatctt ccccatcggt gatgtcggcg atataggcgc cagcaaccgc acctgtggcg    5100
ccggtgatgc cggccacgat gcgtccggcg tagaggatcg agatctcgat cccgcgaaat    5160
taatacgact cactataggg gaattgtgag cggataacaa ttcccctcta gaaataattt    5220
tgtttaactt taagaaggag atataccatg gccgccgccg ccgccgcctc cgacctcctc    5280
tacgccgcac cctccctcaa gtccggctc gccgccgggg agaccctgta cgggctcttc    5340
ctcctctcct tctcccccac gctcgccgag ctcgccgccc tcgccggcta cgactacgtc    5400
gtcgtcgaca tggagcacgg ccccggcggc gttcccgagg cgctggcctg cctccgcgcc    5460
ctcgacgccg cccgtacccc agccgtcatc cgcctcccg aggccggccc catctgggcc    5520
aagaaggccc tcgacctcgg ccccgcgggc ctcatggtcc ccgccgtcga gtcccccgcc    5580
gccgcggccg ccgccgtgtc gcactgccgc tacccgcccc gaggcgttcg cggcgccgcc    5640
caccccatcg tccgcgcctc cgcgtacggc ctcgacgact cctacctctc ccgctgcgag    5700
gacgagacgc taatcatctg ccaggtcgag accgccgctg gcattgcgga ggtcgacgcc    5760
attgccgccg tcgacggcgt cgacgtcgtc cagatgggac cgctcgactt gtcagccagc    5820
atggggtacc tgtgggaccc agggaacagg aaggtgcgag ccaggctgag ggaggccgag    5880
aagaaggtgt tggatgccag gaagaagaat gtgacagctt cagatggcaa tgtcgcatat    5940
ctaggcggat cgccatgcc gaacgacccg gcagagcagc tcaagctgag gggttaccac    6000
atggtgtctg gtgcagtgga cattgggatg ttccggaagg cggcgttgga ggatgtcaag    6060
cggttcaagg aggcagtgat ggaaatcggc gaggaggaag gcgaggagga cgatgaaaag    6120
aaggacaagg aagacgacgg gtactggagt gaga                                6154
```

<210> SEQ ID NO 85
<211> LENGTH: 315
<212> TYPE: PRT
<213> ORGANISM: artificial sequence
<220> FEATURE:
<223> OTHER INFORMATION: Os09g36030 His TAG

<400> SEQUENCE: 85

```
Met Ala Ala Ala Ala Ala Ser Asp Leu Leu Tyr Ala Ala Pro Ser
1               5                   10                  15

Leu Lys Ser Arg Leu Ala Ala Gly Glu Thr Leu Tyr Gly Leu Phe Leu
            20                  25                  30

Leu Ser Phe Ser Pro Thr Leu Ala Glu Leu Ala Ala Leu Ala Gly Tyr
        35                  40                  45

Asp Tyr Val Val Val Asp Met Glu His Gly Pro Gly Gly Val Pro Glu
    50                  55                  60

Ala Leu Ala Cys Leu Arg Ala Leu Asp Ala Ala Arg Thr Pro Ala Val
65                  70                  75                  80

Ile Arg Leu Pro Glu Ala Gly Pro Ile Trp Ala Lys Lys Ala Leu Asp
                85                  90                  95

Leu Gly Pro Ala Gly Leu Met Val Pro Ala Val Glu Ser Pro Ala Ala
            100                 105                 110

Ala Ala Ala Ala Val Ser His Cys Arg Tyr Pro Pro Arg Gly Val Arg
        115                 120                 125

Gly Ala Ala His Pro Ile Val Arg Ala Ser Ala Tyr Gly Leu Asp Asp
    130                 135                 140

Ser Tyr Leu Ser Arg Cys Glu Asp Glu Thr Leu Ile Ile Cys Gln Val
145                 150                 155                 160
```

| | | | | | | | | | | | |
|---|---|---|---|---|---|---|---|---|---|---|---|
|Glu|Thr|Ala|Ala|Gly|Ile|Ala|Glu|Val|Asp|Ala|Ile|Ala|Ala|Val|Asp|
| | | |165| | | |170| | | |175|

Gly Val Asp Val Val Gln Met Gly Pro Leu Asp Leu Ser Ala Ser Met
        180                 185                 190

Gly Tyr Leu Trp Asp Pro Gly Asn Arg Lys Val Arg Ala Arg Leu Arg
        195                 200                 205

Glu Ala Glu Lys Lys Val Leu Asp Ala Arg Lys Lys Asn Val Thr Ala
        210                 215                 220

Ser Asp Gly Asn Val Ala Tyr Leu Gly Gly Phe Ala Met Pro Asn Asp
225                 230                 235                 240

Pro Ala Glu Gln Leu Lys Leu Arg Gly Tyr His Met Val Ser Gly Ala
                245                 250                 255

Val Asp Ile Gly Met Phe Arg Lys Ala Ala Leu Glu Asp Val Lys Arg
                260                 265                 270

Phe Lys Glu Ala Val Met Glu Ile Gly Glu Glu Gly Glu Glu Asp
        275                 280                 285

Asp Glu Lys Lys Asp Lys Glu Asp Asp Gly Tyr Trp Ser Glu Lys Leu
290                 295                 300

Ala Ala Ala Leu Glu His His His His His His
305                 310                 315

<210> SEQ ID NO 86
<211> LENGTH: 30
<212> TYPE: DNA
<213> ORGANISM: artificial sequence
<220> FEATURE:
<223> OTHER INFORMATION: PP FWD primer

<400> SEQUENCE: 86
cgactacgac atgctcggcg ccatcgcctg                                    30

<210> SEQ ID NO 87
<211> LENGTH: 29
<212> TYPE: DNA
<213> ORGANISM: artificial sequence
<220> FEATURE:
<223> OTHER INFORMATION: PP REV primer

<400> SEQUENCE: 87
ggatggcacc ggagaggccg gtgccatcc                                     29

<210> SEQ ID NO 88
<211> LENGTH: 4395
<212> TYPE: DNA
<213> ORGANISM: artificial sequence
<220> FEATURE:
<223> OTHER INFORMATION: pCR blunt HpaI PP

<400> SEQUENCE: 88
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagctat    240 taggtgacg cgttagaata ctcaagctat gcatcaagct tggtaccgag ctcggatcca    300
ctagtaacgg ccgccagtgt gctggaattc aggcgactac gacatgctcg gcgccatcgc    360
ctgccgcttc gtttaaggac ctgctcatgg acatgcccat caaccacttc aagcgacgcc    420
tgcacagcgg tgaaccgcaa atcggcctgt ggctcggcct ggccgatgcc tactgcgccg    480

```
agctggcggc caatgccggt ttcgactggc tgctgatcga cggcgaacac gcgcccaacg    540
acctgcgcgg catgctcgcc cagttgcagg cggtggcacc ctaccccagc caggcagtga    600
tccgcccggt gatcggcgat accgcgctga tcaagcaggt gctggatatc ggcgcacaaa    660
ccttgctggt gccgatggtg aaactgccga acaggcgcg gcaactggtc aaggccatgc     720
attacccgcc caagggcatt cgcggggtgg gcagcgcgct ggcgagggct cgcgctgga     780
acaccctccc cggttacctg gaccacgccg atgagcaaat gtgcctgctg gtgcagatcg    840
agaacaagga aggcctggcc aacctggacg agatcgttgc ggtggaaggt gtggatggcg    900
tgttcatcgg gcctgcagac ctgagtgcgc ccatggggca tcgcggcaac cccgggcacc    960
cggaggtgca ggcggcgatt gaagacgcga tcgtgcgcat tggcaaggcg ggcaaagccg   1020
ccggcattct cagcgcggac gagaaactgg cgcgacgcta catcgagctg gtgcgcgcgt   1080
tgtggcggt gggtgtggat accacggtgc tgatgcgcgg gctgcgcgag ctggcgggga   1140
agttcaagga tacagtggta gtccctagtg ccggggtag tgtctactga ggcttctggt    1200
tggatggcac cggcctcctg aattctgcag atatccatca cactggcggc cgctcgagca   1260
tgcatctaga gggcccaatt cgccctatag tgagtcgtat tacaattcac tggccgtcgt   1320
tttacaacgt cgtgactggg aaaaccctgg cgttacccaa cttaatcgcc ttgcagcaca   1380
tccccctttc gccagctggc gtaatagcga agaggcccgc accgatcgcc cttcccaaca   1440
gttgcgcagc ctatacgtac ggcagtttaa ggtttacacc tataaaagag agagccgtta   1500
tcgtctgttt gtggatgtac agagtgatat tattgcacg ccggggcgac ggatggtgat   1560
cccctggcc agtgcacgtc tgctgtcaga taaagtctcc cgtgaacttt acccggtggt   1620
gcatatcggg gatgaaagct ggcgcatgat gaccaccgat atggccagtg tgccggtctc   1680
cgttatcggg gaagaagtgg ctgatctcag ccaccgcgaa aatgacatca aaaacgccat   1740
taacctgatg ttctggggaa tataaatgtc aggcatgaga ttatcaaaaa ggatcttcac   1800
ctagatcctt ttcacgtaga aagccagtcc gcagaaacgg tgctgacccc ggatgaatgt   1860
cagctactgg gctatctgga caagggaaaa cgcaagcgca aagagaaagc aggtagcttg   1920
cagtgggctt acatggcgat agctagactg ggcggtttta tggacagcaa gcgaaccgga   1980
attgccagct ggggcgccct ctggtaaggt tgggaagccc tgcaaagtaa actggatggc   2040
tttcttgccg ccaaggatct gatggcgcag gggatcaagc tctgatcaag agacaggatg   2100
aggatcgttt cgcatgattg aacaagatgg attgcacgca ggttctccgg ccgcttgggt   2160
ggagaggcta ttcggctatg actgggcaca acagacaatc ggctgctctg atgccgccgt   2220
gttccggctg tcagcgcagg ggcgcccggt tctttttgtc aagaccgacc tgtccggtgc   2280
cctgaatgaa ctgcaagacg aggcagcgcg gctatcgtgg ctggccacga cgggcgttcc   2340
ttgcgcagct gtgctcgacg ttgtcactga agcgggaagg gactggctgc tattgggcga   2400
agtgccgggg caggatctcc tgtcatctca ccttgctcct gccgagaaag tatccatcat   2460
ggctgatgca atgcggcggc tgcatacgct tgatccggct acctgcccat tcgaccacca   2520
agcgaaacat cgcatcgagc gagcacgtac tcggatggaa gccggtcttg tcgatcagga   2580
tgatctggac gaagagcatc aggggctcgc gccagccgaa ctgttcgcca ggctcaaggc   2640
gagcatgccc gacggcgagg atctcgtcgt gacccatggc gatgcctgct tgccgaatat   2700
catggtggaa aatggccgct tttctggatt catcgactgt ggccggctgg gtgtggcgga   2760
ccgctatcag gacatagcgt tggctacccg tgatattgct gaagagcttg gcggcgaatg   2820
```

```
ggctgaccgc ttcctcgtgc tttacggtat cgccgctccc gattcgcagc gcatcgcctt    2880
ctatcgcctt cttgacgagt tcttctgaat tattaacgct tacaatttcc tgatgcggta    2940
ttttctcctt acgcatctgt gcggtatttc acaccgcatc aggtggcact tttcggggaa    3000
atgtgcgcgg aaccctatt tgtttatttt tctaaataca ttcaaatatg tatccgctca    3060
tgagacaata accctgataa atgcttcaat aatagcacgt gaggagggcc accatggcca    3120
agttgaccag tgccgttccg gtgctcaccg cgcgcgacgt cgccgagcg gtcgagttct    3180 ggaccgaccg gctcgggttc tcccgggact tcgtggagga cgacttcgcc ggtgtggtcc    3240
gggacgacgt gaccctgttc atcagcgcgt tccaggacca ggtggtgccg gacaacaccc    3300
tggcctgggt gtgggtgcgc ggcctggacg agctgtacgc cgagtggtcg gaggtcgtgt    3360
ccacgaactt ccgggacgcc tccggccgg ccatgaccga gatcggcgag cagccgtggg    3420
ggcgggagtt cgccctgcgc gacccggccg gcaactgcgt gcacttcgtg gccgaggagc    3480
aggactgaca cgtgctaaaa cttcattttt aatttaaaag gatctaggtg aagatccttt    3540
ttgataatct catgaccaaa atcccttaac gtgagttttc gttccactga gcgtcagacc    3600
ccgtagaaaa gatcaaagga tcttcttgag atccttttt tctgcgcgta atctgctgct    3660
tgcaaacaaa aaaaccaccg ctaccagcgg tggtttgttt gccggatcaa gagctaccaa    3720 ctcttttcc gaaggtaact ggcttcagca gagcgcagat accaaatact gttcttctag    3780
tgtagccgta gttaggccac cacttcaaga actctgtagc accgcctaca tacctcgctc    3840
tgctaatcct gttaccagtg gctgctgcca gtggcgataa gtcgtgtctt accgggttgg    3900
actcaagacg atagttaccg gataaggcgc agcggtcggg ctgaacgggg gttcgtgca    3960 cacagcccag cttggagcga acgacctaca ccgaactgag atacctacag cgtgagctat    4020
gagaaagcgc cacgcttccc gaagggagaa aggcggacag gtatccggta agcggcaggg    4080
tcggaacagg agagcgcacg agggagcttc caggggga aacgcctggtat ctttatagtc    4140 ctgtcgggtt cgccacctc tgacttgagc gtcgattttt gtgatgctcg tcagggggc    4200 ggagcctatg gaaaaacgcc agcaacgcgg cctttttacg gttcctggcc ttttgctggc    4260
cttttgctca catgttcttt cctgcgttat cccctgattc tgtggataac cgtattaccg    4320
cctttgagtg agctgatacc gctcgccgca gccgaacgac cgagcgcagc gagtcagtga    4380
gcgaggaagc ggaag                                                     4395

<210> SEQ ID NO 89
<211> LENGTH: 804
<212> TYPE: DNA
<213> ORGANISM: Pseudomonas putida

<400> SEQUENCE: 89
atggacatgc ccatcaacca cttcaagcga cgcctgcaca gcggtgaacc gcaaatcggc      60
ctgtggctcg gcctggccga tgcctactgc gccgagctgg cggccaatgc cggtttcgac     120
tggctgctga tcgacggcga acacgcgccc aacgacctgc gcggcatgct cgcccagttg     180
caggcggtgg caccctaccc cagccaggca gtgatccgcc cggtgatcgg cgataccgcg     240
ctgatcaagc aggtgctgga tatcggcgca caaaccttgc tggtgccgat ggtgaaaact     300
gccgaacagg cgcggcaact ggtcaaggcc atgcattacc cgcccaaggg cattcgcggg     360
gtgggcagcg cgctggcgag ggcttcgcgc tggaacaccc tccccggtta cctggaccac     420
gccgatgagc aaatgtgcct gctggtgcag atcgagaaca aggaaggcct ggccaacctg     480
gacgagatcg ttgcggtgga aggtgtggat ggcgtgttca tcgggcctgc agacctgagt     540
```

```
gcggccatgg ggcatcgcgg caaccccggg cacccggagg tgcaggcggc gattgaagac      600
gcgatcgtgc gcattggcaa ggcgggcaaa gccgccggca ttctcagcgc ggacgagaaa      660
ctggcgcgac gctacatcga gctgggtgcg gcgtttgtgg cggtgggtgt ggataccacg      720
gtgctgatgc gcgggctgcg cgagctggcg gggaagttca aggatacagt ggtagtccct      780
agtgccgggg gtagtgtcta ctga                                             804
```

<210> SEQ ID NO 90
<211> LENGTH: 267
<212> TYPE: PRT
<213> ORGANISM: Pseudomonas putida

<400> SEQUENCE: 90

```
Met Asp Met Pro Ile Asn His Phe Lys Arg Arg Leu His Ser Gly Glu
1               5                   10                  15

Pro Gln Ile Gly Leu Trp Leu Gly Leu Ala Asp Ala Tyr Cys Ala Glu
            20                  25                  30

Leu Ala Ala Asn Ala Gly Phe Asp Trp Leu Leu Ile Asp Gly Glu His
        35                  40                  45

Ala Pro Asn Asp Leu Arg Gly Met Leu Ala Gln Leu Gln Ala Val Ala
    50                  55                  60

Pro Tyr Pro Ser Gln Ala Val Ile Arg Pro Val Ile Gly Asp Thr Ala
65                  70                  75                  80

Leu Ile Lys Gln Val Leu Asp Ile Gly Ala Gln Thr Leu Leu Val Pro
                85                  90                  95

Met Val Glu Thr Ala Glu Gln Ala Arg Gln Leu Val Lys Ala Met His
            100                 105                 110

Tyr Pro Pro Lys Gly Ile Arg Gly Val Gly Ser Ala Leu Ala Arg Ala
        115                 120                 125

Ser Arg Trp Asn Thr Leu Pro Gly Tyr Leu Asp His Ala Asp Glu Gln
    130                 135                 140

Met Cys Leu Leu Val Gln Ile Glu Asn Lys Glu Gly Leu Ala Asn Leu
145                 150                 155                 160

Asp Glu Ile Val Ala Val Glu Gly Val Asp Gly Val Phe Ile Gly Pro
                165                 170                 175

Ala Asp Leu Ser Ala Ala Met Gly His Arg Gly Asn Pro Gly His Pro
            180                 185                 190

Glu Val Gln Ala Ala Ile Glu Asp Ala Ile Val Arg Ile Gly Lys Ala
        195                 200                 205

Gly Lys Ala Ala Gly Ile Leu Ser Ala Asp Glu Lys Leu Ala Arg Arg
    210                 215                 220

Tyr Ile Glu Leu Gly Ala Ala Phe Val Ala Val Gly Val Asp Thr Thr
225                 230                 235                 240

Val Leu Met Arg Gly Leu Arg Glu Leu Ala Gly Lys Phe Lys Asp Thr
                245                 250                 255

Val Val Val Pro Ser Ala Gly Gly Ser Val Tyr
            260                 265
```

<210> SEQ ID NO 91
<211> LENGTH: 27
<212> TYPE: DNA
<213> ORGANISM: artificial sequence
<220> FEATURE:
<223> OTHER INFORMATION: HpaI PP fwd primer

<400> SEQUENCE: 91
catatggaca tgcccatcaa ccacttc    27

<210> SEQ ID NO 92
<211> LENGTH: 26
<212> TYPE: DNA
<213> ORGANISM: artificial sequence
<220> FEATURE:
<223> OTHER INFORMATION: HpaI PP rev primer

<400> SEQUENCE: 92
gagctcgggt agacactacc cccggc    26

<210> SEQ ID NO 93
<211> LENGTH: 3829
<212> TYPE: DNA
<213> ORGANISM: artificial sequence
<220> FEATURE:
<223> OTHER INFORMATION: pGEM-T HpaI PP  plasmid

<400> SEQUENCE: 93
catatggaca tgcccatcaa ccacttcaag cgacgcctgc acagcggtga accgcaaatc    60
ggcctgtggc tcggcctggc cgatgcctac tgcgccgagc tggcgccaa tgccggtttc    120 gactggctgc tgatcgacgg cgaacacgcg cccaacgacc tgcgcggcat gctcgcccag    180
ttgcaggcgg tggcacccta ccccagccag gcagtgatcc gccggtgat cggcgatacc    240 gcgctgatca agcaggtgct ggatatcggc gcacaaacct tgctggtgcc gatggtggaa    300
actgccgaac aggcgcggca actggtcaag gccatgcatt accgcccaa gggcattcgc    360 ggggtgggca gcgcgctggc gagggcttcg cgctggaaca ccctccccgg ttacctggac    420
cacgccgatg agcaaatgtg cctgctggtg cagatcgaga acaaggaagg cctggccaac    480
ctggacgaga tcgttgcggt ggaaggtgtg gatggcgtgt tcatcgggcc tgcagacctg    540
agtgcggcca tggggcatcg cggcaacccc gggcacccgg aggtgcaggc ggcgattgaa    600
gacgcgatcg tgcgcattgg caaggcgggc aaagccgccg gcattctcag cgcggacgag    660
aaactggcgc gacgctacat cgagctgggt gcggcgtttg tggcggtggg tgtggatacc    720
acggtgctga tgcgcgggct gcgcgagctg gcggggaagt tcaaggatac agtggtagtc    780
cctagtgccg ggggtagtgt ctacccgagc tcaatcacta gtgaattcgc ggccgcctgc    840
aggtcgacca tatgggagag ctcccaacgc gttggatgca tagcttgagt attctatagt    900
gtcacctaaa tagcttggcg taatcatggt catagctgtt tcctgtgtga aattgttatc    960
cgctcacaat tccacacaac atacgagccg gaagcataaa gtgtaaagcc tggggtgcct    1020
aatgagtgag ctaactcaca ttaattgcgt tgcgctcact gcccgctttc cagtcgggaa    1080
acctgtcgtg ccagctgcat taatgaatcg gccaacgcgc ggggagaggc ggtttgcgta    1140
ttgggcgctc ttccgcttcc tcgctcactg actcgctgcg ctcggtcgtt cggctgcggc    1200
gagcggtatc agctcactca aaggcggtaa tacggttatc cacagaatca ggggataacg    1260
caggaaagaa catgtgagca aaaggccagc aaaaggccag gaaccgtaaa aaggccgcgt    1320
tgctggcgtt tttccatagg ctccgccccc ctgacgagca tcacaaaaat cgacgctcaa    1380
gtcagaggtg gcgaaacccg acaggactat aaagatacca ggcgtttccc cctggaagct    1440
ccctcgtgcg ctctcctgtt ccgaccctgc cgcttaccgg atacctgtcc gcctttctcc    1500
cttcgggaag cgtggcgctt tctcatagct cacgctgtag gtatctcagt tcggtgtagg    1560
tcgttcgctc caagctgggc tgtgtgcacg aaccccccgt tcagcccgac cgctgcgcct    1620

```
tatccggtaa ctatcgtctt gagtccaacc cggtaagaca cgacttatcg ccactggcag    1680
cagccactgg taacaggatt agcagagcga ggtatgtagg cggtgctaca gagttcttga    1740
agtggtggcc taactacggc tacactagaa gaacagtatt tggtatctgc gctctgctga    1800
agccagttac cttcggaaaa agagttggta gctcttgatc cggcaaacaa accaccgctg    1860
gtagcggtgg tttttttgtt tgcaagcagc agattacgcg cagaaaaaaa ggatctcaag    1920
aagatccttt gatcttttct acggggtctg acgctcagtg gaacgaaaac tcacgttaag    1980
ggattttggt catgagatta tcaaaaagga tcttcaccta gatcctttta aattaaaaat    2040
gaagttttaa atcaatctaa agtatatatg agtaaacttg gtctgacagt taccaatgct    2100
taatcagtga ggcacctatc tcagcgatct gtctatttcg ttcatccata gttgcctgac    2160
tccccgtcgt gtagataact acgatacggg agggcttacc atctggcccc agtgctgcaa    2220
tgataccgcg agacccacgc tcaccggctc cagatttatc agcaataaac cagccagccg    2280
gaagggccga gcgcagaagt ggtcctgcaa ctttatccgc ctccatccag tctattaatt    2340
gttgccggga agctagagta agtagttcgc cagttaatag tttgcgcaac gttgttgcca    2400
ttgctacagg catcgtggtg tcacgctcgt cgtttggtat ggcttcattc agctccggtt    2460
cccaacgatc aaggcgagtt acatgatccc ccatgttgtg caaaaaagcg gttagctcct    2520
tcggtcctcc gatcgttgtc agaagtaagt tggccgcagt gttatcactc atggttatgg    2580
cagcactgca taattctctt actgtcatgc catccgtaag atgcttttct gtgactggtg    2640
agtactcaac caagtcattc tgagaatagt gtatgcggcg accgagttgc tcttgcccgg    2700
cgtcaatacg ggataatacc gcgccacata gcagaacttt aaaagtgctc atcattggaa    2760
aacgttcttc ggggcgaaaa ctctcaagga tcttaccgct gttgagatcc agttcgatgt    2820
aacccactcg tgcacccaac tgatcttcag catcttttac tttcaccagc gtttctgggt    2880
gagcaaaaac aggaaggcaa aatgccgcaa aaaagggaat aagggcgaca cggaaatgtt    2940
gaatactcat actcttcctt tttcaatatt attgaagcat ttatcagggt tattgtctca    3000
tgagcggata catatttgaa tgtatttaga aaaataaaca ataggggtt ccgcgcacat    3060 ttccccgaaa agtgccacct gatgcggtgt gaaataccgc acagatgcgt aaggagaaaa    3120
taccgcatca ggaaattgta agcgttaata ttttgttaaa attcgcgtta aattttttgtt    3180 aaatcagctc attttttaac caataggccg aaatcggcaa aatcccttat aaatcaaaag    3240
aatagaccga gatagggttg agtgttgttc cagtttggaa caagagtcca ctattaaaga    3300
acgtggactc caacgtcaaa gggcgaaaaa ccgtctatca gggcgatggc ccactacgtg    3360
aaccatcacc ctaatcaagt tttttggggt cgaggtgccg taaagcacta aatcggaacc    3420
ctaaagggag cccccgattt agagcttgac ggggaaagcc ggcgaacgtg gcgagaaagg    3480
aagggaagaa agcgaaagga gcgggcgcta gggcgctggc aagtgtagcg gtcacgctgc    3540
gcgtaaccac cacacccgcc gcgcttaatg cgccgctaca gggcgcgtcc attcgccatt    3600
caggctgcgc aactgttggg aagggcgatc ggtgcgggcc tcttcgctat tacgccagct    3660
ggcgaaaggg ggatgtgctg caaggcgatt aagttgggta acgccagggt tttcccagtc    3720
acgacgttgt aaaacgacgg ccagtgaatt gtaatacgac tcactatagg gcgaattggg    3780
cccgacgtcg catgctcccg gccgccatgg cggccgcggg aattcgatt                3829
```

<210> SEQ ID NO 94
<211> LENGTH: 6069
<212> TYPE: DNA
<213> ORGANISM: artificial sequence
<220> FEATURE:
<223> OTHER INFORMATION: pET29a HpaI PP plasmid

<400> SEQUENCE: 94

```
tatggacatg cccatcaacc acttcaagcg acgcctgcac agcggtgaac cgcaaatcgg     60
cctgtggctc ggcctggccg atgcctactg cgccgagctg gcggccaatg ccggtttcga   120
ctggctgctg atcgacggcg aacacgcgcc caacgacctg cgcggcatgc tcgcccagtt   180
gcaggcggtg gcaccctacc ccagccaggc agtgatccgc cggtgatcg gcgataccgc    240
gctgatcaag caggtgctgg atatcggcgc acaaaccttg ctggtgccga tggtggaaac   300
tgccgaacag gcgcggcaac tggtcaaggc catgcattac ccgcccaagg gcattcgcgg   360
ggtgggcagc gcgctggcga gggcttcgcg ctggaacacc ctccccggtt acctggacca   420
cgccgatgag caaatgtgcc tgctggtgca gatcgagaac aaggaaggcc tggccaacct   480
ggacgagatc gttgcggtgg aaggtgtgga tggcgtgttc atcgggcctg cagacctgag   540
tgcggccatg gggcatcgcg gcaaccccgg gcacccggag gtgcaggcgg cgattgaaga   600
cgcgatcgtg cgcattggca aggcgggcaa agccgccggc attctcagcg cggacgagaa   660
actggcgcga cgctacatcg agctgggtgc ggcgtttgtg gcggtgggtg tggataccac   720
ggtgctgatg cgcgggctgc gcgagctggc ggggaagttc aaggatacag tggtagtccc   780
tagtgccggg ggtagtgtct acccgagctc cgtcgacaag cttgcggccg cactcgagca   840
ccaccaccac caccactgag atccggctgc taacaaagcc cgaaaggaag ctgagttggc   900
tgctgccacc gctgagcaat aactagcata accccttggg gcctctaaac gggtcttgag   960
gggttttttg ctgaaaggag gaactatatc cggattggcg aatgggacgc gccctgtagc  1020
ggcgcattaa gcgcggcggg tgtggtggtt acgcgcagcg tgaccgctac acttgccagc  1080
gccctagcgc ccgctccttt cgctttcttc ccttcctttc tcgccacgtt cgccggcttt  1140
ccccgtcaag ctctaaatcg ggggctccct ttagggttcc gatttagtgc tttacggcac  1200
ctcgacccca aaaaacttga ttagggtgat ggttcacgta gtgggccatc gccctgatag  1260
acggttttc gccctttgac gttggagtcc acgttcttta atagtggact cttgttccaa   1320
actggaacaa cactcaaccc tatctcggtc tattcttttg atttataagg gattttgccg  1380
atttcggcct attggttaaa aaatgagctg atttaacaaa aatttaacgc gaattttaac   1440
aaaatattaa cgtttacaat ttcaggtggc acttttcggg gaaatgtgcg cggaacccct  1500
atttgtttat ttttctaaat acattcaaat atgtatccgc tcatgaatta attcttagaa  1560
aaactcatcg agcatcaaat gaaactgcaa tttattcata tcaggattat caataccata  1620
tttttgaaaa agccgtttct gtaatgaagg agaaaactca ccgaggcagt tccataggat  1680
ggcaagatcc tggtatcggt ctgcgattcc gactcgtcca acatcaatac aacctattaa  1740
tttcccctcg tcaaaaataa ggttatcaag tgagaaatca ccatgagtga cgactgaatc  1800
cggtgagaat ggcaaaagtt tatgcatttc tttccagact tgttcaacag gccagccatt  1860
acgctcgtca tcaaaatcac tcgcatcaac caaaccgtta ttcattcgtg attgcgcctg  1920
agcgagacga aatacgcgat cgctgttaaa aggacaatta caaacaggaa tcgaatgcaa  1980
ccggcgcagg aacactgcca gcgcatcaac aatattttca cctgaatcag gatattcttc  2040
taatacctgg aatgctgttt tcccggggat cgcagtggtg agtaaccatg catcatcagg  2100
agtacggata aaatgcttga tggtcggaag aggcataaat tccgtcagcc agtttagtct  2160
gaccatctca tctgtaacat cattggcaac gctacctttg ccatgtttca gaaacaactc  2220
```

-continued

```
tggcgcatcg ggcttcccat acaatcgata gattgtcgca cctgattgcc cgacattatc    2280
gcgagcccat ttatacccat ataaatcagc atccatgttg gaatttaatc gcggcctaga    2340
gcaagacgtt tcccgttgaa tatggctcat aacaccccct gtattactgt ttatgtaagc    2400
agacagtttt attgttcatg accaaaatcc cttaacgtga gttttcgttc cactgagcgt    2460 cagacccgt agaaaagatc aaaggatctt cttgagatcc ttttttttctg cgcgtaatct    2520 gctgcttgca acaaaaaaa ccaccgctac cagcggtggt ttgtttgccg gatcaagagc    2580
taccaactct ttttccgaag gtaactggct tcagcagagc gcagatacca aatactgtcc    2640
ttctagtgta gccgtagtta ggccaccact tcaagaactc tgtagcaccg cctacatacc    2700
tcgctctgct aatcctgtta ccagtggctg ctgccagtgg cgataagtcg tgtcttaccg    2760
ggttggactc aagacgatag ttaccggata aggcgcagcg gtcgggctga acggggggtt    2820
cgtgcacaca gcccagcttg gagcgaacga cctacaccga actgagatac ctacagcgtg    2880
agctatgaga aagcgccacg cttcccgaag ggagaaaggc ggacaggtat ccggtaagcg    2940
gcagggtcgg aacaggagag cgcacgaggg agcttccagg gggaaacgcc tggtatcttt    3000
atagtcctgt cgggtttcgc cacctctgac ttgagcgtcg attttttgtga tgctcgtcag    3060 gggggcggag cctatggaaa aacgccagca acgcggcctt tttacggttc ctggccttt    3120 gctggccttt tgctcacatg ttcttttcctg cgttatcccc tgattctgtg gataaccgta    3180
ttaccgcctt tgagtgagct gataccgctc gccgcagccg aacgaccgag cgcagcgagt    3240
cagtgagcga ggaagcggaa gagcgcctga tgcggtattt tctccttacg catctgtgcg    3300
gtatttcaca ccgcatatat ggtgcactct cagtacaatc tgctctgatg ccgcatagtt    3360
aagccagtat acactccgct atcgctacgt gactgggtca tggctgcgcc ccgacacccg    3420
ccaacacccg ctgacgcgcc ctgacgggct tgtctgctcc cggcatccgc ttacagacaa    3480
gctgtgaccg tctccgggag ctgcatgtgt cagaggtttt caccgtcatc accgaaacgc    3540
gcgaggcagc tgcggtaaag ctcatcagcg tggtcgtgaa gcgattcaca gatgtctgcc    3600
tgttcatccg cgtccagctc gttgagtttc tccagaagcg ttaatgtctg gcttctgata    3660
aagcgggcca tgttaagggc ggttttttcc tgtttggtca ctgatgcctc cgtgtaaggg    3720
ggatttctgt tcatgggggt aatgataccg atgaaacgag agaggatgct cacgatacgg    3780
gttactgatg atgaacatgc ccggttactg gaacgttgtg agggtaaaca actggcggta    3840
tggatgcggc gggaccagag aaaaatcact cagggtcaat gccagcgctt cgttaataca    3900
gatgtaggtg ttccacaggg tagccagcag catcctgcga tgcagatccg gaacataatg    3960
gtgcagggcg ctgacttccg cgtttccaga ctttacgaaa cacggaaacc gaagaccatt    4020
catgttgttg ctcaggtcgc agacgttttg cagcagcagt cgcttcacgt tcgctcgcgt    4080
atcggtgatt cattctgcta accagtaagg caaccccgcc agcctagccg ggtcctcaac    4140
gacaggagca cgatcatgcg cacccgtggg gccgccatgc cggcgataat ggcctgcttc    4200
tcgccgaaac gtttggtggc gggaccagtg acgaaggctt gagcgagggc gtgcaagatt    4260
ccgaataccg caagcgacag gccgatcatc gtcgcgctcc agcgaaagcg gtcctcgccg    4320
aaaatgaccc agagcgctgc cggcacctgt cctacgagtt gcatgataaa gaagacagtc    4380
ataagtgcgg cgacgatagt catgccccgc gcccaccgga aggagctgac tgggttgaag    4440
gctctcaagg gcatcggtcg agatcccggt gcctaatgag tgagctaact tacattaatt    4500
gcgttgcgct cactgcccgc tttccagtcg ggaaacctgt cgtgccagct gcattaatga    4560
atcggccaac gcgcggggag aggcggtttg cgtattgggc gccagggtgg ttttttcttt    4620
```

```
caccagtgag acgggcaaca gctgattgcc cttcaccgcc tggccctgag agagttgcag    4680
caagcggtcc acgctggttt gccccagcag gcgaaaatcc tgtttgatgg tggttaacgg    4740
cgggatataa catgagctgt cttcggtatc gtcgtatccc actaccgaga tgtccgcacc    4800
aacgcgcagc ccggactcgg taatggcgcg cattgcgccc agcgccatct gatcgttggc    4860
aaccagcatc gcagtgggaa cgatgccctc attcagcatt gcatggtttt gttgaaaacc    4920
ggacatggca ctccagtcgc cttcccgttc cgctatcggc tgaatttgat tgcgagtgag    4980
atatttatgc cagccagcca gacgcagacg cgccgagaca gaacttaatg ggcccgctaa    5040
cagcgcgatt tgctggtgac ccaatgcgac cagatgctcc acgcccagtc gcgtaccgtc    5100
ttcatgggag aaaataatac tgttgatggg tgtctggtca gagacatcaa gaaataacgc    5160
cggaacatta gtgcaggcag cttccacagc aatggcatcc tggtcatcca gcggatagtt    5220
aatgatcagc ccactgacgc gttgcgcgag aagattgtgc accgccgctt acaggcttc    5280 gacgccgctt cgttctacca tcgacaccac cacgctggca cccagttgat cggcgcgaga    5340
tttaatcgcc gcgacaattt cgacggcgc gtgcagggcc agactggagg tggcaacgcc    5400
aatcagcaac gactgtttgc cgccagttg ttgtgccacg cggttgggaa tgtaattcag    5460
ctccgccatc gccgcttcca cttttttccg cgttttcgca gaaacgtggc tggcctggtt    5520
caccacgcgg gaaacggtct gataagagac accggcatac tctgcgacat cgtataacgt    5580
tactggtttc acattcacca ccctgaattg actctcttcc gggcgctatc atgccatacc    5640
gcgaaaggtt ttgcgccatt cgatggtgtc cgggatctcg acgctctccc ttatgcgact    5700
cctgcattag gaagcagccc agtagtaggt tgaggccgtt gagcaccgcc gccgcaagga    5760
atggtgcatg caaggagatg cgcccaaca gtccccgggc cacggggcct gccaccatac    5820
ccacgccgaa acaagcgctc atgagcccga agtggcgagc ccgatcttcc ccatcggtga    5880
tgtcggcgat ataggcgcca gcaaccgcac ctgtggcgcc ggtgatgccg gccacgatgc    5940
gtccggcgta gaggatcgag atcgatctcg atcccgcgaa attaatacga ctcactatag    6000 ggaattgtg agcggataac aattcccctc tagaaataat tttgtttaac tttaagaagg    6060
agatataca                                                            6069
```

<210> SEQ ID NO 95
<211> LENGTH: 285
<212> TYPE: PRT
<213> ORGANISM: artificial sequence
<220> FEATURE:
<223> OTHER INFORMATION: HpaI PP His TAG

<400> SEQUENCE: 95

```
Met Asp Met Pro Ile Asn His Phe Lys Arg Arg Leu His Ser Gly Glu
1               5                   10                  15

Pro Gln Ile Gly Leu Trp Leu Gly Leu Ala Asp Ala Tyr Cys Ala Glu
                20                  25                  30

Leu Ala Ala Asn Ala Gly Phe Asp Trp Leu Leu Ile Asp Gly Glu His
            35                  40                  45

Ala Pro Asn Asp Leu Arg Gly Met Leu Ala Gln Leu Gln Ala Val Ala
        50                  55                  60

Pro Tyr Pro Ser Gln Ala Val Ile Arg Pro Val Ile Gly Asp Thr Ala
65                  70                  75                  80

Leu Ile Lys Gln Val Leu Asp Ile Gly Ala Gln Thr Leu Leu Val Pro
                85                  90                  95
```

Met Val Glu Thr Ala Glu Gln Ala Arg Gln Leu Val Lys Ala Met His
            100                 105                 110

Tyr Pro Pro Lys Gly Ile Arg Gly Val Gly Ser Ala Leu Ala Arg Ala
        115                 120                 125

Ser Arg Trp Asn Thr Leu Pro Gly Tyr Leu Asp His Ala Asp Glu Gln
130                 135                 140

Met Cys Leu Leu Val Gln Ile Glu Asn Lys Glu Gly Leu Ala Asn Leu
145                 150                 155                 160

Asp Glu Ile Val Ala Val Glu Gly Val Asp Gly Val Phe Ile Gly Pro
                165                 170                 175

Ala Asp Leu Ser Ala Ala Met Gly His Arg Gly Asn Pro Gly His Pro
            180                 185                 190

Glu Val Gln Ala Ala Ile Glu Asp Ala Ile Val Arg Ile Gly Lys Ala
        195                 200                 205

Gly Lys Ala Ala Gly Ile Leu Ser Ala Asp Glu Lys Leu Ala Arg Arg
    210                 215                 220

Tyr Ile Glu Leu Gly Ala Ala Phe Val Ala Val Gly Val Asp Thr Thr
225                 230                 235                 240

Val Leu Met Arg Gly Leu Arg Glu Leu Ala Gly Lys Phe Lys Asp Thr
                245                 250                 255

Val Val Val Pro Ser Ala Gly Gly Ser Val Tyr Pro Ser Ser Val Asp
            260                 265                 270

Lys Leu Ala Ala Ala Leu Glu His His His His His
            275                 280                 285

<210> SEQ ID NO 96
<211> LENGTH: 33
<212> TYPE: DNA
<213> ORGANISM: artificial sequence
<220> FEATURE:
<223> OTHER INFORMATION: AthHpaIL G83 rev primer

<400> SEQUENCE: 96
gttttccggt aatccgagaa tggctgatgt tcc     33

<210> SEQ ID NO 97
<211> LENGTH: 33
<212> TYPE: DNA
<213> ORGANISM: artificial sequence
<220> FEATURE:
<223> OTHER INFORMATION: AthHpaIL G83 fwd primer

<400> SEQUENCE: 97
ggaacatcag ccattctcgg attccggaaa ac     33

<210> SEQ ID NO 98
<211> LENGTH: 3913
<212> TYPE: DNA
<213> ORGANISM: artificial sequence
<220> FEATURE:
<223> OTHER INFORMATION: pGEM-T At4g10750-G83-plasmid

<400> SEQUENCE: 98
aatcactagt gaattcgcgg ccgcctgcag gtcgaccata tgggagagct cccaacgcgt     60
tggatgcata gcttgagtat tctatagtgt cacctaaata gcttggcgta atcatggtca    120
tagctgtttc ctgtgtgaaa ttgttatccg ctcacaattc cacacaacat acgagccgga    180
agcataaagt gtaaagcctg gggtgcctaa tgagtgagct aactcacatt aattgcgttg    240
cgctcactgc ccgctttcca gtcgggaaac ctgtcgtgcc agctgcatta atgaatcggc    300

-continued

```
caacgcgcgg ggagaggcgg tttgcgtatt gggcgctctt ccgcttcctc gctcactgac      360
tcgctgcgct cggtcgttcg gctgcggcga gcggtatcag ctcactcaaa ggcggtaata      420
cggttatcca cagaatcagg ggataacgca ggaaagaaca tgtgagcaaa aggccagcaa      480
aaggccagga accgtaaaaa ggccgcgttg ctggcgtttt tccataggct ccgcccccct      540
gacgagcatc acaaaaatcg acgctcaagt cagaggtggc gaaacccgac aggactataa      600
agataccagg cgtttccccc tggaagctcc ctcgtgcgct ctcctgttcc gaccctgccg      660
cttaccggat acctgtccgc ctttctccct tcgggaagcg tggcgctttc tcatagctca      720
cgctgtaggt atctcagttc ggtgtaggtc gttcgctcca agctgggctg tgtgcacgaa      780
ccccccgttc agcccgaccg ctgcgcctta tccggtaact atcgtcttga gtccaacccg      840
gtaagacacg acttatcgcc actggcagca gccactggta acaggattag cagagcgagg      900
tatgtaggcg gtgctacaga gttcttgaag tggtggccta actacggcta cactagaaga      960
acagtatttg gtatctgcgc tctgctgaag ccagttacct tcggaaaaag agttggtagc     1020
tcttgatccg gcaaacaaac caccgctggt agcggtggtt tttttgtttg caagcagcag     1080
attacgcgca gaaaaaaagg atctcaagaa gatcctttga tcttttctac ggggtctgac     1140
gctcagtgga acgaaaactc acgttaaggg attttggtca tgagattatc aaaaaggatc     1200
ttcacctaga tccttttaaa ttaaaaatga agttttaaat caatctaaag tatatatgag     1260
taaacttggt ctgacagtta ccaatgctta atcagtgagg cacctatctc agcgatctgt     1320
ctatttcgtt catccatagt tgcctgactc cccgtcgtgt agataactac gatacgggag     1380
ggcttaccat ctggccccag tgctgcaatg ataccgcgag acccacgctc accggctcca     1440
gatttatcag caataaacca gccagccgga agggccgagc gcagaagtgg tcctgcaact     1500
ttatccgcct ccatccagtc tattaattgt tgccgggaag ctagagtaag tagttcgcca     1560
gttaatagtt tgcgcaacgt tgttgccatt gctacaggca tcgtggtgtc acgctcgtcg     1620
tttggtatgg cttcattcag ctccggttcc caacgatcaa ggcgagttac atgatccccc     1680
atgttgtgca aaaaagcggt tagctccttc ggtcctccga tcgttgtcag aagtaagttg     1740
gccgcagtgt tatcactcat ggttatggca gcactgcata attctcttac tgtcatgcca     1800
tccgtaagat gcttttctgt gactggtgag tactcaacca agtcattctg agaatagtgt     1860
atgcggcgac cgagttgctc ttgcccggcg tcaatacggg ataataccgc gccacatagc     1920
agaactttaa aagtgctcat cattggaaaa cgttcttcgg ggcgaaaact ctcaaggatc     1980
ttaccgctgt tgagatccag ttcgatgtaa cccactcgtg cacccaactg atcttcagca     2040
tcttttactt tcaccagcgt ttctgggtga gcaaaaacag gaaggcaaaa tgccgcaaaa     2100
aagggaataa gggcgacacg gaaatgttga atactcatac tcttcctttt tcaatattat     2160
tgaagcattt atcagggtta ttgtctcatg agcggataca tatttgaatg tatttagaaa     2220
aataaacaaa taggggttcc gcgcacattt ccccgaaaag tgccacctga tgcggtgtga     2280
aataccgcac agatgcgtaa ggagaaaata ccgcatcagg aaattgtaag cgttaatatt     2340
ttgttaaaat tcgcgttaaa ttttgttaa atcagctcat ttttaaccaa ataggccgaa     2400
atcggcaaaa tcccttataa atcaaaagaa tagaccgaga tagggttgag tgttgttcca     2460
gtttggaaca agagtccact attaaagaac gtggactcca acgtcaaagg gcgaaaaacc     2520
gtctatcagg gcgatggccc actacgtgaa ccatcaccct aatcaagttt tttggggtcg     2580
aggtgccgta aagcactaaa tcggaaccct aaagggagcc cccgatttag agcttgacgg     2640
```

-continued

```
ggaaagccgg cgaacgtggc gagaaaggaa gggaagaaag cgaaaggagc gggcgctagg    2700
gcgctggcaa gtgtagcggt cacgctgcgc gtaaccacca cacccgccgc gcttaatgcg    2760
ccgctacagg gcgcgtccat cgccattcca ggctgcgcaa ctgttgggaa gggcgatcgg    2820
tgcgggcctc ttcgctatta cgccagctgg cgaaagggg atgtgctgca aggcgattaa     2880
gttgggtaac gccagggttt tcccagtcac gacgttgtaa aacgacggcc agtgaattgt    2940
aatacgactc actatagggc gaattgggcc cgacgtcgca tgctcccggc cgccatggcg    3000
gccgcgggaa ttcgattcca tggggcccgc caccgccgtg gaagcgatca cgaatcgatc    3060
caaaaactcc ttgaaatctc gtctccgtgg aggagaaact ctctacggtc tcttttact     3120 ctccttctcg ccgacattag ccgagatcgc tgctcacgcc ggttacgatt acgtcgtcgt    3180
tgatatggaa catggtcccg gaggtatacc ggaagctttg gattgtattc gagctcttaa    3240
cgccgccgga acatcagcca ttctcggatt accggaaaac tcaccaacct gggctaaaaa    3300
agctctagat ctaggtccac aaggaatcat gttcccaatg atcgaatctc gtaaagacgc    3360
taccaaagcg gtgtcgtatt gccggtttcc tcccgacggt atccgtggat cggcgcacac    3420
ggtggtgaga gcttctaact acggaatcga tgaagggtat ttaagtaatt acgcagagga    3480
gattctgatt atgtgccagg tggaatcagg tgaaggagtg aagaaagctg atgaaatcgc    3540
agccgttgat ggtgttgact gtgtgcaaat gggaccgttg gatcttagtg cgagtttagg    3600
gtatttgtgg gatcctggac ataagaaagt gagagagatg atgaagaagg ctgagaaatc    3660
tgtgctgagc actgatccgg cgaaaggcgg ggcttacttg tcgggtttcg cgatgccgca    3720
cgatggagct ggtgagattc ggggacgtgg ttaccatatg gtcgccggag ctgttgatgt    3780
tggattgttt aggaatgctg ctgttgaaga tgtgaggaga ttcaagatgg gtttggtcaa    3840
tgaatcggac agtgaggatt cgtcggaaca tgataaagat gttgatgatg agaagtactg    3900
gagcgaagtc gac                                                       3913
```

<210> SEQ ID NO 99
<211> LENGTH: 6142
<212> TYPE: DNA
<213> ORGANISM: artificial sequence
<220> FEATURE:
<223> OTHER INFORMATION: pET28a At4g10750-G83 -plasmid

<400> SEQUENCE: 99

```
catgggcccg ccaccgccg tggaagcgat cacgaatcga tccaaaaact ccttgaaatc    60
tcgtctccgt ggaggagaaa ctctctacgg tctcttttta ctctccttct cgccgacatt    120
agccgagatc gctgctcacg ccggttacga ttacgtcgtc gttgatatgg aacatggtcc    180
cggaggtata ccggaagctt tggattgtat tcgagctctt aacgccgccg gaacatcagc    240
cattctcgga ttaccggaaa actcaccaac ctgggctaaa aaagctctag atctaggtcc    300
acaaggaatc atgttcccaa tgatcgaatc tcgtaaagac gctaccaaag cggtgtcgta    360
ttgccggttt cctcccgacg gtatccgtgg atcggcgcac acggtggtga gagcttctaa    420
ctacggaatc gatgaagggt atttaagtaa ttacgcagag gagattctga ttatgtgcca    480
ggtggaatca ggtgaaggag tgaagaaagc tgatgaaatc gcagccgttg atggtgttga    540
ctgtgtgcaa atgggaccgt tggatcttag tgcgagttta gggtatttgt gggatcctgg    600
acataagaaa gtgagagaga tgatgaagaa ggctgagaaa tctgtgctga gcactgatcc    660
ggcgaaaggc ggggcttact tgtcgggttt cgcgatgccg cacgatggag ctggtgagat    720
tcggggacgt ggttaccata tggtcgccgg agctgttgat gttggattgt ttaggaatgc    780
```

```
tgctgttgaa gatgtgagga gattcaagat gggtttggtc aatgaatcgg acagtgagga    840
ttcgtcggaa catgataaag atgttgatga tgagaagtac tggagcgaag tcgacaagct    900
tgcggccgca ctcgagcacc accaccacca ccactgagat ccggctgcta acaaagcccg    960
aaaggaagct gagttggctg ctgccaccgc tgagcaataa ctagcataac cccttggggc   1020
ctctaaacgg gtcttgaggg gttttttgct gaaaggagga actatatccg gattggcgaa   1080
tgggacgcgc cctgtagcgg cgcattaagc gcggcgggtg tggtggttac gcgcagcgtg   1140
accgctacac ttgccagcgc cctagcgccc gctcctttcg ctttcttccc ttcctttctc   1200
gccacgttcg ccggctttcc ccgtcaagct ctaaatcggg gctccctttt agggttccga   1260
tttagtgctt tacggcacct cgaccccaaa aaacttgatt agggtgatgg ttcacgtagt   1320
gggccatcgc cctgatagac ggttttttcgc cctttgacgt tggagtccac gttctttaat   1380
agtggactct tgttccaaac tggaacaaca ctcaaccta tctcggtcta ttcttttgat   1440
ttataaggga ttttgccgat tcggcctat tggttaaaaa atgagctgat ttaacaaaaa   1500
tttaacgcga attttaacaa atattaacg tttacaattt caggtggcac ttttcgggga   1560
aatgtgcgcg gaacccctat ttgttttattt ttctaaatac attcaaatat gtatccgctc   1620
atgaattaat tcttagaaaa actcatcgag catcaaatga aactgcaatt tattcatatc   1680
aggattatca ataccatatt tttgaaaaag ccgtttctgt aatgaaggag aaaactcacc   1740
gaggcagttc cataggatgg caagatcctg gtatcggtct gcgattccga ctcgtccaac   1800
atcaatacaa cctattaatt tcccctcgtc aaaaataagg ttatcaagtg agaaatcacc   1860
atgagtgacg actgaatccg gtgagaatgg caaaagttta tgcatttctt tccagacttg   1920
ttcaacaggc cagccattac gctcgtcatc aaaatcactc gcatcaacca aaccgttatt   1980
cattcgtgat tgcgcctgag cgagacgaaa tacgcgatcg ctgttaaaag gacaattaca   2040
aacaggaatc gaatgcaacc ggcgcaggaa cactgccagc gcatcaacaa tattttcacc   2100
tgaatcagga tattcttcta atacctggaa tgctgttttc ccggggatcg cagtggtgag   2160
taaccatgca tcatcaggag tacgataaaa atgcttgatg gtcggaagag gcataaattc   2220
cgtcagccag tttagtctga ccatctcatc tgtaacatca ttggcaacgc tacctttgcc   2280
atgtttcaga aacaactctg gcgcatcggg cttcccatac aatcgataga ttgtcgcacc   2340
tgattgcccg acattatcgc gagcccattt atacccatat aaatcagcat ccatgttgga   2400
atttaatcgc ggcctagagc aagacgtttc ccgttgaata tggctcataa caccccttgt   2460
attactgttt atgtaagcag acagttttat tgttcatgac caaatccct taacgtgagt   2520 tttcgttcca ctgagcgtca gaccccgtag aaaagatcaa aggatcttct tgagatcctt   2580 ttttctgcg cgtaatctgc tgcttgcaaa caaaaaaacc accgctacca gcggtggttt   2640
gtttgccgga tcaagagcta ccaactcttt ttccgaaggt aactggcttc agcagagcgc   2700
agataccaaa tactgtcctt ctagtgtagc cgtagttagg ccaccacttc aagaactctg   2760
tagcaccgcc tacatacctc gctctgctaa tcctgttacc agtggctgct gccagtggcg   2820
ataagtcgtg tcttaccggg ttggactcaa gacgatagtt accggataag gcgcagcggt   2880
cgggctgaac ggggggttcg tgcacacagc ccagcttgga gcgaacgacc tacaccgaac   2940
tgagatacct acagcgtgag ctatgagaaa gcgccacgct tcccgaaggg agaaaggcgg   3000
acaggtatcc ggtaagcggc agggtcggaa caggagagcg cacgagggag cttccagggg   3060
gaaacgcctg gtatctttat agtcctgtcg ggtttcgcca cctctgactt gagcgtcgat   3120
```

-continued

```
ttttgtgatg ctcgtcaggg gggcggagcc tatggaaaaa cgccagcaac gcggccttttt    3180
tacggttcct ggccttttgc tggcttttgt ctcacatgtt ctttcctgcg ttatcccctg    3240
attctgtgga taaccgtatt accgcctttg agtgagctga taccgctcgc cgcagccgaa    3300
cgaccgagcg cagcgagtca gtgagcgagg aagcggaaga gcgcctgatg cggtattttc    3360
tccttacgca tctgtgcggt atttcacacc gcatatatgg tgcactctca gtacaatctg    3420
ctctgatgcc gcatagttaa gccagtatac actccgctat cgctacgtga ctgggtcatg    3480
gctgcgcccc gacacccgcc aacacccgct gacgcgccct gacgggcttg tctgctcccg    3540
gcatccgctt acagacaagc tgtgaccgtc tccgggagct gcatgtgtca gaggttttca    3600
ccgtcatcac cgaaacgcgc gaggcagctg cggtaaagct catcagcgtg gtcgtgaagc    3660
gattcacaga tgtctgcctg ttcatccgcg tccagctcgt tgagtttctc cagaagcgtt    3720
aatgtctggc ttctgataaa gcgggccatg ttaagggcgg ttttttcctg tttggtcact    3780
gatgcctccg tgtaagggggg atttctgttc atggggtaa tgataccgat gaaacgagag    3840
aggatgctca cgatacgggt tactgatgat gaacatgccc ggttactgga acgttgtgag    3900
ggtaaacaac tggcggtatg gatgcggcgg gaccagagaa aaatcactca gggtcaatgc    3960
cagcgcttcg ttaatacaga tgtaggtgtt ccacagggta gccagcagca tcctgcgatg    4020
cagatccgga acataatggt gcagggcgct gacttccgcg tttccagact ttacgaaaca    4080
cggaaaccga agaccattca tgttgttgct caggtcgcag acgttttgca gcagcagtcg    4140
cttcacgttc gctcgcgtat cggtgattca ttctgctaac cagtaaggca accccgccag    4200
cctagccggg tcctcaacga caggagcacg atcatgcgca cccgtggggc cgccatgccg    4260
gcgataatgg cctgcttctc gccgaaacgt ttggtggcgg gaccagtgac gaaggcttga    4320
gcgagggcgt gcaagattcc gaataccgca agcgacaggc cgatcatcgt cgcgctccag    4380
cgaaagcggt cctcgccgaa aatgacccag agcgctgccg gcacctgtcc tacgagttgc    4440
atgataaaga agacagtcat aagtgcggcg acgatagtca tgccccgcgc ccaccggaag    4500
gagctgactg ggttgaaggc tctcaagggc atcggtcgag atcccggtgc ctaatgagtg    4560
agctaactta cattaattgc gttgcgctca ctgcccgctt ccagtcgggg aaacctgtcg    4620
tgccagctgc attaatgaat cggccaacgc gcggggagag gcggtttgcg tattgggcgc    4680
cagggtggtt tttcttttca ccagtgagac gggcaacagc tgattgccct tcaccgcctg    4740
gccctgagag agttgcagca agcggtccac gctggtttgc cccagcaggc gaaaatcctg    4800
tttgatggtg gttaacggcg ggatataaca tgagctgtct tcggtatcgt cgtatcccac    4860
taccgagata tccgcaccaa cgcgcagccc ggactcggta atggcgcgca ttgcgcccag    4920
cgccatctga tcgttggcaa ccagcatcgc agtgggaacg atgccctcat tcagcatttg    4980
catggtttgt tgaaaaccgg acatggcact ccagtcgcct tcccgttccg ctatcggctg    5040
aatttgattg cgagtgagat atttatgcca gccagccaga cgcagacgcg ccgagacaga    5100
acttaatggg cccgctaaca gcgcgatttg ctggtgaccc aatgcgacca gatgctccac    5160
gcccagtcgc gtaccgtctt catgggagaa ataatactg ttgatgggtg tctggtcaga    5220
gacatcaaga aataacgccg gaacattagt gcaggcagct tccacagcaa tggcatcctg    5280
gtcatccagc ggatagttaa tgatcagccc actgacgcgt tgcgcgagaa gattgtgcac    5340
cgccgcttta caggcttcga cgccgcttcg ttctaccatc gacaccacca cgctggcacc    5400
cagttgatcg gcgcgagatt taatcgccgc gacaatttgc gacggcgcgt gcagggccag    5460
actggaggtg gcaacgccaa tcagcaacga ctgtttgccc gccagttgtt gtgccacgcg    5520
```

-continued

```
gttgggaatg taattcagct ccgccatcgc cgcttccact ttttcccgcg ttttcgcaga      5580
aacgtggctg gcctggttca ccacgcggga acggtctga  taagagacac cggcatactc      5640
tgcgacatcg tataacgtta ctggtttcac attcaccacc ctgaattgac tctcttccgg      5700
gcgctatcat gccataccgc gaaaggtttt gcgccattcg atggtgtccg ggatctcgac      5760
gctctccctt atgcgactcc tgcattagga agcagcccag tagtaggttg aggccgttga      5820
gcaccgccgc cgcaaggaat ggtgcatgca aggagatggc gcccaacagt cccccggcca      5880
cggggcctgc caccataccc acgccgaaac aagcgctcat gagcccgaag tggcgagccc      5940
gatcttcccc atcggtgatg tcggcgtatat aggcgccagc aaccgcacct gtggcgccgg      6000
tgatgccggc cacgatgcgt ccggcgtaga ggatcgagat ctcgatcccg cgaaattaat      6060
acgactcact ataggggaat tgtgagcgga taacaattcc cctctagaaa taattttgtt      6120
taactttaag aaggagatat ac                                                6142
```

<210> SEQ ID NO 100
<211> LENGTH: 311
<212> TYPE: PRT
<213> ORGANISM: artificial sequence
<220> FEATURE:
<223> OTHER INFORMATION: At4g10750-G83 His TAG

<400> SEQUENCE: 100

```
Met Gly Pro Ala Thr Ala Val Glu Ala Ile Thr Asn Arg Ser Lys Asn
1               5                   10                  15

Ser Leu Lys Ser Arg Leu Arg Gly Gly Glu Thr Leu Tyr Gly Leu Phe
            20                  25                  30

Leu Leu Ser Phe Ser Pro Thr Leu Ala Glu Ile Ala Ala His Ala Gly
        35                  40                  45

Tyr Asp Tyr Val Val Asp Met Glu His Gly Pro Gly Gly Ile Pro
    50                  55                  60

Glu Ala Leu Asp Cys Ile Arg Ala Leu Asn Ala Ala Gly Thr Ser Ala
65                  70                  75                  80

Ile Leu Gly Leu Pro Glu Asn Ser Pro Thr Trp Ala Lys Lys Ala Leu
                85                  90                  95

Asp Leu Gly Pro Gln Gly Ile Met Phe Pro Met Ile Glu Ser Arg Lys
            100                 105                 110

Asp Ala Thr Lys Ala Val Ser Tyr Cys Arg Phe Pro Pro Asp Gly Ile
        115                 120                 125

Arg Gly Ser Ala His Thr Val Val Arg Ala Ser Asn Tyr Gly Ile Asp
    130                 135                 140

Glu Gly Tyr Leu Ser Asn Tyr Ala Glu Glu Ile Leu Ile Met Cys Gln
145                 150                 155                 160

Val Glu Ser Gly Glu Gly Val Lys Lys Ala Asp Glu Ile Ala Ala Val
                165                 170                 175

Asp Gly Val Asp Cys Val Gln Met Gly Pro Leu Asp Leu Ser Ala Ser
            180                 185                 190

Leu Gly Tyr Leu Trp Asp Pro Gly His Lys Lys Val Arg Glu Met Met
        195                 200                 205

Lys Lys Ala Glu Lys Ser Val Leu Ser Thr Asp Pro Ala Lys Gly Gly
    210                 215                 220

Ala Tyr Leu Ser Gly Phe Ala Met Pro His Asp Gly Ala Gly Glu Ile
225                 230                 235                 240

Arg Gly Arg Gly Tyr His Met Val Ala Gly Ala Val Asp Val Gly Leu
```

```
                    245                 250                 255
Phe Arg Asn Ala Ala Val Glu Asp Val Arg Arg Phe Lys Met Gly Leu
            260                 265                 270

Val Asn Glu Ser Asp Ser Glu Asp Ser Ser Glu His Asp Lys Asp Val
        275                 280                 285

Asp Asp Glu Lys Tyr Trp Ser Glu Val Asp Lys Leu Ala Ala Ala Leu
    290                 295                 300

Glu His His His His His His
305                 310

<210> SEQ ID NO 101
<211> LENGTH: 30
<212> TYPE: DNA
<213> ORGANISM: artificial sequence
<220> FEATURE:
<223> OTHER INFORMATION: FUSION REV primer

<400> SEQUENCE: 101
gatgggcatg tccatcgtga tcgcttccac                                      30

<210> SEQ ID NO 102
<211> LENGTH: 30
<212> TYPE: DNA
<213> ORGANISM: artificial sequence
<220> FEATURE:
<223> OTHER INFORMATION: FUSION FWD primer

<400> SEQUENCE: 102
gtggaagcga tcacgatgga catgcccatc                                      30

<210> SEQ ID NO 103
<211> LENGTH: 26
<212> TYPE: DNA
<213> ORGANISM: artificial sequence
<220> FEATURE:
<223> OTHER INFORMATION: pET29a 3prime

<400> SEQUENCE: 103
ccaactcagc ttcctttcgg gctttg                                          26

<210> SEQ ID NO 104
<211> LENGTH: 3938
<212> TYPE: DNA
<213> ORGANISM: artificial sequence
<220> FEATURE:
<223> OTHER INFORMATION: pCR8GW- plastid HpaI PP

<400> SEQUENCE: 104
caccatggcc accgcttcaa tcttccccgc cgccgtgacc gtcaccagag atgtgacatc      60
tcttcttaat ccatcttctc tgatcatcgg aaaatcatta tctccttcaa agttcagctc     120
aatcaaatcc tccgtttcat tttcccgcaa aaccctaact ccaattcgat actcttcatc     180
tcccgccgat cactcacccg ccaccgcygt ggaagcgatc acgatggaca tgcccatcaa     240
ccacttcaag cgacgcctgc acagcggtga accgcaaatc ggcctgtggc tcggcctggc     300
cgatgcctac tgcgccgagc tggcggccaa tgccggtttc gactggctgc tgatcgacgg     360
cgaacacgcg cccaacgacc tgcgcggcat gctcgcccag ttgcaggcgg tggcacccta     420
cccccagcca gcagtgatcc ggcccggtga tcggcgatacc gcgctgatca agcaggtgct     480
ggatatcggc gcacaaacct tgctggtgcc gatggtggaa actgccgaac aggcgcggca     540
actggtcaag gccatgcatt acccgcccaa gggcattcgc ggggtgggca gcgcgctggc     600
```

```
gagggcttcg cgctggaaca ccctccccgg ttacctggac cacgccgatg agcaaatgtg    660
cctgctggtg cagatcgaga caaggaagg cctggccaac ctggacgaga tcgttgcggt     720
ggaaggtgtg gatggcgtgt tcatcgggcc tgcagacctg agtgcggcca tggggcatcg    780 cggcaaccc gggcacccgg aggtgcaggc ggcgattgaa gacgcgatcg tgcgcattgg     840
caaggcgggc aaagccgccg gcattctcag cgcggacgag aaactggcgc gacgctacat    900
cgagctgggt gcggcgtttg tggcggtggg tgtggatacc acggtgctga tgcgcgggct    960
gcgcgagctg gcggggaagt tcaaggatac agtggtagtc cctagtgccg ggggtagtgt    1020
ctacccgagc tccgtcgaca agcttgcggc cgcactcgag caccaccacc accaccactg    1080
agatccggct gctaacaaag cccgaaagga agctgagttg aagggcgaa ttcgacccag     1140 ctttcttgta caaagttggc attataaaaa ataattgctc atcaatttgt tgcaacgaac    1200
aggtcactat cagtcaaaat aaaatcatta tttgccatcc agctgatatc ccctatagtg    1260
agtcgtatta catggtcata gctgtttcct ggcagctctg cccgtgtct caaaatctct     1320 gatgttacat tgcacaagat aaaaatatat catcatgcct cctctagacc agccaggaca    1380
gaaatgcctc gacttcgctg ctgcccaagg ttgccgggtg acgcacaccg tggaaacgga    1440
tgaaggcacg aacccagtgg acataagcct gttcggttcg taagctgtaa tgcaagtagc    1500
gtatgcgctc acgcaactgg tccagaacct tgaccgaacg cagcggtggt aacgcgcag    1560 tggcggtttt catggcttgt tatgactgtt tttttgggt acagtctatg cctcgggcat     1620
ccaagcagca agcgcgttac gccgtgggtc gatgtttgat gttatggagc agcaacgatg    1680
ttacgcagca gggcagtcgc cctaaaacaa agttaaacat catgagggaa gcggtgatcg    1740
ccgaagtatc gactcaacta tcagaggtag ttggcgtcat cgagcgccat ctcgaaccga    1800
cgttgctggc cgtacatttg tacggctccg cagtggatgg cggcctgaag ccacacagtg    1860
atattgattt gctggttacg gtgaccgtaa ggcttgatga acaacgcgg cgagctttga    1920 tcaacgacct tttggaaact tcggcttccc ctggagagag cgagattctc cgcgctgtag    1980
aagtcaccat tgttgtgcac gacgacatca ttccgtggcg ttatccagct aagcgcgaac    2040
tgcaatttgg agaatggcag cgcaatgaca ttcttgcagg tatcttcgag ccagccacga    2100
tcgacattga tctggctatc ttgctgacaa aagcaagaga acatagcgtt gccttggtag    2160
gtccagcggc ggaggaactc tttgatccgg ttcctgaaca ggatctattt gaggcgctaa    2220
atgaaacctt aacgctatgg aactcgccgc ccgactgggc tggcgatgag cgaaatgtag    2280
tgcttacgtt gtcccgcatt tggtacagcg cagtaaccgg caaaatcgcg ccgaaggatg    2340
tcgctgccga ctgggcaatg gagcgcctgc cggcccagta tcagcccgtc atacttgaag    2400
ctagacaggc ttatcttgga caagaagaag atcgcttggc ctcgcgcgca gatcagttgg    2460
aagaatttgt ccactacgtg aaaggcgaga tcaccaaggt agtcggcaaa taaccctcga    2520
gccacccatg accaaaatcc cttaacgtga gttacgcgtc gttccactga gcgtcagacc    2580
ccgtagaaaa gatcaaagga tcttcttgag atccttttt tctgcgcgta atctgctgct    2640
tgcaaacaaa aaaaccaccg ctaccagcgg tggtttgttt gccggatcaa gagctaccaa    2700
ctctttttcc gaaggtaact ggcttcagca gagcgcagat accaaatact gtccttctag    2760
tgtagccgta gttaggccac cacttcaaga actctgtagc accgcctaca tacctcgctc    2820
tgctaatcct gttaccagtg gctgctgcca gtggcgataa gtcgtgtctt accgggttgg    2880
actcaagacg atagttaccg gataaggcgc agcggtcggg ctgaacgggg ggttcgtgca    2940
```

| | |
|---|---|
| cacagcccag cttggagcga acgacctaca ccgaactgag atacctacag cgtgagcatt | 3000 |
| gagaaagcgc cacgcttccc gaagggagaa aggcggacag gtatccggta agcggcaggg | 3060 |
| tcggaacagg agagcgcacg agggagcttc caggggggaaa cgcctggtat ctttatagtc | 3120 |
| ctgtcgggtt tcgccacctc tgacttgagc gtcgattttt gtgatgctcg tcagggggc | 3180 |
| ggagcctatg gaaaaacgcc agcaacgcgg cctttttacg gttcctggcc ttttgctggc | 3240 |
| cttttgctca catgttcttt cctgcgttat cccctgattc tgtggataac cgtattaccg | 3300 |
| cctttgagtg agctgatacc gctcgccgca gccgaacgac cgagcgcagc gagtcagtga | 3360 |
| gcgaggaagc ggaagagcgc ccaatacgca aaccgcctct ccccgcgcgt tggccgattc | 3420 |
| attaatgcag ctggcacgac aggtttcccg actggaaagc gggcagtgag cgcaacgcaa | 3480 |
| ttaatacgcg taccgctagc caggaagagt ttgtagaaac gcaaaaaggc catccgtcag | 3540 |
| gatggccttc tgcttagttt gatgcctggc agtttatggc gggcgtcctg cccgccaccc | 3600 |
| tccgggccgt tgcttcacaa cgttcaaatc cgctcccggc ggatttgtcc tactcaggag | 3660 |
| agcgttcacc gacaaacaac agataaaacg aaaggcccag tcttccgact gagcctttcg | 3720 |
| ttttatttga tgcctggcag ttccctactc tcgcgttaac gctagcatgg atgttttccc | 3780 |
| agtcacgacg ttgtaaaacg acggccagtc ttaagctcgg gccccaaata atgatttat | 3840 |
| tttgactgat agtgacctgt tcgttgcaac aaattgatga gcaatgcttt tttataatgc | 3900 |
| caactttgta caaaaaagca ggctccgaat tcgcccttt | 3938 |

<210> SEQ ID NO 105
<211> LENGTH: 15983
<212> TYPE: DNA
<213> ORGANISM: artificial sequence
<220> FEATURE:
<223> OTHER INFORMATION: pKR1478 - plastid HpaI PP

<400> SEQUENCE: 105

| | |
|---|---|
| acccagcttt cttgtacaaa gtggtgatgg ccgcatttcg caccaaatca atgaaagtaa | 60 |
| taatgaaaag tctgaataag aatacttagg cttagatgcc tttgttactt gtgtaaaata | 120 |
| acttgagtca tgtaccttg gcggaaacag aataaataaa aggtgaaatt ccaatgctct | 180 |
| atgtataagt tagtaatact taatgtgttc tacggttgtt tcaatatcat caaactctaa | 240 |
| ttgaaacttt agaaccacaa atctcaatct tttcttaatg aaatgaaaaa tcttaattgt | 300 |
| accatgttta tgttaaacac cttacaattg gttggagagg aggaccaacc gatgggacaa | 360 |
| cattgggaga aagagattca atggagattt ggataggaga acaacattct ttttcacttc | 420 |
| aatacaagat gagtgcaaca ctaaggatat gtatgagact ttcagaagct acgacaacat | 480 |
| agatgagtga ggtggtgatt cctagcaaga aagacattag aggaagccaa atcgaacaa | 540 |
| ggaagacatc aagggcaaga gacaggacca tccatctcag gaaaaggagc tttgggatag | 600 |
| tccgagaagt tgtacaagaa atttttggga gggtgagtga tgcattgctg gtgactttaa | 660 |
| ctcaatcaaa attgagaaag aaagaaaagg gaggggctc acatgtgaat agaagggaaa | 720 |
| cgggagaatt ttacagtttt gatctaatgg gcatcccagc tagtggtaac atattcacca | 780 |
| tgtttaacct tcacgtacgt ctagaggatc cgtcgacggc gcgccagatc ctctagagtc | 840 |
| gacctgcagg catgcaagct tggcgtaatc atggtcatag ctgtttcctg tgtgaaattg | 900 |
| ttatccgctc acaattccac acaacatacg agccggaagc ataaagtgta aagcctgggg | 960 |
| tgcctaatga gtgagctaac tcacattaat tgcgttgcgc tcactgcccg ctttccagtc | 1020 |
| gggaaacctg tcgtgccagc tgcattaatg aatcggccaa cgcgcgggga gaggcggttt | 1080 |

```
gcgtattgga tcgatccctg aaagcgacgt tggatgttaa catctacaaa ttgccttttc    1140
ttatcgacca tgtacgtaag cgcttacgtt tttggtggac ccttgaggaa actggtagct    1200
gttgtgggcc tgtggtctca agatggatca ttaatttcca ccttcaccta cgatgggggg    1260
catcgcaccg gtgagtaata ttgtacggct aagagcgaat ttggcctgta gacctcaatt    1320
gcgagctttc taatttcaaa ctattcgggc ctaacttttg gtgtgatgat gctgactggc    1380
aggatatata ccgttgtaat ttgagctcgt gtgaataagt cgctgtgtat gtttgtttga    1440
ttgtttctgt tggagtgcag cccatttcac cggacaagtc ggctagattg atttagccct    1500
gatgaactgc cgaggggaag ccatcttgag cgcggaatgg gaatggattt cgttgtacaa    1560
cgagacgaca gaacacccac gggaccgagc ttcgcgagct tttgtatccg tggcatcctt    1620
ggtccgggcg atttgttcac gtccatgagg cgctctccaa aggaacgcat attttccggt    1680
gcaacctttc cggttcttcc tctactcgac ctcttgaagt cccagcatga atgttcgacc    1740
gctccgcaag cggatctttg gcgcaaccag ccggtttcgc acgtcgattc tcgcgagcct    1800
gcatactttg gcaagattgc tgaatgacgc tgatgcttca tcgcaatctg cgataatggg    1860
gtaagtatcc ggtgaaggcc gcaggtcagg ccgcctgagc actcagtgtc ttggatgtcc    1920
agttccacgg cagctgttgc tcaagcctgc tgatcggagc gtccgcaagg tcggcgcgga    1980
cgtcggcaag ccaggcctgc ggatcgatgt tattgagctt ggcgctcatg atcagtgtcg    2040
ccatgaacgc cgcacgttca gcacaacgat ccgatccggc aaacagccat gacttcctgc    2100
cgagtacata gcctctgagc gttcgttcgg cagcattgtt cgtcaggcaa atcgggccgt    2160
catcgaggaa tgacgtaatg ccatcccatc gcttgagcat gtaatttatc gcctcggcga    2220
cgggagaact gcgcgacaat ttcccccgct cggtttcgag ccaatcatgc agctcttcgg    2280
cgagtgacct tgatcaggcc accgccacga ccgcggaaga cgaacagatg cctgcgcatc    2340
ggatcgcgct tcagcgtctc ttgcaccatc agcgacaaac cgggaaagcc tttgcgcatg    2400
tccgtactta tgtcgccact tgggagggct tcgtctacgt ggccttcgtg atcgacgtct    2460
tcgcccgtcg cattgtcgga tggcgggcga ccggacagc acatgcaggc tttgtcctcg    2520
atgccctcga ggaggctcat catgatcggc gtcccgctca tggcggccta gtgcatcact    2580
cggatcgcgg tgttcaatac gtgtcctttc gctattccga gcggttggca gaagcaggta    2640
tcgagccatc tatcggaagc gtcggcgaca gcacgacaac gccctcgcag aagcgatcaa    2700
cggtctttac aaggccgagg tcattcatcg gcgtggacca tggaggagct tcgaagcggt    2760
cgagttcgct accttggaat ggatagactg gttcaaccac ggcggctttt gaagcccatc    2820
ggcaatatac cgccagccga agacgaggat cagtattacg ccatgctgga cgaagcagcc    2880
atggctgcgc atttttaacga aatggcctcc ggcaaacccg gtgcggttca cttgttgcgt    2940
gggaaagttc acgggactcc gcgcacgagc cttcttcgta atagccatat cgaccgaatt    3000
gacctgcagg ggggggggg aaagccacgt tgtgtctcaa aatctctgat gttacattgc    3060
acaagataaa aatatatcat catgaacaat aaaactgtct gcttacataa acagtaatac    3120 aagggggtgtt atgagccata ttcaacggga aacgtcttgc tcgaggccgc gattaaattc    3180
caacatggat gctgatttat atgggtataa atgggctcgc gataatgtcg ggcaatcagg    3240
tgcgacaatc tatcgattgt atgggaagcc cgatgcgcca gagttgtttc tgaaacatgg    3300
caaaggtagc gttgccaatg atgttacaga tgagatggtc agactaaaact ggctgacgga    3360 atttatgcct cttccgacca tcaagcattt tatccgtact cctgatgatg catggttact    3420
```

```
caccactgcg atccccggga aaacagcatt ccaggtatta gaagaatatc ctgattcagg    3480
tgaaaatatt gttgatgcgc tggcagtgtt cctgcgccgg ttgcattcga ttcctgtttg    3540
taattgtcct tttaacagcg atcgcgtatt tcgtctcgct caggcgcaat cacgaatgaa    3600
taacggtttg gttgatgcga gtgattttga tgacgagcgt aatggctggc ctgttgaaca    3660
agtctggaaa gaaatgcata agcttttgcc attctcaccg gattcagtcg tcactcatgg    3720
tgatttctca cttgataacc ttattttga cgagggaaa ttaataggtt gtattgatgt    3780
tggacgagtc ggaatcgcag accgatacca ggatcttgcc atcctatgga actgcctcgg    3840
tgagttttct ccttcattac agaaacggct ttttcaaaaa tatggtattg ataatcctga    3900
tatgaataaa ttgcagtttc atttgatgct cgatgagttt ttctaatcag aattggttaa    3960
ttggttgtaa cactggcaga gcattacgct gacttgacgg gacggcggct tgttgaata    4020 aatcgaactt ttgctgagtt gaaggatcag atcacgcatc ttcccgacaa cgcagaccgt    4080
tccgtggcaa agcaaaagtt caaaatcacc aactggtcca cctacaacaa agctctcatc    4140
aaccgtggct ccctcacttt ctggctggat gatggggcga ttcaggcctg gtatgagtca    4200
gcaacacctt cttcacgagg cagacctcag cgccccccc ccctgcagg tcttttccaa    4260 tgatgagcac ttttaaagtt ctgctatgtg gcgcggtatt atcccgtgtt gacgccgggc    4320
aagagcaact cggtcgccgc atacactatt ctcagaatga cttggttgag tactcaccag    4380
tcacagaaaa gcatcttacg gatggcatga cagtaagaga attatgcagt gctgccataa    4440
ccatgagtga taacactgcg gccaacttac ttctgacaac gatcggagga ccgaaggagc    4500
taaccgcttt tttgcacaac atggggatc atgtaactcg ccttgatcgt tgggaaccgg    4560
agctgaatga agccatacca aacgacgagc gtgacaccac gatgcctgta gcaatggcaa    4620
caacgttgcg caaactatta actggcgaac tacttactct agcttcccgg caacaattaa    4680
tagactggat ggaggcggat aaagttgcag gaccacttct gcgctcggcc cttccggctg    4740
gctggtttat tgctgataaa tctggagccg gtgagcgtgg gtctcgcggt atcattgcag    4800
cactggggcc agatggtaag ccctcccgta tcgtagttat ctacacgacg gggagtcagg    4860
caactatgga tgaacgaaat agacagatcg ctgagatagg tgcctcactg attaagcatt    4920
ggtaactgtc agaccaagtt tactcatata ctttagat tgatttaaaa cttcattttt    4980
aatttaaaag gatctaggtg aagatccttt ttgataatct catgaccaaa atcccttaac    5040
gtgagttttc gttccactga gcgtcagacc ccgtagaaaa gatcaaagga tcttcttgag    5100 atccttttt tctgcgcgta atctgctgct tgcaaacaaa aaaaccaccg ctaccagcgg    5160
tggtttgttt gccggatcaa gagctaccaa ctctttttcc gaaggtaact ggcttcagca    5220
gagcgcagat accaaatact gtccttctag tgtagccgta gttaggccac cacttcaaga    5280
actctgtagc accgcctaca tacctcgctc tgctaatcct gttaccagtg gctgctgcca    5340
gtggcgataa gtcgtgtctt accgggttgg actcaagacg atagttaccg gataaggcgc    5400
agcggtcggg ctgaacgggg ggttcgtgca cacagcccag cttggagcga acgacctaca    5460
ccgaactgag atacctacag cgtgagctat gagaaagcgc cacgcttccc gaagggagaa    5520
aggcggacag gtatccggta agcggcaggg tcggaacagg agagcgcacg agggagcttc    5580
caggggaaac gcctggtat ctttatagtc ctgtcgggtt tcgccacctc tgacttgagc    5640 gtcgatttt tgtgatgctcg tcaggggggc ggagcctatg gaaaaacgcc agcaacgcgg    5700
cctttttacg gttcctggcc ttttgctggc cttttgctca catgttcttt cctgcgttat    5760
cccctgattc tgtggataac cgtattaccg cctttgagtg agctgatacc gctcgccgca    5820
```

```
gccgaacgac cgagcgcagc gagtcagtga gcgaggaagc ggaagagcgc ctgatgcggt    5880
attttctcct tacgcatctg tgcggtattt cacaccgcat atggtgcact ctcagtacaa    5940
tctgctctga tgccgcatag ttaagccagt atacactccg ctatcgctac gtgactgggt    6000
catggctgcg ccccgacacc cgccaacacc cgctgacgcg ccctgacggg cttgtctgct    6060
cccggcatcc gcttacagac aagctgtgac cgtctccggg agctgcatgt gtcagaggtt    6120
ttcaccgtca tcaccgaaac gcgcgaggca gggtgccttg atgtgggcgc cggcggtcga    6180
gtggcgacgg cgcggcttgt ccgcgccctg gtagattgcc tggccgtagg ccagccattt    6240
ttgagcggcc agcggccgcg ataggccgac gcgaagcggc ggggcgtagg gagcgcagcg    6300
accgaagggt aggcgctttt tgcagctctt cggctgtgcg ctggccagac agttatgcac    6360
aggccaggcg ggttttaaga gttttaataa gttttaaaga gttttaggcg gaaaaatcgc    6420
cttttttctc ttttatatca gtcacttaca tgtgtgaccg gttcccaatg tacggctttg    6480
ggttcccaat gtacgggttc cggttcccaa tgtacggctt tgggttccca atgtacgtgc    6540
tatccacagg aaagagacct tttcgacctt ttccccctgc tagggcaatt tgccctagca    6600
tctgctccgt acattaggaa ccggcggatg cttcgccctc gatcaggttg cggtagcgca    6660
tgactaggat cgggccagcc tgccccgcct cctccttcaa atcgtactcc ggcaggtcat    6720
ttgacccgat cagcttgcgc acggtgaaac agaacttctt gaactctccg gcgctgccac    6780
tgcgttcgta gatcgtcttg aacaaccatc tggcttctgc cttgcctgcg gcgcggcgtg    6840
ccaggcggta gagaaaacgg ccgatgccgg gatcgatcaa aaagtaatcg gggtgaaccg    6900
tcagcacgtc cgggttcttg ccttctgtga tctcgcggta catccaatca gctagctcga    6960
tctcgatgta ctccggccgc ccggtttcgc tctttacgat cttgtagcgg ctaatcaagg    7020
cttcaccctc ggataccgtc accaggcggc cgttcttggc cttcttcgta cgctgcatgg    7080
caacgtgcgt ggtgtttaac cgaatgcagg tttctaccag gtcgtctttc tgctttccgc    7140
catcggctcg ccggcagaac ttgagtacgt ccgcaacgtg tggacggaac acgcggccgg    7200
gcttgtctcc cttcccttcc cggtatcggt tcatggattc ggttagatgg gaaaccgcca    7260
tcagtaccag gtcgtaatcc cacacactgg ccatgccggc cggccctgcg gaaacctcta    7320
cgtgcccgtc tggaagctcg tagcggatca cctcgccagc tcgtcggtca cgcttcgaca    7380
gacgaaaaac ggccacgtcc atgatgctgc gactatcgcg ggtgcccacg tcatagagca    7440
tcggaacgaa aaaatctggt tgctcgtcgc ccttgggcgg cttcctaatc gacggcgcac    7500
cggctgccgg cggttgccgg gattctttgc ggattcgatc agcggccgct tgccacgatt    7560
caccggggcg tgcttctgcc tcgatgcgtt gccgctgggc ggcctgcgcg gccttcaact    7620
tctccaccag gtcatcaccc agcgccgcgc cgatttgtac cggccggat ggtttgcgac    7680 cgctcacgcc gattcctcgg gcttgggggt tccagtgcca ttgcagggcc ggcagacaac    7740
ccagccgctt acgcctggcc aaccgcccgt tcctccacac atgggcatt ccacggcgtc    7800 ggtgcctggt tgttcttgat tttccatgcc gcctccttta gccgctaaaa ttcatctact    7860
catttattca tttgctcatt tactctggta gctgcgcgat gtattcagat agcagctcgg    7920
taatggtctt gccttggcgt accgcgtaca tcttcagctt ggtgtgatcc tccgccggca    7980
actgaaagtt gacccgcttc atggctggcg tgtctgccag gctggccaac gttgcagcct    8040
tgctgctgcg tgcgctcgga cggccggcac ttagcgtgtt tgtgcttttg ctcatttttct    8100 ctttacctca ttaactcaaa tgagttttga tttaatttca gcggccagcg cctggacctc    8160
```

```
gcgggcagcg tcgccctcgg gttctgattc aagaacggtt gtgccggcgg cggcagtgcc   8220
tgggtagctc acgcgctgcg tgatacggga ctcaagaatg ggcagctcgt acccggccag   8280
cgcctcggca acctcaccgc cgatgcgcgt gcctttgatc gcccgcgaca cgacaaaggc   8340
cgcttgtagc cttccatccg tgacctcaat gcgctgctta accagctcca ccaggtcggc   8400
ggtggcccat atgtcgtaag ggcttggctg caccggaatc agcacgaagt cggctgcctt   8460
gatcgcggac acagccaagt ccgccgcctg gggcgctccg tcgatcacta cgaagtcgcg   8520
ccggccgatg gccttcacgt cgcggtcaat cgtcgggcgg tcgatgccga caacggttag   8580
cggttgatct tcccgcacgg ccgcccaatc gcgggcactg ccctggggat cggaatcgac   8640
taacagaaca tcggccccgg cgagttgcag ggcgcgggct agatgggttg cgatggtcgt   8700
cttgcctgac ccgcctttct ggttaagtac agcgataact tcatgcgttc ccttgcgtat   8760
ttgtttattt actcatcgca tcatatacgc agcgaccgca tgacgcaagc tgttttactc   8820
aaatacacat cacctttta dacggcggcg ctcggtttct tcagcggcca agctggccgg   8880
ccaggccgcc agcttggcat cagacaaacc ggccaggatt tcatgcagcc gcacggttga   8940
gacgtgcgcg gcggctcga acacgtaccc ggccgcgatc atctccgcct cgatctcttc   9000
ggtaatgaaa aacggttcgt cctggccgtc ctggtgcggt ttcatgcttg ttcctcttgg   9060
cgttcattct cggcggccgc cagggcgtcg gcctcggtca atgcgtcctc acggaaggca   9120
ccgcgccgcc tggcctcggt gggcgtcact tcctcgctgc gctcaagtgc gcggtacagg   9180
gtcgagcgat gcacgccaag cagtgcagcc gcctctttca cggtgcggcc ttcctggtcg   9240
atcagctcgc gggcgtgcgc gatctgtgcc ggggtgaggg tagggcgggg gccaaacttc   9300
acgcctcggg ccttggcggc ctcgcgcccg ctccgggtgc ggtcgatgat tagggaacgc   9360
tcgaactcgg caatgccggc gaacacggtc aacaccatgc ggccggccgg cgtggtggtg   9420
tcggcccacg gctctgccag gctacgcagg cccgcgccgg cctcctggat gcgctcggca   9480
atgtccagta ggtcgcgggt gctgcgggcc aggcggtcta gcctggtcac tgtcacaacg   9540
tcgccagggc gtaggtggtc aagcatcctg gccagctccg ggcggtcgcg cctggtgccg   9600
gtgatcttct cggaaaacag cttggtgcag ccggccgcgt gcagttcggc ccgttggttg   9660
gtcaagtcct ggtcgtcggt gctgacgcgg gcatagccca gcaggccagc ggcggcgctc   9720
ttgttcatgg cgtaatgtct ccggttctag tcgcaagtat tctactttat gcgactaaaa   9780
cacgcgacaa gaaaacgcca ggaaaagggc agggcggcag cctgtcgcgt aacttaggac   9840
ttgtgcgaca tgtcgttttc agaagacggc tgcactgaac gtcagaagcc gactgcacta   9900
tagcagcgga ggggttggac cacaggacgg gtgtggtcgc catgatcgcg tagtcgatag   9960
tggctccaag tagcgaagcg agcaggactg ggcggcggcc aaagcggtcg acagtgctc   10020 cgagaacggg tgcgcataga aattgcatca acgcatatag cgctagcagc acgccatagt   10080
gactggcgat gctgtcggaa tggacgatat cccgcaagag gcccggcagt accggcataa   10140
ccaagcctat gcctacagca tccagggtga cggtgccgag gatgacgatg agcgcattgt   10200
tagatttcat acacggtgcc tgactgcgtt agcaatttaa ctgtgataaa ctaccgcatt   10260
aaagctagct tgcttggtcg ttccgcgtga acgtcggctc gattgtacct gcgttcaaat   10320
actttgcgat cgtgttgcgc gcctgcccgg tgcgtcggct gatctcacgg atcgactgct   10380
tctctcgcaa cgccatccga cggatgatgt ttaaaagtcc catgtggatc actccgttgc   10440
cccgtcgctc accgtgttgg ggggaaggtg cacatggctc agttctcaat ggaaattatc   10500
tgcctaaccg gctcagttct gcgtagaaac caacatgcaa gctccaccgg gtgcaaagcg   10560
```

```
gcagcggcgg caggatatat tcaattgtaa atggcttcat gtccgggaaa tctacatgga   10620
tcagcaatga gtatgatggt caatatggag aaaagaaag agtaattacc aattttttt    10680 caattcaaaa atgtagatgt ccgcagcgtt attataaaat gaaagtacat tttgataaaa   10740
cgacaaatta cgatccgtcg tatttatagg cgaaagcaat aaacaaatta ttctaattcg   10800
gaaatcttta tttcgacgtg tctacattca cgtccaaatg ggggcttaga tgagaaactt   10860
cacgatcgat gccttgattt cgccattccc agatacccat ttcatcttca gattggtctg   10920
agattatgcg aaaatataca ctcatataca taaatactga cagtttgagc taccaattca   10980
gtgtagccca ttacctcaca taattcactc aaatgctagg cagtctgtca actcggcgtc   11040
aatttgtcgg ccactatacg atagttgcgc aaattttcaa agtcctggcc taacatcaca   11100
cctctgtcgg cggcgggtcc catttgtgat aaatccacca tatcgaatta attcagactc   11160
ctttgcccca gagatcacaa tggacgactt cctctatctc tacgatctag tcaggaagtt   11220
cgacggagaa ggtgacgata ccatgttcac cactgataat gagaagatta gccttttcaa   11280
tttcagaaag aatgctaacc cacagatggt tagagaggct tacgcagcag gtctcatcaa   11340
gacgatctac ccgagcaata atctccagga gatcaaatac cttcccaaga aggttaaaga   11400
tgcagtcaaa agattcagga ctaactgcat caagaacaca gagaaagata tatttctcaa   11460
gatcagaagt actattccag tatggacgat tcaaggcttg cttcacaaac caaggcaagt   11520
aatagagatt ggagtctcta aaaaggtagt tcccactgaa tcaaaggcca tggagtcaaa   11580
gattcaaata gaggacctaa cagaactcgc cgtaaagact ggcgaacagt tcatacagag   11640
tctcttacga ctcaatgaca agaagaaaat cttcgtcaac atggtggagc acgacacgct   11700
tgtctactcc aaaaatatca agatacagt ctcagaagac caaagggcaa ttgagacttt    11760
tcaacaaagg gtaatatccg gaaacctcct cggattccat tgcccagcta tctgtcactt   11820
tattgtgaag atagtggaaa aggaaggtgg ctcctacaaa tgccatcatt gcgataaagg   11880
aaaggccatc gttgaagatg cctctgccga cagtggtccc aaagatggac ccccacccac   11940
gaggagcatc gtggaaaaag aagacgttcc aaccacgtct tcaaagcaag tggattgatg   12000
tgatatctcc actgacgtaa gggatgacgc acaatcccac tatccttcgc aagacccttc   12060
ctctatataa ggaagttcat ttcatttgga gaggacacgc tgaaatcacc agtctccaag   12120
cttgcgggga tcgtttcgca tgattgaaca agatggattg cacgcaggtt ctccggccgc   12180
ttgggtggag aggctattcg gctatgactg ggcacaacag acaatcggct gctctgatgc   12240
cgccgtgttc cggctgtcag cgcaggggcg cccggttctt tttgtcaaga ccgacctgtc   12300
cggtgccctg aatgaactgc aggacgaggc agcgcggcta tcgtggctgg ccacgacggg   12360
cgttccttgc gcagctgtgc tcgacgttgt cactgaagcg ggaagggact ggctgctatt   12420
gggcgaagtg ccggggcagg atctcctgtc atctcacctt gctcctgccg agaaagtatc   12480
catcatggct gatgcaatgc ggcggctgca tacgcttgat ccggctacct gcccattcga   12540
ccaccaagcg aaacatcgca tcgagcgagc acgtactcgg atggaagccg gtcttgtcga   12600
tcaggatgat ctggacgaag agcatcaggg gctcgcgcca gccgaactgt tcgccaggct   12660
caaggcgcgc atgcccgacg gcgaggatct cgtcgtgacc catggcgatg cctgcttgcc   12720
gaatatcatg gtggaaaatg gccgcttttc tggattcatc gactgtggcc ggctgggtgt   12780
ggcggaccgc tatcaggaca tagcgttggc tacccgtgat attgctgaag agcttggcgg   12840
cgaatgggct gaccgcttcc tcgtgcttta cggtatcgcc gctcccgatt cgcagcgcat   12900
```

```
cgccttctat cgccttcttg acgagttctt ctgagcggga ctctggggtt cgaaatgacc    12960
gaccaagcga cgcccaacct gccatcacga gatttcgatt ccaccgccgc cttctatgaa    13020
aggttgggct tcggaatcgt tttccgggac gccggctgga tgatcctcca gcgcggggat    13080
ctcatgctgg agttcttcgc ccaccccgga tcgatccaac acttacgttt gcaacgtcca    13140
agagcaaata gaccacgaac gccggaaggt tgccgcagcg tgtggattgc gtctcaattc    13200
tctcttgcag gaatgcaatg atgaaatatga tactgactat gaaactttga gggaatactg    13260
cctagcaccg tcacctcata acgtgcatca tgcatgccct gacaacatgg aacatcgcta    13320
tttttctgaa gaattatgct cgttggagga tgtcgcggca attgcagcta ttgccaacat    13380
cgaactaccc ctcacgcatg cattcatcaa tattattcat gcggggaaag gcaagattaa    13440
tccaactggc aaatcatcca gcgtgattgg taacttcagt tccagcgact tgattcgttt    13500
tggtgctacc cacgttttca ataaggacga gatggtggag taaagaagga gtgcgtcgaa    13560
gcagatcgtt caaacatttg gcaataaagt ttcttaagat tgaatcctgt tgccggtctt    13620
gcgatgatta tcatataatt tctgttgaat tacgttaagc atgtaataat taacatgtaa    13680
tgcatgacgt tatttatgag atgggttttt atgattagag tcccgcaatt atacatttaa    13740
tacgcgatag aaaacaaaat atagcgcgca aactaggata aattatcgcg cgcggtgtca    13800
tctatgttac tagatcgatc aaacttcggt actgtgtaat gacgatgagc aatcgagagg    13860
ctgactaaca aaaggtacat cgcgatggat cgatccattc gccattcagg ctgcgcaact    13920
gttgggaagg gcgatcggtg cgggcctctt cgctattacg ccagctggcg aaaggggat    13980 gtgctgcaag gcgattaagt tgggtaacgc cagggttttc ccagtcacga cgttgtaaaa    14040
cgacggccag tgaattcctg cagcccgggg gatccgccca ctcgaggcgc gccaagcttg    14100
catgcctgca ggctagccta agtacgtact caaaatgcca acaataaaa aaaagttgc    14160 tttaataatg ccaaaacaaa ttaataaaac acttacaaca ccggattttt tttaattaaa    14220
atgtgccatt taggataaat agttaatatt tttaataatt attaaaaag ccgtatctac    14280 taaaatgatt tttatttggt tgaaatatt aatatgttta aatcaacaca atctatcaaa    14340
attaaactaa aaaaaaaata agtgtacgtg gttaacatta gtacagtaat ataagaggaa    14400
aatgagaaat taagaaattg aaagcgagtc taatttttaa attatgaacc tgcatatata    14460
aaaggaaaga aagaatccag gaagaaaaga aatgaaacca tgcatggtcc cctcgtcatc    14520
acgagtttct gccatttgca atagaaacac tgaaacacct ttctctttgt cacttaattg    14580
agatgccgaa gccacctcac accatgaact tcatgaggtg tagcacccaa ggcttccata    14640
gccatgcata ctgaagaatg tctcaagctc agcaccctac ttctgtgacg tgtccctcat    14700
tcaccttcct ctcttcccta taaataacca cgcctcaggt tctccgcttc acaactcaaa    14760
cattctctcc attggtcctt aaacactcat cagtcatcac cgcggccatc acaagtttgt    14820
acaaaaaagc aggctccgaa ttcgcccttc accatggcca ccgcttcaat cttcccccgcc    14880 gccgtgaccg tcaccagaga tgtgacatct cttcttaatc catcttctct gatcatcgga    14940
aaatcattat ctccttcaaa gttcagctca atcaaatcct ccgtttcatt ttcccgcaaa    15000
accctaactc caattcgata ctcttcatct cccgccgatc actcacccgc caccgcygtg    15060
gaagcgatca cgatggacat gcccatcaac cacttcaagc gacgcctgca cagcggtgaa    15120
ccgcaaatcg gcctgtggct cggcctggcc gatgcctact cgccgagct ggcggccaat    15180 gccggtttcg actggctgct gatcgacggc gaacacgcgc caacgacct gcgcggcatg    15240 ctcgcccagt tgcaggcggt ggcaccctac cccagccagg cagtgatccg cccggtgatc    15300
```

```
ggcgataccg cgctgatcaa gcaggtgctg gatatcggcg cacaaacctt gctggtgccg  15360
atggtggaaa ctgccgaaca ggcgcggcaa ctggtcaagg ccatgcatta cccgcccaag  15420
ggcattcgcg gggtgggcag cgcgctggcg agggcttcgc gctggaacac cctccccggt  15480
tacctggacc acgccgatga gcaaatgtgc ctgctggtgc agatcgagaa caaggaaggc  15540
ctggccaacc tggacgagat cgttgcggtg gaaggtgtgg atggcgtgtt catcgggcct  15600
gcagacctga gtgcggccat ggggcatcgc ggcaaccccg ggcacccgga ggtgcaggcg  15660
gcgattgaag acgcgatcgt gcgcattggc aaggcgggca aagccgccgg cattctcagc  15720
gcggacgaga aactggcgcg acgctacatc gagctgggtg cggcgtttgt ggcggtgggt  15780
gtggatacca cggtgctgat gcgcgggctg cgcgagctgg cggggaagtt caaggataca  15840
gtggtagtcc ctagtgccgg gggtagtgtc tacccgagct ccgtcgacaa gcttgcggcc  15900
gcactcgagc accaccacca ccaccactga gatccggctg ctaacaaagc ccgaaaggaa  15960
gctgagttgg aagggcgaat tcg                                          15983
```

<210> SEQ ID NO 106
<211> LENGTH: 358
<212> TYPE: PRT
<213> ORGANISM: Pseudomonas putida

<400> SEQUENCE: 106

```
Met Ala Thr Ala Ser Ile Phe Pro Ala Ala Val Thr Val Thr Arg Asp
1               5                   10                  15

Val Thr Ser Leu Leu Asn Pro Ser Ser Leu Ile Ile Gly Lys Ser Leu
            20                  25                  30

Ser Pro Ser Lys Phe Ser Ser Ile Lys Ser Ser Val Ser Phe Ser Arg
        35                  40                  45

Lys Thr Leu Thr Pro Ile Arg Tyr Ser Ser Ser Pro Ala Asp His Ser
    50                  55                  60

Pro Ala Thr Ala Val Glu Ala Ile Thr Met Asp Met Pro Ile Asn His
65                  70                  75                  80

Phe Lys Arg Arg Leu His Ser Gly Glu Pro Gln Ile Gly Leu Trp Leu
                85                  90                  95

Gly Leu Ala Asp Ala Tyr Cys Ala Glu Leu Ala Ala Asn Ala Gly Phe
            100                 105                 110

Asp Trp Leu Leu Ile Asp Gly Glu His Ala Pro Asn Asp Leu Arg Gly
        115                 120                 125

Met Leu Ala Gln Leu Gln Ala Val Ala Pro Tyr Pro Ser Gln Ala Val
    130                 135                 140

Ile Arg Pro Val Ile Gly Asp Thr Ala Leu Ile Lys Gln Val Leu Asp
145                 150                 155                 160

Ile Gly Ala Gln Thr Leu Leu Val Pro Met Val Glu Thr Ala Glu Gln
                165                 170                 175

Ala Arg Gln Leu Val Lys Ala Met His Tyr Pro Pro Lys Gly Ile Arg
            180                 185                 190

Gly Val Gly Ser Ala Leu Ala Arg Ala Ser Arg Trp Asn Thr Leu Pro
        195                 200                 205

Gly Tyr Leu Asp His Ala Asp Glu Gln Met Cys Leu Leu Val Gln Ile
    210                 215                 220

Glu Asn Lys Glu Gly Leu Ala Asn Leu Asp Glu Ile Val Ala Val Glu
225                 230                 235                 240

Gly Val Asp Gly Val Phe Ile Gly Pro Ala Asp Leu Ser Ala Ala Met
```

```
                        245                 250                 255
Gly His Arg Gly Asn Pro Gly His Pro Glu Val Gln Ala Ala Ile Glu
            260                 265                 270

Asp Ala Ile Val Arg Ile Gly Lys Ala Gly Lys Ala Ala Gly Ile Leu
            275                 280                 285

Ser Ala Asp Glu Lys Leu Ala Arg Arg Tyr Ile Glu Leu Gly Ala Ala
            290                 295                 300

Phe Val Ala Val Gly Val Asp Thr Thr Val Leu Met Arg Gly Leu Arg
305                 310                 315                 320

Glu Leu Ala Gly Lys Phe Lys Asp Thr Val Val Pro Ser Ala Gly
            325                 330                 335

Gly Ser Val Tyr Pro Ser Ser Val Asp Lys Leu Ala Ala Ala Leu Glu
            340                 345                 350

His His His His His His
            355

<210> SEQ ID NO 107
<211> LENGTH: 358
<212> TYPE: PRT
<213> ORGANISM: Arabidopsis lyrata

<400> SEQUENCE: 107

Met Thr Thr Ala Ser Ile Phe Pro Ala Ala Val Val Thr Thr Asp
1               5                   10                  15

Val Thr Ser Leu Leu Asn Pro Ser Ser Leu Ile Ile Gly Lys Ser Leu
            20                  25                  30

Ser Pro Ser Lys Phe Ser Ser Ile Arg Ser Ser Val Ser Phe Ser Arg
            35                  40                  45

Lys Thr Leu Thr Pro Ile Arg Tyr Ser Ser Ser Pro Ala Asp His Ser
50                  55                  60

Pro Val Ala Ala Val Glu Ala Ile Thr Asn Arg Ser Lys Thr Ser Leu
65                  70                  75                  80

Lys Ser Arg Leu Arg Gly Gly Glu Thr Leu Tyr Gly Leu Phe Leu Leu
            85                  90                  95

Ser Phe Ser Pro Thr Leu Ala Glu Ile Ala Ala His Ala Gly Tyr Asp
            100                 105                 110

Tyr Val Val Val Asp Met Glu His Gly Pro Gly Gly Ile Pro Glu Ala
            115                 120                 125

Leu Asp Cys Ile Arg Ala Leu Asn Ala Ala Gly Thr Ser Ala Ile Leu
130                 135                 140

Arg Leu Pro Glu Asn Ser Ser Thr Trp Ala Lys Lys Ala Leu Asp Leu
145                 150                 155                 160

Gly Pro Gln Gly Ile Met Phe Pro Met Ile Glu Ser Arg Lys Asp Ala
            165                 170                 175

Thr Lys Ala Val Ser Tyr Cys Arg Phe Pro Pro Asp Gly Ile Arg Gly
            180                 185                 190

Ser Ala His Thr Val Val Arg Ala Ser Asn Tyr Gly Ile Asp Glu Gly
            195                 200                 205

Tyr Leu Ser Asn Tyr Ala Glu Glu Ile Leu Ile Met Cys Gln Val Glu
            210                 215                 220

Ser Ser Glu Gly Val Lys Lys Ala Asp Glu Ile Ala Ala Val Asp Gly
225                 230                 235                 240

Val Asp Cys Val Gln Met Gly Pro Leu Asp Leu Ser Ala Ser Leu Gly
            245                 250                 255
```

Tyr Leu Trp Asp Pro Gly His Lys Lys Val Arg Glu Met Met Lys Lys
            260                 265                 270

Ala Glu Lys Ser Val Leu Thr Ser Asp Pro Ala Lys Gly Gly Ala Tyr
        275                 280                 285

Leu Ser Gly Phe Ala Met Pro His Asp Gly Ala Val Glu Ile Arg Gly
    290                 295                 300

Arg Gly Tyr His Met Val Ala Gly Ala Val Asp Val Gly Leu Phe Arg
305                 310                 315                 320

Asn Ala Ala Val Glu Asp Val Arg Arg Phe Lys Met Gly Leu Val Asn
                325                 330                 335

Glu Ser Asp Gly Glu Asp Ser Leu Glu His Asp Lys Asp Val Asp Asp
            340                 345                 350

Glu Lys Tyr Trp Ser Glu
            355

<210> SEQ ID NO 108
<211> LENGTH: 346
<212> TYPE: PRT
<213> ORGANISM: Theobroma cacao

<400> SEQUENCE: 108

Met Ala Thr Leu Thr Tyr Thr Ala Ala Ala Ala Ser Pro Lys Leu
1               5                   10                  15

Ser Leu Arg Asn Pro Leu Ser Phe Ile Ser Ser Lys Ser Leu Ser Phe
            20                  25                  30

Pro Ser Ser Lys Pro Ser Ile Ser Leu Leu Lys Pro Leu Asn Ser Thr
        35                  40                  45

Lys Phe Pro Thr Leu Ser Pro Leu Lys Cys Ser Pro Asn Pro Ser Pro
    50                  55                  60

Ser Pro Ser Thr Ser Ser Leu Lys Ser Arg Leu Arg Asn Gly Glu Thr
65                  70                  75                  80

Leu Tyr Gly Ile Phe Leu Leu Ser Phe Ser Pro Thr Leu Ala Glu Ile
                85                  90                  95

Ala Ala Leu Ser Gly Tyr Asp Phe Val Val Ile Asp Met Glu His Gly
            100                 105                 110

Pro Gly Gly Ile His Glu Ser Leu Gln Ile Leu Arg Thr Leu Ser Pro
        115                 120                 125

Thr Asn Thr Pro Ala Ile Ile Arg Leu Pro Glu Phe Ser Ala Ala Trp
    130                 135                 140

Ala Lys Lys Ala Leu Asp Leu Gly Pro Gln Gly Ile Met Phe Pro Met
145                 150                 155                 160

Ile Asp Ser Pro Lys Asp Ala Lys Ala Val Ser Tyr Cys Arg Phe
                165                 170                 175

Pro Pro Asp Gly Ile Arg Gly Ser Ala His Thr Val Val Arg Ala Ser
            180                 185                 190

Asn Tyr Gly Ile Asn Glu Gly Tyr Leu Ser Asn Tyr Met Glu Asp Leu
        195                 200                 205

Leu Ile Met Cys Gln Val Glu Thr Val Asp Ala Val Lys Lys Val Glu
    210                 215                 220

Glu Ile Ala Ala Val Asp Gly Val Asp Cys Val Gln Met Gly Pro Leu
225                 230                 235                 240

Asp Leu Ser Ala Ser Leu Gly Tyr Leu Trp Asp Pro Gly His Lys Asn
                245                 250                 255

Val Arg Glu Met Leu Arg Thr Ala Glu Arg Gly Val Leu Lys Ser Asp
            260                 265                 270

```
Pro Gly Asp Gly Gly Ala Phe Leu Ala Gly Phe Ala Met Pro His Asp
        275                 280                 285

Pro Pro Val Glu Leu Gly Arg Arg Gly Tyr His Met Val Ser Gly Ala
290                 295                 300

Val Asp Phe Ala Leu Phe Arg Asn Ala Ala Leu Ala Asp Val Lys Ser
305                 310                 315                 320

Phe Lys Asn Ser Val Thr Val Gly Phe Asp Asp Gly Glu Glu Asp
                325                 330                 335

Lys Asp Gly Asp Glu Lys Tyr Trp Ser Glu
        340                 345

<210> SEQ ID NO 109
<211> LENGTH: 357
<212> TYPE: PRT
<213> ORGANISM: Ricinus communis

<400> SEQUENCE: 109

Met Pro Ala Leu Thr Ala Ala Thr Thr Phe Phe Ser Leu Ser Ser
1               5                   10                  15

Asn His Gln Asn Pro Asn Lys Pro Gln Cys Ser Ser Leu Pro Asn Leu
                20                  25                  30

Pro Phe Asn Phe Lys Thr Leu Asn Pro Asn Thr Ile Ile Thr Thr Thr
            35                  40                  45

Thr Phe Lys Thr Leu Thr Pro Leu Lys Ser Ser Thr Ser Ser Asp Val
        50                  55                  60

Asp Pro Thr Ser Ser Thr Thr Pro Ile Ser Ala Ala Ser Ser Phe
65                  70                  75                  80

Ser Leu Lys Ser Arg Leu Arg Asn Gly Glu Thr Leu Tyr Gly Ile Phe
                85                  90                  95

Leu Leu Ser Phe Ser Pro Thr Leu Ala Glu Ile Ser Gly Leu Ala Gly
            100                 105                 110

Tyr Asp Phe Ala Val Val Asp Met Glu His Gly Pro Gly Gly Ile Thr
        115                 120                 125

Glu Ala Leu Asn Cys Leu Arg Ala Leu Ala Ser Thr Gln Thr Pro Ala
130                 135                 140

Ile Ile Arg Leu Pro Glu Thr Cys Pro Thr Trp Ala Lys Lys Ala Leu
145                 150                 155                 160

Asp Leu Gly Pro Gln Gly Ile Met Phe Pro Met Val Glu Ser Pro Lys
                165                 170                 175

Met Ala Lys Lys Ala Val Ser Tyr Cys Arg Phe Pro Pro Glu Gly Ile
            180                 185                 190

Arg Gly Ser Ala His Thr Val Val Arg Ala Ser Ser Tyr Gly Ile Asp
        195                 200                 205

Glu Gly Tyr Leu Ser Asn Tyr Gly Asp Glu Leu Leu Ile Met Cys Gln
210                 215                 220

Val Glu Ser Glu Glu Gly Val Lys Lys Ala Asp Glu Ile Ala Ala Val
225                 230                 235                 240

Asp Gly Val Asp Cys Ile Gln Met Gly Pro Leu Asp Leu Ser Ala Ser
                245                 250                 255

Met Gly Tyr Leu Trp Asp Pro Gly His Lys Lys Val Arg Glu Met Met
            260                 265                 270

Arg Ala Ala Glu Lys Ala Val Leu Gly Ser Lys Lys Gly Gly Gly
        275                 280                 285

Ala Tyr Leu Ala Gly Phe Ser Met Pro His Asp Gly Pro Ile Asp Leu
```

```
            290                 295                 300
Lys Ser Arg Gly Tyr Asn Met Val Ala Gly Thr Val Asp Val Gly Leu
305                 310                 315                 320

Phe Arg Ser Ala Ala Val Asp Asp Val Lys Lys Phe Lys Met Ser Leu
                325                 330                 335

Val Gln Gly Ser Asp Asp Glu Glu Glu His Asp Lys Asp Ala Asp Glu
                340                 345                 350

Lys Tyr Trp Ser Glu
            355

<210> SEQ ID NO 110
<211> LENGTH: 351
<212> TYPE: PRT
<213> ORGANISM: Solanum lycopersicum

<400> SEQUENCE: 110

Met Ala Ala Met Ala Gly Phe Ser Ser Ser Ser Ser Ser Ser Leu Ser
1               5                   10                  15

Thr Leu Arg Lys Ser Phe Thr Ser Ser Pro Ile Phe Pro Ser Phe
            20                  25                  30

His Ser Leu Leu Pro Arg Ile Pro Lys Pro Ser Ser Leu Lys Thr Val
            35                  40                  45

Asn Pro Ile Phe Lys Pro Ser Leu Pro Arg Arg Phe Ser Ser Ala Val
50                  55                  60

Ala Ala Thr Ala Asp Ser Ala Glu Val Arg Gln Ser Leu Lys Thr Arg
65                  70                  75                  80

Leu Lys Asn Gly Glu Thr Leu Tyr Gly Ile Phe Leu Leu Gly Phe Ser
                85                  90                  95

Pro Thr Leu Ala Glu Ile Ala Gly Leu Ala Gly Tyr Asp Phe Ala Val
            100                 105                 110

Val Asp Met Glu His Gly His Gly Ile Ser Asp Ala Leu Pro Cys
            115                 120                 125

Leu His Ala Leu Ala Ala Thr Gln Thr Pro Ala Ile Leu Arg Ile Pro
130                 135                 140

Glu Ser Ser Ala Thr Trp Ala Lys Lys Ala Leu Asp Leu Gly Pro Gln
145                 150                 155                 160

Gly Ile Met Phe Pro Met Ile Asp Gly Pro Lys Ser Ala Arg Lys Ala
                165                 170                 175

Val Ser Tyr Cys Arg Phe Pro Pro Asn Gly Val Arg Gly Ser Ala His
            180                 185                 190

Thr Val Val Arg Ala Ser Ser Tyr Gly Ile Asp Glu Gly Tyr Leu Ser
            195                 200                 205

Asn Tyr Glu Asp Asp Leu Leu Ile Met Cys Gln Val Glu Cys Val Asp
210                 215                 220

Gly Val Lys Lys Ile Asp Glu Ile Ala Ala Val Glu Gly Val Asp Cys
225                 230                 235                 240

Ile Gln Met Gly Pro Leu Asp Leu Ser Ala Ser Leu Gly Tyr Leu Trp
                245                 250                 255

Asp Pro Gly Asn Lys Lys Val Lys Glu Met Met Asn Thr Ala Glu Lys
            260                 265                 270

Gly Ala Leu Lys Lys Lys Pro Leu Asp Gly Gly Ala Tyr Leu Ser Gly
            275                 280                 285

Phe Ala Met Pro His Asp Ser Pro Glu Asn Leu Lys Ser Arg Gly Tyr
            290                 295                 300
```

```
His Met Val Ser Gly Ala Val Asp Ile Ala Leu Phe Arg Asn Ala Ala
305                 310                 315                 320

Val Glu Asp Val Asn Lys Phe Lys Met Ser Leu Asp Lys Gly Phe Glu
                325                 330                 335

Asp Gln Lys Asp His Lys Asp Gly Glu Glu Lys Tyr Trp Ser Glu
            340                 345                 350

<210> SEQ ID NO 111
<211> LENGTH: 359
<212> TYPE: PRT
<213> ORGANISM: Vitis vinifera

<400> SEQUENCE: 111

Met Ala Thr Val Thr Phe Pro Pro Ser Ser Leu Ser Thr Pro Pro Lys
1               5                   10                  15

Pro His Phe Pro Lys Pro Ser Lys Thr Leu Ile His Leu Pro Ser Pro
                20                  25                  30

Lys Phe Ser Phe Ser Lys Pro Ala Phe Asn Leu Lys Thr Leu Asn Pro
            35                  40                  45

Ile Leu Ser Gln Ser Pro Ala Pro Leu Arg Leu Ser Asn Thr Thr Ser
50                  55                  60

Asp Leu Ile Ala Tyr Asp Asn Ser Val Pro Val Pro Val Pro Val Pro
65                  70                  75                  80

Ser Arg Ser Leu Lys Ser Arg Leu His Asp Gly Glu Thr Leu Tyr Gly
                85                  90                  95

Leu Phe Leu Leu Ser Phe Ser Pro Thr Leu Ala Glu Ile Ala Gly Leu
            100                 105                 110

Ala Gly Tyr Asp Phe Val Val Asp Met Glu His Gly His Gly Gly
            115                 120                 125

Val Ser Asp Ala Leu Pro Cys Leu His Ala Leu Ala Ala Thr Arg Thr
130                 135                 140

Pro Ala Ile Ile Arg Leu Pro Glu Ser Cys Pro Thr Trp Ala Lys Lys
145                 150                 155                 160

Ala Leu Asp Leu Gly Pro Gln Gly Ile Met Phe Pro Met Ile Asp Ser
                165                 170                 175

Pro Lys Leu Ala Arg Lys Ala Val Ser Tyr Cys Arg Phe Pro Pro Ala
            180                 185                 190

Gly Val Arg Gly Ser Ala His Thr Val Val Arg Ala Ser Ser Tyr Gly
            195                 200                 205

Ile Asp Ala Gly Tyr Leu Ser Asn Tyr Glu Glu Leu Leu Ile Met
210                 215                 220

Cys Gln Val Glu Ser Glu Glu Ala Val Lys Lys Ile Glu Asp Ile Ala
225                 230                 235                 240

Ala Val Asp Gly Val Asp Cys Ile Gln Met Gly Pro Met Asp Leu Ser
                245                 250                 255

Ala Ser Met Gly Tyr Leu Trp Asp Pro Gly Asn Lys Lys Val Arg Glu
            260                 265                 270

Met Met Lys Val Ala Glu Lys Gly Val Leu Gly Thr Lys Lys Lys Pro
            275                 280                 285

Arg Glu Gly Ala Tyr Leu Ala Gly Phe Ala Met Pro His Asp Ser Pro
290                 295                 300

Asp Asp Leu Arg Ser Arg Gly Tyr His Met Val Ser Gly Ala Val Asp
305                 310                 315                 320

Val Gly Leu Phe Arg Ser Ala Ala Val Glu Asp Val Lys Lys Phe Lys
                325                 330                 335
```

Met Gly Leu Lys Glu Ala Ser Asp Asp Glu Lys Glu Asn Ala Lys Glu
            340                 345                 350

Asp Glu Lys Tyr Trp Ser Glu
        355

<210> SEQ ID NO 112
<211> LENGTH: 348
<212> TYPE: PRT
<213> ORGANISM: Carica papaya

<400> SEQUENCE: 112

Met Ala Ala Arg Ala Ile Leu Ser Asp Leu Pro Leu Ser Ser Ser Phe
1               5                   10                  15

Thr Lys Pro Ser Ser Ser Thr Ser Phe Ser Pro Arg Pro Pro Pro Leu
            20                  25                  30

Ser Phe Pro Phe Ser Leu Pro Arg Leu Lys Thr Leu Thr Phe Asn Ser
        35                  40                  45

Pro Ser His Leu Ser Pro Thr Ile Thr Thr Ala Ala Val Thr Ser Ala
    50                  55                  60

Ser Val Ser Ser Ser Ser Leu Lys Ser Arg Leu Arg Asn Gly Asp
65                  70                  75                  80

Thr Leu Tyr Gly Leu Phe Leu Leu Ser Phe Ser Pro Thr Leu Ala Glu
                85                  90                  95

Ile Ala Ala Leu Ala Gly Tyr Asp Phe Val Val Ile Asp Met Glu His
            100                 105                 110

Gly Pro Gly Gly Ile Ser Glu Ala Leu His Cys Leu Arg Ala Leu Ser
        115                 120                 125

Ala Ala Gly Thr Pro Gly Ile Leu Arg Leu Pro Glu Ser Cys Pro Thr
    130                 135                 140

Trp Ala Lys Lys Ala Leu Asp Leu Gly Pro Gln Gly Ile Met Phe Pro
145                 150                 155                 160

Met Ile Asp Ser Pro Lys Asp Ala Lys Ala Val Ser Tyr Cys His
                165                 170                 175

Phe Pro Pro Lys Gly Ile Arg Gly Ser Ala His Thr Val Val Arg Ala
            180                 185                 190

Ser Asn Tyr Gly Val Asp Glu Glu Tyr Leu Ser Thr Tyr Glu Glu Glu
        195                 200                 205

Gln Leu Ile Met Cys Gln Val Glu Ser Glu Glu Gly Val Lys Lys Val
    210                 215                 220

Glu Asp Ile Ala Ala Val Glu Gly Val Asp Cys Ile Gln Met Gly Pro
225                 230                 235                 240

Leu Asp Leu Ser Ala Ser Met Gly Tyr Leu Trp Asp Pro Gly His Lys
                245                 250                 255

Lys Val Arg Glu Met Met Gly Val Ala Glu Lys Arg Val Leu Gly Thr
            260                 265                 270

Lys Pro Gly Asn Gly Gly Ala Tyr Leu Ala Gly Phe Ala Met Pro His
        275                 280                 285

Asp Gly Pro Asp Leu Arg Ala Arg Gly Tyr His Met Val Ser Gly
    290                 295                 300

Ala Val Asp Val Gly Met Phe Arg Asn Ala Val Glu Asp Val Arg
305                 310                 315                 320

Arg Phe Lys Met Gly Leu Met Gln Gly Ser Asp Asp Glu Lys Glu Arg
                325                 330                 335

Gly Arg Asp Gly Glu Asp Glu Lys Tyr Trp Ser Glu

<210> SEQ ID NO 113
<211> LENGTH: 336
<212> TYPE: PRT
<213> ORGANISM: Citrus clementina

<400> SEQUENCE: 113

Ala Ala Ala Val Thr Lys Leu Ala Gln Asn Lys Ile Ile Ser Phe Pro
1               5                   10                  15

Lys Ser Pro Leu Phe Asn Leu Asn Gly Asn Lys Ser Lys Ile Val Phe
            20                  25                  30

Pro Lys Leu Lys Leu Thr Pro Ser Val Ser Arg Ser Pro Ser Asp Leu
        35                  40                  45

Ser Pro Gly Asp Pro Leu Ser Pro Ser Pro Ser Pro Ser Pro Glu Ser
    50                  55                  60

Leu Lys Tyr Arg Leu Gln Ser Asn Glu Thr Leu Tyr Gly Leu Phe Leu
65                  70                  75                  80

Leu Ser Phe Ser Pro Thr Leu Ala Glu Ile Ser Gly Leu Ala Gly Tyr
                85                  90                  95

Asp Phe Val Val Val Asp Met Glu His Gly Pro Gly Gly Ile Ser Asp
            100                 105                 110

Ala Leu Ala Cys Leu His Ala Leu Ala Ala Thr Gly Thr Pro Ala Ile
        115                 120                 125

Leu Arg Leu Pro Glu Ser Cys Pro Thr Trp Ala Lys Lys Ala Leu Asp
130                 135                 140

Leu Gly Pro Gln Gly Val Met Phe Pro Met Ile Asp Ser Pro Glu Ala
145                 150                 155                 160

Ala Lys Glu Ala Val Ser Tyr Cys Arg Phe Pro Pro Ser Gly Val Arg
                165                 170                 175

Gly Ser Ala His Thr Val Val Arg Ala Ser Gly Tyr Gly Ile Asp Glu
            180                 185                 190

Gly Tyr Leu Ser Asn Tyr Glu Glu Glu Leu Leu Ile Met Cys Gln Val
        195                 200                 205

Glu Ser Glu Glu Gly Val Lys Arg Ala Glu Asp Ile Ala Ala Val Ala
    210                 215                 220

Gly Val Asp Cys Val Gln Met Gly Pro Leu Asp Leu Ser Ala Ser Met
225                 230                 235                 240

Gly Tyr Leu Trp Asp Pro Gly His Arg Lys Val Arg Glu Met Met Arg
                245                 250                 255

Val Ala Glu Lys Gly Val Leu Gly Gly Lys Ala Tyr Leu Ala Gly
            260                 265                 270

Phe Ala Met Pro His Asp Ala Pro Leu Glu Met Lys Ser Arg Gly Tyr
        275                 280                 285

His Met Val Ser Gly Ala Val Asp Val Gly Leu Phe Arg Asn Ala Ala
    290                 295                 300

Val Glu Asp Val Ala Arg Phe Lys Met Asn Leu Thr Asp Ala Asp
305                 310                 315                 320

Asp Met Thr Asn Ile Met Met Met Leu Gly Gly Lys Gly Leu Arg Cys
                325                 330                 335

<210> SEQ ID NO 114
<211> LENGTH: 346
<212> TYPE: PRT
<213> ORGANISM: Citrus clementina

<400> SEQUENCE: 114

| | | | | | | | | | | | | | | |
|---|---|---|---|---|---|---|---|---|---|---|---|---|---|---|
|Met|Thr|Thr|Leu|Thr|Cys|Ser|Gly|Ser|Gly|Thr|Ala|Ala|Thr|Val|Ala|
|1| | | |5| | | | |10| | | | |15| |

Lys Leu Ala Gln Asn Lys Ile Ser Ser Phe Pro Lys Ala Pro Leu Phe
              20                    25                30

Thr Leu Asn Gly Asn Lys Ser Lys Ile Val Phe Pro Lys Leu Lys Leu
        35                    40                45

Thr Pro Ser Val Ser Arg Ser Pro Ser Asp Leu Ser Pro Gly Asp Pro
 50                      55                    60

Leu Ser Pro Ser Pro Ser Pro Glu Ser Leu Lys Tyr Arg Leu
 65                 70              75              80

Gln Ser Asn Glu Thr Leu Tyr Gly Leu Phe Leu Leu Ser Phe Ser Pro
              85                    90              95

Thr Leu Ala Glu Ile Ser Gly Leu Ala Gly Tyr Asp Phe Val Val Val
         100                  105             110

Asp Met Glu His Gly Pro Gly Gly Ile Ser Asp Ala Leu Ala Cys Leu
          115                120              125

His Ala Leu Ala Ala Thr Gly Thr Pro Ala Ile Leu Arg Leu Pro Glu
130                    135              140

Ser Cys Pro Thr Trp Ala Lys Lys Ala Leu Asp Leu Gly Pro Gln Gly
145               150              155              160

Val Met Phe Pro Met Ile Asp Ser Pro Glu Ala Lys Glu Ala Val
             165                170              175

Ser Tyr Cys Arg Phe Pro Pro Ser Gly Val Arg Gly Ser Ala His Thr
         180                185              190

Val Val Arg Ala Ser Gly Tyr Gly Ile Asp Glu Gly Tyr Leu Ser Asn
        195                200              205

Tyr Glu Glu Leu Leu Ile Met Cys Gln Val Glu Ser Glu Glu Gly
    210                215              220

Val Lys Arg Ala Glu Asp Ile Ala Ala Val Asp Gly Val Asp Cys Val
225                    230              235              240

Gln Met Gly Pro Leu Asp Leu Ser Ala Ser Met Gly Tyr Leu Trp Asp
             245                250              255

Pro Gly His Arg Lys Val Arg Glu Met Met Arg Val Ala Glu Lys Gly
         260                265              270

Val Leu Gly Gly Gly Lys Ala Tyr Leu Ala Gly Phe Ala Met Pro His
        275                280              285

Asp Glu Pro Leu Glu Met Lys Ser Arg Gly Tyr His Met Val Val Gly
    290                295              300

Ala Val Glu Leu Gly Leu Val Lys Asn Ala Ala Val Lys Glu Val Ala
305                    310              315              320

Arg Phe Ile Lys Asn Leu Asn Glu Lys Cys Gln Ile Ile Lys Lys Ile
                 325                330              335

Lys Leu Gly Gly Glu Arg Ile Lys Lys Ser
            340                345

<210> SEQ ID NO 115
<211> LENGTH: 347
<212> TYPE: PRT
<213> ORGANISM: Oryza brachata

<400> SEQUENCE: 115

Met Ala Ala Phe Ala Ser Ser Ser Ala Ser Leu Ser Arg Leu Leu Arg
1              5                    10              15

```
Ala Arg Lys Pro Ser Pro Ser Ser Pro Pro Ser Arg Arg Ala Pro
            20                  25                  30

Ala Leu Leu Pro Leu Pro Arg Arg Gly Arg Arg Ser Ala Ser Ala Val
        35                  40                  45

Ser Ala Ala Thr Ser Glu Leu Leu Ser Ala Ala Pro Ser Leu Lys Ser
    50                  55                  60

Arg Leu Ala Ala Gly Lys Thr Leu Tyr Gly Leu Phe Leu Leu Ser Phe
65                  70                  75                  80

Ser Pro Thr Leu Ala Glu Leu Ala Ala Leu Ala Gly Tyr Asp Tyr Val
                85                  90                  95

Val Val Asp Met Glu His Gly Pro Gly Gly Ile Pro Glu Ala Leu Ala
            100                 105                 110

Cys Leu Arg Ala Leu Asp Ala Ala Arg Thr Pro Ala Ile Leu Arg Leu
        115                 120                 125

Pro Glu Ala Cys Ser Ile Trp Ala Lys Lys Ala Leu Asp Leu Gly Pro
    130                 135                 140

Ala Gly Leu Met Leu Pro Ala Val Glu Ser Pro Ala Ala Ala Ala Ala
145                 150                 155                 160

Ala Val Ser His Cys Arg Tyr Pro Pro Arg Gly Val Arg Gly Ala Ala
                165                 170                 175

His Pro Ile Val Arg Ala Ser Val Tyr Gly Leu Asp Asp Ser Tyr Leu
            180                 185                 190

Ser Arg Cys Glu Asp Asp Thr Leu Ile Ile Cys Gln Val Glu Thr Ala
        195                 200                 205

Ala Gly Ile Ala Glu Val Asp Ala Ile Ala Ala Val Asp Gly Val Asp
    210                 215                 220

Val Val Gln Met Gly Pro Leu Asp Leu Ser Ala Ser Met Gly Tyr Leu
225                 230                 235                 240

Trp Asp Pro Gly Asn Arg Lys Val Arg Ala Arg Leu Arg Glu Ala Glu
                245                 250                 255

Lys Lys Val Leu Asp Ala Arg Lys Lys Val Thr Ala Ser Asp Gly
            260                 265                 270

Asn Val Ala Tyr Leu Gly Gly Phe Ala Met Pro Asn Asp Pro Ala Glu
        275                 280                 285

Gln Leu Lys Leu Arg Gly Tyr His Met Val Ala Gly Ala Ala Asp Ile
    290                 295                 300

Gly Met Phe Arg Lys Ala Ala Leu Glu Asp Val Lys Arg Phe Lys Glu
305                 310                 315                 320

Ala Val Met Glu Ile Gly Glu Glu Gly Asp Glu Tyr Gly Asp Glu Lys
                325                 330                 335

Lys Asp Lys Glu Asp Asp Gly Tyr Trp Ser Glu
            340                 345

<210> SEQ ID NO 116
<211> LENGTH: 342
<212> TYPE: PRT
<213> ORGANISM: Brachypodium distachyon

<400> SEQUENCE: 116

Met Ala Val Ser Ala Thr Ala Thr Ser Leu Ser His Leu Leu Pro Ala
1               5                   10                  15

Pro Lys Pro Lys Pro Arg Thr Pro Pro Arg Leu Ser Leu Leu Pro Ser
            20                  25                  30

Asn Arg Lys Pro Ser Arg Ala Ala Thr Ser Ala Ile Phe Ala Ala Ala
        35                  40                  45
```

```
Ala Ala Ala Ser Asp Phe Leu Ser Pro Val Pro Ser Leu Lys Ser Arg
        50                  55                  60

Leu Ala Ala Gly Asp Thr Leu Tyr Gly Leu Phe Leu Leu Ser Phe Ser
 65                  70                  75                  80

Pro Thr Leu Ala Glu Ile Ala Ala Leu Ala Gly Tyr Asp Tyr Val Val
                     85                  90                  95

Val Asp Met Glu His Gly Pro Gly Ser Ile Thr Glu Ala Leu Ala Cys
                100                 105                 110

Leu Arg Ala Leu Asp Ala Ala Arg Thr Pro Ala Val Leu Arg Leu Pro
            115                 120                 125

Glu Ala Cys Pro Val Trp Ala Lys Lys Ala Leu Asp Leu Gly Pro Ala
        130                 135                 140

Gly Leu Met Leu Pro Ala Ile Glu Ser Pro Ala Ala Ala Glu Ala
145                 150                 155                 160

Val Ser His Cys Arg Tyr Pro Pro Arg Gly Val Arg Gly Ala Ala Tyr
                165                 170                 175

Pro Ile Val Arg Ala Ser Ala Tyr Gly Leu Asp Asp Ser Tyr Val Ser
                180                 185                 190

Arg Cys Glu Asp Asp Thr Leu Ile Ile Cys Gln Val Glu Thr Ala Ala
            195                 200                 205

Gly Val Ala Glu Val Asp Ala Ile Ala Ala Val Asp Gly Val Asp Val
        210                 215                 220

Val Gln Met Gly Pro Leu Asp Leu Ser Ala Ser Met Gly Tyr Leu Trp
225                 230                 235                 240

Asp Pro Gly Asn Arg Lys Val Arg Ala Ala Leu Arg Glu Ala Glu Arg
                245                 250                 255

Lys Val Leu Glu Ala Arg Lys Lys Lys Val Thr Ala Ser Ala Gly Asn
            260                 265                 270

Ala Ala Tyr Leu Gly Gly Phe Ala Met Pro Asn Asp Pro Pro Glu Gln
        275                 280                 285

Leu Lys Met Arg Gly Tyr His Met Val Ala Gly Ala Val Asp Ile Gly
        290                 295                 300

Leu Phe Arg Lys Ala Ala Leu Glu Asp Val Lys Trp Phe Lys Glu Ala
305                 310                 315                 320

Val Met Glu Ile Gly Glu Glu Glu Gly Glu Glu Asp Glu Lys Asp
                325                 330                 335

Asp Gly Tyr Trp Ser Glu
            340

<210> SEQ ID NO 117
<211> LENGTH: 346
<212> TYPE: PRT
<213> ORGANISM: Sorghum

<400> SEQUENCE: 117

Met Ala Ala Thr Ala Ser Ser Leu Ser His Leu Leu Leu Ala Pro Lys
 1               5                  10                  15

Pro Arg Pro Lys Ala Gln Pro Asn Pro Ser His Leu Arg Ser His Ser
            20                  25                  30

Ile Thr Ser Pro Leu Pro Cys Arg Gly Arg Arg Ser Ser Leu Gly Val
            35                  40                  45

Ser Ala Ala Ala Ser Asp Leu Leu Ser Pro Ala Pro Ser Leu Lys Ser
        50                  55                  60

Arg Leu Ala Ala Gly Asp Thr Leu Tyr Gly Leu Phe Leu Leu Ser Phe
```

```
            65                  70                  75                  80
        Ser Pro Thr Leu Ala Glu Leu Ala Ala Leu Ala Gly Tyr Asp Tyr Val
                        85                  90                  95

Val Val Asp Met Glu His Gly Pro Gly Ile Pro Glu Ala Leu Ala
                    100                 105                 110

Cys Leu Arg Ala Leu Asp Ala Arg Thr Pro Ala Val Leu Arg Leu
                    115                 120                 125

Pro Glu Ala Ser Ala Val Trp Ala Lys Lys Ala Leu Asp Leu Gly Pro
                    130                 135                 140

Ala Gly Leu Met Leu Pro Ala Ile Glu Ser Pro Ala Ala Ala Glu
        145                 150                 155                 160

Ala Val Ser His Cys Arg Tyr Pro Pro Arg Gly Val Arg Gly Ala Ala
                            165                 170                 175

His Pro Ile Val Arg Ala Ser Ala Tyr Gly Phe Asp Asp Ser Tyr Ile
                    180                 185                 190

Ser Arg Cys Glu Asp Asp Thr Leu Val Ile Cys Gln Val Glu Thr Ala
                    195                 200                 205

Thr Gly Ile Ala Glu Ile Asp Ala Ile Ala Ile Asp Gly Val Asp
            210                 215                 220

Val Val Gln Met Gly Pro Leu Asp Leu Ser Ala Ser Met Gly Tyr Leu
        225                 230                 235                 240

Trp Asp Pro Gly Asn Arg Lys Val Arg Ala Ala Leu Arg Glu Ala Glu
                            245                 250                 255

Arg Lys Val Leu Glu Ala Arg Lys Lys Val Ala Ala Ala Ser Asp
                    260                 265                 270

Gly Asn Ala Ala Tyr Leu Gly Gly Phe Ala Met Gln Asn Asp Pro Pro
                    275                 280                 285

Glu Gln Leu Lys Leu Arg Gly Tyr His Met Val Ala Gly Ala Val Asp
                290                 295                 300

Ile Ala Met Phe Arg Lys Ala Ala Leu Asp Asp Val Lys Arg Phe Arg
        305                 310                 315                 320

Glu Ala Val Met Glu Ile Gly Glu Gly Asp Glu Asp Glu Lys Asp
                        325                 330                 335

Glu Lys Glu Asn Asp Gly Tyr Trp Ser Glu
                    340                 345

<210> SEQ ID NO 118
<211> LENGTH: 341
<212> TYPE: PRT
<213> ORGANISM: Paspalum notatum

<400> SEQUENCE: 118

Met Ala Ala Ser Ser Leu Ser His Pro Leu Leu Ala Pro Lys Thr Gln
1               5                   10                  15

Pro Asn Pro Ser Pro Leu Pro Ser Arg His Ile Ala Thr Pro Leu Pro
            20                  25                  30

Arg Arg Gly Arg Arg Ser Ala His Ala Val Ser Ala Ala Ser Asp
        35                  40                  45

Leu Leu Ser Pro Ala Pro Ser Leu Lys Ser Arg Leu Ala Ala Gly Asp
    50                  55                  60

Thr Leu Tyr Gly Leu Phe Leu Leu Ser Phe Ser Pro Thr Leu Ala Glu
65                  70                  75                  80

Leu Ala Ala Leu Ala Gly Tyr Asp Tyr Val Val Asp Met Glu His
                85                  90                  95
```

Gly Pro Gly Gly Ile Pro Glu Ala Leu Ser Cys Leu Arg Ala Leu Asp
             100                 105                 110

Ala Ala Arg Thr Pro Ala Val Leu Arg Leu Pro Glu Ala Ser Ala Val
         115                 120                 125

Trp Ala Lys Lys Ala Leu Asp Leu Gly Pro Ala Gly Leu Met Ile Pro
130                 135                 140

Ala Val Glu Ser Pro Ala Ala Ala Glu Ala Val Ser Tyr Cys Arg
145                 150                 155                 160

Tyr Pro Pro Arg Gly Val Arg Gly Ala His Pro Ile Val Arg Ala
             165                 170                 175

Ser Ala Tyr Gly Leu Asp Asp Ser Tyr Leu Ser Arg Cys Glu Asp Asp
         180                 185                 190

Thr Leu Leu Ile Cys Gln Val Glu Thr Ala Ala Gly Ile Ala Glu Val
         195                 200                 205

Asp Ala Ile Ala Ser Val Asp Gly Val Asp Val Val Gln Met Gly Pro
210                 215                 220

Leu Asp Met Ser Ala Ser Met Gly Tyr Leu Trp Asp Pro Gly Asn Arg
225                 230                 235                 240

Lys Val Arg Ala Ala Leu Arg Glu Ala Glu Arg Lys Val Leu Glu Ala
             245                 250                 255

Arg Lys Lys Val Ala Ala Pro Ser Asp Gly Asn Ala Ala Tyr Leu Gly
         260                 265                 270

Gly Phe Ala Met Gln Asn Asp Pro Pro Glu Gln Leu Lys Leu Arg Gly
         275                 280                 285

Tyr His Met Val Ala Gly Ala Val Asp Ile Gly Met Phe Arg Lys Ala
290                 295                 300

Ala Leu Asp Asp Val Lys Arg Phe Arg Glu Ala Val Met Glu Ile Gly
305                 310                 315                 320

Glu Glu Gly Asp Asp Glu Asp Glu Lys Asp Glu Lys Gln Asn Asp
             325                 330                 335

Gly Tyr Trp Ser Glu
            340

<210> SEQ ID NO 119
<211> LENGTH: 343
<212> TYPE: PRT
<213> ORGANISM: Eragrostis nindensis

<400> SEQUENCE: 119

Met Ala Ala Ala Ser Leu Ser His Leu Leu Leu Ala Pro Lys Leu
1                5                  10                  15

Lys Ser Lys Pro Asn Pro Thr Pro Leu Pro Ser Arg Arg Ala Cys Val
             20                  25                  30

Pro Leu Pro Arg Ser Arg Arg Pro Thr Gln Ala Ile Ser Ala Ala Ala
         35                  40                  45

Ser Asp Leu Leu Ala Pro Ala Pro Thr Leu Lys Ser Arg Leu Ala Ala
         50                  55                  60

Gly Asp Thr Leu Tyr Gly Leu Phe Leu Leu Ser Phe Ser Pro Thr Leu
65                  70                  75                  80

Ala Glu Leu Ala Ala Leu Ala Gly Tyr Asp Tyr Val Val Val Asp Met
             85                  90                  95

Glu His Gly Pro Gly Gly Ile Pro Glu Ala Leu Ala Cys Leu Arg Ala
             100                 105                 110

Leu Asp Ala Ala Arg Thr Pro Ala Val Leu Arg Leu Pro Glu Ala Ser
         115                 120                 125

Pro Val Trp Ala Lys Lys Ala Leu Asp Leu Gly Pro Ala Gly Leu Met
            130                 135                 140

Leu Pro Ala Val Glu Ser Pro Ala Ala Ala Glu Ala Val Ser Tyr
145                 150                 155                 160

Cys Arg Tyr Pro Pro Arg Gly Val Arg Gly Ala Ala His Thr Val Val
                165                 170                 175

Arg Ala Ser Ala Tyr Gly Leu Asp Asp Ser Tyr Leu Ser Arg Cys Glu
            180                 185                 190

Asp Glu Thr Leu Ile Met Cys Gln Val Glu Thr Ala Ala Gly Ile Ala
        195                 200                 205

Glu Val Glu Ala Ile Ala Ala Val Asp Gly Val Asp Val Val Gln Met
210                 215                 220

Gly Pro Leu Asp Leu Ser Ala Ser Met Gly Tyr Leu Trp Asp Pro Gly
225                 230                 235                 240

Asn Arg Lys Val Arg Ala Thr Leu Arg Glu Ala Glu Arg Lys Val Leu
                245                 250                 255

Ala Ala Arg Lys Lys Asp Ala Ser Ser Asp Gly Asn Ala Ala Tyr
            260                 265                 270

Leu Gly Gly Phe Ala Met Pro Asn Asp Gln Ala Glu Gln Leu Lys Leu
        275                 280                 285

Arg Gly Tyr His Met Val Ala Gly Ala Val Asp Val Gly Leu Phe Arg
290                 295                 300

Lys Ala Ala Leu Asp Asp Ile Lys Arg Phe Arg Glu Ala Val Met Glu
305                 310                 315                 320

Ile Gly Glu Glu Gly Asp Glu Glu Asp Lys Leu Glu Lys Glu
                325                 330                 335

Ala Asp Gly Tyr Trp Ser Glu
            340

<210> SEQ ID NO 120
<211> LENGTH: 291
<212> TYPE: PRT
<213> ORGANISM: Tulipa gesneriana

<400> SEQUENCE: 120

Thr Arg Gln Ser Leu Lys Ser Arg Leu Ala Ser Gly Asp Thr Leu Leu
1               5                   10                  15

Gly Ile Phe Leu Val Ser Asn Ser Pro Thr Leu Ala Glu Ile Val Gly
            20                  25                  30

Leu Ser Gly Tyr Asp Tyr Val Val Ile Asp Met Glu His Gly Pro Gly
        35                  40                  45

Gly Ile Pro Glu Ala Ile Ala Cys Leu Arg Ala Leu Ala Val Thr Gly
    50                  55                  60

Thr Pro Ala Ile Ile Arg Val Pro Glu Leu Cys Ala Ala Leu Ala Lys
65                  70                  75                  80

Lys Ala Leu Asp Ile Gly Pro Gln Gly Ile Met Phe Pro Met Ile Glu
                85                  90                  95

Ser Ala Asp Gln Ala Glu Leu Ala Val Ser Tyr Cys Arg Tyr Pro Pro
            100                 105                 110

Lys Gly Ile Arg Gly Ala Ala Asn Val Val Arg Ala Ser Ala Tyr Gly
        115                 120                 125

Phe Asp Glu Gly Tyr Leu Lys Trp Cys Arg Glu Glu Leu Ile Val Phe
    130                 135                 140

Cys Gln Val Glu Ser Glu Ala Gly Val Ala Glu Leu Asp Ala Ile Ala

```
                145                 150                 155                 160
Ala Val Asp Gly Val Gly Gly Ile Gln Ile Gly Pro Arg Asp Leu Ser
                165                 170                 175

Ala Ser Met Gly Cys Leu Glu Glu Pro Asp Asn Pro Ala Val Met Glu
                180                 185                 190

Thr Leu Arg Thr Ala Glu Arg Arg Ala Leu Ala Ala Gly Lys Lys Ser
                195                 200                 205

Thr Gly Pro Tyr Leu Ala Gly Met Ala Thr Ala Leu Asp Ser Pro Gly
                210                 215                 220

Glu Leu Arg Arg Gly Tyr His Met Val Gly Ser Gly Ala Asp Leu
225                 230                 235                 240

Ser Leu Phe Arg Lys Ala Ala Leu Gln Asp Val Glu Ser Phe Gln Lys
                245                 250                 255

Ala Lys Leu Ala Ala Ala Thr Gly Asp Glu Gly Val Lys Glu Arg His
                260                 265                 270

Thr Ser Asn Gly Val Val Lys Asn Arg Ser Tyr Gly Ser Gln Met Ser
                275                 280                 285

Asn Gly Tyr
    290

<210> SEQ ID NO 121
<211> LENGTH: 291
<212> TYPE: PRT
<213> ORGANISM: Tulipa gesneriana

<400> SEQUENCE: 121

Thr Arg Gln Ser Leu Lys Ser Arg Leu Ala Ser Gly Asp Thr Leu Leu
1               5                   10                  15

Gly Ile Phe Leu Val Ser Asn Ser Pro Thr Leu Ala Glu Ile Val Gly
                20                  25                  30

Leu Ser Gly Tyr Asp Tyr Val Val Ile Asp Met Glu His Gly Pro Gly
                35                  40                  45

Gly Ile Pro Glu Ala Ile Ala Cys Leu Arg Ala Leu Ala Val Thr Gly
    50                  55                  60

Thr Pro Ala Ile Ile Arg Val Pro Glu Leu Cys Ala Ala Leu Ala Lys
65                  70                  75                  80

Lys Ala Leu Asp Ile Gly Pro Gln Gly Ile Met Phe Pro Met Ile Glu
                85                  90                  95

Ser Ala Asp Gln Ala Glu Leu Ala Val Ser Tyr Cys Arg Tyr Pro Pro
                100                 105                 110

Lys Gly Ile Arg Gly Ala Ala Asn Val Val Arg Ala Ser Ala Tyr Gly
                115                 120                 125

Phe Asp Glu Gly Tyr Leu Lys Trp Cys Arg Glu Glu Leu Ile Val Phe
                130                 135                 140

Cys Gln Val Glu Ser Glu Ala Gly Val Ala Glu Leu Asp Ala Ile Ala
145                 150                 155                 160

Ala Val Asp Gly Val Gly Gly Ile Gln Ile Gly Pro Arg Asp Leu Ser
                165                 170                 175

Ala Ser Met Gly Cys Leu Glu Glu Pro Asp Asn Pro Ala Val Met Glu
                180                 185                 190

Thr Leu Arg Thr Ala Glu Arg Arg Ala Leu Ala Ala Gly Lys Lys Ser
                195                 200                 205

Thr Gly Pro Tyr Leu Ala Gly Met Ala Thr Ala Leu Asp Ser Pro Gly
                210                 215                 220
```

```
Glu Leu Leu Arg Arg Gly Tyr His Met Val Gly Ser Gly Ala Asp Leu
225                 230                 235                 240

Ser Leu Phe Arg Lys Ala Ala Leu Gln Asp Val Glu Ser Phe Gln Lys
            245                 250                 255

Ala Lys Leu Ala Ala Thr Gly Asp Glu Gly Val Lys Glu Arg His
            260                 265                 270

Thr Ser Asn Gly Val Val Lys Asn Arg Ser Tyr Gly Ser Gln Met Ser
            275                 280                 285

Asn Gly Tyr
    290
```

<210> SEQ ID NO 122
<211> LENGTH: 364
<212> TYPE: PRT
<213> ORGANISM: Asclepias syriaca

<400> SEQUENCE: 122

```
Met Ala Ile Leu Lys Phe Ser Thr Ala Thr Ala Ser Leu Ser Thr
1               5                   10                  15

Phe Arg Gln Pro Ser Leu Ser Phe Ser Val Lys Lys Ser Pro Ser Ile
                20                  25                  30

Gln His Leu Ser Ser Pro Thr Ala Lys Ser Pro Leu Thr Leu Lys Thr
            35                  40                  45

Ile Asn Leu Asn Glu Asp Gln Arg Ser Pro Phe Pro Ile Cys Ser Ser
50                  55                  60

Ser Ser Thr Ser Ala Tyr Ile Ala Ala Ala Ala Thr Ala Val Gly
65                  70                  75                  80

Pro Gln Ser Leu Lys Ala Arg Leu Lys Asn Gly Glu Thr Leu Tyr Gly
                85                  90                  95

Ile Phe Leu Leu Ser Phe Ser Pro Thr Ile Ala Glu Ile Ala Gly Leu
            100                 105                 110

Ala Gly Tyr Asp Phe Ala Val Val Asp Met Glu His Gly Pro Gly Gly
            115                 120                 125

Ile Ala Glu Ala Leu Ser Cys Leu Arg Ala Leu Lys Ala Thr Lys Thr
130                 135                 140

Ala Ala Ile Leu Arg Val Pro Glu Thr Ser Asp Thr Trp Ala Lys Lys
145                 150                 155                 160

Ala Leu Asp Leu Gly Pro Glu Gly Ile Met Phe Pro Met Ile Asp Ser
                165                 170                 175

Pro Lys Ala Ala Arg Lys Ala Val Ser Tyr Cys Arg Phe Pro Pro Lys
            180                 185                 190

Gly Val Arg Gly Ser Ala His Thr Val Val Arg Ala Ser Ser Tyr Gly
            195                 200                 205

Ile Asp Glu Gly Tyr Leu Ser Asn Tyr Glu Asp Glu Leu Leu Ile Met
210                 215                 220

Cys Gln Val Glu Cys Gln Glu Gly Val Lys Lys Ile Glu Asp Ile Ala
225                 230                 235                 240

Ala Val Glu Gly Val Asp Cys Ile Glu Met Gly Pro Leu Asp Leu Ser
                245                 250                 255

Ala Ser Met Gly Tyr Leu Trp Asp Pro Gly His Arg Lys Val Arg Glu
            260                 265                 270

Leu Met Arg Lys Ala Glu Ala Val Leu Arg Ser Asn Pro Asp Glu
            275                 280                 285

Gly Gly Ala Tyr Leu Ala Gly Phe Ala Met Pro His Asp Ser Pro Ile
290                 295                 300
```

```
Ala Leu Lys Ser Arg Gly Tyr His Met Val Ser Gly Ala Val Asp Thr
305                 310                 315                 320

Ala Val Phe Arg Asn Ser Ala Val Asp Asp Val Lys Asn Phe Lys Met
            325                 330                 335

Ser Leu Glu Ser Ile Glu Glu Glu Asp Asp Leu Gln Ala Thr Ile
        340                 345                 350

Gln Lys Glu Asp Asp Glu Gly Tyr Trp Ser Glu
    355                 360
```

<210> SEQ ID NO 123
<211> LENGTH: 355
<212> TYPE: PRT
<213> ORGANISM: Momordica charantia

<400> SEQUENCE: 123

```
Met Ala Ile Pro Ser Ser Phe Thr Ile Ser Pro Ser Phe Leu Ser Ser
1               5                   10                  15

Ser Lys Leu Leu Pro Thr Lys Ser Leu Ser Phe Ser Arg Ser Ala Pro
            20                  25                  30

Phe Leu Ser Pro Phe Arg Thr Leu Phe Pro Ile Ser Ser Asn Ser Ser
        35                  40                  45

Ser Asn Pro Ser Ile Pro Ser Pro Ile Asp Ser Ser Asp Ser Phe Ala
50                  55                  60

Ala Pro Ser Pro Ala Val Asn Arg Asn Leu Lys Ser Arg Leu Arg Asn
65                  70                  75                  80

Gly Asp Thr Leu Tyr Gly Leu Phe Leu Ser Phe Ser Pro Ser Leu
            85                  90                  95

Ala Glu Ile Ala Gly Leu Ala Gly Tyr Asp Phe Val Val Asp Met
            100                 105                 110

Glu His Gly Tyr Gly Gly Ile Ser Asp Ala Leu Pro Cys Leu His Ala
            115                 120                 125

Leu Ala Ala Ala Gln Thr Ala Ala Ile Leu Arg Leu Pro Glu Ser Ser
    130                 135                 140

Ala Ala Trp Ala Lys Lys Ala Leu Asp Leu Gly Pro Gln Gly Ile Met
145                 150                 155                 160

Phe Pro Met Ile Asp Ser Ser Lys Glu Ala Lys Lys Ala Val Ser Tyr
                165                 170                 175

Cys Arg Phe Pro Pro Ala Gly Val Arg Gly Ser Ala His Pro Val Val
            180                 185                 190

Arg Ala Ser Lys Tyr Gly Ile Asp Glu Gly Tyr Leu Ser Asn Tyr Glu
        195                 200                 205

Asp Glu Leu Leu Ile Met Cys Gln Val Glu Ser Glu Gln Ala Val Lys
210                 215                 220

Lys Ile Glu Glu Ile Met Glu Val Asp Gly Val Asp Cys Ile Gln Met
225                 230                 235                 240

Gly Pro Leu Asp Met Ser Gly Ser Met Gly Tyr Leu Trp Asp Pro Gly
                245                 250                 255

His Lys Lys Val Arg Glu Met Met Arg Arg Ala Glu Lys Ala Val Leu
            260                 265                 270

Gln Ser Lys Gly Asp Asn Gly Glu Gly Ala Phe Leu Ala Gly Phe
        275                 280                 285

Ser Met Pro His Asp Gly Pro Ile Asp Met Arg Lys Arg Gly Tyr Arg
290                 295                 300

Met Ile Ser Gly Ala Val Asp Leu Gly Leu Phe Arg Thr Ala Ala Val
```

```
                305                 310                 315                 320
Glu Asp Val Arg Lys Phe Lys Met Ser Glu Ile Ser Gly Ser Glu Asp
                    325                 330                 335
Glu Asp Gln Pro Leu Thr His Ile Glu Glu Asp Glu Glu Asp Lys Tyr
                    340                 345                 350
Trp Ser Glu
        355

<210> SEQ ID NO 124
<211> LENGTH: 1050
<212> TYPE: DNA
<213> ORGANISM: Tulipa gesneriana

<400> SEQUENCE: 124
gcacgaggca gagcctcaag tcccgcctcg cctcaggcga caccctcctc ggcatcttcc      60
ttgtcagcaa ctcccccacc ctcgctgaaa tcgtcggcct ctctggatac gactatgtcg     120
tcatcgacat ggagcacggc cccgggggca tcccagaggc catcgcctgc ctccgtgctc     180
tagctgtcac cggtaccccg gccatcatcc gcgtcccaga gctctgtgcc gccctagcca     240
agaaagccct cgacatcggc cctcagggga tcatgttccc aatgatcgag tccgccgatc     300
aagccgagct cgccgtctcc tactgccgct acccaccaaa gggaattcgt ggggcggcta     360
atgttgtcag agcctctgcc tacgggttcg acgaagggta cctgaaatgg tgccgggagg     420
agctgattgt gttctgtcag gttgagtcgg aggctggggt ggcagagctg gacgcgattg     480
cggctgttga cggggttggg ggtatacaga ttggaccaag ggatctaagt gccagcatgg     540
ggtgcctgga ggaacctgat aacccggcgg tgatggagac gctgaggacg ccgagcgga      600 gggcgcttgc ggcggggaag aagagtacag ggccgtatct cgcggggatg cgacggcgc      660 tggatagccc cggggagctg ctgaggaggg ggtaccatat ggtgggcagt ggggcggatt     720
tgtctttgtt tcggaaggct gccctgcagg acgtggagag ttttcagaag gcgaagttgg     780
cggcggcgac cggagatgaa ggtgtgaaag aacgtcatac ttccaacgga gtcgtgaaga     840
accgtagtta tggctctcaa atgagcaatg gatactaaac cccgcggcca actctttgct     900
gctttaggtt tggttaatat ttacaaaacc tgaaacagct cgtgtagcca tgaattaagc     960
tagtttattt tttcattgtt ggggacaaca tggattatat atgaacttca attaagcgta    1020
cttctattaa aaaaaaaaaa aaaaaaaaaa                                     1050

<210> SEQ ID NO 125
<211> LENGTH: 1108
<212> TYPE: DNA
<213> ORGANISM: Tulipa gesneriana

<400> SEQUENCE: 125
gcacgaggct cttatctctc attctcactg ccatcccgaa gctcctgctg ctcttcatca      60
atggctcctc tcctccaatc aaatataacc ctcaagtctc gggttgcctc cggcgagacc     120
ctctacggac tcttcctaat gagcgcctcc cccaccatcg ccgagatcgc cggccttgcc     180
ggctacgact tcgtcgtcgt cgacatggag cacggccccg agacatcat cgactccctc      240 tcctcaatcc gcgcactagc tgccgctggc accccagcca tcatccgtgt cccggagaaa     300
tctgctgcct gggctaaaaa ggcccttgac ctgggtcctc agggaatcat gttccccatg     360
gtggagaacg ccaagactgc agagcagctt gtctcctact gccgctaccc tcctcgcggc     420
atccgtggca ccgcccatgt catggtgcga gcctctggct acggcaccga cgacacctac     480
```

```
gtccaccgct gcgaggagga cctcctcatc ctctgcatgg ttgagactga aaccggagtc    540
gacaacattg aggaaatcgc atcagttgac ggtgtcgacg gcatccagat gggcccccgg    600
gacctcgggg caagcatggg atacctcaag gatccggga atcccaaggc taggaaagtg     660
ctcctggcgg cggagaagag ggtggtcgcc ttgcaaaagg ctggaaaggg gccgtttctc    720
gggggtatct ccacccagca acacaagccc gaggaactta gggagcgcgg gtacaacatc    780
atcgccggag gagtggacgt ggggctgttc cggcaggcgg cggtggagga tgttcaaaga    840
ttccgccgtg gagctgctac tccagcgaac aagaatcata atatcgtcaa tggagtccat    900
gtcccatcag ctgcctagtt atcaaacaag agtcccggcc gcctttgagg atctatgttt    960
atcatttccg ggcttttttta ctttcaccct tgagattctt cctcatatct aattttcaaa   1020 tttattttt  tgtgcatatt atgcaaataa agcattctca ttaaaagaca atctttggaa    1080
attctattcc aaaaaaaaaa aaaaaaaa                                       1108

<210> SEQ ID NO 126
<211> LENGTH: 1543
<212> TYPE: DNA
<213> ORGANISM: Asclepias syriaca

<400> SEQUENCE: 126
ggggacagaa atctctccac tttgagattc gtaacaagaa agaatccatg gcaattttga     60
agttttccac cgcaactact gcttccctct ctactttcag acaaccctct ctttcttttt    120
ctgtcaagaa atcgccttca atccaacact tgtcttctcc gactgctaaa tcgcctctga    180
cccttaaaac aattaatctc aacgaagatc agagaagccc atttccaatc tgttcctcta    240
gcagcacctc cgcatacatt gcagccgccg ccgccacagc cgtcggtcca caatctctta    300
aagcccggct caaaaacggc gagactcttt atggtatctt cctgctcagc ttctccccta    360
cgatcgccga aattgcaggc ctcgctggat atgatttcgc cgtcgtcgac atggagcatg    420
gtcccggtgg gatcgccgaa gccctatctt gtctccgagc tcttaaagcc accaaaacag    480
cggcgattct ccgtgttccg gaaacgtccg atacctgggc aaagaaggcc ctggatctgg    540
gtccagaagg cattatgttc ccgatgatcg acagtccaaa ggcggcgcga aaagcagtgt    600
cttattgccg atttccacct aagggtgtcc ggggatcggc ccacacagtt gttcgagctt    660
ccagttacgg cattgatgaa gggtacttga gtaattacga ggacgagctt ctgatcatgt    720
gccaagtaga gtgccaagaa ggagtgaaga aaattgagga catagctgca gttgaaggag    780
tagattgcat tgaaatgggg ccattagatt tgagtgctag catgggttat ctatgggatc    840
cagggcatag gaaggtgagg gagttgatga ggaaagcaga ggcagcggtg ctacgatcaa    900
atcccgatga aggcggcgcc tatttggccg gatttgccat gccgcacgat agtccaattg    960
ccttgaaatc aagagggtac catatggtgt ccggcgcggt ggataccgcc gtgttcagaa    1020
atagtgcagt ggatgatgtt aagaacttca aatgagtttt ggagtccatt gaagaagaag    1080
aagatgatct gcaagcaacc attcaaaagg aggatgatga tgaaggatat tggagcgaat    1140
gaacaaatat ttaccatgtt ttgatcctaa aattaatgca ttacaacagt gtgtcaacca    1200
ctatcaagat cttgcatttg agttgaattg atcagtttct ttaattccaa agaatcatgt    1260
ttagctgttc attgttgtgt tgttcatat ggcttggaac ttgaacaaa ccttctttca     1320 tccttgttaa ggtcaccaaa tgcagaactg cagatatatt gattgttcgt ttctgttgtg    1380
tttgagaagc ctatggaatt agaatttgaa gggtggtgaa cttggaaatc tatatctcat    1440
ttggacaagg aaaaatgtaa ataatttccc tttctttac aagtacttga atcaaatgac    1500
```
tagacattta tataaaaaaa aaaaaaaaaa aaaaaaaaaa aaa                1543

<210> SEQ ID NO 127
<211> LENGTH: 1330
<212> TYPE: DNA
<213> ORGANISM: Momordica charantia

<400> SEQUENCE: 127
gcacgaggct gatctcctct gttcctccag gctccaacaa tggcgattcc ttcctccttc    60
accatttctc cctccttcct ctcttcttcc aaacttctcc ccaccaaatc cctctccttc   120
tctcgctccg ctccatttct ctctcctttc agaaccctat tccccatttc atccaattcc   180
tcctccaacc cctcaattcc ttcccccatt gattcctcag attcattcgc cgccccttcc   240
ccggccgtca atcggaatct caagtcccgt ctccgcaatg cgacaccct ctacggcctc    300
ttccttctct ccttctcccc ctccctcgcc gagatcgccg gtctcgccgg ctacgacttc   360
gtcgtcgtcg acatggaaca cggctacggt ggcatctccg acgccctccc ctgcctccac   420
gccctcgccg ccgctcaaac agccgccatt ctccgccttc ccgagagctc cgccgcgtgg   480
gcgaagaaag cgctagattt gggcccgcag ggtataatgt tcccgatgat cgattcgtcg   540
aaagaggcga agaaagcggt gtcgtactgc agattccctc ccgccggagt ccgaggatcg   600
gcccacccgg tggtcagagc atccaaatac gggattgacg aagggtactt gagcaattac   660
gaggacgagt tgctgatcat gtgtcaggtg gaatcggagc aagcggtgaa gaagatagaa   720
gagataatgg aagtggatgg cgtggattgc attcaaatgg ggccattgga catgagcggg   780
agcatggggt atctatggga tccggggcac aagaaggtga gggagatgat gaggagggcc   840
gagaaagctg tactgcagag caaaggcgat aatggtgaag agggtgcctt tttggctgga   900
ttctcaatgc cccacgatgg cccaattgac atgagaaaac gtggatatcg gatgatttct   960
ggggctgtgg atttgggttt gtttcgaact gctgctgtag aggatgtgag aaagtttaag  1020
atgagtgaaa tcagtggctc tgaggatgag gatcagccgc taactcacat tgaggaggat  1080
gaagaagaca gtactggagc gaatgaaac aaccttttg ttttttccatc ttttttggtat  1140
tcttctttat ctttcaagta cataagtaga gcttggagag ttgcatttct tgacatgggt  1200
ctttataaat catgctcata tgtggatgtg gatatgcact ttctcctgtt ctcaatgttt  1260
ttacatacaa tttttcagtc tactctcttt tttttgctta ctgaaaaaaa aaaaaaaaaa  1320
aaaaaaaaaa                                                           1330

<210> SEQ ID NO 128
<211> LENGTH: 25
<212> TYPE: PRT
<213> ORGANISM: Artificial Sequence
<220> FEATURE:
<223> OTHER INFORMATION: conserved sequence motif for identifying HpaIL
      family
<220> FEATURE:
<221> NAME/KEY: DOMAIN
<222> LOCATION: (1)..(25)
<223> OTHER INFORMATION: Xaa= any amino acid

<400> SEQUENCE: 128

Leu Lys Xaa Arg Xaa Xaa Xaa Xaa Thr Leu Tyr Gly Xaa Phe Leu Xaa
1               5                   10                  15

Xaa Xaa Ser Pro Thr Xaa Ala Glu Xaa
            20                  25

-continued

```
<210> SEQ ID NO 129
<211> LENGTH: 20
<212> TYPE: PRT
<213> ORGANISM: Artificial Sequence
<220> FEATURE:
<223> OTHER INFORMATION: conserved sequence motif for identifying HpaIL
      family
<220> FEATURE:
<221> NAME/KEY: DOMAIN
<222> LOCATION: (1)..(20)
<223> OTHER INFORMATION: Xaa= any amino acid

<400> SEQUENCE: 129

Tyr Asp Xaa Xaa Val Xaa Asp Met Glu His Gly Xaa Gly Xaa Xaa Xaa
1               5                   10                  15

Xaa Xaa Xaa Xaa
            20

<210> SEQ ID NO 130
<211> LENGTH: 29
<212> TYPE: PRT
<213> ORGANISM: Artificial Sequence
<220> FEATURE:
<223> OTHER INFORMATION: conserved sequence motif for identifying HpaIL
      family
<220> FEATURE:
<221> NAME/KEY: DOMAIN
<222> LOCATION: (1)..(29)
<223> OTHER INFORMATION: Xaa= any amino acid

<400> SEQUENCE: 130

Xaa Xaa Xaa Arg Xaa Pro Glu Xaa Xaa Xaa Xaa Xaa Ala Lys Lys Ala
1               5                   10                  15

Leu Asp Leu Gly Pro Xaa Gly Xaa Met Xaa Pro Xaa Xaa
            20                  25

<210> SEQ ID NO 131
<211> LENGTH: 51
<212> TYPE: PRT
<213> ORGANISM: Artificial Sequence
<220> FEATURE:
<223> OTHER INFORMATION: conserved sequence motif for identifying HpaIL
      family
<220> FEATURE:
<221> NAME/KEY: DOMAIN
<222> LOCATION: (1)..(51)
<223> OTHER INFORMATION: Xaa= any amino acid

<400> SEQUENCE: 131

Xaa Val Ser Xaa Cys Arg Xaa Pro Pro Xaa Gly Xaa Arg Gly Xaa Ala
1               5                   10                  15

Xaa Xaa Xaa Val Arg Ala Ser Xaa Tyr Gly Xaa Xaa Xaa Xaa Tyr Xaa
            20                  25                  30

Xaa Xaa Xaa Xaa Xaa Xaa Xaa Xaa Cys Xaa Val Glu Xaa Xaa
        35                  40                  45

Xaa Xaa Xaa
    50

<210> SEQ ID NO 132
<211> LENGTH: 27
<212> TYPE: PRT
<213> ORGANISM: Artificial Sequence
<220> FEATURE:
<223> OTHER INFORMATION: conserved sequence motif for identifying HpaIL
      family
<220> FEATURE:
<221> NAME/KEY: DOMAIN
<222> LOCATION: (1)..(27)
```

<223> OTHER INFORMATION: Xaa= any amino acid

<400> SEQUENCE: 132

Ile Ala Ala Xaa Xaa Gly Val Xaa Xaa Xaa Gln Xaa Gly Pro Xaa Asp
1               5                   10                  15

Xaa Xaa Ala Ser Xaa Gly Xaa Leu Xaa Xaa Pro
            20                  25

<210> SEQ ID NO 133
<211> LENGTH: 1077
<212> TYPE: DNA
<213> ORGANISM: Arabidopsis lyrata

<400> SEQUENCE: 133

```
atgaccaccg cttcaatctt ccccgccgcc gtcgtcgtca ccacagatgt gacatctctg      60
cttaatccat cttctctgat catcggaaaa tcattatctc cttcgaagtt cagctcaatc     120
agatcctcag tttcattctc ccgcaaaacg ctaactccaa tccgatactc ttcctctccc     180
gccgatcact cacccgtcgc cgccgtggaa gcgatcacga atcgatccaa aacctccttg     240
aaatctcgtc tccgtggagg agaaactctc tacggcctct ttttactctc cttctcgccg     300
acattagccg agatcgctgc tcacgccggt tacgattacg tcgtcgttga catggaacac     360
ggtcccggag gcataccgga agctttggat tgtattcgag ctcttaacgc cgccggaaca     420
tccgcaattc tccgattacc ggaaaaactcc tcaacctggg ctaaaaaagc cctagatcta     480
ggtcctcaag gaatcatgtt cccaatgatt gagtctcgca agacgctac caaagcggtg      540
tcgtattgcc ggtttcctcc cgacggcatc cgtggatcgg cgcacacggt ggtgcgagct     600
tcgaactacg gaatcgacga agggtattta agtaattacg cagaggagat tctgattatg     660
tgccaggtgg aatcatctga aggagtgaag aaagctgatg aaatcgcagc cgttgatggt     720
gttgactgtg tgcaaatggg accgttggat cttagtgcga gtttggggta tttgtgggat     780
ccgggacata agaaagtgag agagatgatg aagaaagctg agaaatcgtg tctgacgtca     840
gacccggcga aaggcgggggc ttatttgtcg ggtttcgcga tgccgcacga cggagctgtt     900
gagatccggg acgtggtta tcatatggtc gccggagctg ttgatgttgg attgtttagg     960
aatgctgctg ttgaagatgt gaggagattc aagatgggtt tggtcaatga atcggatggt    1020
gaggattcgt tggaacatga taaagatgtt gacgatgaga agtactggag cgaataa      1077
```

<210> SEQ ID NO 134
<211> LENGTH: 1231
<212> TYPE: DNA
<213> ORGANISM: Theobroma cacao

<400> SEQUENCE: 134

```
tttttttttt tttttttccga actcaaagtc tcaatctcga tttcattgtc gaataggaaa      60
cgatgctgct caacatgtac aaaaacttgc aaccaaatag acaccaaaag gaaaagcaaa     120
gtaaaactcc atctattttt attcactcca atacttctca tcaccatctt tatcctcttc     180
cccatcatca tcaaaaccca ccgtcacact attcttaaaa cttttaacat ccgccaaagc     240
cgcatttctg aacaacgcaa atcaacggc gccagaaacc atgtgatacc cgcgcctccc     300
gagctccacc ggcggatcat gcggcattgc aaaaccagcc aagaaggctc caccgtcccc     360
agggtccgac ttaagcactc ctctctccgc cgtcctcaac atctcccctaa cgttcttgtg     420
acccgggtcc cacaagtaac ccaagctagc gcttaaatcc aacgggccca tttgaacaca     480
gtcgacccca tcaacggcgg cgatctcttc cactttttc accgcatcta ccgtctccac     540
```

```
ctggcacatt attaacagat cctccatgta attactcaaa tacccttcgt tgattccgta    600
gttggaagct ctcactaccg tgtgagcgga gccacggatt ccgtcaggag ggaaacggca    660
ataagacacc gccttttag cgtctttagg ggagtcaatc atagggaaca tgatcccttg    720
tggaccgagg tcaagagctt ttttggccca agcagcggag aattcaggga ggcggatgat    780
ggctggggta ttggtcgggg agagagtgcg taggatttgg agggattcgt ggattcctcc    840
agggccgtgt tccatgtcga tgactacaaa gtcgtagcca gagagtgcgg cgatctcggc    900
cagagtggga gagaaggaaa ggaggaagat accgtagagg gtttcgccgt tgcggaggcg    960
ggatttgaga gaggatgtgg agggagaagg tgaaggatta ggggaacatt tgagagggga   1020
gagggtgggg aatttggtag agtttaaggg tttgagtaag gaaatggaag gcttggaaga   1080
aggaaaggag agggatttgg aggaaatgaa tgaaagagga tttctaaggg aaagtttggg   1140
gctggcggca gcggcggcgg tgtatgtgag agtggccatg gcttgtggtg caggggatg    1200
gtggggaatt tggggttatt aaccaacccc g                                  1231
```

<210> SEQ ID NO 135
<211> LENGTH: 1074
<212> TYPE: DNA
<213> ORGANISM: Ricinus communis

<400> SEQUENCE: 135

```
atgcccgctc tcaccgccgc cgccaccact ttcttttccc tctcttcaaa tcatcaaaat     60
cctaataagc cccagtgctc ttcacttcct aacctaccct tcaatttcaa aaccctaaac    120
cctaacacca tcatcaccac caccacattc aaaaccctaa ctccactcaa atcctcgacc    180
tcctctgatg ttgaccctac ctcctcatcc accactccca tttcggccgc ctcctctttc    240
tctctcaaat ctcgtctccg taacggcgaa actctgtacg gcatattcct cctcagcttc    300
tccccaactc tagccgaaat ctccggcctc gccggctacg atttcgcggt tgtggacatg    360
gaacacggtc ccggcggcat caccgaagct cttaactgtc tccgcgcgct cgcctccact    420
caaacgccgg cgatcattag attgccgaaa acctgcccta cgtgggcgaa aaaagcgcta    480
gatctcggtc cgcaggggat aatgtttccg atggttgaga gtcccaaaat ggctaaaaag    540
gcggtgtcgt attgccggtt tccaccggag ggaatacgcg atcggcgca tacggtggtg     600
agagcgtcga gttatgggat agatgaaggg tatttaagta attacggaga cgagttgttg    660
ataatgtgcc aagtagagag cgaagaaggc gttaaaaaag cagatgaaat tgcagccgtc    720
gatggggtga actgtataca aatgggaccg ttagatttaa gtgctagtat ggggtatttg    780
tgggacccag gcataagaa agttagagag atgatgagag ctgctgagaa ggctgtttta    840
ggatctaaga aagtggcgg tggggcctac ttggctgggt tctctatgcc acatgatgga    900
cccattgatt tgaaatcaag aggatataat atggtagcag aaccgtcga tgttgggctg    960
tttagaagtg ctgccgttga tgatgttaag aagtttaaga tgagtttagt tcaagggtct   1020
gacgatgagg aggagcatga taaggatgct gatgagaagt actggagcga gtaa          1074
```

<210> SEQ ID NO 136
<211> LENGTH: 1227
<212> TYPE: DNA
<213> ORGANISM: Solanum lycopersicum

<400> SEQUENCE: 136

```
ggacccaaac agtattgaca ctaaaatggc tgccatggcc ggattttctt cttcttcttc     60
```

```
ttcatctcta tcaactcttc gaaaatcctt tacttccact tcgcctatttt tcccttcatt    120
ccattctctg cttccgcgaa ttccaaaacc ttcatcactc aaaacggtaa acccaatctt    180
caaaccctcc ctaccacgcc gattctcctc cgctgttgcc gccaccgccg attccgccga    240
agttagacaa tccctcaaaa ctcgcttgaa aaatggagaa acccttacg gcattttcct    300
tctcggtttc tctccaaccc tcgctgagat cgctggactc gccggatacg acttcgccgt    360
cgtcgatatg gaacatggtc acggaggtat ctccgatgca ctcccttgtc ttcatgcctt    420
agccgctact caaaccccag ctattctccg tatccctgaa tcctcagcta cttgggctaa    480
aaaagccctc gatctcggcc cacagggcat tatgttttccg atgatcgacg gtccgaaatc    540
agcccgaaag gcagtgtctt actgccgttt cccgcctaat ggcgtacgtg gatctgctca    600
tactgttgtt agagcttcga gctatggaat tgatgaaggg tatttgagta attacgagga    660
tgatctactg atcatgtgtc aagttgagtg tgtagatgga gtgaagaaga ttgatgaaat    720
tgcagcagtg gaaggggttg attgtattca aatgggacca ttggatttga gtgcgagttt    780
agggtactta tgggatcctg ggataagaa agtgaaggag atgatgaata cagctgaaaa    840
aggagcattg aagaagaagc cacttgacgg tggggcgtat ttatctggat ttgcaatgcc    900
tcatgatagt cctgagaatt tgaaatcaag agggtaccat atggtttcag gagcagtaga    960
tatcgcgttg tttagaaatg cagctgtgga ggatgtgaac aagtttaaga tgagtttgga   1020
taaaggattt gaagatcaaa aagatcataa agatggtgaa gagaagtact ggagtgagta   1080
aaaatttgaa cttttgttac attacatcct agttttttgaa gtattatgtt ctgcttttttg   1140
ttgattatga gtcttggaga ttaacttaag tttcgaattt gagctactta tgcaatacag   1200
ccttttttttt agaaaaaaaa aaaaaaa                                       1227

<210> SEQ ID NO 137
<211> LENGTH: 1080
<212> TYPE: DNA
<213> ORGANISM: vitis vinifera

<400> SEQUENCE: 137
atggctacgg tgaccttccc cccttcgtct ctctcaaccc caccgaaacc ccactttcct     60
aaaccctcca aaaccctaat tcaccttcct tctccgaagt tttctttctc aaagccagca    120
ttcaacctca aaaccctaaa ccccattctc tcgcaatccc cagctccact ccggcttttcc   180
aacacgactt ctgatctcat cgcctacgac aattcggtgc cggtgccggt gccggtgcct    240
tctcgatccc tgaagtctcg tctccacgat ggcgaaaccc tttatggcct cttcctcctc    300
agcttctctc ccactctcgc tgagatcgcc ggcctcgctg ctacgacttt cgtcgtcgtt    360
gatatggagc acggccacgg aggcgtctcc gacgccctac cctgcctcca cgccctcgcc    420
gctactcgga ctccggcaat cattcggctc ccagagagtt gtccaacgtg ggcgaaaaag    480
gccctcgatc tgggtccaca agggatcatg tttccgatga tcgacagccc taaattggcg    540
aggaaagccg tctcgtactg ccggttttcca ccggcggggg ttcgtgggtc ggcgcacact    600
gtcgtgaggg cgtcgagcta cggcatcgac gctgggtatc tgagcaatta cgaggaggag    660
ttgttgatca tgtgccaggt cgagtctgaa gaggctgtga agaagatcga agacatcgcc    720
gccgtcgatg gggtcgactg catccaaatg gggcccatgg atctgagcgc gagtatggga    780
tatttgtggg atccagggaa caagaaggtg agagagatga tgaaggttgc agagaagggc    840
gtgttgggga cgaagaaaaa acccagggaa ggcgcctact ggctggcctt cgctatgccg    900
catgattccc cagatgatct aaggtcgcga ggctatcaca tggtttctgg tgcagtcgat    960
```

```
gtggggttgt tcaggagtgc tgcggtcgag gatgtgaaga agttcaagat ggggttgaag    1020
gaggcctctg acgatgagaa agagaatgct aaagaagatg agaagtactg gagcgagtaa    1080

<210> SEQ ID NO 138
<211> LENGTH: 1047
<212> TYPE: DNA
<213> ORGANISM: Carica papaya

<400> SEQUENCE: 138
atggctgcca gagctatcct ctccgatctc cctctctcat cgtccttcac caaaccttct      60
tcttccacat ccttctcccc aagaccccct cctctctcat tccctttctc cttacctcgc     120
cttaaaaccc taaccttcaa ttccccctct cacctctccc ccaccatcac cacagccgcc     180
gttacttccg cttctgtttc ttcctcctca tccttgaaat cccgcctccg gaacggggat     240 acccttttacg ggcttttcct cctatcattc tccccaactc tcgcagagat tgccgccctc     300
gccggctacg atttcgtcgt tatcgacatg gagcatggtc cgggggggcat ttccgaggcc     360 ttacactgcc tccgcgctct ctccgctgct ggtacccctg gtatcctccg cctcccagag     420
agctgtccca cgtgggcgaa gaaggccctc gatcttggtc cccagggcat catgttcccc     480
atgatcgatt cccctaaaga cgcgaagaag gcggtttcgt actgtcattt tccccccaaa     540
gggatccgtg atcggcgca cactgttgtg agagcttcga attacggggt ggatgaagag     600
tatctgagta cttacgagga ggagcaactg ataatgtgcc aggtagagtc tgaggaggga     660
gtgaaaaaag tggaagacat tgcggctgtt gaaggggttg actgcataca gatgggtcct     720
ttagatctga gcgcgagcat ggggtacttg tgggatccag ggcacaagaa ggttagagag     780
atgatgggag tggcagagaa gagggtgttg ggtacgaagc ctggcaatgg cggagcctac     840
ttagcgggtt ttgcaatgcc gcatgatggg ccggatgatc tgcgggcgcg aggttatcac     900
atggtgtctg gtgcggttga tgttgggatg ttcagaaatg ctgctgtgga agatgtaagg     960
aggtttaaga tgggtttgat gcagggttcg gatgatgaga aggaacgggg aagggatggt    1020
gaagatgaaa agtactggag cgagtga                                        1047

<210> SEQ ID NO 139
<211> LENGTH: 1194
<212> TYPE: DNA
<213> ORGANISM: Citrus clemetina

<400> SEQUENCE: 139
gccgccgccg tcaccaaaact tgcacaaaat aagatcattt catttccaaa atcacccttg      60
ttcaacctca acggcaacaa atccaaaatc gttttcccaa aactgaaatt gacccccctca    120 gtctcacgct caccctcgga tctgtcgcca ggcgatcccc tttccccatc tccatcaccc    180
tcgcccgaat cactcaagta tcgtctccaa agcaacgaaa ccctgtacgg actcttcctc    240
ctctctttct ccccaactct tgccgaaatt tcgggcctcg ccggttacga tttcgtcgtc    300
gtagacatgg agcacggccc tggcggcatt tccgatgctc tcgcttgcct tcacgctctt    360
gccgccacgg ggacaccggc cattctgcgg ctccctgaaa gttgcccaac ttgggctaaa    420
aaggccctcg atctgggccc acaaggggtc atgttcccta tgattgactc cccagaagcc    480
gccaaggaag cggtgtcgta ttgccggttc ccgccttctg gagtgcgggg atccgctcac    540
acggtggtga gagcgtccgg ttacgggatt gatgagggat acttgagtaa ttacgaggag    600
gagttgttga ttatgtgcca ggtggagagc gaggaaggcg tcaagcgagc cgaagacatc    660
```

```
gcggcggttg ctggggttga ctgcgtgcaa atgggaccgt tggatttgag tgcgagtatg    720
gggtacttgt gggatccagg gcacaggaag gtgagggaga tgatgagggt ggcggagaaa    780
ggggttttgg gcggtggcaa ggcttacttg gctgggtttg ctatgcctca tgatgcgcct    840
cttgagatga agtcacgtgg ataccacatg gtgtccggtg ccgttgacgt ggggctgttt    900
agaaatgcgg ctgtggagga cgtggcaaga tttaagatga atttgacgga tgatgccgac    960
gatatgacaa acataatgat gatgcttgga gggaaaggat taagatgctg atgacagtac   1020
tggaacgaaa aataatggta agggcatgaa tgaaaaaata tcatgaaaat gaagatgaaa   1080
ggcatgctaa gggcatcaat cttaacaatc accaaaaact taagttttgt gaattccaat   1140 tttttttatat aaactttctt tgaataaacc ccaggcggga agttttctat cgtg         1194
```

<210> SEQ ID NO 140
<211> LENGTH: 1143
<212> TYPE: DNA
<213> ORGANISM: Citrus clementina

<400> SEQUENCE: 140

```
cttcacactt gacgaagacg aactgagcgg aactgaaact gagacaatta caaaagcaac     60
catgaccacg ctcacttgct cgggctccgg cactgccgcc actgtcgcca agcttgcaca    120
aaataaaatc agttcatttc caaaagcacc cttgttcacc ctcaacggca acaaatcgaa    180
aatcgttttc ccaaaactga aattgacccc ctcagtctca cgctcaccct cggatctgtc    240
gccaggcgat ccccttttccc catctccatc accctcgccc gaatcactca agtatcgcct    300
ccaaagcaac gaaaccctgt acggactctt cctcctctct ttctcccaa ctcttgccga    360 aatttcgggc ctggccggtt acgatttcgt cgtcgtagac atggagcacg ccctggcgg    420 catttccgat gctctcgctt gccttcacgc tcttgccgcc acggggacgc cggccattct    480
gcggctccct gaaagttgcc caacttgggc taaaaaggcc ctcgatctgg gcccacaagg    540
ggtcatgttc cctatgattg actccccaga agccgccaag gaagcggtgt cgtattgccg    600
gttcccgcct tctggagtgc ggggatccgc tcacacggtg gtgagagcgt ccggttacgg    660
gattgatgag ggatacttga gtaattacga ggaggagttg ttgattatgt gccaggtgga    720
gagcgaggaa ggcgtcaagc gagccgaaga catcgcggcg gttgatgggg ttgactgcgt    780
gcaaatggga ccgttggatt tgagtgcgag tatggggtac ttgtgggacc cagggcacag    840
gaaagtgagg gagatgatga gggtggcgga gaaggggggtt ttgggcggtg gcaaggctta    900
cttggctggg tttgctatgc ctcatgatga acctcttgag atgaaatcac gtggatacca    960
catggtggtc ggtgccgttg aactggggct ggttaaaaat gcggctgtga aggaagtggc   1020
aagatttata aagaatttaa acgaaaaatg ccaaataata aaaagataa agcttggagg   1080 ggaaaggatt aaaaaatctt aataaaaaga tacgtgaacc aaaaaaaaaa ggggtaatgg   1140
cag                                                                 1143
```

<210> SEQ ID NO 141
<211> LENGTH: 1044
<212> TYPE: DNA
<213> ORGANISM: Oryza brachyata

<400> SEQUENCE: 141

```
ttactcactc cagtacccgt catcctcctt gtccttcttt tcatcccat attcatctcc      60 ctcctcacca atttccatca ctgcctcctt gaaccgctta acatcctcca atgccgcctt    120
tcggaacatc ccaatgtccg ctgcaccagc caccatatgg taccccctca acttgagctg    180
```

```
ctcagctggg tcattcggca tcgcaaatcc gcctaaatat gccacgttgc catctgaagc      240
agtcaccttc ttcttcctgg catccaacac cttcttctcg gcctccctca gcctggctcg      300
caccttcctg ttccctgggt cccacaggta ccccatgctg gctgacaagt cgagtggccc      360
catttggacg acgtcgacgc catcaacggc ggcaatggcg tcgacctctg caatgccagc      420
ggcagtctcg acttggcaaa tgatcagggt gtcgtcctcg cagcgggaga ggtaggagtc      480
gtcgaggcca tacacggagg cgcggacgat ggggtgggcg cgccacgaa ccccacgggg       540 cgggtatcgg cagtgcgaca cggcggcggc cgcagcagcg ggggactcga cggcgggaag      600
catgagaccc gcggggccga gtcgagcgc cttcttggcc cagatggagc aggcctcggg       660
gaggcggagg atcgcggggg tgcgggcagc gtcgagggcg cggagacagg cgagcgcctc      720
gggaatgccg ccggggccgt gctccatgtc gacgacgacg tagtcgtagc cggcgagcgc      780
ggcgagctcg gcgagggtgg gggagaagga gaggaggaac aagccataca gggtcttccc      840
ggcggcgagg cgtgacttga gtgaaggggc agcggagagg agctcggagg tggcggcgga      900
gacggcagag gctgagcgcc gcccgcgtcg cggcagggg agcagggcgg gggcgcggcg       960
ggatggagga ggcgacgagg ggcttggctt gcgcgcgcgg aggaggcggg agagcgaggc     1020
cgaggacgag gcgaaggcgg ccat                                            1044
```

<210> SEQ ID NO 142
<211> LENGTH: 1029
<212> TYPE: DNA
<213> ORGANISM: Brachypodium distachyon

<400> SEQUENCE: 142

```
atggcagtct ccgccaccgc cacttccctc tcccacctcc tccccgcgcc gaaacccaaa       60
cccagaaccc cgcctcgcct ctccctcctg cccagcaacc gcaagccctc ccgcgccgcc      120
accagtgcca tatttgccgc cgcggccgcg gcctccgact tcctctcccc ggtcccctcc      180
ctcaagtccc gcctggcagc cggcgacacc ctctacggcc tcttcctcct ctccttctcc      240 cccacccctcg ccgagatcgc cgcgctcgct ggctacgact acgtggtcgt cgacatggag      300
cacgggcccg gtagcatcac ggaggccctt gcctgcctcc gcgccctcga cgccgcccgc      360 accccgccg ttctccgcct cccagaggcc tgccccgtct gggcgaagaa ggcgctcgac       420
ctcggtcctg caggcctcat gctcccagcc atcgagtccc cggccgccgc cgccgaggcc      480
gtatcgcact gccggtaccc gccccggggc gtccgtggcg ccgcctaccc gatcgtccgc      540
gcatccgctt atggcctcga cgactcctac gtctcccgct gtgaggacga cccctcatc      600 atctgccagg tcgagaccgc cgcaggtgtt gcagaggtcg acgccatcgc cgctgtcgac      660
ggtgtcgacg tcgtccagat gggcccgctc gacctgtcgg cgagcatggg gtacctatgg      720
gatcccggta acaggaaggt gcgagcagcg ctgagggaag ccgagaggaa ggtgttggag      780
gccaggaaga agaaggttac agcttcggcg ggtaatgcag cttacttggg tggatttgcc      840
atgccgaatg acccacctga gcagctcaag atgaggggt accatatggt ggccggtgct       900
gtggacattg ggttgttccg gaaggcagca ttggaggatg tcaagtggtt caaggaggcg      960
gtaatgaaaa tcggggaaga ggagggcgag gaggaggatg agaaggacga tgggtattgg     1020
agtgagtga                                                             1029
```

<210> SEQ ID NO 143
<211> LENGTH: 1041
<212> TYPE: DNA

<213> ORGANISM: Sorghum

<400> SEQUENCE: 143

```
atggccgcca ctgcctcctc cctctcccac ctcctcctcg cccccaagcc cagacccaaa    60
gctcaaccaa acccctcgca tctccgctcc cacagcatca cgagcccgct cccctgccgt   120
gggcggcgct cctccctcgg ggtctccgcc gcggcatccg acctcctctc tcccgcgccc   180
tccctcaagt cccgcctcgc cgccggggac accctctacg gctgttcct cctctccttc    240
tccccgaccc tcgccgagct cgccgccctc gccggctacg actacgtcgt cgtcgacatg   300
gagcacgggc ccggcgggat ccccgaggcg ctcgcctgcc tccgcgcgct cgacgccgcg   360
cgcaccccg ccgtcctccg cctcccggag gctagcgccg tctgggccaa gaaggcgctg    420
gacctcggcc ccgcgggcct catgctcccc gccatcgagt ccccgccggc cgccgccgag   480
gcggtctccc actgccgcta cccgccgcgc ggggtccgcg gcgccgcgca ccccatcgtc   540
cgcgcctccg cctacggctt cgacgactcc tacatctccc gctgcgagga cgatacgctc   600
gtcatctgcc aggtcgagac cgccaccggg atcgcggaga tcgacgccat cgccgccatc   660
gacggcgtgg acgtcgtgca gatgggcccg ctcgacctgt cggctagcat gggatacctg   720
tgggaccctg gaacaggaa ggtccgggcg gcgctgaggg aggccgagag gaaggtgctg    780
gaggccagga agaagaaggt ggcagcggcc tcggatggca atgctgctta cttgggtggg   840
tttgcaatgc agaatgaccc gccagagcag ctcaagttga ggggttacca tatggtggct   900
ggcgcagtgg acattgccat gttccgcaag gcggcattgg atgatgtcaa gcggtttcga   960
gaggcagtga tggagatcgg cgaggaaggt gatgaggatg agaaggatga aaggaaaat  1020
gacgggtact ggagtgagtg a                                          1041
```

<210> SEQ ID NO 144
<211> LENGTH: 1419
<212> TYPE: DNA
<213> ORGANISM: Paspalum notatum
<220> FEATURE:
<221> NAME/KEY: misc_feature
<222> LOCATION: (595)..(595)
<223> OTHER INFORMATION: y=t/u or c

<400> SEQUENCE: 144

```
cacgcggcgg ccgccggcct ggacaaccac tcccccactc ggcatcggca gtcgagatcc    60
ccaaaaccaa gccaccgtcg acatcgaggc gccgccccgc ccaccggctt ctctcgccat   120
ggccgcctcc tccctctccc accccctcct cgcgcccaaa acacaaccaa accccctcacc  180
tctcccctcc cgccacatcg ccaccccgct cccccgccgc gggcggcgct ccgcccacgc   240
ggtctccgcc gctgcatccg atctcctctc cccgcgccc tccctcaagt cccgactcgc    300
cgccggggac accctctacg gctgttcct cctctccttc tccccgacgc tcgccgagct   360
cgctgccctc gccggctacg actacgtcgt cgtcgacatg gagcacgggc cgggcgggat   420
tcccgaggcg ctcctctgcc tgcgcgcact cgacgccgcg cgcaccccgg ccgtgctccg   480
cctcccggag gccagcgccg tctgggccaa gaaggcgctc gacctcggcc cggcgggcct   540
catgatcccg gccgtcgagt ccccgccggc cgctgccgag gcagtctcct actgycgcta   600
cccgccgcgc ggggtccggg gcgcggccca ccccatcgtc cgcgcctccg cctacggcct   660
cgacgactcc tacctctccc gctgcgagga cgacacgctc ctcatctgcc aggtcgagac   720
cgccgccggg atcgcggagg tcgacgccat cgcctctgtc gacggcgtgg acgtcgtgca   780
gatgggcccg ctcgacatgt cggccagcat ggggtacctt tgggaccctg gaacaggaa    840
```

```
ggtgcgggcg gcgctgaggg aggcggagag gaaggtgctg gaggccagga aaaaggtggc    900
ggcgccttcg gatggcaatg ctgcttactt gggcgggttt gcaatgcaga atgacccacc    960
ggagcagctc aagttgaggg gttaccatat ggtggctggt gcagttgaca ttgggatgtt   1020
ccgaaaggcg gcattggatg acgtcaagag gttccgggag gcggtgatgg agatcggtga   1080
ggagggtgay gatgaggaag atgagaagga tgagaagcaa aatgatgggt actggagtga   1140
gtgagcagag cataacaaat ctaagctgtg gcttggctga aaactggtta tggagttttg   1200
ttgtggtgtt gttttgttct gaattgagag ggagtaagcc atcttaactc ttaaggagcc   1260
caagaatctc ctggtttagc tgtacccttt ttatttcttc atttgatttt caggtgaaca   1320
gtctgtgggc accgtgtatc cccattttgt aggaagaaac ttcgaactgg tggctaccaa   1380
taaagcattg aattagaaag aatggccttt atttttttc                          1419

<210> SEQ ID NO 145
<211> LENGTH: 1211
<212> TYPE: DNA
<213> ORGANISM: Eragrostis nindensis

<400> SEQUENCE: 145 ccccaaaacca ccgcctccac ccaccggcag cgctcgccat ggccgccgcc gcctccctct    60
cccacctcct cctcgctccc aaactcaaat cgaagccgaa ccccacgcct ctcccctccc   120
gtcgcgcctg cgtcccctttg ccccgcagca ggcgcccccac tcaagcgatc tccgccgcgg   180
catccgacct cctcgccccc gcgccgaccc tcaagtcccg cctcgccgcg ggcgacaccc   240
tctacggcct cttcctcctc tccttctccc ccaccctcgc cgagctcgcc gcccttgcgg   300
ggtacgacta cgtcgtcgtc gacatggagc acgggccggg cggcatcccc gaggcgctcg   360
cctgcctccg cgcgctcgac gccgcgcgca ccccggccgt gctccgcctc cccgaggcca   420
gccccgtctg ggccaagaag cgctcgacc tcggccccgc gggcctcatg ctccccgccg   480
tcgagtcgcc cgccgcagcc gccgaggccg tctcctactg ccgctacccg ccgcgcggcg   540
tccgcggcgc ggcgcacacc gtcgtccgcg cctccgccta cggcctcgac gactcatacc   600
tctcccgctg cgaggacgag accctcatca tgtgccaggt cgagaccgcc gccggcatcg   660
cggaggtgga agccatcgcc gccgtcgacg gcgtcgacgt cgtgcagatg ggcccgctcg   720
acctgtcagc cagcatgggg tacctgtggg atccggggaa caggaaggtg cgggcgacgc   780
tgagggaggc cgagaggaag gtgctggcag ccaggaagaa gaaggatgca tcctcggatg   840
gcaatgctgc ttatttgggc ggctttgcga tgccgaatga ccaagcggag cagctcaagc   900 tgagggggtta ccatatggtg gctggcgcag tggacgttgg gctgttccgg aaagcagcac   960
tggatgacat caagcggttc cggaggcag tgatggagat tggcgaggag ggagacgagg  1020
aggaggatga aaagttggag aaggaagctg acgggtattg gagcgagtga gcacaggctc  1080
agctgagctg aaacagagcg atgaactgat tgtggtgtct tttctggtga tttggaatcc  1140
tgttctgaac tgagagggtc taaatgatca taagtggcct cggagtttct ggattttggt  1200
gtactcttgt t                                                       1211

<210> SEQ ID NO 146
<211> LENGTH: 1519
<212> TYPE: DNA
<213> ORGANISM: Zea mays

<400> SEQUENCE: 146
```

-continued

```
gccacgccag caagcgcacg gcggcaccgc agcacgtgac aaaacagtca cgccccacgc    60
ggccccactt ctccggccgc cggactcgcc gttcggcttg cagtcgcag acggcagatc   120
ccaaaatcga acaaccacca cctcccccctc cgccgaccgg ccggccggct cgctcgcca   180
tggccgccac cgcttccttc ctctcccacc tcctcctcgc ccccaagcgc agacccaaaa   240
ctcagccaaa cccctcgcat cttccctccc agcgcatcac ggaccggctt ccctgccgtg   300
ggcggcgctc ctccgtcgcg gtctccgccg cggcatccga cctcctctct cccgcgccct   360
ccctcaagtc ccgcctcgcc gccggagaca ccctgtacgg tctgttcctc ctctccttct   420
cccctacccct cgccgagctc gccgcccctcg ccggctacga ctacgtcgtc gtcgacatgg   480
agcacgggcc gggcgggatc cccgaggcgc tcgcctgcct tcgcgcgctg gacgccgcgc   540
gcaccccgc cgtgctccgc ctcccggagg ccagcgccgt ctgggccaag aaggcgctgg   600
acctcggccc cgcgggcctc atgctccccg ccatcgagtc ccccgaggcc gccgcggagg   660
cggtctccca ctgccgctac ccgccgcgcg gggtccgcgg cgccgcacac cccatcgtcc   720
gcgcctccgc ctacggcttc gacgactcct acctctcccg ctgcgaggac gatacccctcg   780
tcatctgcca ggtcgagacc gccaccgcga tcgcggagat cgacgccatc gccgccgtcg   840
acggcgtgga cgtcgtgcgg atgggcccgc tcgacctgtc ggctagcatg ggataccctgt   900
gggaccccgg gaacaggaag gtccgggcta cgctgaggga ggccgagagg aaggtgctgg   960
aggccaagaa gaagaagaag gcggcggcag cagcctcggg tggcaatgct gcttacctgg  1020
gcgggtttgc aatgcagaat gacccgccgg agcagctcaa attgaggggt taccatatgg  1080
tagctggcgc agtagacatt gctatgttcc ggaaggcggc attggatgat gtcaggcggt  1140
tccgagaggc agtgatggag atcggcgagg aggatgatga ggatgaggtt gagaaatgtg  1200
agaaggaaaa tgacgggtac tggagtgagt gagtgaacag tgtagaacag agctgagctg  1260
aagcatggag agaagtggct atgggttttg ttctggtgat atgtttttg ttctgaattc  1320
agaggattta ttcgagatct taaggagccc aagaatttct agcttagct gtactcttgt  1380
ttaggtcatc atttgatttt caggtgaaca atccggttgg gcatcttaaa catccctatt  1440
tgtaggatga aactcagaac tggtggctac caataaagtg ctgtttttt tcaaaaaaaa  1500
aaaaaaaaaa aaaaaaaa                                                1519
```

<210> SEQ ID NO 147
<211> LENGTH: 350
<212> TYPE: PRT
<213> ORGANISM: Zea mays
<400> SEQUENCE: 147

```
Met Ala Ala Thr Ala Ser Phe Leu Ser His Leu Leu Leu Ala Pro Lys
1               5                  10                  15

Arg Arg Pro Lys Thr Gln Pro Asn Pro Ser His Leu Pro Ser Gln Arg
            20                  25                  30

Ile Thr Asp Arg Leu Pro Cys Arg Gly Arg Arg Ser Val Ala Val
        35                  40                  45

Ser Ala Ala Ala Ser Asp Leu Leu Ser Pro Ala Ser Leu Lys Ser
    50                  55                  60

Arg Leu Ala Ala Gly Asp Thr Leu Tyr Gly Leu Phe Leu Leu Ser Phe
65                  70                  75                  80

Ser Pro Thr Leu Ala Glu Leu Ala Ala Leu Ala Gly Tyr Asp Tyr Val
                85                  90                  95

Val Val Asp Met Glu His Gly Pro Gly Gly Ile Pro Glu Ala Leu Ala
```

```
               100                 105                 110
Cys Leu Arg Ala Leu Asp Ala Ala Arg Thr Pro Ala Val Leu Arg Leu
        115                 120                 125

Pro Glu Ala Ser Ala Val Trp Ala Lys Lys Ala Leu Asp Leu Gly Pro
130                 135                 140

Ala Gly Leu Met Leu Pro Ala Ile Glu Ser Pro Glu Ala Ala Ala Glu
145                 150                 155                 160

Ala Val Ser His Cys Arg Tyr Pro Pro Arg Gly Val Arg Gly Ala Ala
                165                 170                 175

His Pro Ile Val Arg Ala Ser Ala Tyr Gly Phe Asp Asp Ser Tyr Leu
            180                 185                 190

Ser Arg Cys Glu Asp Asp Thr Leu Val Ile Cys Gln Val Glu Thr Ala
                195                 200                 205

Thr Ala Ile Ala Glu Ile Asp Ala Ile Ala Ala Val Asp Gly Val Asp
        210                 215                 220

Val Val Arg Met Gly Pro Leu Asp Leu Ser Ala Ser Met Gly Tyr Leu
225                 230                 235                 240

Trp Asp Pro Gly Asn Arg Lys Val Arg Ala Thr Leu Arg Glu Ala Glu
                245                 250                 255

Arg Lys Val Leu Glu Ala Lys Lys Lys Lys Ala Ala Ala Ala
            260                 265                 270

Ser Gly Gly Asn Ala Ala Tyr Leu Gly Gly Phe Ala Met Gln Asn Asp
                275                 280                 285

Pro Pro Glu Gln Leu Lys Leu Arg Gly Tyr His Met Val Ala Gly Ala
        290                 295                 300

Val Asp Ile Ala Met Phe Arg Lys Ala Ala Leu Asp Val Arg Arg
305                 310                 315                 320

Phe Arg Glu Ala Val Met Glu Ile Gly Glu Asp Asp Glu Asp Glu
                325                 330                 335

Val Glu Lys Cys Glu Lys Glu Asn Asp Gly Tyr Trp Ser Glu
            340                 345                 350

<210> SEQ ID NO 148
<211> LENGTH: 10
<212> TYPE: PRT
<213> ORGANISM: artificial sequence
<220> FEATURE:
<223> OTHER INFORMATION: motif

<400> SEQUENCE: 148

Glu Leu Val Ile Ser Leu Ile Val Glu Ser
1               5                   10

<210> SEQ ID NO 149
<211> LENGTH: 10
<212> TYPE: PRT
<213> ORGANISM: artificial sequence
<220> FEATURE:
<223> OTHER INFORMATION: motif

<400> SEQUENCE: 149

Ser Glu Val Ile Leu Ser Ile Val Leu Glu
1               5                   10

<210> SEQ ID NO 150
<211> LENGTH: 5
<212> TYPE: PRT
<213> ORGANISM: artificial sequence
<220> FEATURE:
```

```
<223> OTHER INFORMATION: motif

<400> SEQUENCE: 150

Glu Leu Val Ile Ser
1               5

<210> SEQ ID NO 151
<211> LENGTH: 5
<212> TYPE: PRT
<213> ORGANISM: artificial sequence
<220> FEATURE:
<223> OTHER INFORMATION: motif

<400> SEQUENCE: 151

Leu Ile Val Glu Ser
1               5
```